(12) United States Patent
Vignuzzi et al.

(10) Patent No.: US 10,206,994 B2
(45) Date of Patent: Feb. 19, 2019

(54) RNA VIRUS ATTENUATION BY ALTERATION OF MUTATIONAL ROBUSTNESS AND SEQUENCE SPACE

(71) Applicant: INSTITUT PASTEUR, Paris (FR)

(72) Inventors: Marco Vignuzzi, Noyers-sur-Serein (FR); Cyril Barbezange, Tours (FR); Gonzalo Moratorio, Paris (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 15/545,481

(22) PCT Filed: Jan. 28, 2016

(86) PCT No.: PCT/EP2016/051849
§ 371 (c)(1),
(2) Date: Jul. 21, 2017

(87) PCT Pub. No.: WO2016/120412
PCT Pub. Date: Aug. 4, 2016

(65) Prior Publication Data
US 2018/0008689 A1  Jan. 11, 2018

(30) Foreign Application Priority Data
Jan. 28, 2015  (EP) ..................................... 15305098

(51) Int. Cl.
| | | |
|---|---|---|
| C12Q 1/68 | (2018.01) | |
| C12P 19/34 | (2006.01) | |
| C12Q 1/70 | (2006.01) | |
| C07H 21/04 | (2006.01) | |
| A61K 48/00 | (2006.01) | |
| A61K 39/12 | (2006.01) | |
| C12N 7/00 | (2006.01) | |
| A61K 39/00 | (2006.01) | |

(52) U.S. Cl.
CPC ................ *A61K 39/12* (2013.01); *C12N 7/00* (2013.01); *A61K 2039/5254* (2013.01); *C12N 2760/00062* (2013.01); *C12N 2760/16134* (2013.01); *C12N 2760/16162* (2013.01); *C12N 2770/00062* (2013.01); *C12N 2770/24134* (2013.01); *C12N 2770/24162* (2013.01); *C12N 2770/32334* (2013.01); *C12N 2770/32362* (2013.01); *Y02A 50/383* (2018.01); *Y02A 50/388* (2018.01)

(58) Field of Classification Search
None
See application file for complete search history.

(56) References Cited

FOREIGN PATENT DOCUMENTS

| | | | |
|---|---|---|---|
| WO | 2006/042156 A2 | 4/2006 | |
| WO | 2008/121992 A2 | 10/2008 | |
| WO | WO2008/121992 | * 10/2008 | |
| WO | 2011/044561 A1 | 4/2011 | |

OTHER PUBLICATIONS

Nougairede A, et al., "Random Codon Re-encoding Induces Stable Reduction of Replicative Fitness of Chikungunya Virus in Primate and Mosquito Cells", PLOS Pathogens, vol. 9, No. 2, Feb. 21, 2013 (Feb. 21, 2013), p. el003172.
Gnadig N F, et al., "Coxsackievirus B3 mutator strains are attenuated in vivo", Proceedinogfs T Hen Ationaalc Ademofy Sciences, vol. 109, No. 34, Aug. 21, 2012 (Aug. 21, 2012), pp. E2294-E2303.
Graci J D, et al., "Mutational Robustness of an RNA Virus Influences Sensitivity to Lethal Mutagenesis," Journal of Virology, vol. 86, No. 5., Mar. 1, 2012 (Mar. 1, 2012), pp. 2869-2873.
Moratorio G, et al., Towards empirically-derived sequence space and fitness landscapes occupied by RNA viruses 11. 22nd International HIV Dynamics & Evolution . May 13-16, 2015. Budapest. Hungary. May 13, 2015 (May 13, 2015). p. 11.

* cited by examiner

*Primary Examiner* — Barry A Chestnut
(74) *Attorney, Agent, or Firm* — Arrigo, Lee, Guttman & Mouta-Bellum LLP

(57) ABSTRACT

The application generally relates to the attenuation of a RNA virus or of a clone thereof and involves the alteration of sequence space, more particularly the reduction, of mutational robustness of said RNA virus or clone. The means of the application are more particularly dedicated to the attenuation of an infectious RNA virus or clone, for the production of immunogenic composition or vaccine. More particularly, the means of the application involve the replacement of codon(s) by different codon(s), which is(are) selected to differ by only one nucleotide from a codon STOP, more particularly by different but synonymous codon(s), which is(are) selected to differ by only one nucleotide from a codon STOP.

28 Claims, 27 Drawing Sheets
Specification includes a Sequence Listing.

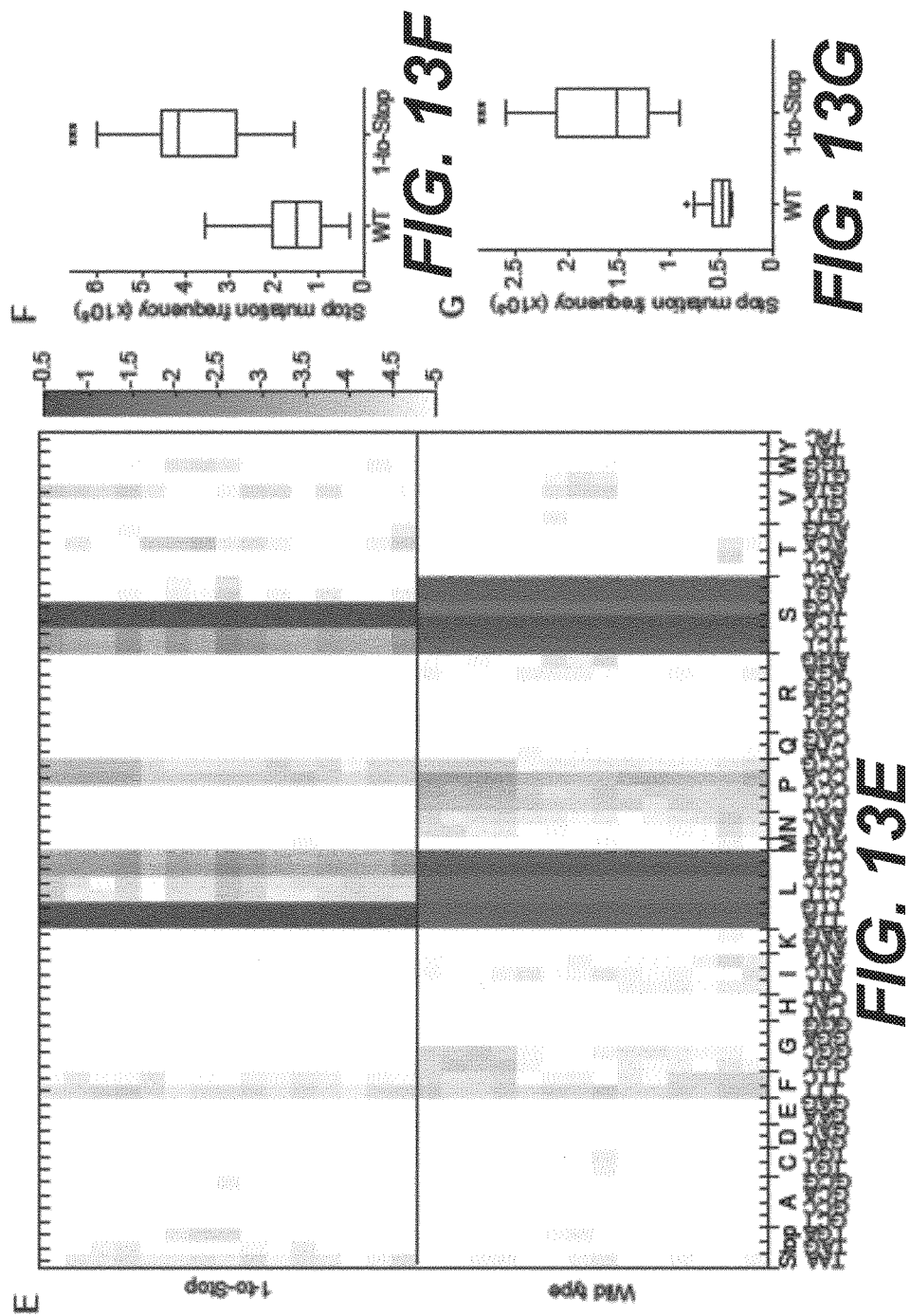

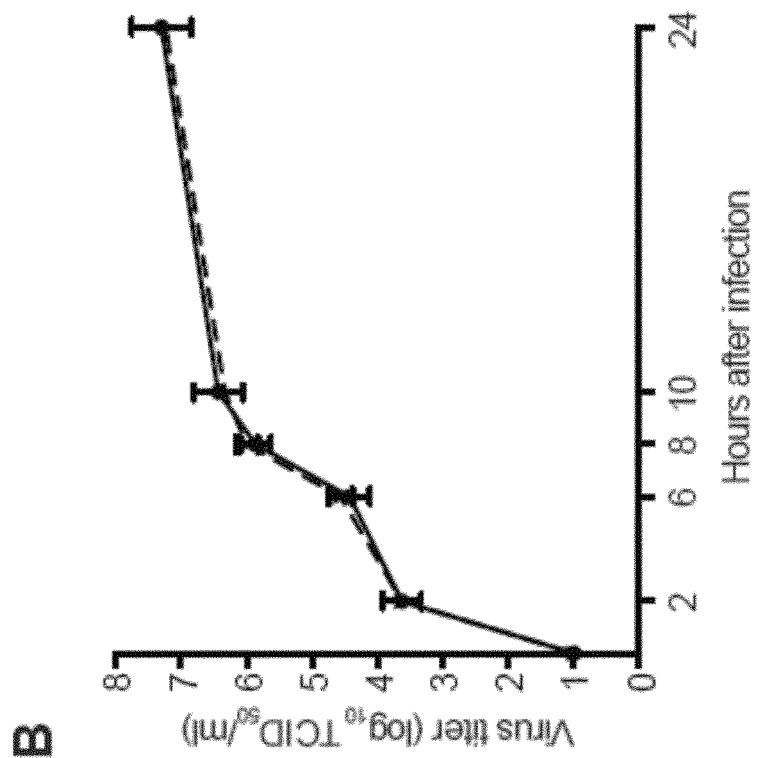
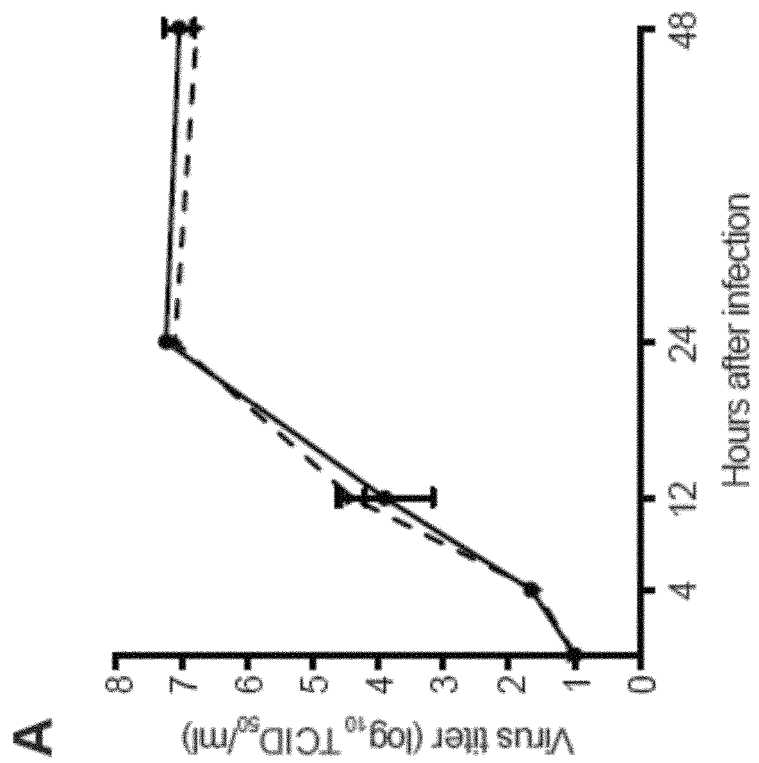

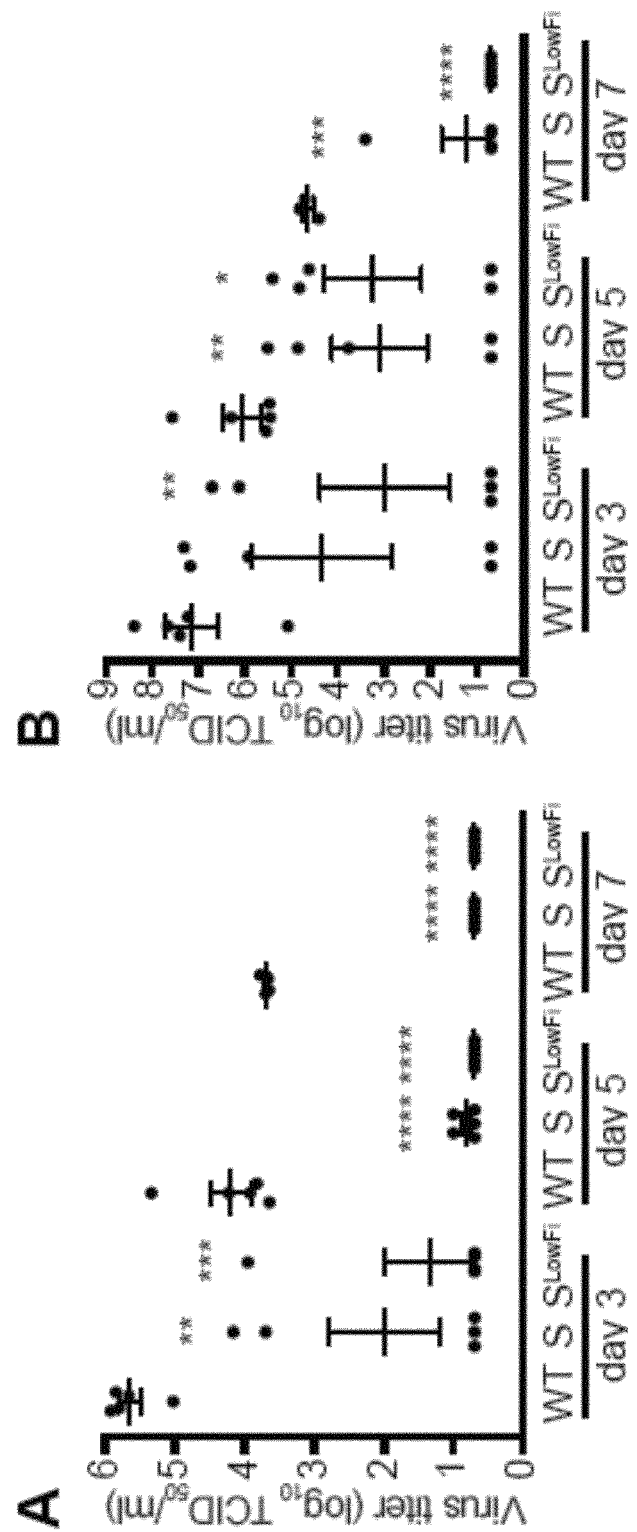

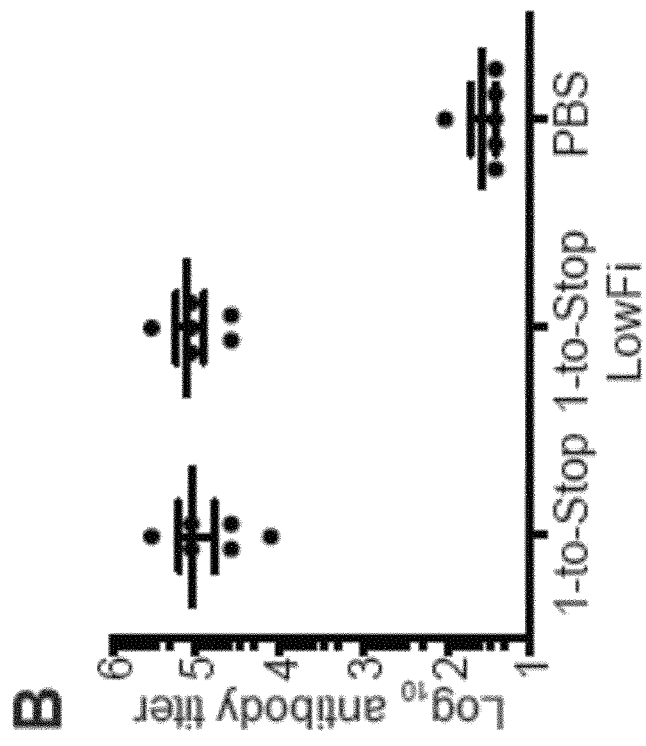
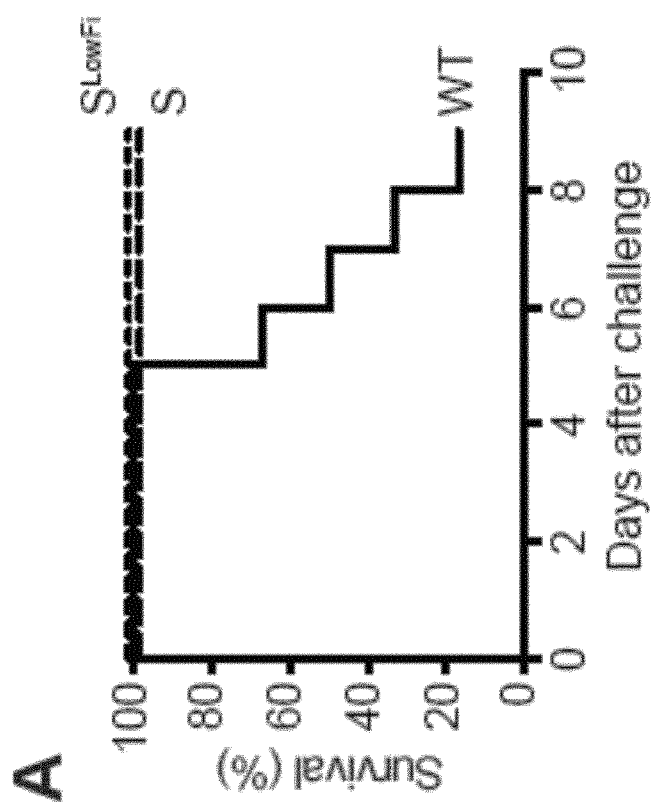
FIG. 17A
FIG. 17B

RNA VIRUS ATTENUATION BY ALTERATION OF MUTATIONAL ROBUSTNESS AND SEQUENCE SPACE

FIELD OF THE INVENTION

The application generally relates to the attenuation of a RNA virus or of a clone thereof and involves the alteration, more particularly the reduction, of mutational robustness of said RNA virus or clone. The means of the application are more particularly dedicated to the attenuation of an infectious RNA virus or clone, for the production of immunogenic composition or vaccine.

BACKGROUND OF THE INVENTION

RNA viruses have very high mutation frequencies. When a RNA virus replicates, nucleotide mutations are generated resulting in a population of variants. The consensus sequence, which is used to define a RNA virus, represents the genetic average of every nucleotide position along the genome. The population of RNA virus variants is a network of variants organized in sequence space around the consensus sequence. This mutant spectrum is often referred to as quasispecies.

This genetic diversity creates a cloud of mutations that are potentially beneficial to viral survival, whereby creating an antigenic drift that requires frequent updates of vaccines and providing the basis for resistance to antivirals. It is known that altering the ability of a RNA virus to generate a normal mutation frequency, reduces viral fitness (i.e., the relative ability of a given virus to generate progeny viruses, taking into account all aspects of the virus life cycle including replication) and attenuates the virus during in vivo infection.

Reducing the fitness of RNA viruses may also be achieved by affecting replication or translation, through a variety of means, including altering codon pair bias.

Another feature that may affect RNA virus fitness is mutational robustness and/or sequence space. Mutational robustness is the ability to conserve phenotype in light of genetic changes (neutral mutation). However, little is known about the effects induced by alteration of RNA virus mutational robustness. Some studies addressed the indirect alteration of RNA virus mutational robustness, using constructs designed to alter fitness by other mechanisms, such as codon deoptimization (e.g., alteration of codon bias and codon pair bias). Therefore, these studies did not address mutational robustness per se (Lauring et al. 2012; Coleman et al. 2008).

The attenuation of RNA viruses for vaccine production faces the problem of genetic instability and of the associated risk of genetic reversion or mutation to a pathogenic phenotype.

The conventional method for RNA virus attenuation currently involves the introduction of random gene mutation or passages in unnatural conditions, whereby introducing more mutations than those actually required for attenuation, but lowering the risk of genetic reversion. This step is mostly empirical and is rather specific of the particular RNA virus type or species under attenuation.

Hence, the current method for RNA virus attenuation involves events, which depend on chance and cannot be universally applied to a variety of virus types.

The application provides means for RNA virus attenuation, which are non-empirical and which can be applied to all RNA viruses.

The means of the application are rationally based on the alteration of mutational robustness and/or of the localization of the virus in sequence space.

SUMMARY OF THE INVENTION

The application provides means for attenuation of RNA virus, which involve mutational robustness as modifiable trait.

The inventors demonstrate that the mutational robustness (and sequence space) of a RNA virus population can be modified without affecting protein replication and packaging of virus progeny, and without necessarily affecting protein sequence.

The means of the application involves decreasing mutational robustness (or restricting viable sequence space). They rely on the framework of the RNA virus quasispecies, by placing the RNA virus in a precarious region of its genetic sequence space, where it becomes victim of its naturally high mutation rate such that mutations are no longer tolerated and neutral, but become lethal or detrimental to the RNA virus. The means of the application thereby achieves attenuation of the RNA virus.

More particularly, the means of the application involve the replacement of codon(s), which codes(code) for Leu, Ser, Arg or Gly, by different but synonymous codon(s). These different but synonymous codon(s) is(are) selected to differ by only one nucleotide from a codon STOP. For example, the CUU codon, which codes for Leu, is replaced by the codon UUA, which also codes for Leu, but which (contrary to the CUU codon) differs by only one nucleotide from a STOP codon (i.e., from the STOP codon UAA). A thus modified RNA virus or clone of the application differs from the wild-type (e.g., infectious) RNA virus or clone by nucleotide sequence, but not by amino acid sequence (at least not before the first replication cycle).

Alternatively or complementarily, more particularly complementarily, the means of the application may involve the replacement of codon(s), which codes(code) for Thr or Ala, by different and non-synonymous codon(s), wherein these different and non-synonymous codon(s) codes(code) for Ser and differs(differ) by only one nucleotide from a STOP codon. For example, the ACA codon, which codes for Thr, may be replaced by the UCA codon, which codes for Ser, which in turns differs from the UAA STOP codon by only one nucleotide. Such codon replacement modify the amino acid sequence of the encoded protein(s) and therefore are selected to not (substantially) modify the antigenicity of this (these) protein(s).

The modified RNA virus (or clone) of the application is hyper-sensitive to mutation, whilst still retaining the replication capacity that is required for vaccine production and whilst being recognized by the immune system of the host similarly to how the wild-type (infectious) RNA virus would.

The means of the application have the advantage of being applicable to any RNA virus, and enable efficient and safe RNA virus attenuation for antiviral immunogenic composition or vaccine.

The application thus relates to an attenuated RNA virus or an attenuated clone thereof, as well as to means deriving, comprising or involving said attenuated RNA virus or attenuated clone, such as an immunogenic composition or vaccine comprising an attenuated RNA virus or an an attenuated clone of the application.

The application relates more particularly to means for producing said attenuated RNA virus or attenuated clone, including computer means.

The application notably relates to a process of production of an attenuated RNA virus or of an attenuated clone thereof, to a process of attenuation of a RNA virus or clone thereof, more particularly a process of attenuation of an infectious RNA virus or infectious clone thereof, as well as to a process of production of RNA virus immunogenic composition or vaccine.

BRIEF DESCRIPTION OF THE FIGURES

Some of the figures, to which the present application refers, are in color. The application as filed contains the color print-out of the figures, which can therefore be accessed by inspection of the file of the application at the patent office.

In FIG. 1, the colors of the codons are, from left to right:
for "wt" (wild-type sequence): red green red purple green purple red and purple;
for "stop" (1-to-Stop sequence): purple, purple, purple, purple, purple, purple and purple;
for "More" (More-i sequence): red, red, red, red, red, red and red;
for "Less" (Less-I sequence): green, green, green, green, green, green and green.

FIG. 5A, from left to right: WT=wild-type; P1Less=Less-i; P1More=More-i; P1Stop=1-to-Stop; bars of FIG. 5B follow the same order (from left to right: WT, P1Less, P1More, P1Stop).

FIG. 11A: Less=Less-i; FIG. 11B: More=More-i; FIG. 11C: WT=wild-type; FIG. 11D: Stop=1-to-Stop.

FIGS. 13A, 13B, 13C, 13D, 13E, 13F and 13G. 1-to-Stop virus is hyper-sensitive to mutation. (A) Relative fitness by direct competition assay. Wild type (open bars) and 1-to-Stop virus (solid bars) were competed against a marked reference wild type Coxsackie virus. The relative fitness of 1-to-Stop is significantly lower than wild type in the presence of 200 µM of either ribavirin (riba, P<0.0005), 5-fluorouracil (5-FU, P<0.0005), 5-azacytidine (AZC, P=0.0004), or amiloride (P=0.0011), or 1 mM manganese (P=0.0017). Mean and SEM are shown, n=3, two-tailed unpaired t test. (B) Plaque size as an alternative measure of fitness. Viruses were grown in the presence of 200 µM of three different mutagens, and the mean plaque size and SEM was determined. Mann Whitney test, n=1000,  P=0.0026; * P<0.0001. (C) Distribution of fitness values. The proportion (y-axis, number of samples) of individual fitness values (x-axis, log 10 Fitness), of wild type and 1-to-Stop populations derived from mock or mutagenic conditions. (D) The relative change in fitness of 1-to-Stop compared to wildtype, under each growth condition. The differences between wild type and 1-to-Stop are significant (P=9.656077e-08, two-tailed t test). (E) Coxsackie virus exploration of sequence space. Heat map interrogating the 117 Ser/Leu codons in 15 wildtype and 15 1-to-Stop populations (1 population per row) passaged 5 times in tissue culture. The columns show each of the 64 possible codons that can be generated, and the colour intensity reveals those that occur with the highest frequency. (F-G) The frequency of Stop mutations observed in sequence reads from the wild type and 1-to-Stop populations passaged in 50 µM (F) and 200 µM (G) of RNA mutagens, all mutagenic conditions combined. Box plots show mean values and 25% and 75% confidence intervals, whiskers show min. and max. values, outliers are shown as + symbols; n=45, *** p<0.0001, two-tailed unpaired t test.

FIGS. 15A, 15B, 15C, 15D and 15E. Influenza A virus 1-to-Stop construct performs similarly (PA region). (A-B) Replication kinetics of passage 5 wild type (solid line) and 1-to-Stop (dashed line) viruses at low moi=0.1 (A) and high moi=10 (B) in MDCK cells. No statistical significance observed for A, P=0.962 and B, P=0.695, two-tailed paired t test, n=3. (C) Heat map interrogating the 100 Ser/Leu codons in 20 wild type and 20 1-to-Stop populations (1 population per row) passaged 5 times in tissue culture. The columns show each of the 64 possible codons that can be generated, and the colour intensity reveals those that occur with the highest frequency. (D) The frequency of Stop mutations observed in sequence reads from the wild type and 1-to-Stop populations passaged in 50 µM of RNA mutagens, all mutagenic conditions combined. Box plots show mean values and 25% and 75% confidence intervals, whiskers show min. and max. values, outliers are shown as + symbols; n=20, *** p<0.0001, two-tailed unpaired t test. (E) In vivo titers in respiratory tract (PFU/g organ) of mice infected intranasally with either wild type (WT) or 1-to-Stop (Stop) virus. Tissues were harvested after 3 and 5 days of infection. Mean values (bars) and individual values (dots) are shown.

FIGS. 16A, 16B, 16C and 16D. "Suicidal" construct: 1-to-Stop coupled with mutator polymerase. (A-C) Virus titres in mouse spleens (A) pancreata (B) and hearts (C) infected with $10^5$ TCID$_{50}$ of wild type (WT), 1-to-Stop (S) or 1-to-Stop coupled with the low fidelity polymerase mutation RdRp-I230F (SLowFi) viruses. Scatter plots indicate individual values (dots), means (bar) and SEM. 1-to-Stop day 7 values are set at the limit of detection. For A,  P=0.002, * P=0.0002, **** P<0.0001; for B, * P=0.03,  P=0.02, * P=0.003, **** P<0.0001; for C, * P=0.05,  P=0.001, ** P<0.0001; n=5, two-tailed unpaired t test. (D) Survival curve of mice infected with either $10^6$ TCID$_{50}$ of wildtype (solid line), 1-to-Stop (long dashes) or 1-to-Stop-Low-Fidelity (short dashes) viruses. * P=<0.0001, n=17, Mantel-Cox test.

FIGS. 17A and 17B. (A) Survival rate of mice that received a lethal dose of wild-type Coxsackie virus (WT), or of 1-to-Stop Coxsackie virus of the application (S), or of 1-to-Stop Coxsackie virus of the application wherein the polymerase 3D has been mutated into the I230F low-fidelity polymerase ($S^{LowFi}$). (B) Neutralizing antibody after immunization of mice with 1-to-Stop Coxsackie virus of the application (1-to-Stop), or with 1-to-Stop Coxsackie virus of the application wherein the low-fidelity polymerase (1-to-Stop LowFi), or with PBS.

DETAILED DESCRIPTION OF THE INVENTION

Figure 1:
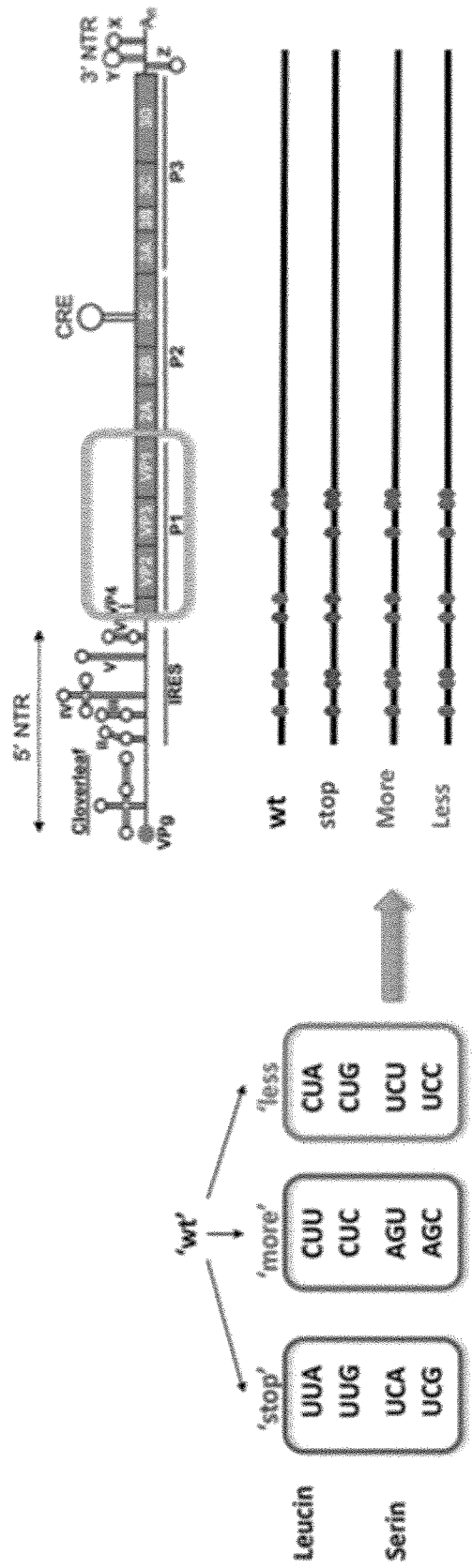
FIG. 1. The genetic organization of the Coxsackie virus B3 genome is shown, with the RNA structure known to be required for replication, translation and packaging. The P1 region (outlined in pink) codes for the structural proteins. 117 leucine and serine codons belonging to all three robustness categories are found within this region, and have been converted exclusively into 'stop' (i.e., 1-to-Stop), 'more' volatile (i.e., More-i) and 'less' volatile (i.e., Less-i) codons in each of three constructs (SynSyn viruses), without altering the amino acid coding sequences of the genome.

The application relates to the subject-matter as defined in the claims as filed and as herein described. In the application, unless specified otherwise or unless a context dictates otherwise, all the terms have their ordinary meaning in the relevant field(s).

A universal method of attenuation of RNA virus for vaccine purposes was a long-standing goal that could not be attained by conventional mutation, because conventional mutation involves the introduction of random gene mutation or passages in unnatural conditions, i.e., virus-specific steps, which often fails beyond the species level. Altering codon usage has been explored in terms of: a) using deoptimized codons, b) using optimized codons, c) using rare codon-pairing, d) codon reshuffling. All these approaches were based on perturbing RNA structure and/or protein translation.

By contrast, the means of the application do not require altering RNA structure and do not necessarily require altering protein translation. Rather, the means of the application involve the replacement of codon(s) by different codon(s), which is (are) selected to differ by only one nucleotide from a codon STOP.

Said different codon(s), which differs(differ) by only one nucleotide from a codon STOP, may herein be referred to as "1-to-Stop" codon(s).

The codon replacement of the application places the RNA virus in a precarious region of its sequence space, where it becomes victim of its naturally high mutation rate such that STOP codon(s) are generated by mutation of said "1-to-Stop" codon(s).

Advantageously, the means of the application involve the replacement of codon(s) by codon(s), which differs(differ) from the codon(s) it (they respectively) replaces(replace) and is(are) selected to differ by only one nucleotide from a codon STOP, and which further is(are) synonymous to the codon(s) it (they respectively) replaces(replace). More particularly, the means of the application involve the replacement of codon(s) which codes(code) for Leu, Ser, Arg or Gly, by codon(s), which is(are) synonymous to the codon(s) it (they respectively) replaces(replace) and which differs (differ) by only one nucleotide from a STOP codon The initial sequence of RNA virus, which is thus modified by synonymous codon(s), codes for the same amino acid sequence as the unmodified (i.e., wild-type and/or infectious) RNA virus. Therefore, at least before the first replication cycle, the thus modified RNA virus of the application codes for the same proteins as the wild-type and/or infectious RNA virus, and therefore is recognized by the host organism similarly to how the unmodified (i.e., wild-type and/or infectious) RNA virus would. Hence, the thus modified RNA virus of the application induces an immune response, which is the same (type of) immune response as the one that would be induced by the wild-type and/or infectious RNA virus. More particularly, it induces at least one antibody (or antibodies), which has(have) the same antigenicity as an antibody (antibodies) that would be induced by the wild-type (i.e., infectious) virus or clone.

Alternatively or complementarily, the means of the application may involve the replacement of codon(s) by codon(s), which differs(differ) from the codon(s) it (they respectively) replaces(replace) and is(are) selected to differ by only one nucleotide from a codon STOP, and which further is(are) non-synonymous to the codon(s) it (they respectively) replaces(replace). More particularly, the means of the application may involve the replacement of codon(s) which codes(code) for Thr or Ala by codon(s), which codes (code) for Ser and which differs(differ) by only one nucleotide from a STOP codon. Such a non-synonymous codon replacement modifies the amino acid sequence of the encoded protein(s) and therefore are selected to not (substantially) modify the antigenicity of the encoded protein(s).

The modified virus of the application is hyper-sensititive to detrimental or lethal mutation. Mutation is induced by the insufficient or deficient fidelity of viral replication, and may be accelerated or further increased by the application of mutagenic agent(s) or factor(s).

Hence, the modified RNA virus of the application loses fitness over time (by mutation of the "1-to-Stop" codon(s) into STOP codon(s)), i.e., the thus modified RNA virus of the application is a virulent or non pathogenic, with a high degree of certainty.

Furthermore, because the codon replacement is performed in the coding region, the 5' and 3' (non-coding) regions, which are required for virus replication and packaging, are unaffected. The modified virus of the application thus retains the replication capacity that is required for vaccine production.

In the application, when reference is made a (RNA) virus, reference is equally (and implicitly) made to a clone of said (RNA) virus, such as a RNA, DNA or cDNA clone, more particularly a DNA or cDNA clone, more particularly a cDNA clone.

The application thus relates to a process of production of an attenuated RNA virus or of an attenuated clone thereof, as well as to a process of attenuation of a RNA virus or clone thereof, more particularly a process of attenuation of an infectious RNA virus or infectious clone thereof.

The application also relates to the attenuated RNA virus or clone as such.

The process of the application involves the attenuation, more particularly the genetic attenuation, of a RNA virus or of a clone thereof, more particularly of an infectious RNA virus or of an infectious clone thereof. Said attenuation or genetic attenuation notably involves the alteration, more particularly the reduction of, the mutational robustness of said RNA virus or clone thereof.

Said (infectious) RNA virus or clone thereof is a RNA virus or clone, which comprises a RNA-dependent DNA polymerase (e.g., a retrovirus, such as HIV) or which comprises a RNA-dependent RNA polymerase.

Advantageously, said (infectious) RNA virus or clone thereof is a RNA virus or clone, which comprises a RNA-dependent RNA polymerase.

More particularly, said (infectious) RNA virus or clone thereof is a RNA virus or clone, which implements a RNA-dependent RNA polymerase for replication.

The process of the application thus comprises (or consists of) modifying the RNA genome of an (infectious) RNA virus, more particularly modifying the coding sequence of said RNA genome, i.e., the CDS sequence, which codes for the RNA virus polyprotein.

The application also relates to the modified virus or clone as such.

An (infectious) clone may be used instead of said (infectious) RNA virus. The term "clone" is herein intended in accordance with its ordinary meaning in the field and encompasses a RNA, DNA or cDNA clone, more particularly a DNA or cDNA clone, more particularly a cDNA clone. A clone is a recombinant cell. A RNA, DNA or cDNA clone comprises a recombinant RNA, DNA or cDNA sequence, respectively.

More particularly, a RNA clone of a virus is a recombinant cell, which comprises a (recombinant) RNA sequence, which is the coding sequence of the genome of said RNA virus (i.e., which is the CDS, which codes for the polyprotein of the RNA virus). A RNA clone may thus (recombinantly) comprise the full-length RNA genome or a fragment thereof, which has retained the CDS thereof (e.g., wherein said genome fragment has retained the sequence, which codes for the polyprotein of said RNA virus).

More particularly, a DNA clone of a virus is a recombinant cell, which comprises a (recombinant) DNA sequence, which is the DNA version of the CDS of the genome of said RNA virus (i.e., the RNA sequence modified by replacement of each nucleotide U by a nucleotide T). Said DNA clone may thus (recombinantly) comprise the DNA version of the full-length genome of said RNA virus, or of a fragment of the full-length genome of said RNA virus, wherein said genome fragment has retained the CDS sequence of said genome (e.g., wherein said genome fragment has retained the sequence, which codes for the polyprotein of said RNA virus).

More particularly, a cDNA clone of a virus is a recombinant cell, which comprises a (recombinant) cDNA sequence, which is the retrotranscript of the CDS of the genome of said RNA virus. Said cDNA clone may thus (recombinantly) comprise the cDNA sequence, which is the retrotranscript of the full-length genome of said RNA virus, or the retrotranscript of a fragment of the full-length genome of said RNA virus, wherein said genome fragment has retained the CDS sequence of said genome (e.g., wherein said genome fragment has retained the sequence, which codes for the polyprotein of said RNA virus).

More particularly, said (RNA, DNA or cDNA) clone comprises and can express said (RNA, DNA or cDNA) sequence. More particularly, said (RNA, DNA or cDNA) clone comprises said (RNA, DNA or cDNA) sequence as an expression insert in an expression vector, such as a plasmid. More particularly, said (RNA, DNA or cDNA) clone codes for (or expresses) viral particles of a RNA virus.

Said (RNA, DNA or cDNA) clone may e.g., be a recombinant human cell, such as a recombinant HeLa cell (ATCC® CCL-2™).

Said expression vector, more particularly said plasmid, may thus e.g., be an expression vector, more particularly a plasmid, for recombinant expression in a human cell, such as a HeLa cell (ATCC® CCL-2™). Said expression vector, more particularly said plasmid, may thus comprise a promoter for recombinant expression of said (RNA, DNA or cDNA) sequence in said cell.

The clone of an infectious RNA virus is an infectious clone.

Hence, when starting from an (infectious) clone of said (infectious) RNA virus, the process of the application thus comprises (or consist of) modifying the (recombinant) sequence (i.e., the sequence which is recombinantly carried by the (infectious) clone and which comprises the coding sequence of the (infectious) of the (infectious) RNA virus or the DNA or cDNA version thereof), more particularly the (recombinant) coding sequence of said clone.

The term "infectious" is herein intended in accordance with its ordinary meaning in the field, and is intended to encompass "virulent" or the capacity of inducing a pathogenic phenotype, more particularly a disease or disorder. An infectious (RNA) virus can infect a target organism, more particularly a target animal (target human and/or target non-human animal). More particularly, an infectious (RNA) virus can cause a disease or disorder in said target animal. For example, an infectious Influenza virus is an Influenza virus, which can infect a human or a non-human mammal or a bird (e.g., a human), more particularly which can cause influenza in a human or a non-human mammal or a bird (e.g., a human).

Attenuation is herein intended in accordance with its ordinary meaning in the field. More particularly, the expression "attenuated (RNA) virus" or "attenuated (RNA, DNA or cDNA) clone" designates a (RNA) virus or (RNA, DNA or cDNA) clone, which has a reduced pathogenic phenotype compared to a wild-type virus (i.e., compared to an infectious and/or virulent virus), more particularly compared to a wild-type virus of the same genus, species, type or subtype (i.e., compared to an infectious and/or virulent virus of the same genus, species, type or subtype).

The terms "genus", "species," "type" and "subtype" are herein intended in accordance with their ordinary meaning in the field. For example:
Influenza virus A is a genus, whereas Influenza virus A H1N1 is a subtype,
Coxsackie virus is a virus type, whereas Coxsackie virus B is a subtype,
Yellow fever virus is a virus species (of the Flavivirus genus),
Chikungunya virus is a virus species (of the Alphavirus genus),
O'Nyong Nyong virus is a virus species (of the Alphavirus genus).

The terms "genus", "species," "type" and "subtype" thus encompass Coxsackie virus (more particularly Coxsackie virus A or B, more particularly Coxsackie virus A2, B or A1, more particularly Coxsackie virus A2 or B, more particularly Coxsackie virus B, more particularly Coxsackie virus B1, B2, B3, B4, B4 or B6, more particularly Coxsackie virus B3), Yellow fever virus, Chikungunya virus, O'Nyong Nyong virus and Influenza virus (more particularly, Influenza virus A, B or C, more particularly Influenza virus A, more particularly Influenza virus A subtype H1N1 or H3N2, more particularly Influenza virus A subtype H1N1).

For example:
an attenuated Coxsackie virus or clone is a Coxsackie virus or clone, which has a reduced pathogenic phenotype compared to an infectious Coxsackie virus or clone;
an attenuated Coxsackie virus B or clone is a Coxsackie virus B or clone thereof, which has a reduced pathogenic phenotype compared to an infectious Coxsackie virus B or clone;
an attenuated Yellow fever virus or clone is a Yellow fever virus or clone thereof, which has a reduced pathogenic phenotype compared to infectious Yellow fever virus or clone;
an attenuated Chikungunya virus or clone is a Chikungunya virus or clone thereof, which has a reduced pathogenic phenotype compared to infectious Chikungunya virus or clone;
an attenuated O'Nyong Nyong virus or clone is a O'Nyong Nyong virus or clone thereof, which has a reduced pathogenic phenotype compared to infectious O'Nyong Nyong virus or clone;
an attenuated Influenza virus or clone is an Influenza virus or clone thereof, which has a reduced pathogenic phenotype compared to an infectious Influenza virus or clone;
an attenuated Influenza virus A or clone is an Influenza virus A or clone thereof, which has a reduced pathogenic phenotype compared to an infectious Influenza virus A or clone; and
an attenuated Influenza virus A subtype H1N1 or clone is an Influenza virus A subtype H1N1 or clone thereof, which has a reduced pathogenic phenotype compared to an infectious Influenza virus A subtype H1N1 or clone.

The terms "genus", "species," "type" and "subtype" similarly encompass Poliovirus (more particularly, Poliovirus sub-types I, II and III), Enterovirus 71 (EV71), Enterovirus 68 (EV68), the Foot-and-mouth disease virus, Hepatitis A virus, Chikungunya virus, Venezuelan Equine Encephalitis Virus (VEEV), Eastern Equine Encephalitis Virus (EEEV), Western Equine Encephalitis Virus (WEEV), Severe Acute Respiratory Syndrome (SARS) coronavirus, Middle East Respiratory Syndrome (MERS) coronavirus, Japanese Encephalitis Virus (JEV), Dengue fever virus, West Nile virus, Zika virus (ZIKV), Ebola virus, Lassa fever virus, Lyssa virus.

A reduced pathogenic phenotype encompasses a reduced infection capacity and/or a reduced replication capacity, and/or a reduced and/or restricted tissue tropism, and/or a default or defect in the assembly of the viral particles, more particularly a reduced infection capacity.

A reduced pathogenic phenotype, more particularly a reduced infection capacity, encompasses a (viral) infection, which is impeded, obstructed or delayed, especially when the symptoms accompanying or following the infection are attenuated, delayed or alleviated or when the infecting virus is cleared from the host.

For example, an attenuated Coxsackie virus or clone is a Coxsackie virus or clone, which does not cause the symptoms of a Coxsackie virus disease, or causes attenuated, delayed or alleviated symptoms of a Coxsackie virus disease.

For example, an attenuated Yellow fever virus or clone is a Yellow fever virus or clone, which does not cause the symptoms of yellow fever, or causes attenuated, delayed or alleviated symptoms of yellow fever.

For example, an attenuated Chikungunya virus or clone is a Chikungunya virus or clone, which does not cause the symptoms of Chikungunya virus disease, or causes attenuated, delayed or alleviated symptoms of Ckikungunya disease.

For example, an attenuated O'Nyong Nyong virus or clone is a O'Nyong Nyong virus or clone, which does not cause the symptoms of O'Nyong Nyong disease, or causes attenuated, delayed or alleviated symptoms of O'Nyong Nyong disease.

For example, an attenuated Influenza virus or clone, is an Influenza virus or clone, which does not cause the symptoms of influenza disease, or causes attenuated, delayed or alleviated symptoms of influenza disease.

In accordance with the application, said modification comprises, or consists of, replacing at least one codon, i.e., one or more codons, more particularly more than two codons, in said (infectious) RNA virus or (infectious) clone. Each codon that is replaced is replaced by a codon, which is different.

Said different codon can be a synonymous codon or a non-synonymous codon, but always differs by only one nucleotide from a STOP codon.

The STOP codons are UAA, UAG and UGA. The DNA or cDNA version of the STOP codons is TAA, TAG and TGA.

Advantageously, said different codon is a synonymous codon, which differs by only one nucleotide from a STOP codon. Replacement by a different but synonymous codon notably applies to codon(s), which codes(code) for Leu, Ser, Arg or Gly.

For example, the CUU codon (coding for Leu) and the AGU codon (coding for Ser) are replaced by the UUA and UCG codons respectively, because:
UUA codes for Leu and differs by only one nucleotide from the STOP codon UAA (or from the STOP codon UGA), and because
UCG codes for Ser and differs by only one nucleotide from the STOP codon UAG.

Replacement by synonymous codon(s) does not modify the amino acid sequence of the encoded protein(s), at least not before the first replication cycle (i.e., at least not before mutation into STOP codon(s) takes place).

Hence, a modified RNA virus or clone of the application, which is modified only by such synonymous codon replacement(s), differs by nucleotide sequence from the parent (infectious) RNA virus or clone, but at least before the first replication cycle it does not differ by amino acid sequence (i.e., it encodes the same viral particles as the parent (infectious) RNA virus or clone).

Alternatively or complementarily, more particularly complementarily, said different codon(s) can be a non-synonymous codon, which differs by only one nucleotide from a STOP codon. Replacement by a different but non-synonymous codon notably applies to codon(s), which codes (code) for Thr or Ala, more particularly to codon(s), which codes(code) for Thr or Ala and which differs by only one nucleotide from a Ser codon. The codon(s), which replaces it(each of them), advantageously is(are) a codon, which codes for Ser and which differs by only one nucleotide from a STOP codon (i.e., the UCA or UCG codon).

For example, the ACA codon, which codes for Thr, can be replaced by the UCA codon, which differs only by one nucleotide from the ACA codon, but which codes for Ser and differs from the UAA STOP codon by only one nucleotide.

Replacement by synonymous codon(s) modifies the amino acid sequence of the encoded protein(s). More particularly, it increases the number or proportion of Ser codon(s). Non-synonymous codon replacement is advantageously selected to not (substantially) modify the antigenicity of the protein(s) that are coded by the thus modified CDS.

In other words, an attenuated virus or clone of the application differs by nucleotide sequence but not necessarily by amino acid sequence (at least not before the first replication cycle) from the wild-type virus, compared to which it has a reduced pathogenic phenotype.

The synonymous and/or non-synonymous, more particularly the synonymous codon replacement of the application drastically increases the sensitivity of the (infectious) virus or clone to detrimental or lethal mutation, i.e., to mutation which introduces STOP codon(s) instead of amino acid codon(s).

The modified virus or modified clone, which results from said codon replacement, has an attenuated pathogenic phenotype compared to the parent (infectious) RNA virus or clone.

Replacing codons by codons, which differ by only one nucleotide from a STOP codon, increases the chance that said replaced codons mutate into a STOP codon after one or several replication cycle(s).

It is all the more true since the RNA-dependent DNA polymerase and the RNA-dependent RNA polymerase, more particularly the RNA-dependent RNA polymerase, are polymerases of low incorporation fidelity, i.e., polymerases, which tend to introduce replication error(s) or mutation(s) in the coding sequence. The error rate of viral RNA-dependent RNA polymerase is estimated to be as high as $10^{-3}$ to $10^{-6}$ per nucleotide copied (compared to $10^{-8}$ to $10^{-11}$ for DNA-dependent DNA polymerase). The higher the number of replication cycles, the higher the chance to have STOP codons being generated (by mutation of the "1-to-Stop" codons).

The application thus provides means for genetic attenuation of an (infectious) RNA virus or of an (infectious) clone thereof, which enable the attenuated RNA virus or clone to replicate to an extent that is sufficient for inducing an immune response but that is not sufficient for inducing the disease.

A codon, which differs only by one nucleotide from a STOP codon, may herein be referred to as a "1-to-Stop" codon.

Said at least one codon, which is replaced by a "1-to-Stop" but synonymous codon, advantageously is at least one codon, which codes for Leu, Ser, Arg or Gly in said infectious RNA virus or infectious clone.

Table 4 below shows the different codons that code for Leu, Ser, Arg and Gly, and identifies those codons, which are "1-to-Stop" codons (identified by "+" in the right-hand column).

TABLE 4

"1-to-Stop" (synonymous) codons

| Amino acid | | (RNA) codon [*] | 1-to-Stop |
|---|---|---|---|
| Leu | L | UUA | + |
|  |  | UUG | + |
|  |  | CUU |  |
|  |  | CUC |  |
|  |  | CUA |  |
|  |  | CUG |  |
| Ser | S | UCU |  |
|  |  | UCC |  |
|  |  | UCA | + |
|  |  | UCG | + |
|  |  | AGU |  |
|  |  | AGC |  |
| Arg | R | CGU |  |
|  |  | CGC |  |
|  |  | CGA | + |
|  |  | CGG |  |
|  |  | AGA |  |
|  |  | AGG |  |
| Gly | G | GGU |  |
|  |  | GGC |  |
|  |  | GGA | + |
|  |  | GGG |  |

[*] The DNA (or cDNA) codon is identical to the RNA codon except for nucleotide U, which is to be replaced by nucleotide T.

For example, among the codons, which code for Leu, the codons CUU, CUC, CUA and CUG are suitable for replacement by the "1-to-Stop" codon UUA or UUG.

Similarly, among the codons, which code for Ser, the codons UCU, UCC, AGU and AGC are suitable for replacement by the "1-to-Stop" codon UCA or UCG.

Among the codons, which code for Arg, the codons CGU, CGC, CGG, AGA, AGG are suitable for replacement by the "1-to-Stop" codon CGA.

Among the codons, which code for Gly, the codons GGU, GGC and GGG are suitable for replacement by the "1-to-Stop" codon GGA.

In other words, said at least one codon, which codes for Leu in said infectious RNA virus or in said infectious RNA, DNA or cDNA clone (more particularly in said cDNA clone), and which is replaced by a different but synonymous "1-to-Stop" codon, is advantageously selected from CUU, CUC, CUA and CUG in said infectious RNA virus or in said RNA clone, or from CTT, CTC, CTA and CTG in said infectious DNA or cDNA clone. The different but synonymous Leu codon, which replaces it, is selected from UUA or UUG for attenuation of said RNA virus or said RNA clone, or from TTA and TTG for attenuation of said DNA or cDNA clone, respectively.

Said at least one codon, which codes for Ser in said infectious RNA virus or in said infectious RNA, DNA or cDNA clone (more particularly in said cDNA clone), and which is replaced by a different but synonymous "1-to-Stop" codon, is advantageously selected from AGU, AGC, UCU and UCC in said infectious RNA virus or in said RNA clone, or from AGT, AGC, TCT and TCC in said infectious DNA or cDNA clone. The different but synonymous Ser codon, which replaces it, is selected from UCA and UCG for attenuation of said RNA virus or said RNA clone, or from TCA and TCG for attenuation of said DNA or cDNA clone, respectively.

Said at least one codon, which codes for Arg in said infectious RNA virus or in said infectious RNA, DNA or cDNA clone (more particularly in said cDNA clone), and which is replaced by a different but synonymous "1-to-Stop" codon, is advantageously selected from AGA, AGG, CGU, CGC or CGG in said infectious RNA virus or in said RNA clone, or from AGA, AGG, CGT, CGC or CGG in said infectious DNA or cDNA clone. The different but synonymous Arg codon, which replaces it, is CGA for attenuation of said RNA virus or RNA clone or for attenuation of said DNA or cDNA clone, respectively. Said at least one codon, which codes for Gly in said infectious RNA virus or in said infectious RNA, DNA or cDNA clone (more particularly in said cDNA clone), and which is replaced by a different but synonymous "1-to-Stop" codon, is advantageously selected from GGG, GGU or GGC in said infectious RNA virus or in said RNA clone, or from GGG, GGT or GGC in said infectious DNA or cDNA clone. The different but synonymous Gly codon, which replaces it, is GGA for attenuation of said RNA virus or said RNA clone or for attenuation of said DNA or cDNA clone, respectively.

More particularly, said at least one codon, which codes for Ser in said infectious RNA virus or in said infectious RNA, DNA or cDNA clone (more particularly in said cDNA clone), and which is replaced by a different but synonymous "1-to-Stop" codon, is selected from AGU and AGC in said infectious RNA virus or in said RNA clone, or from AGT and AGC in said infectious DNA or cDNA clone. The different but synonymous Ser codon, which replaces it, is selected from UCA and UCG for attenuation of said RNA virus or in said RNA clone, or from TCA and TCG for attenuation of said DNA or cDNA clone, respectively.

More particularly, said at least one codon, which codes for Arg in said infectious RNA virus or in said infectious RNA, DNA or cDNA clone (more particularly in said cDNA clone), and which is replaced by a different but synonymous "1-to-Stop" codon, is selected from AGA and AGG in said infectious RNA virus or in said infectious RNA, DNA or cDNA clone. The different but synonymous Arg codon, which replaces it, is CGA for attenuation of said RNA virus or for attenuation of said RNA, DNA or cDNA clone, respectively.

In accordance with the application, said synonymous codon replacement (i.e., said replacement by different but synonymous "1-to-Stop" codons) may comprise the replacement of:
  at least one codon, which codes for Leu or
  at least one codon which codes for Ser or
  at least one codon, which codes for Arg or
  at least one codon, which codes for Gly.

In accordance with the application, said synonymous codon replacement (i.e., said replacement by different but synonymous "1-to-Stop" codons) may comprise the replacement of:
  at least one codon, which codes for Leu and
  at least one codon which codes for Ser and
  at least one codon, which codes for Arg.

In accordance with the application, said synonymous codon replacement (i.e., said replacement by different but synonymous "1-to-Stop" codons) may comprise the replacement of:
  at least one codon which codes for Ser and
  at least one codon, which codes for Arg and
  at least one codon, which codes for Gly.

In accordance with the application, said synonymous codon replacement (i.e., said replacement by different but synonymous "1-to-Stop" codons) may comprise the replacement of:
  at least one codon, which codes for Leu and
  at least one codon, which codes for Arg and
  at least one codon, which codes for Gly.

In accordance with the application, said synonymous codon replacement (i.e., said replacement by different but synonymous "1-to-Stop" codons) may comprise the replacement of:
  at least one codon, which codes for Leu and
  at least one codon which codes for Ser and
  at least one codon, which codes for Gly.

In accordance with the application, said synonymous codon replacement (i.e., said replacement by different but synonymous "1-to-Stop" codons) may comprise the replacement of:
  at least one codon, which codes for Leu and
  at least one codon which codes for Ser and
  at least one codon, which codes for Arg and
  at least one codon, which codes for Gly.

In accordance with the application, said synonymous codon replacement (i.e., said replacement by different but synonymous "1-to-Stop" codons) may comprise the replacement of:
  at least one codon, which codes for Leu and
  at least one codon which codes for Ser.

In accordance with the application, said synonymous codon replacement (i.e., said replacement by different but synonymous "1-to-Stop" codons) may comprise the replacement of:
  at least one codon, which codes for Arg and
  at least one codon, which codes for Gly.

In accordance with the application, said synonymous codon replacement (i.e., said replacement by different but synonymous "1-to-Stop" codons) may comprise the replacement of:
  at least one codon, which codes for Leu and
  at least one codon, which codes for Arg.

In accordance with the application, said synonymous codon replacement (i.e., said replacement by different but synonymous "1-to-Stop" codons) may comprise the replacement of:
  at least one codon, which codes for Leu and
  at least one codon, which codes for Gly.

In accordance with the application, said synonymous codon replacement (i.e., said replacement by different but synonymous "1-to-Stop" codons) may comprise the replacement of:
  at least one codon which codes for Ser and
  at least one codon, which codes for Arg.

In accordance with the application, said synonymous codon replacement (i.e., said replacement by different but synonymous "1-to-Stop" codons) may comprise the replacement of:
  at least one codon which codes for Ser and
  at least one codon, which codes for Gly.

Alternatively or complementarily, more particularly complementarily, to said synonymous codon replacement, the means of the application may comprise the replacement of codon(s) by "1-to-Stop" codon(s), which is(are) not synonymous to the codon(s) it (they respectively) replaces (replace).

Said at least one codon, which is replaced by a "1-to-Stop" but non-synonymous codon, advantageously is at least one codon, which codes Thr or Ala in said infectious RNA virus or infectious clone. Said at least one codon, which codes Thr or Ala in said infectious RNA virus or infectious clone, and which is to be replaced by a non-synonymous "1-to-Stop" Ser codon, advantageously is a Thr or Ala codon, which differs only by one nucleotide from a Ser codon.

The "1-to-Stop" but non-synonymous codon(s), which replaces(replace) it(them), is(are) codon(s), which codes (code) for Ser and which differs(differ) by only one nucleotide from a STOP codon, i.e., the "1-to-Stop" but non-synonymous codon(s), which replaces(replace) it(them), is(are) a codon, which is (each independently) selected from the UCA or UCG codons.

In accordance with the application, said non-synonymous codon replacement may comprise the replacement of:
  at least one codon, which codes for Thr in said infectious RNA virus or infectious cDNA clone, and which is ACA, wherein the codon, which codes for Ser and which replaces it, is UCA for attenuation of said RNA virus or TCA for attenuation of said cDNA clone, and/or
  at least one codon, which codes for Thr in said infectious RNA virus or infectious cDNA clone, and which is ACG, wherein the codon, which codes for Ser and which replaces it, is UCG for attenuation of said RNA virus or TCG for attenuation of said cDNA clone, and/or
  at least one codon, which codes for Ala in said infectious RNA virus or infectious cDNA clone, and which is GCA, wherein the codon, which codes for Ser and which replaces it, is UCA for attenuation of said RNA virus or TCA for attenuation of said cDNA clone, and/or
  at least one codon, which codes for Ala in said infectious RNA virus or infectious cDNA clone, and which is GCG, wherein the codon, which codes for Ser and which replaces it, is UCG for attenuation of said RNA virus or TCG for attenuation of said cDNA clone.

Throughout the application, the terms "at least one codon" (or equivalent expressions, such as codon(s)) each independently encompass one or more codon, more particularly several codons, i.e., at least two codons, more particularly at least 10 codons, more particularly at least 20 codons, more particularly at least 30 codons, more particularly at least 40 codons.

A number of at least 50 codons, or at least 60, or at least 70, or at least 80, or at least 90, or at least 100, or at least 110 codons, e.g., a number of 117 codons, or a number of at least 150, is also herein independently encompassed by each term "at least one codon".

A number of at least 500, or at least 550, or at least 600 codons, is also herein independently encompassed by each term "at least one codon".

The codon replacement of the application (i.e., the replacement of at least one (Leu, Ser, Arg, Gly) codon by a synonymous "1-to-Stop" codon and/or the replacement of at least one (Thr, Ala) codon by a non-synonymous "1-to-Stop" (Ser) codon, more particularly the replacement of at least one (Leu, Ser, Arg, Gly) codon by a synonymous "1-to-Stop" codon) advantageously comprises the replacement of several of said at least one codon.

For example, at least two codons selected from Leu, Ser, Arg and Gly codons are each replaced by a different but synonymous codon (cf. Table 4 above).

For example, at least two codons selected from Thr and Ala codons, which each differ by only one nucleotide from a Ser codon, are each replaced by a Ser codon, which does itself differ only by one nucleotide from a STOP codon (i.e., by the UCA or UCG codon).

For example, at least two codons selected from Leu, Ser, Arg and Gly codons are each replaced by a different but synonymous codon (cf. Table 4 above) and at least one or two codon(s) selected from Thr and Ala codons, which each differ by only one nucleotide from a Ser codon, is (are each)

replaced by a Ser codon, which differs only by one nucleotide from a STOP codon (i.e., by the UCA or UCG codon).

Advantageously, not all of the Leu, Ser, Arg and Gly codons of the virus genome are replaced by a synonymous "1-to-Stop" codon.

Advantageously, not all of the Thr and Ala codons of the virus genome are replaced by a non-synonymous (Ser) "1-to-Stop" codon.

Advantageously, said codon replacement is performed in a nucleotide region of said RNA virus or clone, the secondary structure of which is not involved in the viral replication and/or in the packaging of the viral particles.

Hence, all the codons, which are selected for replacement in accordance with the application, more particularly for synonymous "1-to-Stop" codon replacement in accordance with the application, are advantageously located in a nucleotide region of said RNA virus or clone, the secondary structure of which is not involved in the viral replication and/or in the packaging of the viral particles.

Examples of secondary structures, which are involved in the viral replication and/or in the packaging of the viral particles notably comprise a loop (such as a hairpin loop, bulge loop, interior loop or multibranched loop), a pseudoknot, a stem, a stem-loop.

These secondary structures are generally located at the 5'- and 3' termini of the RNA genome (5'-untranslated region or UTR and 3'-untranslated region or 3'-UTR).

Some secondary structures, which are involved in the viral replication and/or in the packaging of the viral particles, may also be found in the coding region of the RNA genome (e.g., the Cis-acting Replication Element (CRE) in Picornaviruses).

Advantageously, the codon replacements of the application (by "1-to-Stop codons) are performed in a coding region, which does not comprise any secondary structure that is involved in the viral replication and/or in the packaging of the viral particles. For example, in case of the Coxsackie virus, the P1 region of the polyprotein does not comprise any secondary structure that is involved in the viral replication and/or in the packaging of the viral particles, and therefore is an advantageous target for codon replacement in accordance with the application.

For example, in case of the Influenza virus, more particularly of Influenza A virus, more particularly of Influenza virus A subtype H1N1, the PA region does not comprise any secondary structure that is involved in the viral replication and/or in the packaging of the viral particles, and therefore is an advantageous target for codon replacement in accordance with the application (cf. example 5 below). Similarly, the HA region of Influenza virus, more particularly of Influenza A virus, more particularly of Influenza virus A subtype H1N1, does not comprise any secondary structure that is involved in the viral replication and/or in the packaging of the viral particles, and therefore is an advantageous target for codon replacement in accordance with the application (cf. example 7 below).

For example, in the case of the Chikungunya virus, the C-E3-E2-6K-E1 polyprotein, more particularly the E2-6K-E1 region of the polyprotein, more particularly the E1 protein and/or the E2 protein, does not comprise any secondary structure that is involved in the viral replication and/or in the packaging of the viral particles, and therefore is an advantageous target for codon replacement in accordance with the application (cf. example 8 below).

In accordance with the application, the codons that are replaced by "1-to-Stop" (synonymous and/or non-synonymous) codons, more particularly at least the codons that are replaced by synonymous "1-to-Stop" codons, may be located in the same protein coding sequence within the polyprotein coded by the RNA genome of said infectious RNA virus or coded by the recombinant sequence of said clone, respectively (e.g., coded by the retro-transcribed cDNA sequence of said cDNA clone).

For example, in the case of the Coxsackie virus, the codons that are replaced by synonymous "1-to-Stop" codons may all be located in the P1 protein.

For example, in the case of the Influenza virus, more particularly of Influenza A virus, more particularly of Influenza virus A subtype H1N1, the codons that are replaced by synonymous "1-to-Stop" codons may all be located in the PA protein and/or in the HA protein.

For example, in the case of the Chikungunya virus, the codons that are replaced by synonymous "1-to-Stop" codons may all be located in the C-E3-E2-6K-E1 polyprotein, more particularly in the E2-6K-E1 region of the polyprotein, more particularly in the E1 protein and/or in the E2 protein.

The proportion of codons that are replaced in accordance with the application (i.e., by "1-to-Stop" synonymous and/or non-synonymous codons), more particularly the proportion of codons that are replaced by "1-to-Stop" synonymous codons in accordance with the application, may e.g., be 2-30%, 2-25%, 2-20%, 2-15% or 2-10%, more particularly 2-10%, of the total number of codons of the genome of said infectious RNA virus, or of the total number of codons of the recombinant sequence of said clone (e.g., of the retro-transcribed cDNA CDS sequence of said cDNA clone). Said proportion may e.g., be a proportion of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30%, more particularly a proportion of 3-29%, 3-24%, 3-19%, 3-14% or 3-9%, or of 4-30%, 4-25%, 4-20%, 4-15% or 4-10%, for example a proportion of 4-28%, 4-23%, 4-18%, 4-13% or 4-8%, for example a proportion of 2-30%, 2-25%, 2-20%, 2-15%, 2-10%, 3-30%, 3-25%, 3-20%, 3-15% or 3-10%, for example a proportion of 4-6% or 5-6%.

The coding sequence (CDS) of the genome of said infectious RNA virus or the recombinant sequence of said clone (e.g., the retro-transcribed cDNA sequence of said cDNA clone) may e.g., comprise more than 2,000 nucleotides. It may e.g., consist of 2,000-30,000 nucleotides, i.e., 666-10,000 codons.

The number of codons that are replaced by (synonymous and/or non-synonymous) "1-to-Stop" codons in accordance with the application, more particularly the number of codons that are replaced by synonymous "1-to-Stop" codons in accordance with the application, may thus range from 13 to 199 codons (2-30%), more particularly from 13 to 66 codons (2-10%), for a genome CDS of 2,000 nucleotides, or from 200 to 3,000 codons (2-30%), more particularly from 200 to 1,000 codons (2-10%), for a genome CDS of 30,000 nucleotides.

The number of codons that are replaced by (synonymous and/or non-synonymous) "1-to-Stop" codons in accordance with the application, more particularly the number of codons that are replaced by synonymous "1-to-Stop" codons in accordance with the application, may e.g., be of 13 or more, 15 or more, 20 or more, 30 or more, 40 or more, 50 or more, 80 or more, 90 or more, 100 or more, 110 or more.

The number of codons that are replaced by (synonymous and/or non-synonymous) "1-to-Stop" codons in accordance with the application, more particularly the number of codons that are replaced by synonymous "1-to-Stop" codons in accordance with the application, may e.g., be of 3,000 or less, 2,500 or less, 2,000 or less, 1,500 or less, 1,000 or less, 900 or less, 800 or less, 700 or less, 600 or less, 500 or less, 400 or less, 300 or less, 200 or less, 150 or less, 120 or less.

Every combination of maximal and minimal number of replaced codons is explicitly encompassed by the application. For example, the number of codons that are replaced by (synonymous and/or non-synonymous) "1-to-Stop" codons in accordance with the application, more particularly the number of codons that are replaced by synonymous "1-to-Stop" codons in accordance with the application, may e.g., be of 13-3,000, 13-2,500, 13-2,000, 13-1,500, 13-1,000, of 13-500, of 15-500, of 20-200, of 80-200, or of 100-120, for example of 117 or 110.

The number or proportion of codons that are replaced by (synonymous and/or non-synonymous) "1-to-Stop" codons in accordance with the application, more particularly the number or proportion of codons that are replaced by synonymous "1-to-Stop" codons in accordance with the application, is selected to be sufficiently high to achieve the desired level of reduction of pathogenic phenotype (e.g., reduction of the tissue tropism and/or of replication capacity), but sufficiently low to avoid viral inactivation (i.e., to achieve attenuation, whilst retaining viability of the modified virus or clone). The number or proportion of codons that are replaced by (synonymous and/or non-synonymous) "1-to-Stop" codons in accordance with the application, more particularly the number of codons that are replaced by synonymous "1-to-Stop" codons in accordance with the application, is advantageously sufficiently low to not lose the capacity to induce an immune response, more particularly to still induce an immune response or a type of immune response, which is similar to the one which would be induced by the infectious (i.e., unmodified) virus or clone.

For example, for a Coxsackie virus, all the Leu and Ser codons, or all the Leu, Ser, Arg and Gly codons, of the P1 protein can be replaced by synonymous "1-to-Stop" codons in accordance with the application (cf. examples 1, 5 and 6 below).

For example, for an Influenza virus, all the Leu and Ser codons, or all the Leu, Ser, Arg and Gly codons, of the PA protein and/or HA protein can be replaced by synonymous "1-to-Stop" codons in accordance with the application (cf. examples 1, 5 and 7 below).

For example, for a Chikungunya virus, all the Leu and Ser codons, or all the Leu, Ser, Arg and Gly codons, of the C-E3-E2-6K-E1 polyprotein can be replaced by synonymous "1-to-Stop" codons in accordance with the application (cf. examples 1, 5 and 8 below).

Advantageously, an attenuated virus or clone of the application still is a live virus or clone. More particularly, an attenuated virus or clone of the application is still capable of achieving at least one replication cycle, for example at least two replication cycles (more particularly at least two replication cycles in the target animal or human, who is the natural target of the infectious virus or clone).

Advantageously, an attenuated virus or clone of the application stimulates or is able to stimulate an immune response when administered to said animal.

The term "immune response" is intended in accordance with its ordinary meaning in the field, and includes one or several from antibody production, induction of cell-mediated immunity, complement activation, development of immunological tolerance, alteration of cytokine production and alteration of chemokine production, more particularly antibody production. Antibody production encompasses neutralizing antibody production, more particularly seroneutralization.

Advantageously, the (synonymous and/or non-synonymous) codon replacement of the application, more particularly at least the synonymous codon replacement of the application, does not (substantially) modify the nature of the humoral immune response that would otherwise be induced by the infectious virus or clone.

Advantageously, the (synonymous and/or non-synonymous) codon replacement of the application, more particularly at least the synonymous codon replacement of the application, does not (substantially) modify the nature of the humoral and cell-mediated immune that would otherwise be induced by the infectious virus or clone.

Advantageously, the (synonymous and/or non-synonymous) codon replacement of the application, more particularly at least the synonymous codon replacement of the application, does not (substantially) modify the nature and extent of the humoral that would otherwise be induced by the infectious virus or clone.

Advantageously, the (synonymous and/or non-synonymous) codon replacement of the application, more particularly at least the synonymous codon replacement of the application, does not (substantially) modify the nature and extent of the humoral and/or cell-mediated immune response that would otherwise be induced by the infectious virus or clone.

More particularly, the (synonymous and/or non-synonymous) codon replacement of the application, more particularly at least the synonymous codon replacement of the application, does not (substantially) modify the antigenic properties of the encoded protein(s), i.e., the antigenic properties of the protein (or of those proteins), which is(are) encoded by a CDS, which has been modified by said codon replacement (i.e., the CDS modified in accordance with the application but before the STOP codon mutation(s)). In other words, said encoded protein(s) (i.e., the(those) protein(s), which is(are) encoded by a CDS, which has been modified by said codon replacement) (all) induces(induce) at least one antibody, which has the same antigenicity (i.e., the same antigen binding property) as an antibody that would otherwise be induced by the infectious virus or clone.

Said infectious RNA virus or infectious clone advantageously is a RNA virus or infectious clone, which is a human pathogen and/or animal pathogen.

In the application, the term "human" encompasses a newborn or neonate (more particularly of 1-day old to less than 4-week old), an infant (more particularly of 4-week old to less than 1-year old), a child (more particularly of 1-year old to less than 12-year old), a teenager (more particularly of 12-year old to less than 18-yearold), an adult (more particularly of 18-year old to 60-year old), and an elderly (above 60-year old, more particularly above 65-year old, more particularly above 70-year old, more particularly above 75-year old, more particularly above 80-year old).

Said human may e.g., be an immuno-depressed human, more particularly an immune-depressed adult.

Said human may e.g., be a newborn or neonate, an infant, an immuno-depressed adult or an elderly.

In the application, the term "animal" encompasses a mammal or a bird, more particularly a non-human mammal or a bird.

Said non-human mammal may e.g., be a horse, a cattle (more particularly a cow), a pig (more particularly *Sus domesticus*), a monkey (more particularly the grivet, the rhesus macaque or the crab-eating macaque) or a rodent (more particularly a mouse).

Said bird may e.g., be poultry, more particularly fowl, more particularly a Galliformes or an Anseriformes, more particularly a Galliformes, more particularly turkey, grouse or chicken, more particularly chicken.

Said (infectious) RNA virus advantageously is a single-stranded RNA virus, more particularly a positive-sense single-stranded RNA virus or a negative-sense single-stranded RNA virus. Advantageously, said (infectious) RNA virus is a positive-sense or negative-sense single-stranded RNA virus, which comprises a RNA-dependent RNA polymerase, more particularly a positive-sense or negative-sense single-stranded RNA virus, which implements a RNA-dependent RNA polymerase for replication.

Said infectious RNA virus advantageously is a RNA virus, more particularly a human and/or animal pathogenic RNA virus, which is of the Picornaviridae family, or of the Togaviridae family, or of the Coronaviridae family or of the Flaviviridae family (positive-sense single-stranded RNA viruses, which comprise a RNA-dependent RNA polymerase).

Said (infectious) RNA virus of the Picornaviridae family advantageously is an Enterovirus, an Aphtovirus or a Hepatovirus.

More particularly, said Enterovirus is an Enterovirus A, B, C or D, more particularly a Coxsackie virus (more particularly a Coxsackie virus A or B, more particularly a Coxsackie virus A2, B or A1, more particularly a Coxsackie virus A2 or B, more particularly a Coxsackie virus A2, B1, B2, B3, B4, B5 or B6, more particularly a Coxsackie virus B, more particularly a Coxsackie virus B1, B2, B3, B4, B5 or B6, more particularly a Coxsackie virus B3), Enterovirus 71 (EV71), a Poliovirus (PV-1, PV-2 or PV-3), or Enterovirus 68 (EV68).

Said Enterovirus advantageously is an Enterovirus A or B, more particularly a Coxsackie virus A2, a Coxsackie virus B (more particularly a Coxsackie virus B1, B2, B3, B4, B5 or B6, more particularly a Coxsackie virus B3), Enterovirus 71 (EV71).

Said Enterovirus advantageously is a Coxsackie virus A2 or a Coxsackie virus B (more particularly a Coxsackie virus B1, B2, B3, B4, B5 or B6, more particularly a Coxsackie virus B3), more particularly a Coxsackie virus B (more particularly a Coxsackie virus B1, B2, B3, B4, B5 or B6, more particularly a Coxsackie virus B3), for example a Coxsackie virus the cDNA CDS sequence of which comprises or consists of SEQ ID NO: 2 (cf. example 1 below).

Said Enterovirus advantageously is a human pathogen.

More particularly, said Aphtovirus is the Foot-and-mouth disease virus, more particularly the virus, which causes Foot-and-mouth disease in cattle, more particularly in cows.

Said Aphtovirus advantageously is an animal pathogen, more particularly a non-human mammal pathogen, more particularly a cattle pathogen, more particularly a cow pathogen.

More particularly, said Hepatovirus is a Hepatitis A virus. Said Hepatovirus advantageously is a human pathogen.

More particularly, said infectious RNA virus of the Togaviridae family is an Alphavirus, more particularly a Chikungunya virus, a O'Nyong Nyong virus (ONNV), a Venezuelan Equine Encephalitis Virus (VEEV), a Eastern Equine Encephalitis Virus (EEEV) or a Western Equine Encephalitis Virus (WEEV).

Said RNA virus of the Togaviridae family advantageously is a human pathogen, such as a Chikungunya virus or a ONNV, more particularly a Chikungunya virus.

For example, said Chikungunya virus is the Chikungunya virus strain CHIKV 06-049 of the Indian Ocean Islands sub-lineage (GENBANK accession number AM258994 version 1), or one of the following Chikungunya virus strains: strain 05-115 (GENBANK accession number AM258990 version 1), strain 05-209 (GENBANK accession number AM258991 version 1), strain 06-021 (GENBANK accession number AM258992 version 1), strain 06-027 (GENBANK accession number AM258993 version 1), strain 06-049 (GENBANK accession number AM258994 version 1), strain 05-061 (GENBANK accession number AM258995 version 1) (cf. Schuffenecker et al. 2006; cf. example 4 below), strain M100 (GENBANK accession number LN898093.1), strain G100 (GENBANK accession number LN898094.1), strain M101 (GENBANK accession number LN898095.1), strain M102 (GENBANK accession number LN898096.1), strain G101 (GENBANK accession number LN898097.1), strain G102 (GENBANK accession number LN898098.1), strain G103 (GENBANK accession number LN898099.1), strain M103 (GENBANK accession number LN898100.1), strain M104 (GENBANK accession number LN898101.1), strain G104 (GENBANK accession number LN898102.1), strain G105 (GENBANK accession number LN898103.1), strain M105 (GENBANK accession number LN898104.1), strain M106 (GENBANK accession number LN898105.1), strain M107 (GENBANK accession number LN898106.1), strain M108 (GENBANK accession number LN898107.1), strain M109 (GENBANK accession number LN898108.1), strain M110 (GENBANK accession number LN898109.1), strain G106 (GENBANK accession number LN898110.1), strain G107 (GENBANK accession number LN898111.1), or strain M111 (GENBANK accession number LN898112.1).

For example, said O'Nyong Nyong virus is the O'Nyong Nyong virus strain (GENBANK accession number M20303.1).

Said infectious RNA virus of the Togaviridae family advantageously is an animal pathogen, more particularly a non-human mammal pathogen, more particularly a horse pathogen, such as a VEEV, EEEV or WEEV.

More particularly, said infectious RNA virus of the Coronaviridae family is a virus of the Coronavirinae sub-family, more particularly a Severe Acute Respiratory Syndrome (SARS) coronavirus or a Middle East Respiratory Syndrome (MERS) coronavirus.

Said infectious RNA virus of the Coronaviridae family advantageously is a human pathogen.

More particularly, said infectious RNA virus of the Flaviviridae family is a Flavivirus, more particularly a Japanese Encephalitis Virus (JEV), a Dengue virus, a West Nile virus, a Yellow fever virus, or a Zika virus (ZIKV). For example, said Yellow fever virus is the Yellow fever virus strain Asibi (GENBANK accession number AY640589; cf. example 3 below).

Said infectious RNA virus of the Flaviviridae family advantageously is a human pathogen.

Said infectious RNA virus advantageously is a RNA virus, more particularly a human and/or animal pathogenic RNA virus, which is of the Orthomyxoviridae family (negative-sense single-stranded RNA viruses, which comprise a RNA-dependent RNA polymerase).

Said infectious RNA virus of the Orthomyxoviridae family advantageously is an Influenza virus A, B or C, more particularly a Influenza virus A or B, more particularly an Influenza virus A, more particularly an Influenza virus A virus subtype H1N1 or H3N2, more particularly an Influenza virus A virus subtype H1N1.

For example, said Influenza virus A is the Influenza virus strain ATCC® VR1337™ (Influenza virus type A subtype H1N1; cf. examples 2 and 5 below).

For example, said Influenza virus A is an Influenza virus type A subtype H1N1, which comprises one or several of the following features:

the PB2 coding sequence is the sequence of SEQ ID NO: 59,
the PB1 coding sequence is the sequence of SEQ ID NO: 62,
the PB1-F2 coding sequence is the sequence of SEQ ID NO: 64,
the NP coding sequence is the sequence of SEQ ID NO: 70,
the NA coding sequence is the sequence of SEQ ID NO: 73,
the M1 coding sequence is the sequence of SEQ ID NO: 76,
the M2 coding sequence is the sequence of SEQ ID NO: 78,
the NS1 coding sequence is the sequence of SEQ ID NO: 81, and
the NS2 coding sequence is the sequence of SEQ ID NO: 83.

Said Influenza virus type A subtype H1N1 may further comprise one of the following features:
the PA coding sequence is the sequence of SEQ ID NO: 49 or 51, or
the HA coding sequence is the sequence of SEQ ID NO: 67.

Said infectious RNA virus of the Orthomyxoviridae family advantageously is a human pathogen and/or an animal pathogen, more particularly a human and/or non-human mammal and/or bird pathogen, more particularly a human and/or pig (*Sus domesticus*) and/or seal and/or horse and/or bird pathogen, more particularly a human pathogen.

The term bird notably encompasses poultry, more particularly fowl, more particularly Galliformes and/or Anseriformes, more particularly Galliformes, more particularly turkey and/or grouse and/or chicken, more particularly chicken.

Said infectious RNA virus advantageously is
a Coxsackie virus (more particularly a Coxsackie virus A or B, more particularly a Coxsackie virus A2, B or A1, more particularly a Coxsackie virus A2 or B, more particularly a Coxsackie virus A2, B1, B2, B3, B4, B5 or B6, more particularly a Coxsackie virus B, more particularly a Coxsackie virus B1, B2, B3, B4, B5 or B6, more particularly a Coxsackie virus B3) or Enterovirus 71 (EV71), or
the Foot-and-mouth disease virus, more particularly the virus, which causes Foot-and-mouth disease in cattle, more particularly in cows, or
a Chikungunya virus, or a O'Nyong Nyong virus, or a VEEV, a EEEV or a WEEV, or
a coronavirus, more particularly a SARS coronavirus or a MERS coronavirus, or
a Japanese Encephalitis Virus (JEV), a Dengue fever virus, a West Nile virus, a Yellow fever virus, or a Zika virus (ZIKV), or
an Influenza virus, more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1.

Said infectious RNA virus advantageously is
a Coxsackie virus (more particularly a Coxsackie virus A or B, more particularly a Coxsackie virus A2, B or A1, more particularly a Coxsackie virus A2 or B, more particularly a Coxsackie virus A2, B1, B2, B3, B4, B5 or B6, more particularly a Coxsackie virus B, more particularly a Coxsackie virus B1, B2, B3, B4, B5 or B6, more particularly a Coxsackie virus B3) or Enterovirus 71 (EV71), or
a Chikungunya virus, or a O'Nyong Nyong virus, or
a coronavirus, more particularly a SARS coronavirus or a MERS coronavirus, or
a Japanese Encephalitis Virus (JEV), a Dengue fever virus, a West Nile virus, a Yellow fever virus, or a Zika virus (ZIKV), or
an Influenza virus (more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1).

Said infectious RNA virus advantageously is
the Foot-and-mouth disease virus, more particularly the virus, which causes Foot-and-mouth disease in cattle, more particularly in cows, or
a VEEV, a EEEV or a WEEV, or
an Influenza virus (more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1).

Said infectious RNA virus advantageously is
a Coxsackie virus (more particularly a Coxsackie virus A or B, more particularly a Coxsackie virus A2, B or A1, more particularly a Coxsackie virus A2 or B, more particularly a Coxsackie virus A2, B1, B2, B3, B4, B5 or B6, more particularly a Coxsackie virus B, more particularly a Coxsackie virus B1, B2, B3, B4, B5 or B6, more particularly a Coxsackie virus B3) or Enterovirus 71 (EV71), or
a Japanese Encephalitis Virus (JEV), a Dengue fever virus, a West Nile virus, a Yellow fever virus, or a Zika virus (ZIKV), or
an Influenza virus (more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1).

Said infectious RNA virus advantageously is
a Coxsackie virus (more particularly a Coxsackie virus A or B, more particularly a Coxsackie virus A2, B or A1, more particularly a Coxsackie virus A2 or B, more particularly a Coxsackie virus A2, B1, B2, B3, B4, B5 or B6, more particularly a Coxsackie virus B, more particularly a Coxsackie virus B1, B2, B3, B4, B5 or B6, more particularly a Coxsackie virus B3) or Enterovirus 71 (EV71), or
a Yellow fever virus, or
an Influenza virus (more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1).

Said infectious RNA virus advantageously is
a Coxsackie virus (more particularly a Coxsackie virus A or B, more particularly a Coxsackie virus A2, B or A1, more particularly a Coxsackie virus A2 or B, more particularly a Coxsackie virus A2, B1, B2, B3, B4, B5 or B6, more particularly a Coxsackie virus B, more particularly a Coxsackie virus B1, B2, B3, B4, B5 or B6, more particularly a Coxsackie virus B3) or a Yellow fever virus, or an Influenza virus (more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1).

Said infectious RNA virus advantageously is a Coxsackie virus B, more particularly a Coxsackie virus B1, B2, B3, B4, B5 or B6, more particularly a Coxsackie virus B3, or a Yellow fever virus, or an Influenza virus (more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1).

Said infectious RNA virus advantageously is a Coxsackie virus, more particularly a Coxsackie virus A or B, more particularly a Coxsackie virus A2, B or A1, more particularly a Coxsackie virus A2 or B, more particularly a Coxsackie virus A2, B1, B2, B3, B4, B5 or B6, more particularly a Coxsackie virus B, more particularly a Coxsackie virus B1, B2, B3, B4, B5 or B6, more particularly a Coxsackie virus B3.

Said infectious RNA virus advantageously is an Influenza virus (more particularly an Influenza virus A, B or C, more particularly an Influenza virus A or B, more particularly an Influenza virus A, more particularly an Influenza virus A subtype H1N1 or H3N2 or H5N1 or H7N2, more particularly an Influenza virus A subtype H1N1 or H3N2, more particularly an Influenza virus A subtype H1N1).

Said infectious RNA virus advantageously is a Chikungunya virus or a O'Nyong Nyong virus, more particularly a Chikungunya virus.

The features of viral family, type or sub-type, which have been indicated above to further define the infectious RNA virus, apply to the infectious clone, as well as to the attenuated virus or clone of the application, *mutatis mutandis*.

An infectious clone of an infectious RNA virus generally is of the same family, genus, species, type or subtype as said infectious RNA virus. The attenuated virus or clone of the application advantageously is of the same family, genus, species, type or subtype as said infectious RNA virus or infectious clone.

For example, when said infectious RNA is an Influenza virus, the attenuated virus of the application is a (live and) attenuated Influenza virus. If said infectious Influenza virus is of the species A, the attenuated virus of the application is a (live and) attenuated virus of the application generally is an Influenza virus of species A. Similarly, if said infectious Influenza virus A is of subtype H1N1, the attenuated virus of the application is a (live and) attenuated virus of the application generally is an Influenza virus A of subtype H1N1.

For example, the infectious RNA can be an Influenza virus (more particularly an Influenza virus A, more particularly an Influenza virus A subtype H1N1), wherein the cDNA sequence coding for the PA protein of said infectious Influenza virus is or comprises the sequence of SEQ ID NO: 49 or 51. The (live and) attenuated Influenza virus of the application can thus be an Influenza virus (more particularly an Influenza virus A, more particularly an Influenza virus A subtype H1N1), wherein the cDNA sequence coding for the PA protein of said attenuated Influenza virus is or comprises the sequence of SEQ ID NO: 54 or 56, respectively (cf. example 5 below).

For example, the infectious RNA can be an Influenza virus (more particularly an Influenza virus A, more particularly an Influenza virus A subtype H1N1), wherein the cDNA sequence coding for the HA protein of said infectious Influenza virus is or comprises the sequence of SEQ ID NO: 67. The (live and) attenuated Influenza virus of the application can thus be an Influenza virus (more particularly an Influenza virus A, more particularly an Influenza virus A subtype H1N1), wherein the cDNA sequence coding for the HA protein of said attenuated Influenza virus is or comprises the sequence of SEQ ID NO: 87 (cf. example 7 below).

Similarly, when said infectious RNA is a Coxsackie virus, the attenuated virus of the application is a (live and) attenuated Coxsackie virus. If said infectious Coxsackie virus is of the subtype B, the attenuated virus of the application is a (live and) attenuated virus of the application generally is a Coxsackie virus of subtype B.

For example, the infectious RNA can be a Coxsackie virus (more particularly a Coxsackie virus B, more particularly a Coxsackie virus B3), wherein the cDNA sequence coding for the P1 protein of said infectious Coxsackie virus is or comprises the sequence of SEQ ID NO: 4. The (live and) attenuated Coxsackie virus of the application can thus be a Coxsackie virus (more particularly a Coxsackie virus B, more particularly a Coxsackie virus B3), wherein the cDNA sequence coding for the P1 protein of said attenuated Coxsackie virus is or comprises he sequence of SEQ ID NO: 14. The sequence of SEQ ID NO: 4 is the wild-type cDNA P1 coding sequence of an infectious Coxsackie virus (more particularly of an infectious Coxsackie virus B, more particularly of an infectious Coxsackie virus B3). The sequence of SEQ ID NO: 14 is the sequence of SEQ ID NO: 4 modified in accordance with the application by the replacement of a total of 117 Leu and Ser codons by "1-to-Stop" (Leu and Ser) codons. Please see example 1 below. Alternatively, the (live and) attenuated Coxsackie virus of the application can be a Coxsackie virus (more particularly a Coxsackie virus B, more particularly a Coxsackie virus B3), wherein the cDNA sequence coding for the P1 protein of said attenuated Coxsackie virus is or comprises the sequence of SEQ ID NO: 85 (cf. example 6 below).

For example, when the infectious RNA is a Coxsackie virus (more particularly a Coxsackie virus B, more particularly a Coxsackie virus B3), wherein the cDNA sequence coding for the polyprotein of said infectious Coxsackie virus is the sequence of SEQ ID NO: 2 or 1, the (live and) attenuated Coxsackie virus of the application can be a Coxsackie virus (more particularly a Coxsackie virus B, more particularly a Coxsackie virus B3), wherein the cDNA sequence coding for the polyprotein of said attenuated Coxsackie virus is the sequence of SEQ ID NO: 13 or 12, respectively.

The sequence of SEQ ID NO: 1 is the cDNA sequence of the full-length genome of an infectious Coxsackie virus (more particularly a Coxsackie virus B, more particularly a Coxsackie virus B3). The sequence of SEQ ID NO: 2 is the cDNA sequence of the CDS of this infectious Coxsackie virus. The sequence of SEQ ID NO: 12 is the sequence of SEQ ID NO: 1 modified in accordance with the application by the replacement of a total of 117 Leu and Ser codons of the P1 protein by "1-to-Stop" (Leu and Ser) codons. The sequence of SEQ ID NO: 13 is the sequence of SEQ ID NO:

2 modified in accordance with the application by the replacement of a total of 117 Leu and Ser codons of the P1 protein by "1-to-Stop" (Leu and Ser) codons. Please see example 1 below.

Similarly, when said infectious RNA is a Chikungunya virus, the attenuated virus of the application is a (live and) attenuated Chikungunya virus.

For example, the infectious RNA is a Chikungunya virus, wherein the cDNA sequence coding for the C-E3-E2-6K-E1 polyprotein of said infectious Chikungunya virus is or comprises the sequence of SEQ ID NO: 104. The (live and) attenuated Chikungunya virus of the application can thus be a Chikungunya virus, wherein the cDNA sequence coding for the C-E3-E2-6K-E1 polyprotein of said attenuated Chikungunya virus is or comprises the sequence of SEQ ID NO: 101 or of SEQ ID NO: 102 (cf. example 8 below).

In the application, the CDS of the infectious RNA virus or of the infectious clone thereof is modified by replacement of certain codons by different but synonymous codons. This codon change may affect some nucleotide sequence features, such as:
- the Codon-Pair Bias (CPB) and/or
- the CpG and/or the UpA dinucleotide bias (the CpG and/or the TpA dinucleotide bias for DNA or cDNA sequences), and/or
- the GC content.

The codon change of the application may result in a (significant) change of the CPB or, to the contrary, in the absence of (significant) change in the CPB.

Codon-Pair Bias (CPB) is intended in accordance with its ordinary meaning in the field. CPB is the observed fact that within a CDS, certain codons, corresponding to two (different) amino acids, are found directly adjacent to one another with frequencies either less or more than expected if these codons were randomly placed next to one another. CPB can be quantified based on statistics and the overall bias of a given CDS (excluding Stop codon-pairs) can be determined by the person of average skill in the art.

In accordance with the application, the CPB of the infectious RNA virus or infectious clone thereof may be not significantly changed, more particularly not changed. Hence, the CPB of the modified virus or modified clone of the application (i.e., the attenuated virus or clone of the application) may be not different or not significantly different from the CPB of said infectious RNA virus or infectious clone.

Alternatively, the CPB of the infectious RNA virus or infectious clone thereof may be changed. Hence, the CPB of the modified virus or modified clone of the application (i.e., the attenuated virus or clone of the application) may be different or significantly different from the CPB of said infectious RNA virus or infectious clone, e.g., to increase the representation of under-represented codon pairs.

CpG and UpA dinucleotide bias is intended in accordance with its ordinary meaning in the field. CpG and UpA dinucleotide bias is the observed fact that these dinucleotides occur with a much lower frequency in the sequence of RNA viruses than would be expected due to random chance.

The codon change of the application may result in a (significant) change of the CpG dinucleotide bias and/or in the UpA (or TpA) dinucleotide bias, or, to the contrary, in the absence of (significant) change in the CpG dinucleotide bias and/or in the UpA (or TpA) dinucleotide bias.

In accordance with the application, the CpG and/or UpA (or TpA) dinucleotide bias of the infectious RNA virus or infectious clone thereof may be not significantly changed, more particularly not changed.

Hence, the CpG and/or UpA (or TpA) dinucleotide bias of the modified virus or modified clone of the application (i.e., of the attenuated virus or clone of the application) may not be (significantly) different from the CpG and/or UpA (or TpA) dinucleotide bias of said infectious RNA virus or infectious clone.

More particularly, the CpG and UpA (or TpA) dinucleotide bias of the modified virus or modified clone of the application (i.e., of the attenuated virus or clone of the application) may not be (significantly) different from the CpG and UpA (or TpA) dinucleotide bias of said infectious RNA virus or infectious clone.

More particularly, the CpG and UpA dinucleotide bias of the modified virus may be not (significantly) different from the CpG and UpA dinucleotide bias of said infectious RNA virus, and the CpG and TpA dinucleotide bias of said modified cDNA clone may be not (significantly) different from the CpG and TpA dinucleotide bias of said infectious cDNA clone.

Alternatively, the CpG and/or UpA (or TpA) dinucleotide bias of the infectious RNA virus or infectious clone thereof may be changed, e.g., to increase the CpG and/or UpA (or TpA) dinucleotide bias.

Hence, the CpG and/or UpA (or TpA) dinucleotide bias of the modified virus or modified clone of the application (i.e., of the attenuated virus or clone of the application) may be (significantly) different from, more particularly (significantly) higher than, the CpG and/or UpA (or TpA) dinucleotide bias of said infectious RNA virus or infectious clone.

More particularly, the CpG and UpA dinucleotide bias of the modified virus may be (significantly) different from, more particularly (significantly) higher than, the CpG and UpA dinucleotide bias of said infectious RNA virus, and the CpG and TpA dinucleotide bias of said modified cDNA clone may be (significantly) different from, more particularly (significantly) higher than, the CpG and TpA dinucleotide bias of said infectious cDNA clone.

The codon change of the application may result in a (significant) change of the GC content or, to the contrary, in the absence of (significant) change in GC content. Hence, the GC content of the modified virus or modified clone of the application (i.e., of the attenuated virus or clone of the application) may be or not be (significantly) different from the GC content of said infectious RNA virus or infectious clone. More particularly, the GC content of the modified virus or modified clone of the application (i.e., of the attenuated virus or clone of the application) is not (significantly) different from the GC content of said infectious RNA virus or infectious clone.

The "1-to-Stop" (synonymous and/or non-synonymous, more particularly synonymous) codon replacement of the application may be the only type modifications made to the nucleotide sequence of said infectious RNA virus or infectious clone.

Alternatively, the modifications made to the nucleotide sequence of said infectious RNA virus or infectious clone may comprise modifications other than said "1-to-Stop" (synonymous and/or non-synonymous, more particularly synonymous) codon replacement of the application. Such other modifications may be made by the person of ordinary skill in the art, for example to lower the fidelity of replication to increase mutation rate, or to increase the fidelity of replication to decrease mutation rate, or to further increase attenuation, or to improve the replication rate.

More particularly, the modifications made to the nucleotide sequence of said infectious RNA virus or infectious clone may comprise replacing the sequence coding for the polymerase (RNA-dependent DNA polymerase or RNA-dependent RNA polymerase) of the infectious virus or clone by a (RNA, DNA or cDNA) sequence coding for a polymerase (RNA-dependent DNA polymerase or RNA-dependent RNA polymerase, respectively), which has lower or higher nucleotide incorporation fidelity.

More particularly, concerning the infectious RNA viruses or clones, which comprise a RNA-dependent RNA polymerase (more particularly, which implement it for replication), the modifications made to the nucleotide sequence of the infectious RNA virus or infectious clone may comprise replacing the sequence coding for the RNA-dependent RNA-polymerase of the infectious virus or clone by a (RNA, DNA or cDNA) sequence coding for a RNA-dependent RNA-polymerase, which has lower or higher nucleotide incorporation fidelity.

At least concerning Coxsackie virus, examples of RNA-dependent RNA-polymerase, which has lower nucleotide incorporation fidelity (i.e., lower copying fidelity), notably comprise the A239G, Y268W, I230F, Y268H, P48K, S299T or F232Y mutant of a wild-type (i.e., infectious) Coxsackie virus B3 RNA-dependent RNA polymerase, for example, the A239G, Y268W, I230F, Y268H, P48K, F232Y or S299T mutant of SEQ ID NO: 15, 16, 17, 18, 19, 20 or 21, respectively.

A239G mutant of the polymerase (i.e., of the 3D protein) of a wild-type (i.e., infectious) human Coxsackie virus B3 [A239G mutant of the sequence of SEQ ID NO: 11; 462 aa]:

```
                                                    SEQ ID NO: 15
GEIEFIESSKDAGFPVINTPSKTKLEPSVFHQVFEGNKEPAVLRSGDPRL        50

KANFEEAIFSKYIGNVNTHVDEYMLEAVDHYAGQLATLDISTEPMKLEDA       100

VYGTEGLEALDLTTSAGYPYVALGIKKRDILSKKTKDLTKLKECMDKYGL       150

NLPMVTYVKDELRSIEKVAKGKSRLIEASSLNDSVAMRQTFGNLYKTFHL       200

NPGVVTGSAVGCDPDLFWSKIPVMLDGHLIAFDYSGYDGSLSPVWFACLK       250

MLLEKLGYTHKETNYIDYLCNSHHLYRDKHYFVRGGMPSGCSGTSIFNSM       300

INNIIIRTLMLKVYKGIDLDQFRMIAYGDDVIASYPWPIDASLLAEAGKG       350

YGLIMTPADKGECFNEVTWTNATFLKRYFRADEQYPFLVHPVMPMKDIHE       400

SIRWTKDPKNTQDHVRSLCLLAWHNGEHEYEEFIRKIRSVPVGRCLTLPA       450

FSTLRRKWLDSF
```

Y268W of the polymerase (i.e., of the 3D protein) of a wild-type (i.e., infectious) human Coxsackie virus B3 [Y268W mutant of the sequence of SEQ ID NO: 11; 462 aa]:

```
                                                    SEQ ID NO: 16
GEIEFIESSKDAGFPVINTPSKTKLEPSVFHQVFEGNKEPAVLRSGDPRL        50

KANFEEAIFSKYIGNVNTHVDEYMLEAVDHYAGQLATLDISTEPMKLEDA       100

VYGTEGLEALDLTTSAGYPYVALGIKKRDILSKKTKDLTKLKECMDKYGL       150

NLPMVTYVKDELRSIEKVAKGKSRLIEASSLNDSVAMRQTFGNLYKTFHL       200

NPGVVTGSAVGCDPDLFWSKIPVMLDGHLIAFDYSGYDASLSPVWFACLK       250

MLLEKLGYTHKETNYIDWLCNSHHLYRDKHYFVRGGMPSGCSGTSIFNSM       300

INNIIIRTLMLKVYKGIDLDQFRMIAYGDDVIASYPWPIDASLLAEAGKG       350

YGLIMTPADKGECFNEVTWTNATFLKRYFRADEQYPFLVHPVMPMKDIHE       400

SIRWTKDPKNTQDHVRSLCLLAWHNGEHEYEEFIRKIRSVPVGRCLTLPA       450

FSTLRRKWLDSF
```

I230F mutant of the polymerase (i.e., of the 3D protein) of a wild-type (i.e., infectious) human Coxsackie virus B3 [I230F mutant of the sequence of SEQ ID NO: 11; 462 aa]:

```
                                                    SEQ ID NO: 17
GEIEFIESSKDAGFPVINTPSKTKLEPSVFHQVFEGNKEPAVLRSGDPRL        50

KANFEEAIFSKYIGNVNTHVDEYMLEAVDHYAGQLATLDISTEPMKLEDA       100

VYGTEGLEALDLTTSAGYPYVALGIKKRDILSKKTKDLTKLKECMDKYGL       150

NLPMVTYVKDELRSIEKVAKGKSRLIEASSLNDSVAMRQTFGNLYKTFHL       200
```

```
NPGVVTGSAVGCDPDLFWSKIPVMLDGHLFAFDYSGYDASLSPVWFACLK      250

MLLEKLGYTHKETNYIDYLCNSHHLYRDKHYFVRGGMPSGCSGTSIFNSM      300

INNIIRTLMLKVYKGIDLDQFRMIAYGDDVIASYPWPIDASLLAEAGKG       350

YGLIMTPADKGECFNEVTWTNATFLKRYFRADEQYPFLVHPVMPMKDIHE      400

SIRWTKDPKNTQDHVRSLCLLAWHNGEHEYEEFIRKIRSVPVGRCLTLPA      450

FSTLRRKWLDSF
```

Y268H mutant of the polymerase (i.e., of the 3D protein) of a wild-type (i.e., infectious) human Coxsackie virus B3 [Y268H mutant of the sequence of SEQ ID NO: 11; 462 aa]:

```
                                                  SEQ ID NO: 18
GEIEFIESSKDAGFPVINTPSKTKLEPSVFHQVFEGNKEPAVLRSGDPRL       50

KANFEEAIFSKYIGNVNTHVDEYMLEAVDHYAGQLATLDISTEPMKLEDA      100

VYGTEGLEALDLTTSAGYPYVALGIKKRDILSKKTKDLTKLKECMDKYGL      150

NLPMVTYVKDELRSIEKVAKGKSRLIEASSLNDSVAMRQTFGNLYKTFHL      200

NPGVVTGSAVGCDPDLFWSKIPVMLDGHLIAFDYSGYDASLSPVWFACLK      250

MLLEKLGYTHKETNYIDHLCNSHHLYRDKHYFVRGGMPSGCSGTSIFNSM      300

INNIIRTLMLKVYKGIDLDQFRMIAYGDDVIASYPWPIDASLLAEAGKG       350

YGLIMTPADKGECFNEVTWTNATFLKRYFRADEQYPFLVHPVMPMKDIHE      400

SIRWTKDPKNTQDHVRSLCLLAWHNGEHEYEEFIRKIRSVPVGRCLTLPA      450

FSTLRRKWLDSF
```

P48K mutant the polymerase (i.e., of the 3D protein) of a wild-type (i.e., infectious) human Coxsackie virus B3 [P48K mutant of the sequence of SEQ ID NO: 11; 462 aa]:

```
                                                  SEQ ID NO: 19
GEIEFIESSKDAGFPVINTPSKTKLEPSVFHQVFEGNKEPAVLRSGDKRL       50

KANFEEAIFSKYIGNVNTHVDEYMLEAVDHYAGQLATLDISTEPMKLEDA      100

VYGTEGLEALDLTTSAGYPYVALGIKKRDILSKKTKDLTKLKECMDKYGL      150

NLPMVTYVKDELRSIEKVAKGKSRLIEASSLNDSVAMRQTFGNLYKTFHL      200

NPGVVTGSAVGCDPDLFWSKIPVMLDGHLIAFDYSGYDASLSPVWFACLK      250

MLLEKLGYTHKETNYIDYLCNSHHLYRDKHYFVRGGMPSGCSGTSIFNSM      300

INNIIRTLMLKVYKGIDLDQFRMIAYGDDVIASYPWPIDASLLAEAGKG       350

YGLIMTPADKGECFNEVTWTNATFLKRYFRADEQYPFLVHPVMPMKDIHE      400

SIRWTKDPKNTQDHVRSLCLLAWHNGEHEYEEFIRKIRSVPVGRCLTLPA      450

FSTLRRKWLDSF
```

F232Y mutant of the polymerase (i.e., of the 3D protein) of a wild-type (i.e., infectious) human Coxsackie virus B3 [F232Y mutant of the sequence of SEQ ID NO: 11; 462 aa]:

```
                                                  SEQ ID NO: 20
GEIEFIESSKDAGFPVINTPSKTKLEPSVFHQVFEGNKEPAVLRSGDPRL       50

KANFEEAIFSKYIGNVNTHVDEYMLEAVDHYAGQLATLDISTEPMKLEDA      100

VYGTEGLEALDLTTSAGYPYVALGIKKRDILSKKTKDLTKLKECMDKYGL      150
```

```
NLPMVTYVKDELRSIEKVAKGKSRLIEASSLNDSVAMRQTFGNLYKTFHL       200

NPGVVTGSAVGCDPDLFWSKIPVMLDGHLIAYDYSGYDASLSPVWFACLK       250

MLLEKLGYTHKETNYIDYLCNSHHLYRDKHYFVRGGMPSGCSGTSIFNSM       300

INNIIRTLMLKVYKGIDLDQFRMIAYGDDVIASYPWPIDASLLAEAGKG        350

YGLIMTPADKGECFNEVTWTNATFLKRYFRADEQYPFLVHPVMPMKDIHE       400

SIRWTKDPKNTQDHVRSLCLLAWHNGEHEYEEFIRKIRSVPVGRCLTLPA       450

FSTLRRKWLDSF
```

S999T mutant of the polymerase (i.e., of the 3D protein) of a wild-type (i.e., infectious) human Coxsackie virus B3 [S299T mutant of the sequence of SEQ ID NO: 11; 462 aa]:

```
                                                    SEQ ID NO: 21
GEIEFIESSKDAGFPVINTPSKTKLEPSVFHQVFEGNKEPAVLRSGDPRL       50

KANFEEAIFSKYIGNVNTHVDEYMLEAVDHYAGQLATLDISTEPMKLEDA       100

VYGTEGLEALDLTTSAGYPYVALGIKKRDILSKKTKDLTKLKECMDKYGL       150

NLPMVTYVKDELRSIEKVAKGKSRLIEASSLNDSVAMRQTFGNLYKTFHL       200

NPGVVTGSAVGCDPDLFWSKIPVMLDGHLIAFDYSGYDASLSPVWFACLK       250

MLLEKLGYTHKETNYIDYLCNSHHLYRDKHYFVRGGMPSGCSGTSIFNTM       300

INNIIRTLMLKVYKGIDLDQFRMIAYGDDVIASYPWPIDASLLAEAGKG        350

YGLIMTPADKGECFNEVTWTNATFLKRYFRADEQYPFLVHPVMPMKDIHE       400

SIRWTKDPKNTQDHVRSLCLLAWHNGEHEYEEFIRKIRSVPVGRCLTLPA       450

FSTLRRKWLDSF
```

At least concerning Chikungunya virus, examples of RNA-dependent RNA-polymerase, which has lower nucleotide incorporation fidelity (i.e., lower copying fidelity), notably comprise the C483A or C483W or C483G mutant of a wild-type (i.e., infectious) Chikungunya virus B3 RNA-dependent RNA polymerase, more particularly the NSp1234 polyprotein.

The sequence of the (wild-type) NSp1234 polyprotein is SEQ ID NO: 89:

```
                                                    SEQ ID NO: 89
MDPVYVDIDADSAFLKALQRAYPMFEVEPRQVTPNDHANARAFSHLAIKL

IEQEIDPDSTILDIGSAPARRMMSDRKYHCVCPMRSAEDPERLANYARKL

ASAAGKVLDRNISGKIGDLQAVMAVPDTETPTFCLHTDVSCRQRADVAIY

QDVYAVHAPTSLYHQAIKGVRVAYWVGFDTTPFMYNAMAGAYPSYSTNWA

DEQVLKAKNIGLCSTDLTEGRRGKLSIMRGKKLKPCDRVLFSVGSTLYPE

SRKLLKSWHLPSVFHLKGKLSFTCRCDTVVSCEGYVVKRITMSPGLYGKT

TGYAVTHHADGFLMCKTTDTVDGERVSFSVCTYVPATICDQMTGILATEV

TPEDAQKLLVGLNQRIVVNGRTQRNTNTMKNYLLPVVAQAFSKWAKECRK

DMEDEKLLGVRERTLTCCCLWAFKKQKTHTVYKRPDTQSIQKVQAEFDSF

VVPSLWSSGLSIPLRTRIKWLLSKVPKTDLIPYSGDAREARDAEKEAEEE

REAELTREALPPLQAAQEDVQVEIDVEQLEDRAGAGIIETPRGAIKVTAQ

PTDHVVGEYLVLSPQTVLRSQKLSLIHALAEQVKTCTHNGRAGRYAVEAY

-continued

DGRVLVPSGYAISPEDFQSLSESATMVYNEREFVNRKLHHIAMHGPALNT

DEESYELVRAERTEHEYVYDVDQRRCCKKEEAAGLVLVGDLTNPPYHEFA

YEGLKIRPACPYKIAVIGVFGVPGSGKSAIIKNLVTRQDLVTSGKKENCQ

EITTDVMRQRGLEISARTVDSLLLNGCNRPVDVLYVDEAFACHSGTLLAL

IALVRPRQKVVLCGDPKQCGFFNMMQMKVNYNHNICTQVYHKSISRRCTL

PVTAIVSSLHYEGKMRTTNEYNKPIVVDTTGSTKPDPGDLVLTCFRGWVK

QLQIDYRGYEVMTAAASQGLTRKGVYAVRQKVNENPLYASTSEHVNVLLT

RTEGKLVWKTLSGDPWIKTLQNPPKGNFKATIKEWEVEHASIMAGICSHQ

MTFDTFQNKANVCWAKSLVPILETAGIKLNDRQWSQIIQAFKEDKAYSPE

VALNEICTRMYGVDLDSGLFSKPLVSVYYADNHWDNRPGGKMFGFNPEAA

SILERKYPFTKGKWNINKQICVTTRRIEDFNPTTNIIPANRRLPHSLVAE

HRPVKGERMEWLVNKINGHHVLLVSGYNLALPTKRVTWVAPLGVRGADYT

YNLELGLPATLGRYDLVVINIHTPFRIHHYQQCVDHAMKLQMLGGDSLRL

LKPGGSLLIRAYGYADRTSERVICVLGRKFRSSRALKPPCVTSNTEMFFL

FSNFDNGRRNFTTHVMNNQLNAAFVGQVTRAGCAPSYRVKRMDIAKNDEE

CVVNAANPRGLPGDGVCKAVYKKWPESFKNSATPVGTAKTVMCGTYPVIH

AVGPNFSNYSESEGDRELAAAYREVAKEVTRLGVNSVAIPLLSTGVYSGG

KDRLTQSLNHLFTAMDSTDADVVIYCRDKEWEKKISEAIQMRTQVELLDE
```

-continued

HISIDCDIVRVHPDSSLAGRKGYSTTEGALYSYLEGTRFHQTAVDMAEIH
TMWPKQTEANEQVCLYALGESIESIRQKCPVDDADASSPPKTVPCLCRYA
MTPERVTRLRMNHVTSIIVCSSFPLPKYKIEGVQKVKCSKVMLFDHNVPS
RVSPREYRSSQESAQEASTITSLTHSQFDLSVDGEILPVPSDLDADAPAL
EPALDDGATHTLPSTTGNLAAVSDWVMSTVPVAPPRRRRGRNLTVTCDER
EGNITPMASVRFFRAELCPVVQETAETRDTAMSLQAPPSTATEPNHPPIS
FGASSETFPITFGDFNEGEIESLSSELLTFGDFLPGEVDDLTDSDWSTCS
DTDDELXLDRAGGYIFSSDTGPGHLQQKSVRQSVLPVNTLEEVHEEKCYP
PKLDEAKEQLLLKKLQESASMANRSRYQSRKVENMKAAIIQRLKRGCRLY
LMSETPKVPTYRTTYPAPVYSPPINVRLSNPESAVAACNEFLARNYPTVS
SYQITDEYDAYLDMVDGSESCLDRATFNPSKLRSYPKQHAYHAPSIRSAV
PSPFQNTLQNVLAAATKRNCNVTQMRELPTLDSAVFNVECFKKFACNQEY
WEEFAASPIRITTENLATYVTKLKGPKAAALFAKTHNLLPLQEVPMDRFT
VDMKRDVKVTPGTKHTEERPKVQVIQAAEPLATAYLCGIHRELVRRLNAV
LLPNVHTLFDMSAEDFDAIIAAHFKPGDTVLETDIASFDKSQDDSLALTA
LMLLEDLGVDHSLLDLIEAAFGEISSCHLPTGTRFKFGAMMKSGMFLTLF
VNTLLNITIASRVLEDRLTKSACAAFIGDDNIIHGVVSDELMAARCATWM
NMEVKIIDAVVSLKAPYFCGGFILHDTVTGTACRVADPLKRLFKLGKPLA
AGDEQDEDRRRALADEVIRWQRTGLIDELEKAVYSRYEVQGISVVVMSMA
TFASSRSNFEKLRGPVITLYGGPK

The sequence of the C483A mutant of NSp1234 polyprotein (encoding the low fidelity polymerase) is SEQ ID NO: 90:

SEQ ID NO: 90

MDPVYVDIDADSAFLKALQRAYPMFEVEPRQVTPNDHANARAFSHLAIKL
IEQEIDPDSTILDIGSAPARRMMSDRKYHCVCPMRSAEDPERLANYARKL
ASAAGKVLDRNISGKIGDLQAVMAVPDTETPTFCLHTDVSCRQRADVAIY
QDVYAVHAPTSLYHQAIKGVRVAYWVGFDTTPFMYNAMAGAYPSYSTNWA
DEQVLKAKNIGLCSTDLTEGRRGKLSIMRGKKLKPCDRVLFSVGSTLYPE
SRKLLKSWHLPSVFHLKGKLSFTCRCDTVVSCEGYVVKRITMSPGLYGKT
TGYAVTHHADGFLMCKTTDTVDGERVSFSVCTYVPATICDQMTGILATEV
TPEDAQKLLVGLNQRIVVNGRTQRNTNTMKNYLLPVVAQAFSKWAKECRK
DMEDEKLLGVRERTLTCCCLWAFKKQKTHTVYKRPDTQSIQKVQAEFDSF
VVPSLWSSGLSIPLRTRIKWLLSKVPKTDLIPYSGDAREARDAEKEAEEE
REAELTREALPPLQAAQEDVQVEIDVEQLEDRAGAGIIETPRGAIKVTAQ
PTDHVVGEYLVLSPQTVLRSQKLSLIHALAEQVKTCTHNGRAGRYAVEAY
DGRVLVPSGYAISPEDFQSLSESATMVYNEREFVNRKLHHIAMHGPALNT
DEESYELVRAERTEHEYVYDVDQRRCCKKEEAAGLVLVGDLTNPPYHEFA
YEGLKIRPACPYKIAVIGVFGVPGSGKSAIIKNLVTRQDLVTSGKKENCQ
EITTDVMRQRGLEISARTVDSLLLNGCNRPVDVLYVDEAFACHSGTLLAL
IALVRPRQKVVLCGDPKQCGFFNMMQMKVNYNHNICTQVYHKSISRRCTL

-continued

PVTAIVSSLHYEGKMRTTNEYNKPIVVDTTGSTKPDPGDLVLTCFRGWVK
QLQIDYRGYEVMTAAASQGLTRKGVYAVRQKVNENPLYASTSEHVNVLLT
RTEGKLVWKTLSGDPWIKTLQNPPKGNFKATIKEWEVEHASIMAGICSHQ
MTFDTFQNKANVCWAKSLVPILETAGIKLNDRQWSQIIQAFKEDKAYSPE
VALNEICTRMYGVDLDSGLFSKPLVSVYYADNHWDNRPGGKMFGFNPEAA
SILERKYPFTKGKWNINKQICVTTRRIEDFNPTTNIIPANRRLPHSLVAE
HRPVKGERMEWLVNKINGHHVLLVSGYNLALPTKRVTWVAPLGVRGADYT
YNLELGLPATLGRYDLVVINIHTPFRIHHYQQCVDHAMKLQMLGGDSLRL
LKPGGSLLIRAYGYADRTSERVICVLGRKFRSSRALKPPCVTSNTEMFFL
FSNFDNGRRNFTTHVMNNQLNAAFVGQVTRAGCAPSYRVKRMDIAKNDEE
CVVNAANPRGLPGDGVCKAVYKKWPESFKNSATPVGTAKTVMCGTYPVIH
AVGPNFSNYSESEGDRELAAAYREVAKEVTRLGVNSVAIPLLSTGVYSGG
KDRLTQSLNHLFTAMDSTDADVVIYCRDKEWEKKISEAIQMRTQVELLDE
HISIDCDIVRVHPDSSLAGRKGYSTTEGALYSYLEGTRFHQTAVDMAEIH
TMWPKQTEANEQVCLYALGESIESIRQKCPVDDADASSPPKTVPCLCRYA
MTPERVTRLRMNHVTSIIVCSSFPLPKYKIEGVQKVKCSKVMLFDHNVPS
RVSPREYRSSQESAQEASTITSLTHSQFDLSVDGEILPVPSDLDADAPAL
EPALDDGATHTLPSTTGNLAAVSDWVMSTVPVAPPRRRRGRNLTVTCDER
EGNITPMASVRFFRAELCPVVQETAETRDTAMSLQAPPSTATEPNHPPIS
FGASSETFPITFGDFNEGEIESLSSELLTFGDFLPGEVDDLTDSDWSTCS
DTDDELXLDRAGGYIFSSDTGPGHLQQKSVRQSVLPVNTLEEVHEEKCYP
PKLDEAKEQLLLKKLQESASMANRSRYQSRKVENMKAAIIQRLKRGCRLY
LMSETPKVPTYRTTYPAPVYSPPINVRLSNPESAVAACNEFLARNYPTVS
SYQITDEYDAYLDMVDGSESCLDRATFNPSKLRSYPKQHAYHAPSIRSAV
PSPFQNTLQNVLAAATKRNCNVTQMRELPTLDSAVFNVECFKKFACNQEY
WEEFAASPIRITTENLATYVTKLKGPKAAALFAKTHNLLPLQEVPMDRFT
VDMKRDVKVTPGTKHTEERPKVQVIQAAEPLATAYLCGIHRELVRRLNAV
LLPNVHTLFDMSAEDFDAIIAAHFKPGDTVLETDIASFDKSQDDSLALTA
LMLLEDLGVDHSLLDLIEAAFGEISSCHLPTGTRFKFGAMMKSGMFLTLF
VNTLLNITIASRVLEDRLTKSACAAFIGDDNIIHGVVSDELMAARAATWM
NMEVKIIDAVVSLKAPYFCGGFILHDTVTGTACRVADPLKRLFKLGKPLA
AGDEQDEDRRRALADEVIRWQRTGLIDELEKAVYSRYEVQGISVVVMSMA
TFASSRSNFEKLRGPVITLYGGPK

The sequence of the C483W mutant of NSp1234 polyprotein (encoding the low fidelity polymerase) is SEQ ID NO: 91:

SEQ ID NO: 91

MDPVYVDIDADSAFLKALQRAYPMFEVEPRQVTPNDHANARAFSHLAIKL
IEQEIDPDSTILDIGSAPARRMMSDRKYHCVCPMRSAEDPERLANYARKL
ASAAGKVLDRNISGKIGDLQAVMAVPDTETPTFCLHTDVSCRQRADVAIY
QDVYAVHAPTSLYHQAIKGVRVAYWVGFDTTPFMYNAMAGAYPSYSTNWA

-continued

DEQVLKAKNIGLCSTDLTEGRRGKLSIMRGKKLKPCDRVLFSVGSTLYPE

SRKLLKSWHLPSVFHLKGKLSFTCRCDTVVSCEGYVVKRITMSPGLYGKT

TGYAVTHHADGFLMCKTTDTVDGERVSFSVCTYVPATICDQMTGILATEV

TPEDAQKLLVGLNQRIVVNGRTQRNTNTMKNYLLPVVAQAFSKWAKECRK

DMEDEKLLGVRERTLTCCCLWAFKKQKTHTVYKRPDTQSIQKVQAEFDSF

VVPSLWSSGLSIPLRTRIKWLLSKVPKTDLIPYSGDAREARDAEKEAEEE

REAELTREALPPLQAAQEDVQVEIDVEQLEDRAGAGIIETPRGAIKVTAQ

PTDHVVGEYLVLSPQTVLRSQKLSLIHALAEQVKTCTHNGRAGRYAVEAY

DGRVLVPSGYAISPEDFQSLSESATMVYNEREFVNRKLHHIAMHGPALNT

DEESYELVRAERTEHEYVYDVDQRRCCKKEEAAGLVLVGDLTNPPYHEFA

YEGLKIRPACPYKIAVIGVFGVPGSGKSAIIKNLVTRQDLVTSGKKENCQ

EITTDVMRQRGLEISARTVDSLLLNGCNRPVDVLYVDEAFACHSGTLLAL

IALVRPRQKVVLCGDPKQCGFFNMMQMKVNYNHNICTQVYHKSISRRCTL

PVTAIVSSLHYEGKMRTTNEYNKPIVVDTTGSTKPDPGDLVLTCFRGWVK

QLQIDYRGYEVMTAAASQGLTRKGVYAVRQKVNENPLYASTSEHVNVLLT

RTEGKLVWKTLSGDPWIKTLQNPPKGNFKATIKEWEVEHASIMAGICSHQ

MTFDTFQNKANVCWAKSLVPILETAGIKLNDRQWSQIIQAFKEDKAYSPE

VALNEICTRMYGVDLDSGLFSKPLVSVYYADNHWDNRPGGKMFGFNPEAA

SILERKYPFTKGKWNINKQICVTTRRIEDFNPTTNIIPANRRLPHSLVAE

HRPVKGERMEWLVNKINGHHVLLVSGYNLALPTKRVTWVAPLGVRGADYT

YNLELGLPATLGRYDLVVINIHTPFRIHHYQQCVDHAMKLQMLGGDSLRL

LKPGGSLLIRAYGYADRTSERVICVLGRKFRSSRALKPPCVTSNTEMFFL

FSNFDNGRRNFTTHVMNNQLNAAFVGQVTRAGCAPSYRVKRMDIAKNDEE

CVVNAANPRGLPGDGVCKAVYKKWPESFKNSATPVGTAKTVMCGTYPVIH

AVGPNFSNYSESEGDRELAAAYREVAKEVTRLGVNSVAIPLLSTGVYSGG

KDRLTQSLNHLFTAMDSTDADVVIYCRDKEWEKKISEAIQMRTQVELLDE

HISIDCDIVRVHPDSSLAGRKGYSTTEGALYSYLEGTRFHQTAVDMAEIH

TMWPKQTEANEQVCLYALGESIESIRQKCPVDDADASSPPKTVPCLCRYA

MTPERVTRLRMNHVTSIIVCSSFPLPKYKIEGVQKVKCSKVMLFDHNVPS

RVSPREYRSSQESAQEASTITSLTHSQFDLSVDGEILPVPSDLDADAPAL

EPALDDGATHTLPSTTGNLAAVSDWVMSTVPVAPPRRRRGRNLTVTCDER

EGNITPMASVRFFRAELCPVVQETAETRDTAMSLQAPPSTATEPNHPPIS

FGASSETFPITFGDFNEGEIESLSSELLTFGDFLPGEVDDLTDSDWSTCS

DTDDELXLDRAGGYIFSSDTGPGHLQQKSVRQSVLPVNTLEEVHEEKCYP

PKLDEAKEQLLLKKLQESASMANRSRYQSRKVENMKAAIIQRLKRGCRLY

LMSETPKVPTYRTTYPAPVYSPPINVRLSNPESAVAACNEFLARNYPTVS

SYQITDEYDAYLDMVDGSESCLDRATFNPSKLRSYPKQHAYHAPSIRSAV

PSPFQNTLQNVLAAATKRNCNVTQMRELPTLDSAVFNVECFKKFACNQEY

WEEFAASPIRITTENLATYVTKLKGPKAAALFAKTHNLLPLQEVPMDRFT

VDMKRDVKVTPGTKHTEERPKVQVIQAAEPLATAYLCGIHRELVRRLNAV

LLPNVHTLFDMSAEDFDAIIAAHFKPGDTVLETDIASFDKSQDDSLALTA

LMLLEDLGVDHSLLDLIEAAFGEISSCHLPTGTRFKFGAMMKSGMFLTLF

VNTLLNITIASRVLEDRLTKSACAAFIGDDNIIHGVVSDELMAARWATWM

NMEVKIIDAVVSLKAPYFCGGFILHDTVTGTACRVADPLKRLFKLGKPLA

AGDEQDEDRRRALADEVIRWQRTGLIDELEKAVYSRYEVQGISVVVMSMA

TFASSRSNFEKLRGPVITLYGGPK

The sequence of the C483G mutant of NSp1234 polyprotein (encoding the low fidelity polymerase) is SEQ ID NO: 92:

SEQ ID NO: 92
MDPVYVDIDADSAFLKALQRAYPMFEVEPRQVTPNDHANARAFSHLAIKL

IEQEIDPDSTILDIGSAPARRMMSDRKYHCVCPMRSAEDPERLANYARKL

ASAAGKVLDRNISGKIGDLQAVMAVPDTETPTFCLHTDVSCRQRADVAIY

QDVYAVHAPTSLYHQAIKGVRVAYWVGFDTTPFMYNAMAGAYPSYSTNWA

DEQVLKAKNIGLCSTDLTEGRRGKLSIMRGKKLKPCDRVLFSVGSTLYPE

SRKLLKSWHLPSVFHLKGKLSFTCRCDTVVSCEGYVVKRITMSPGLYGKT

TGYAVTHHADGFLMCKTTDTVDGERVSFSVCTYVPATICDQMTGILATEV

TPEDAQKLLVGLNQRIVVNGRTQRNTNTMKNYLLPVVAQAFSKWAKECRK

DMEDEKLLGVRERTLTCCCLWAFKKQKTHTVYKRPDTQSIQKVQAEFDSF

VVPSLWSSGLSIPLRTRIKWLLSKVPKTDLIPYSGDAREARDAEKEAEEE

REAELTREALPPLQAAQEDVQVEIDVEQLEDRAGAGIIETPRGAIKVTAQ

PTDHVVGEYLVLSPQTVLRSQKLSLIHALAEQVKTCTHNGRAGRYAVEAY

DGRVLVPSGYAISPEDFQSLSESATMVYNEREFVNRKLHHIAMHGPALNT

DEESYELVRAERTEHEYVYDVDQRRCCKKEEAAGLVLVGDLTNPPYHEFA

YEGLKIRPACPYKIAVIGVFGVPGSGKSAIIKNLVTRQDLVTSGKKENCQ

EITTDVMRQRGLEISARTVDSLLLNGCNRPVDVLYVDEAFACHSGTLLAL

IALVRPRQKVVLCGDPKQCGFFNMMQMKVNYNHNICTQVYHKSISRRCTL

PVTAIVSSLHYEGKMRTTNEYNKPIVVDTTGSTKPDPGDLVLTCFRGWVK

QLQIDYRGYEVMTAAASQGLTRKGVYAVRQKVNENPLYASTSEHVNVLLT

RTEGKLVWKTLSGDPWIKTLQNPPKGNFKATIKEWEVEHASIMAGICSHQ

MTFDTFQNKANVCWAKSLVPILETAGIKLNDRQWSQIIQAFKEDKAYSPE

VALNEICTRMYGVDLDSGLFSKPLVSVYYADNHWDNRPGGKMFGFNPEAA

SILERKYPFTKGKWNINKQICVTTRRIEDFNPTTNIIPANRRLPHSLVAE

HRPVKGERMEWLVNKINGHHVLLVSGYNLALPTKRVTWVAPLGVRGADYT

YNLELGLPATLGRYDLVVINIHTPFRIHHYQQCVDHAMKLQMLGGDSLRL

LKPGGSLLIRAYGYADRTSERVICVLGRKFRSSRALKPPCVTSNTEMFFL

FSNFDNGRRNFTTHVMNNQLNAAFVGQVTRAGCAPSYRVKRMDIAKNDEE

CVVNAANPRGLPGDGVCKAVYKKWPESFKNSATPVGTAKTVMCGTYPVIH

AVGPNFSNYSESEGDRELAAAYREVAKEVTRLGVNSVAIPLLSTGVYSGG

KDRLTQSLNHLFTAMDSTDADVVIYCRDKEWEKKISEAIQMRTQVELLDE

HISIDCDIVRVHPDSSLAGRKGYSTTEGALYSYLEGTRFHQTAVDMAEIH

```
-continued
TMWPKQTEANEQVCLYALGESIESIRQKCPVDDADASSPPKTVPCLCRYA

MTPERVTRLRMNHVTSIIVCSSFPLPKYKIEGVQKVKCSKVMLFDHNVPS

RVSPREYRSSQESAQEASTITSLTHSQFDLSVDGEILPVPSDLDADAPAL

EPALDDGATHTLPSTTGNLAAVSDWVMSTVPVAPPRRRRGRNLTVTCDER

EGNITPMASVRFFRAELCPVVQETAETRDTAMSLQAPPSTATEPNHPPIS

FGASSETFPITFGDFNEGEIESLSSELLTFGDFLPGEVDDLTDSDWSTCS

DTDDELXLDRAGGYIFSSDTGPGHLQQKSVRQSVLPVNTLEEVHEEKCYP

PKLDEAKEQLLLKKLQESASMANRSRYQSRKVENMKAAIIQRLKRGCRLY

LMSETPKVPTYRTTYPAPVYSPPINVRLSNPESAVAACNEFLARNYPTVS

SYQITDEYDAYLDMVDGSESCLDRATFNPSKLRSYPKQHAYHAPSIRSAV

PSPFQNTLQNVLAAATKRNCNVTQMRELPTLDSAVFNVECFKKFACNQEY

WEEFAASPIRITTENLATYVTKLKGPKAAALFAKTHNLLPLQEVPMDRFT

VDMKRDVKVTPGTKHTEERPKVQVIQAAEPLATAYLCGIHRELVRRLNAV

LLPNVHTLFDMSAEDFDAIIAAHFKPGDTVLETDIASFDKSQDDSLALTA

LMLLEDLGVDHSLLDLIEAAFGEISSCHLPTGTRFKFGAMMKSGMFLTLF

VNTLLNITIASRVLEDRLTKSACAAFIGDDNIIHGVVSDELMAARGATWM

NMEVKIIDAVVSLKAPYFCGGFILHDTVTGTACRVADPLKRLFKLGKPLA

AGDEQDEDRRRALADEVIRWQRTGLIDELEKAVYSRYEVQGISVVVMSMA

TFASSRSNFEKLRGPVITLYGGPK
```

The modifications made to the nucleotide sequence of said infectious RNA virus or clone may not comprise any non-synonymous substitution (more particularly any non-synonymous substitution in the coding region of said infectious virus or clone) other than said replacement of polymerase coding sequence (i.e., other than said RNA-dependent DNA polymerase coding sequence or RNA-dependent RNA polymerase coding sequence, respectively).

In accordance with the application, said "1-to-Stop" (synonymous and/or non-synonymous, more particularly synonymous) codon(s) mutates into a STOP codon after one or several replication cycle(s) of said modified virus or modified cDNA clone.

Hence, the nucleotide sequence of the modified virus or modified clone of the application mutates during viral replication: the proportion of STOP codons generated by said nucleotide mutation(s) is higher than the one observed in said infectious RNA virus or infectious clone at the same number of replication cycles.

Indeed, the modified virus or clone of the application is a (live) virus or clone, which is attenuated or which is susceptible to (further) attenuation, e.g., a virus or clone, which is programmed to (further) attenuate in vivo. Indeed, it is (i.e., it has been made) hyper-sensitive to nucleotide mutation(s), more particularly to lethal or detrimental mutation(s).

Said (attenuating or further attenuating) mutation(s), i.e., the mutation(s) of ("1-to-Stop" codon(s)) into STOP codon(s), may occur in vivo, i.e., after the modified virus or clone has been administered (e.g., injected) to a host organism (e.g., to a host non-human animal or a host human, which has to be vaccinated against said infectious RNA virus).

Complementarily or alternatively, said (attenuating or further attenuating) mutation(s) may occur in vitro, e.g., in an in vitro culture medium, which contains at least one mutagenic agent or mutagenic condition, and in the presence of which the modified virus or clone is grown, e.g., for culture passage(s).

Indeed, to increase the mutation rate(s) or the extent of mutation(s), more particularly to increase the number of ("1-to-Stop") codons mutating into STOP codons, the modified virus or clone of the application may be (in vitro) contacted with at least one mutagenic agent or compound, or may be (in vitro) placed under mutagenic conditions.

Examples of said at least one mutagenic agent or compound notably comprise:
Ribavirin IUPAC 1-[(2R,3R,4S,5R)-3,4-dihydroxy-5-(hydroxy-methyl)oxolan-2-yl]-1H-1,2,4-triazole-3-carboxamide),
Favipiravir, also known as T-705 or Avigan, IUPAC 5-Fluoro-2-oxo-1H-pyrazine-3-carboxamide,
5-Fluorouracil IUPAC 5-fluoro-1H-pyrimidine-2,4-dione,
5-Azacitidine IUPAC 4-amino-1-b-D-ribofuranosyl-1,3,5-tria-zin-2(1H)-one, or
Amiloride IUPAC 3,5-diamino-6-chloro-N-(diaminomethylene) pyrazine-2-carboxamide,
a pyrazinecarboximide compound which shows anti-viral activity (more particularly anti-viral activity against one or several Flaviviruses and/or Aphtoviruses and/or Enteroviruses, more particularly against one or several Yellow fever virus and/Foot-and-mounth disease viruses and/or Influenza viruses, more particularly against one or several Influenza viruses), such as Favipiravir (6-fluoro-3-hydroxy-2-pyrazinecarboxamide; cf. Furuta et al. 2009).

Examples of mutagenic conditions notably comprise an increase of the cell culture temperature (e.g., from 37° C. to 39° C.) and/or the alteration of intracellular nucleotides pools (e.g., a nucleotide imbalance, wherein the nucleotides U (or T) and/or A and/or G are in excess compared to the nucleotide C).

Said at least one mutagenic agent may e.g., be contacted with the modified virus or clone of the application during passage in an in vitro cell culture medium, more particularly, an in vitro cell culture medium, which contains cells on which said (modified) virus or clone can be passaged for growth. Said at least one mutagenic agent may then be comprised in said in vitro cell culture medium, advantageously at a concentration which is the virus IC50 inhibitory concentration and/or at a concentration which is not toxic to the cells of the culture medium (more particularly at a concentration which is not toxic to said cells for a period of 72 hours), more particularly at a concentration which is (or is the closest to) the virus IC50 inhibitory concentration without being toxic to the cells of the culture medium for a period of 72 hours.

Said cell is a cell sensitive to infection by said modified virus or clone, for example an animal cell, more particularly a human cell, a non-human mammalian cell, a bird cell, an insect cell.

Said human cell may e.g., be a cell from a human cell line, such as the HeLa cell line [ATCC® CCL-2™]. Said non-human mammalian cell may e.g., be a horse cell, a cattle cell (more particularly a cow cell), a pig cell (more particularly a *Sus domesticus* cell), a monkey cell (more particularly a grivet cell, a rhesus macaque cell or a crab-eating macaque cell, such as the VERO cell line [ATCC® CCL-81TM]) or a rodent cell (more particularly a mouse cell). Said bird cell may e.g., be a poultry cell, more particularly a fowl cell, more particularly a Galliformes cell or an Anseriformes cell, more particularly a Galliformes cell, more particularly a turkey cell, a grouse cell or a chicken cell, more particularly a chicken cell. Said insect cell may e.g., be a mosquito cell, more particularly an *Aedes* sp. or *Anopheles* sp. cell.

Said in vitro culture medium is an in vitro culture medium, which is suitable for the growth of the cells it contains. It may e.g., be an in vitro culture medium, which comprises amino acids, vitamins, inorganic salts and carbon source(s).

Said amino acids may comprise several (more particularly all of the) amino acids selected from the group consisting of Glycine, L-Alanyl-L-Glutamine, L-Arginine hydrochloride, L-Cystine 2HCl, L-Histidine hydrochloride-H2O, L-Isoleucine, L-Leucine, L-Lysine hydrochloride, L-Methionine, L-Phenylalanine, L-Serine, L-Threonine, L-Tryptophan, L-Tyrosine and L-Valine.

Said vitamins may comprise several (more particularly all of the) vitamins selected from the group consisting of choline chloride, D-calcium pantothenate, folic acid, niacinamide, pyridoxine hydrochloride, riboflavin, thiamine hydrochloride and i-inositol.

Said inorganic salts may comprise several (more particularly all of the) inorganic salts selected from the group consisting of calcium chloride (CaCl2-2H2O), ferric nitrate (Fe(NO3)3"9H2O), magnesium sulfate (MgSO4-7H2O), potassium chloride (KCl), sodium bicarbonate (NaHCO3), sodium chloride (NaCl) and sodium phosphate monobasic (NaH2PO4-2H2O).

Said carbon source(s) may comprise one or several of the carbon sources selected from the group consisting of glucose (e.g., D-glucose) and pyruvate (e.g., sodium pyruvate). More particularly, said carbon source(s) may comprise glucose and pyruvate, more particularly D-glucose and sodium pyruvate.

Said in vitro culture medium may e.g., be an in vitro culture medium, such as a Dulbecco's Modified Eagle Medium (DMEM), which contains D-glucose at 4.5 g/l and sodium pyruvate at 110 mg/l, for example the GlutaMAX™ DMEM (SIGMA-ALDRICH Product #31966047).

After said (in vitro) contact with said at least one mutagenic agent, the modified virus or clone of the application is still alive, i.e., it is (further) attenuated but is not killed or inactivated.

The application relates to the modified virus or clone as such.

Said modified virus is a RNA virus. Said modified clone is a RNA, DNA or cDNA clone, more particularly a DNA or cDNA clone, more particularly a cDNA clone. The modified (RNA) virus of the application may be the RNA transcript of a (DNA or) cDNA clone of the application, e.g., the RNA viral transcript, which is obtainable by transcription of a (DNA or) cDNA clone of the application using a DNA-dependent RNA polymerase (such as the T7 RNA polymerase, e.g., from FERMENTAS).

Said modified virus or clone advantageously is an attenuated virus or clone, more particularly a live and attenuated virus or clone.

The modified virus or clone is obtainable by the process of the application, more particularly by the genetic modifications described in the application.

The features described in relation to the process of the application apply to the modified virus or clone mutatis mutandis.

More particularly, the application relates to a modified virus or clone, more particularly to a live and attenuated RNA virus, which is a Coxsackie virus or clone, more particularly a Coxsackie virus or clone of subtype A2, B or A1, more particularly of subtype A1, B1, B2, B3, B4, B5, B6 or A1, more particularly of subtype A1 or B, more particularly of subtype A1, B1, B2, B3, B4, B5 or B6, more particularly of subtype B1, B2, B3, B4, B5 or B6, more particularly a Coxsackie virus B3 or clone.

More particularly, the application relates to a modified virus or clone, more particularly to a live and attenuated RNA virus, which is an Influenza virus or clone, more particularly an Influenza A virus or clone, more particularly an Influenza A subtype H1N1 virus or clone.

More particularly, the application relates to a modified virus or clone, more particularly to a live and attenuated RNA virus, which is a Chikungunya virus or clone or a O'Nyong-Nyong virus or clone, more particularly a Chikungunya virus or clone.

The proportion of codons that are TTA, TTG, TCA, TCG, CGA or GGA codons in the coding sequence of said (modified or) live and attenuated Coxsackie virus of the application, or the proportion of codons that are UUA, UUG, UCA, UCG, CGA or GGA codons in the live and attenuated Coxsackie virus clone of the application, may e.g., be 2-30%, 2-25%, 2-20%, 2-15%, 2-10%, 3-30%, 3-25%, 3-20%, 3-15% or 3-10% higher than the proportion of codons that are TTA, TTG, TCA, TCG, CGA or GGA codons in a (wild-type) infectious Coxsackie virus, more particularly 2-30%, 2-25%, 2-20%, 2-15%, 2-10%, 3-30%, 3-25%, 3-20%, 3-15% or 3-10% higher than the proportion of codons that are TTA, TTG, TCA, TCG, CGA and GGA codons in the sequence of SEQ ID NO: 2 (the sequence of SEQ ID NO: 2 is the wild-type cDNA CDS sequence of an infectious Coxsackie virus).

The expression "proportion of codons in a coding sequence" is intended in accordance with its ordinary meaning in the filed. For example, the proportion of codons that are TTA, TTG, TCA, TCG, CGA or GGA codons in a coding sequence is the ratio of the total number of TTA, TTG, TCA, TCG, CGA and GGA codons in said coding sequence to the total number of codons in said coding sequence, this ratio being multiplied by 100 to express it as a percentage.

More particularly, the proportion of codons that are TTA or TTG codons in the coding sequence of said (modified or) live and attenuated Coxsackie virus of the application, or the proportion of codons that are UUA or UUG codons in the live and attenuated Coxsackie virus clone of the application, may e.g., be 2-30%, 2-25%, 2-20%, 2-15%, 2-10%, 3-30%, 3-25%, 3-20%, 3-15% or 3-10% higher than the proportion of codons that are TTA or TTG codons in a (wild-type) infectious Coxsackie virus, more particularly 2-30%, 2-25%, 2-20%, 2-15%, 2-10%, 3-30%, 3-25%, 3-20%, 3-15% or 3-10% higher than the proportion of codons that are TTA or TTG, codons in the sequence of SEQ ID NO: 2.

More particularly, the proportion of codons that are TCA or TCG, codons in the coding sequence of said (modified or) live and attenuated Coxsackie virus of the application, or the proportion of codons that are UCA or UCG codons in the live and attenuated Coxsackie virus clone of the application, may e.g., be 2-30%, 2-25%, 2-20%, 2-15%, 2-10%, 3-30%, 3-25%, 3-20%, 3-15% or 3-10% higher than the proportion of codons that are TCA or TCG codons in a (wild-type) infectious Coxsackie virus, more particularly 2-30%, 2-25%, 2-20%, 2-15%, 2-10%, 3-30%, 3-25%, 3-20%, 3-15% or 3-10% higher than the proportion of codons that are TCA or TCG codons in the sequence of SEQ ID NO: 2.

More particularly, the proportion of codons that are CGA codons in the coding sequence of said (modified or) live and attenuated Coxsackie virus of the application, or in the live and attenuated Coxsackie virus clone of the application, may e.g., be 2-30%, 2-25%, 2-20%, 2-15%, 2-10%, 3-30%, 3-25%, 3-20%, 3-15% or 3-10% higher than the proportion of codons that are CGA codons in a (wild-type) infectious Coxsackie virus, more particularly 2-30%, 2-25%, 2-20%, 2-15%, 2-10%, 3-30%, 3-25%, 3-20%, 3-15% or 3-10% higher than the proportion of codons that are CGA codons in the sequence of SEQ ID NO: 2 (the sequence of SEQ ID NO: 2 is the wild-type cDNA CDS sequence of an infectious Coxsackie virus).

More particularly, the proportion of codons that are GGA codons in the coding sequence of said (modified or) live and attenuated Coxsackie virus of the application, or in the live and attenuated Coxsackie virus clone of the application, may e.g., be 2-30%, 2-25%, 2-20%, 2-15%, 2-10%, 3-30%, 3-25%, 3-20%, 3-15% or 3-10% higher than the proportion of codons that are GGA codons in a (wild-type) infectious Coxsackie virus, more particularly 2-10% higher than the proportion of codons that are GGA codons in the sequence of SEQ ID NO: 2 (the sequence of SEQ ID NO: 2 is the wild-type cDNA CDS sequence of an infectious Coxsackie virus).

The same feature(s) applies(apply) to Chikungunya virus, O'Nyong-Nyong virus and Influenza virus, mutatis mutandis.

The RNA genome of wild-type Chikungunya virus typically consists of 11,600-12,100 nucleotides, e.g., 11,605-12,005 nucleotides, e.g., 11,805 nucleotides.

Examples of cDNA sequence of wild-type Chikungunya virus comprise the CDS of the sequence GENBANK AM258994 (CDS extending from position 26 to position 7450; SEQ ID NO: 93).

```
SEQ ID NO: 93 is:
                                       atgga tcctgtgtac gtggacatag acgctgacag
   61 cgcctttttg aaggccctgc aacgtgcgta ccccatgttt gaggtggaac caaggcaggt
  121 cacaccgaat gaccatgcta atgctagagc gttctcgcat ctagctataa aactaataga
  181 gcaggaaatt gaccccgact caaccatcct ggatatcggc agtgcgccag caaggaggat
  241 gatgtcggac aggaagtacc actgcgtctg cccgatgcgc agtgcggaag atcccgagag
  301 actcgccaat tatgcgagaa agctagcatc tgccgcagga aaagtcctgg acagaaacat
  361 ctctggaaag atcggggact acaagcagt aatggccgtg ccagacacgg agacgccaac
  421 attctgctta cacacagacg tctcatgtag acagagagca gacgtcgcta tataccaaga
  481 cgtctatgct gtacacgcac ccacgtcgct ataccaccag gcgattaaag gggtccgagt
  541 ggcgtactgg gttgggttcg acacaacccc gttcatgtac aatgccatgg cgggtgccta
  601 cccctcatac tcgacaaaact gggcagatga gcaggactg aaggctaaga cataggatt
  661 atgttcaaca gacctgacgg aaggtagacg aggcaagttg tctattatga gagggaaaaa
  721 gctaaaaccg tgcgaccgtg tgctgttctc agtagggtca acgctctacc cggaaagccg
  781 caagctactt aagagctggc acctgccatc ggtgttccat ttaaagggca aactcagctt
  841 cacatgccgc tgtgatacag tggtttcgtg tgagggctac gtcgttaaga gaataacgat
  901 gagcccaggc ctttatggaa aaaccacagg gtatgcggta acccaccacg cagacggatt
  961 cctgatgtgc aagactaccg acacggttga cggcgaaaga gtgtcattct cggtgtgcac
 1021 atacgtgccg gcgaccattt gtgatcaaat gaccggcatc cttgctacag aagtcacgcc
 1081 ggaggatgca cagaagctgt tggtggggct gaaccagaga atagtggtta acggcagaac
 1141 gcaacggaat acgaacacca tgaaaaatta tctgcttccc gtggtcgccc aagccttcag
 1201 taagtgggca aaggagtgcc ggaaagacat ggaagatgaa aaactcctgg gggtcagaga
 1261 aagaacactg acctgctgct gtctatgggc attcaagaag cagaaaacac acacggtcta
 1321 caagagacct gatacccagt caattcagaa ggttcaggcc gagtttgaca gctttgtggt
 1381 accgagtctg tggtcgtccg ggttgtcaat ccctttgagg actagaatca aatggttgtt
 1441 aagcaaggtg ccaaaaaccg acctgatccc atacagcgga gacgcccgag aagcccggga
 1501 cgcagaaaaa gaagcagagg aagaacgaga agcagaactg actcgcgaag ccctaccacc
 1561 tctacaggca gcacaggaag atgttcaggt cgaaatcgac gtggaacagc ttgaggacag
 1621 agcgggcgca ggaataatag agactccgag aggagctatc aaagttactg cccaaccaac
 1681 agaccacgtc gtgggagagt acctggtact ctccccgcag accgtactac gtagccagaa
 1741 gctcagtctg attcacgctt tggcggagca agtgaagacg tgcacgcaca acggacgagc
 1801 agggaggtat gcggtcgaag cgtacgacgg ccgagtccta gtgccctcag gctatgcaat
```

-continued

```
1861 ctcgcctgaa gacttccaga gtctaagcga aagcgcaacg atggtgtata acgaaagaga
1921 gttcgtaaac agaaagctac accatattgc gatgcacgga ccagccctga acaccgacga
1981 agagtcgtat gagctggtga gggcagagag gacagaacac gagtacgtct acgacgtgga
2041 tcagagaaga tgctgtaaga aggaagaagc cgcaggactg gtactggtgg gcgacttgac
2101 taatccgccc taccacgaat tcgcatatga agggctaaaa atccgccctg cctgcccata
2161 caaaattgca gtcataggag tcttcggagt accgggatct ggcaagtcag ctattatcaa
2221 gaacctagtt accaggcagg acctggtgac tagcggaaag aaagaaaact gccaagaaat
2281 caccaccgac gtgatgagac agagaggtct agagatatct gcacgtacgg ttgactcgct
2341 gctcttgaat ggatgcaaca gaccagtcga cgtgttgtac gtagacgagg cgtttgcgtg
2401 ccactctgga acgctacttg ctttgatcgc cttggtgaga ccaaggcaga aagttgtact
2461 ttgtggtgac ccgaagcagt gcggcttctt caatatgatg cagatgaaag tcaactataa
2521 tcacaacatc tgcacccaag tgtaccacaa aagtatctcc aggcggtgta cactgcctgt
2581 gaccgccatt gtgtcatcgt tgcattacga aggcaaaatg cgcactacga atgagtacaa
2641 caagccgatt gtagtggaca ctacaggctc aacaaaacct gaccctggag acctcgtgtt
2701 aacgtgcttc agagggtggg ttaaacaact gcaaattgac tatcgtggat acgaggtcat
2761 gacagcagcc gcatcccaag ggttaaccag aaaaggagtt tacgcagtta gacaaaaagt
2821 taatgaaaac ccgctctatg catcaacgtc agagcacgtc aacgtactcc taacgcgtac
2881 ggaaggtaaa ctggtatgga agacactttc cggcgacccg tggataaaga cgctgcagaa
2941 cccaccgaaa ggaaacttca aagcaactat taaggagtgg gaggtggagc atgcatcaat
3001 aatggcgggc atctgcagtc accaaatgac cttcgataca ttccaaaata aagccaacgt
3061 ttgttgggct aagagcttgg tccctatcct cgaaacagcg gggataaaac taatgatag
3121 gcagtggtct cagataattc aagccttcaa agaagacaaa gcatactcac ctgaagtagc
3181 cctgaatgaa atatgtacgc gcatgtatgg ggtggatcta gacagcgggc tatttttctaa
3241 accgttggtg tctgtgtatt acgcggataa ccactgggat aataggcctg gagggaaaat
3301 gttcggattt aaccccgagg cagcatccat tctagaaaga aagtatccat tcacaaaagg
3361 gaagtggaac atcaacaagc agatctgcgt gactaccagg aggatagaag actttaaccc
3421 taccaccaac atcataccgg ccaacaggag actaccacac tcattagtgg ccgaacaccg
3481 cccagtaaaa ggggaaagaa tggaatggct ggttaacaag ataaacggcc accacgtgct
3541 cctggtcagt ggctataacc ttgcactgcc tactaagaga gtcacttggg tagcgccgtt
3601 aggtgtccgc ggagcggact acacatacaa cctagagttg ggtctgccag caacgcttgg
3661 taggtatgac ctagtggtca taaacatcca cacaccttt cgcatacacc attaccaaca
3721 gtgcgtcgac cacgcaatga aactgcaaat gctcggggt gactcattga gactgctcaa
3781 accgggcggc tctctattga tcagagcata tggttacgca gatagaacca gtgaacgagt
3841 catctgcgta ttgggacgca gtttagatc gtctagagcg ttgaaaccac catgtgtcac
3901 cagcaaacact gagatgtttt tcctattcag caactttgac aatggcagaa ggaatttcac
3961 aactcatgtc atgaacaatc aactgaatgc agccttcgta ggacaggtca cccgagcagg
4021 atgtgcaccg tcgtacccggg taaaacgcat ggacatcgcg aagaacgatg aagagtgcgt
4081 agtcaacgcc gctaaccctc gcgggttacc gggtgacggt gtttgcaagg cagtatacaa
4141 aaaatggccg gagtccttta agaacagtgc aaccacagtg ggaaccgcaa aaacagttat
4201 gtgcggtacg tatccagtaa tccacgctgt ggaccaaaac ttctctaatt attcggagtc
4261 tgaaggggac cgggaattgg cagctgccta tcgagaagtc gcaaaggaag taactaggct
```

-continued

```
4321 gggagtaaat agtgtagcta tacctctcct ctccacaggt gtatactcag gagggaaaga
4381 caggctgacc cagtcactga accacctctt tacagccatg gactcgacgg atgcagacgt
4441 ggtcatctac tgccgcgaca aagaatggga gaagaaaata tctgaggcca tacagatgcg
4501 gacccaagta gagctgctgg atgagcacat ctccatagac tgcgatattg ttcgcgtgca
4561 ccctgacagc agcttggcag gcagaaaagg atacagcacc acggaaggcg cactgtactc
4621 atatctagaa gggacccgtt ttcatcagac ggctgtggat atggcggaga tacatactat
4681 gtggccaaag caaacagagg ccaatgagca agtctgccta tatgccctgg gggaaagtat
4741 tgaatcgatc aggcagaaat gcccggtgga tgatgcagac gcatcatctc cccccaaaac
4801 tgtcccgtgc ctttgccgtt acgctatgac tccagaacgc gtcacccggc ttcgcatgaa
4861 ccacgtcaca agcataattg tgtgttcttc gtttcccctc ccaaagtaca aaatagaagg
4921 agtgcaaaaa gtcaaatgct ctaaggtaat gctatttgac cacaacgtgc catcgcgcgt
4981 aagtccaagg gaatatagat cttcccagga gtctgcacag gaggcgagta caatcacgtc
5041 actgacgcat agtcaattcg acctaagcgt tgatggcgag atactgcccg tcccgtcaga
5101 cctggatgct gacgcccag ccctagaacc agcactagac gacggggcga cacacacgct
5161 gccatccaca accggaaacc ttgcggccgt gtctgattgg gtaatgagca ccgtacctgt
5221 cgcgccgccc agaagaaggc gagggagaaa cctgactgtg acatgtgacg agagagaagg
5281 gaatataaca cccatggcta gcgtccgatt ctttagggca gagctgtgtc cggtcgtaca
5341 agaaacagcg gagacgcgtg acacagcaat gtctcttcag gcaccaccga gtaccgccac
5401 ggaaccgaat catccgccga tctccttcgg agcatcaagc gagacgttcc ccattacatt
5461 tggggacttc aacgaaggag aaatcgaaag cttgtcttct gagctactaa ctttcggaga
5521 cttcttacca ggagaagtgg atgacttgac agacagcgac tggtccacgt gctcagacac
5581 ggacgacgag ttatgactag acagggcagg tgggtatata ttctcgtcgg acaccggtcc
5641 aggtcattta caacagaagt cagtacgcca gtcagtgctg ccggtgaaca ccctggagga
5701 agtccacgag gagaagtgtt acccacctaa gctggatgaa gcaaaggagc aactattact
5761 taagaaactc caggagagtg catccatggc caacagaagc aggtatcagt cgcgcaaagt
5821 agaaaacatg aaagcagcaa tcatccagag actaaagaga ggctgtagac tatacttaat
5881 gtcagagacc ccaaaagtcc ctacttaccg gactacatat ccggcgcctg tgtactcgcc
5941 tccgatcaac gtccgattgt ccaatcccga gtccgcagtg cagcatgca atgagttctt
6001 agctagaaac tatccaactg tctcatcata ccaaattacc gacgagtatg atgcatatct
6061 agacatggtg gacgggtcgg agagttgcct ggaccgagcg acattcaatc cgtcaaaact
6121 caggagctac ccgaaacagc acgcttacca cgcgccctcc atcagaagcg ctgtaccgtc
6181 cccattccag aacacactac agaatgtact ggcagcagcc acgaaaagaa actgcaacgt
6241 cacacagatg agggaattac ccactttgga ctcagcagta ttcaacgtgg agtgtttcaa
6301 aaaattcgca tgcaaccaag aatactggga agaatttgct gccagcccta ttaggataac
6361 aactgagaat ttagcaacct atgttactaa actaaaaggg ccaaaagcag cagcgctatt
6421 cgcaaaaacc cataatctac tgccactaca ggaagtacca atggataggt tcacagtaga
6481 tatgaaaagg gacgtaaagg tgactcctgg tacaaagcat acagaggaaa gacctaaggt
6541 gcaggttata caggcggctg aaccccttgg cacagcatac ctatgtggga ttcacagaga
6601 gctggttagg aggctgaacg ccgtcctcct acccaatgta catacactat ttgacatgtc
6661 tgccgaggat ttcgatgcca tcatagccgc acactttaag ccaggagaca ctgttttgga
```

-continued

```
6721 aacggacata gcctcctttg ataagagcca agatgattca cttgcgctta ctgctttgat 6781 gctgttagag gatttagggg tggatcactc cctgctggac ttgatagagg ctgctttcgg 6841 agagatttcc agctgtcacc taccgacagg tacgcgcttc aagttcggcg ccatgatgaa 6901 atcaggtatg ttcctaactc tgttcgtcaa cacattgtta aacatcacca tcgccagccg 6961 agtgctggaa gatcgtctga caaaatccgc gtgcgcggcc ttcatcggcg acgacaacat 7021 aatacatgga gtcgtctccg atgaattgat ggcagccaga tgtgccactt ggatgaacat 7081 ggaagtgaag atcatagatg cagttgtatc cttgaaagcc ccttactttt gtggagggtt 7141 tatactgcac gatactgtga caggaacagc ttgcagagtg gcagaccccgc taaaaaggct 7201 ttttaaactg ggcaaaccgc tagcggcagg tgacgaacaa gatgaagata aagacgagc 7261 gctggctgac gaagtgatca gatggcaacg aacagggcta attgatgagc tggagaaagc 7321 ggtatactct aggtacgaag tgcagggtat atcagttgtg gtaatgtcca tggccacctt 7381 tgcaagctcc agatccaact tcgagaagct cagaggaccc gtcataactt tgtacggcgg 7441 tcctaaatag
```

Examples of cDNA sequence of wild-type O'Nyong-Nyong virus comprise the CDS of the sequence GENBANK M20303.1 (CDS extending from position 80 to position 7624 GENBANK M20303.1; SEQ ID NO: 94).

```
SEQ ID NO: 94 is:
                           a tggattcagt gtatgtagac atagatgctg acagcgcgtt
 121 tctgaaggcg ttgcagcaag catacccccat gtttgaggtg gaaccaaagc aggtcacgcc 181 aaatgaccat gcaaacgcta gagcattttc gcatctagca ataaaactga tagagcagga 241 aattgatcca gactcaacca ttctagacat tggtagcgca ccagctagga ggatgatgtc 301 tgatagaaaa taccactgcg tctgcccgat gcgcagcgca aagaccctg agaggctcgc 361 gaattacgcg agaaaacttg cgtcagccgc tggaaaggtg acagataaaa acatctccgg 421 aaaaattaat gatctacaag ctgtgatggc cgtaccgaat atggaaacat ccacattctg 481 cctacacact gatgctacat gcaaacaaag aggagacgtc gccatttatc aagacgtcta 541 cgccgtccat gcacctacct cgctgtacca tcaggcgatt aaaggagtcc gcgtggcata 601 ctggataggg ttcgatacga cacctttcat gtacaatgca atggctggcg catacccatc 661 atattcaaca aactgggctg atgagcaggt actgaaagct aagaacatag gctgtgttc 721 aacagaccta tctgagggta gacgaggcaa actatccatc atgagaggca aaaaattgaa 781 gccatgcgac cgagtgctat tctcggtcgg ctcaacactc taccctgaaa gtcgtaaact 841 tctacaaagc tggcatttac catcggtatt tcatctgaag ggtaaactca gcttcacctg 901 ccgctgtgac acgatcgtct catgcgaagg atacgttgtc aagagagtga ccatgagtcc 961 aggcatctac ggaaagacat cggggtatgc tgtaactcat catgccggcg gcttcctgat 1021 gtgcaagacg acagatacag tagacggcga aagggtatca ttctccgtgt gtacttacgt 1081 accagctact atctgcgacc agatgactgg aatccttgcc actgaggtaa ccccagaaga 1141 cgcacagaaa ctactggttg ggctaaacca acggatagtg gtcaatggca ggacgcaacg 1201 taatacaaac accatgaaaa actacctgct cccaatagtt gctcaggcct tcagcaagtg 1261 ggccaaagaa tgtcgaaagg acatggagga cgaaaaactc ttgggtgtcc gagagaggac 1321 cttaacgtgc tgttgcctat gggcatttag aaagcacaag acgcatacgg tgtacaaaag 1381 accggatacc cagtcaatcc aaaaggtccc tgccgaattt gacagctttg tgataccaag 1441 tctgtggtcg tcaggtttat caattccgct gagaaccaga atcaagtggc tcttgagcaa 1501 agctccaaaa tacgagcaac taccgcacag cggaaacgcc gaggaagcag cccaggctga
```

-continued

```
1561 aacagatgcg gtagaagaac aggaggcaga gctaacccga gaagctatgc caccattgca 1621 ggcgacacag gatgacattc aggtagaaat tgatgtagag caacttgaag accgagcagg 1681 agcgggcata gtcgaaacac caagaggagc aatcaaagtc acagcccaac cgtcagacct 1741 tgttgtcgga gagtacttag tactgacacc gcaggcggtc ctgcgcagcc aaaaactcag 1801 tctgattcac gcgcttgcag agcaggtaaa aacgtgcaca catagtgggc gagcaggcag 1861 gtacgcggtt gaagcatacg atgggcgtgt tctagtgccc tcgggctacg cgataccccca 1921 ggaagacttc cagagcttaa gcgaaagtgc caccatggta tttaacgagc gagagtttgt 1981 gaaccggaag ttacaccaca tcgccatgca cggcccagcg ctgaacactg atgaagagtc 2041 atatgaactg gtaagggtag agaaaacaga acacgagtac gtctatgacg ttgatcagaa 2101 gaaatgttgt aagagggagg aagcaacagg actagtgcta gtaggcgact taactagccc 2161 accataccat gagttcgcct acgaaggact aaaaatccgc ccagcatgtc catacaaaac 2221 ggcagttata ggtgtcttcg gagtaccggg ttctggcaag tcggctataa tcaaaaacct 2281 ggtaaccagg caagacttgg tgactagtgg aaaaaaagaa aactgccaag aaatctccaa 2341 tgacgtaatg cggcaaagga aattggagat atctgcacgt acagtcgact cactactcct 2401 gaatggatgt aacaagccag tggaagtact gtacgtggac gaggcattcg cttgtcattc 2461 gggaaccctg ttggcactga tagccatggt tagaccgcgt cagaaggtcg tactttgtgg 2521 cgacccaaag cagtgcggat tcttcaatat gatgcaaatg aaggtcaact ataatcacaa 2581 catctgcaca caggtgtacc ataaaagcat atcaaggcgg tgtacactgc ctgtaacagc 2641 catcgtgtcc tcgttgcatt acgagagcaa gatgcgcact acaaatgagt acaaccagcc 2701 aatcgtagtg gatactacgg gcataacaaa accagaaccc ggggacttag tgttaacgtg 2761 tttccgggga tgggttaagc agctgcaaat agactaccgt ggaaacgaag tcatgacagc 2821 agctgcttct caggggctga ccagaaaagg tgtttatgca gtaaggcaga aagtcaacga 2881 aaaccctctg tatgcaccaa catcagaaca cgttaacgtg ctattgacac gcacagaggg 2941 caagttgaca tggaagacac tctcaggcga cccatggata aagatactgc agaacccccc 3001 aaaagggac tttaaggcaa caatcaagga gtgggaagca gaacacgcct ccatcatggc 3061 aggaatatgc aatcaccaga tggcttttga cacatttcag aacaaagcta atgtatgctg 3121 ggctaaatgc ctggtcccta ttcttgacac tgctggaatc aaattaagtg acaggcagtg 3181 gtctcagata gtgcaagctt ttaaagaaga tagggcctac tctccagaag ttgcactgaa 3241 tgaaatatgc actcgcatat atgggtaga cctggacagc ggactattct caaagccact 3301 gatatccgtc tactatgcag acaaccactg ggacaataga ccaggaggaa aaatgttcgg 3361 gttcaacccct gaggtggcac ttatgcttga aagaaatat cccttttacaa aaggtaagtg 3421 gaacattaac aagcagatat gtataactac cagaaaggtt gacgaattta ccccgaaaac 3481 caacataata ccggccaacc gcagactgcc gcactcactc gtggctgaac accactcagt 3541 gagagggggaa agaatggaat ggctggtaaa caaaatcagc ggtcaccaca tgttgttggt 3601 tagcggtcat aatctttatat taccaacaaa aagagtcacc tgggtagcac cgttaggcac 3661 ccgaggtgca gactacacat ataacctgga acttggtcta ccagccacac taggcagata 3721 tgacctggta gttatcaata tccatactcc attccgcata catcattacc agcagtgtgt 3781 agatcacgca atgaagctcc agatgctagg ggggactct ctacggctgt taaagccggg 3841 aggttcactt ctgattagag cttacgggta cgccgaccga accagtgaaa gggtcattag 3901 cgtattggga cgcaagttca gatcgtccag ggctctgaaa cctcagtgca tcacgagcaa
```

```
3961 tacagaaatg ttcttcctat ttagccgatt cgacaatgga agaaggaact tcaccacaca 4021 tgttatgaac aaccagctga acgcagtgta tgcaggactg gccactagag cgggctgtgc 4081 cccgtcatac cgagtgaaac ggatggacat cgcaaagaac actgaggaat gcgtggtaaa 4141 cgccgccaat ccgcgcggag taccaggcga tggagtatgt aaagccgtgt atagaaaatg 4201 gccagaatca ttcagaaaca gtgcaacacc agtggggact gcaaagacaa tcatgtgcgg 4261 tcaatacccc gtcatccacg cagtaggccc taacttctca aactattctg aggctgaagg 4321 ggatagggaa ttggcttcag tgtatagaga agtggcgaaa gaagtgtcta ggctaggagt 4381 gagcagtgta gccatccctt tgctctcaac cggtgtgtac tcaggaggca agacagact 4441 gctgcaatca ctaaaccatc ttttcgcagc gatggattcg acagatgcag acgttgtcat 4501 ctactgcagg gacaaggaat gggagaagaa gatcactgaa gccatatcac taagatccca 4561 ggtagaatta ctagatgatc acatctcagt ggattgcgac attgtacgcg ttcatccaga 4621 cagcagcttg gcaggccgaa aggggtacag cacagtagag ggagcactct actcgtacct 4681 agagggaaca agattccacc aaactgcagt agatatggca gagatatata ccatgtggcc 4741 gaaacaaact gaagccaacg aacaggtctg cctatatgct ctgggggaga gtatagagtc 4801 cgtcaggcaa aaatgtcccg tagacgacgc cgacgcctca ttccctccga aaacagtccc 4861 gtgcctatgc cgttatgcta tgacgcctga acgagttgca cgtctacgca tgaatcatac 4921 caccagcatc atagtgtgct cgtcttttcc gctgccgaaa tacaaaatcg agggcgtgca 4981 aaaagtaaaa tgttcgaaag cactcttgtt tgatcacaac gtaccgtctc gagtgagccc 5041 gagaacgtac aggcctgcgg acgaaatcat cagacacct caaacaccaa ctgaagcgtg 5101 tcaggacgca caactcgtgc agtcaataaa tgatgaagca gtgccagttc cctcagactt 5161 agaggcttgt gacgcaacta tggactggcc ctctatcggc accgtatcaa caagacaaag 5221 acacgactca tctgacagcg agtatagtgg ctccagaagt aacatacaac tagtgacggc 5281 ggacgtgcat gcaccaatgt acgcacattc gctggcgtcc agcggaggtt caatgctgtc 5341 gctgtccagt gaaccagctc agaacggcac aatgatacta cttgactcag aagacacaga 5401 cagtataagc agagtaagca caccgatcgc cccgcccaga agacgtttgg gaaggaccat 5461 aaatgtgacc tgcgacgagc gggaagggaa aatactccct atggccagcg acaggttctt 5521 cactgctaag ccatacactg tcgcactgag cgtatcaaca gcagatatga ctgtgtatcc 5581 catccaggca ccgctaggat tgataccacc acctaccctc gaaccgatca ctttcggaga 5641 cttcgccgaa ggtgaaatag acaacctcct gacaggggca ttgacatttg ggacttcga 5701 gccaggtgaa gtggaagagc tgacggatag cgagtggtca acgtgctcgg acacagacga 5761 agagttacga ctagacagag caggggtta catattctcc tctgacactg gtcaaggtca 5821 tctacagcaa aaatcagtac gtcaaacgac gctaccggta acattgttg aagaggtcca 5881 cgaagagaaa tgctatccac ctaaattgga tgagatcaaa gagcaactac tacttaagag 5941 acttcaggag agtgcttcca cggctaaccg gagtaggtac caatctagaa aagtggaaaa 6001 catgaaagcc acgattatcc acagactgaa agagggttgc agactctatt ggcgtcaga 6061 aacaccgagg gtcccatctt accgagtcac atacccggcg cccatctact cgccttcaat 6121 caatatcaaa ctgactaacc cagagactgc agtagcagtg tgtaacgagt ttttggccag 6181 aaactatcca actgtggcat cctaccaagt cactgacgag tacgacgcgt acttggatat 6241 ggtagacggg tccgaaagtt gcctagacag agctacattc aacccgtcta aactcaggag 6301 ttacccaaaa caacactctt accacgcacc caccatcaga agtgcagtgc catcaccatt 6361 ccaaaatacg ttgcagaatg tcttggcagc ggccacaaaa agaaactgca acgtaacgca
```

```
-continued
6421 gatgagggaa ctacccacta tggactccgc agtgtttaac gtggagtgtt ttaagaagta 6481 cgcttgcaac caagagtact ggagagagtt cgcctcaagc cctataaggg taacgacaga 6541 gaatctgaca atgtatgtga cgaaactaaa ggggcctaaa gcggcggcac tcttcgcaaa 6601 aacacacaac ttgctgccgc tacaagaggt accgatggac aggttcacaa tggacatgaa 6661 acgtgatgtg aaagtgacac caggtacaaa gcacaccgag gaaaggccga aagtacaggt 6721 catacaggcg gcagaaccac tggcaacagc ataccgtgt ggcatacaca gagagttggt 6781 gagaagacta aatgcagttc tgctaccgaa tgtccacaca ctgttcgata tgtcagccga 6841 agacttcgat gcaattatag ccacccattt caaaccgggc gatgctgtac tagaaactga 6901 catagcctca tttgataaga gtcaagacga ctcgcttgcg tcgaccgcca tgatgttgct 6961 agaagacctt ggggtagatc aacctatcct ggatctgata gaagcagcat tcggcgaaat 7021 atccagttgt catctaccga cgggtacgcg gttcaagttc ggcgcaatga tgaaatcagg 7081 catgttctta accctgtttg tcaatacct cctgaacatc accattgcca gtcgggtgtt 7141 agaggagcga ttgactactt cagcctgtgc agctttcatt ggggacgaca acataataca 7201 tggggttgtc tctgacgcac taatggctgc acgttgtgct acgtggatga acatggaagt 7261 gaaaatcatc gatgcagtag tgtcagagaa ggcgccatac ttctgtgggg gatttatttt 7321 acacgacacg gtgacaggca cgtcgtgcag agtagcagac cctttaaaga gactgttcaa 7381 gctaggcaaa cctctggcag ctggagacga acaggatgag gacagaagac gtgctctggc 7441 agatgaggtt actagatggc aaagaaccgg cttagtcaca gaattggaaa aagcagtata 7501 ttcaaggtat gaagtacaag gaataacagc cgtaataaca tcaatggcta cctttgcgaa 7561 tagcaaagaa aactttaaga aactaagagg gcccgtcgta accttgtacg gcggacctaa 7621 atag
```

The RNA genome of wild-type Influenza virus typically consists of 13,300-13,800 nucleotides, e.g., 13,388-13,788 nucletides, e.g., 13,588 nucleotides.

Examples of cDNA sequence of wild-type Influenza virus comprise the CDS of the RNA genome of strain ATCC® VR-1337™ (Influenza virus type A subtype H1N1), or of an Influenza virus type A subtype H1N1, which comprises:
the PB2 coding sequence is the sequence of SEQ ID NO: 59,
the PB1 coding sequence is the sequence of SEQ ID NO: 62,
the PB1-F2 coding sequence is the sequence of SEQ ID NO: 64,
the NP coding sequence is the sequence of SEQ ID NO: 70,
the NA coding sequence is the sequence of SEQ ID NO: 73,
the M1 coding sequence is the sequence of SEQ ID NO: 76,
the M2 coding sequence is the sequence of SEQ ID NO: 78,
the NS1 coding sequence is the sequence of SEQ ID NO: 81,
the NS2 coding sequence is the sequence of SEQ ID NO: 83,
the PA coding sequence is the sequence of SEQ ID NO: 49 or 51, and
the HA coding sequence is the sequence of SEQ ID NO: 67 (cf. examples 2 and 5 below).

In the (modified or) live and attenuated (RNA) Coxsackie virus of the application, the cDNA version of the sequence coding for Coxsackie virus P1 protein may comprise or consist of the sequence of SEQ ID NO: 14. Similarly, in the (modified or) live and attenuated (DNA or cDNA) clone of Coxsackie virus of the application, the sequence coding for Coxsackie virus P1 protein may comprise or consist of the sequence of SEQ ID NO: 14.

The (modified or) live and attenuated (RNA) Coxsackie virus of the application may advantageously not comprise the (endogenous) Coxsackie virus P1 protein coding sequence of said infectious RNA virus, more particularly may advantageously not comprise the RNA version of the sequence of SEQ ID NO: 4. Similarly, the (modified or) live and attenuated (DNA or cDNA) clone of Coxsackie virus of the application, may advantageously not comprise the DNA or cDNA retrotranscript of the (endogenous) Coxsackie virus P1 protein coding sequence of an infectious RNA virus, more particularly may advantageously not comprise the sequence of SEQ ID NO: 4. The sequence of SEQ ID NO: 4 is the wild-type cDNA P1 coding sequence of an infectious Coxsackie virus. The sequence of SEQ ID NO: 14 is the sequence of SEQ ID NO: 4 modified in accordance with the application by the replacement of a total of 117 Leu and Ser codons by "1-to-Stop" (Leu and Ser) codons. Please see example 1 below.

In the (modified or) live and attenuated (RNA) Coxsackie virus of the application, the cDNA version of the sequence coding for Coxsackie virus polyprotein may advantageously comprise or consist of the sequence of SEQ ID NO: 13 or 12, more particularly of SEQ ID NO: 13. Similarly, in the (modified or) live and attenuated (DNA or cDNA) clone of Coxsackie virus of the application, the sequence coding for Coxsackie virus polyprotein may advantageously comprise or consist of the sequence of SEQ ID NO: 13 or 12, more particularly of SEQ ID NO: 13.

The (modified or) live and attenuated Coxsackie virus of the application may advantageously not comprise the (endogenous) Coxsackie virus polyprotein coding sequence of said infectious RNA virus, more particularly may advantageously not comprise the RNA version of the sequence of SEQ ID NO: 2 or 1, more particularly the RNA version of the sequence of SEQ ID NO: 2. Similarly, the (modified or) live and attenuated (DNA or cDNA) clone of Coxsackie virus of the application, may advantageously not comprise the DNA or cDNA retrotranscript of the (endogenous) Coxsackie virus polyprotein coding sequence of an infectious RNA virus, more particularly may advantageously not comprise the sequence of SEQ ID NO: 2 or 1, more particularly the sequence of SEQ ID NO: 2.

The sequence of SEQ ID NO: 1 is the cDNA sequence of the full-length genome of an infectious Coxsackie virus. The sequence of SEQ ID NO: 2 is the cDNA sequence of the CDS of these infectious Coxsackie virus. The sequence of SEQ ID NO: 12 is the sequence of SEQ ID NO: 1 modified in accordance with the application by the replacement of a total of 117 Leu and Ser codons of the P1 protein by "1-to-Stop" (Leu and Ser synonymous) codons. The sequence of SEQ ID NO: 13 is the sequence of SEQ ID NO: 2 modified in accordance with the application by the replacement of a total of 117 Leu and Ser codons of the P1 protein by "1-to-Stop" (Leu and Ser synonymous) codons. Please see example 1 below.

In the (modified or) live and attenuated (RNA) Coxsackie virus of the application, the cDNA version of the sequence coding for Coxsackie virus P1 protein may comprise or consist of the sequence of SEQ ID NO: 85 (cf. example 6 below). Similarly, in the (modified or) live and attenuated (DNA or cDNA) clone of Coxsackie virus of the application, the sequence coding for Coxsackie virus P1 protein may comprise or consist of the sequence of SEQ ID NO: 85.

The (modified or) live and attenuated (RNA) Coxsackie virus of the application may advantageously not comprise the (endogenous) Coxsackie virus P1 protein coding sequence of said infectious RNA virus, more particularly may advantageously not comprise the RNA version of the sequence of SEQ ID NO: 4. Similarly, the (modified or) live and attenuated (DNA or cDNA) clone of Coxsackie virus of the application, may advantageously not comprise the DNA or cDNA retrotranscript of the (endogenous) Coxsackie virus P1 protein coding sequence of an infectious RNA virus, more particularly may advantageously not comprise the sequence of SEQ ID NO: 4.

In the (modified or) live and attenuated (RNA) Influenza virus of the application, the cDNA version of the sequence coding for Inluenza virus PA protein may comprise or consist of the sequence of SEQ ID NO: 54 or 56. Similarly, in the (modified or) live and attenuated (DNA or cDNA) clone of Influenza virus of the application, the sequence coding for Influenza virus PA protein may comprise or consist of the sequence of SEQ ID NO: 54 or 56.

The (modified or) live and attenuated (RNA) Influenza virus of the application may advantageously not comprise the (endogenous) Influenza virus PA protein coding sequence of said infectious RNA virus, more particularly may advantageously not comprise the RNA version of the sequence of SEQ ID NO: 49 or 51. Similarly, the (modified or) live and attenuated (DNA or cDNA) clone of Influenza virus of the application, may advantageously not comprise the DNA or cDNA retrotranscript of the (endogenous) Influenza virus PA protein coding sequence of an infectious RNA virus, more particularly may advantageously not comprise the sequence of SEQ ID NO: 49 or 51.

The (modified or) live and attenuated (RNA) Influenza virus of the application may comprise the wild-type PB2, PB1, NP, NA, M and NS segments of Influenza, e.g., the PB2 genomic segment of SEQ ID NO: 59, the PB1 genomic segment of SEQ ID NO: 62, the NP genomic segment of SEQ ID NO: 70, the NA genomic segment of SEQ ID NO: 73, the M1 genomic segment of SEQ ID NO: 76, the M2 genomic segment of SEQ ID NO: 78, the NS1 genomic segment of SEQ ID NO: 81 and the NS2 genomic segment of SEQ ID NO: 83.

Please see example 5 below.

The (modified or) live and attenuated (RNA) Influenza virus of the application may comprise the wild-type HA segment (SEQ ID NO: 67) or a mutated HA (such as SEQ ID NO: 87; cf. example 7 below).

In the (modified or) live and attenuated (RNA) Influenza virus of the application, the cDNA version of the sequence coding for Inluenza virus PA protein may comprise or consist of the sequence of SEQ ID NO: 87. Similarly, in the (modified or) live and attenuated (DNA or cDNA) clone of Influenza virus of the application, the sequence coding for Influenza virus PA protein may comprise or consist of the sequence of SEQ ID NO: 87.

The (modified or) live and attenuated (RNA) Influenza virus of the application may advantageously not comprise the (endogenous) Influenza virus PA protein coding sequence of said infectious RNA virus, more particularly may advantageously not comprise the RNA version of the sequence of SEQ ID NO: 67. Similarly, the (modified or) live and attenuated (DNA or cDNA) clone of Influenza virus of the application, may advantageously not comprise the DNA or cDNA retrotranscript of the (endogenous) Influenza virus PA protein coding sequence of an infectious RNA virus, more particularly may advantageously not comprise the sequence of SEQ ID NO: 67. The (modified or) live and attenuated (RNA) Influenza virus of the application may comprise the wild-type PB2, PB1, NP, NA, M and NS segments of Influenza, e.g., the PB2 genomic segment of SEQ ID NO: 59, the PB1 genomic segment of SEQ ID NO: 62, the NP genomic segment of SEQ ID NO: 70, the NA genomic segment of SEQ ID NO: 73, the M1 genomic segment of SEQ ID NO: 76, the M2 genomic segment of SEQ ID NO: 78, the NS1 genomic segment of SEQ ID NO: 81 and the NS2 genomic segment of SEQ ID NO: 83.

Please see example 7 below.

The (modified or) live and attenuated (RNA) Influenza virus of the application may comprise the wild-type PA genomic segment of SEQ ID NO: 49 or 51, or may comprise a mutated PA segment (such as SEQ ID NO: 54 or 56; cf. example 3 below).

In the (modified or) live and attenuated (RNA) Chikungunya virus of the application, the cDNA version of the sequence coding for Chikungunya virus C-E3-E2-6K-E1 polyprotein may comprise or consist of the sequence of SEQ ID NO: 101 (cf. example 8 below). Similarly, in the (modified or) live and attenuated (DNA or cDNA) clone of Chikungunya virus of the application, the sequence coding for Chikungunya virus C-E3-E2-6K-E1 polyprotein may comprise or consist of the sequence of SEQ ID NO: 101. The (modified or) live and attenuated (RNA) Chikungunya virus of the application may advantageously not comprise the (endogenous) Chikungunya virus C-E3-E2-6K-E1 polyprotein coding sequence of said infectious RNA virus, more particularly may advantageously not comprise the RNA version of the sequence of SEQ ID NO: 104. Similarly, the (modified or) live and attenuated (DNA or cDNA) clone of Chikungunya virus of the application, may advantageously not comprise the DNA or cDNA retrotranscript of the (endogenous) Chikungunya virus C-E3-E2-6K-E1 polyprotein coding sequence of an infectious RNA virus, more particularly may advantageously not comprise the sequence of SEQ ID NO: 104.

In the (modified or) live and attenuated (RNA) Chikungunya virus of the application, the cDNA version of the sequence coding for Chikungunya virus C-E3-E2-6K-E1 polyprotein may comprise or consist of the sequence of SEQ ID NO: 102 (cf. example 8 below). Similarly, in the (modified or) live and attenuated (DNA or cDNA) clone of Chikungunya virus of the application, the sequence coding for Chikungunya virus C-E3-E2-6K-E1 polyprotein may comprise or consist of the sequence of SEQ ID NO: 102. The (modified or) live and attenuated (RNA) Chikungunya virus of the application may advantageously not comprise the (endogenous) Chikungunya virus C-E3-E2-6K-E1 polyprotein coding sequence of said infectious RNA virus, more particularly may advantageously not comprise the RNA version of the sequence of SEQ ID NO: 100. Similarly, the (modified or) live and attenuated (DNA or cDNA) clone of Chikungunya virus of the application, may advantageously not comprise the DNA or cDNA retrotranscript of the (endogenous) Chikungunya virus C-E3-E2-6K-E1 polyprotein coding sequence of an infectious RNA virus, more particularly may advantageously not comprise the sequence of SEQ ID NO: 100.

The application relates more particularly to a live and attenuated virus or to a live and attenuated cDNA clone of virus, which is a live and attenuated Coxsackie virus or a live and attenuated cDNA clone thereof, wherein the codons that codes for Leu in the P1 protein of said live and attenuated Coxsackie virus or cDNA clone thereof are all selected from UUA and UUG for said live and attenuated virus, or from TTA and TTG for said live and attenuated cDNA clone, and wherein the codons that codes for Ser in the P1 protein of said live and attenuated Coxsackie virus or cDNA clone thereof are all selected from UCA and UCG for said live and attenuated virus, or from TCA and TCG for said live and attenuated cDNA clone.

For example, the application relates to a live and attenuated Coxsackie virus or to a live and attenuated cDNA clone thereof, wherein the sequence coding for Coxsackie virus P1 protein is or comprises the RNA transcript of the cDNA sequence of SEQ ID NO: 14, or the cDNA sequence of SEQ ID NO: 14, respectively.

Alternatively or complementarily to said Ser and Leu codons, the Arg and Gly codons may be codons that differ by only one nucleotide from a STOP codon (cf. example 6 below). The live and attenuated Coxsackie virus or the live and attenuated cDNA clone thereof may e.g., be a Coxsackie virus or clone, wherein the codons that codes for Arg in the P1 protein of said live and attenuated Coxsackie virus or cDNA clone thereof all are CGA, and the wherein codons that codes for Gly in the P1 protein of said live and attenuated Coxsackie virus or cDNA clone thereof all are GGA. For example, the live and attenuated Coxsackie virus or the live and attenuated cDNA clone thereof is a Coxsackie virus or clone, wherein the sequence coding for Coxsackie virus P1 protein is or comprises the RNA transcript of the cDNA sequence of SEQ ID NO: 85, or the cDNA sequence of SEQ ID NO: 85, respectively.

Such a live and attenuated virus or cDNA clone is obtainable by the process of the application.

The application relates more particularly to a live and attenuated virus or to a live and attenuated cDNA clone of virus, which is a live and attenuated Influenza virus or a live and attenuated cDNA clone thereof, wherein the codons that codes for Leu in the PA and/or HA protein(s) of said live and attenuated Influenza virus or cDNA clone thereof are all selected from UUA and UUG for said live and attenuated virus, or from TTA and TTG for said live and attenuated cDNA clone, and wherein the codons that codes for Ser in the PA and/or HA protein(s) of said live and attenuated Influenza virus or cDNA clone thereof are all selected from UCA and UCG for said live and attenuated virus, or from TCA and TCG for said live and attenuated cDNA clone. For example, the application relates to a live and attenuated Influenza virus or to a live and attenuated cDNA clone thereof, wherein the sequence coding for the Influenza PA protein is or comprises the RNA transcript of the cDNA sequence of SEQ ID NO: 54 or 56, or the cDNA sequence of SEQ ID NO: 54 or 56, respectively; or wherein the sequence coding for the Influenza HA protein is or comprises the RNA transcript of the cDNA sequence of SEQ ID NO: 87, or the cDNA sequence of SEQ ID NO: 87, respectively; or wherein the sequence coding for the Influenza PA protein is or comprises the RNA transcript of the cDNA sequence of SEQ ID NO: 54 or 56, or the cDNA sequence of SEQ ID NO: 54 or 56, respectively, and wherein the sequence coding for the Influenza HA protein is or comprises the RNA transcript of the cDNA sequence of SEQ ID NO: 87, or the cDNA sequence of SEQ ID NO: 87, respectively.

Alternatively or complementarily to said Ser and Leu codons, the Arg and Gly codons may be codons that differ by only one nucleotide from a STOP codon (cf. example 8 below). The live and attenuated Influenza virus or the live and attenuated cDNA clone thereof may e.g., be a Influenza virus or clone, wherein the codons that codes for Arg in the PA and/or HA protein(s) of said live and attenuated Influenza virus or cDNA clone thereof all are CGA, and wherein the codons that codes for Gly in the PA and/or HA protein(s) of said live and attenuated Influenza virus or cDNA clone thereof all are GGA.

Such a live and attenuated virus or cDNA clone is obtainable by the process of the application.

The application relates more particularly to a live and attenuated virus or to a live and attenuated cDNA clone of virus, which is a live and attenuated Chikungunya virus or a live and attenuated cDNA clone thereof, wherein the codons that codes for Leu in the E1 and/or E2 protein(s) of said live and attenuated Chikungunya virus or cDNA clone thereof are all selected from UUA and UUG for said live and attenuated virus, or from TTA and TTG for said live and attenuated cDNA clone, and wherein the codons that codes for Ser in the E1 and/or E2 protein(s) of said live and attenuated Chikungunya virus or cDNA clone thereof are all selected from UCA and UCG for said live and attenuated virus, or from TCA and TCG for said live and attenuated cDNA clone.

For example, the application relates to a live and attenuated Chikungunya virus or to a live and attenuated cDNA clone thereof, wherein the sequence coding for Chikungunya virus polyprotein C-E3-E2-6K-E1 is or comprises the RNA transcript of the cDNA sequence of SEQ ID NO: 101 or the cDNA sequence of SEQ ID NO: 101, respectively.

Alternatively or complementarily to said Ser and Leu codons, the Arg and Gly codons may be codons that differ by only one nucleotide from a STOP codon (cf. example 8 below). The live and attenuated Chikungunya virus or the live and attenuated cDNA clone thereof may e.g., be a Chikungunya virus or clone, wherein the codons that codes for Arg in the E1 and/or E2 protein(s) of said live and attenuated Chikungunya virus or cDNA clone thereof all are CGA, and wherein the codons that codes for Gly in the E1 and/or E2 protein(s) of said live and attenuated Chikungunya virus or cDNA clone thereof all are GGA.

For example, the live and attenuated Coxsackie virus or the live and attenuated cDNA clone thereof is a Chikungunya virus or clone, wherein the sequence coding for Chikungunya virus polyprotein C-E3-E2-6K-E1 comprises the RNA transcript of the cDNA sequence of SEQ ID NO: 102 or the cDNA sequence of SEQ ID NO: 102, respectively.

Such a live and attenuated virus or cDNA clone is obtainable by the process of the application.

Advantageously, a live and attenuated virus or a live and attenuated cDNA clone of the application generates STOP codons by mutation after one or several replication cycle(s).

The application also relates to the nucleic acids (e.g., cDNA) of said attenuated virus or clones, more particularly to each of the nucleic acids of SEQ ID NO: 14, 54, 56, 85 87, 101 and 102. The application also relates to a nucleic acid vector, such as a plasmid, which comprises at least one these nucleic acids (e.g., cDNA).

The application also relates to a culture medium, more particularly a cell culture medium, which comprises at least one (modified or attenuated) virus or clone of the application. Said culture medium may e.g., be an in vitro and/or non-naturally occurring culture medium. More particularly, said (cell) culture medium can be the above-described in vitro (cell) culture medium, e.g., an in vitro (cell) culture medium, which comprises amino acids, vitamins, inorganic salts and carbon source(s) as above-described, e.g., a DMEM culture medium such as the GlutaMAX™ DMEM. In addition to said at least one (modified or attenuated) virus or clone of the application, said culture medium may comprise said cell(s). Said cell may e.g., be a cell, which is sentitive to infection by said (modified or attenuated) virus or clone of the application, and which can grow in said (cell) culture medium. Said cell may e.g., be a cell as described above for the in vitro (cell) culture medium, e.g., a mammalian cell, more particularly a human cell (e.g., from a human cell line, such as the HeLa cell line [ATCC® CCL-2™]) or a non-human animal cell (e.g., from a non-human mammalian cell line, such as the VERO cell line [ATCC® CCL-81™]).

The application also relates to a composition. The term "composition" encompasses pharmaceutical composition, antiviral composition, immunogenic composition and vaccine, more particularly antiviral composition, immunogenic composition and vaccine, more particularly immunogenic composition and vaccine.

The composition of the application comprises at least one (modified or attenuated) virus or clone of the application, more particularly at least one live and attenuated virus or (DNA or cDNA) clone of the application.

The composition of the application can be used in the prevention and/or treatment and/or palliation, more particularly in the prevention, of a RNA virus infection or of a disease or disorder induced by a RNA virus. For example, a composition of the application, which comprises at least one (modified or attenuated) Coxsackie virus or (DNA or cDNA) clone of the application, can be used in the prevention and/or treatment and/or palliation, more particularly in the prevention, of a Coxsackie virus infection or of a disease or disorder induced by a Coxsackie virus. For example, a composition of the application, which comprises at least one (modified or attenuated) Influenza virus or (DNA or cDNA) clone of the application, can be used in the prevention and/or treatment and/or palliation, more particularly in the prevention, of a Influenza virus infection or of a disease or disorder induced by a Influenza virus. For example, a composition of the application, which comprises at least one (modified or attenuated) Chikungunya virus or (DNA or cDNA) clone of the application, can be used in the prevention and/or treatment and/or palliation, more particularly in the prevention, of a Chikungunya virus infection or of a disease or disorder induced by a Chikungunya virus. For example, a composition of the application, which comprises at least one (modified or attenuated) O'Nyong-Nyong virus or (DNA or cDNA) clone of the application, can be used in the prevention and/or treatment and/or palliation, more particularly in the prevention, of a O'Nyong-Nyong virus infection or of a disease or disorder induced by a O'Nyong-Nyong virus.

Advantageously, said composition of the application is suitable for administration into a host, in particular in a mammalian host, especially in a human or an animal host.

Said composition of the application may further comprise a pharmaceutically suitable excipient or carrier and/or vehicle, when used for systemic or local administration. A pharmaceutically suitable excipient or carrier and/or vehicle refers to a non-toxic solid, semisolid or liquid filler, diluent, encapsulating material or formulation auxiliary of any conventional type. A "pharmaceutically acceptable carrier" is non-toxic to recipients at the dosages and concentrations employed and is compatible with other ingredients of the formulation; suitable carriers include, but are not limited to, phosphate buffered saline solutions, distilled water, emulsions such as an oil/water emulsions, various types of wetting agents sterile solutions and the like, dextrose, glycerol, saline, ethanol, and combinations thereof.

Said composition of the application may further comprise an immunogenic adjuvant, such as Freund type adjuvants, generally used in the form of an emulsion with an aqueous phase or can comprise water-insoluble inorganic salts, such as aluminium hydroxide, zinc sulphate, colloidal iron hydroxide, calcium phosphate or calcium chloride.

In the composition of the application, the virus or clone of the application is advantageously contained in a dose sufficient to elicit an immune antibody response, more particularly an immune antibody response against at least one polyprotein, protein or polypeptide expressed by said virus or clone of the application. In a particular embodiment, said immune antibody response is a protective humoral response. The protective humoral response results mainly in maturated antibodies, having a high affinity for their antigen, such as IgG. In a particular embodiment, the protective humoral response induces the production of neutralizing antibodies.

It is considered that the composition of the application can have a protective capacity against RNA virus infection when after challenge of immunized host with said RNA virus, said composition delays and/or attenuates the symptoms usually elicited (in an unprotected animal host) after infection with said RNA virus against which protection is sought by the administration of the composition of the application. According to a particular embodiment, said composition of the application is formulated for an administration through parental route such as subcutaneous (s.c.), intradermal (i.d.), intramuscular (i.m.), intraperitoneal (i.p.) or intravenous (i.v.) injection, more particularly intradermal (i.d.) injection.

According to another particular embodiment, said composition of the application is administered in one or multiple administration dose(s), in particular in a prime-boost administration regime. The term "prime-boost regimen" generally encompasses a first administration step eliciting an immune response and one or several later administration step(s) boosting the immune reaction. Accordingly, an efficient prime-boost system can be used for iterative administration, enabling successively priming and boosting the immune response in a host, especially after injections in a host in need thereof. The term "iterative" means that the active principle is administered twice or more to the host. The priming and boosting immunization can be administered to the host at different or identical doses, and injections can be administered at intervals of several weeks, in particular at intervals of four weeks or more.

The quantity to be administered (dosage) depends on the subject to be treated, including the condition of the patient, the state of the individual's immune system, the route of administration and the size of the host. Suitable dosages can be adjusted by the person of average skill in the art.

The application also relates to a method to treat, prevent or protect, more particularly to prevent or protect against a RNA virus infection in a mammalian host, especially in a human or a non-human animal host, comprising administering said virus or clone of the application to said mammalian host.

As used herein, the expression "to protect against a RNA virus infection" refers to a method by which a RNA virus infection is obstructed or delayed, especially when the symptoms accompanying or following the infection are attenuated, delayed or alleviated or when the infecting RNA virus is cleared from the host.

The application also relates to a method to produce a composition, more particularly an immunogenic composition or vaccine against RNA virus infection, which comprises producing said virus or clone of the application, e.g., as a clone or cDNA clone in a culture medium, optionally collecting the viral particles or virions produced by said virus or clone, and formulating said cultured virus or clone (or said collected viral particles) in a composition suitable for administration to an animal, more particularly to a human or to a non-human animal.

The application also relates to a computer program product, for storage in a memory of a processing unit or on a removable memory support for cooperation with a reader of said processing unit, wherein said computer program product comprises instructions.

Said instructions can e.g., be instructions for carrying out a process of the application. Said instructions can e.g., be instructions for identifying codons, which code for Leu, Ser, Arg or Gly in the nucleic acid sequence of an infectious RNA virus or infectious (cDNA) clone thereof, and for replacing a proportion of them by a different but synonymous codon, wherein (each of) said different but synonymous codon is a codon, which differs by only one nucleotide from a STOP codon ("1-to-Stop" codon; cf. above). Said proportion is different from 0% and different from 100%. For example, said proportion is a proportion of 2-30%, 2-25%, 2-20%, 2-15%, 2-10%, 3-30%, 3-25%, 3-20%, 3-15% or 3-10% of the total number of codons of the genome of said infectious RNA virus, or of the total number of codons of the retro-transcribed cDNA CDS sequence of said cDNA clone, respectively (cf. above).

Alternatively or complementarily, more particularly complementarily, said instructions can e.g., be instructions for identifying codons, which code for Thr or Ala in the nucleic acid sequence of an infectious RNA virus or infectious (cDNA) clone thereof, and which differs by only one nucleotide from a Ser codon, and for replacing a proportion of these Thr or Ala by a different but non-synonymous codon, wherein (each of) said different but non-synonymous codon is a codon, which codes for Ser and which differs by only one nucleotide from a STOP codon (cf. above). Said proportion is different from 0% and different from 100%. For example, said proportion is a proportion of 2-30%, 2-25%, 2-20%, 2-15%, 2-10%, 3-30%, 3-25%, 3-20%, 3-15% or 3-10% of the total number of codons of the genome of said infectious RNA virus, or of the total number of codons of the retro-transcribed cDNA CDS sequence of said cDNA clone, respectively (cf. above).

The application also relates to a computer device, comprising a processing unit in the memory of which is stored a computer program product of the application. The computer device of the application may further comprise the nucleotide sequence of an (infectious) RNA virus or clone, and/or measurement instructions or values for implementation of the process or means of the application, e.g., measurement instructions or values for the number of codons, which code for Leu, Ser, Arg or Gly in the nucleic acid sequence of an infectious RNA virus or infectious (cDNA) clone thereof and/or for the number of codons, which code for Thr or Ala in the nucleic acid sequence of an infectious RNA virus or infectious (cDNA) clone thereof and which differ by only one nucleotide from a Ser codon.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the menas of the application.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

In an attempt to help the reader of the present application, the description has been separated in various paragraphs or sections. These separations should not be considered as disconnecting the substance of a paragraph or section from the substance of another paragraph or section. To the contrary, the present description encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Example 1

The genetic architecture of RNA virus populations can be described as a network of variants organized in sequence space around a master sequence(s), a mutant spectrum often referred to as quasispecies. Because of their extreme mutation rates, RNA virus populations exist perilously close to a threshold of extinction, as has been demonstrated by numerous studies of lethal mutagenesis. Population genetic models suggest that error-prone replication near this extinction threshold will favor the evolution of mutational robustness, whereby populations buffer the negative effects of mutation by migrating to regions of sequence space corresponding to more neutral fitness landscapes. In turn, robustness may facilitate evolvability by increasing the number of adaptive pathways available within a given landscape. It is thus hypothesized that viruses have evolved genome sequences to be positioned within optimal regions of sequence space where the largest networks of neighboring sequences are accessible through neutral fitness mutations.

In experimental virology, the concept of the master sequence is generally represented by the consensus, which is the genetic average of every nucleotide at each nucleotide position along the genome. Studies of mutational robustness in experimental systems have generally relied on demonstrating differences between different virus from different taxonomic families or at best, between different members of the same taxonomic family. In result, these viruses are not occupying the same sequence space and thus, robustness in these studies cannot be directly addressed.

In a recent study, Lauring et al. 2012 experimentally tested the robustness of poliovirus genomes presenting codon-shuffled sequences, suggesting that robustness was indeed altered and could potentially explain the attenuation of these variants in vivo. However, the laboratory that initially constructed these variants provides an alternative explanation for attenuation based on codon pair deoptimization (Coleman et al. 2008). The validity of robustness as an evolvable and modifiable trait thus remains to be directly addressed and confirmed.

In evolutionary models, robustness can be linked to the degeneracy of the genetic code. That is, multiple sequences can give rise to the same amino acid and thus, the same phenotype. While synonymous mutation is often thought to be selectively neutral, the observed variation in codon usage across both viral and organismal taxa suggests the presence of mutational bias and/or selective pressure. In RNA viruses, constraints on RNA structures, the availability of tRNAs, CpG dinucleotide content, deoptimized codon pairing have all been considered the reasons for codon bias, and have impeded and confounded attempts to demonstrate the role of genetic or mutational robustness on virus fitness.

Here, we address robustness directly and experimentally, and unequivocally show that indeed robustness is an evolvable, optimized trait that if modified results in the attenuation of RNA viruses.

Materials and Methods

Generation of Virus Stocks and Infections

Based on McLachlan's chemical similarity matrix for amino acids (McLachan, 1971; McLachlan 1972; accession number MCLA720101) and Archetti's mathematical framework to predict the effect of point mutation on synonymous codons (Archetti 2009), we generated Synthetic Synonymous viruses (or SynSyn) that bear 117 different synonymous codons, in other words different nucleotide sequences, while encoding the same amino acid sequence. All SynSyn Variants were genetically engineered using "de novo" synthetic gene technology (EUROGENTEC) and the CVB3-Nancy cDNA infectious clone (cDNA genomic sequence of SEQ ID NO: 1; cDNA CDS sequence of SEQ ID NO: 2). All newly generated DNA plasmids were Sanger-sequenced in full (GATC BIOTECH) to confirm that each of the 117 positions were introduced. Our strategy was based on the two amino acids with the greatest range of exploration of sequence space, i.e., serine and leucine, because they are encoded by six different codons. Importantly, these codons were altered without affecting RNA structure, replication, translation, as well as dinucleotide frequencies. These codons can be classified into three categories (cf. FIG. 1):

A-Group "1 to Stop", for one change away from Stop codon, such that a mutation at this codon has the highest likelihood of changing into a stop codon after a single point mutation.

B-Group "More-i", for more volatile, means that a new mutation at this codon has a higher likehood of changing to an amino acid with different chemical properties (more volatile amino acids), and C-Group "Less-i", for less volatile, means that a mutation at this codon has a higher likelihood to be silent or to maintain close physico-chemical properties with the original amino acid. A detailed list of all changes introduced is shown in Table 1 below.

TABLE 1 list of the changes introduced in SynSyn Viruses ("1-to-Stop" mutants)

| Position of the first nucleotide of the codon within SEQ ID NO: 1 | Wild-type (infectious) | Less-i | More-i | 1-to-Stop | Coded amino acid |
|---|---|---|---|---|---|
| 789 | TCA | TCT | AGT | TCA | S |
| 822 | CTG | CTG | CTC | TTG | L |
| 831 | AGC | TCC | AGC | TCG | S |
| 840 | TCC | TCC | AGC | TCG | S |
| 885 | TCC | TCC | AGC | TCG | S |
| 891 | TCA | TCT | AGT | TCA | S |
| 963 | TCA | TCT | AGT | TCA | S |
| 966 | CTA | CTA | CTT | TTA | L |
| 975 | CTC | CTG | CTC | TTG | L |
| 981 | TCC | TCC | AGC | TCG | S |
| 1008 | AGT | TCT | AGT | TCA | S |
| 1023 | TCA | TCT | AGT | TCA | S |
| 1032 | TTA | CTA | CTT | TTA | L |
| 1041 | TCC | TCC | AGC | TCG | S |
| 1104 | CTA | CTA | CTT | TTA | L |
| 1113 | AGT | TCT | AGT | TCA | S |
| 1176 | CTT | CTA | CTT | TTA | L |
| 1182 | TCT | TCT | AGT | TCA | S |
| 1203 | TCA | TCT | AGT | TCA | S |
| 1224 | CTG | CTG | CTC | TTG | L |
| 1236 | TTG | CTG | CTC | TTG | L |
| 1239 | TCG | TCC | AGC | TCG | S |
| 1245 | TTA | CTA | CTT | TTA | L |
| 1251 | CTG | CTG | CTC | TTG | L |
| 1281 | TTA | CTA | CTT | TTA | L |
| 1323 | TCT | TCT | AGT | TCA | S |
| 1344 | TTG | CTG | CTC | TTG | L |
| 1347 | CTA | CTA | CTT | TTA | L |
| 1389 | CTA | CTA | CTT | TTA | L |
| 1404 | TCC | TCC | AGC | TCG | S |
| 1407 | AGT | TCT | AGT | TCA | S |
| 1416 | TTG | CTG | CTC | TTG | L |
| 1419 | CTG | CTG | CTC | TTG | L |
| 1464 | TCC | TCC | AGC | TCG | S |
| 1470 | TCC | TCC | AGC | TCG | S |
| 1479 | TTG | CTG | CTC | TTG | L |
| 1530 | CTC | CTG | CTC | TTG | L |
| 1560 | CTA | CTA | CTT | TTA | L |
| 1575 | AGT | TCT | AGT | TCA | S |
| 1605 | AGT | TCT | AGT | TCA | S |
| 1647 | CTA | CTA | CTT | TTA | L |
| 1671 | CTA | CTA | CTT | TTA | L |
| 1689 | TCC | TCC | AGC | TCA | S |
| 1749 | TTA | CTA | CTT | TTA | L |
| 1755 | TTA | CTA | CTT | TTA | L |
| 1773 | TTA | CTA | CTT | TTA | L |
| 1797 | AGC | TCC | AGC | TCG | S |
| 1809 | CTG | CTG | CTC | TTG | L |
| 1815 | TCA | TCT | AGT | TCA | S |
| 1830 | TCA | TCT | AGT | TCA | S |
| 1836 | TCC | TCC | AGC | TCG | S |
| 1896 | TTG | CTG | CTC | TTG | L |
| 1920 | TCA | TCT | AGT | TCA | S |

TABLE 1-continued list of the changes introduced in SynSyn Viruses ("1-to-Stop" mutants)

| Position of the first nucleotide of the codon within SEQ ID NO: 1 | Wild-type (infectious) | Less-i | More-i | 1-to-Stop | Coded amino acid |
|---|---|---|---|---|---|
| 1959 | TCT | TCT | AGT | TCA | S |
| 1989 | TCC | TCC | AGC | TCG | S |
| 2001 | TCT | TCT | AGT | TCA | S |
| 2028 | CTG | CTG | CTC | TTG | L |
| 2043 | TCG | TCC | AGC | TCG | S |
| 2046 | AGT | TCT | AGT | TCA | S |
| 2064 | CTC | TCG | AGT | TTG | S |
| 2067 | CTA | CTA | CTC | TTA | L |
| 2079 | TTG | CTG | CTT | TTG | L |
| 2100 | TCA | TCT | CTC | TCA | L |
| 2106 | AGC | TCC | AGT | TCG | S |
| 2115 | CTT | CTA | AGC | TTA | S |
| 2136 | TCG | TCC | CTT | TCG | L |
| 2160 | CTT | CTA | AGC | TTA | S |
| 2163 | TTG | CTG | CTT | TTG | L |
| 2172 | TCA | TCT | CTC | TCA | L |
| 2217 | CTT | CTA | AGT | TTA | S |
| 2247 | CTA | CTA | CTT | TTA | L |
| 2253 | TCA | TCT | CTT | TCA | L |
| 2256 | AGT | TCT | AGT | TCA | S |
| 2265 | CTG | CTG | AGT | TTG | S |
| 2283 | AGC | TCC | CTC | TCG | L |
| 2310 | TCA | TCT | AGC | TCA | S |
| 2385 | AGC | TCC | AGT | TCG | S |
| 2388 | TCC | TCC | AGC | TCG | S |
| 2412 | TCA | TCT | AGC | TCA | S |
| 2430 | TCT | TCT | AGT | TCA | S |
| 2439 | CTA | CTA | CTT | TTA | L |
| 2442 | TTG | CTG | CTC | TTG | L |
| 2463 | TCG | TCC | AGC | TCG | S |
| 2556 | TCA | TCT | AGT | TCA | S |
| 2574 | CTC | CTG | CTC | TTG | L |
| 2601 | TCA | TCT | AGT | TCA | S |
| 2655 | TCA | TCT | AGT | TCA | S |
| 2661 | TCC | TCC | AGC | TCG | S |
| 2667 | TCA | TCT | AGT | TCA | S |
| 2685 | CTA | CTA | CTT | TTA | L |
| 2694 | TCA | TCT | AGT | TCA | S |
| 2727 | TCA | TCT | AGT | TCA | S |
| 2757 | TTA | CTA | CTT | TTA | L |
| 2781 | CTT | CTA | CTT | TTA | L |
| 2793 | CTA | CTA | CTT | TTA | L |
| 2823 | CTG | CTG | CTC | TTG | L |
| 2829 | CTG | CTG | CTC | TTG | L |
| 2847 | AGT | TCT | AGT | TCA | S |
| 2862 | TCA | TCT | AGT | TCA | S |
| 2892 | CTA | CTA | CTT | TTA | L |
| 2949 | TCA | TCT | AGT | TCA | S |
| 2967 | TCT | TCT | AGT | TCA | S |
| 2979 | AGT | TCT | AGT | TCA | S |
| 3018 | TCC | TCC | AGC | TCG | S |
| 3030 | TTG | CTG | CTC | TTG | L |
| 3033 | AGC | TCC | AGC | TCG | S |
| 3051 | TCA | TCT | AGT | TCA | S |
| 3072 | TCT | TCT | AGT | TCA | S |
| 3081 | TCC | TCC | AGC | TCG | S |
| 3111 | CTA | CTA | CTT | TTA | L |
| 3129 | CTA | CTA | CTT | TTA | L |
| 3156 | AGC | TCC | AGC | TCG | S |
| 3174 | AGC | TCC | AGC | TCG | S |
| 3237 | CTC | CTG | CTC | TTG | L |
| 3279 | AGC | TCC | AGC | TCG | S |
| 3303 | AGC | TCC | AGC | TCG | S |

The codon positions within the CDS sequence of SEQ ID NO: 2 are equal to those within SEQ ID NO: 1 minus 774.

CVB3 cDNA plasmids were linearized with Sal I. Linearized plasmids were purified with the MACHEREY-NAGEL PCR purification kit. 5 µg of linearized plasmid was in vitro transcribed using T7 RNA polymerase (FERMENTAS). 10 µg of transcript was electroporated into HeLa cells that were washed twice in PBS (w/o $Ca^{2+}$ and $Mg^{2+}$) and resuspended in PBS (w/o $Ca^{2+}$ and $Mg^{2+}$) at $10^7$ cells/ml. Electroporation conditions were as follows: 0.4 mm cuvette, 25 mF, 700 V, maximum resistance, exponential decay in a BIO-RAD GenePulser XCell electroporator. Cells were recovered in DMEM (GlutaMAX™; SIGMA-ALDRICH Product #31966047, which is at 4.5 g/l D-glucose and which contains sodium pyruvate at 110 mg/l). 500 µl of p0 virus stocks were used to infect fresh HeLa cells monolayers for three more passages. For each passage, virus was harvested by one freeze-thaw cycle and clarified by spinning at 10 K rpm for 10 minutes. Three independent stocks were generated for each virus. Consensus sequencing of virus stocks used in downstream experiments confirmed the stability of the engineered mutations and did not detect any additional mutations across the genome.

Determination of Viral Titers:

By TCID50: Ten-fold serial dilutions of virus were prepared in 96-well round bottom plates in free DMEM media. Dilutions were performed in 12 replicates and 100 µl of dilution were transferred to $10^4$ Vero cells plated in 100 µl of DMEM. After 5 days living cell monolayers were colored by crystal violet. TCID50 values were determined by the Reed and Muensch method.

By Plaque Assay: Vero or HeLa cells were seeded into 6-well plates and virus preparations were serially diluted (10-fold) in DMEM free media. Cells were washed twice with PBS and infected with 250 µl of dilution for 30 minutes at 37° C., after which a solid overlay comprising DMEM medium and 1% w/v agarose (INVITROGEN) was added. 2 days after infection, cells were fixed and stained with crystal violet 0.2%, and plaques were enumerated.

Viral Passages Under Mutagenic Conditions

Drugs (SIGMA ALDRICH)

Ribavirin IUPAC 1-[(2R,3R,4S,5R)-3,4-dihydroxy-5-(hydroxy-methyl)oxolan-2-yl]-1H-1,2,4-triazole-3-carboxamide);

5-Fluorouracil IUPAC 5-fluoro-1H-pyrimidine-2,4-dione;

5-Azacitidine IUPAC 4-amino-1-b-D-ribofuranosyl-1,3,5-tria-zin-2(1H)-one;

Amiloride IUPAC 3,5-diamino-6-chloro-N-(diaminomethylene) pyrazine-2-carboxamide.

HeLa cell monolayers in 6-well plates were pretreated for 4 hours (ribavirin, AZC, 5FU, MnCl2 and amiloride compounds with different concentrations, from 50 to 300 µl of each). We chose and verified concentrations of compounds that were not toxic to cells over a 72 hours period. For amiloride compounds, we chose and confirmed concentrations corresponding to virus inhibitory concentration (IC50) values that were not toxic to cells, as determined by Harrison et al. 2008. Cells were then infected at an MOI=0.1 with passage 2 virus. 48 hours post-infection, virus was harvested by one freeze-thaw cycle and virus titers (TCID50 or plaque assay) were determined. The same procedure was performed for five passages under each different mutagenic condition in three biological replicates.

Replication Kinetics and Quantification of Total Viral Genomes

For growth kinetics, HeLa cells were infected at MOI of 0.1 and 1, frozen at different time points after infection, and later, titered by $TCID_{50}$ assay. For qRT-PCR analysis, total RNA from infected cell supernatants was extracted by TRIzol reagent (INVITROGEN) and purified. The TaqMan RNA-to-C$_t$one-step RT-PCR kit (APPLIED BIOSYS- TEMS) was used to quantify viral RNA. Each 25-μL reaction contained 5 μL RNA, 100 μM each primer (forward 5'-GCATATGGTGATGATGTGATCGCTAGC-3' SEQ ID NO: 95 and reverse 5'-GGGGTACTGTTCATCT-GCTCTAAA-3' SEQ ID NO: 96), and 25 pmol probe 5'-[6-Fam] GGTTACGGGCTGATCATG-3' in an ABI 7000 machine. Reverse transcription was performed at 50° C. for 30 min and 95° C. for 10 min, and it was followed by 40 cycles at 95° C. for 15 s and 60° C. for 1 min. A standard curve (y=−0.2837x+12,611, $R^2$=0.99912) was generated using in vitro-transcribed genomic RNA.

Quantitative Estimate of Fitness

Relative fitness values were obtained by competing each SynSyn Virus, obtained from different passages under each different mutagen/compound assay, with a marked reference virus that contains four adjacent silent mutations in the polymerase region introduced by direct mutagenesis. Co-infections were performed in triplicate at MOI of 0.01 using a 1:1 mixture of each variant with the reference virus. After 24h, supernatants were harvested and a mix 1:1 with TRIzol reagent (INVITROGEN) was performed to keep the viral RNA. The proportion of each virus was determined by real time RT-PCR on extracted RNA using a mixture of Taqman probes labeled with two different fluorescent reporter dyes. MGB_CVB3_WT detects WT virus (including the SynSyn variants) with the sequence CGCATCGTACCCATGG (SEQ ID NO: 97), and it is labeled at the 5' end with a 6FAM dye (6-carboxyfluorescein) and MGB_CVB3_Ref containing the four silent mutations; CGCTAGCTACCCATGG (SEQ ID NO: 98) was labeled with a 5' VIC dye. Each 25 μL-reaction contained 5 μL RNA, 900 nM each primer (forward primer, 5'-GATCGCATATGGTGATGATGTGA-3' SEQ ID NO: 99; reverse primer, 5'-AGCTTCAGCGAG-TAAAGATGCA-3' SEQ ID NO: 100), and 150 nM each probe. Using a known standard for the WT and reference virus during the q-RT-PCR we were able to calculate the RNA concentration for each viral variant with extremely good sensitivity. The relative fitness was determined by the method described in the work by Carrasco et al, using the RNA determinations for each virus. Briefly, the formula $$W = \left[\frac{R(t)}{R(0)}\right]^{1/t}$$

represents the fitness W of each mutant genotype relative to the common competitor reference sequence, where R(0) and R(t) represent the ratio of mutant to reference virus densities in the inoculation mixture and t days post-inoculation (1 day in this case), respectively. It is important to mention that the fitness of the normal WT to reference virus was 1.019, indicating no significant differences in fitness caused by the silent mutations engineered in the reference virus (competitor).

Infection of Mice

Mice were kept in the PASTEUR Institute animal facilities in biosafety level 2 conditions, with water and food supplied ad libitum, and they were handled in accordance with institutional guidelines for animal welfare. All studies were carried out in BALB/c male mice between 5 and 6 week old. Mice were infected i.p. with $10^5$ $TCID_{50}$ in 0.20 ml. For tissue tropism studies, we harvested whole organs (spleen, pancreas and heart) and sera that were homogenized in PBS using a Precellys 24 tissue homogenizer (BERTIN TECHNOLOGIES). Viral RNA was extracted using TRIzol reagent (INVITROGEN). Full genome PCR, viral titers by $TCID_{50}$ as well as real-time PCR, was performed as described above.

Full Genome Analysis by Deep Sequencing

To estimate the population diversity of variants by deep sequencing, cDNA libraries were prepared by H-minus RT (THERMOFISHER) from RNA extracted from virus generated in Hela cells or different mice organs, and the viral genome was amplified using a high fidelity polymerase (PHUSION®) to generate 1 amplicon of 7.4 kb in length (full-length genome). PCRs were fragmented (Fragmentase), multiplexed, clustered, sequenced in the same lane with ILLUMINA cBot and GAIIX technology and analyzed with established deep sequencing data analysis tools and in house scripts.

Sequence Space

We propose a sequence space representation designed to capture the diversity due to differences in mutational robustness of the SynSyn viruses. For each of the 117-codon positions that were modified in our SynSyn viruses, the fraction of mutants using each of the 64 codons was estimated from deep sequencing data. Taking the mean value over the 117 positions, we obtained mean codon usage frequencies, giving a sequence space representation of the samples in 64-dimensions. While this representation does not truly reflect the full sequence space, it is suitable to study the effects of robustness changes in a neighborhood containing mutant swarms around the 4 viruses.

Dimension Reduction

Principal Component Analysis (PCA) was applied to the log-transformed sequence space data to find structure and construct a low-dimensional representation. The performance of the PCA was measured by the amount of variance captured in the components used for the low-dimensional representation and could be visualized by a screen plot.

Fitness Landscape Reconstruction

Coupling the low-dimensional (preferably 2D) representation of each sample with the fitness value of the sample, interpolation methods were used to assign a fitness value to any point in the low-dimensional space. All points in the sequence space mapping to a specific point in the low-dimensional space were assumed to have the same fitness. Reconstruction of the landscape was done with a Gaussian kernel smoother. The fitness of a point was estimated as a weighted average of the neighboring samples, where the weights are given by Gaussian kernels centered at each sample and then normalized to sum to one. The width of the kernel determines the landscape smoothness. Cross validation was employed to find the kernel width that maximizes the predictive power of the landscape.

Sequence Data (Wild-type Sequences)

cDNA sequence of the RNA genome of a wild-type (i.e., infectious) human Coxsackie virus B3 [7452 nt]:

SEQ ID NO: 1
gggagacccgaattctccaagacatcccccccccaaaacagcctgtgggt tgatcccacccacaggcccattgggcgctagcactctggtatcacggtac ctttgtgcgcctgtttttatacccctcccccaactgtaacttagaagtaa cacacaccgatcaacagtcagcgtggcacaccagccacgttttgatcaag cacttctgttaccccggactgagtatcaatagactgctcacgcggttgaa ggagaaagcgttcgttatccggccaactacttcgaaaaacctagtaacac cgtggaagttgcagagtgtttcgctcagcactacccagtgtagatcagg
tcgatgagtcaccgcattcccacgggcgaccgtggcggtggctgcgttg
gcggcctgcccatggggaaacccatgggacgctctaatacagacatggtg
cgaagagtctattgagctagttggtagtcctccggcccctgaatgcggct
aatcctaactgcggagcacacaccctcaagccagagggcagtgtgtcgta
acgggcaactctgcagcggaaccgactactttggggtgtccgtgtttcatt
ttattcctatactggctgcttatggtgacaattgagagatcgttaccata
tagctattggattggccatccggtgactaatagagctattatatatccct
ttgttgggtttataccacttagcttgaaagaggttaaaacattacaattc
attgttaagttgaatacagcaaaatgggagctcaagtatcaacgcaaaag
actgggcacatgagaccaggctgaatgctagcggcaattccatcattca
ctacacaaatattaattattacaaggatgccgcatccaactcagccaatc
ggcaggatttcactcaagacccgggcaagttcacagaaccagtgaaagat
atcatgattaaatcactaccagctctcaactcccccacagtagaggagtg
cggatacagtgacagggcgagatcaatcacattaggtaactccaccataa
cgactcaggaatgcgccaacgtggtggtgggctatggagtatggccagat
tatctaaaggatagtgaggcaacagcagaggaccaaccgacccaaccaga
cgttgccacatgtaggttctataccccttgactctgtgcaatggcagaaaa
cctcaccaggatggtggtgaagctgcccgatgctttgtcgaacttagga
ctgtttgggcagaacatgcagtaccactacttaggccgaactgggtatac
cgtacatgtgcagtgcaatgcatctaagttccaccaaggatgcttgctag
tagtgtgtgtaccggaagctgagatggggttgcgcaacgctagacaacacc
ccatccagtgcagaattgctgggggcgatagcgcaaaggagtttgcgga
caaaccggtcgcatccgggtccaacaagttggtacagagggtggtgtata
atgcaggcatggggtgggtgttggaaacctcaccattttcccccaccaa
tggatcaacctacgcaccaataatagtgctacaattgtgatgccatacac
caacagtgtacctatggataacatgtttaggcataacaacgtcaccctaa
tggttatcccatttgtaccgctagattactgccctgggtccaccacgtac
gtcccaattacggtcacgtagcccaatgtgtgccgagtacaatgggtt
acgtttagcagggcaccagggcttaccaaccatgaatactccggggagct
gtcaatttctgacatcagacgacttccaatcaccatccgccatgccgaa
tatgacgtcacaccagagatgaggatacctggtgaggtgaaaaacttgat
ggaaatagctgaggttgactcagttgtcccagtccaaaatgttggagaga
aggtcaactctatggaagcataccagatacctgtgagatccaacgaagga
tctggaacgcaagtattcggctttccactgcaaccagggtactcgagtgt
ttttagtcggacgctcctaggagagatcttgaactattatacacattggt
caggcagcataaagcttacgtttatgttctgtggttcggccatggctact
ggaaaattccttttggcatactcaccaccaggtgctggagctcctacaaa
aagggttgatgctatgcttggtactcatgtaatttgggacgtggggctac
aatcaagttgcgtgctgtgtataccctggataagccaaacacactaccgg
tttgttgcttcagatgagtataccgcaggggggttttattacgtgctggta tcaaacaaacatagtggtcccagcggatgcccaaagctcctgttacatca
tgtgtttcgtgtcagcatgcaatgacttctctgtcaggctattgaaggac
actcctttcatttcgcagcaaaacttttccagggcccagtggaagacgc
gataacagccgctatagggagagttgcggataccgtgggtacagggccaa
ccaactcagaagctataccagcactcactgctgctgagacgggtcacacg
tcacaagtagtgccgggtgacactatgcagacacgccacgttaagaacta
ccattcaaggtccgagtcaaccatagagaacttcctatgtaggtcagcat
gcgtgtactttacggagtataaaaactcaggtgccaagcggtatgctgaa
tgggtattaacaccacgacaagcagcacaacttaggagaaagctagaatt
ctttacctacgtccggttcgacctggagctgacgtttgtcataacaagta
ctcaacagccctcaaccacacagaaccaagatgcacagatcctaacacac
caaattatgtatgtaccaccaggtggacctgtaccagataaagttgattc
atacgtgtggcaaacatctacgaatcccagtgtgttttggaccgagggaa
acgcccgccgcgcatgtccataccgttttgagcattggcaacgcctat
tcaaatttctatgacggatggtctgaattttccaggaacggagtttacgg
catcaacacgctaaacaacatgggcacgctatatgcaagacatgtcaacg
ctggaagcacgggtccaataaaaagcaccattagaatctacttcaaaccg
aagcatgtcaaagcgtggatacctagaccacctagactctgccaatacga
gaaggcaaagaacgtgaacttccaacccagcggagttaccactactaggc
aaagcatcactacaatgacaaatacgggcgcatttggacaacaatcaggg
gcagtgtatgtggggaactacagggtggtaaatagacatctagctaccag
tgctgactggcaaaactgtgtgtgggaaagttacaacagagacctcttag
tgagcacgaccacagcacatggatgtgatattatagccagatgtcagtgc
acaacgggagtgtactttttgtgcgtccaaaaacaagcactacccaatttc
gtttgaaggaccaggtctagtagaggtccaagagagtgaatactacccca
ggagataccaatcccatgtgcttttagcagctggattttccgaaccaggt
gactgtggcggtatcctaaggtgtgagcatggtgtcattggcattgtgac
catgggggggtgaaggcgtggtcggctttgcagacatccgtgatctcctgt
ggctggaagatgatgcaatggaacagggagtgaaggactatgtggaacag
cttggaaatgcattcggctccggctttactaaccaaatatgtgagcaagt
caacctcctgaaagaatcactagtgggtcaagactccatcttagagaaat
ctctaaaagccttagttaagataatatcagccttagtaattgtggtgagg
aaccacgatgacctgatcactgtgactgccacactagcccttatcggttg
tacctcgtccccgtggcggtggctcaaacagaaggtgtcacaatattacg
gaatccctatggctgaacgccaaaacaatagctggcttaagaaatttact
gaaatgacaaatgcttgcaagggtatggaatggatagctgtcaaaattca
gaaattcattgaatggctcaaagtaaaaattttgccagaggtcagagaaa
aacacgagttcctgaacagacttaaacaactccccttattagaaagtcag
atcgccacaatcgagcagagcgcgccatcccaaagtgaccaggaacaatt
attttccaatgtccaatactttgcccactattgcagaaagtacgctcccc -continued

```
tctacgcagctgaagcaaagagggtgttctcccttgagaagaagatgagc
aattacatacagttcaagtccaaatgccgtattgaacctgtatgtttgct
cctgcacgggagccctggtgccggcaagtcggtggcaacaaacttaattg
gaaggtcgcttgctgagaaactcaacagctcagtgtactcactaccgcca
gacccagatcacttcgacggatacaaacagcaggccgtggtgattatgga
cgatctatgccagaatcctgatgggaaagacgtctccttgttctgccaaa
tggtttccagtgtagattttgtaccacccatggctgccctagaagagaaa
ggcattctgttcacctaccgtttgtcttggcatcgaccaatgcaggatc
tattaatgctccaaccgtgtcagatagcagagccttggcaaggagatttc
actttgacatgaacatcgaggttatttccatgtacagtcagaatggcaag
ataaacatgccatgtcagtcaagacttgtgacgatgagtgttgcccggt
caattttaaaaagtgctgccctcttgtgtgtgggaaggctatacaattca
ttgatagaagaacaggtcagatactctctagacatgctagtcaccgag
atgtttagggagtacaatcatagacatagcgtggggaccacgcttgaggc
actgttccagggaccaccagtatacagagagatcaaaattagcgttgcac
cagagacaccaccaccgcccgccattgcggacctgctcaaatcggtagac
agtgaggctgtgagggagtactgcaaagaaaaaggatggttggttcctga
gatcaactccaccctccaaattgagaaacatgtcagtcgggctttcattt
gcttacaggcattgaccacatttgtgtcagtggctggaatcatatatata
atatataagctctttgcgggttttcaaggtgcttatacaggagtgcccaa
ccagaagcccagagtgcctaccctgaggcaagcaaagtgcaaggccctg
cctttgagttcgccgtcgcaatgatgaaaaggaactcaagcacggtgaaa
actgaatatggcgagtttaccatgctgggcatctatgacaggtgggccgt
tttgccacgccacgccaaacctgggccaaccatcttgatgaatgatcaag
aggttggtgtgctagatgccaaggagctagtagacaaggacggcaccaac
ttagaactgacactactcaaattgaaccggaatgagaagttcagagacat
cagaggcttcttagccaaggaggaagtggaggttaatgaggcagtgctag
caattaacaccagcaagtttcccaacatgtacattccagtaggacaggtc
acagaatacggcttcctaaacctaggtggcacacccaccaagagaatgct
tatgtacaacttccccacaagagcaggccagtgtggtggagtgctcatgt
ccaccggcaaggtactgggtatccatgttggtggaaatggccatcagggc
ttctcagcagcactcctcaaacactacttcaatgatgagcaaggtgaaat
agaatttattgagagctcaaaggacgccgggtttccagtcatcaacacac
caagtaaaacaaagttggagcctagtgttttccaccaggtctttgagggg
aacaaagaaccagcagtactcaggagtggggatccacgtctcaaggccaa
ttttgaagaggctatattttccaagtatataggaaatgtcaacacacacg
tggatgagtacatgctggaagcagtggaccactacgcaggccaactagcc
accctagatatcagcactgaaccaatgaaactggaggacgcagtgtacgg
taccgagggtcttgaggcgcttgatctaacaacgagtgccggttacccat
atgttgcactgggtatcaagaagagggacatcctctctaagaagactaag
gacctaacaaagttaaaggaatgtatggacaagtatggcctgaacctacc
```

-continued

```
aatggtgacttatgtaaaagatgagctcaggtccatagagaaggtagcga
aaggaaagtctaggctgattgaggcgtccagtttgaatgattcagtggcg
atgagacagacatttggtaatctgtacaaaacttttccacctaaacccagg
ggttgtgactggtagtgctgttgggtgtgacccagacctcttttggagca
agataccagtgatgttagatggacatctcatagcatttgattactctggg
tacgatgctagcttaagccctgtctggtttgcttgcctaaaaatgttact
tgagaagcttggatacacgcacaaagagacaaactacattgactacttgt
gcaactcccatcacctgtacagggataaacattactttgtgaggggtggc
atgccctcgggatgttctggtaccagtattttcaactcaatgattaacaa
tatcataattaggacactaatgctaaaagtgtacaaagggattgacttgg
accaattcaggatgatcgcatatggtgatgatgtgatcgcatcgtaccca
tggcctatagatgcatctttactcgctgaagctggtaagggttacgggct
gatcatgacaccagcagataagggagagtgctttaacgaagttacctgga
ccaacgccacttttcctaaagaggtattttagagcagatgaacagtacccc
ttcctggtgcatcctgttatgcccatgaaagacatacacgaatcaattag
atggaccaaggatccaaagaacacccaagatcacgtgcgctcactgtgtc
tattagcttggcataacggggagcacgaatatgaggagttcatccgtaaa
attagaagcgtcccagtcggacgttgtttgaccctccccgcgttttcaac
tctacgcaggaagtggttggactccttttagattagagacaatttgaaat
aatttagattggcttaaccctactgtgctaaccgaaccagataacggtac
agtaggggtaaattctccgcattcggtgcggaaaaaaaaaaaaaaaag
aa
``` cDNA sequence of the CDS of the RNA genome of a wild-type (i.e., infectious) human Coxsackie virus B3 [fragment 774-7331 from SEQ ID NO: 1; 6558 nt]:

SEQ ID NO: 2
```
atgggagctcaagtatcaacgcaaaagactggggcacatgagaccaggct
gaatgctagcggcaattccatcattcactacacaaatattaattattaca
aggatgccgcatccaactcagccaatcggcaggatttcactcaagacccg
ggcaagttcacagaaccagtgaaagatatcatgattaaatcactaccagc
tctcaactcccccacagtagaggagtgcggatacagtgacagggcgagat
caatcacattaggtaactccaccataacgactcaggaatgcgccaacgtg
gtggtgggctatggagtatggccagattatctaaaggatagtgaggcaac
agcagaggaccaaccgacccaaccagacgttgccacatgtaggttctata
cccttgactctgtgcaatggcagaaaacctcaccaggatggtggtggaag
ctgcccgatgctttgtcgaacttaggactgtttgggcagaacatgcagta
ccactacttaggccgaactgggtataccgtacatgtgcagtgcaatgcat
ctaagttccaccaaggatgcttgctagtagtgtgtgtaccggaagctgag
atgggttgcgcaacgctagacaacaccccatccagtgcagaattgctggg
gggcgatagcgcaaaggagtttgcggacaaaccggtcgcatccgggtcca
acaagttggtacagagggtggtgtataatgcaggcatgggggtgggtgtt
``` ggaaacctcaccattttcccccaccaatggatcaacctacgcaccaataa tagtgctacaattgtgatgccatacaccaacagtgtacctatggataaca tgtttaggcataacaacgtcaccctaatggttatcccatttgtaccgcta gattactgccctgggtccaccacgtacgtcccaattacggtcacgatagc cccaatgtgtgccgagtacaatgggttacgtttagcagggcaccagggct taccaaccatgaatactccggggagctgtcaatttctgacatcagacgac ttccaatcaccatccgccatgccgcaatatgacgtcacaccagagatgag gatacctggtgaggtgaaaaacttgatggaaatagctgaggttgactcag ttgtcccagtccaaaatgttggagagaaggtcaactctatggaagcatac cagatacctgtgagatccaacgaaggatctggaacgcaagtattcggctt tccactgcaaccagggtactcgagtgttttagtcggacgctcctaggag agatcttgaactattatacacattggtcaggcagcataaagcttacgttt atgttctgtggttcggccatggctactggaaaattccttttggcatactc accaccaggtgctggagctcctacaaaaagggttgatgctatgcttggta ctcatgtaatttgggacgtggggctacaatcaagttgcgtgctgtgtata ccctggataagccaaacacactaccggtttgttgcttcagatgagtatac cgcagggggttttattacgtgctggtatcaaacaaacatagtggtcccag cggatgcccaaagctcctgttacatcatgtgtttcgtgtcagcatgcaat gacttctctgtcaggctattgaaggacactccttcatttcgcagcaaaa cttttccagggccagtggaagacgcgataacagccgctatagggagag ttgcggataccgtgggtacagggccaaccaactcagaagctataccagca ctcactgctgctgagacgggtcacacgtcacaagtagtgccgggtgacac tatgcagacacgccacgttaagaactaccattcaaggtccgagtcaacca tagagaacttcctatgtaggtcagcatgcgtgtactttacggagtataaa aactcaggtgccaagcggtatgctgaatgggtattaacaccacgacaagc agcacaacttaggagaaagctagaattctttacctacgtccggttcgacc tggagctgacgtttgtcataacaagtactcaacagccctcaaccacacag aaccaagatgcacagatcctaacacaccaaattatgtatgtaccaccagg tggacctgtaccagataaagttgattcatacgtgtggcaaacatctacga atcccagtgtgttttggaccgagggaaacgccccgccgcgcatgtccata ccgttttttgagcattggcaacgcctattcaaatttctatgacggatggtc tgaattttccaggaacggagtttacggcatcaacacgctaaacaacatgg gcacgctatatgcaagacatgtcaacgctggaagcacgggtccaataaaa agcaccattagaatctacttcaaaccgaagcatgtcaaagcgtggatacc tagaccacctagactctgccaatacgagaaggcaaagaacgtgaacttcc aacccagcggagttaccactactaggcaaagcatcactacaatgacaaat acgggcgcatttggacaacaatcaggggcagtgtatgtggggaactacag ggtggtaaatagacatctagctaccagtgctgactggcaaaactgtgtgt gggaaagttacaacagagacctcttagtgagcacgaccacagcacatgga tgtgatattatagccagatgtcagtgcacaacgggagtgtacttttgtgc gtccaaaaacaagcactacccaatttcgtttgaaggaccaggtctagtag aggtccaagagagtgaatactaccccaggagataccaatcccatgtgctt ttagcagctggattttccgaaccaggtgactgtggcggtatcctaaggtg tgagcatggtgtcattggcattgtgaccatgggggtgaaggcgtggtcg gctttgcagacatccgtgatctcctgtggctggaagatgatgcaatggaa cagggagtgaaggactatgtggaacagcttggaaatgcattcggctccgg ctttactaaccaaatatgtgagcaagtcaacctcctgaaagaatcactag tgggtcaagactccatcttagagaaatctctaaaagccttagttaagata atatcagcctagtaattgtggtgaggaaccacgatgacctgatcactgt gactgccacactagccctatcggttgtacctcgtcccgtggcggtggc tcaaacagaaggtgtcacaatattacggaatccctatggctgaacgccaa aacaatagctggcttaagaaatttactgaaatgacaaatgcttgcaaggg tatggaatggatagctgtcaaaattcagaaattcattgaatggctcaaag taaaaattttgccagaggtcagagaaaaacacgagttcctgaacagactt aaacaactcccccttattagaaagtcagatcgccacaatcgagcagagcgc gccatcccaaagtgaccaggaacaattattttccaatgtccaatactttg cccactattgcagaaagtacgctcccctctacgcagctgaagcaaagagg gtgttctcccttgagaagaagatgagcaattacatacagttcaagtccaa atgccgtattgaacctgtatgtttgctcctgcacggagccctggtgccg gcaagtcggtggcaacaaacttaattggaaggtcgcttgctgagaaactc aacagctcagtgtactcactaccgccagacccagatcacttcgacggata caaacagcaggccgtggtgattatggacgatctatgccagaatcctgatg ggaaagacgtctccttgttctgccaaatggtttccagtgtagattttgta ccacccatggctgccctagaagagaaaggcattctgttcacctcaccgtt tgtcttggcatcgaccaatgcaggatctattaatgctccaaccgtgtcag atagcagagccttggcaaggagatttcactttgacatgaacatcgaggtt atttccatgtacagtcagaatggcaagataaacatgcccatgtcagtcaa gacttgtgacgatgagtgttgcccggtcaattttaaaaagtgctgccctc ttgtgtgtgggaaggctatacaattcattgatagaagaacacaggtcaga tactctctagacatgctagtcaccgagatgtttagggagtacaatcatag acatagcgtgggaccacgcttgaggcactgttccagggaccaccagtat acagagagatcaaaattagcgttgcaccagagacaccaccaccgcccgcc attgcggacctgctcaaatcggtagacagtgaggctgtgagggagtactg caaagaaaaggatggttggttcctgagatcaactccaccctccaaattg agaaacatgtcagtcgggcttcatttgcttacaggcattgaccacattt gtgtcagtggctggaatcatatatataatatataagctctttgcgggttt tcaaggtgcttatacaggagtgcccaaccagaagcccagagtgcctaccc tgaggcaagcaaaagtgcaaggccctgcctttgagttcgccgtcgcaatg atgaaaaggaactcaagcacggtgaaaactgaatatggcgagtttaccat gctgggcatctatgacaggtgggccgttttgccacgccacgccaaacctg ggccaaccatcttgatgaatgatcaagaggttggtgtgctagatgccaag -continued

```
gagctagtagacaaggacggcaccaacttagaactgacactactcaaatt gaaccggaatgagaagttcagagacatcagaggcttcttagccaaggag aagtggaggttaatgaggcagtgctagcaattaacaccagcaagtttccc aacatgtacattccagtaggacaggtcacagaatacggcttcctaaacct aggtggcacacccaccaagagaatgcttatgtacaacttccccacaagag caggccagtgtggtggagtgctcatgtccaccggcaaggtactgggtatc catgttggtggaaatggccatcagggcttctcagcagcactcctcaaaca ctacttcaatgatgagcaaggtgaaatagaatttattgagagctcaaagg acgccgggtttccagtcatcaacacaccaagtaaaacaaagttggagcct agtgttttccaccaggtctttgaggggaacaaagaaccagcagtactcag gagtggggatccacgtctcaaggccaattttgaagaggctatattttcca agtatataggaaatgtcaacacacacgtggatgagtacatgctggaagca gtggaccactacgcaggccaactagccaccctagatatcagcactgaacc aatgaaactggaggacgcagtgtacgtaccgagggtcttgaggcgcttg atctaacaacgagtgccggttacccatatgttgcactgggtatcaagaag agggacatcctctctaagaagactaaggacctaacaaagttaaaggaatg tatggacaagtatgcctgaacctaccaatggtgacttatgtaaaagatg agctcaggtccatagagaaggtagcgaaaggaaagtctaggctgattgag gcgtccagtttgaatgattcagtggcgatgagacagacatttggtaatct gtacaaaactttccacctaaacccagggggttgtgactggtagtgctgttg ggtgtgacccagacctcttttggagcaagataccagtgatgttagatgga catctcatagcatttgattactctgggtacgatgctagcttaagccctgt ctggtttgcttgcctaaaaatgttacttgagaagcttggatacacgcaca aagagacaaactacattgactacttgtgcaactcccatcacctgtacagg
```

```
gataaacattactttgtgaggggtggcatgccctcgggatgttctggtac cagtattttcaactcaatgattaacaatatcataattaggacactaatgc taaaagtgtacaaagggattgacttggaccaattcaggatgatcgcatat ggtgatgatgtgatcgcatcgtacccatggcctatagatgcatctttact cgctgaagctggtaagggttacgggctgatcatgacaccagcagataagg gagagtgctttaacgaagttacctggaccaacgccacttcctaaagagg tattttagagcagatgaacagtacccttcctggtgcatcctgttatgcc catgaaagacatacacgaatcaattagatggaccaaggatccaaagaaca cccaagatcacgtgcgctcactgtgtctattagcttggcataacggggag cacgaatatgaggagttcatccgtaaaattagaagcgtcccagtcggacg ttgtttgaccctccccgcgttttcaactctacgcaggaagtggttggact ccttttag
```

TABLE 2 wild-type (i.e., infectious) Coxsackie virus B3

| cDNA sequences coding for: | | Positions within the (wild-type) CDS sequence of SEQ ID NO: 2 |
|---|---|---|
| wild-type P1 (SEQ ID NO: 4) | wild-type region VP4 | 1-207 |
| | wild-type region VP2 | 208-996 |
| | wild-type region VP3 | 997-1710 |
| | wild-type region VP1 | 1711-2562 |
| wild-type P2 (SEQ ID NO: 6) | wild-type region 2A | 2563-3003 |
| | wild-type region 2B | 3004-3300 |
| | wild-type region 2C | 3301-4287 |
| wild-type P3 (SEQ ID NO: 8) | wild-type region 3A | 4288-4554 |
| | wild-type region 3B | 4555-4620 |
| | wild-type region 3C | 4621-5169 |
| | wild-type region 3D = wild-type polymerase (SEQ ID NO: 10) | 5170-6555 |

Polyprotein of a wild-type (i.e., infectious) human Coxsackie virus B3 [coded by CDS of SEQ ID NO: 2; 2185 aa]:

SEQ ID NO: 3

```
MGAQVSTQKTGAHETRLNASGNSIIHYTNINYYKDAASNSANRQDFTQDP      50

GKFTEPVKDIMIKSLPALNSPTVEECGYSDRARSITLGNSTITTQECANV     100

VVGYGVWPDYLKDSEATAEDQPTQPDVATCRFYTLDSVQWQKTSPGWWWK     150

LPDALSNLGLFGQNMQYHYLGRTGYTVHVQCNASKFHQGCLLVVCVPEAE     200

MGCATLDNTPSSAELLGGDSAKEFADKPVASGSNKLVQRVVYNAGMGVGV     250

GNLTIFPHQWINLRTNNSATIVMPYTNSVPMDNMFRHNNVTLMVIPFVPL     300

DYCPGSTTYVPITVTIAPMCAEYNGLRLAGHQGLPTMNTPGSCQFLTSDD     350

FQSPSAMPQYDVTPEMRIPGEVKNLMEIAEVDSVVPVQNVGEKVNSMEAY     400

QIPVRSNEGSGTQVFGFPLQPGYSSVFSRTLLGEILNYYTHWSGSIKLTF     450

MFCGSAMATGKFLLAYSPPGAGAPTKRVDAMLGTHVIWDVGLQSSCVLCI     500

PWISQTHYRFVASDEYTAGGFITCWYQTNIVVPADAQSSCYIMCFVSACN     550

DFSVRLLKDTPFISQQNFFQGPVEDAITAAIGRVADTVGTGPTNSEAIPA     600

LTAAETGHTSQVVPGDTMQTRHVKNYHSRSESTIENFLCRSACVYFTEYK     650

NSGAKRYAEWVLTPRQAAQLRRKLEFFTYVRFDLELTFVITSTQQPSTTQ     700
```

-continued

```
NQDAQILTHQIMYVPPGGPVPDKVDSYVWQTSTNPSVFWTEGNAPPRMSI        750

PFLSIGNAYSNFYDGWSEFSRNGVYGINTLNNMGTLYARHVNAGSTGPIK        800

STIRIYFKPKHVKAWIPRPPRLCQYEKAKNVNFQPSGVTTTRQSITTMTN        850

TGAFGQQSGAVYVGNYRVVNRHLATSADWQNCVWESYNRDLLVSTTTAHG        900

CDIIARCQCTTGVYFCASKNKHYPISFEGPGLVEVQESEYYPRRYQSHVL        950

LAAGFSEPGDCGGILRCEHGVIGIVTMGGEGVVGFADIRDLLWLEDDAME       1000

QGVKDYVEQLGNAFGSGFTNQICEQVNLLKESLVGQDSILEKSLKALVKI       1050

ISALVIVVRNHDDLITVTATLALIGCTSSPWRWLKQKVSQYYGIPMAERQ       1100

NNSWLKKFTEMTNACKGMEWIAVKIQKFIEWLKVKILPEVREKHEFLNRL       1150

KQLPLLESQIATIEQSAPSQSDQEQLFSNVQYFAHYCRKYAPLYAAEAKR       1200

VFSLEKKMSNYIQFKSKCRIEPVCLLLHGSPGAGKSVATNLIGRSLAEKL       1250

NSSVYSLPPDPDHFDGYKQQAVVIMDDLCQNPDGKDVSLFCQMVSSVDFV       1300

PPMAALEEKGILFTSPFVLASTNAGSINAPTVSDSRALARRFHFDMNIEV       1350

ISMYSQNGKINMPMSVKTCDDECCPVNFKKCCPLVCGKAIQFIDRRTQVR       1400

YSLDMLVTEMFREYNHRHSVGTTLEALFQGPPVYREIKISVAPETPPPPA       1450

IADLLKSVDSEAVREYCKEKGWLVPEINSTLQIEKHVSRAFICLQALTTF       1500

VSVAGIIYIIYKLFAGFQGAYTGVPNQKPRVPTLRQAKVQGPAFEFAVAM       1550

MKRNSSTVKTEYGEFTMLGIYDRWAVLPRHAKPGPTILMNDQEVGVLDAK       1600

ELVDKDGTNLELTLLKLNRNEKFRDIRGFLAKEEVEVNEAVLAINTSKFP       1650

NMYIPVGQVTEYGFLNLGGTPTKRMLMYNFPTRAGQCGGVLMSTGKVLGI       1700

HVGGNGHQGFSAALLKHYFNDEQGEIEFIESSKDAGFPVINTPSKTKLEP       1750

SVFHQVFEGNKEPAVLRSGDPRLKANFEEAIFSKYIGNVNTHVDEYMLEA       1800

VDHYAGQLATLDISTEPMKLEDAVYGTEGLEALDLTTSAGYPYVALGIKK       1850

RDILSKKTKDLTKLKECMDKYGLNLPMVTYVKDELRSIEKVAKGKSRLIE       1900

ASSLNDSVAMRQTFGNLYKTFHLNPGVVTGSAVGCDPDLFWSKIPVMLDG       1950

HLIAFDYSGYDASLSPVWFACLKMLLEKLGYTHKETNYIDYLCNSHHLYR       2000

DKHYFVRGGMPSGCSGTSIFNSMINNIIIRTLMLKVYKGIDLDQFRMIAY       2050

GDDVIASYPWPIDASLLAEAGKGYGLIMTPADKGECFNEVTWTNATFLKR       2100

YFRADEQYPFLVHPVMPMKDIHESIRWTKDPKNTQDHVRSLCLLAWHNGE       2150

HEYEEFIRKIRSVPVGRCLTLPAFSTLRRKWLDSF
```

TABLE 3

| | wild-type (i.e., infectious) Coxsackie virus B3 |
|---|---|
| Amino acid sequences of: | Positions within the (wild-type) polyprotein sequence of SEQ ID NO: 3 |
| Wild-type P1 (SEQ ID NO: 5) | 1-854 |
| Wild-type P2 (SEQ ID NO: 7) | 855-1429 |
| Wild-type P3 (SEQ ID NO: 9) | 1430-2185 |
| Wild-type polymerase (SEQ ID NO: 11) = wild-type region 3D | 1724-2185 | cDNA sequence coding for the P1 region of a wild-type (i.e., infectious) human Coxsackie virus B3 [fragment 1-2562 from SEQ ID NO: 2; 2562 nt]:

SEQ ID NO: 4
```
atgggagctcaagtatcaacgcaaaagactggggcacatgagaccaggct
gaatgctagcggcaattccatcattcactacacaaatattaattattaca
aggatgccgcatccaactcagccaatcggcaggatttcactcaagacccg
ggcaagttcacagaaccagtgaaagatatcatgattaaatcactaccagc
tctcaactcccccacagtagaggagtgcggatacagtgacagggcgagat
caatcacattaggtaactccaccataacgactcaggaatgcgccaacgtg
gtggtgggctatggagtatggccagattatctaaaggatagtgaggcaac
agcagaggaccaaccgacccaaccagacgttgccacatgtaggttctata
```

-continued

```
cccttgactctgtgcaatggcagaaaacctcaccaggatggtggtggaag
ctgcccgatgctttgtcgaacttaggactgtttgggcagaacatgcagta
ccactacttaggccgaactgggtataccgtacatgtgcagtgcaatgcat
ctaagttccaccaaggatgcttgctagtagtgtgtgtaccggaagctgag
atggggttgcgcaacgctagacaacaccccatccagtgcagaattgctggg
gggcgatagcgcaaaggagtttgcggacaaaccggtcgcatccgggtcca
acaagttggtacagagggtggtgtataatgcaggcatgggggtgggtgtt
ggaaacctcaccatttttcccccaccaatggatcaacctacgcaccaataa
tagtgctacaattgtgatgccatacaccaacagtgtacctatggataaca
tgtttaggcataacaacgtcacccctaatggttatcccatttgtaccgcta
gattactgccctgggtccaccacgtacgtcccaattacggtcacgatagc
cccaatgtgtgccgagtacaatgggttacgtttagcagggcaccagggct
taccaaccatgaatactccggggagctgtcaatttctgacatcagacgac
ttccaatcaccatccgccatgccgcaatatgacgtcacaccagagatgag
gatacctggtgaggtgaaaaacttgatggaaatagctgaggttgactcag
ttgtcccagtccaaaatgttggagagaaggtcaactctatggaagcatac
cagatacctgtgagatccaacgaaggatctggaacgcaagtattcggctt
tccactgcaaccagggtactcgagtgttttagtcggacgctcctaggag
agatcttgaactattatacacattggtcaggcagcataaagcttacgttt
atgttctgtggttcggccatggctactggaaaattccttttggcatactc
accaccaggtgctggagctcctacaaaaagggttgatgctatgcttggta
ctcatgtaatttgggacgtggggctacaatcaagttgcgtgctgtgtata
ccctggataagccaaacacactaccggtttgttgcttcagatgagtatac
```

```
cgcagggggttttattacgtgctggtatcaaacaaacatagtggtcccag
cggatgcccaaagctcctgttacatcatgtgtttcgtgtcagcatgcaat
gacttctctgtcaggctattgaaggacactccttttcatttcgcagcaaaa
cttttccagggcccagtggaagacgcgataacagccgctatagggagag
ttgcggataccgtgggtacagggccaaccaactcagaagctataccagca
ctcactgctgctgagacgggtcacacgtcacaagtagtgccgggtgacac
tatgcagacacgccacgttaagaactaccattcaaggtccgagtcaacca
tagagaacttcctatgtaggtcagcatgcgtgtactttacggagtataaa
aactcaggtgccaagcggtatgctgaatgggtattaacaccacgacaagc
agcacaacttaggagaaagctagaattctttacctacgtccggttcgacc
tggagctgacgtttgtcataacaagtactcaacagccctcaaccacacag
aaccaagatgcacagatcctaacacaccaaattatgtatgtaccaccagg
tggacctgtaccagataaagttgattcatacgtgtggcaaacatctacga
atcccagtgtgttttggaccgagggaaacgccccgcgcgcatgtccata
ccgttttttgagcattggcaacgcctattcaaatttctatgacggatggtc
tgaattttccaggaacggagtttacggcatcaacacgctaaacaacatgg
gcacgctatatgcaagacatgtcaacgctggaagcacgggtccaataaaa
agcaccattagaatctacttcaaaccgaagcatgtcaaagcgtggatacc
tagaccacctagactctgccaatacgagaaggcaaagaacgtgaacttcc
aacccagcggagttaccactactaggcaaagcatcactacaatgacaaat
acgggcgcattt
```

P1 region of a wild-type (i.e., infectious) human Coxsackie virus B3 [coded by SEQ ID NO: 4; 854 aa]:

SEQ ID NO: 5

| | |
|---|---:|
| MGAQVSTQKTGAHETRLNASGNSIIHYTNINYYKDAASNSANRQDFTQDP | 50 |
| GKFTEPVKDIMIKSLPALNSPTVEECGYSDRARSITLGNSTITTQECANV | 100 |
| VVGYGVWPDYLKDSEATAEDQPTQPDVATCRFYTLDSVQWQKTSPGWWWK | 150 |
| LPDALSNLGLFGQNMQYHYLGRTGYTVHVQCNASKFHQGCLLVVCVPEAE | 200 |
| MGCATLDNTPSSAELLGGDSAKEFADKPVASGSNKLVQRVVYNAGMGVGV | 250 |
| GNLTIFPHQWINLRTNNSATIVMPYTNSVPMDNMFRHNNVTLMVIPFVPL | 300 |
| DYCPGSTTYVPITVTIAPMCAEYNGLRLAGHQGLPTMNTPGSCQFLTSDD | 350 |
| FQSPSAMPQYDVTPEMRIPGEVKNLMEIAEVDSVVPVQNVGEKVNSMEAY | 400 |
| QIPVRSNEGSGTQVFGFPLQPGYSSVFSRTLLGEILNYYTHWSGSIKLTF | 450 |
| MFCGSAMATGKFLLAYSPPGAGAPTKRVDAMLGTHVIWDVGLQSSCVLCI | 500 |
| PWISQTHYRFVASDEYTAGGFITCWYQTNIVVPADAQSSCYIMCFVSACN | 550 |
| DFSVRLLKDTPFISQQNFFQGPVEDAITAAIGRVADTVGTGPTNSEAIPA | 600 |
| LTAAETGHTSQVVPGDTMQTRHVKNYHSRSESTIENFLCRSACVYFTEYK | 650 |
| NSGAKRYAEWVLTPRQAAQLRRKLEFFTYVRFDLELTFVITSTQQPSTTQ | 700 |
| NQDAQILTHQIMYVPPGGPVPDKVDSYVWQTSTNPSVFWTEGNAPPRMSI | 750 |

```
PFLSIGNAYSNFYDGWSEFSRNGVYGINTLNNMGTLYARHVNAGSTGPIK          800

STIRIYFKPKHVKAWIPRPPRLCQYEKAKNVNFQPSGVTTTRQSITTMTN          850

TGAF
``` cDNA sequence coding for the P2 region of a wild-type (i.e., infectious) human Coxsackie virus B3 [fragment 2563-4287 from SEQ ID NO: 2; 1725 nt]:

```
                                              SEQ ID NO: 6
ggacaacaatcaggggcagtgtatgtggggaactacagggtggtaaatag acatctagctaccagtgctgactggcaaaactgtgtgtgggaaagttaca acagagacctcttagtgagcacgaccacagcacatggatgtgatattata gccagatgtcagtgcacaacgggagtgtacttttgtgcgtccaaaaacaa gcactacccaatttcgtttgaaggaccaggtctagtagaggtccaagaga gtgaatactaccccaggagataccaatcccatgtgcttttagcagctgga ttttccgaaccaggtgactgtggcggtatcctaaggtgtgagcatggtgt cattggcattgtgaccatgggggtgaaggcgtggtcggctttgcagaca tccgtgatctcctgtggctggaagatgatgcaatggaacagggagtgaag gactatgtggaacagctggaaatgcattcggctccggctttactaacca aatatgtgagcaagtcaacctcctgaaagaatcactagtgggtcaagact ccatcttagagaaatctctaaaagccttagttaagataatatcagcctta gtaattgtggtgaggaaccacgatgacctgatcactgtgactgccacact agcccctatcggttgtacctcgtcccgtggcggtggctcaaacagaagg tgtcacaatattacggaatccctatggctgaacgccaaaacaatagctgg cttaagaaatttactgaaatgacaaatgcttgcaagggtatggaatggat agctgtcaaaattcagaaattcattgaatggctcaaagtaaaaattttgc
```

```
                                              -continued
cagaggtcagagaaaaacacgagttcctgaacagacttaaacaactcccc ttattagaaagtcagatcgccacaatcgagcagagcgcgccatcccaaag tgaccaggaacaattattttccaatgtccaatactttgcccactattgca gaaagtacgctccctctacgcagctgaagcaaagagggtgttctccctt gagaagaagatgagcaattacatacagttcaagtccaaatgccgtattga acctgtatgtttgctcctgcacgggagccctggtgccggcaagtcggtgg caacaaacttaattggaaggtcgcttgctgagaaactcaacagctcagtg tactcactaccgccagacccagatcacttcgacggatacaaacagcaggc cgtggtgatttatggacgatctatgccagaatcctgatgggaaagacgtct ccttgttctgccaaatggtttccagtgtagattttgtaccacccatggct gccctagaagagaaaggcattctgttcacctcaccgtttgtcttggcatc gaccaatgcaggatctattaatgctccaaccgtgtcagatagcagagcct tggcaaggagatttcactttgacatgaacatcgaggttatttccatgtac agtcagaatggcaagataaacatgcccatgtcagtcaagacttgtgacga tgagtgttgcccggtcaattttaaaaagtgctgccctcttgtgtgtggga aggctatacaattcattgatagaagaacacaggtcagatactctctagac atgctagtcaccgagatgtttagggagtacaatcatagacatagcgtggg gaccacgcttgaggcactgttccag
```

P2 region of a wild-type (i.e., infectious) human Coxsackie virus B3 [coded by SEQ ID NO: 6; 575 aa]:

```
                                              SEQ ID NO: 7
GQQSGAVYVGNYRVVNRHLATSADWQNCVWESYNRDLLVSTTTAHGCDII          50

ARCQCTTGVYFCASKNKHYPISFEGPGLVEVQESEYYPRRYQSHVLLAAG         100

FSEPGDCGGILRCEHGVIGIVTMGGEGVVGFADIRDLLWLEDDAMEQGVK         150

DYVEQLGNAFGSGFTNQICEQVNLLKESLVGQDSILEKSLKALVKIISAL         200

VIVVRNHDDLITVTATLALIGCTSSPWRWLKQKVSQYYGIPMAERQNNSW         250

LKKFTEMTNACKGMEWIAVKIQKFIEWLKVKILPEVREKHEFLNRLKQLP         300

LLESQIATIEQSAPSQSDQEQLFSNVQYFAHYCRKYAPLYAAEAKRVFSL         350

EKKMSNYIQFKSKCRIEPVCLLLHGSPGAGKSVATNLIGRSLAEKLNSSV         400

YSLPPDPDHFDGYKQQAVVIMDDLCQNPDGKDVSLFCQMVSSVDFVPPMA         450

ALEEKGILFTSPFVLASTNAGSINAPTVSDSRALARRFHFDMNIEVISMY         500

SQNGKINMPMSVKTCDDECCPVNFKKCCPLVCGKAIQFIDRRTQVRYSLD         550

MLVTEMFREYNHRHSVGTTLEALFQ
``` cDNA sequence coding for the P3 region of a wild-type (i.e., infectious) human Coxsackie virus B3 [fragment 4288-6555 from SEQ ID NO: 2; 2268 nt]:

SEQ ID NO: 8 ggaccaccagtatacagagagatcaaaattagcgttgcaccagagacacc
accaccgcccgccattgcggacctgctcaaatcggtagacagtgaggctg
tgagggagtactgcaaagaaaaaggatggttggttcctgagatcaactcc
accctccaaattgagaaacatgtcagtcgggctttcatttgcttacaggc
attgaccacatttgtgtcagtggctggaatcatatatataatatataagc
tctttgcgggttttcaaggtgcttatacaggagtgcccaaccagaagccc
agagtgcctaccctgaggcaagcaaaagtgcaaggccctgcctttgagtt
cgccgtcgcaatgatgaaaaggaactcaagcacggtgaaaactgaatatg
gcgagtttaccatgctgggcatctatgacaggtgggccgttttgccacgc
cacgccaaacctgggccaaccatcttgatgaatgatcaagaggttggtgt
gctagatgccaaggagctagtagacaaggacggcaccaacttagaactga
cactactcaaattgaaccggaatgagaagttcagagacatcagaggcttc
ttagccaaggaggaagtggaggttaatgaggcagtgctagcaattaacac
cagcaagtttcccaacatgtacattccagtaggacaggtcacagaatacg
gcttcctaaacctaggtggcacacccaccaagagaatgcttatgtacaac
ttccccacaagagcaggccagtgtggtggagtgctcatgtccaccggcaa
ggtactgggtatccatgttggtggaaatggccatcagggcttctcagcag
cactcctcaaacactacttcaatgatgagcaaggtgaaatagaatttatt
gagagctcaaaggacgccgggtttccagtcatcaacacaccaagtaaaac
aaagttggagcctagtgttttccaccaggtctttgagggaacaaagaac
cagcagtactcaggagtggggatccacgtctcaaggccaattttgaagag
gctatattttccaagtatataggaaatgtcaacacacacgtggatgagta
catgctggaagcagtggaccactacgcaggccaactagccaccctagata
tcagcactgaaccaatgaaactggaggacgcagtgtacggtaccgagggt
cttgaggcgcttgatctaacaacgagtgccggttacccatatgttgcact
gggtatcaagaagagggacatcctctctaagaagactaaggacctaacaa
agttaaaggaatgtatggacaagtatggcctgaacctaccaatggtgact
tatgtaaaagatgagctcaggtccatagagaaggtagcgaaaggaaagtc
taggctgattgaggcgtccagtttgaatgattcagtggcgatgagacaga
catttggtaatctgtacaaaactttccacctaaacccaggggttgtgact
ggtagtgctgttgggtgtgacccagacctcttttggagcaagataccagt
gatgttagatggacatctcatagcatttgattactctgggtacgatgcta
gcttaagccctgtctggtttgcttgcctaaaaatgttacttgagaagctt
ggatacacgcacaaagagacaaactacattgactacttgtgcaactccca
tcacctgtacagggataaacattactttgtgagggtggcatgccctcgg
gatgttctggtaccagtattttcaactcaatgattaacaatatcataatt
aggacactaatgctaaaagtgtacaaagggattgacttggaccaattcag
gatgatcgcatggtgatgatgtgatcgcatcgtacccatggcctatag
atgcatctttactcgctgaagctggtaagggttacgggctgatcatgaca
ccagcagataagggagagtgctttaacgaagttacctggaccaacgccac
tttcctaaagaggtattttagagcagatgaacagtacccttcctggtgc
atcctgttatgcccatgaaagacatacacgaatcaattagatggaccaag
gatccaaagaacacccaagatcacgtgcgctcactgtgtctattagcttg
gcataacggggagcacgaatatgaggagttcatccgtaaaattagaagcg
tcccagtcggacgttgtttgaccctccccgcgttttcaactctacgcagg
aagtggttggactccttt P3 region of a wild-type (i.e., infectious) Coxsackie virus B3 [coded by SEQ ID NO: 8; 756 aa]:

SEQ ID NO: 9

```
GPPVYREIKISVAPETPPPPAIADLLKSVDSEAVREYCKEKGWLVPEINS      50
TLQIEKHVSRAFICLQALTTFVSVAGIIYIIYKLFAGFQGAYTGVPNQKP     100
RVPTLRQAKVQGPAFEFAVAMMKRNSSTVKTEYGEFTMLGIYDRWAVLPR     150
HAKPGPTILMNDQEVGVLDAKELVDKDGTNLELTLLKLNRNEKFRDIRGF     200
LAKEEVEVNEAVLAINTSKFPNMYIPVGQVTEYGFLNLGGTPTKRMLMYN     250
FPTRAGQCGGVLMSTGKVLGIHVGGNGHQGFSAALLKHYFNDEQGEIEFI     300
ESSKDAGFPVINTPSKTKLEPSVFHQVFEGNKEPAVLRSGDPRLKANFEE     350
AIFSKYIGNVNTHVDEYMLEAVDHYAGQLATLDISTEPMKLEDAVYGTEG     400
LEALDLTTSAGYPYVALGIKKRDILSKKTKDLTKLKECMDKYGLNLPMVT     450
YVKDELRSIEKVAKGKSRLIEASSLNDSVAMRQTFGNLYKTFHLNPGVVT     500
```

```
-continued
GSAVGCDPDLFWSKIPVMLDGHLIAFDYSGYDASLSPVWFACLKMLLEKL        550

GYTHKETNYIDYLCNSHHLYRDKHYFVRGGMPSGCSGTSIFNSMINNIII        600

RTLMLKVYKGIDLDQFRMIAYGDDVIASYPWPIDASLLAEAGKGYGLIMT        650

PADKGECFNEVTWTNATFLKRYFRADEQYPFLVHPVMPMKDIHESIRWTK        700

DPKNTQDHVRSLCLLAWHNGEHEYEEFIRKIRSVPVGRCLTLPAFSTLRR        750

KWLDSF
``` cDNA sequence coding for the polymerase (i.e., for the 3D protein) of a wild-type (i.e., infectious) human Coxsackie virus B3 [fragment 5170-6555 from SEQ ID NO: 2; 1386 nt]

```
                                                 SEQ ID NO: 10
ggtgaaatagaatttattgagagctcaaaggacgccgggtttccagtcat caacacaccaagtaaaacaaagttggagcctagtgttttccaccaggtct ttgaggggaacaaagaaccagcagtactcaggagtggggatccacgtctc aaggccaattttgaagaggctatattttccaagtatataggaaatgtcaa cacacacgtggatgagtacatgctggaagcagtggaccactacgcaggcc aactagccaccctagatatcagcactgaaccaatgaaactggaggacgca gtgtacggtaccgagggtcttgaggcgcttgatctaacaacgagtgccgg ttacccatatgttgcactgggtatcaagaagagggacatcctctctaaga agactaaggacctaacaaagttaaaggaatgtatggacaagtatggcctg aacctaccaatggtgacttatgtaaaagatgagctcaggtccatagagaa
```

```
                         -continued
ggtagcgaaaggaaagtctaggctgattgaggcgtccagtttgaatgatt cagtggcgatgagacagacatttggtaatctgtacaaaactttccaccta aacccagggggttgtgactggtagtgctgttgggtgtgacccagacctctt ttggagcaagataccagtgatgttagatggacatctcatagcatttgatt actctgggtacgatgctagcttaagccctgtctggtttgcttgcctaaaa atgttacttgagaagcttggatacacgcacaaagagacaaactacattga ctacttgtgcaactcccatcacctgtacagggataaacattactttgtga
```

```
                         -continued
ggggtggcatgccctcgggatgttctggtaccagtattttcaactcaatg attaacaatatcataattaggacactaatgctaaaagtgtacaaagggat tgacttggaccaattcaggatgatcgcatatggtgatgatgtgatcgcat cgtacccatggcctatagatgcatctttactcgctgaagctggtaagggt tacgggctgatcatgacaccagcagataagggagagtgctttaacgaagt tacctggaccaacgccactttcctaaagaggtattttagagcagatgaac agtacccttcctggtgcatcctgttatgcccatgaaagacatacacgaa tcaattagatggaccaaggatccaaagaacacccaagatcacgtgcgctc actgtgtctattagcttggcataacggggagcacgaatatgaggagttca tccgtaaaattagaagcgtcccagtcggacgttgtttgaccctccccgcg ttttcaactctacgcaggaagtggttggactccttt
```

Polymerase (i.e., 3D protein) of a wild-type (i.e., infectious) human Coxsackie virus B3 [coded by SEQ ID NO: 10; 462 aa]

```
                                                 SEQ ID NO: 11
GEIEFIESSKDAGFPVINTPSKTKLEPSVFHQVFEGNKEPAVLRSGDPRL         50

KANFEEAIFSKYIGNVNTHVDEYMLEAVDHYAGQLATLDISTEPMKLEDA        100

VYGTEGLEALDLTTSAGYPYVALGIKKRDILSKKTKDLTKLKECMDKYGL        150

NLPMVTYVKDELRSIEKVAKGKSRLIEASSLNDSVAMRQTFGNLYKTFHL        200

NPGVVTGSAVGCDPDLFWSKIPVMLDGHLIAFDYSGYDASLSPVWFACLK        250

MLLEKLGYTHKETNYIDYLCNSHHLYRDKHYFVRGGMPSGCSGTSIFNSM        300

INNIIRTLMLKVYKGIDLDQFRMIAYGDDVIASYPWPIDASLLAEAGKG        350

YGLIMTPADKGECFNEVTWTNATFLKRYFRADEQYPFLVHPVMPMKDIHE        400

SIRWTKDPKNTQDHVRSLCLLAWHNGEHEYEEFIRKIRSVPVGRCLTLPA        450

FSTLRRKWLDSF
```

Sequence Data (1-to-Stop Sequences)

"1-to-Stop" mutant of the cDNA sequence of the RNA genome of a wild-type (i.e., infectious) human Coxsackie virus B3 [1-to-Stop" mutant of the sequence of SEQ ID NO: 1; 7452 nt]:

```
                                                 SEQ ID NO: 12
GGGAGACCCGAATTCTCCAAGACATCCCCCCCCCAAAACAGCCTGTGGGT

TGATCCCACCCACAGGCCCATTGGGCGCTAGCACTCTGGTATCACGGTAC

CTTTGTGCGCCTGTTTTATACCCCCTCCCCCAACTGTAACTTAGAAGTAA
```

```
CACACACCGATCAACAGTCAGCGTGGCACACCAGCCACGTTTTGATCAAG
CACTTCTGTTACCCCGGACTGAGTATCAATAGACTGCTCACGCGGTTGAA
GGAGAAAGCGTTCGTTATCCGGCCAACTACTTCGAAAAACCTAGTAACAC
CGTGGAAGTTGCAGAGTGTTTCGCTCAGCACTACCCCAGTGTAGATCAGG
TCGATGAGTCACCGCATTCCCCACGGGCGACCGTGGCGGTGGCTGCGTTG
GCGGCCTGCCCATGGGGAAACCCATGGGACGCTCTAATACAGACATGGTG
CGAAGAGTCTATTGAGCTAGTTGGTAGTCCTCCGGCCCCTGAATGCGGCT
AATCCTAACTGCGGAGCACACACCCTCAAGCCAGAGGGCAGTGTGTCGTA
ACGGGCAACTCTGCAGCGGAACCGACTACTTTGGGTGTCCGTGTTTCATT
TTATTCCTATACTGGCTGCTTATGGTGACAATTGAGAGATCGTTACCATA
TAGCTATTGGATTGGCCATCCGGTGACTAATAGAGCTATTATATATCCCT
TTGTTGGGTTTATACCACTTAGCTTGAAAGAGGTTAAAACATTACAATTC
ATTGTTAAGTTGAATACAGCAAAATGGGAGCTCAAGTATCAACGCAAAAG
ACTGGGGCACATGAGACCAGGTTGAATGCTTCGGGCAATTCGATCATTCA
CTACACAAATATTAATTATTACAAGGATGCCGCATCGAACTCAGCCAATC
GGCAGGATTTCACTCAAGACCCGGGCAAGTTCACAGAACCAGTGAAAGAT
ATCATGATTAAATCATTACCAGCTTTGAACTCGCCCACAGTAGAGGAGTG
CGGATACTCAGACAGGGCGAGATCAATCACATTAGGTAACTCGACCATAA
CGACTCAGGAATGCGCCAACGTGGTGGTGGGCTATGGAGTATGGCCAGAT
TATTTAAAGGATTCAGAGGCAACAGCAGAGGACCAACCGACCCAACCAGA
CGTTGCCACATGTAGGTTCTATACCTTAGACTCAGTGCAATGGCAGAAAA
CCTCACCAGGATGGTGGTGGAAGTTGCCCGATGCTTTGTCGAACTTAGGA
TTGTTTGGGCAGAACATGCAGTACCACTACTTAGGCCGAACTGGGTATAC
CGTACATGTGCAGTGCAATGCATCAAAGTTCCACCAAGGATGCTTGTTAG
TAGTGTGTGTACCGGAAGCTGAGATGGGTTGCGCAACGTTAGACAACACC
CCATCGTCAGCAGAATTGTTGGGGGGCGATACGGCAAAGGAGTTTGCGGA
CAAACCGGTCGCATCGGGGTCGAACAAGTTGGTACAGAGGGTGGTGTATA
ATGCAGGCATGGGGTGGGTGTTGGAAACTTGACCATTTTCCCCCACCAA
TGGATCAACTTACGCACCAATAATTCAGCTACAATTGTGATGCCATACAC
CAACTCAGTACCTATGGATAACATGTTTAGGCATAACAACGTCACCTTAA
TGGTTATCCCATTTGTACCGTTAGATTACTGCCCTGGGTCAACCACGTAC
GTCCCAATTACGGTCACGATAGCCCCAATGTGTGCCGAGTACAATGGGTT
ACGTTTAGCAGGGCACCAGGGCTTACCAACCATGAATACTCCGGGTCGT
GTCAATTTTTGACATCAGACGACTTCCAATCACCATCGGCCATGCCGCAA
TATGACGTCACACCAGAGATGAGGATACCTGGTGAGGTGAAAAACTTGAT
GGAAATAGCTGAGGTTGACTCAGTTGTCCCAGTCCAAAATGTTGGAGAGA
AGGTCAACTCAATGGAAGCATACCAGATACCTGTGAGATCGAACGAAGGA
TCAGGAACGCAAGTATTCGGCTTTCCATTGCAACCAGGGTACTCGTCAGT
TTTTTCACGGACGTTGTTAGGAGAGATCTTGAACTATTATACACATTGGT
CAGGCTCGATAAAGTTAACGTTTATGTTCTGTGGTTCGGCCATGGCTACT
GGAAAATTCTTATTGGCATACTCACCACCAGGTGCTGGAGCTCCTACAAA
AAGGGGTTGATGCTATGTTAGGTACTCATGTAATTTGGGACGTGGGGTTAC
AATCATCATGCGTGTTGTGTATACCCTGGATATCGCAAACACACTACCGG
TTTGTTGCTTCAGATGAGTATACCGCAGGGGGTTTTATTACGTGCTGGTA
TCAAACAAACATAGTGGTCCCAGCGGATGCCCAATCGTCGTGTTACATCA
TGTGTTTCGTGTCAGCATGCAATGACTTCTCAGTCAGGTTATTGAAGGAC
ACTCCTTTCATTTCGCAGCAAAACTTTTTCCAGGGCCCAGTGGAAGACGC
GATAACAGCCGCTATAGGGAGAGTTGCGGATACCGTGGGTACAGGGCCAA
CCAACTCAGAAGCTATACCAGCATTGACTGCTGCTGAGACGGGTCACACG
TCACAAGTAGTGCCGGGTGACACTATGCAGACACGCCACGTTAAGAACTA
CCATTCAAGGTCGGAGTCAACCATAGAGAACTTCTTATGTAGGTCAGCAT
GCGTGTACTTTACGGAGTATAAAAACTCAGGTGCCAAGCGGTATGCTGAA
TGGGTATTAACACCACGACAAGCAGCACAATTAAGGAGAAAGTTAGAATT
CTTTACCTACGTCCGGTTCGACTTGGAGTTGACGTTTGTCATAACATCAA
CTCAACAGCCCTCAACCACACAGAACCAAGATGCACAGATCTTAACACAC
CAAATTATGTATGTACCACCAGGTGGACCTGTACCAGATAAAGTTGATTC
ATACGTGTGGCAAACATCAACGAATCCCTCAGTGTTTTGGACCGAGGGAA
ACGCCCCGCCGCGCATGTCGATACCGTTTTTGTCGATTGGCAACGCCTAT
TCAAATTTCTATGACGGATGGTCAGAATTTTCGAGGAACGGAGTTTACGG
CATCAACACGTTAAACAACATGGGCACGTTATATGCAAGACATGTCAACG
CTGGATCGACGGGTCCAATAAAATCGACCATTAGAATCTACTTCAAACCG
AAGCATGTCAAAGCGTGGATACCTAGACCACCTAGATTGTGCCAATACGA
GAAGGCAAAGAACGTGAACTTCCAACCCTCGGGAGTTACCACTACTAGGC
AATCGATCACTACAATGACAAATACGGGCGCATTTGGACAACAATCAGGG
GCAGTGTATGTGGGGAACTACAGGGTGGTAAATAGACATCTAGCTACCAG
TGCTGACTGGCAAAACTGTGTGTGGGAAAGTTACAACAGAGACCTCTTAG
TGAGCACGACCACAGCACATGGATGTGATATTATAGCCAGATGTCAGTGC
ACAACGGGAGTGTACTTTTGTGCGTCCAAAAACAAGCACTACCCAATTTC
GTTTGAAGGACCAGGTCTAGTAGAGGTCCAAGAGAGTGAATACTACCCCA
GGAGATACCAATCCCATGTGCTTTTAGCAGCTGGATTTTCCGAACCAGGT
GACTGTGGCGGTATCCTAAGGTGTGAGCATGGTGTCATTGGCATTGTGAC
CATGGGGGGTGAAGGCGTGGTCGGCTTTGCAGACATCCGTGATCTCCTGT
GGCTGGAAGATGATGCAATGGAACAGGGAGTGAAGGACTATGTGGAACAG
CTTGGAAATGCATTCGGCTCCGGCTTTACTAACCAAATATGTGAGCAAGT
CAACCTCCTGAAAGAATCACTAGTGGGTCAAGACTCCATCTTAGAGAAAT
CTCTAAAAGCCTTAGTTAAGATAATATCAGCCTTAGTAATTGTGGTGAGG
AACCACGATGACCTGATCACTGTGACTGCCACACTAGCCCTTATCGGTTG
TACCTCGTCCCCGTGGCGGTGGCTCAAACAGAAGGTGTCACAATATTACG
GAATCCCTATGGCTGAACGCCAAAACAATAGCTGGCTTAAGAAATTTACT
GAAATGACAAATGCTTGCAAGGGTATGGAATGGATAGCTGTCAAAATTCA
GAAATTCATTGAATGGCTCAAAGTAAAAATTTTGCCAGAGGTCAGAGAAA
```

-continued

```
AACACGAGTTCCTGAACAGACTTAAACAACTCCCCTTATTAGAAAGTCAG

ATCGCCACAATCGAGCAGAGCGCGCCATCCCAAAGTGACCAGGAACAATT

ATTTTCCAATGTCCAATACTTTGCCCACTATTGCAGAAAGTACGCTCCCC

TCTACGCAGCTGAAGCAAAGAGGGTGTTCTCCCTTGAGAAGAAGATGAGC

AATTACATACAGTTCAAGTCCAAATGCCGTATTGAACCTGTATGTTTGCT

CCTGCACGGGAGCCCTGGTGCCGGCAAGTCGGTGGCAACAAACTTAATTG

GAAGGTCGCTTGCTGAGAAACTCAACAGCTCAGTGTACTCACTACCGCCA

GACCCAGATCACTTCGACGGATACAAACAGCAGGCCGTGGTGATTATGGA

CGATCTATGCCAGAATCCTGATGGGAAAGACGTCTCCTTGTTCTGCCAAA

TGGTTTCCAGTGTAGATTTTGTACCACCCATGGCTGCCCTAGAAGAGAAA

GGCATTCTGTTCACCTCACCGTTTGTCTTGGCATCGACCAATGCAGGATC

TATTAATGCTCCAACCGTGTCAGATAGCAGAGCCTTGGCAAGGAGATTTC

ACTTTGACATGAACATCGAGGTTATTTCCATGTACAGTCAGAATGGCAAG

ATAAACATGCCCATGTCAGTCAAGACTTGTGACGATGAGTGTTGCCCGGT

CAATTTTAAAAAGTGCTGCCCTCTTGTGTGTGGGAAGGCTATACAATTCA

TTGATAGAAGAACACAGGTCAGATACTCTCTAGACATGCTAGTCACCGAG

ATGTTTAGGGAGTACAATCATAGACATAGCGTGGGGACCACGCTTGAGGC

ACTGTTCCAGGGACCACCAGTATACAGAGAGATCAAAATTAGCGTTGCAC

CAGAGACACCACCACCGCCCGCCATTGCGGACCTGCTCAAATCGGTAGAC

AGTGAGGCTGTGAGGGAGTACTGCAAAGAAAAAGGATGGTTGGTTCCTGA

GATCAACTCCACCCTCCAAATTGAGAAACATGTCAGTCGGGCTTTCATTT

GCTTACAGGCATTGACCACATTTGTGTCAGTGGCTGGAATCATATATATA

ATATATAAGCTCTTTGCGGGTTTTCAAGGTGCTTATACAGGAGTGCCCAA

CCAGAAGCCCAGAGTGCCTACCCTGAGGCAAGCAAAAGTGCAAGGCCCTG

CCTTTGAGTTCGCCGTCGCAATGATGAAAAGGAACTCAAGCACGGTGAAA

ACTGAATATGGCGAGTTTACCATGCTGGGCATCTATGACAGGTGGGCCGT

TTTGCCACGCCACGCCAAACCTGGGCCAACCATCTTGATGAATGATCAAG

AGGTTGGTGTGCTAGATGCCAAGGAGCTAGTAGACAAGGACGGCACCAAC

TTAGAACTGACACTACTCAAATTGAACCGGAATGAGAAGTTCAGAGACAT

CAGAGGCTTCTTAGCCAAGGAGGAAGTGGAGGTTAATGAGGCAGTGCTAG

CAATTAACACCAGCAAGTTTCCCAACATGTACATTCCAGTAGGACAGGTC

ACAGAATACGGCTTCCTAAACCTAGGTGGCACACCCACCAAGAGAATGCT

TATGTACAACTTCCCCACAAGAGCAGGCCAGTGTGGTGGAGTGCTCATGT

CCACCGGCAAGGTACTGGGTATCCATGTTGGTGGAAATGGCCATCAGGGC

TTCTCAGCAGCACTCCTCAAACACTACTTCAATGATGAGCAAGGTGAAAT

AGAATTTATTGAGAGCTCAAAGGACGCCGGGTTCCAGTCATCAACACAC

CAAGTAAAACAAAGTTGGAGCCTAGTGTTTTCCACCAGGTCTTTGAGGGG

AACAAAGAACCAGCAGTACTCAGGAGTGGGGATCCACGTCTCAAGGCCAA

TTTTGAAGAGGCTATATTTTCCAAGTATATAGGAAATGTCAACACACACG

TGGATGAGTACATGCTGGAAGCAGTGGACCACTACGCAGGCCAACTAGCC

ACCCTAGATATCAGCACTGAACCAATGAAACTGGAGGACGCAGTGTACGG

TACCGAGGGTCTTGAGGCGCTTGATCTAACAACGAGTGCCGGTTACCCAT

ATGTTGCACTGGGTATCAAGAAGAGGGACATCCTCTCTAAGAAGACTAAG

GACCTAACAAAGTTAAAGGAATGTATGGACAAGTATGGCCTGAACCTACC

AATGGTGACTTATGTAAAAGATGAGCTCAGGTCCATAGAGAAGGTAGCGA

AAGGAAAGTCTAGGCTGATTGAGGCGTCCAGTTTGAATGATTCAGTGGCG

ATGAGACAGACATTTGGTAATCTGTACAAAACTTTCCACCTAAACCCAGG

GGTTGTGACTGGTAGTGCTGTTGGGTGTGACCCAGACCTCTTTTGGAGCA

AGATACCAGTGATGTTAGATGGACATCTCATAGCATTTGATTACTCTGGG

TACGATGCTAGCTTAAGCCCTGTCTGGTTTGCTTGCCTAAAAATGTTACT

TGAGAAGCTTGGATACACGCACAAAGAGACAAACTACATTGACTACTTGT

GCAACTCCCATCACCTGTACAGGGATAAACATTACTTTGTGAGGGGTGGC

ATGCCCTCGGGATGTTCTGGTACCAGTATTTTCAACTCAATGATTAACAA

TATCATAATTAGGACACTAATGCTAAAAGTGTACAAAGGGATTGACTTGG

ACCAATTCAGGATGATCGCATATGGTGATGATGTGATCGCATCGTACCCA

TGGCCTATAGATGCATCTTTACTCGCTGAAGCTGGTAAGGGTTACGGGCT

GATCATGACACCAGCAGATAAGGGAGAGTGCTTTAACGAAGTTACCTGGA

CCAACGCCACTTTCCTAAAGAGGTATTTTAGAGCAGATGAACAGTACCCC

TTCCTGGTGCATCCTGTTATGCCCATGAAAGACATACACGAATCAATTAG

ATGGACCAAGGATCCAAAGAACACCCAAGATCACGTGCGCTCACTGTGTC

TATTAGCTTGGCATAACGGGGAGCACGAATATGAGGAGTTCATCCGTAAA

ATTAGAAGCGTCCCAGTCGGACGTTGTTTGACCCTCCCCGCGTTTTCAAC

TCTACGCAGGAAGTGGTTGGACTCCTTTTAGATTAGAGACAATTTGAAAT

AATTTAGATTGGCTTAACCCTACTGTGCTAACCGAACCAGATAACGGTAC

AGTAGGGGTAAATTCTCCGCATTCGGTGCGGAAAAAAAAAAAAAAAAAG

AA
```

The "1-to-Stop" mutant of SEQ ID NO: 12 still codes for the (wild-type) polyprotein of SEQ ID NO: 3.

"1-to-Stop" mutant of the cDNA sequence of the CDS of the RNA genome of a wild-type (i.e., infectious) human Coxsackie virus B3 ["1-to-Stop" mutant of the sequence of SEQ ID NO: 2; fragment 774-7331 from the sequence of SEQ ID NO: 12; 6558 nt]:

SEQ ID NO: 13
```
ATGGGAGCTCAAGTATCAACGCAAAAGACTGGGGCACATGAGACCAGGTT

GAATGCTTCGGGCAATTCGATCATTCACTACACAAATATTAATTATTACA

AGGATGCCGCATCGAACTCAGCCAATCGGCAGGATTTCACTCAAGACCCG

GGCAAGTTCACAGAACCAGTGAAAGATATCATGATTAAATCATTACCAGC

TTTGAACTCGCCCACAGTAGAGGAGTGCGGATACTCAGACAGGGCGAGAT

CAATCACATTAGGTAACTCGACCATAACGACTCAGGAATGCGCCAACGTG

GTGGTGGGCTATGGAGTATGGCCAGATTATTTAAAGGATTCAGAGGCAAC

AGCAGAGGACCAACCGACCCAACCAGACGTTGCCACATGTAGGTTCTATA

CCTTAGACTCAGTGCAATGGCAGAAAACCTCACCAGGATGGTGGTGGAAG
```

-continued

TTGCCCGATGCTTTGTCGAACTTAGGATTGTTTGGGCAGAACATGCAGTA
CCACTACTTAGGCCGAACTGGGTATACCGTACATGTGCAGTGCAATGCAT
CAAAGTTCCACCAAGGATGCTTGTTAGTAGTGTGTGTACCGGAAGCTGAG
ATGGGTTGCGCAACGTTAGACAACACCCCATCGTCAGCAGAATTGTTGGG
GGGCGATACGGCAAAGGAGTTTGCGGACAAACCGGTCGCATCGGGGTCGA
ACAAGTTGGTACAGAGGGTGGTGTATAATGCAGGCATGGGGGTGGGTGTT
GGAAACTTGACCATTTTCCCCCACCAATGGATCAACTTACGCACCAATAA
TTCAGCTACAATTGTGATGCCATACACCAACTCAGTACCTATGGATAACA
TGTTTAGGCATAACAACGTCACCTTAATGGTTATCCCATTTGTACCGTTA
GATTACTGCCCTGGGTCAACCACGTACGTCCCAATTACGGTCACGATAGC
CCCAATGTGTGCCGAGTACAATGGGTTACGTTTAGCAGGGCACCAGGGCT
TACCAACCATGAATACTCCGGGGTCGTGTCAATTTTTGACATCAGACGAC
TTCCAATCACCATCGGCCATGCCGCAATATGACGTCACACCAGAGATGAG
GATACCTGGTGAGGTGAAAAACTTGATGGAAATAGCTGAGGTTGACTCAG
TTGTCCCAGTCCAAAATGTTGGAGAGAAGGTCAACTCAATGGAAGCATAC
CAGATACCTGTGAGATCGAACGAAGGATCAGGAACGCAAGTATTCGGCTT
TCCATTGCAACCAGGGTACTCGTCAGTTTTTTCACGGACGTTGTTAGGAG
AGATCTTGAACTATTATACACATTGGTCAGGCTCGATAAAGTTAACGTTT
ATGTTCTGTGGTTCGGCCATGGCTACTGGAAAATTCTTATTGGCATACTC
ACCACCAGGTGCTGGAGCTCCTACAAAAAGGGTTGATGCTATGTTAGGTA
CTCATGTAATTTGGGACGTGGGGTTACAATCATCATGCGTGTTGTGTATA
CCCTGGATATCGCAAACACACTACCGGTTTGTTGCTTCAGATGAGTATAC
CGCAGGGGGTTTTATTACGTGCTGGTATCAAACAAACATAGTGGTCCCAG
CGGATGCCCAATCGTCGTGTTACATCATGTGTTTCGTGTCAGCATGCAAT
GACTTCTCAGTCAGGTTATTGAAGGACACTCCTTTCATTTCGCAGCAAAA
CTTTTTCCAGGGCCCAGTGGAAGACGCGATAACAGCCGCTATAGGGAGAG
TTGCGGATACCGTGGGTACAGGGCCAACCAACTCAGAAGCTATACCAGCA
TTGACTGCTGCTGAGACGGGTCACACGTCACAAGTAGTGCCGGGTGACAC
TATGCAGACACGCCACGTTAAGAACTACCATTCAAGGTCGGAGTCAACCA
TAGAGAACTTCTTATGTAGGTCAGCATGCGTGTACTTTACGGAGTATAAA
AACTCAGGTGCCAAGCGGTATGCTGAATGGGTATTAACACCACGACAAGC
AGCACAATTAAGGAGAAAGTTAGAATTCTTTACCTACGTCCGGTTCGACT
TGGAGTTGACGTTTGTCATAACATCAACTCAACAGCCCTCAACCACACAG
AACCAAGATGCACAGATCTTAACACACCAAATTATGTATGTACCACCAGG
TGGACCTGTACCAGATAAAGTTGATTCATACGTGTGGCAAACATCAACGA
ATCCCTCAGTGTTTTGGACCGAGGGAAACGCCCCGCCGCGCATGTCGATA
CCGTTTTTGTCGATTGGCAACGCCTATTCAAATTTCTATGACGGATGGTC
AGAATTTTCGAGGAACGGAGTTTACGGCATCAACACGTTAAACAACATGG
GCACGTTATATGCAAGACATGTCAACGCTGGATCGACGGGTCCAATAAAA
TCGACCATTAGAATCTACTTCAAACCGAAGCATGTCAAAGCGTGGATACC

-continued

TAGACCACCTAGATTGTGCCAATACGAGAAGGCAAAGAACGTGAACTTCC
AACCCTCGGGAGTTACCACTACTAGGCAATCGATCACTACAATGACAAAT
ACGGGCGCATTTGGACAACAATCAGGGGCAGTGTATGTGGGGAACTACAG
GGTGGTAAATAGACATCTAGCTACCAGTGCTGACTGGCAAAACTGTGTGT
GGGAAAGTTACAACAGAGACCTCTTAGTGAGCACGACCACAGCACATGGA
TGTGATATTATAGCCAGATGTCAGTGCACAACGGGAGTGTACTTTTGTGC
GTCCAAAAACAAGCACTACCCAATTTCGTTTGAAGGACCAGGTCTAGTAG
AGGTCCAAGAGAGTGAATACTACCCCAGGAGATACCAATCCCATGTGCTT
TTAGCAGCTGGATTTTCCGAACCAGGTGACTGTGGCGGTATCCTAAGGTG
TGAGCATGGTGTCATTGGCATTGTGACCATGGGGGGTGAAGGCGTGGTCG
GCTTTGCAGACATCCGTGATCTCCTGTGGCTGGAAGATGATGCAATGGAA
CAGGGAGTGAAGGACTATGTGGAACAGCTTGGAAATGCATTCGGCTCCGG
CTTTACTAACCAAATATGTGAGCAAGTCAACCTCCTGAAAGAATCACTAG
TGGGTCAAGACTCCATCTTAGAGAAATCTCTAAAAGCCTTAGTTAAGATA
ATATCAGCCTTAGTAATTGTGGTGAGGAACCACGATGACCTGATCACTGT
GACTGCCACACTAGCCCTTATCGGTTGTACCTCGTCCCCGTGGCGGTGGC
TCAAACAGAAGGTGTCACAATATTACGGAATCCCTATGGCTGAACGCCAA
AACAATAGCTGGCTTAAGAAATTTACTGAAATGACAAATGCTTGCAAGGG
TATGGAATGGATAGCTGTCAAAATTCAGAAATTCATTGAATGGCTCAAAG
TAAAAATTTTGCCAGAGGTCAGAGAAAAACACGAGTTCCTGAACAGACTT
AAACAACTCCCCTTATTAGAAAGTCAGATCGCCACAATCGAGCAGAGCGC
GCCATCCCAAAGTGACCAGGAACAATTATTTTCCAATGTCCAATACTTTG
CCCACTATTGCAGAAAGTACGCTCCCCTCTACGCAGCTGAAGCAAAGAGG
GTGTTCTCCCTTGAGAAGAAGATGAGCAATTACATACAGTTCAAGTCCAA
ATGCCGTATTGAACCTGTATGTTTGCTCCTGCACGGGAGCCCTGGTGCCG
GCAAGTCGGTGGCAACAAACTTAATTGGAAGGTCGCTTGCTGAGAAACTC
AACAGCTCAGTGTACTCACTACCGCCAGACCCAGATCACTTCGACGGATA
CAAACAGCAGGCCGTGGTGATTATGGACGATCTATGCCAGAATCCTGATG
GGAAAGACGTCTCCTTGTTCTGCCAAATGGTTTCCAGTGTAGATTTTGTA
CCACCCATGGCTGCCCTAGAAGAGAAAGGCATTCTGTTCACCTCACCGTT
TGTCTTGGCATCGACCAATGCAGGATCTATTAATGCTCCAACCGTGTCAG
ATAGCAGAGCCTTGGCAAGGAGATTTCACTTTGACATGAACATCGAGGTT
ATTTCCATGTACAGTCAGAATGGCAAGATAAACATGCCCATGTCAGTCAA
GACTTGTGACGATGAGTGTTGCCCGGTCAATTTTAAAAAGTGCTGCCCTC
TTGTGTGTGGGAAGGCTATACAATTCATTGATAGAAGAACACAGGTCAGA
TACTCTCTAGACATGCTAGTCACCGAGATGTTTAGGGAGTACAATCATAG
ACATAGCGTGGGACCACGCTTGAGGCACTGTTCCAGGGACCACCAGTAT
ACAGAGAGATCAAAATTAGCGTTGCACCAGAGACACCACCACCGCCCGCC
ATTGCGGACCTGCTCAAATCGGTAGACAGTGAGGCTGTGAGGGAGTACTG
CAAAGAAAAAGGATGGTTGGTTCCTGAGATCAACTCCACCCTCCAAATTG
AGAAACATGTCAGTCGGGCTTTCATTTGCTTACAGGCATTGACCACATTT

-continued
GTGTCAGTGGCTGGAATCATATATATAATATATAAGCTCTTTGCGGGTTT

TCAAGGTGCTTATACAGGAGTGCCCAACCAGAAGCCCAGAGTGCCTACCC

TGAGGCAAGCAAAAGTGCAAGGCCCTGCCTTTGAGTTCGCCGTCGCAATG

ATGAAAAGGAACTCAAGCACGGTGAAAACTGAATATGGCGAGTTTACCAT

GCTGGGCATCTATGACAGGTGGGCCGTTTTGCCACGCCACGCCAAACCTG

GGCCAACCATCTTGATGAATGATCAAGAGGTTGGTGTGCTAGATGCCAAG

GAGCTAGTAGACAAGGACGGCACCAACTTAGAACTGACACTACTCAAATT

GAACCGGAATGAGAAGTTCAGAGACATCAGAGGCTTCTTAGCCAAGGAGG

AAGTGGAGGTTAATGAGGCAGTGCTAGCAATTAACACCAGCAAGTTTCCC

AACATGTACATTCCAGTAGGACAGGTCACAGAATACGGCTTCCTAAACCT

AGGTGGCACACCCACCAAGAGAATGCTTATGTACAACTTCCCCACAAGAG

CAGGCCAGTGTGGTGGAGTGCTCATGTCCACCGGCAAGGTACTGGGTATC

CATGTTGGTGGAAATGGCCATCAGGGCTTCTCAGCAGCACTCCTCAAACA

CTACTTCAATGATGAGCAAGGTGAAATAGAATTTATTGAGAGCTCAAAGG

ACGCCGGGTTTCCAGTCATCAACACACCAAGTAAAACAAAGTTGGAGCCT

AGTGTTTTCCACCAGGTCTTTGAGGGGAACAAAGAACCAGCAGTACTCAG

GAGTGGGGATCCACGTCTCAAGGCCAATTTTGAAGAGGCTATATTTTCCA

AGTATATAGGAAATGTCAACACACACGTGGATGAGTACATGCTGGAAGCA

GTGGACCACTACGCAGGCCAACTAGCCACCCTAGATATCAGCACTGAACC

AATGAAACTGGAGGACGCAGTGTACGGTACCGAGGGTCTTGAGGCGCTTG

ATCTAACAACGAGTGCCGGTTACCCATATGTTGCACTGGGTATCAAGAAG

AGGGACATCCTCTCTAAGAAGACTAAGGACCTAACAAAGTTAAAGGAATG

TATGGACAAGTATGGCCTGAACCTACCAATGGTGACTTATGTAAAAGATG

AGCTCAGGTCCATAGAGAAGGTAGCGAAAGGAAAGTCTAGGCTGATTGAG

GCGTCCAGTTTGAATGATTCAGTGGCGATGAGACAGACATTTGGTAATCT

GTACAAAACTTTCCACCTAAACCCAGGGGTTGTGACTGGTAGTGCTGTTG

GGTGTGACCCAGACCTCTTTTGGAGCAAGATACCAGTGATGTTAGATGGA

CATCTCATAGCATTTGATTACTCTGGGTACGATGCTAGCTTAAGCCCTGT

CTGGTTTGCTTGCCTAAAAATGTTACTTGAGAAGCTTGGATACACGCACA

AAGAGACAAACTACATTGACTACTTGTGCAACTCCCATCACCTGTACAGG

GATAAACATTACTTTGTGAGGGGTGGCATGCCCTCGGGATGTTCGGTAC

CAGTATTTTCAACTCAATGATTAACAATATCATAATTAGGACACTAATGC

TAAAAGTGTACAAAGGGATTGACTTGGACCAATTCAGGATGATCGCATAT

GGTGATGATGTGATCGCATCGTACCCATGGCCTATAGATGCATCTTTACT

CGCTGAAGCTGGTAAGGGTTACGGGCTGATCATGACACCAGCAGATAAGG

GAGAGTGCTTTAACGAAGTTACCTGGACCAACGCCACTTTCCTAAAGAGG

TATTTTAGAGCAGATGAACAGTACCCCTTCCTGGTGCATCCTGTTATGCC

CATGAAAGACATACACGAATCAATTAGATGGACCAAGGATCCAAAGAACA

CCCAAGATCACGTGCGCTCACTGTGTCTATTAGCTTGGCATAACGGGGAG

CACGAATATGAGGAGTTCATCCGTAAAATTAGAAGCGTCCCAGTCGGACG

TTGTTTGACCCTCCCCGCGTTTTCAACTCTACGCAGGAAGTGGTTGGACT

CCTTTTAG

The "1-to-Stop" mutant of SEQ ID NO: 13 still codes for the (wild-type) polyprotein of SEQ ID NO: 3.

1-to-Stop" mutant of the cDNA sequence coding for the P1 region of a wild-type (i.e., infectious) human Coxsackie virus B3 ["1-to-Stop" mutant of the sequence of SEQ ID NO: 4; fragment 1-2562 from the sequence of SEQ ID NO: 13; 2562 nt]:

SEQ ID NO: 14
ATGGGAGCTCAAGTATCAACGCAAAAGACTGGGGCACATGAGACCAGGTT

GAATGCTTCGGGCAATTCGATCATTCACTACACAAATATTAATTATTACA

AGGATGCCGCATCGAACTCAGCCAATCGGCAGGATTTCACTCAAGACCCG

GGCAAGTTCACAGAACCAGTGAAAGATATCATGATTAAATCATTACCAGC

TTTGAACTCGCCCACAGTAGAGGAGTGCGGATACTCAGACAGGGCGAGAT

CAATCACATTAGGTAACTCGACCATAACGACTCAGGAATGCGCCAACGTG

GTGGTGGGCTATGGAGTATGGCCAGATTATTTAAAGGATTCAGAGGCAAC

AGCAGAGGACCAACCGACCCAACCAGACGTTGCCACATGTAGGTTCTATA

CCTTAGACTCAGTGCAATGGCAGAAAACCTCACCAGGATGGTGGTGGAAG

TTGCCCGATGCTTTGTCGAACTTAGGATTGTTTGGGCAGAACATGCAGTA

CCACTACTTAGGCCGAACTGGGTATACCGTACATGTGCAGTGCAATGCAT

CAAAGTTCCACCAAGGATGCTTGTTAGTAGTGTGTGTACCGGAAGCTGAG

ATGGGTTGCGCAACGTTAGACAACACCCCATCGTCAGCAGAATTGTTGGG

GGGCGATACGGCAAAGGAGTTTGCGGACAAACCGGTCGCATCGGGGTCGA

ACAAGTTGGTACGAGGGTGGTGTATAATGCAGGCATGGGGGTGGGTGTT

GGAAACTTGACCATTTTCCCCCACCAATGGATCAACTTACGCACCAATAA

TTCAGCTACAATTGTGATGCCATACACCAACTCAGTACCTATGGATAACA

TGTTTAGGCATAACAACGTCACCTTAATGGTTATCCCATTTGTACCGTTA

GATTACTGCCCTGGGTCAACCACGTACGTCCCAATTACGGTCACGATAGC

CCCAATGTGTGCCGAGTACAATGGGTTACGTTTAGCAGGGCACCAGGGCT

TACCAACCATGAATACTCCGGGGTCGTGTCAATTTTTGACATCAGACGAC

TTCCAATCACCATCGGCCATGCCGCAATATGACGTCACACCAGAGATGAG

GATACCTGGTGAGGTGAAAAACTTGATGGAAATAGCTGAGGTTGACTCAG

TTGTCCCAGTCCAAATGTTGGAGAGAAGGTCAACTCAATGGAAGCATAC

CAGATACCTGTGAGATCGAACGAAGGATCAGGAACGCAAGTATTCGGCTT

TCCATTGCAACCAGGGTACTCGTCAGTTTTTTCACGGACGTTGTTAGGAG

AGATCTTGAACTATTATACACATTGGTCAGGCTCGATAAAGTTAACGTTT

ATGTTCTGTGGTTCGGCCATGGCTACTGGAAAATTCTTATTGGCATACTC

ACCACCAGGTGCTGGAGCTCCTACAAAAAGGGTTGATGCTATGTTAGGTA

CTCATGTAATTTGGGACGTGGGGTTACAATCATCATGCGTGTTGTGTATA

CCCTGGATATCGCAAACACACTACCGGTTTGTTGCTTCAGATGAGTATAC

CGCAGGGGGTTTTATTACGTGCTGGTATCAAACAAACATAGTGGTCCCAG

CGGATGCCCAATCGTCGTGTTACATCATGTGTTTCGTGTCAGCATGCAAT

-continued

```
GACTTCTCAGTCAGGTTATTGAAGGACACTCCTTTCATTTCGCAGCAAAA

CTTTTTCCAGGGCCCAGTGGAAGACGCGATAACAGCCGCTATAGGGAGAG

TTGCGGATACCGTGGGTACAGGGCCAACCAACTCAGAAGCTATACCAGCA

TTGACTGCTGCTGAGACGGGTCACACGTCACAAGTAGTGCCGGGTGACAC

TATGCAGACACGCCACGTTAAGAACTACCATTCAAGGTCGGAGTCAACCA

TAGAGAACTTCTTATGTAGGTCAGCATGCGTGTACTTTACGGAGTATAAA

AACTCAGGTGCCAAGCGGTATGCTGAATGGGTATTAACACCACGACAAGC

AGCACAATTAAGGAGAAAGTTAGAATTCTTTACCTACGTCCGGTTCGACT

TGGAGTTGACGTTTGTCATAACATCAACTCAACAGCCCTCAACCACACAG

AACCAAGATGCACAGATCTTAACACACCAAATTATGTATGTACCACCAGG

TGGACCTGTACCAGATAAAGTTGATTCATACGTGTGGCAAACATCAACGA

ATCCCTCAGTGTTTTGGACCGAGGGAAACGCCCCGCCGCGCATGTCGATA

CCGTTTTTGTCGATTGGCAACGCCTATTCAAATTTCTATGACGGATGGTC

AGAATTTTCGAGGAACGGAGTTTACGGCATCAACACGTTAAACAACATGG

GCACGTTATATGCAAGACATGTCAACGCTGGATCGACGGGTCCAATAAAA

TCGACCATTAGAATCTACTTCAAACCGAAGCATGTCAAAGCGTGGATACC

TAGACCACCTAGATTGTGCCAATACGAGAAGGCAAAGAACGTGAACTTCC

AACCCTCGGGAGTTACCACTACTAGGCAATCGATCACTACAATGACAAAT

ACGGGCGCATTT
```

The "1-to-Stop" mutant of SEQ ID NO: 14 still codes for the (wild-type) P1 region of SEQ ID NO: 4.

Results

Construction of Coxsackie Virus B3 (CVB3) Genomes with Altered Theoretical Robustness and Sequence Space In order to alter the genetic robustness of the CVB3 genome, without changing the amino acid sequence of the virus, we applied McLachlan's chemical similarity matrix for amino acids (McLachlan 1971; McLachlan 1972; accession number MCLA720101) and the mathematical framework designed by Archetti that predicts the potential effect of a point mutation over synonymous codons for every amino acid (Archetti 2009). To avoid the confounding effects of changing every codon, and to more directly address the question of robustness, we first focused our approach on two amino acids with the greatest degeneracy of the genetic code and theoretical potential for robustness: serine and leucine, because they are encoded by six different codons. These codons can thus be classified into three categories (FIG. 1):

A-Group "1-to Stop" (purple), for one change away from Stop, such that a mutation at this codon has the highest likelihood of changing into a stop codon after only a single point mutation;

B-Group "More-i" (red), for more impact by point mutations, means that a new mutation at this codon has a higher likelihood of changing to an amino acid with different chemical properties (more volatile amino acids);

C-Group "Less-i" (green), for less impact by point mutations, means that a mutation at this codon has a higher likelihood to be silent or to maintain close physicochemical properties with the original amino acid (less volatile).

Replication Characteristics of Robustness Variants

Figure 2:
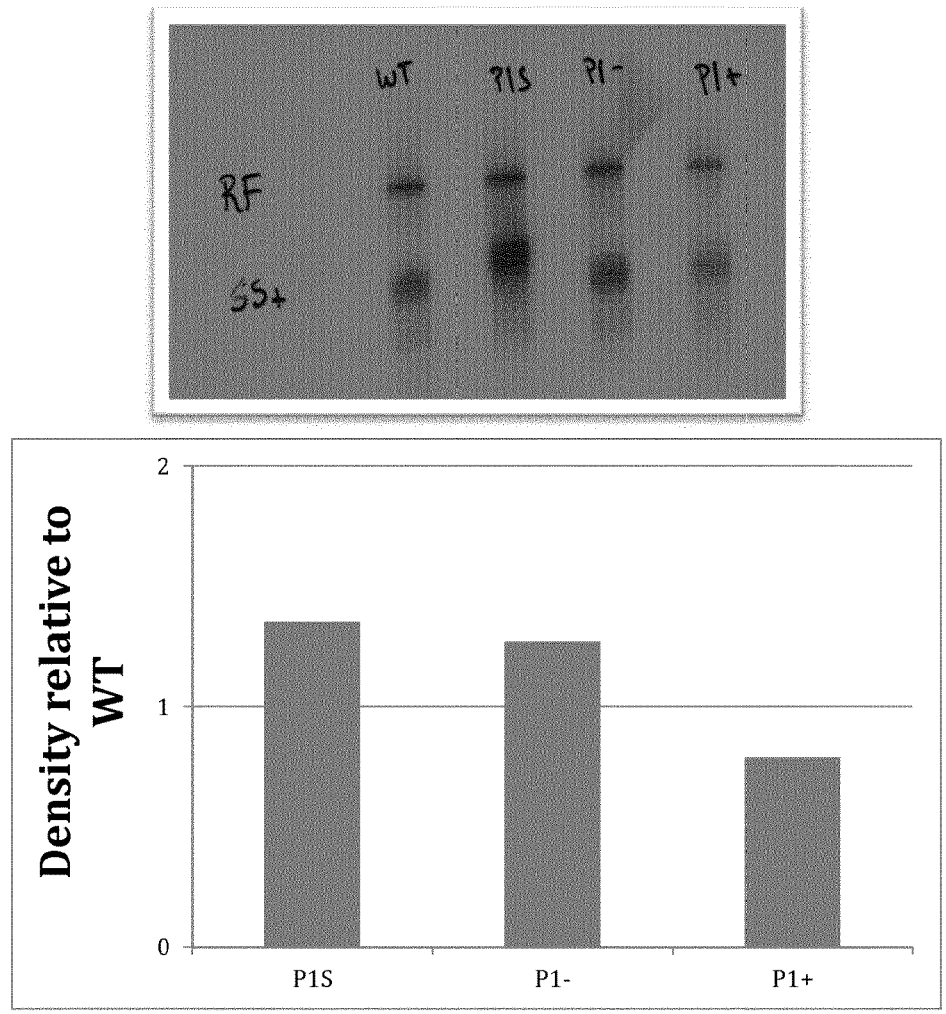
FIG. 2. Codon swapping does not alter RNA synthesis during genome replication. In vitro replication assays were performed using HeLa cell extracts and in vitro transcribed genomic RNA. Single strand, positive sense (SS+) and replicative forms (RF) are visualized by northern blot, quantified and normalized to wild type (WT) virus. No significant differences observed for either of three constructs.
(WT=wild-type; P1+=More-i; P1−=Less-i; P1S=1-to-Stop)
Figure 3:
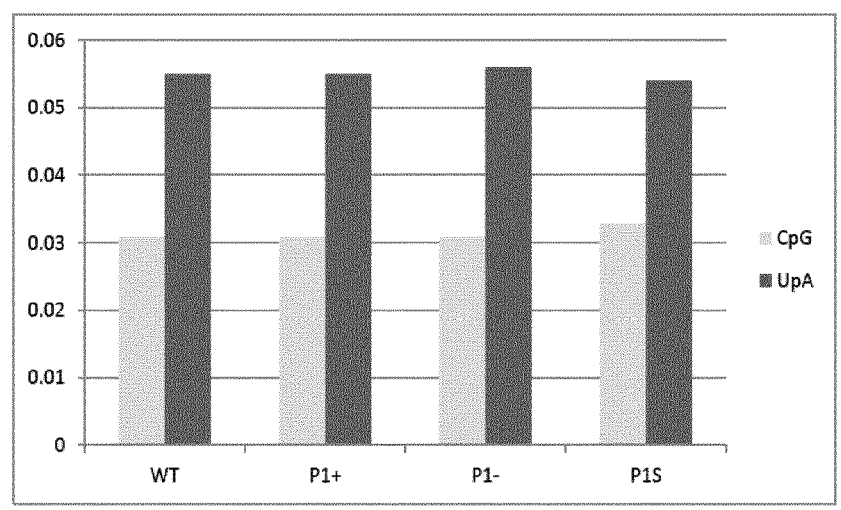
FIG. 3. Codon swapping to alter serine and leucine codons in our constructs does not alter the CpG and UpA frequency (y-axis), shown to attenuate viruses. No significant differences observed between wild type (WT), 'more' (P1+), 'less' (P1−) and 'stop' (P1S) constructs (left bar CpG; right bar UpA).
(WT=wild-type; P1+=More-i; P1−=Less-i; P1S=1-to-Stop)

We thus altered 117 serine and leucine codons present in the P1 region of the genome, representing approximately 5% of the total genomic sequence, to generate constructs that exclusively contain one of the three categories of codon listed above. This region does not contain any known RNA structures required for virus replication or packaging. Indeed, we observed no differences in RNA synthesis that would suggest defects in RNA structure (FIG. 2). Furthermore, our altered codon sequences did not affect the codon pair bias described by Coleman et al. 2008, nor the CpG and UpA dinucleotide bias shown to affect virus fitness by Atkinson et al. 2014 (FIG. 3). Taken together, our results suggest that the altered codons did not negatively impact any of the properties that have been shown to result in attenuation in other codon de-optimization studies, indicating that our constructs will allow us to address robustness in absence of confounding effects.

Figure 4A:
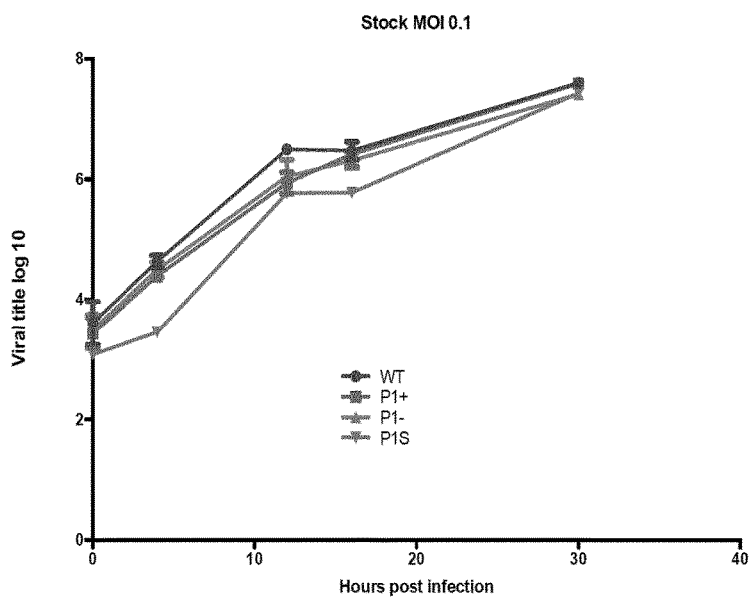
FIGS. 4A, 4B and 4C. Replication kinetics of robustness variants. (4A and 4B) HeLa cells were infected at MOI of 0.1 or MOI of 1 with passage 1 stocks of wild type (WT) or other variants and at times indicated post infection, the viral progeny was quantified by standard plaque assay. (4C) Growth curves using passage 5 stocks of the same variants. (A, B and C: WT=●; P1+=■; P1−=▲; P1S=▼)
(WT=wild-type; P1+=More-i; P1−=Less-i; P1S=1-to-Stop)
Figure 4B:
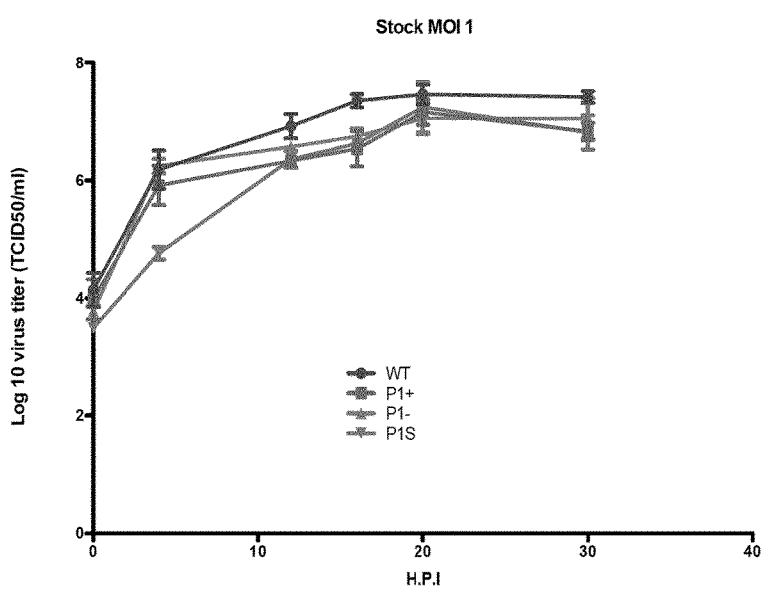
Figure 4C:
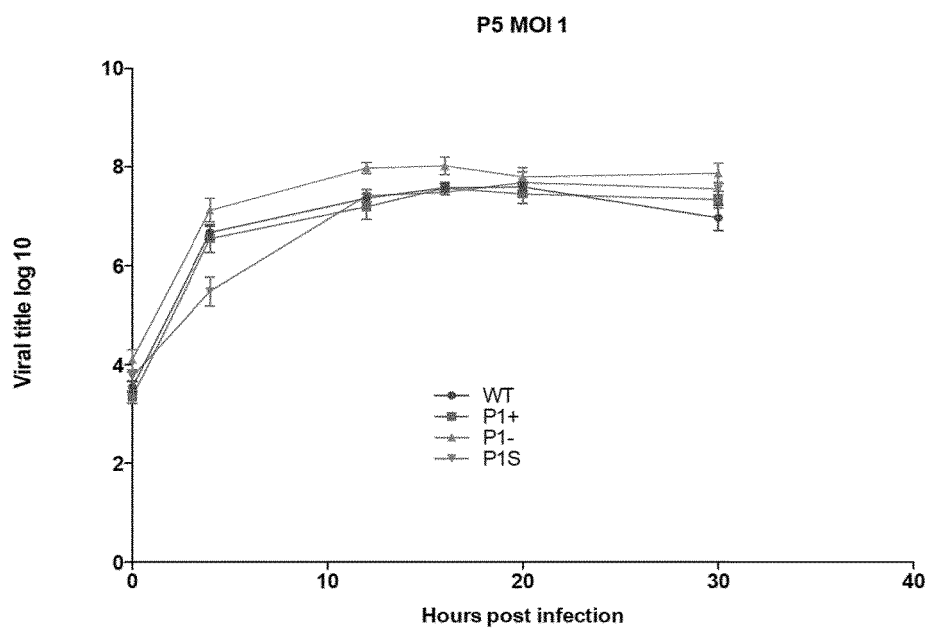

Next, we checked whether our variants retained wild-type-like replication dynamics under normal cell growth conditions. Both at low (0.1) and high (1) MOI, all viruses reached the same final viral titers and replicated with similar dynamics to wild-type (not significantly different), indicating that all constructs would be appropriate vaccine seeds for building larger virus stocks (FIGS. 4A and 4B). Interestingly, the P1S construct containing codons most likely to result in stop mutations (i.e., the 1-to-Stop construct) was the only variant to present significantly lower titers at the initial replication cycle (at 6 hours post infection). To test the genetic and phenotypic stability, each variant was passaged 5 times in HeLa cells, and a growth curve was performed using passage 5 stocks (FIG. 4C). Once more, each virus replicated similar to wild type and retained the same kinetics as the passage 1 stocks, confirming overall stability. Interestingly, the 'less' constructs (i.e., the Less-i constructs) designed to be more robust than wild type virus achieved the highest replicative capacity in the passage 5 stock.

Direct Evidence that Decreasing Mutational Robustness of a RNA Virus Results in Reduced Viability.

Figures 5A, 5B:
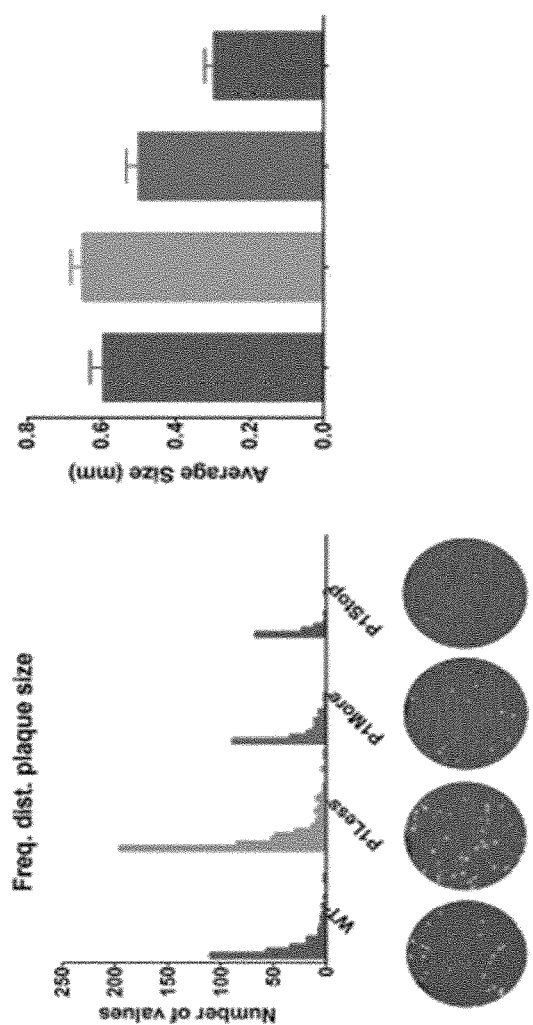
FIGS. 5A and 5B. Individual (5A) and average (5B) fitness of wild type and robustness variant populations, as measured by plaque size. HeLa cells were infected with serial dilutions of each virus population and standard plaque assay was performed. Plaques were then visualized and measured by ImageJ software (Rasband 1997-2014; Schneider et al. 2012; Abramoff et al. 2004). Each plaque was categorized according to size. (5A) The number of plaques (y-axis) presenting small->large plaques (y-axis) for each variant is shown. (5B) The average plaque size of the population was determined from values in (5A).

Theoretically, altering genetic robustness will render the virus population more or less sensitive to mutation and consequently, less or more fit. Since the ability of a virus to generate an infectious plaque in cell culture is a strong correlate of virus fitness, we measured plaque size for several hundred individual plaques from the wild-type and robustness variant populations (FIGS. 5A and 5B). In agreement with theory, wild type displayed a broad range of fitness (plaque sizes). The 'less' construct (i.e., the Less-i construct), expected to be more robust and have less negative impact of mutation presented more individual plaques of size that was even larger than wild type (higher fitness). The 'more' construct (i.e., the More-i construct), presented a wide range of fitness values, but not as wide as wild type, as expected since its volatile codons have a greater chance of resulting in non-compatible changes. Finally, the 'stop' population (i.e., the 1-to-Stop population) presented significantly smaller plaque sizes, indicative of low fitness variants or aborted replication, hypothetically the result of stop codons.

Figure 6:
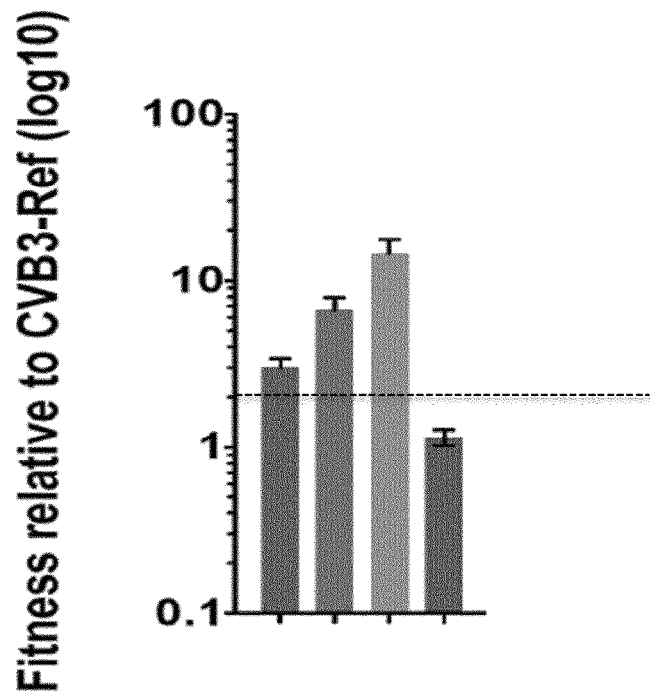
FIG. 6. Relative fitness of wild type (blue), 'more' (red), 'less' (green) and 'stop' (purple) constructs. The dotted line indicates the neutral fitness of the reference genome. From left to right: first bar=wild-type; second bar=More-i; third bar=Less-i; fourth bar=1-to-Stop.

To further confirm these presumed differences in fitness, more direct fitness assays in which each population was competed against a wild type-like neutral reference sequence and the relative fitness of each construct was determined using a well-established quantitative assay (Gnädig et al. 2012) (FIG. 6). The results confirm the neutral fitness of wild type, the higher fitness of 'more' viruses (i.e., of the More-i viruses) and the highest fitness of 'less' viruses (i.e., of the Less-i viruses). Importantly, the 'stop' construct (i.e., the 1-to-Stop construct) has significantly lower fitness than wild type.

Figure 7:
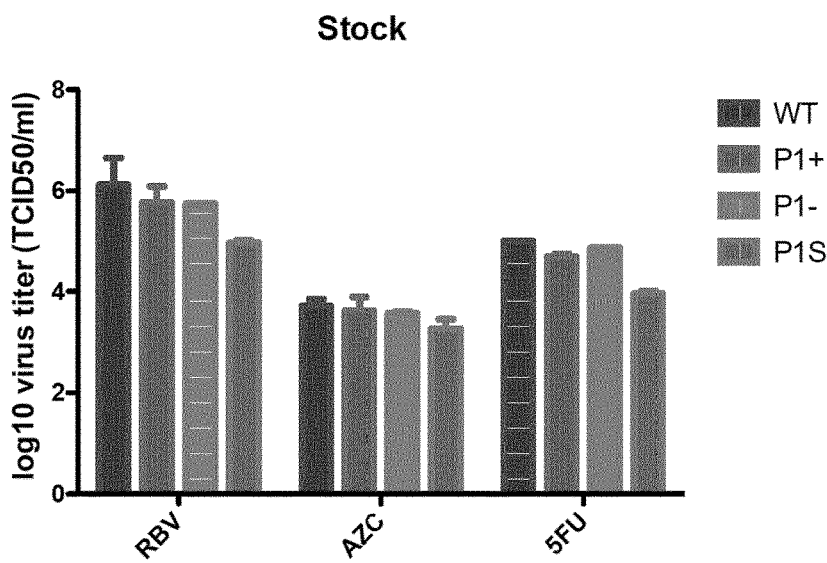
FIG. 7. Direct evidence of decreased mutational robustness by codon swapping. HeLa cells were treated with either ribavirin (RBV), 5-fluorouracil (5-FU) or 5-Azacytidine (AZC), infected with virus stocks, and the surviving infectious progeny virus was quantified by plaque assay. (WT=wild-type; P1+=More-i; P1−=Less-i; P1S=1-to-Stop; for each of RBV, AZC and 5FU, the bars are in the following order from left to right: WR; P1+; P1−; P1S).

Finally, to obtain direct evidence that the reduction in fitness observed for the 'stop' variant (i.e., of the 1-to-Stop variant) was indeed the result of an increased incidence of stop mutations, we compared the ability of each variant to grow under three mutagenic conditions (FIG. 7): ribavirin (RBV), which biases towards G-A and C-U transition mutations; 5-fluorouracil (5FU), which biases heavily towards U-C and A-G mutations; and 5-Azacytidine (AZC), which biases towards C-A and C-G mutations. Under these conditions in which the virus mutation frequency is artificially enhanced, the heightened sensitivity of the 'stop' construct (i.e., of the 1-to-Stop construct) is evident in all three treatments.

Figure 8:
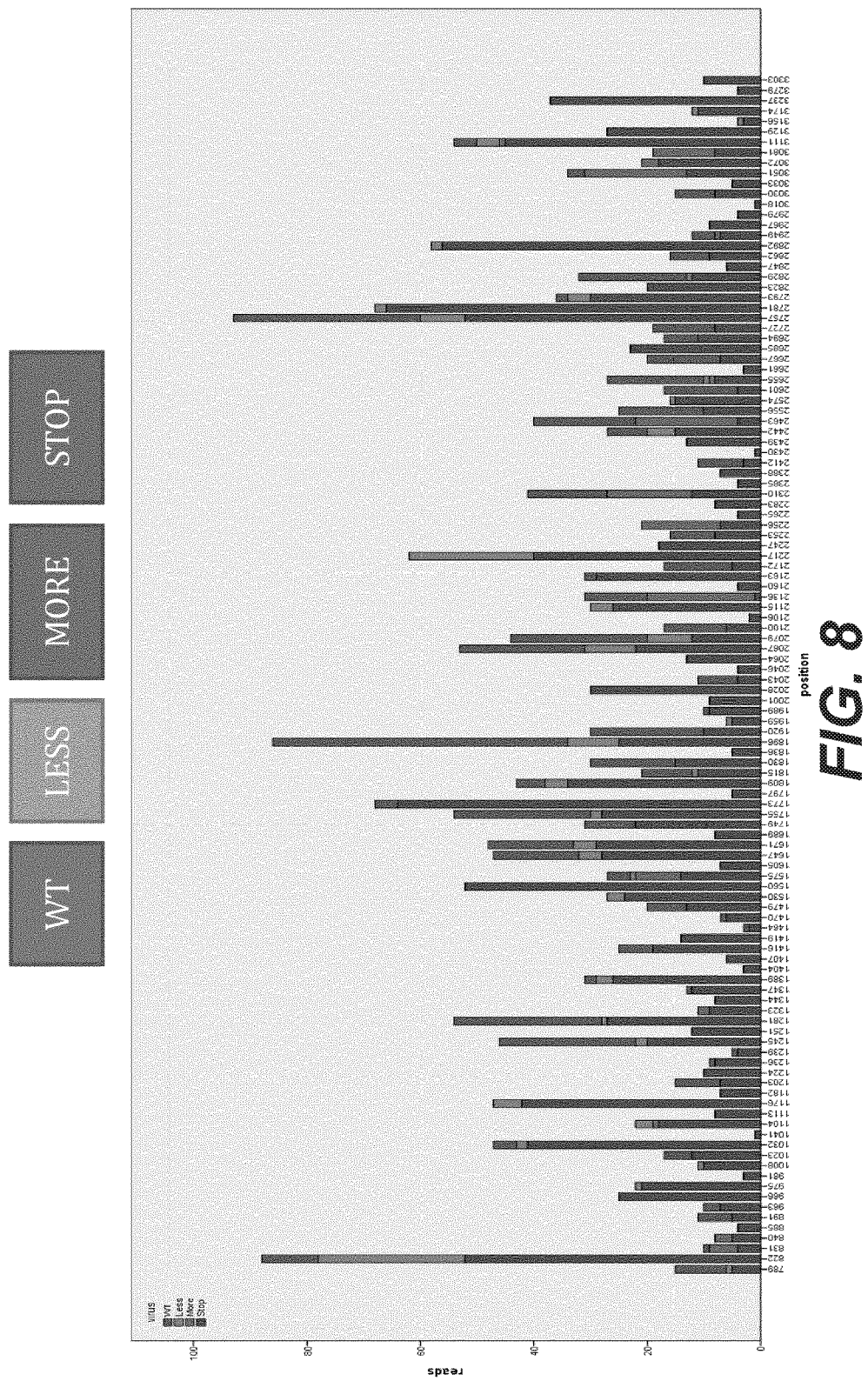
FIG. 8. Total number of STOP codons observed in the progeny virus populations. Deep sequencing was performed on wildtype (blue), 'less' (green), 'more' (red) and 'stop' (purple) viruses that were passaged for 5 generations in low mutagenic conditions. The total number of reads presenting Leu/Ser codons that have mutated into STOP codons were analyzed for the 117 altered sites in the P1 region. (WT=wild-type; P1+=More-i; P1−=Less-i; P1S=1-to-Stop).

To further confirm the link between the theoretical propensity of these constructs to mutate into STOP codons experimentally, we deep sequenced whole-genome virus populations that had been passaged under mutagenic conditions, and quantified the number of reads that had indeed mutated to STOP (FIG. 8, FIG. 11). As expected, wild type virus presented STOP mutations throughout the P1 region, as this virus naturally contains a proportion of Ser/Leu belonging to the 'stop' category (i.e., the 1-to-Stop category). On the other hand, 'less' and 'more' populations (i.e., the Less-i and More-i populations) presenting significantly fewer STOP mutations, as their codon usage no longer permits these mutations with just one nucleotide change. Importantly, the 'stop' virus population (i.e., the 1-to-Stop population) presented a significantly higher proportion of STOP mutations at every Ser/Leu codon in the P1 region; while it presented the same number of STOP mutations as wild type in the P2 and P3 regions, which were not genetically altered to modify mutational robustness (not shown).

Taken together these results demonstrate and confirm that the mutational robustness of a virus population can indeed be modified, without affecting protein sequence, replication and packaging of virus progeny.

Attenuation in Vivo by Reduction of Mutational Robustness.

Figure 9A:
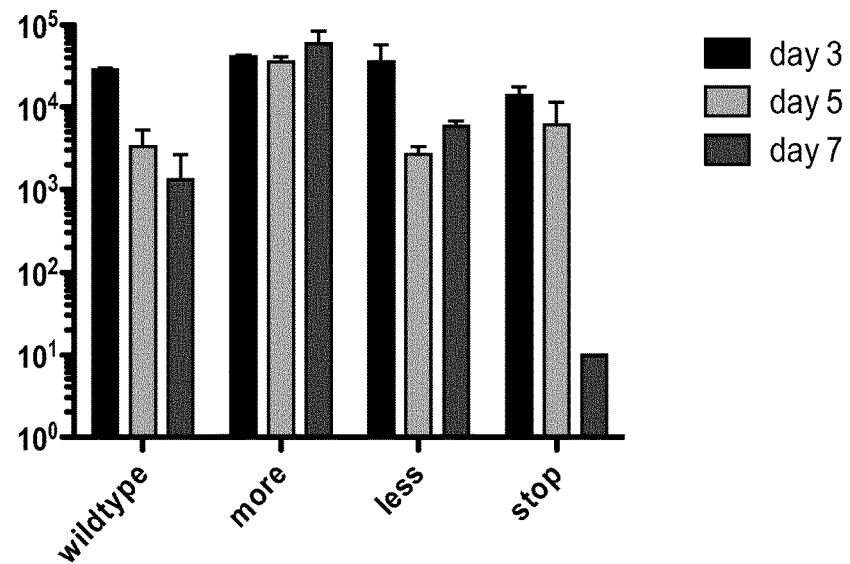
FIGS. 9A and 9B. Attenuation of Coxsackie virus B3 by reduction of mutational robustness. Mice were infected with $10^6$ PFU of each virus construct and the titers of progeny virus in the key target organs, heart (9A) and pancreas (9B), were determined by standard plaque assay. No virus was detected for day 7 'stop' construct, shown as value 10, the limit of detection. (WT=wild-type; more=More-i; less=Less-i; stop=1-to-Stop).
Figure 9B:
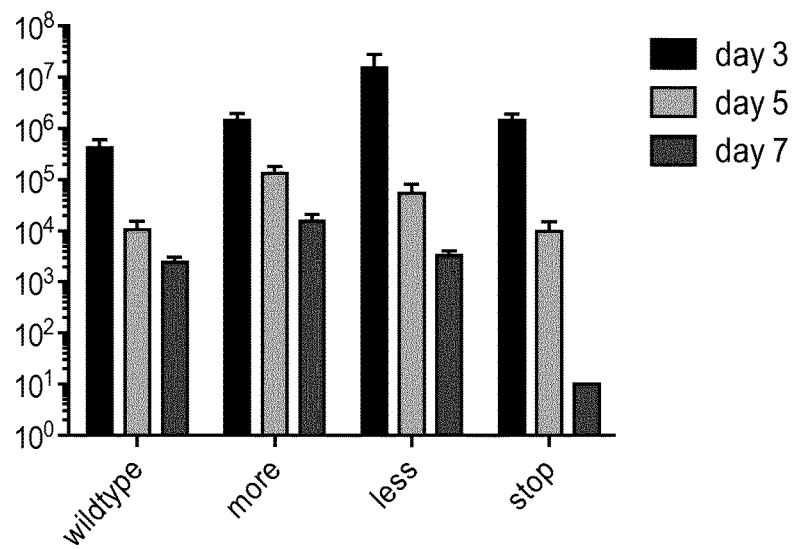
Figure 10:
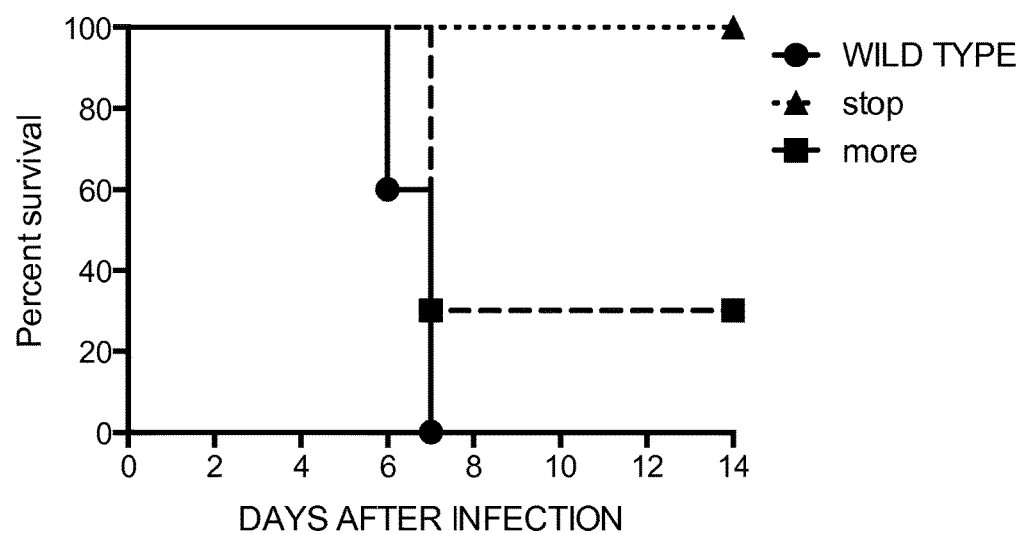
FIG. 10. Survival curve of mice infected with robustness variants. Mice were infected i.p. with $10^5$ TCID$_{50}$ in 0.20 ml of each virus population and survival was monitored over a 14 day period. x axis: percent survival; y axis: days after infection; stop=1-to-Stop; more=More-i.
Figure 11A:
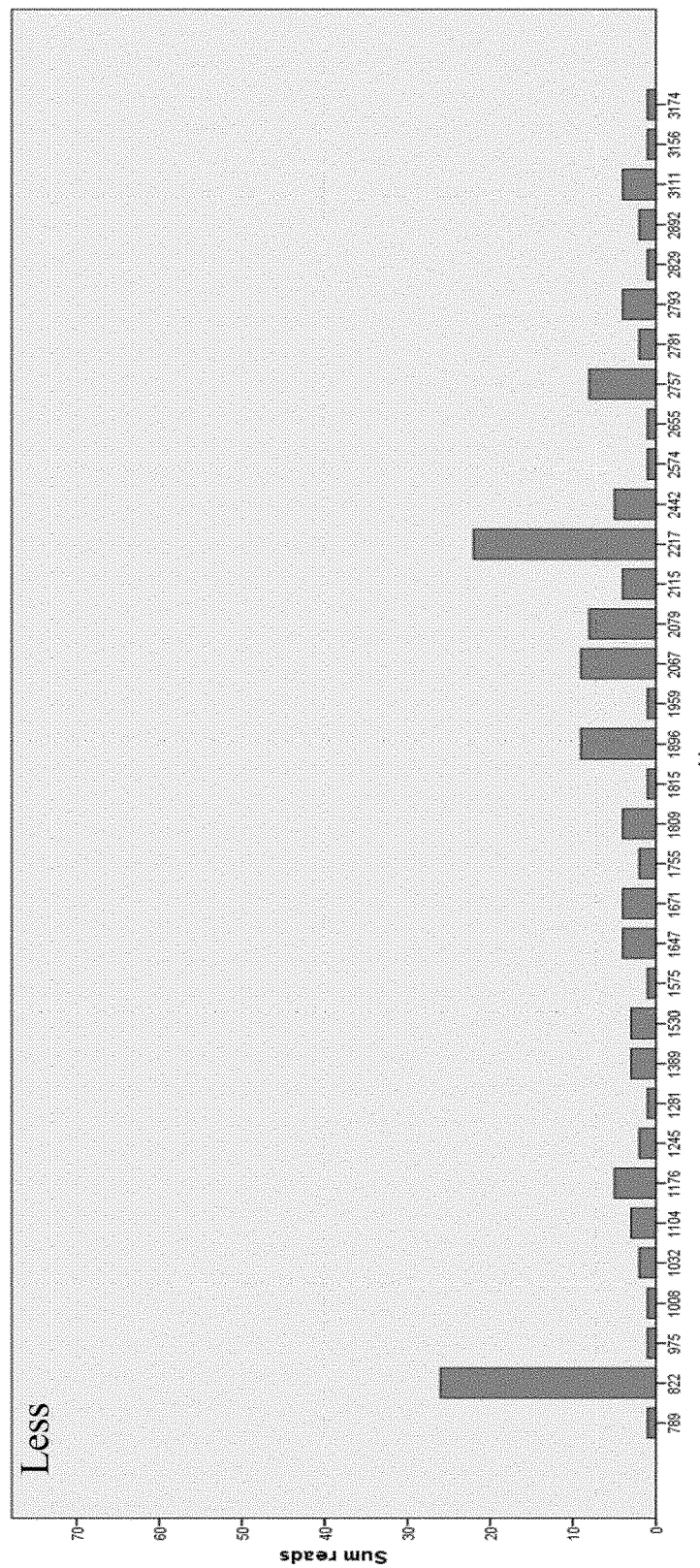
FIGS. 11A, 11B, 11C and 11D. Individual values for each construct of the number of STOP mutations presented in the progeny virus population.
Figure 11B:
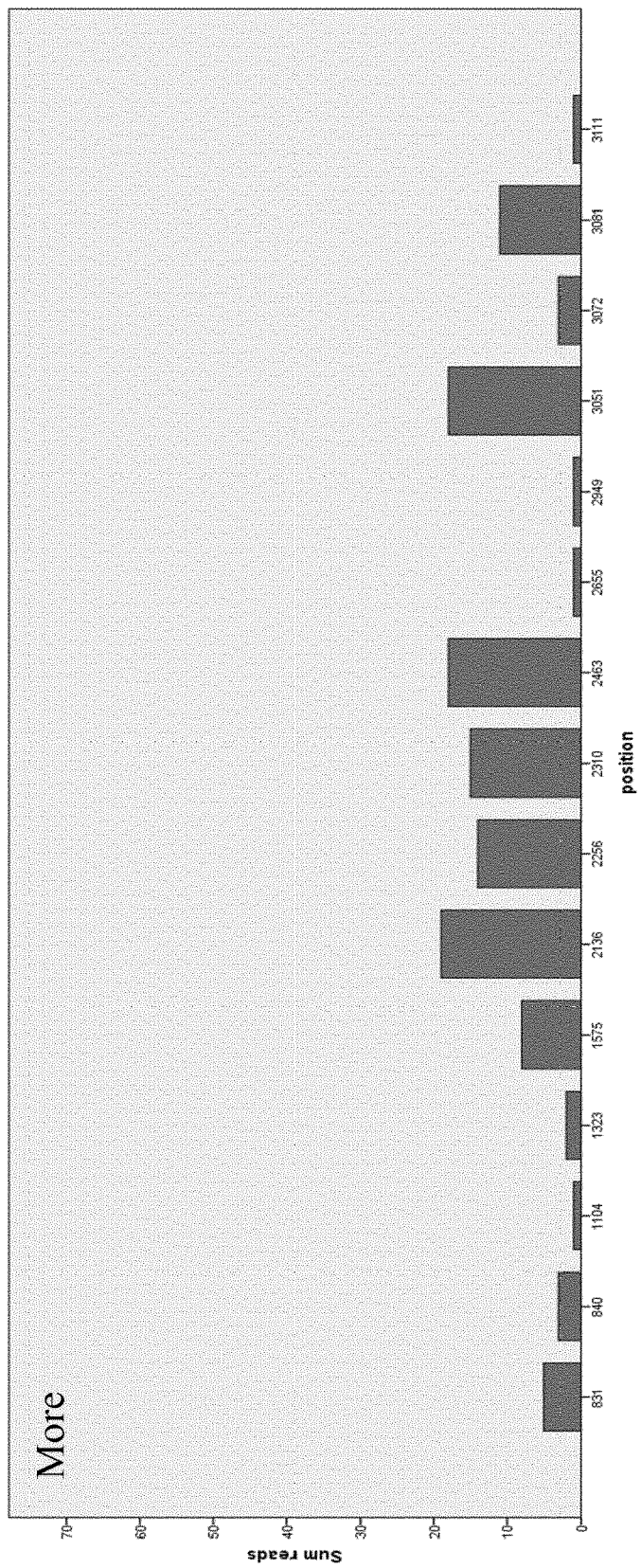
Figure 11C:
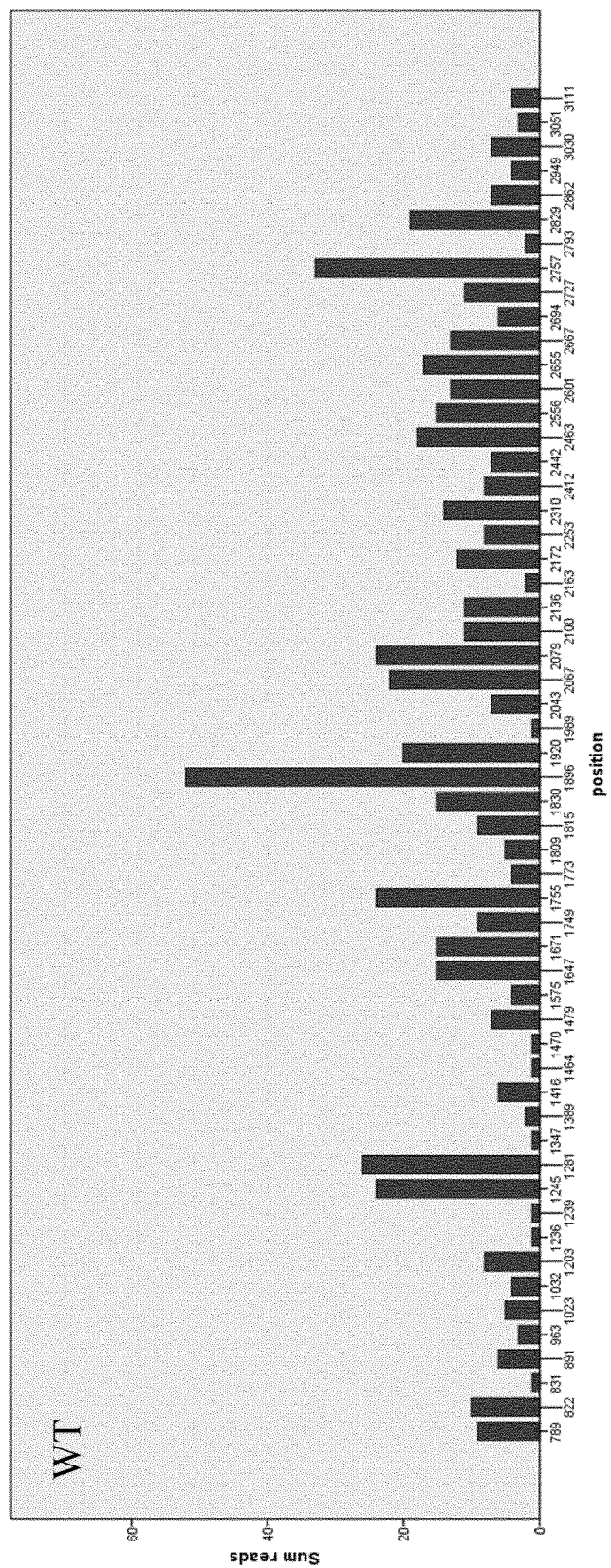
Figure 11D:
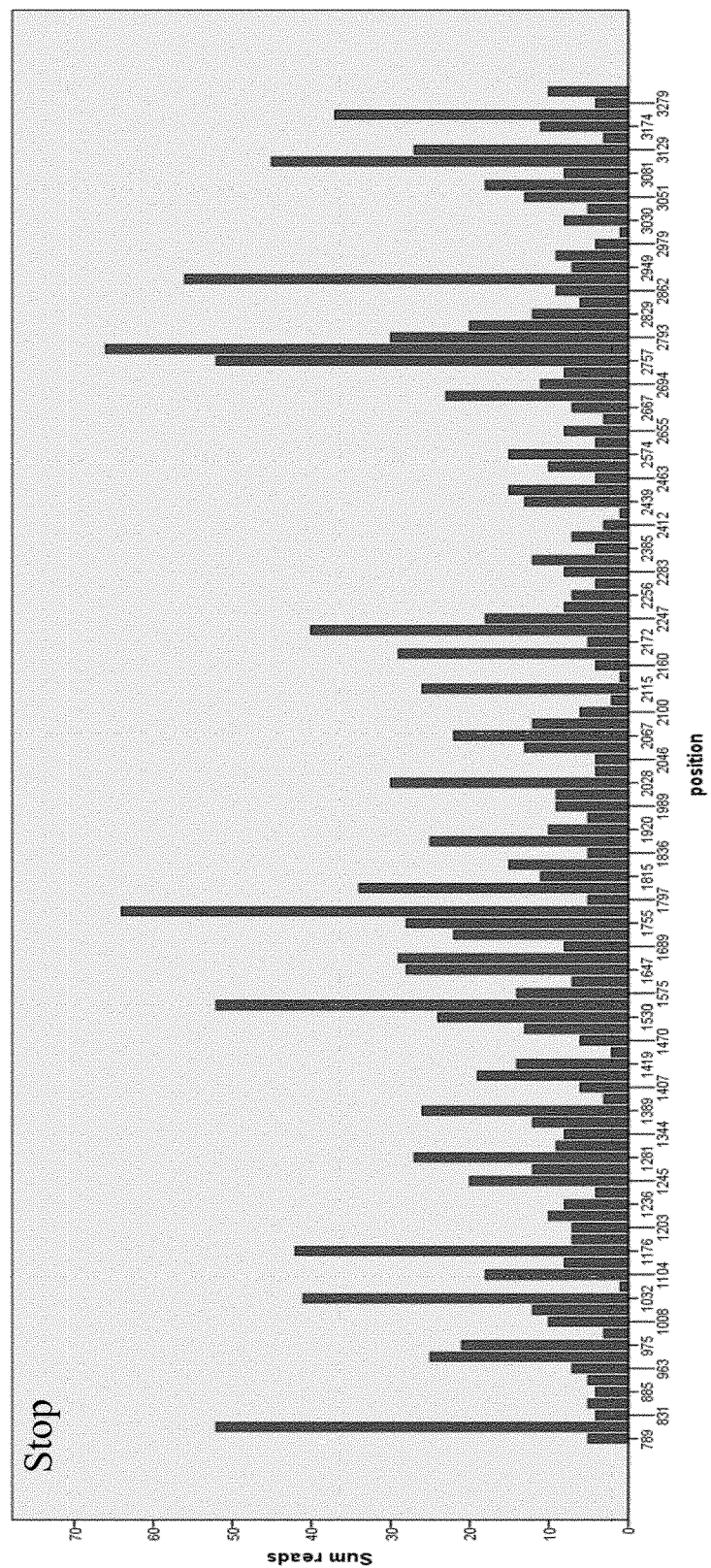

We next determined whether the 'stop' construct (i.e., the 1-to-Stop construct) with a confirmed decrease in mutational robustness was indeed attenuated in vivo. 3-4 week old mice were infected with $10^6$ PFU of wild type virus or each robustness variant and virus titer was determined during the one week course of acute infection (FIGS. 9A and 9B). Wild type virus presented high viral titers in both target organs throughout the infection, with a characteristic decline in titer of the seven day period. No significant differences were observed for the 'less' construct (i.e., for the Less-i construct). Interestingly, the 'more' construct (i.e., for the More-i construct) displayed a sustained level of intense replication throughout the seven day period, with values significantly higher than wild type. Importantly, the 'stop' construct replicated well for the first 5 days, but was undetectable in both organs by day seven, confirming that the reduction of robustness in this construct attenuates this virus.

To further confirm the attenuation of the 'stop' variant (i.e., of the 1-to-Stop variant) with reduced mutational robustness in vivo, mice were administered a lethal dose of wild type virus and the same dose of the 'more' and 'stop' variants (i.e., of the More-i and Less-i variants) and survival was monitored daily over a two week period. All mice infected with wild type virus succumbed to infection within seven days. For the 'more' construct which titered higher than wild type in our previous experiment (FIGS. 9A and 9B), 70% of mice succumbed to infection. Importantly, all of the mice that received the 'stop' construct survived infection.

Discussion

In this work, we provide direct proof that the mutational robustness of an organism can indeed be modified without altering the protein coding sequence. We show that increasing the theoretical robustness of an RNA virus ('less' construct) does result in a virus population that is more tolerant (resistant) to the effects of mutation. We also show that rendering a virus more plastic ('more' construct) results in a virus population that is significantly more diverse than wild type. Moreover, although most mutations in RNA viruses are expected to be detrimental, the overall greater diversity in this population may in some situations be beneficial—e.g., this population replicated better than wild type virus in the main target tissues in vivo.

The most significant aspect of this work is the biological confirmation that decreasing the theoretical robustness of an organism ('stop' construct) does in fact render the virus hyper-sensitive to its own already high mutation rates. In vivo, this virus population was significantly attenuated, did not cause disease in mice and was cleared by day seven post-infection. Our results show that decreasing robustness is a valid, novel approach to attenuate live virus vaccines. Because this approach is based on the universal genetic code, and since all RNA viruses have extreme mutation frequencies, this approach is applicable to any RNA virus for which reverse genetic and other engineering techniques are available.

It is expected that the degree of attenuation will be a function of the number of altered codons, such that an optimum between attenuation and replicative capacity can be determined for each virus. Furthermore, the large number of sites that can be altered while still maintaining viability (in this case, 117 codons) renders these vaccine candidates genetically stable. Unlike traditional live virus vaccines whose attenuation can be attributed to a few key nucleotides that can quickly revert to wild type (e.g., oral polio vaccines), these candidates are unable to do so, because each of the >100 codons contributes equally to the attenuation.

Finally, these studies were performed using a RNA virus with its naturally high mutation rate. An option to further adjust attenuation is to include fidelity altering amino acid changes that either increase or decrease mutation rates, as we have previously described (Gnädig et al. 2012). Coupling low replication fidelity with low robustness would further and more quickly attenuate a virus; while increasing fidelity would generate an even more genetically stable construct. For example, the 1-to-Stop construct can be coupled to a low-fidelity RNA-dependent RNA polymerase, such as the A239G, Y268W, I230F, Y268H, P48K or F232Y mutant of Coxsackie virus B3 RNA-dependent RNA polymerase (SEQ ID NOs: 15, 16, 17, 18, 19 or 20, respectively).

Example 2

Influenza Virus 1-to-Stop mutants of Influenza virus have been produced by applying the procedure described in example 1 to the infectious Influenza virus strain ATCC® VR-1737™ (Influenza virus type A subtype H1N1 [pdm09]).

Example 3

Yellow Fever Virus 1-to-Stop mutants of Yellow fever virus have been produced by applying the procedure described in example 1 to the infectious Yellow fever virus strain Asibi (GENBANK accession number AY640589).

Example 4

Chikungunya Virus 1-to-Stop mutants of Chikungunya viruses have been produced by applying the procedure described in example 1 to the infectious Chikungunya virus strain CHIKV 06-049 of the Indian Ocean Islands sub-lineage, within the ECSA (Eastern, Central and South African) lineage (GENBANK accession number AM258994 version 1), and to the following Chikungunya virus strains: strain 05-115 (GENBANK accession number AM258990 version 1), strain 05-209 (GENBANK accession number AM258991 version 1), strain 06-021 (GENBANK accession number AM258992 version 1), strain 06-027 (GENBANK accession number AM258993 version 1), strain 06-049 (GENBANK accession number AM258994 version 1), strain 05-061 (GENBANK accession number AM258995 version 1).

Example 5

1-to-Stop Mutants of COXSACKIE VIRUS (P1 Region) and of INFLUENZA VIRUS (PA Region); in Vivo Experiments Experimental Procedures Cells and viruses. HeLa and HEK293T cells (ATCC® CCL-2™ and ATCC® CRL-3216™) were maintained in DMEM medium (GlutaMAX™; SIGMA-ALDRICH Product #31966047, which is at 4.5 g/l D-glucose and which contains sodium pyruvate at 110 mg/l) with 10% new born calf serum, while MDCK and MDCK-SIAT cells (SIGMA-ALDRICH Product #85011435 and Product #05071502) were maintained in MEM medium (MEM with Earle's salts, L-glutamine and sodium bicarbonate; SIGMA-ALDRICH Product # M4655) with 5% foetal calf serum. Wild type Coxsackie virus B3 (Nancy strain; cDNA genomic sequence of SEQ ID NO: 1; cDNA CDS sequence of SEQ ID NO: 2) and SynSyn variants were generated from a pCB3-Nancy infectious cDNA plasmid. Wild-type Influenza A virus (A/Paris/2590/2009 (H1N1pdm09); ATCC® VR1337™) and SynSyn variants were generated from bidirectional reverse genetics plasmids (Hoffmann et al. 2000), provided by the Molecular Genetics of RNA Viruses unit at INSTITUT PASTEUR (Paris, France).

We generated Coxsackie and Influenza A 1-to-Stop viruses that bear 117 and 110 different synonymous codons, respectively, by "de novo" synthetic gene technology (EUROGENTEC). All newly generated DNA plasmids were Sanger sequenced in full (GATC Biotech) to confirm each of the 117/110-positions. The list of the codon changes introduced in Coxsackie virus is given in Table 1 above (cf. example 1). The low-fidelity 1-to-Stop virus was generated by insertion of the I230F mutation in the viral polymerase 3D gene by site-directed mutagenesis of the 1-to-Stop infectious clone.

The list of the codon changes introduced in Influenza virus is given in Table 5 below.

TABLE 5

| Position of the first nucleotide of the codon within SEQ ID NO: 49 (wildtype Influenza PA coding segment) | Wild-type (infectious) | 1-to-Stop | Coded amino acid |
|---|---|---|---|
| 46 | CTT | CTA | leucine |
| 124 | TTG | CTG | leucine |
| 145 | TCG | TCC | serine |
| 178 | TCA | TCT | serine |
| 193 | TCT | TCT | serine |
| 211 | CTA | CTA | leucine |
| 214 | TTG | CTG | leucine |
| 277 | AGT | TCT | serine |
| 316 | CTT | CTA | leucine |
| 325 | TTG | CTG | leucine |
| 394 | CTA | CTA | leucine |
| 418 | TCT | TCT | serine |
| 445 | TCA | TCT | serine |
| 487 | CTT | CTA | leucine |
| 499 | AGC | TCC | serine |
| 523 | CTT | CTA | leucine |
| 550 | AGT | TCT | serine |
| 556 | AGT | TCT | serine |
| 559 | CTA | CTA | leucine |
| 568 | TCC | TCC | serine |
| 580 | TCC | TCC | serine |
| 640 | CTT | CTA | leucine |
| 652 | AGT | TCT | serine |
| 655 | CTC | CTG | leucine |
| 670 | TCC | TCC | serine |
| 673 | AGC | TCC | serine |
| 676 | CTT | CTA | leucine |
| 736 | CTT | CTA | leucine |
| 739 | TCC | TCC | serine |
| 748 | TCA | TCT | serine |
| 781 | TTG | CTG | leucine |
| 802 | CTC | CTG | leucine |
| 808 | TTG | CTG | leucine |
| 823 | CTT | CTA | leucine |
| 838 | TCA | TCT | serine |
| 847 | CTG | CTG | leucine |
| 850 | CTG | CTG | leucine |
| 862 | CTG | CTG | leucine |
| 868 | TTA | CTA | leucine |
| 871 | AGT | TCT | serine |
| 886 | AGT | TCT | serine |
| 910 | CTA | CTA | leucine |
| 1003 | CTC | CTG | leucine |
| 1024 | CTA | CTA | leucine |
| 1033 | CTA | CTA | leucine |
| 1090 | AGC | TCC | serine |
| 1096 | TTG | CTG | leucine |
| 1108 | CTC | CTG | leucine |
| 1168 | CTT | CTA | leucine |
| 1183 | AGT | TCT | serine |
| 1204 | TCT | TCT | serine |
| 1207 | CTA | CTA | leucine |
| 1213 | AGC | TCC | serine |
| 1249 | TTG | CTG | leucine |
| 1258 | TCA | TCT | serine |
| 1261 | AGC | TCC | serine |
| 1273 | CTT | CTA | leucine |
| 1318 | AGC | TCC | serine |
| 1351 | TCC | TCC | serine |
| 1405 | TTG | CTG | leucine |
| 1408 | CTC | CTG | leucine |
| 1417 | TCC | TCC | serine |
| 1444 | CTG | CTG | leucine |
| 1459 | AGC | TCC | serine |
| 1498 | CTG | CTG | leucine |
| 1525 | TCT | TCT | serine |
| 1531 | TTG | CTG | leucine |
| 1564 | AGT | TCT | serine |
| 1576 | TCA | TCT | serine |
| 1579 | CTC | CTG | leucine |
| 1594 | CTG | CTG | leucine |
| 1627 | CTT | CTA | leucine |
| 1645 | CTC | CTG | leucine |

TABLE 5-continued

| Position of the first nucleotide of the codon within SEQ ID NO: 49 (wildtype Influenza PA coding segment) | Wild-type (infectious) | 1-to-Stop | Coded amino acid |
|---|---|---|---|
| 1648 | TTG | CTG | leucine |
| 1672 | TCG | TCC | serine |
| 1687 | CTA | CTA | leucine |
| 1711 | TCC | TCC | serine |
| 1753 | CTT | CTA | leucine |
| 1756 | CTT | CTA | leucine |
| 1762 | TCT | TCT | serine |
| 1765 | CTT | CTA | leucine |
| 1780 | AGC | TCC | serine |
| 1798 | TCT | TCT | serine |
| 1801 | TCT | TCT | serine |
| 1846 | TCG | TCC | serine |
| 1870 | TCA | TCT | serine |
| 1894 | TCT | TCT | serine |
| 1918 | TTA | CTA | leucine |
| 1921 | CTG | CTG | leucine |
| 1930 | TCT | TCT | serine |
| 1942 | AGT | TCT | serine |
| 1945 | CTA | CTA | leucine |
| 1954 | TCT | TCC | serine |
| 1963 | CTT | CTA | leucine |
| 1975 | TCG | TCC | serine |
| 1984 | TCG | TCC | serine |
| 1993 | TTG | CTG | leucine |
| 1996 | CTT | CTA | leucine |
| 1999 | CTC | CTG | leucine |
| 2014 | CTT | CTA | leucine |
| 2026 | CTG | CTG | leucine |
| 2047 | CTT | CTA | leucine |
| 2056 | CTA | CTA | leucine |
| 2080 | CTG | CTG | leucine |
| 2101 | TTG | CTG | leucine |
| 2104 | CTT | CTA | leucine |
| 2113 | TCT | TCT | serine |
| 2125 | TCC | TCC | serine |
| 2131 | CTC | CTG | leucine |
| 2143 | CTG | CTG | leucine |

Generation of Coxsackie Virus Stocks by in Vitro Transcription and Transfection. CVB3 cDNA plasmids were linearized with Sal I. Linearized plasmids were purified with the MACHEREY-NAGEL PCR purification kit. 5 μg of linearized plasmid was in vitro transcribed using T7 RNA polymerase (FERMENTAS). 10 μg of transcript was electroporated into HeLa cells that were washed twice in PBS (w/o $Ca^{2+}$ and $Mg^{2+}$) and resuspended in PBS (w/o $Ca^{2+}$ and $Mg^{2+}$) at $10^7$ cells/ml. Electroporation conditions were as follows: 0.4 mm cuvette, 25 mF, 700 V, maximum resistance, exponential decay in a BIO-RAD GenePulser XCell electroporator. Cells were recovered in DMEM (GlutaMAX™; SIGMA-ALDRICH Product #31966047, which is at 4.5 g/l D-glucose and which contains sodium pyruvate at 110 mg/l). 500 μl of p0 virus stocks were used to infect fresh HeLa cells monolayers for three more passages. For each passage, virus was harvested by one freeze-thaw cycle and clarified by spinning at 10 K rpm for 10 minutes. Three independent stocks were generated for each virus. Consensus sequencing of virus stocks used in downstream experiments confirmed the stability of the engineered mutations and did not detect any additional mutations across the genome.

Generation of influenza A virus stocks by reverse genetics. Using 35 mm plates and DMEM (GlutaMAX™; SIGMA-ALDRICH Product #31966047, which is at 4.5 g/l D-glucose and which contains sodium pyruvate at 110 mg/l) supplemented with 10% FCS, co-cultures of 293T ($4.10^5$/well) and MDCK cells ($3.10^5$/well) were transfected with the eight bidirectional plasmids both driving protein expression and directing vRNA template synthesis, using 0.5 mg of each plasmid and 18 μl of FUGENE HD (ROCHE). DNA and transfection reagent were first mixed, then incubated at room temperature for 15 min, and finally added to cells, which were then incubated at 35° C. Sixteen hours later, the DNA-transfection reagent mix was removed, cells were washed twice in DMEM, and 2 mL of DMEM containing 1 μg/ml of L-1-tosylamido-2-phenyl chloromethyl ketone treated trypsin (TPCK-trypsin, Sigma-Aldrich) were added. Cells were incubated at 35° C. for 2 more days, supernatants were collected and clarified, and virus was titrated by $TCID_{50}$ as described below. Three independent stocks were generated for each virus. Consensus sequencing of virus stocks used in downstream experiments confirmed the stability of the engineered mutations and did not detect any additional mutations across the genome.

Viral titres by $TCID_{50}$. Ten-fold serial dilutions of virus were prepared in 96-well round bottom plates in serum-free DMEM media. Dilutions were performed in 12 replicates and 100 μl of dilution were transferred to $10^4$ Vero cells (ATCC® CCL-81™) for Coxsachie virus or to $10^4$ MDCK (ATCC® CCL-34™) for Influenza A virus, plated in 100 μl of DMEM. After 5 days living cell monolayers were coloured by crystal violet.

Viral titres by plaque assay. HeLa cells (ATCC® CCL-2™)—for Coxsackie virus—or MDCK-SIAT cells (SIGMA-ALDRICH product #05071502)—for Influenza A virus-were seeded into 6-well plates and virus preparations were serially diluted (10-fold) in DMEM free media. Cells were washed twice with PBS and infected with 250 μl of dilution for 30 minutes at 37° C., after which a solid overlay comprising DMEM medium and 1% w/v agarose (INVITROGEN) was added. 2 days after infection, cells were fixed and stained with crystal violet 0.2%, and plaques were enumerated.

Replication kinetics and quantification of total viral genomes. For growth kinetics, HeLa cells (for Coxsackie virus) or MDCK cells (for Influenza A virus) were infected at MOI of 1, frozen at different time points after infection, and later, tittered by $TCID_{50}$ assay. Coxsackie viruses were harvested by one freeze-thaw cycle and Influenza A viruses were harvested in clarified supernatant. For qRT-PCR analysis, total RNA from infected cell supernatants was extracted by TRIzol reagent (INVITROGEN) and purified. The TaqMan RNA-to-$C_t$ one-step RT-PCR kit (APPLIED BIOSYSTEMS) was used to quantify viral RNA. Each 25-μL reaction contained 5 μL RNA, 100 μM each primer (forward 5"-GCATATGGTGATGATGTGATCGCTAGC-3" SEQ ID NO: 22 and reverse 5"-GGGGTACTGTTCATCTGCTCTAAA-3" SEQ ID NO: 23), and 25 pmol probe 5"-[6-Fam]-GGTTACGGGCTGATCATG-3" (SEQ ID NO: 24) in an ABI 7000 machine. Reverse transcription was performed at 50° C. for 30 min and 95° C. for 10 min, and it was followed by 40 cycles at 95° C. for 15 s and 60° C. for 1 min. A standard curve ($y=-0.2837x+12{,}611$; $R^2=0.99912$) was generated using in vitro-transcribed genomic RNA.

Viral passages under mutagenic conditions. The mutagenic compounds (SIGMA ALDRICH) used were:

Ribavirin IUPAC 1-[(2R,3R,4S,5R)-3,4-dihydroxy-5-(hydroxy-methyl)oxolan-2-yl]-1H-1,2,4-triazole-3-carboxamide); 50, 100 and 200 μM for Coxsackie viruses; 5 and 20 μM for influenza A viruses;

5-Fluorouracil IUPAC 5-fluoro-1H-pyrimidine-2,4-dione; 50, 100 and 200 µM for Coxsackie viruses; 5 and 30 µM for influenza A viruses;

5-Azacitidine IUPAC 4-amino-1-b-D-ribofuranosyl-1,3,5-tria-zin-2(1H)-one; 50, 100 and 200 µM for Coxsackie viruses; 5 and 15 µM for influenza A viruses;

Amiloride IUPAC 3,5-diamino-6-chloro-N-(diaminomethylene) pyrazine-2-carboxamide; 100 and 200 µM for Coxsackie viruses;

Manganese (Mn2+); 0.5 mM and 1 mM for Coxsackie viruses.

HeLa (Coxsackie virus) or MDCK (influenza A virus) cell monolayers in 6-well plates were pretreated for 4 hours with ribavirin, AZC, 5FU, MnCl2 and amiloride compounds with different concentrations. Cells were then infected at an MOI=0.1 for Coxsackie and 0.001 for influenza A virus with passage 2 viruses. 48 hours postinfection, Coxsackie viruses were harvested by one freeze-thaw cycle and influenza A viruses were harvested in clarified supernatant. Virus titres (TCID$_{50}$ or plaque assay) were determined. The same procedure was performed for five passages under each different mutagenic condition in three biological replicates, except for Influenza A viruses that were passaged only in low mutagenic conditions in ribavirin, 5-fluorouracil and 5-azacytidine.

Measurement of plaque size. Coxsackie virus plaque measurements were performed on sub confluent monolayers of 10$^7$ HeLa cells in 10 cm dishes. To ensure non-overlapping plaques the amount of virus was determined empirically (40-70 per dish for Coxsackie). Each plate was scanned individually after 30 h post infection at 300 dpi. Sixteen bit image files were analysed using ImageJ™. The same protocol was used to measure the plaque phenotype of pretreated viral populations. WT and 1-to-Stop viruses were submitted to high concentrations of Ribavirin, 5FU and AZC, and time post infection was increased to 40 h in order to better recover viral viability to perform plaque measures.

Quantitative measurement of fitness. For Coxsackie virus, relative fitness values were obtained by competing each WT and 1-to-Stop virus, obtained from different passages under each different mutagen/compound assay, with a marked reference virus that contains four adjacent silent mutations in the polymerase region introduced by direct mutagenesis. Co-infections were performed in triplicate at MOI of 0.01 using a 1:1 mixture of each variant with the reference virus. After 24 h, supernatants were harvested and a mix 1:1 with TRIzol reagent (INVITROGEN) was performed to keep the viral RNA. The proportion of each virus was determined by real time RT-PCR on extracted RNA using a mixture of TAQMAN™ probes labelled with two different fluorescent reporter dyes. MGB_CVB3_WT detects WT and 1-to-Stop viruses with the sequence CGCATCGTACCCATGG (SEQ ID NO: 25), and is labelled at the 5' end with a 6FAM dye (6-carboxyfluorescein) and MGB_CVB3_Ref containing the four silent mutations; CGCTAGCTACCCATGG (SEQ ID NO: 26) was labelled with a 5' VIC dye. Each 25 µL-reaction contained 5 µL RNA, 900 nM each primer (forward primer, 5"-GATCGCATATGGTGATGATGTGA-3"(SEQ ID NO: 27); reverse primer, 5"-AGCTTCAGC-GAGTAAAGATGCA-3"(SEQ ID NO: 28)), and 150 nM each probe. Using a known standard for the WT and reference virus during the q-RT-PCR we were able to calculate the RNA concentration for each viral variant with high sensitivity. The relative fitness was determined by the method described in the work by Carrasco et al. 2007, using the RNA determinations for each virus. Briefly, the formula $$W = \left[\frac{R(t)}{R(0)}\right]^{1/t}$$

represents the fitness W of each mutant genotype relative to the common competitor reference sequence, where R(0) and R(t) represent the ratio of mutant to reference virus densities in the inoculation mixture and t days post-inoculation (1 day in this case), respectively. It is important to mention that the fitness of the normal WT to reference virus was 1.019, indicating no significant differences in fitness caused by the silent mutations engineered in the reference virus (competitor).

Mouse husbandry and ethics. Mice were kept in the animal facilities of INSTITUT PASTEUR (Paris, France) in biosafety level 2 conditions, with water and food supplied ad libitum, and they were handled in accordance with the Animal Committee regulations of INSTITUT PASTEUR (Paris, France) in accordance with the directive EU 2010/63 adopted on 22 Sep. 2010 by the European Parliament and the European Union Council. Mouse protocols 2013-0101 and 2013-0021 were evaluated and approved by the Ethics Committee on Animal Experimentation CETEA no. 89 (INSTITUT PASTEUR), working under the French national Ministère de l'Enseignement Supérieur et de la Recherche (MESR). All studies were carried out in BALB/c male mice between 5 and 6 week old.

Coxsackie virus infections in vivo. Mice were infected intra-peritoneally with 10$^5$ TCID$_{50}$ WT or 1-to-Stop viruses in 0.20 ml. For tissue tropism studies, we harvested whole organs (spleen, pancreas and heart) 3, 5 and 7 days post infection and homogenized them in PBS using a Precellys 24 tissue homogenizer (BERTIN TECHNOLOGIES). Viral RNA was extracted using TRIzol reagent (INVITROGEN). Full genome PCR, viral titres by TCID$_{50}$ as well as real-time PCR, was performed as described above. Survival curves were generated by injecting 4-week-old mice (n=8 mice per virus) with 5×10$^6$ TCID$_{50}$ of virus and monitoring morbidity and mortality for 10 days after infection. For protection studies, mice were immunized with PBS or 5×10$^5$ TCID$_{50}$ of 1-to-Stop or 1-to-Stop$^{LowFi}$ virus. 21 days after immunization serum was collected to quantify the production of neutralizing antibodies. Mice were then challenged with 1×10$^6$ of wild-type virus (hyper virulent strain 372V of wild type Coxsackie virus B3) and survival was monitored over the following 10 days.

Neutralization assay. At 3 weeks after immunization, serum was collected and serially diluted with DMEM and heat-inactivated at 56° C. for 30 min, while the CVB3 stock was diluted to a working concentration of 3×10$^3$ TCID$_{50}$. Neutralizing antibody titers were determined by TCID$_{50}$ reduction assay in Vero cells, 50 µL of each diluted serum sample was mixed with 50 µL of CVB3 at working concentration and added to 96-well plates for incubation at 37° C. for 2 h. Following the incubation, 8 replicates of each dilutions were used to infect 10$^4$ Vero cells seeded in a 96-well plate. At 6 days post-infection, the cells were observed under a microscope for the presence of CPEs. Neutralization titers were determined as the highest serum dilution that could prevent CPE in >50% of cells.

Influenza virus infection in vivo. Mice were anesthetized and infected intra-nasally with 10$^5$ TCID$_{50}$ WT or 1-to-Stop viruses in 20 microliters (diluted in PBS). Lungs and trachea were harvested at three and five days post infection and were homogenized in PBS using a Precellys 24 tissue homogenizer (BERTIN TECHNOLOGIES). Infectious virus within homogenized tissues was titrated by plaque assay and titers were expressed as plaque-forming units per gramme of organ (pfu/g). Viral RNA was extracted using TRIzol reagent (INVITROGEN). Virus genomic variability was evaluated by deep sequencing, as described below, but targeting only the PA segment of positive samples.

Full genome analysis by deep sequencing. To estimate the population diversity of variants by deep sequencing, Coxsackie virus cDNA libraries were performed using the kit Maxima H Minus First Strand cDNA Synthesis (THERMOFISHER) and oligo dT as a primer from RNA extracted from virus generated in HeLa cells or different mouse organs. The viral genome was amplified using a high fidelity polymerase (PHUSION®) to generate an amplicon of 7.2 kb in length (full-length genome). The primers and PCR were designed and optimized in the lab (5'-GAAAACGCGGGGAGGGTCAAA-3' (SEQ ID NO: 29) and 5'-ACCCCCTCCCCCAACTGTAA-3' (SEQ ID NO: 30)). For influenza A virus harvested after five serial passages in mild mutagenic conditions, viral RNA genome was extracted for infected-cell supernatants (MACHEREY-NAGEL), reverse transcribed with Accuscript High Fidelity 1st strand cDNA Synthesis kit (AGILENT) using 5'-AGCRAAAGCAGG-3' (SEQ ID NO: 31) primer (where R=A or G), and amplified by PCR using PHUSION® High-Fidelity DNA Polymerase (THERMOSCIENTIFIC). Eight PCRs were designed to cover the coding regions of the eight genomic segments (PB2, PB1, PA, HA, NP, NA, M and NS). The primer sets, one per genomic segment, were used on the two contructed viruses (wildtype; 1-to-Stop). The sequences of the primers are:

```
PB2
>H1N1s/pPB2-2f
                                    (SEQ ID NO: 32)
GCAAAAGCAGGTCAATTATATTC

>H1N1pPN2-2333r
                                    (SEQ ID NO: 33)
CAAGGTCGTTTTTAAACAATTCG

PB1
>H1N1pPB1-3f
                                    (SEQ ID NO: 34)
CAAAAGCAGGCAAACCATTT

>H1N1pPB1-2302r
                                    (SEQ ID NO: 35)
TTCATTATTTTTGCCGTCTGAG

PA
>H1N1pPA-1f
                                    (SEQ ID NO: 36)
AGCAAAAGCAGGTACTGATCCA

>H1N1pPA-2216r
                                    (SEQ ID NO: 37)
TTTTTGGACAGTATGGATAGCAAA

HA
>H1N1pHA-4f
                                    (SEQ ID NO: 38)
AAAAGCAGGGGAAAACAAAAG

>H1N1pHA-1770r
                                    (SEQ ID NO: 39)
ACAAGGGTGTTTTTCTCATGCT

NP
>H1N1s/pNP-2f
                                    (SEQ ID NO: 40)
GCAAAAGCAGGGTAGATAATCA
```

-continued

```
>H1N1pNP-1561r
                                    (SEQ ID NO: 41)
GAAACAAGGGTATTTTTCCTCAAC

NA
>H1N1pNA-7f
                                    (SEQ ID NO: 42)
AGCAGGAGTTTAAAATGAATCC

>H1N1pNA-1425r
                                    (SEQ ID NO: 43)
TGTCAATGGTAAATGGCAACTC

M
>H1N1pM-23f
                                    (SEQ ID NO: 44)
AAGATGAGTCTTCTAACCGAGGTC

>H1N1pM-987r
                                    (SEQ ID NO: 45)
CAAAATGACCATCGTCAACATC

NS
>H1N1pNS-2f
                                    (SEQ ID NO: 46)
GCAAAAGCAGGGTGACAAA

>H1N1pNS-860r
                                    (SEQ ID NO: 47)
ATAAGCTGAAACGAGAAAGCTC
```

For mouse organs, RNA was extracted with TRIzol reagent (INVITROGEN) and only PA was targeted by PCR. The PCR products were fragmented (Fragmentase), multiplexed, clustered, sequenced in the same lane with ILLUMINA cBot and GAIIX technology and analysed with established deep sequencing data analysis tools and in house scripts.

Codon frequencies. The sequenced reads for each sample were aligned to their respective reference genomes using BWA (Li 2013). Per-site codon frequencies were estimated for each sample by considering the reads covering the given site. Only reads with all Phred base quality scores within the codon exceeding 30 were used. The ML (Maximum Likelihood) estimates of the codon frequencies, based on number of observed codon counts and their quality scores, were then computed numerically.

Heat map reconstruction. Each row in the heat maps shows a single sample. The samples are grouped by construct. The color intensity depicts the log-transformed mean codon frequencies for all 64 codons over the 117 (Coxsackie virus) or 110 (Influenza virus) codon sites that were changed in the constructs.

Stop codons. The mean frequency of observed stop codons were computed for all wild type and 1-to-Stop samples, where the mean was taken over the 117/110 modified positions. Box plots are used to show the frequency distribution over the wild type and 1-to-Stop samples respectively.

Fitness distribution graphs. Histograms showing empirical fitness values with the samples grouped by construct and mutagenic conditions were generated. The difference in fitness (ΔFitness) between pairs of wild type and 1-to-Stop codons from the same experimental conditions were also computed and shown in histograms, again grouped by mutagen.

Virus sequence data. The Coxsackie virus sequence data are provided in example 1 above. The Influenza virus sequence data are as follows.

Wildtype Influenza PA Segments:

>wildtype genomic RNA (vRNA) PA sequence
coding protein PA and protein PA_X          (SEQ ID NO: 48)
5'-

AGUAGAAACAAGGUACUUUUUUGGACAGUAUGGAUAGCAAAUAGUAGCAU

UGCCACAACUACUUCAGUGCAUGUGUGAGGAAGGAGUUGAACCAAGAUGC

AUUAAGCAAAACCCAGGGAUCAUUAAUCAGGCACUCCUCGAUUGCUUCAU

AUAGCCCCCAAGAUCGAAGGUUCCAGGUUCCAGGUUGUCCCUAAGUGCC

UGAACAAUGAGAAGCAAUUUUCUCGAUUCAGCCGAAAACCCCUCAAGUUG

UGGAGACGCAUAUAGACUGUUGAAUACAGAUUUUGCCAGUAAGGUCCUGC

ACACUUUCCCAAUAGAGCCUUCCUCCACUCCCCGGGUGACUCUCCGAUU

GGCCAUGUUUCCGAUUUGUUUUCAAAGAAUUCCUUGGUCAUGUCUUUCUC

UUUGACAGAAGACUCGGCCUCAAUCAUGCUCUCAAUCUGCUGAAGAGACU

GAAGAAGGCAGCGCCUCAUUUCCAUGCCCCAUUUCAUCUUGAUCUUGGAG

GUUCCAUUGGUUCUCACAUAUAGGAACAUGGGCCUCGACACUUGGCCUAU

CGCAGUCCUCAAGAGCAUGUCUCCUAUUUCAAGAACACAGUAUUUUUCCC

AUUUGUGUGGCUCCAGUCUCGGGUCAGUGAGUGAGAACUCCAUACUUACA

AAGUUCACCACAUCAGUAUCAUUUCUCAAAUGAGACCUUCCUUUUAUAAU

GAACCCAUACAGGUUUGUUUUCCGUCUUCCUUCUUUGGUCCUACAUUUGC

UUAUCAUUGGGAUCAGCUGAAAGUCAUCCAUGGCUGCACAGGAUGCAUUG

AGCAAGGCCGUAUUUAUGUACACUCCCUUCAUUAUGUAUUCAGUAGCCU

GCAGUGGACACUUCUGCUGUAAAAUAGUUCCUCCUCAUGCUUGCGAUAU

GUUCAAUCGGGGCAACAUCUUCUCCUAUUUCAUCAAGUUCUAUCCAGCUU

GAAUCAGUCAAUUCACAUGCCUUAUUGAAUUCAUUUUGGACCCAGCUUGC

UAGAGAUCUGGGCUCUGGCUCAUCACUGUCAUACUGUUUAAGGUCUCCAA

CAUCUUUGCAGUCAUCAAAGUCUACUUUUUCGGUGCCAUAUUUUCACCG

AGUGCCCACUUCAAUUGGCUUGUUCUCUUCAUGUUCUUUGUCCUUGGGAU

CUUCUCUUCAUUUUCAAUGUCCUGUAGCUCUGCUAGCACUUGCUUCCAAG

CCAUGAGGUAAUUGGGAUUUAUGCCUUUCCCAUGUGGUUUGACUAUGUUA

GGCUCUUUCCAGCCAAAGAAUGUCUUCAUGCAUUUGAUUGCAUCAUAUAG

UGGUAUUCCCUCCCCCUCGUGACUCGGGUCUUCAAUACUUAAUUUCAGAG

CAUCCAUCAGCAGGAACUUUGACCGCUGAUGGCAAAGAGGCCCAUCAGGC

AAUCUGAGGGGCGUGGUGUCGUCCUCAAGAAUGGUUCAAUUUUGGCGUU

CACUUCUUUUGACAUUUGGGAAAGCUUGCCCUCAAUGCAGCCGUUCGGCU

CGAAUCCAUCUACAUAGGCUCUAAAGUUUUCAAGGCUGGAGAAGUUCGGU

GGGAGACUUUGGUCGGCAAGCUUGCGCAUAGUUCCUGUAAUCUCAAAUUU

UUCUUCAAUUGUCUCUUCGCCUCUUUCGGACUGACGAAAGGAAUCCAUA

GACUCCUACUGGCCAUUUCUUGUCUUAUAGUGAAAAGCCUAGUUUUGAUU

CUUGCCCUGCUCUUCGUCAAGGGUGUAGUCCGCUUUGGUGGCCAUCUC

CUCUCCAGUGAAUGAAAGAUGUGAAUGUGUGUCUUCUCAGAUUUUAUUU

UGUUGGCUUUCUCUAGGUAAUAUAUGUGGACUUCCCUCCGUGUUACUCCA

AUUUCAAUGAACCGGUUCUCUUUGUAAUCAUACAAAUCAGGAAGAAAUUU

AGGCUUCUCUACCCCUGUUGUGUUACAUAUACUGUUCACCACUGUCCAGG

CCAUGAUUCGGUCUCUUCCUUCAAUUAUCUCAAAUCGGUGCUUCAAUAGU

GCAUUCGGGUCACCAGAUUCUACAAUUAUUGAUUCACCCCGUUCGUCGAU

GAAAUGGAAAUCCGAAUACAUGAAACAAACUUCCAAAUGUGUGCAUAUUG

CAGCAAACUUGUUAGUUUCGAUUUUCGGAUCUUCCCCAUAUUCUUUCAUU

GCCUUUUCCGCAAGCUCGACGAUCAUUGGAUUGAAGCAUUGUCGCACAAA

GUCUUCCAUUUUGGAUCAGUACCUGCUUUCGCU

>PA_CDS                                     (SEQ ID NO: 49)
coding protein PA
5'-

ATGGAAGACTTTGTGCGACAATGCTTCAATCCAATGATCGTCGAGCTTGC

GGAAAAGGCAATGAAAGAATATGGGGAAGATCCGAAAATCGAAACTAACA

AGTTTGCTGCAATATGCACACATTTGGAAGTTTGTTTCATGTATTCGGAT

TTCCATTTCATCGACGAACGGGGTGAATCAATAATTGTAGAATCTGGTGA

CCCGAATGCACTATTGAAGCACCGATTTGAGATAATTGAAGGAAGAGACC

GAATCATGGCCTGGACAGTGGTGAACAGTATATGTAACACAACAGGGGTA

GAGAAGCCTAAATTTCTTCCTGATTTGTATGATTACAAAGAGAACCGGTT

CATTGAAATTGGAGTAACACGGAGGGAAGTTCACATATATTACCTAGAGA

AAGCCAACAAAATAAAATCTGAGAAGACACACATTCACATCTTTTCATTC

ACTGGAGAGGAGATGGCCACCAAAGCGGACTACACCCTTGACGAAGAGAG

CAGGGCAAGAATCAAAACTAGGCTTTTCACTATAAGACAAGAAATGGCCA

GTAGGAGTCTATGGGATTCCTTTCGTCAGTCCGAAAGAGGCGAAGAGACA

ATTGAAGAAAATTTGAGATTACAGGAACTATGCGCAAGCTTGCCGACCA

AAGTCTCCCACCGAACTTCTCCAGCCTTGAAAACTTTAGAGCCTATGTAG

ATGGATTCGAGCCGAACGGCTGCATTGAGGGCAAGCTTTCCCAAATGTCA

AAAGAAGTGAACGCCAAAATTGAACCATTCTTGAGGACGACACCACGCCC

CCTCAGATTGCCTGATGGGCCTCTTTGCCATCAGCGGTCAAAGTTCCTGC

TGATGGATGCTCTGAAATTAAGTATTGAAGACCCGAGTCACGAGGGGGAG

GGAATACCACTATATGATGCAATCAAATGCATGAAGACATTCTTTGGCTG

GAAAGAGCCTAACATAGTCAAACCACATGGGAAAGGCATAAATCCCAATT

ACCTCATGGCTTGGAAGCAAGTGCTAGCAGAGCTACAGGACATTGAAAAT

GAAGAGAAGATCCCAAGGACAAAGAACATGAAGAGAACAAGCCAATTGAA

GTGGGCACTCGGTGAAAATATGGCACCAGAAAAGTAGACTTTGATGACT

GCAAAGATGTTGGAGACCTTAAACAGTATGACAGTGATGAGCCAGAGCCC

AGATCTCTAGCAAGCTGGGTCCAAAATGAATTCAATAAGGCATGTGAATT

GACTGATTCAAGCTGGATAGAACTTGATGAAATAGGAGAAGATGTTGCCC

CGATTGAACATATCGCAAGCATGAGGAGGAACTATTTTACAGCAGAAGTG

TCCCACTGCAGGGCTACTGAATACATAATGAAGGGAGTGTACATAAATAC

GGCCTTGCTCAATGCATCCTGTGCAGCCATGGATGACTTTCAGCTGATCC

CAATGATAAGCAAATGTAGGACCAAAGAAGGAAGACGGAAAACAAACCTG

TATGGGTTCATTATAAAAGGAAGGTCTCATTTGAGAAATGATACTGATGT

GGTGAACTTTGTAAGTATGGAGTTCTCACTCACTGACCCGAGACTGGAGC

CACACAAATGGGAAAAATACTGTGTTCTTGAAATAGGAGACATGCTCTTG

AGGACTGCGATAGGCCAAGTGTCGAGGCCCATGTTCCTATATGTGAGAAC

CAATGGAACCTCCAAGATCAAGATGAAATGGGGCATGGAAATGAGGCGCT

GCCTTCTTCAGTCTCTTCAGCAGATTGAGAGCATGATTGAGGCCGAGTCT

TCTGTCAAAGAGAAAGACATGACCAAGGAATTCTTTGAAAACAAATCGGA

AACATGGCCAATCGGAGAGTCACCCAGGGGAGTGGAGGAAGGCTCTATTG

GGAAAGTGTGCAGGACCTTACTGGCAAAATCTGTATTCAACAGTCTATAT

GCGTCTCCACAACTTGAGGGGTTTTCGGCTGAATCGAGAAAATTGCTTCT

CATTGTTCAGGCACTTAGGGACAACCTGGAACCTGGAACCTTCGATCTTG

GGGGGCTATATGAAGCAATCGAGGAGTGCCTGATTAATGATCCCTGGGTT

TTGCTTAATGCATCTTGGTTCAACTCCTTCCTCACACATGCACTGAAGTA

G

>PA_protein (SEQ ID NO: 50)

MEDFVRQCFNPMIVELAEKAMKEYGEDPKIETNKFAAICTHLEVCFMYSD

FHFIDERGESIIVESGDPNALLKHRFEIIEGRDRIMAWTVVNSICNTTGV

EKPKFLPDLYDYKENRFIEIGVTRREVHIYYLEKANKIKSEKTHIHIFSF

TGEEMATKADYTLDEESRARIKTRLFTIRQEMASRSLWDSFRQSERGEET

IEEKFEITGTMRKLADQSLPPNFSSLENFRAYVDGFEPNGCIEGKLSQMS

KEVNAKIEPFLRTTPRPLRLPDGPLCHQRSKFLLMDALKLSIEDPSHEGE

GIPLYDAIKCMKTFFGWKEPNIVKPHGKGINPNYLMAWKQVLAELQDIEN

EEKIPRTKNMKRTSQLKWALGENMAPEKVDFDDCKDVGDLKQYDSDEPEP

RSLASWVQNEFNKACELTDSSWIELDEIGEDVAPIEHIASMRRNYFTAEV

SHCRATEYIMKGVYINTALLNASCAAMDDFQLIPMISKCRTKEGRRKTNL

YGFIIKGRSHLRNDTDVVNFVSMEFSLTDPRLEPHKWEKYCVLEIGDMLL

RTAIGQVSRPMFLYVRTNGTSKIKMKWGMEMRRCLLQSLQQIESMIEAES

SVKEKDMTKEFFENKSETWPIGESPRGVEEGSIGKVCRTLLAKSVFNSLY

ASPQLEGFSAESRKLLLIVQALRDNLEPGTFDLGGLYEAIEECLINDPWV

LLNASWFNSFLTHALK*

>PA-X_CDS (SEQ ID NO: 51)

coding protein PA_X (cDNA sequence = fragment
1-700 from SEQ ID NO: 50 + deletion of
nucleotide 571)

5'-

ATGGAAGACTTTGTGCGACAATGCTTCAATCCAATGATCGTCGAGCTTGC

GGAAAAGGCAATGAAAGAATATGGGGAAGATCCGAAAATCGAAACTAACA

AGTTTGCTGCAATATGCACACATTTGGAAGTTTGTTTCATGTATTCGGAT

TTCCATTTCATCGACGAACGGGGTGAATCAATAATTGTGAATCTGGTGA

CCCGAATGCACTATTGAAGCACCGATTTGAGATAATTGAAGGAAGAGACC

GAATCATGGCCTGGACAGTGGTGAACAGTATATGTAACACAACAGGGGTA

GAGAAGCCTAAATTTCTTCCTGATTTGTATGATTACAAAGAGAACCGGTT

CATTGAAATTGGAGTAACACGGAGGGAAGTCCACATATATTACCTAGAGA

AAGCCAACAAAATAAAATCTGAGAAGACACACATTCACATCTTTTCATTC

ACTGGAGAGGAGATGGCCACCAAAGCGGACTACACCCTTGACGAAGAGAG

CAGGGCAAGAATCAAAACTAGGCTTTTCACTATAAGACAAGAAATGGCCA

GTAGGAGTCTATGGGATTCCTTCGTCAGTCCGAAAGAGGCGAAGAGACAA

TTGAAGAAAAATTTGAGATTACAGGAACTATGCGCAAGCTTGCCGACCAA

AGTCTCCCACCGAACTTCTCCAGCCTTGAAAACTTTAGAGCCTATGTAG

>PA-X_protein (SEQ ID NO: 52)

MEDFVRQCFNPMIVELAEKAMKEYGEDPKIETNKFAAICTHLEVCFMYSD

FHFIDERGESIIVESGDPNALLKHRFEIIEGRDRIMAWTVVNSICNTTGV

EKPKFLPDLYDYKENRFIEIGVTRREVHIYYLEKANKIKSEKTHIHIFSF

TGEEMATKADYTLDEESRARIKTRLFTIRQEMASRSLWDSFVSPKEAKRQ

LKKNLRLQELCASLPTKVSHRTSPALKTLEPM*

1-to-Stop PA Segments:

>genomic RNA (vRNA) PA sequence (SEQ ID NO: 53)

5'-

AGUAGAAACAAGGUACUUUUUUGGACAGUAUGGAUAGCAAAUAGUAGCAU

UGCCACAACUACUUCAaUGCAUGUGUcAaGAAcGAGUUGAACCAuGAUGC

AUUuAaCAAAACCCAGGGAUCAUUAAUCAaGCACUCCUCGAUUGCUUCAU

AUAaCCCCCCuAaAUCGAAGGUUCCAGGUUCCAaGUUGUCCCUuAaUGCC

UGAACAAUcAauAaCAAUUUUCUCGAUUCAGCCGAAAACCCCUCuAaUUG

UGGuGACGCAUAUAaugaGUUGAAUACuGAUUUUGCCAaUAAGGUCCUGC

ACACUUUCCCAAUuGAGCCUUCCUCCACUCCCCUGGGUGACUCUCCGAUU

GGCCAUGUUUCCGAUUUGUUUUCAAAGAAUUCCUUGGUCAUGUCUUUCUC

UUUGACuGAuGACUCGGCCUCAAUCAUcgaCUCAAUCUGCUGuAauGACU

GuAauAaGCAGCGCCUCAUUUCCAUGCCCCAUUUCAUCUUGAUCUUcGAG

GUUCCAUUGGUUCUCACAUAUAaGAACAUGGGCCUCGACACUUGGCCUAU

CGCAGUCCUCAAcAaCAUGUCUCCUAUUUCuAaAACACAGUAUUUUUCCC

AUUUGUGUGGCUCCAaUCUCGGGUCAGUcAaUGAGAACUCCAUugaUACA

AAGUUCACCACAUCAGUAUCAUUUCUCAAAUGuGACCUUCCUUUUAUAAU

GAACCCAUACAaGUUUGUUUUCCGUCUUCCUUCUUUGGUCCUACAUUUcg aUAUCAUUGGGAUCAaCUGAAAGUCAUCCAUGGCUGCACAcGAUGCAUUc

AaCAAGGCCGUAUUUAUGUACACUCCCUUCAUUAUGUAUUCAGUAGCCCU

GCAGUGcGACACUUCUGCUGUAAAAUAGUUCCUCCUCAUcgaUGCGAUAU

GUUCAAUCGGGGCAACAUCUUCUCCUAUUUCAUCuAaUUCUAUCCAcgaU

GAAUCAGUCAAUUCACAUGCCUUAUUGAAUUCAUUUUGGACCCAcgaUGC

UAauGAUCUGGGCUCUGGCUCAUCugaGUCAUACUGUUUuAaGUCUCCAA

CAUCUUUGCAGUCAUCAAAGUCUACUUUUUCUGGUGCCAUAUUUUCACCc

AaUGCCCACUUCAAUUGcgaUGUUCUCUUCAUGUUCUUUGUCCUUGGGAU

-continued

CUUCUCUUCAUUUUCAAUGUCCUGUAaCUCUGCUAaCACUUGCUUCCAAG
CCAUcAaGUAAUUGGGAUUUAUGCCUUUCCCAUGUGGUUUGACUAUGUUA
GGCUCUUUCCAGCCAAAGAAUGUCUUCAUGCAUUUGAUUGCAUCAUAUAa
UGGUAUUCCCUCCCCCUCGUGugaCGGGUCUUCAAUugaUAAUUUCAaAG
CAUCCAUCAaCAaGAACUUUGACCGCUGAUGGCAuAaAGGCCCAUCAGGC
AAUCUcAaGGGGCGUGGUGUCGUCCUCAAGAAUGGUUCAAUUUUGGCGUU
CACUUCUUUUGACAUUUGcGAuAaCUUGCCCUCAAUGCAGCCGUUCGGCU
CGAAUCCAUCUACAUAGGCUCUAAAGUUUUCuAacgacGAGAAGUUCGGU
GGcAaugaUUGGUCGGCuAaCUUGCGCAUAGUUCCUGUAAUCUCAAAUUU
UUCUUCAAUUGUCUCUUCGCCUCUUUCcGACUGACGAAAcGAAUCCCAUA
augaCCUugaGGCCAUUUCUUGUCUUAUAGUGAAuAaCCUAGUUUUGAUU
CUUGCCCUcgaCUCUUCGUCuAaGGUGUAGUCCGCUUUGGUGGCCAUCUC
CUCUCCAGUGAAUGAAAAGAUGUGAAUGUGUGUCUUCUCuGAUUUUAUUU
UGUUGGCUUUCUCUAaGUAAUAUAUGUGGACUUCCCUCCGUGUUACUCCA
AUUUCAAUGAACCGGUUCUCUUUGUAAUCAUACAAAUCAGGuAaAAAUUU
AGGCUUCUCUACCCCUGUUGUGUUACAUAUugaGUUCACCACUGUCCAGG
CCAUGAUUCGGUCUCUUCCUUCAAUUAUCUCAAAUCGGUGCUUCAAUAaU
GCAUUCGGGUCACCuGAUUCUACAAUUAUUGAUUCACCCCGUUCGUCGAU
GAAAUGGAAAUCCGAAUACAUGAAACAAACUUCCAAAUGUGUGCAUAUUG
CAGCAAACUUGUUAGUUUCGAUUUUCGGAUCUUCCCCAUAUUCUUUCAUU
GCCUUUUCCGCuAaCUCGACGAUCAUUGGAUUGAAGCAUUGUCGCACAAA
GUCUUCCAUUUUGGAUCAGUACCUGCUUUCGCU

>PA_CDS (SEQ ID NO: 54)

5'-

ATGGAAGACTTTGTGCGACAATGCTTCAATCCAATGATCGTCGAGtTaGC
GGAAAAGGCAATGAAAGAATATGGGGAAGATCCGAAAATCGAAACTAACA
AGTTTGCTGCAATATGCACACATTTGGAAGTTTGTTTCATGTATTCGGAT
TTCCATTTCATCGACGAACGGGGTGAATCAATAATTGTAGAATCaGGTGA
CCCGAATGCAtTATTGAAGCACCGATTTGAGATAATTGAAGGAAGAGACC
GAATCATGGCCTGGACAGTGGTGAACtcaATATGTAACACAACAGGGGTA
GAGAAGCCTAAATTTtTaCCTGATTTGTATGATTACAAAGAGAACCGGTT
CATTGAAATTGGAGTAACACGGAGGGAAGTCCACATATATTACtTAGAGA
AAGCCAACAAAATAAAATCaGAGAAGACACACATTCACATCTTTTCATTC
ACTGGAGAGGAGATGGCCACCAAAGCGGACTACACCtTaGACGAAGAGtc
gAGGGCAAGAATCAAAACTAGGtTaTTCACTATAAGACAAGAAATGGCCt
caAGGtcatTATGGGATTCgTTTCGTCAGTCgGAAAGAGGCGAAGAGACA
ATTGAAGAAAAATTTGAGATTACAGGAACTATGCGCAAGtTaGCCGACCA
AtcatTgCCACCGAACTTCTCgtcgtTaGAAAACTTTAGAGCCTATGTAG
ATGGATTCGAGCCGAACGGCTGCATTGAGGGCAAGtTaTCgCAAATGTCA
AAAGAAGTGAACGCCAAAATTGAACCATTCTTGAGGACGACACCACGCCC
CtTgAGATTGCCTGATGGGCCTtTaTGCCATCAGCGGTCAAAGTTCtTGt
TGATGGATGCTtTGAAATTAtcaATTGAAGACCCGtcaCACGAGGGGGAG
GGAATACCAtTATATGATGCAATCAAATGCATGAAGACATTCTTTGGCTG
GAAAGAGCCTAACATAGTCAAACCACATGGGAAAGGCATAAATCCCAATT
ACtTgATGGCTTGGAAGCAAGTGtTAGCAGAGtTACAGGACATTGAAAAT
GAAGAGAAGATCCCAAGGACAAAGAACATGAAGAGAACAtcgCAATTGAA
GTGGGCAtTgGGTGAAAATATGGCACCAGAAAAAGTAGACTTTGATGACT
GCAAAGATGTTGGAGACtTaAAACAGTATGACtcaGATGAGCCAGAGCCC
AGATCatTAGCAtcgTGGGTCCAAAATGAATTCAATAAGGCATGTGAATT
GACTGATTCAtcgTGGATAGAAtTaGATGAAATAGGAGAAGATGTTGCCC
CGATTGAACATATCGCAtcgATGAGGAGGAACTATTTTACAGCAGAAGTG
TCgCACTGCAGGGCTACTGAATACATAATGAAGGGAGTGTACATAAATAC
GGCCTTGtTgAATGCATCgTGTGCAGCCATGGATGACTTTCAGtTGATCC
CAATGATAtcgAAATGTAGGACCAAAGAAGGAAGACGGAAAACAAACtTG
TATGGGTTCATTATAAAAGGAAGGTCaCATTTGAGAAATGATACTGATGT
GGTGAACTTTGTAtcaATGGAGTTCTCAtTgACTGACCCGAGAtTGGAGC
CACACAAATGGGAAAAATACTGTGTTtTaGAAATAGGAGACATGtTgTTG
AGGACTGCGATAGGCCAAGTGTCGAGGCCCATGTTCtTATATGTGAGAAC
CAATGGAACCTCgAAGATCAAGATGAAATGGGGCATGGAAATGAGGCGCT
GCtTatTaCAGTCatTaCAGCAGATTGAGtcgATGATTGAGGCCGAGTCa
TCaGTCAAAGAGAAAGACATGACCAAGGAATTCTTTGAAAACAAATCGGA
AACATGGCCAATCGGAGAGTCACCCAGGGGAGTGGAGGAAGGCTCaATTG
GGAAAGTGTGCAGGACCTTAtTGGCAAAATCaGTATTCAACtcatTATAT
GCGTCaCCACAAtTaGAGGGGTTTTCGGCTGAATCGAGAAAATTGtTatT
gATTGTTCAGGCAtTaAGGGACAACtTGGAACCTGGAACCTTCGATtTaG
GGGGGtTATATGAAGCAATCGAGGAGTGCtTGATTAATGATCCCTGGGTT
TTGtTaAATGCATCaTGGTTCAACTCgTTCtTgACACATGCAtTGAAGTA
G >PA_protein (SEQ ID NO: 55)

MEDFVRQCFNPMIVELAEKAMKEYGEDPKIETNKFAAICTHLEVCFMYSD
FHFIDERGESIIVESGDPNALLKHRFEIIEGRDRIMAWTVVNSICNTTGV
EKPKFLPDLYDYKENRFIEIGVTRREVHIYYLEKANKIKSEKTHIHIFSF
TGEEMATKADYTLDEESRARIKTRLFTIRQEMASRSLWDSFRQSERGEET
IEEKFEITGTMRKLADQSLPPNFSSLENFRAYVDGFEPNGCIEGKLSQMS
KEVNAKIEPFLRTTPRPLRLPDGPLCHQRSKFLLMDALKLSIEDPSHEGE
GIPLYDAIKCMKTFFGWKEPNIVKPHGKGINPNYLMAWKQVLAELQDIEN
EEKIPRTKNMKRTSQLKWALGENMAPEKVDFDDCKDVGDLKQYDSDEPEP
RSLASWVQNEFNKACELTDSSWIELDEIGEDVAPIEHIASMRRNYFTAEV
SHCRATEYIMKGVYINTALLNASCAAMDDFQLIPMISKCRTKEGRRKTNL
YGFIIKGRSHLRNDTDVVNFVSMEFSLTDPRLEPHKWEKYCVLEIGDMLL
RTAIGQVSRPMFLYVRTNGTSKIKMKWGMEMRRCLLQSLQQIESMIEAES

-continued
SVKEKDMTKEFFENKSETWPIGESPRGVEEGSIGKVCRTLLAKSVFNSLY
ASPQLEGFSAESRKLLLIVQALRDNLEPGTFDLGGLYEAIEECLINDPWV
LLNASWFNSFLTHALK*

>PA-X_CDS
(SEQ ID NO: 56)
5'-
ATGGAAGACTTTGTGCGACAATGCTTCAATCCAATGATCGTCGAGtTaGC
GGAAAAGGCAATGAAAGAATATGGGGAAGATCCGAAAATCGAAACTAACA
AGTTTGCTGCAATATGCACACATTTGGAAGTTTGTTTCATGTATTCGGAT
TTCCATTTCATCGACGAACGGGGTGAATCAATAATTGTAGAATCaGGTGA
CCCGAATGCAtTATTGAAGCACCGATTTGAGATAATTGAAGGAAGAGACC
GAATCATGGCCTGGACAGTGGTGAACtcaATATGTAACACAACAGGGGTA
GAGAAGCCTAAATTTtTaCCTGATTTGTATGATTACAAAGAGAACCGGTT
CATTGAAATTGGAGTAACACGGAGGGAAGTCCACATATATTACtTAGAGA
AAGCCAACAAAATAAAATCaGAGAAGACACACATTCACATCTTTTCATTC
ACTGGAGAGGAGATGGCCACCAAAGCGGACTACACCtTaGACGAAGAGtc
gAGGGCAAGAATCAAAACTAGGtTaTTCACTATAAGACAAGAAATGGCCt
caAGGtcatTATGGGATTCgTTCGTCAGTCgGAAAGAGGCGAAGAGACAA
TTGAAGAAAAATTTGAGATTACAGGAACTATGCGCAAGtTaGCCGACCAA
tcatTgCCACCGAACTTCTCgtcgtTaGAAAACTTTAGAGCCTATGTAG >PA-X_protein
(SEQ ID NO: 57)
MEDFVRQCFNPMIVELAEKAMKEYGEDPKIETNKFAAICTHLEVCFMYSD
FHFIDERGESIIVESGDPNALLKHRFEIIEGRDRIMAWTVVNSICNTTGV
EKPKFLPDLYDYKENRFIEIGVTRREVHIYYLEKANKIKSEKTHIHIFSF
TGEEMATKADYTLDEESRARIKTRLFTIRQEMASRSLWDSFVSRKEAKRQ
LKKNLRLQELCAS*

Other Influenza Segments (Commun to Wt, 1-to-Stop, MoreV and LessV Constructs):
Influenza PB2 Segment:

>genomic RNA (vRNA) PB2 sequence (SEQ ID NO: 58)

5'-

AGUAGAAACAAGGUCGUUUUUAAACAAUUCGACACUAAUUGAUGGCCAUC

CGAAUUCUUUUGGUCGCUGUCUGGCUGUCAGUAAGUAUGCUAGAGUCCCG

UUUUCGUUUCAUUACCAACACUACGUCCCCUUGCCCAAUUAGCACAUUAG

CCUUCUCUCCUUUUGCAAGAUUGCUCAGUUCAUUGAUGCUUAAUGCUGGG

CCAUAUCUCUUGUCUUCUUUGCCCAAAAUGAGAAAUCCUCUCAGGACAGC

AGACUCCACCCCAGAUGUGCCUUCAUCUGGAUCUUCAGUCAAUGCACCUG

CAUCCUUUCCAAGAACUGUAAGUCGUUUGGUUGCCUUGUUGUAAUUGAAU

ACUGGAGAAUUGCCUCUUACCAGUAUCCUCAACCCUGAUCCUCUCACAUU

CACAGUCAAUGAGGAAAAUUGCAUCCUACUCUGUUCUGGUGGAGCAGCAG

CAAAGGGGAGAAGUUUUAUUAUUUGGACAGUGUCAAAUGUCCCAAGCACA

UCCCGCAUUUGCUGGAACAGUGUCCUUACGAAUCCACUGUACCGGCUUCU

-continued

GGUUGCCUUAGGGACAAGAGACUGAAAUGGUUCAAAUUCCAUUUUGUUGU

AUAACAUUGUGGGAUCUUGUGACCAUUGAAUUUUCACAAUUUCCCAGUUC

CUGAUUAUCCAUUGAUAAGUGUUGACUAGCACUGACUCAGGGCCAUUGAU

CUCCCACAUCAUUGAUGACGAAUAAGUUAUUGUCAACUUCUCAGUUCCUU

GCGUUUCACUGACUUCUUCGGGAGACAAUAAUACGUUCCCUCUUUGAUCU

CUAACCCUUAAAAAUCGGUCAAUACUCACUACCACUCUCUCCGUGCUGGA

GUAUUCAUCUACUCCCAUUUUGCUGACUCUUAUCCCUCUCAGCGACAUCU

CCGUGCUUGGGGUCAUGUCGGGCAGUAUUCCGAUCAUUCCCAUCACAUUG

UCGAUGGAUUCAAUUCCCCAGUUCUGGAAAAGCACUUUUGCAUCUUUUUG

GAAAUGCCUCAAGAGUUGGUGCAUGGGGUUCAGUCGCUGGUUUGCCCUAU

UGACAAAGUUCAGAUCGCCCCUAACUGCCUUGAUCAUGCAAUCCUCUUGU

GAGAAUACCAUGGCCACAAUUAUUGCCUCAGCAAUUGACUGCUCGUCUCU

CCCGCUUACUAUCAACUGGAUCAAUCUCCUGGUUGCCUUUCUGAGAAUAG

CUGUUGCUCUUCUCCCAACCAUUGUGAAUUCUUCAUACCCUUCAUGUACU

CUUAUUUUCAGUGUUUGGAGGUUGCCCGUUAGCACUUCUUCUUCUUUCUU

GACUGAUGAUCCGCUUGUCCUUUUGAAAGUGAACCCACCAAAACUGAAAG

AUGAGCUAAUCCUCAACCCUAUUGCUGCCUUGCAUAUGUCUACGGCUUGU

UCCUCAGUUGGAUUCUGUCUAAGGAUGUCCACCAUCCUUACUCCUCCAAU

CUGUGUGCUGUGGCACAUUUCCAAGAGAGAUGCUAAUGGGUCUGCUGACA

CUGCUGCUCUUCUUACUAUGUUUCUAGCAGCGAUAAUCAAACUUUGGUCA

ACAUCAUCAUUUCUCACUUCUCCUCCUGGAGUGUACAUCUGCUCCCAGCA

CGUCCCUUGGGUUAAGUGCAACACUUCAAUAUAAACACUGCCUGUUCCGC

CGGCUACUGGGAGAAACCUUGUUUUACGGACCAAUUCUCUUUCUAGCAUG

UACGCCACCAUCAAGGGAGCAAUUUUACAAUCCUGGAGCUCUUCUUUCUU

CUCUUUUGUUAUUGCCAUUUGUGACUCUGAUGUCAGUAUUCUUGCCCCCA

CUUCAUUUGGGAAAACAACUUCCAUAAUCACAUCCUGUGCCUCCUUGGCA

CUGAGAUCUGCAUGGCCAGGGUUUGUAUCAACUCUCCUCCUUAUUUUAAC

UUGAUUUCUGAAGUGGACAGGGCCGAAGGUACCAUGUUUCAACCUUUCGA

CCUUUUCGAAAUAAGUUUUAUAUACCUUAGGGUAAUGAACUGUACUUGUU

GUUGGGCCAUUCCUAUUCCACCAUGUUACGGCCAGAGGUGAUACCAUCAC

UCGGUCUGAUCCAGCAUCGUUUGUUUUGCUCCAGAGGGUUUGUCCUUGUU

CAUUCCUCUCUGGAAUCAUGUCCAUUAUUCUCUUGUCUGCUGUAAUUGGG

UAUCUCAUUGCCAUCAUCCACUUCAUUCUGAGUGCGGGGUUCUUCUCUUG

CCUUCCUGAUGUGUACUUUUUGAUUAUGGCCAUAUGGUCCACAGUGGUCU

UAGUGAGUAUCUCGCGAGUGCGGGACUGCGACAUUAGAUCUCUCAGUUCU

UUUAUUCUCUCCAUAUUGAAUAUAUUUGACCUGCUUUCGCU

>PB2_CDS (SEQ ID NO: 59)

5'-

ATGGAGAGAATAAAAGAACTGAGAGATCTAATGTCGCAGTCCCGCACTCG

CGAGATACTCACTAAGACCACTGTGGACCATATGGCCATAATCAAAAAGT

-continued
```
ACACATCAGGAAGGCAAGAGAAGAACCCCGCACTCAGAATGAAGTGGATG
ATGGCAATGAGATACCCAATTACAGCAGACAAGAGAATAATGGACATGAT
TCCAGAGAGGAATGAACAAGGACAAACCCTCTGGAGCAAAACAAACGATG
CTGGATCAGACCGAGTGATGGTATCACCTCTGGCCGTAACATGGTGGAAT
AGGAATGGCCCAACAACAAGTACAGTTCATTACCCTAAGGTATATAAAAC
TTATTTCGAAAAGGTCGAAAGGTTGAAACATGGTACCTTCGGCCCTGTCC
ACTTCAGAAATCAAGTTAAAATAAGGAGGAGAGTTGATACAAACCCTGGC
CATGCAGATCTCAGTGCCAAGGAGGCACAGGATGTGATTATGGAAGTTGT
TTTCCCAAATGAAGTGGGGGCAAGAATACTGACATCAGAGTCACAAATGG
CAATAACAAAAGAGAAGAAAGAAGAGCTCCAGGATTGTAAAATTGCTCCC
TTGATGGTGGCGTACATGCTAGAAAGAGAATTGGTCCGTAAAACAAGGTT
TCTCCCAGTAGCCGGCGGAACAGGCAGTGTTTATATTGAAGTGTTGCACT
TAACCCAAGGGACGTGCTGGGAGCAGATGTACACTCCAGGAGGAGAAGTG
AGAAATGATGATGTTGACCAAAGTTTGATTATCGCTGCTAGAAACATAGT
AAGAAGAGCAGCAGTGTCAGCAGACCCATTAGCATCTCTCTTGGAAATGT
GCCACAGCACACAGATTGGAGGAGTAAGGATGGTGGACATCCTTAGACAG
AATCCAACTGAGGAACAAGCCGTAGACATATGCAAGGCAGCAATAGGGTT
GAGGATTAGCTCATCTTTCAGTTTTGGTGGGTTCACTTTCAAAAGGACAA
GCGGATCATCAGTCAAGAAGAAGAAGAAGTGCTAACGGGCAACCTCCAA
ACACTGAAAATAAGAGTACATGAAGGGTATGAAGAATTCACAATGGTTGG
GAGAAGAGCAACAGCTATTCTCAGAAAGGCAACCAGGAGATTGATCCAGT
TGATAGTAAGCGGGAGAGACGAGCAGTCAATTGCTGAGGCAATAATTGTG
GCCATGGTATTCTCACAAGAGGATTGCATGATCAAGGCAGTTAGGGGCGA
TCTGAACTTTGTCAATAGGGCAAACCAGCGACTGAACCCCATGCACCAAC
TCTTGAGGCATTTCCAAAAAGATGCAAAAGTGCTTTTCCAGAACTGGGGA
ATTGAATCCATCGACAATGTGATGGGAATGATCGGAATACTGCCCGACAT
GACCCCAAGCACGGAGATGTCGCTGAGAGGGATAAGAGTCAGCAAAATGG
GAGTAGATGAATACTCCAGCACGGAGAGAGTGGTAGTGAGTATTGACCGA
TTTTTAAGGGTTAGAGATCAAAGAGGGAACGTATTATTGTCTCCCGAAGA
AGTCAGTGAAACGCAAGGAACTGAGAAGTTGACAATAACTTATTCGTCAT
CAATGATGTGGGAGATCAATGGCCCTGAGTCAGTGCTAGTCAACACTTAT
CAATGGATAATCAGGAACTGGGAAATTGTGAAATTCAATGGTCACAAGA
TCCCACAATGTTATACAACAAAATGGAATTTGAACCATTTCAGTCTCTTG
TCCCTAAGGCAACCAGAAGCCGGTACAGTGGATTCGTAAGGACACTGTTC
CAGCAAATGCGGGATGTGCTTGGGACATTTGACACTGTCCAAATAATAAA
ACTTCTCCCCTTTGCTGCTGCTCCACCAGAACAGAGTAGGATGCAATTTT
CCTCATTGACTGTGAATGTGAGAGGATCAGGGTTGAGGATACTGGTAAGA
GGCAATTCTCCAGTATTCAATTACAACAAGGCAACCAAACGACTTACAGT
TCTTGGAAAGGATGCAGGTGCATTGACTGAAGATCCAGATGAAGGCACAT
CTGGGGTGGAGTCTGCTGTCCTGAGAGGATTTCTCATTTTGGGCAAAGAA
GACAAGAGATATGGCCCAGCATTAAGCATCAATGAACTGAGCAATCTTGC
AAAAGGAGAGAAGGCTAATGTGCTAATTGGGCAAGGGGACGTAGTGTTGG
TAATGAAACGAAAACGGGACTCTAGCATACTTACTGACAGCCAGACAGCG
ACCAAAAGAATTCGGATGGCCATCAATTAG
```

>PB2_protein (SEQ ID NO: 60)

MERIKELRDLMSQSRTREILTKTTVDHMAIIKKYTSGRQEKNPALRMKWM
MAMRYPITADKRIMDMIPERNEQGQTLWSKTNDAGSDRVMVSPLAVTWWN
RNGPTTSTVHYPKVYKTYFEKVERLKHGTFGPVHFRNQVKIRRRVDTNPG
HADLSAKEAQDVIMEVVFPNEVGARILTSESQMAITKEKKEELQDCKIAP
LMVAYMLERELVRKTRFLPVAGGTGSVYIEVLHLTQGTCWEQMYTPGGEV
RNDDVDQSLIIAARNIVRRAAVSADPLASLLEMCHSTQIGGVRMVDILRQ
NPTEEQAVDICKAAIGLRISSSFSFGGFTFKRTSGSSVKKEEEVLTGNLQ
TLKIRVHEGYEEFTMVGRRATAILRKATRRLIQLIVSGRDEQSIAEAIIV
AMVFSQEDCMIKAVRGDLNFVNRANQRLNPMHQLLRHFQKDAKVLFQNWG
IESIDNVMGMIGILPDMTPSTEMSLRGIRVSKMGVDEYSSTERVVVSIDR
FLRVRDQRGNVLLSPEEVSETQGTEKLTITYSSSMMWEINGPESVLVNTY
QWIIRNWEIVKIQWSQDPTMLYNKMEFEPFQSLVPKATRSRYSGFVRTLF
QQMRDVLGTFDTVQIIKLLPFAAAPPEQSRMQFSSLTVNVRGSGLRILVR
GNSPVFNYNKATKRLTVLGKDAGALTEDPDEGTSGVESAVLRGFLILGKE
DKRYGPALSINELSNLAKGEKANVLIGQGDVVLVMKRKRDSSILTDSQTA
TKRIRMAIN*

Influenza PB1 Segment:

>genomic RNA (vRNA) PB1 sequence (SEQ ID NO: 61)
```
5'-
AGUAGAAACAAGGCAUUUUUUCAUGAAGGACAAGUUAAAUUCAUUAUUUU
UGCCGUCUGAGUUCUUCAAUGGUGGAACAGAUCUUCAUGAUCUCAGAGAA
CUCUUCUUUCUUGAUCCGUCCAGACUCGAAGUCGACCCUGGCAUCAAUCC
GGGCCCUAGACACCAUGGCCUCCACCAUGCUAGAAAUUCCAACCGGUCUC
CUAUAUGAACUGCUAGGGAAAAAUUUCUCGAAUAGAUUGCAGCACUUCUG
GUACAUCUGUUCAUCCUCAAGAAUUCCCCUUUGGCUUGUGUUGAGAAUAG
AACGAUUCCUCUUGGGAAUCCAGGAAUGUGUAGUUGCAACGGCAUCAUAU
UCCAUGCUUUUGGCUGGACCAUGGGCUGGCAUUACCACAGCAUUGUUUAC
AGAAUCAAUCUCUUUAUGACUGACAAAGGGAUUCAGGGGAUUACAAAGUC
UUCCCCGAUAAUCAUCAUCCAUUAGCUCCCAUUUUAAGCAGACUUCAGGA
AUGUGAAGAUUCCGUAUAUUGUAUAAGUUUGGUCCUCCAUCUGAUACUAA
UAGCCCUACCUUUGAUUGGGUUUGAUCCCACAGCUUCUUUAACUCAAAUG
AUCUUCUCGUCUGAAUUUGUGUGUCUCCCCUAUGGCACCUAUAUGUGUAU
CUGUAGUCUUUGAUGAACAAUUGAAGAGCCAUCUGGGCCGUUGCAGGUCC
AAGGUCAUUGUUUAUCAUGUUGUUCUUUAUCACUGUUACUCCAAUACUCA
UGUCAGCUGAUUCAUUUACUCCAGACACUCCAAAGCUGGGUAGCUCCAUG
```

CUAAAAUUAGCCACAAAUCCAUAGCGAUAAAAAAAGCUUGUGAAUUCAAA
UGUCCCUGUCUUAUUUAUAUAGGACUUCUUUUUUGCUCAUGUUGAUUCCA
CUAACUUGCAGGUCCUGUAGAAUCUGUCCACUCCUGCUUGUAUUCCCUCA
UGGUUUGGUGCAUUCACUAUGAGAGCAAAAUCGUCGGAUGAUUGGAGCCC
AUCCCACCAGUAUAUUGUCUUGGUGUAUUUCUUUUGUCCAAGAUUCAGUA
UCGAGACUCCCAAGACCGUACUUAGCAUGUUGAACAUGCCCAUCAUCAUC
CCAGGACUCAGUGAUGCUGUGCCAUCUAUUAGAAGAGGCCUUAUUUUCUC
AAUUUUCUUCUUUGUUGAUUCAUUGAAGUACUUCAGGUCAAUGCUUGCUA
GCAUUUCUGCUGGUAUUUGUGUUCGAAUCUUCAUUCUUUUACUCUCGAAC
AUGUACCCUUUCCCUAGUCUUGCCAUUUUGUUUGAGAACAUUAUGGGUGC
CAUGCUCAGGAUGUUUCUGAACCACUCGGGUUGAUUUCUGGUGAUAUAUG
UAAUCAUCGCCAGGAACAUUCGAGGAUUUUGAUUUUCAUUCCACUUAGUG
UUGUCCCCAGUGAUUGUGAAAGAAAUCUCUGUGUCUUGUGAAUUAGUCAU
CAUCUUUCUCACAACAUUUGCCAGUUUGGCCUUCUUUUCAUUGCCCCCUA
CUGGGAGCCCAGACUGUUCAAGCUUUUCGCAAAUGCUCCUAGCUAAAGUU
UCAACAAAGUAUACGAAACCUCUAAUCUGCAUCCCAGGUGUUGCGAUAGC
CCUUCUUUUUAACUUGCUCUCUCUGCAUCUUUGGUCAUCGUAUUUAAUG
UCAGGGCUCUUAUUAGAUAGCCUCUCUUAUUCAGUCUUUGUUUUUUCUUC
CCUAUUGUUCUUUGCGUGACCAUCUUCUUGGUCAUGUUGUCUCUUACUCU
CCUUUUUCUUUGAAAGUGGGUUGUUAUCUCUAUUUCCUCUUUGUUCAUUG
AUUCCAUUACAUCCUUUAAGAAAUCUAUUAGCCUUCCUGACUCAUUAGCU
GUUAGGCCAUUCGAUCUAAAGACUUCUAUGGUGUUGGCCAAUGCAGUUGC
UGCCGGUUGAUUUCUGUUUAAUGUCCAAUCAUAAGUCUGGCGACCUUGAG
UUAGUUUAUCUACCCUUGUUUGUUGAACAACUUCCAUUGUUUCAAGGCAU
GAAUUCUCAAAUAUUCCUGGGUGGGAUUCUUCAAGGAAAGCCAUAGCCUC
UAGAACACAGUCUGUUUGUGCAUACCCACUUGGUUCAUUAUCCUCAGGUA
GUGGUCCAUCAACUGGGUUGAGCUGGGGUGCACCAGUCUCUGUGUUUGUC
GUCCACUUUCCCUUUUCUGAGUAUGGUGUGUUCUGUUUACUGUGUCCAU
GGUGUAUCCUGUUCCUGUUCCAUGGCUGUAUGGAGGAUCUCCAGUAUAAG
GGAAUGUGGUGCUUAUGGCAUUUGCGCUGGAAUUUUUAAGAAAAGUAGA
GUCGGAUUGACAUCCAUUCAAAUGGUUUGCCUGCUUUCGCU
>PB1_CDS
                                         (SEQ ID NO: 62)
5'-
ATGGATGTCAATCCGACTCTACTTTTCTTAAAAATTCCAGCGCAAAATGC
CATAAGCACCACATTCCCTTATACTGGAGATCCTCCATACAGCCATGGAA
CAGGAACAGGATACACCATGGACACAGTAAACAGAACACACCAATACTCA
GAAAAGGGAAAGTGGACGACAAACACAGAGACTGGTGCACCCCAGCTCAA
CCCGATTGATGGACCACTACCTGAGGATAATGAACCAAGTGGGTATGCAC
AAACAGACTGTGTTCTAGAGGCTATGGCTTTCCTTGAAGAATCCCACCCA
GGAATATTTGAGAATTCATGCCTTGAAACAATGGAAGTTGTTCAACAAAC
AAGGGTAGATAAACTAACTCAAGGTCGCCAGACTTATGATTGGACATTAA

ACAGAAATCAACCGGCAGCAACTGCATTGGCCAACACCATAGAAGTCTTT
AGATCGAATGGCCTAACAGCTAATGAGTCAGGAAGGCTAATAGATTTCTT
AAAGGATGTAATGGAATCAATGAACAAAGAGGAAATAGAGATAACAACCC
ACTTTCAAAGAAAAGGAGAGTAAGAGACAACATGACCAAGAAGATGGTC
ACGCAAAGAACAATAGGGAAGAAAAAACAAAGACTGAATAAGAGAGGCTA
TCTAATAAGAGCCCTGACATTAAATACGATGACCAAAGATGCAGAGAGAG
GCAAGTTAAAAAGAAGGGCTATCGCAACACCTGGGATGCAGATTAGAGGT
TTCGTATACTTTGTTGAAACTTTAGCTAGGAGCATTTGCGAAAAGCTTGA
ACAGTCTGGGCTCCCAGTAGGGGGCAATGAAAAGAAGGCCAAACTGGCAA
ATGTTGTGAGAAAGATGATGACTAATTCACAAGACACAGAGATTTCTTTC
ACAATCACTGGGGACAACACTAAGTGGAATGAAAATCAAATCCTCGAAT
GTTCCTGGCGATGATTACATATATCACCAGAAATCAACCCGAGTGGTTCA
GAAACATCCTGAGCATGGCACCCATAATGTTCTCAAACAAAATGGCAAGA
CTAGGGAAAGGGTACATGTTCGAGAGTAAAAGAATGAAGATTCGAACACA
AATACCAGCAGAAATGCTAGCAAGCATTGACCTGAAGTACTTCAATGAAT
CAACAAAGAAGAAAATTGAGAAAATAAGGCCTCTTCTAATAGATGGCACA
GCATCACTGAGTCCTGGGATGATGATGGGCATGTTCAACATGCTAAGTAC
GGTCTTGGGAGTCTCGATACTGAATCTTGGACAAAAGAAATACACCAAGA
CAATATACTGGTGGGATGGGCTCCAATCATCCGACGATTTTGCTCTCATA
GTGAATGCACCAAACCATGAGGGAATACAAGCAGGAGTGGACAGATTCTA
CAGGACCTGCAAGTTAGTGGGAATCAACATGAGCAAAAAGAAGTCCTATA
TAAATAAGACAGGGACATTTGAATTCACAAGCTTTTTTTATCGCTATGGA
TTTGTGGCTAATTTTAGCATGGAGCTACCCAGCTTTGGAGTGTCTGGAGT
AAATGAATCAGCTGACATGAGTATTGGAGTAACAGTGATAAAGAACAACA
TGATAAACAATGACCTTGGACCTGCAACGGCCCAGATGGCTCTTCAATTG
TTCATCAAAGACTACAGATACACATATAGGTGCCATAGGGGAGACACACA
AATTCAGACGAGAAGATCATTTGAGTTAAAGAAGCTGTGGGATCAAACCC
AATCAAAGGTAGGGCTATTAGTATCAGATGGAGGACCAAACTTATACAAT
ATACGGAATCTTCACATTCCTGAAGTCTGCTTAAAATGGGAGCTAATGGA
TGATGATTATCGGGGAAGACTTTGTAATCCCCTGAATCCCTTTGTCAGTC
ATAAAGAGATTGATTCTGTAAACAATGCTGTGGTAATGCCAGCCCATGGT
CCAGCCAAAAGCATGGAATATGATGCCGTTGCAACTACACATTCCTGGAT
TCCCAAGAGGAATCGTTCTATTCTCAACACAAGCCAAAGGGGAATTCTTG
AGGATGAACAGATGTACCAGAAGTGCTGCAATCTATTCGAGAAATTTTTC
CCTAGCAGTTCATATAGGAGACCGGTTGGAATTTCTAGCATGGTGGAGGC
CATGGTGTCTAGGGCCCGGATTGATGCCAGGGTCGACTTCGAGTCTGGAC
GGATCAAGAAAGAAGAGTTCTCTGAGATCATGAAGATCGTTCCACCATT
GAAGAACTCAGACGGCAAAAATAA

-continued

>PB1_protein (SEQ ID NO: 63)
MDVNPTLLFLKIPAQNAISTTFPYTGDPPYSHGTGTGYTMDTVNRTHQYS
EKGKWTTNTETGAPQLNPIDGPLPEDNEPSGYAQTDCVLEAMAFLEESHP
GIFENSCLETMEVVQQTRVDKLTQGRQTYDWTLNRNQPAATALANTIEVF
RSNGLTANESGRLIDFLKDVMESMNKEEIEITTHFQRKRRVRDNMTKKMV
TQRTIGKKKQRLNKRGYLIRALTLNTMTKDAERGKLKRRAIATPGMQIRG
FVYFVETLARSICEKLEQSGLPVGGNEKKAKLANVVRKMMTNSQDTEISF
TITGDNTKWNENQNPRMFLAMITYITRNQPEWFRNILSMAPIMFSNKMAR
LGKGYMFESKRMKIRTQIPAEMLASIDLKYFNESTKKKIEKIRPLLIDGT
ASLSPGMMMGMFNMLSTVLGVSILNLGQKKYTKTIYWWDGLQSSDDFALI
VNAPNHEGIQAGVDRFYRTCKLVGINMSKKKSYINKTGTFEFTSFFYRYG
FVANFSMELPSFGVSGVNESADMSIGVTVIKNNMINNDLGPATAQMALQL
FIKDYRYTYRCHRGDTQIQTRRSFELKKLWDQTQSKVGLLVSDGGPNLYN
IRNLHIPEVCLKWELMDDDYRGRLCNPLNPFVSHKEIDSVNNAVVMPAHG
PAKSMEYDAVATTHSWIPKRNRSILNTSQRGILEDEQMYQKCCNLFEKFF
PSSSYRRPVGISSMVEAMVSRARIDARVDFESGRIKKEEFSEIMKICSTI
EELRRQK*

>PB1-F2_CDS (SEQ ID NO: 64)
ATGGAACAGGAACAGGATACACCATGGACACAGTAA

>PB1-F2_protein (SEQ ID NO: 65)
MEQEQDTPWTQ*

Influenza HA Segment:

>genomic RNA (vRNA) HA sequence (SEQ ID NO: 66)

5'-

AGUAGAAACAAGGGUGUUUUUCUCAUGCUUCUGAAAUCCUAAUGUUAAAU
ACAUAUUCUACACUGUAGAGACCCAUUAGAGCACAUCCAGAAACUGAUUG
CCCCCAGGGAGACUACCAGUACCAAUGAACUGGCGACAGUUGAAUAGAUC
GCCAAAAUCUGGUAAAUCCUUGUUGAUUCCAGCUUUACCCCAUCUAUUUC
UUCUCUGUUUAAUUUUGCUUCCUCUGAGUAUUUUGGGUAGUCAUAAGUCC
CAUUUUUGACACUUUCCAUGCACGUGUUAUCGCAUUUGUGGUAAAAUUCA
AAGCAGCCGUUUCCAAUUUCCUUGGCAUUGUUUUUUAGCUGGCUUCUUAC
CUUUUCAUAUAAGUUCUUCACAUUUGAAUCGUGGUAGUCCAAAGUUCUUU
CAUUUUCCAAUAGAACCAACAGUUCGGCAUUGUAAGUCCAAAUGUCCAGG
AAACCAUCAUCAACUUUUUUAUUUAAAUUCUCUAUUCUUUUUUCCAGGUG
GUUGAACUCUUUACCUACUGCUGUGAACUGUGUAUUCAUCUUUUCAAUAA
CAGAAUUUACUUUGUUAGUAAUCUCGUCAAUGGCAUUCUGUGUGCUCUUC
AGGUCGGCUGCAUAUCCUGACCCCUGCUCAUUUUGAUGGUGAUAACCGUA
CCAUCCAUCUACCAUCCCUGUCCACCCCCCUUCAAUGAAACCGGCAAUGG
CCCCAAAUAGGCCUCUAGAUUGAAUAGACGGGACAUUCCUCAAUCCUGUG
GCCAGUCUCAAUUUUGUGCUUUUUACAUAUUUUGGACAUUUUCCAAUUGU
GAUCGGAUGUAUAUUCUGAAAUGGGAGGCUGGUGUUUAUAGCACCCUUGG
GUGUCUGACAAGUUGUAUUGCAAUCGUGGACUGGUGUAUCUGAAAUGAUA
AUACCAGAUCCAGCAUUUCUUUCCAUUGCGAAUGCAUAUCUCGGUACCAC
UAGAUUUCCAGUUGCUUCGAAUGUUAUUUUGUCUCCCGGCUCUACUAGUG
UCCAGUAAUAGUUCAUUCUCCCCUCUUGAUCCCUCACUUUGGGUCUUAUU
GCUAUUUCCGGCUUGAACUUCUUGCUGUAUCUUGAUGACCCCACAAAAAC
AUAUGCAUCUGCAUUCUGAUAGAGACUUUGUUGGUCAGCACUAGUAGAUG
GAUGGUGAAUGCCCCAUAGCACGAGGACUUCUUUCCCUUUAUCAUUAAUG
UAGGAUUUGCUGAGCUUUGGGUAUGAAUUUCCUUUUUUAACUAGCCAUAU
UAAAUUUUUGUAGAAGCUUUUUGCUCCAGCAUGAGGACAUGCUGCCGUUA
CACCUUUGUUCGAGUCAUGAUUGGGCCAUGAACUUGUCUUGGGGAAUAUC
UCAAACCUUUCAAAUGAUGACACUGAGCUCAAUUGCUCUCUUAGCUCCUC
AUAAUCGAUGAAAUCUCCUGGGUAACACGUUCCAUUGUCUGAACUAGAUG
UUUCCACAAUGUAGGACCAUGAGCUUGCUGUGGAGAGUGAUUCACACUCU
GGAUUUCCCAGGAUCCAGCCAGCAAUGUUACAUUUACCCAAAUGCAAUGG
GGCUACCCCUCUUAGUUUGCAUAGUUUCCCGUUAUGCUUGUCUUCUAGAA
GGUUAACAGAGUGUGUUACUGUUACAUUCUUUUCUAGUACUGUGUCUACA
GUGUCUGUUGAAUUGUUCGCAUGAUAACCUAUACAUAAUGUGUCUGCAUU
UGCGGUUGCAAAUGUAUAUAGCAGAACUACUAGUAUUGCCUUCAUUUUUG
UUGCUUUUGUUUUCCCCUGCUUUUGCU

>HA_CDS (SEQ ID NO: 67)

5'-

ATGAAGGCAATACTAGTAGTTCTGCTATATACATTTGCAACCGCAAATGC
AGACACATTATGTATAGGTTATCATGCGAACAATTCAACAGACACTGTAG
ACACAGTACTAGAAAAGAATGTAACAGTAACACACTCTGTTAACCTTCTA
GAAGACAAGCATAACGGGAAACTATGCAAACTAAGAGGGGTAGCCCCATT
GCATTTGGGTAAATGTAACATTGCTGGCTGGATCCTGGGAAATCCAGAGT
GTGAATCACTCTCCACAGCAAGCTCATGGTCCTACATTGTGGAAACATCT
AGTTCAGACAATGGAACGTGTTACCCAGGAGATTTCATCGATTATGAGGA
GCTAAGAGAGCAATTGAGCTCAGTGTCATCATTTGAAAGGTTTGAGATAT
TCCCCAAGACAAGTTCATGGCCCAATCATGACTCGAACAAAGGTGTAACG
GCAGCATGTCCTCATGCTGGAGCAAAAAGCTTCTACAAAAATTTAATATG
GCTAGTTAAAAAAGGAAATTCATACCCAAAGCTCAGCAAATCCTACATTA
ATGATAAAGGGAAAGAAGTCCTCGTGCTATGGGGCATTCACCATCCATCT
ACTAGTGCTGACCAACAAAGTCTCTATCAGAATGCAGATGCATATGTTTT
TGTGGGGTCATCAAGATACAGCAAGAAGTTCAAGCCGGAAATAGCAATAA
GACCCAAAGTGAGGGATCAAGAGGGGAGAATGAACTATTACTGGACACTA
GTAGAGCCGGGAGACAAAATAACATTCGAAGCAACTGGAAATCTAGTGGT
ACCGAGATATGCATTCGCAATGGAAAGAAATGCTGGATCTGGTATTATCA
TTTCAGATACACCAGTCCACGATTGCAATACAACTTGTCAGACACCCAAG

-continued

GGTGCTATAAACACCAGCCTCCCATTTCAGAATATACATCCGATCACAAT

TGGAAAATGTCCAAAATATGTAAAAAGCACAAAATTGAGACTGGCCACAG

GATTGAGGAATGTCCCGTCTATTCAATCTAGAGGCCTATTTGGGGCCATT

GCCGGTTTCATTGAAGGGGGGTGGACAGGGATGGTAGATGGATGGTACGG

TTATCACCATCAAAATGAGCAGGGGTCAGGATATGCAGCCGACCTGAAGA

GCACACAGAATGCCATTGACGAGATTACTAACAAAGTAAATTCTGTTATT

GAAAAGATGAATACACAGTTCACAGCAGTAGGTAAAGAGTTCAACCACCT

GGAAAAAAGAATAGAGAATTTAAATAAAAAAGTTGATGATGGTTTCCTGG

ACATTTGGACTTACAATGCCGAACTGTTGGTTCTATTGGAAAATGAAAGA

ACTTTGGACTACCACGATTCAAATGTGAAGAACTTATATGAAAAGGTAAG

AAGCCAGCTAAAAAACAATGCCAAGGAAATTGGAAACGGCTGCTTTGAAT

TTTACCACAAATGCGATAACACGTGCATGGAAAGTGTCAAAAATGGGACT

TATGACTACCCAAAATACTCAGAGGAAGCAAAATTAAACAGAGAAGAAAT

AGATGGGGTAAAGCTGGAATCAACAAGGATTTACCAGATTTTGGCGATCT

ATTCAACTGTCGCCAGTTCATTGGTACTGGTAGTCTCCCTGGGGGCAATC

AGTTTCTGGATGTGCTCTAATGGGTCTCTACAGTGTAGAATATGTATTTA

A

>HA_protein (SEQ ID NO: 68)

MKAILVVLLYTFATANADTLCIGYHANNSTDTVDTVLEKNVTVTHSVNLL

EDKHNGKLCKLRGVAPLHLGKCNIAGWILGNPECESLSTASSWSYIVETS

SSDNGTCYPGDFIDYEELREQLSSVSSFERFEIFPKTSSWPNHDSNKGVT

AACPHAGAKSFYKNLIWLVKKGNSYPKLSKSYINDKGKEVLVLWGIHHPS

TSADQQSLYQNADAYVFVGSSRYSKKFKPEIAIRPKVRDQEGRMNYYWTL

VEPGDKITFEATGNLVVPRYAFAMERNAGSGIIISDTPVHDCNTTCQTPK

GAINTSLPFQNIHPITIGKCPKYVKSTKLRLATGLRNVPSIQSRGLFGAI

AGFIEGGWTGMVDGWYGYHHQNEQGSGYAADLKSTQNAIDEITNKVNSVI

EKMNTQFTAVGKEFNHLEKRIENLNKKVDDGFLDIWTYNAELLVLLENER

TLDYHDSNVKNLYEKVRSQLKNNAKEIGNGCFEFYHKCDNTCMESVKNGT

YDYPKYSEEAKLNREEIDGVKLESTRIYQILAIYSTVASSLVLVVSLGAI

SFWMCSNGSLQCRICI*

Influenza NP Segment:

>genomic RNA (vRNA) NP sequence (SEQ ID NO: 69)

5'-
AGUAGAAACAAGGGUAUUUUUCCUCAACUGUCAUACUCCUCUGCAUUGUC

UCCGAAGAAAUAAGACCCUUCAUUACUCAUGUCAAAGGAAGGCACGAUCG

GGUUCGUUGCCUUUUCGUCCGAGAGCUCGAAGACUCCCCGCCCCUGGAAG

GACAAAUCUUCUGGCUUUGCACUUUCCAUCAUUCUUAUAACUUCUGUUCG

CAUGUCGGAUGUCCGUCCUUCAUUGUUCCCGCUGAAUGCUGCCAUAACGG

UUGCUCUUUCAAAAGGGAGAUUCCGCUGCACUGAGAAUGUAGGCUGCACA

CUGAUCUGGCCUGCGGAUGCCUUUUGUUGAUUGGUAUUUCCUCCACUCCU

-continued

GGUCCUUAUGGCCCAGUAUCUGCUUCUCAGUUCCAGGGUAUUGGAGUCCA

UGGUUUCCACAUUCUCAUUUGAAGCAAUCUGGACCCCUCUUGUGGAAAGC

UUUCCUCUUGGAAUCACUUUCUUUCCUCUUAUGAAACUUGAUACUCUUAA

AUCUUCAAAUGCAGCAGAGUGGCAUGCCAUCCACACCAAUUGACUCUUGU

GAGCUGGGUUUUCAUUUGGCCUCAUCAGGCUGACCACUUGGCUGUUUUGG

AGUAAUUUGAAUGGGUCUAUCCCGACCAGUGAGUACCCUUCCCUUUCAAA

GUCAUGCCCACUUGCUACUGCAAGCCCAUACACACAAGCAGGCAGGCAGG

AUUUAUGUGCAACUGAUCCCCUCAGAAUGAGUGCUGACCGUGCCAGGAAA

AUGAGGUCUUCAAUCUCAGCGUUUCCUGGGUUUCGACUUUCUCUUACUUG

AUCCAUCAUUGCCCUCUGGGCAGCUGUUUGAAAUUUUCCUUUGAGGAUAU

UGCACAUUCUUUCAUAAGCAACCCUUGUCCUUCGUCCAUUUUCACCCCUC

CAGAAAUUUCGGUCAUUGAUUCCACGUUUGAUCAUUCUGAUUAACUCCAU

UGCUAUUGUUCCAACUCCUUUCACCGCAGCACCUGCGGCACCAGACCUUC

UGGGAAGUGUUGAACCUUGCAUUAGAGAGCACAUUCUGGGAUCCAUUCCG

GUGCGAACAAGCGCUCUUGUUCUCUGAUAUGUGGCAUCAUUCAGGUUGGA

AUGCCAAAUCAUGAUAUGAGUAAGACCUGCUGUUGCAUCUUCGCCAUUGU

UUGCUUGGCGCCAAACUCUCCUUAUUUCUUCUUUGUCAUAAAGGAUGAGU

UCUCUCAUCCACUUUCCGUCUACUCUUCUAUAUAUGGGUCCUCCUGUUUU

CUUAGGGUCCUUCCCAGCACUGGGAUGCUCUUCUAGGUAUUUAUUUCUUC

UCUCAUCAAAAGCAGAAAGCACCAUCCUCUCUAUUGUUAUGCUAUUCUGG

AUUAGUCGUCCAUCAUAAUCACUGAGUUUGAGUUCAGUGCACAUUUGGAU

GUAGAAUCUCCCGAUUCCACCAAUCAUUCUUCCGACAGAUGCUCUGAUUU

CUGUGGCAUCCUGGCGCUCCCCACCAGUCUCCAUUUGUUCAUAUGAUCGU

UUGGUGCCUUGAGACGCCAUGGCUUCGAUGUCACUCAUUGAGUGAUUAUC

UACCCUGCUUUUGCU

>NP_CDS (SEQ ID NO: 70)

5'-

ATGGCGTCTCAAGGCACCAAACGATCATATGAACAAATGGAGACTGGTGG

GGAGCGCCAGGATGCCACAGAAATCAGAGCATCTGTCGGAAGAATGATTG

GTGGAATCGGGAGATTCTACATCCAAATGTGCACTGAACTCAAACTCAGT

GATTATGATGGACGACTAATCCAGAATAGCATAACAATAGAGAGGATGGT

GCTTTCTGCTTTTGATGAGAGAAGAAATAAATACCTAGAAGAGCATCCCA

GTGCTGGGAAGGACCCTAAGAAAACAGGAGGACCCATATATAGAAGAGTA

GACGGAAAGTGGATGAGAGAACTCATCCTTTATGACAAAGAAGAAATAAG

GAGAGTTTGGCGCCAAGCAAACAATGGCGAAGATGCAACAGCAGGTCTTA

CTCATATCATGATTTGGCATTCCAACCTGAATGATGCCACATATCAGAGA

ACAAGAGCGCTTGTTCGCACCGGAATGGATCCCAGAATGTGCTCTCTAAT

GCAAGGTTCAACACTTCCCAGAAGGTCTGGTGCCGCAGGTGCTGCGGTGA

AAGGAGTTGGAACAATAGCAATGGAGTTAATCAGAATGATCAAACGTGGA

ATCAATGACCGAAATTTCTGGAGGGGTGAAAATGGACGAAGGACAAGGGT

```
TGCTTATGAAAGAATGTGCAATATCCTCAAAGGAAAATTTCAAACAGCTG
CCCAGAGGGCAATGATGGATCAAGTAAGAGAAAGTCGAAACCCAGGAAAC
GCTGAGATTGAAGACCTCATTTTCCTGGCACGGTCAGCACTCATTCTGAG
GGGATCAGTTGCACATAAATCCTGCCTGCCTGCTTGTGTGTATGGGCTTG
CAGTAGCAAGTGGGCATGACTTTGAAAGGGAAGGGTACTCACTGGTCGGG
ATAGACCCATTCAAATTACTCCAAAACAGCCAAGTGGTCAGCCTGATGAG
GCCAAATGAAAACCCAGCTCACAAGAGTCAATTGGTGTGGATGGCATGCC
ACTCTGCTGCATTTGAAGATTTAAGAGTATCAAGTTTCATAAGAGGAAAG
AAAGTGATTCCAAGAGGAAAGCTTTCCACAAGAGGGGTCCAGATTGCTTC
AAATGAGAATGTGGAAACCATGGACTCCAATACCCTGGAACTGAGAAGCA
GATACTGGGCCATAAGGACCAGGAGTGGAGGAAATACCAATCAACAAAAG
GCATCCGCAGGCCAGATCAGTGTGCAGCCTACATTCTCAGTGCAGCGGAA
TCTCCCTTTTGAAAGAGCAACCGTTATGGCAGCATTCAGCGGGAACAATG
AAGGACGGACATCCGACATGCGAACAGAAGTTATAAGAATGATGGAAAGT
GCAAAGCCAGAAGATTTGTCCTTCCAGGGGCGGGAGTCTTCGAGCTCTC
GGACGAAAAGGCAACGAACCCGATCGTGCCTTCCTTTGACATGAGTAATG
AAGGGTCTTATTTCTTCGGAGACAATGCAGAGGAGTATGACAGTTGA
>NP_protein
                                        (SEQ ID NO: 71)
MASQGTKRSYEQMETGGERQDATEIRASVGRMIGGIGRFYIQMCTELKLS
DYDGRLIQNSITIERMVLSAFDERRNKYLEEHPSAGKDPKKTGGPIYRRV
DGKWMRELILYDKEEIRRVWRQANNGEDATAGLTHIMIWHSNLNDATYQR
TRALVRTGMDPRMCSLMQGSTLPRRSGAAGAAVKGVGTIAMELIRMIKRG
INDRNFWRGENGRRTRVAYERMCNILKGKFQTAAQRAMMDQVRESRNPGN
AEIEDLIFLARSALILRGSVAHKSCLPACVYGLAVASGHDFEREGYSLVG
IDPFKLLQNSQVVSLMRPNENPAHKSQLVWMACHSAAFEDLRVSSFIRGK
KVIPRGKLSTRGVQIASNENVETMDSNTLELRSRYWAIRTRSGGNTNQQK
ASAGQISVQPTFSVQRNLPFERATVMAAFSGNNEGRTSDMRTEVIRMMES
AKPEDLSFQGRGVFELSDEKATNPIVPSFDMSNEGSYFFGDNAEEYDS*
```

Influenza NA Segment:

```
>genomic RNA (vRNA) NA sequence
                                        (SEQ ID NO: 72)
5'-AGUAGAAACAAGGAGUUUUUUGAACAAAUUACUUGUCAAUGGUAAAU
GGCAACUCAGCACCGUCUGGCCAAGACCAACCCACAGUGUCACUGUUUAC
ACCACAAAAGGAUAUGCUGCUCCCGCUAGUCCAGAUUGUGUUCUCUUUGG
GUCGCCCUCUGAUUAGUUCAACCCAGAAGCAAGGUCUUAUACAAUCCAGC
CCUGUUAGUUCUGGAUGCUGAACAAAACUCCCGCUAUAUCCUGACCACUC
AUUUAUUCCUACGAUAUCUUGCUUUAUUGAGAAGUUAUUGUCUGUCCCAG
UCCAUCCGUUCGGAUCCCAAAUCAUCUCAAAACCGUUUCUUGAACUAAUG
CUUUUAGUUCUCCCUAUCCAAACACCAUUGCCGUAUUUGAAUGAAAAUCC
UUUUACUCCAUUGCUCCAUUAGACGAUACUGGACCACAACUGCCUGUCU
UAUCAUUAGGGCGUGGAUUGUCUCCGAAAAUCCCACUGCAUAUGUAUCCU
AUCUGAUAUUCCAGAUUCUGGUUGAAAGACACCCACGGUCGAUUCGAGCC
AUGCCAGUUAUCCCUGCACACACAUGUGAUUUCACUAGAAUCAGGAUAAC
AGGAGCAUUCCUCAUAGUGAUAAUUAGGGGCAUUCAUUUCGACUGAUUUG
ACUAUCUUUCCCUUUUCUAUUCUGAAGAUCUUGUAUGAGGCCUGUCCAUU
ACUUGGUCCAUCGGUCAUUACAGUAAAGCAAGAACCAUUUACACAUGCAC
AUUCAGACUCUUGUGUUCUCAAUAUAUUGUUUCUCCAACUCUUGAUAGUG
UCUGUUAUUAUGCCGUUGUACUUUAACACAGCCACUGCCCCAUUGUCUGG
GCCAGAAAUUCCAAUUGUUAGCCAAUUGAUGCCAUCAUGACAAGCACUUG
CUGACCAAGCGACUGACUCAAAUCUUGAGUUGUAUGGAGAGGGAACUUCA
CCAAUAGGACAGCUCAUUAGGGUUCGAUAUGGGCUCCUGUCUUUAAUGGU
UCCAUUGGAAUGUUUGUCAUUUAGCAAGGCCCCUUGAGUCAAGAAGAAGG
UUCUGCAUUCCAAGGGGGAGCAUGAUAUGAAUGGUUCCCUUAUGACAAAC
ACAUCCCCUUGGAACCGAUUCUUACACUGUUGUCUUUACUGUAUAUAGC
CCAUCCACUAACAGGGCAGAGAGAGGAAUUGCCCGCUAAUUUCACGGAAA
CCACUGACUGUCCAGCAGCAAAGUUGGUGUUGCUGAUGUUAACAUAUGUC
UGAUUUACCCAAGUGUUGUUUUCAUAAGUAAUGACGCUUUGAUUGCAUGU
UUCAAUCUGAUUUUGAUUCCCAAGUUGAAUUGAGUGGCUAAUCCAUAUUG
AGAUUAUGUUUCCAAUUUGUAAUAUUAAGUUAGCCAUUCCAAUUGUCAUA
CAGACCGAACCAAUGGUUAUUAUCUUUUGGUUUGGAUUCAUUUUAAACUC
CUGCUUUUGCU
>NA_CDS
                                        (SEQ ID NO: 73)
5'-ATGAATCCAAACCAAAAGATAATAACCATTGGTTCGGTCTGTATGAC
AATTGGAATGGCTAACTTAATATTACAAATTGGAAACATAATCTCAATAT
GGATTAGCCACTCAATTCAACTTGGGAATCAAAATCAGATTGAAACATGC
AATCAAAGCGTCATTACTTATGAAAACAACACTTGGGTAAATCAGACATA
TGTTAACATCAGCAACACCAACTTTGCTGCTGGACAGTCAGTGGTTTCCG
TGAAATTAGCGGGCAATTCCTCTCTCTGCCCTGTTAGTGGATGGGCTATA
TACAGTAAAGACAACAGTGTAAGAATCGGTTCCAAGGGGGATGTGTTTGT
CATAAGGGAACCATTCATATCATGCTCCCCCTTGGAATGCAGAACCTTCT
TCTTGACTCAAGGGGCCTTGCTAAATGACAAACATTCCAATGGAACCATT
AAAGACAGGAGCCCATATCGAACCCTAATGAGCTGTCCTATTGGTGAAGT
TCCCTCTCCATACAACTCAAGATTTGAGTCAGTCGCTTGGTCAGCAAGTG
CTTGTCATGATGGCATCAATTGGCTAACAATTGGAATTTCTGGCCCAGAC
AATGGGGCAGTGGCTGTGTTAAAGTACAACGGCATAATAACAGACACTAT
CAAGAGTTGGAGAAACAATATATTGAGAACACAAGAGTCTGAATGTGCAT
GTGTAAATGGTTCTTGCTTTACTGTAATGACCGATGGACCAAGTAATGGA
CAGGCCTCATACAAGATCTTCAGAATAGAAAAGGGAAAGATAGTCAAATC
AGTCGAAATGAATGCCCCTAATTATCACTATGAGGAATGCTCCTGTTATC
CTGATTCTAGTGAAATCACATGTGTGTGCAGGGATAACTGGCATGGCTCG
AATCGACCGTGGGTGTCTTTCAACCAGAATCTGGAATATCAGATAGGATA
```

```
CATATGCAGTGGGATTTTCGGAGACAATCCACGCCCTAATGATAAGACAG
GCAGTTGTGGTCCAGTATCGTCTAATGGAGCAAATGGAGTAAAAGGATTT
TCATTCAAATACGGCAATGGTGTTTGGATAGGGAGAACTAAAAGCATTAG
TTCAAGAAACGGTTTTGAGATGATTTGGGATCCGAACGGATGGACTGGGA
CAGACAATAACTTCTCAATAAAGCAAGATATCGTAGGAATAAATGAGTGG
TCAGGATATAGCGGGAGTTTTGTTCAGCATCCAGAACTAACAGGGCTGGA
TTGTATAAGACCTTGCTTCTGGGTTGAACTAATCAGAGGGCGACCCAAAG
AGAACACAATCTGGACTAGCGGGAGCAGCATATCCTTTTGTGGTGTAAAC
AGTGACACTGTGGGTTGGTCTTGGCCAGACGGTGCTGAGTTGCCATTTAC
CATTGACAAGTAA
```

>NA_protein (SEQ ID NO: 74)

MNPNQKIITIGSVCMTIGMANLILQIGNIISIWISHSIQLGNQNQIETCN
QSVITYENNTWVNQTYVNISNTNFAAGQSVVSVKLAGNSSLCPVSGWAIY
SKDNSVRIGSKGDVFVIREPFISCSPLECRTFFLTQGALLNDKHSNGTIK
DRSPYRTLMSCPIGEVPSPYNSRFESVAWSASACHDGINWLTIGISGPDN
GAVAVLKYNGIITDTIKSWRNNILRTQESECACVNGSCFTVMTDGPSNGQ
ASYKIFRIEKGKIVKSVEMNAPNYHYEECSCYPDSSEITCVCRDNWHGSN
RPWVSFNQNLEYQIGYICSGIFGDNPRPNDKTGSCGPVSSNGANGVKGFS
FKYGNGVWIGRTKSISSRNGFEMIWDPNGWTGTDNNFSIKQDIVGINEWS
GYSGSFVQHPELTGLDCIRPCFWVELIRGRPKENTIWTSGSSISFCGVNS
DTVGWSWPDGAELPFTIDK*

Influenza M Segment:

>genomic RNA (vRNA) M sequence (SEQ ID NO: 75)
```
5'-AGUAGAAACAAGGUAGUUUUUUACUCUAGCUCUAUGUUGACAAAAUG
ACCAUCGUCAACAUCCACAGCACUCUGCUGUUCCUGUUGAUAUUCUUCCC
UCAUGGACUCAGGCACUCCUUCCGUAGAAGGCCCUCUUUUCAAACCGUAU
UUAAAGCGACGAUAAAUACAUUUGAAAAAAAGACGAUCAGUAAUCCACAA
UAUCAGGUGCAAGAUCCCAAUGAUAUUUGCUGCAAUGACGAGAGGAUCAC
UUGAAUCGCUGCAUCUGCACUCCCAUUCGCUUCUGGUAGGCCUGCAAAUU
UUCAAGAAGGUCAUCUUUCAGACCAGCACUGGAGCUAGGAUGAGUCCCAA
UAGUUCUCAUUGCAUGUACCAUCUGCCUAGUCUGAUUAGCAACCUCCAUG
GCCUCCGCUGCCUGUUCACUCGAUCCAGCCAUCUGUUCCAUAGCCUUUGC
CGUAGUGCUAGCCAGCACCAUUCUGUUUUCAUGCCUGAUUAGUGGAUUGG
UGGUAGUAGCCAUCUGUCUGUGAGACCGAUGCUGUGAAUCAGCAAUCUGU
UCACAAGUGGCACACACUAGACCAAAAGCAGCUUCUGUGGUCACUGUUCC
CAUCCUGUUGUAUAUGAGGCCCAUGCAACUGGCAAGUGCACCAGUUGAAU
AGCUUAGUGACACCUCCUUGGCCCCAUGGAACGUUAUUUCUCUUUUUGAGC
UUCUUGUAUAGUUUAACUGCUCUAUCCAUGUUGUUCGGUCCCCAUUCCC
AUUUAGGGCAUUUUGGACAAAGCGUCUACGCUGCAGUCCUCGCUCACUGG
GCACGGUGAGCGUGAACACAAAUCCUAAAAUUCCCUUAGUCAGAGGUGAC
```
```
AAGAUUGGUCUUGUCUUUAGCCAUUCCAUGAGAGCCUCAAGAUCUGUGUU
CUUUCCUGCAAAGACACUUUCCAGUCUCUGCGCGAUCUCGGCUUUGAGGG
GGCCUGACGGGAUGAUAGAAAGAACGUACGUUUCGACCUCGGUUAGAAGA
CUCAUCUUUAAAUAUCUACCUGCUUUUGCU
```

>M1_CDS (SEQ ID NO: 76)
```
5'-ATGAGTCTTCTAACCGAGGTCGAAACGTACGTTCTTTCTATCATCCC
GTCAGGCCCCCTCAAAGCCGAGATCGCGCAGAGACTGGAAAGTGTCTTTG
CAGGAAAGAACACAGATCTTGAGGCTCTCATGGAATGGCTAAAGACAAGA
CCAATCTTGTCACCTCTGACTAAGGGAATTTTAGGATTTGTGTTCACGCT
CACCGTGCCCAGTGAGCGAGGACTGCAGCGTAGACGCTTTGTCCAAAATG
CCCTAAATGGGAATGGGGACCCGAACAACATGGATAGAGCAGTTAAACTA
TACAAGAAGCTCAAAAGAGAAATAACGTTCCATGGGGCCAAGGAGGTGTC
ACTAAGCTATTCAACTGGTGCACTTGCCAGTTGCATGGGCCTCATATACA
ACAGGATGGGAACAGTGACCACAGAAGCTGCTTTTGGTCTAGTGTGTGCC
ACTTGTGAACAGATTGCTGATTCACAGCATCGGTCTCACAGACAGATGGC
TACTACCACCAATCCACTAATCAGGCATGAAAACAGAATGGTGCTGGCTA
GCACTACGGCAAAGGCTATGGAACAGATGGCTGGATCGAGTGAACAGGCA
GCGGAGGCCATGGAGGTTGCTAATCAGACTAGGCAGATGGTACATGCAAT
GAGAACTATTGGGACTCATCCTAGCTCCAGTGCTGGTCTGAAAGATGACC
TTCTTGAAAATTTGCAGGCCTACCAGAAGCGAATGGGAGTGCAGATGCAG
CGATTCAAGTGA
```

>M1_protein (SEQ ID NO: 77)

MSLLTEVETYVLSIIPSGPLKAEIAQRLESVFAGKNTDLEALMEWLKTRP
ILSPLTKGILGFVFTLTVPSERGLQRRRFVQNALNGNGDPNNMDRAVKLY
KKLKREITFHGAKEVSLSYSTGALASCMGLIYNRMGTVTTEAAFGLVCAT
CEQIADSQHRSHRQMATTTNPLIRHENRMVLASTTAKAMEQMAGSSEQAA
EAMEVANQTRQMVHAMRTIGTHPSSSAGLKDDLLENLQAYQKRMGVQMQR
FK*

>M2_CDS (SEQ ID NO: 78)
```
5'-ATGAGTCTTCTAACCGAGGTCGAAACGCCTACCAGAAGCGAATGGGA
GTGCAGATGCAGCGATTCAAGTGATCCTCTCGTCATTGCAGCAAATATCA
TTGGGATCTTGCACCTGATATTGTGGATTACTGATCGTCTTTTTTTCAAA
TGTATTTATCGTCGCTTTAAATACGGTTTGAAAAGAGGGCCTTCTACGGA
AGGAGTGCCTGAGTCCATGAGGGAAGAATATCAACAGGAACAGCAGAGTG
CTGTGGATGTTGACGATGGTCATTTTGTCAACATAGAGCTAGAGTAA
```

>M2_protein (SEQ ID NO: 79)

MSLLTEVETPTRSEWECRCSDSSDPLVIAANIIGILHLILWITDRLFFKC
IYRRFKYGLKRGPSTEGVPESMREEYQQEQQSAVDVDDGHFVNIELE*

Influenza NS Segment:

>genomic RNA (vRNA) NS sequence
(SEQ ID NO: 80)
5'-AGUAGAAACAAGGGUGUUUUUUAUCAUUAAAUAAGCUGAAACGAGAA

AGCUCUUAUCUCUUGUUCUACUUCAAGCAGUAGUUGUAAGGCUUGCAUAA

AUGUUAUUUGUUCGAAACUAUUCUCUGUCGCUUUCAAUCUGUGCCGCAUU

UCUUCAAUUAACCACCUUAUUUCCUCAAAUUUCUGUCCCAAUUGCUCUCG

CCACUUUUCAUUUCUGCUCUGGAGGUAGUGAAGGUCUCCCAUUCUCAUCA

CAGUUUCUCCAAGCGAAUCUCUGUAUAUUUUCAGAGACUCGAACCGUGUU

ACCAUUCCAUUCAAGUCCUCCGAUGAGGACCCCAACUGCAUUUUUGACAU

CCUCAUAAGUAUGUCCUGGAAGAGAAGGUGAUGGUGAAAUUUCUCCAACU

AUUGCUCCCUCCUCAGUGAAAGCCCUUAGUAGUAUCAAGGUCUCUAAUCG

GUUAAAGAUUACACUGAAGUUCGCUUUCAGUACUAUGUUCUUUUCCAUGA

UCGCCUGGUCCAAUCGCACGCAAAGAGGGCCUAUUAUCUUUUGCCUAGGC

AUGAGCAUGAACCAGUCUCGUGACAUUUCCUCGAGGGUCAUGUCAGAAAG

GUAGCGCGAAGUAGGUACAGAUGCAAUUGUCAUUCUAAGUGUCUCGCUGG

AUUCCUCUUUCAAUAUCCAUUCCACGAUUUGUUUCCCAACAAGAGUGGCU

GUUUCGAUAUCGAGGCCAAGGGUGUUGCCUCUUCCUUUUAAGGACUUUUG

AUCUCGGCGGAGCCGAUCAAGGAAUGGGGCAUCACCCAAUCCAUUGUCUG

CAAAUCGCUUGCGGAUAUGCCAAAGGAAACAGUCUACCUGAAAGCUUGAC

AUGGUGUUGGAGUCCAUUAUGUUUUUGUCACCCUGCUUUUGCU

>NS1_CDS
(SEQ ID NO: 81)
5'-ATGGACTCCAACACCATGTCAAGCTTTCAGGTAGACTGTTTCCTTTG

GCATATCCGCAAGCGATTTGCAGACAATGGATTGGGTGATGCCCCATTCC

TTGATCGGCTCCGCCGAGATCAAAAGTCCTTAAAAGGAAGAGGCAACACC

CTTGGCCTCGATATCGAAACAGCCACTCTTGTTGGGAAACAAATCGTGGA

ATGGATATTGAAAGAGGAATCCAGCGAGACACTTAGAATGACAATTGCAT

CTGTACCTACTTCGCGCTACCTTTCTGACATGACCCTCGAGGAAATGTCA

CGAGACTGGTTCATGCTCATGCCTAGGCAAAAGATAATAGGCCCTCTTTG

CGTGCGATTGGACCAGGCGATCATGGAAAAGAACATAGTACTGAAAGCGA

ACTTCAGTGTAATCTTTAACCGATTAGAGACCTTGATACTACTAAGGGCT

TTCACTGAGGAGGGAGCAATAGTTGGAGAAATTTCACCATCACCTTCTCT

TCCAGGACATACTTATGAGGATGTCAAAAATGCAGTTGGGGTCCTCATCG

GAGGACTTGAATGGAATGGTAACACGGTTCGAGTCTCTGAAAATATACAG

AGATTCGCTTGGAGAAACTGTGATGAGAATGGGAGACCTTCACTACCTCC

AGAGCAGAAATGA

>NS1_protein
(SEQ ID NO: 82)
MDSNTMSSFQVDCFLWHIRKRFADNGLGDAPFLDRLRRDQKSLKGRGNTL

GLDIETATLVGKQIVEWILKEESSETLRMTIASVPTSRYLSDMTLEEMSR

-continued
DWFMLMPRQKIIGPLCVRLDQAIMEKNIVLKANFSVIFNRLETLILLRAF

TEEGAIVGEISPSPSLPGHTYEDVKNAVGVLIGGLEWNGNTVRVSENIQR

FAWRNCDENGRPSLPPEQK*

>NS2_CDS
(SEQ ID NO: 83)
5'-ATGGACTCCAACACCATGTCAAGCTTTCAGGACATACTTATGAGGAT

GTCAAAAATGCAGTTGGGGTCCTCATCGGAGGACTTGAATGGAATGGTAA

CACGGTTCGAGTCTCTGAAAATATACAGAGATTCGCTTGGAGAAACTGTG

ATGAGAATGGGAGACCTTCACTACCTCCAGAGCAGAAATGAAAAGTGGCG

AGAGCAATTGGGACAGAAATTTGAGGAAATAAGGTGGTTAATTGAAGAAA

TGCGGCACAGATTGAAAGCGACAGAGAATAGTTTCGAACAAATAACATTT

ATGCAAGCCTTACAACTACTGCTTGAAGTAGAACAAGAGATAAGAGCTTT

CTCGTTTCAGCTTATTTAA

>NS2_protein
(SEQ ID NO: 84)
MDSNTMSSFQDILMRMSKMQLGSSSEDLNGMVTRFESLKIYRDSLGETVM

RMGDLHYLQSRNEKWREQLGQKFEEIRWLIEEMRHRLKATENSFEQITFM

QALQLLLEVEQEIRAFSFQLI*

Results

Figure 12A:
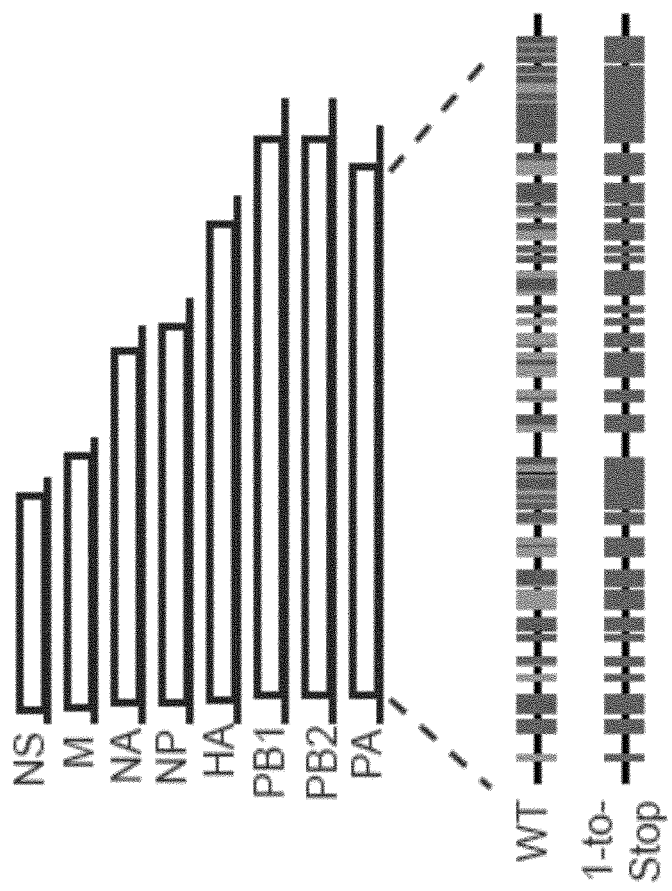
FIGS. 12A, 12B and 12C. (A) Schematic of the Influenza A virus genome's 8 individual segments with open reading frames encoding each protein. The PA gene, in expanded view, shows the 110 Ser/Leu codons that were altered for each 1-to-Stop virus. (B) Dinucleotide frequency of CpG (solid bars) and UpA (open bars) in wild type and 1-to-Stop Coxsackie virus (CVB3) constructs, relative to previously published wild type E7 virus and its constructs shown to affect virus attenuation. The values indicate the actual number of dinucleotides present in the wild type genome and increase or decrease (+/−n) in the altered region of genetically engineered variants. (C) Codon pair bias of wild type and 1-to-Stop CVB3, compared to wild type poliovirus (PV) and previously published constructs engineered to attenuate virus through codon pair deoptimization: PV-AB, construct containing only rare codons; PV-SD, in which codons were randomly shuffled; PV-Max, in which codon pair bias was maximized; PV-Min, in which codon pair bias was minimized.
Figures 12B, 12C:
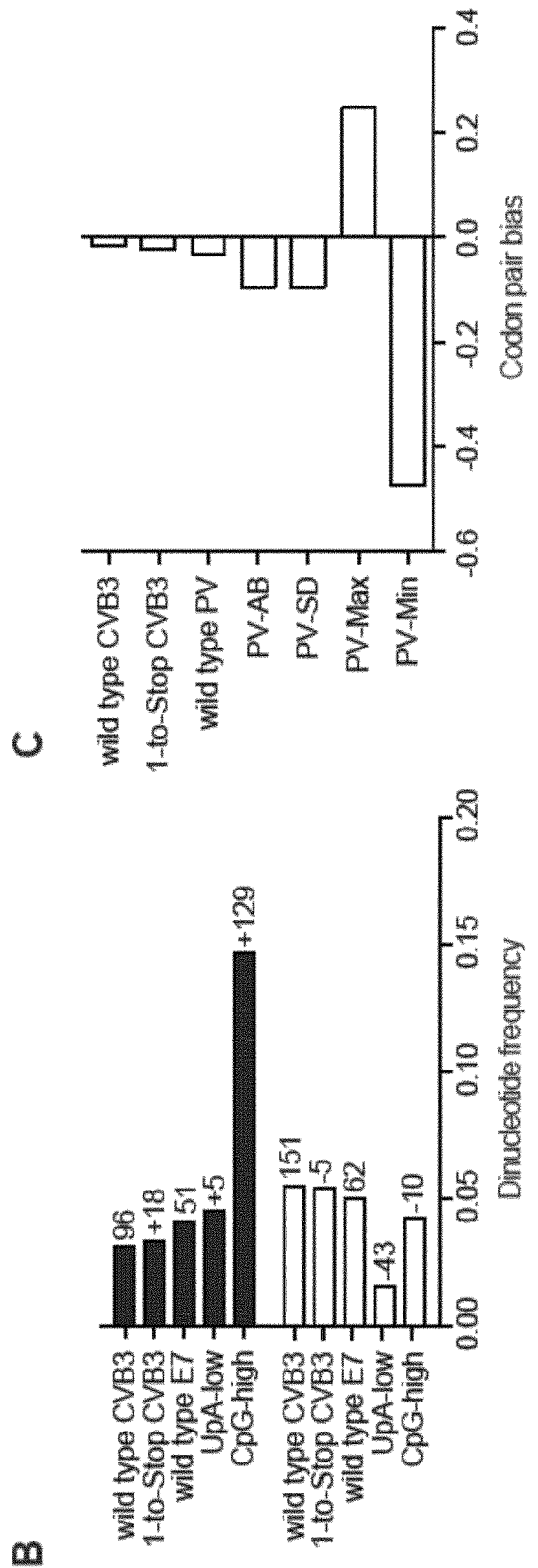

Reprogramming a viral genome to have enhanced proclivity for non-sense mutations, without impacting replication kinetics. Our goal was to assess the effect of shifting a virus location in sequence space to less 'hospitable' regions that increase its propensity to generate non-sense mutations. However, altering location in sequence space requires changes in nucleotide sequence, which can result in confounding factors such as changes in amino acid sequence or RNA structure, or introduction of nucleotide and codon bias. To minimize these factors, we chose the P1 structural protein-coding region of the genome (cf. example 1 above), which does not contain significant RNA structure or replication/translation elements. Indeed, this region can be entirely deleted or replaced by exogenous sequences without affecting genome replication or packaging. We chose to introduce only synonymous changes, so that the proteins produced by the new virus have the same amino acid sequence and retain the same functions as wild type virus. We also elected to change the codons for only two amino acids with the highest codon redundancy (Leucine and Serine) for two reasons: 1) we wanted the overall change in nucleotide sequence to be limited to less than 5% of the total genome sequence and 2) we chose codons on which mutations would have the most significant impact on viability. Of the six Leu and six Ser codons, we identified a category that we termed '1-to-Stop', because single nucleotide changes on these codons would result in Stop mutations (cf. example 1 above; cf. FIG. 1). Since the viral genome is translated into a single polyprotein that is cleaved into individual viral proteins required to replicate the virus, a stop mutation in the P1 region would 'kill' the virus. We thus generated a '1-to-Stop' Coxsackie virus in which the 117 Ser and Leu codons of wild type virus were all synonymously changed to the '1-to-Stop' category of codons. Previously, Atkinson et al. demonstrated that the increases in CpG and UpA dinucleotides as a result of codon reshuffling could account for the observed attenuation of RNA viruses in cell culture, while decreases could improve replication kinetics (Atkinson et al. 2014). In comparison, no significant changes in CpG and UpA dinucleotide frequency were introduced in the 1-to-Stop (FIG. 12B) that would confound our observations. In other codon re-shuffling studies, the introduction of codon pair bias was found to be responsible for virus attenuation. Once more, we confirmed that the 1-to-Stop virus did not present a significant change in codon pair bias (FIG. 12C). Furthermore, we confirmed the aforementioned factors and potential alterations in RNA folding did not significantly alter the replication kinetics of the 1-to-Stop virus stock and after five passages in tissue culture (cf. FIGS. 4A-4E; cf. example 1). None of the 117 Leu and Ser codon changes had reverted or mutated at the consensus level during passage, indicating that the genome modifications were genetically stable. The retention of wild type-like replicative capacity was further confirmed by in vitro replication assays, in which in vitro transcribed virus RNA was allowed to replicate in the presence of replication complexes isolated from infected cells (cf. FIG. 2, cf. example 1).

Figures 13A, 13B:
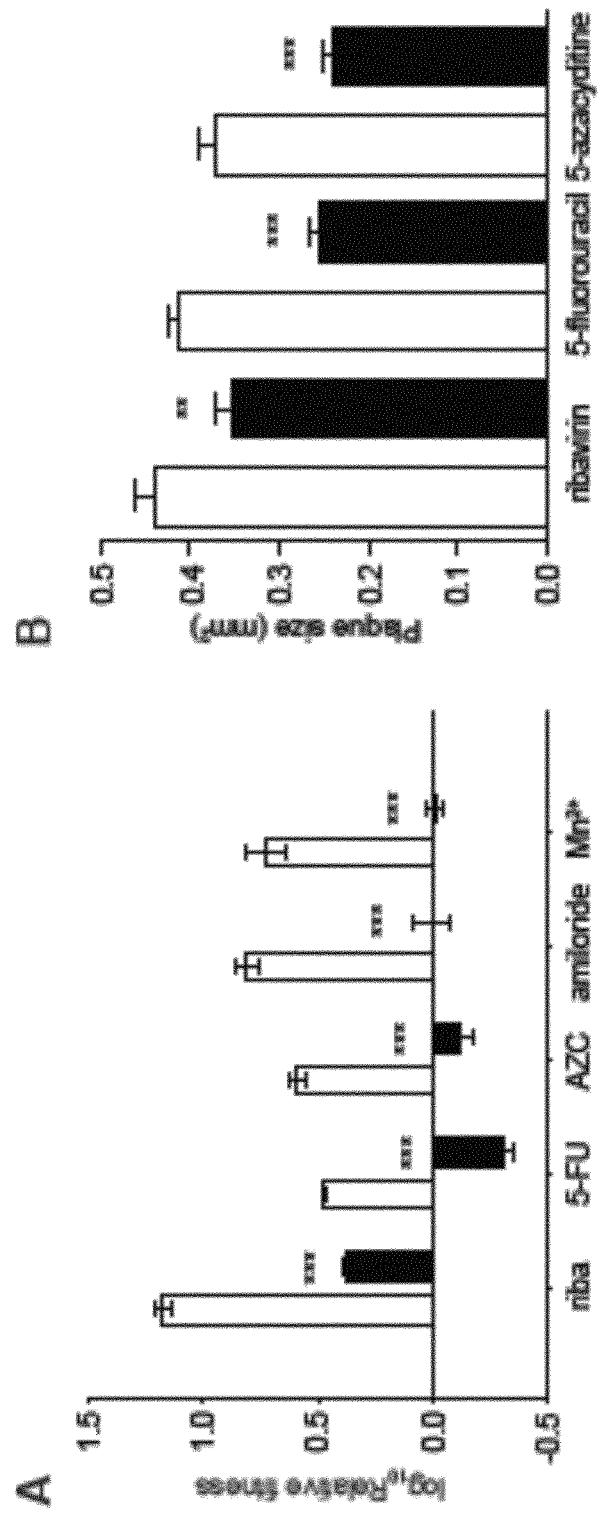
Figures 13C, 13D:
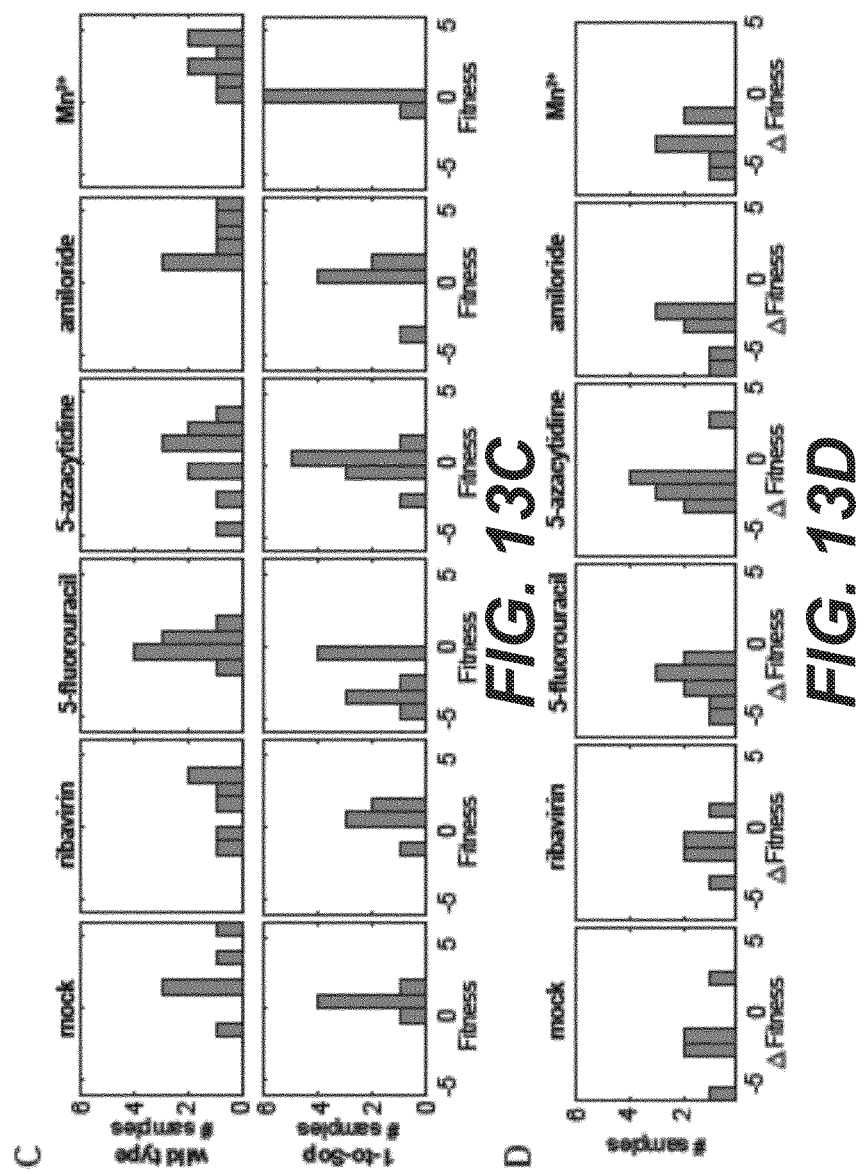

The 1-to-Stop virus has lower fitness and is hyper-sensitive to mutation. Given the high mutation rates of RNA viruses, the 1-to-Stop virus would expectedly be more sensitive to the effects of mutation (lower mutational robustness) because of its higher likelihood of generating stop mutations. This effect would be exacerbated when mutation rate is increased. We thus determined the relative fitness of wild type and 1-to-Stop virus when grown under five different mutagenic treatments: the mutagenic base analogs ribavirin, 5-fluorouracil and 5-azacytidine; amiloride, which perturbs intracellular concentrations of Mg2+ and Mn2+ that are essential co-factors of the viral polymerase; and Mn2+ itself, which increases the polymerase error rate. In all five cases, the 1-to-Stop virus presented significantly lower fitness (FIG. 13A). As another measure of the effect of mutation on virus fitness, the mean plaque size was determined for virus treated with the three mutagenic base analogs. The 1-to-Stop virus produced significantly smaller plaques in all three cases (FIG. 13B). The distribution of fitness values between wild type and the 1-to-Stop virus under mutagenic conditions reveals that a greater proportion of wild type samples present positive fitness compared to the 1-to-Stop virus (FIG. 13C), and that the relative change in fitness for the 1-to-Stop virus compared to wild type is highly significant (FIG. 13D). Since the synonymous codon changes of the 1-to-Stop virus are expected to alter the sequence space available to the virus, and thus, the mutants this population can generate, we passaged 15 wild type and 15 1-to-Stop virus populations for five passages and characterized the changes that emerged by mutation at the 117 altered Leu/Ser codon sites (FIG. 13E). The data show that although relatively stable, the 1-to-Stop viruses do present variants that have regenerated some wild type-like codons at low frequency: for example, the '1-to-Stop' TTA/TTG Leucine codons have mutated to CTA/CTG. Additionally, changing the sequence space of the 1-to-Stop virus has impeded its ability to generate amino acid mutations found in all wild type virus populations: for example, the isoleucine and proline mutants. Importantly, the data show that the 1-to-Stop virus populations generate more Stop mutations than wild type viruses. To better quantify this observation, we deep sequenced wild type and 1-to-Stop viruses grown in low (FIG. 13F) and high (FIG. 13G) concentrations of RNA mutagens. The 1-to-Stop virus populations contain a significantly higher proportion of genomes with Stop mutations compared to wild type.

Figures 14A, 14B, 14C:
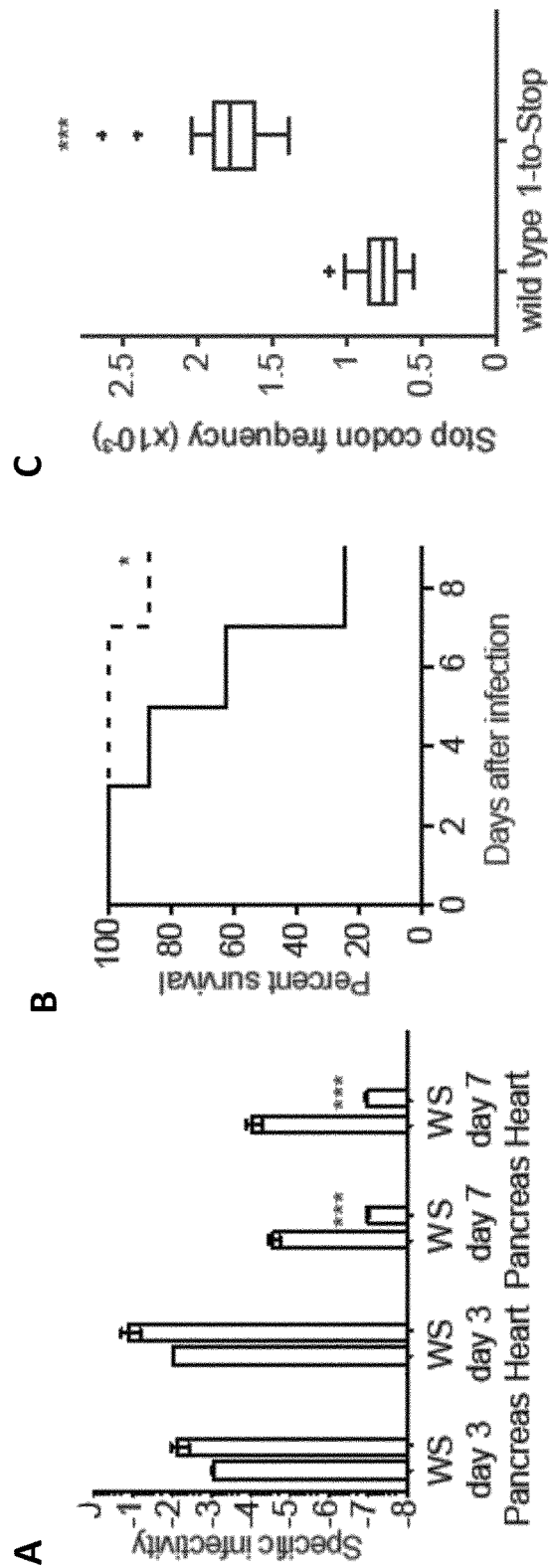
FIGS. 14A, 14B and 14C. 1-to-Stop is attenuated in vivo. (A) Specific infectivity of wild type (W) and 1-to-Stop (S) viruses from day 3 and 7 samples from pancreas and heart. *** P<0.0001, n=6, two-tailed t test. (B) Survival curve of mice infected with either $10^6$ TCID$_{50}$ of wildtype (solid line) or 1-to-Stop (dashed line) viruses. * P=0.011, n=10, Mantel-Cox test. (C) The frequency of stop mutations observed in sequence reads from the wildtype and 1-to-Stop populations from infected tissues (hearts and pancreata combined). Box plot shows mean values and 25% and 75% confidence intervals, whiskers show min. and max. values, outliers are shown as + symbols; n=62, *** P<0.0001, two-tailed unpaired t test.

The 1-to-Stop virus is attenuated and generates more stop mutations in vivo. To evaluate whether repositioning a virus in a region of sequence space that increases its propensity for non-sense mutations may lead to attenuation, mice were given a sub-lethal dose of wild type or 1-to-Stop virus, and viral titres were determined over the seven days of acute infection. While the 1-to-Stop virus replicated with wild type-like kinetics during the first five days of infection, it was no longer detectable in neither the pancreata nor hearts by day seven (cf. FIGS. 9A-9B; cf. example 1). While RNA could still be detected at seven days of infection, viable virus could not be recovered from the tissues, and the specific infectivity of the progeny virus population was significantly lower than wild type (FIG. 14A). The attenuated profile of the 1-to-Stop virus was further assessed in mice given a lethal dose of wild type virus and the equivalent dose of 1-to-Stop virus, for which a significantly higher proportion of survival was observed (FIG. 14B). Finally, virus samples from the heart and pancreas of infected mice were deep sequenced to confirm that the 1-to-Stop virus generated more stop mutations in vivo (FIG. 14C), as was observed in tissue culture (FIG. 13E-G).

Figure 15C:
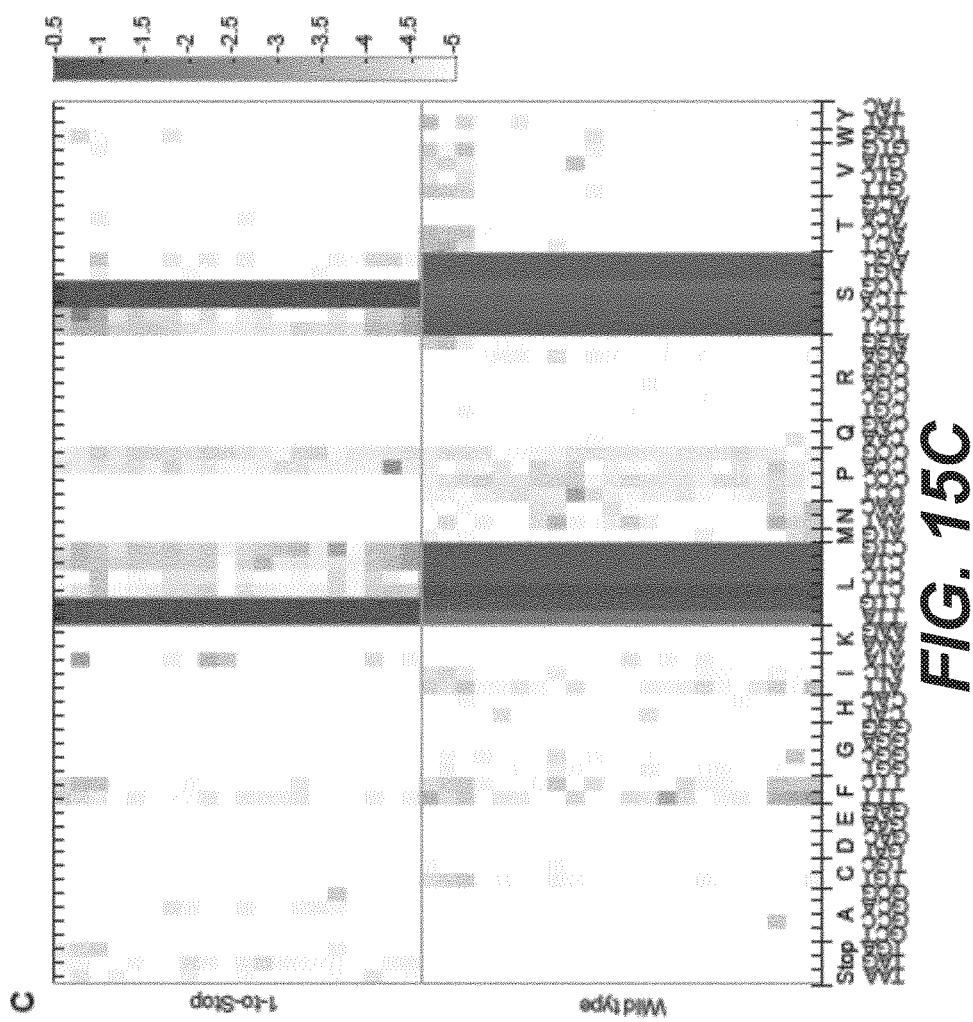
Figures 15D, 15E:
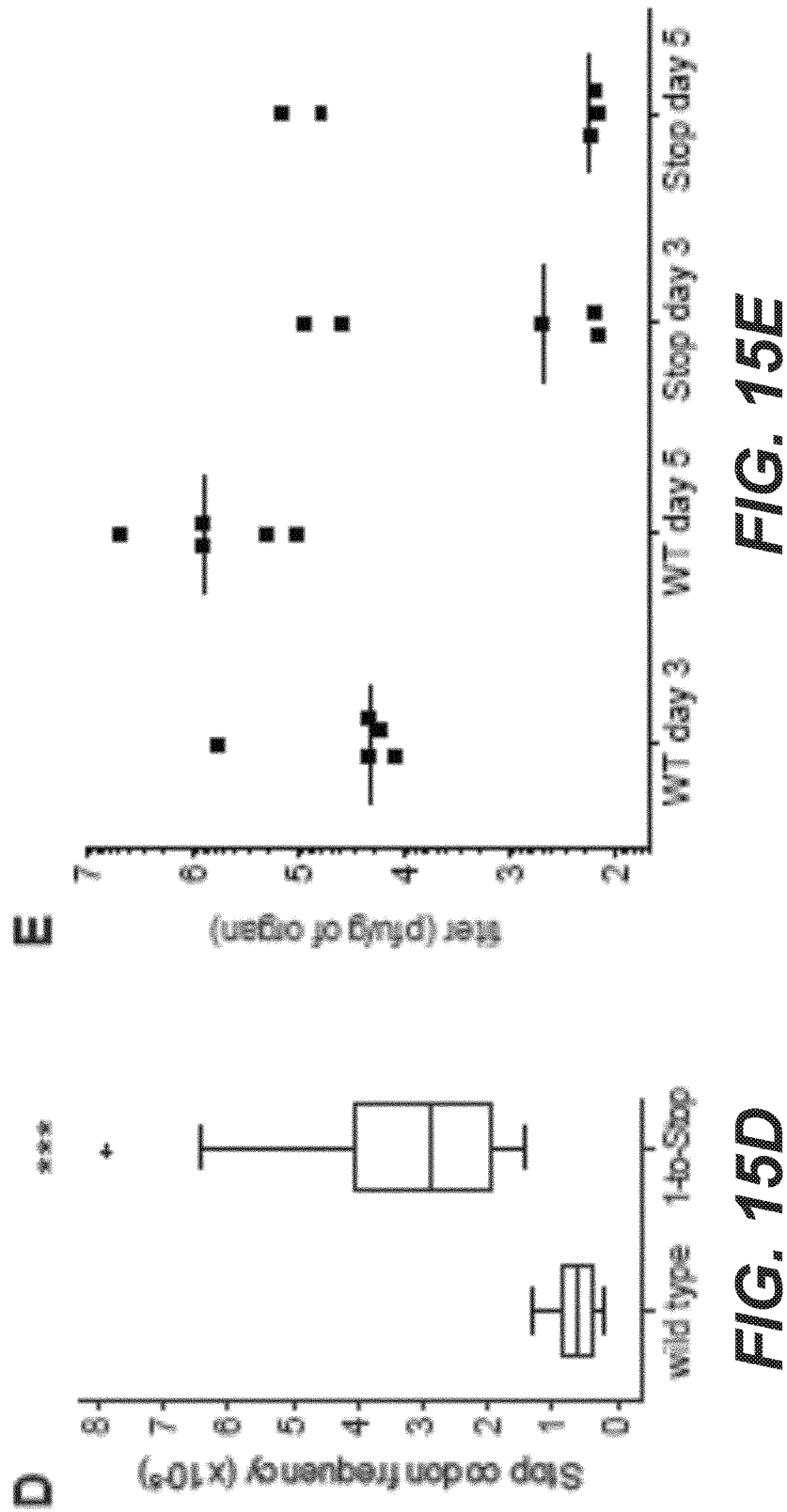

Non-sense mutation targeting of virus in sequence space can be more generally applied. To investigate the feasibility of altering sequence space to render a virus more prone to non-sense mutations in a more general manner, we applied a similar strategy to Influenza A virus, a considerably different RNA virus with a segmented, negative sense genome. In this case, the segment encoding the PA polymerase gene was altered at all of its 100 Ser/Leu codons to present only 1-to-Stop category codons (FIG. 12A). Virus stocks were generated and we determined the replication kinetics of passage five virus at low (FIG. 15A) and high (FIG. 15B) multiplicity of infection. No significant difference was observed between the 1-to-Stop and wild type virus. We passaged 20 wild type and 20 1-to-Stop virus replicates five times in tissue culture and deep sequenced the populations to evaluate the minority mutations emerging in each population at the 100 altered codon sites, as was performed for Coxsackie virus (FIG. 13E). The resulting profiles were similar to what was observed for Coxsackie virus: tendency to regenerate some wild type-like Ser/Leu codons; inability to generate some other amino acids (e.g., Prolines, Glutamines, Isoleucines); an increased incidence of Stop mutations (FIG. 15C). We passaged wild type and 1-to-Stop virus in low concentrations of mutagenic compounds and quantified the number of Stop codons within sequence reads of these samples. The 1-to-Stop populations presented a significantly higher frequency of Stop mutations in the sequencing reads compared to wild type virus (FIG. 15D). Finally, mice were infected intranasally with $10^5$ $TCID_{50}$ wildtype or 1-to-Stop viruses, and whole respiratory tract tissue was harvested at three and five days after infection. The titers of virus in these tissues were lower in 1-to-Stop virus-infected mice (FIG. 15E), confirming its attenuation in vivo.

Figures 16C, 16D:
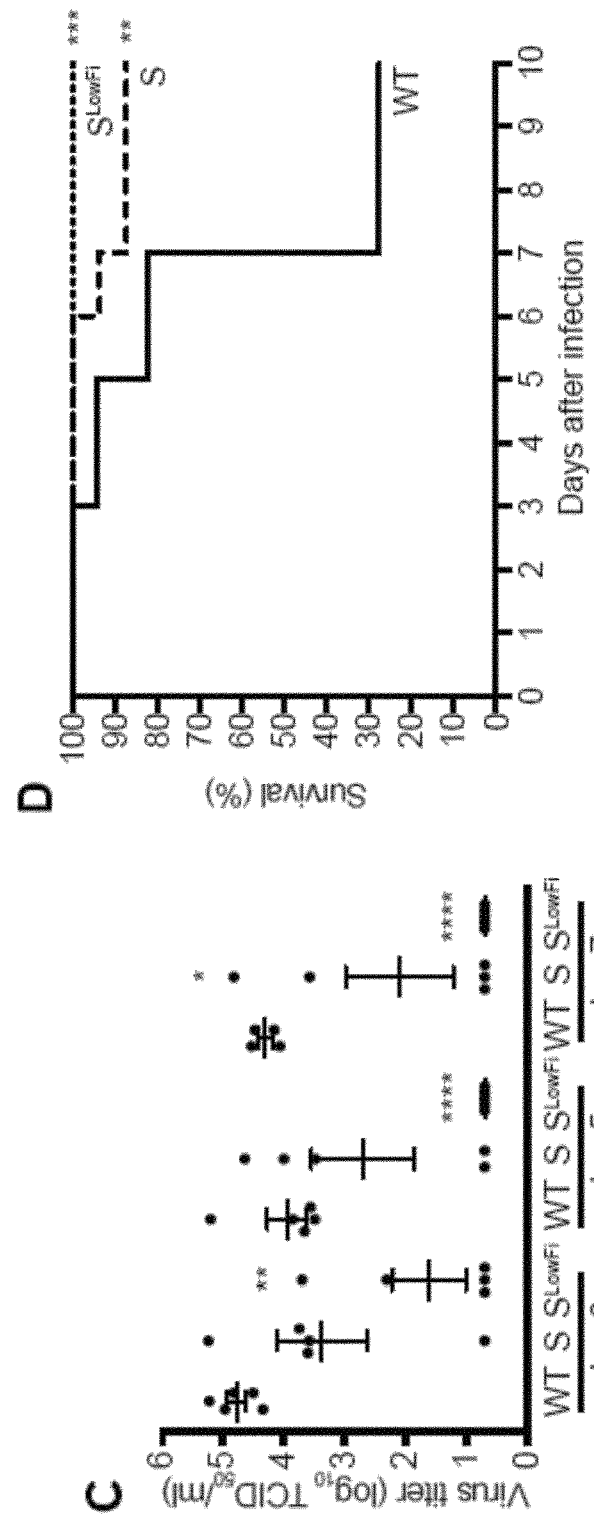

The combination of defavorizing sequence space and intrinsically increasing mutation rate results in an optimally attenuated virus. Our results demonstrate that relocalizing a virus in an unfavorable region of sequence space, where copy error has a higher likelihood of generating non-sense mutations, can attenuate viruses. The treatment of these viruses with RNA mutagens to extrinsically increase error rates resulted in even greater loss of infectivity in tissue culture. Previously, we isolated and characterized viral polymerase variants that intrinsically increase mutations with error frequencies that resemble mutagenic treatment (Gnadig et al. 2012). We thus combined these approaches, by inserting the viral polymerase I230F amino acid change, that confers low-fidelity and increases mutation frequency by 3-fold, into the 1-to-Stop virus. We then infected mice with wild type, 1-to-Stop or the 1-to-Stop+I230F Low-Fidelity viruses and quantified viral titers in pancreata (FIG. 16A), hearts (FIG. 16B) and spleens (FIG. 16C) over the seven days of infection. The results indicate that the degree of attenuation is significantly increased for the low-fidelity version of the 1-to-Stop virus. Virus titers are undetectable in the organs of mice as early as three days after infection, and are not detectable in any organ of any mice by seven days of infection. Accordingly, a survival curve of mice receiving a lethal dose of wild type and equivalent dose of low-fidelity 1-to-Stop virus revealed the latter to be completely attenuated (FIG. 16D).

The 1-to-Stop and 1-to-StopLowFidelity viruses protect against lethal challenge and generate high levels of neutralizing antibodies. To confirm that the 1-to-StopLowFidelity variant was also attenuated at high doses, mice were infected with a lethal dose of wildtype and the equivalent dose of both 1-to-Stop constructs. The survival curve showed that both 1-to-Stop viruses were highly attenuated (FIG. 17A). Prior to challenge infection, blood was harvested from mice and the amount of neutralizing antibody was quantified (FIG. 17B). All mice immunized with either of the 1-to-Stop constructs produced high levels of neutralizing antibody.

Example 6

"Super-Stop" Mutants of Coxsackie Virus (P1 Region)

A "Super-Stop" mutant of Coxsackie virus was generated as described in example 1 above by replacing the Leu and Ser codons of the P1 coding sequence by 1-to-Stop synonymous codons (as described in example 1 above), and further by replacing the Arg and Gly codons of the P1 coding sequence by 1-to-Stop synonymous codons.

The sequence of the P1 coding sequence of this "Super-Stop" mutant of Coxsackie virus is shown below.
>CVB3superstop DNA sequence (2562nt; SEQ ID NO: 85)

```
                                        SEQ ID NO: 85
ATGGGAGCTCAAGTATCAACGCAAAAGACTGGAGCACATGAGACCAGATT

GAATGCTTCGGGAAATTCGATCATTCACTACACAAATATTAATTATTACA

AGGATGCCGCATCGAACTCAGCCAATCGACAGGATTTCACTCAAGACCCG

GGAAAGTTCACAGAACCAGTGAAAGATATCATGATTAAATCATTACCAGC

TTTGAACTCGCCCACAGTAGAGGAGTGCGGATACTCAGACAGAGCGAGAT

CAATCACATTAGGAAACTCGACCATAACGACTCAGGAATGCGCCAACGTG

GTGGTGGGATATGGAGTATGGCCAGATTATTTAAAGGATTCAGAGGCAAC

AGCAGAGGACCAACCGACCCAACCAGACGTTGCCACATGTAGATTCTATA

CCTTAGACTCAGTGCAATGGCAGAAAACCTCACCAGGATGGTGGTGGAAG

TTGCCCGATGCTTTGTCGAACTTAGGATTGTTTGGACAGAACATGCAGTA

CCACTACTTAGGACGAACTGGATATACCGTACATGTGCAGTGCAATGCAT

CAAAGTTCCACCAAGGATGCTTGTTAGTAGTGTGTGTACCGGAAGCTGAG

ATGGGATGCGCAACGTTAGACAACACCCCATCGTCAGCAGAATTGTTGGG

AGGAGATACGGCAAAGGAGTTTGCGGACAAACCGGTCGCATCGGGATCGA

ACAAGTTGGTACAGAGAGTGGTGTATAATGCAGGAATGGGAGTGGGAGTT

GGAAACTTGACCATTTTCCCCCACCAATGGATCAACTTACGAACCAATAA

TTCAGCTACAATTGTGATGCCATACACCAACTCAGTACCTATGGATAACA

TGTTTAGACATAACAACGTCACCTTAATGGTTATCCCATTTGTACCGTTA

GATTACTGCCCTGGATCAACCACGTACGTCCCAATTACGGTCACGATAGC

CCCAATGTGTGCCGAGTACAATGGATTACGATTAGCAGGACACCAGGGAT

TACCAACCATGAATACTCCGGGATCGTGTCAATTTTTGACATCAGACGAC

TTCCAATCACCATCGGCCATGCCGCAATATGACGTCACACCAGAGATGAG

AATACCTGGAGAGGTGAAAAACTTGATGGAAATAGCTGAGGTTGACTCAG

TTGTCCCAGTCCAAAATGTTGGAGAGAAGGTCAACTCAATGGAAGCATAC

CAGATACCTGTGAGATCGAACGAAGGATCAGGAACGCAAGTATTCGGATT

TCCATTGCAACCAGGATACTCGTCAGTTTTTTCACGAACGTTGTTAGGAG

AGATCTTGAACTATTATACACATTGGTCAGGATCGATAAAGTTAACGTTT

ATGTTCTGTGGATCGGCCATGGCTACTGGAAAATTCTTATTGGCATACTC

ACCACCAGGAGCTGGAGCTCCTACAAAAAGAGTTGATGCTATGTTAGGAA

CTCATGTAATTTGGGACGTGGGATTACAATCATCATGCGTGTTGTGTATA

CCCTGGATATCGCAAACACACTACCGATTTGTTGCTTCAGATGAGTATAC

CGCAGGAGGATTTATTACGTGCTGGTATCAAACAAACATAGTGGTCCCAG

CGGATGCCCAATCGTCGTGTTACATCATGTGTTTCGTGTCAGCATGCAAT

GACTTCTCAGTCAGATTATTGAAGGACACTCCTTTCATTTCGCAGCAAAA

CTTTTTCCAGGGACCAGTGGAAGACGCGATAACAGCCGCTATAGGAAGAG

TTGCGGATACCGTGGGAACAGGACCAACCAACTCAGAAGCTATACCAGCA

TTGACTGCTGCTGAGACGGGACACACGTCACAAGTAGTGCCGGGAGACAC

TATGCAGACACGACACGTTAAGAACTACCATTCAAGATCGGAGTCAACCA

TAGAGAACTTCTTATGTAGATCAGCATGCGTGTACTTTACGGAGTATAAA

AACTCAGGAGCCAAGCGATATGCTGAATGGGTATTAACACCACGACAAGC

AGCACAATTAAGAAGAAAGTTAGAATTCTTTACCTACGTCCGATTCGACT

TGGAGTTGACGTTTGTCATAACATCAACTCAACAGCCCTCAACCACACAG

AACCAAGATGCACAGATCTTAACACACCAAATTATGTATGTACCACCAGG

AGGACCTGTACCAGATAAAGTTGATTCATACGTGTGGCAAACATCAACGA

ATCCCTCAGTGTTTTGGACCGAGGGAAACGCCCCGCCGCGAATGTCGATA

CCGTTTTTGTCGATTGGAAACGCCTATTCAAATTTCTATGACGGATGGTC

AGAATTTTCGAGAAACGGAGTTTACGGAATCAACACGTTAAACAACATGG

GAACGTTATATGCAAGACATGTCAACGCTGGATCGACGGGACCAATAAAA

TCGACCATTAGAATCTACTTCAAACCGAAGCATGTCAAAGCGTGGATACC

TAGACCACCTAGATTGTGCCAATACGAGAAGGCAAAGAACGTGAACTTCC

AACCCTCGGGAGTTACCACTACTAGACAATCGATCACTACAATGACAAAT

ACGGGCGCATTT
```

SEQ ID NO: 85 codes for the (wild-type) P1 protein of SEQ ID NO: 105:

```
                                             SEQ ID NO: 105
MGAQVSTQKTGAHETRLNASGNSIIHYTNINYYKDAASNSANRQDFTQDP

GKFTEPVKDIMIKSLPALNSPTVEECGYSDRARSITLGNSTITTQECANV

VVGYGVWPDYLKDSEATAEDQPTQPDVATCRFYTLDSVQWQKTSPGWWWK

LPDALSNLGLFGQNMQYHYLGRTGYTVHVQCNASKFHQGCLLVVCVPEAE

MGCATLDNTPSSAELLGGDTAKEFADKPVASGSNKLVQRVVYNAGMGVGV

GNLTIFPHQWINLRTNNSATIVMPYTNSVPMDNMFRHNNVTLMVIPFVPL

DYCPGSTTYVPITVTIAPMCAEYNGLRLAGHQGLPTMNTPGSCQFLTSDD

FQSPSAMPQYDVTPEMRIPGEVKNLMEIAEVDSVVPVQNVGEKVNSMEAY

QIPVRSNEGSGTQVFGFPLQPGYSSVFSRTLLGEILNYYTHWSGSIKLTF

MFCGSAMATGKFLLAYSPPGAGAPTKRVDAMLGTHVIWDVGLQSSCVLCI

PWISQTHYRFVASDEYTAGGFITCWYQTNIVVPADAQSSCYIMCFVSACN

DFSVRLLKDTPFISQQNFFQGPVEDAITAAIGRVADTVGTGPTNSEAIPA

LTAAETGHTSQVVPGDTMQTRHVKNYHSRSESTIENFLCRSACVYFTEYK

NSGAKRYAEWVLTPRQAAQLRRKLEFFTYVRFDLELTFVITSTQQPSTTQ

NQDAQILTHQIMYVPPGGPVPDKVDSYVWQTSTNPSVFWTEGNAPPRMSI

PFLSIGNAYSNFYDGWSEFSRNGVYGINTLNNMGTLYARHVNAGSTGPIK

STIRIYFKPKHVKAWIPRPPRLCQYEKAKNVNFQPSGVTTTRQSITTMTN

TGAF
```

Example 7

1-to-Stop Mutants of Influenza (HA Region)

A 1-to-Stop mutant of Influenza A virus was generated as described in example 5 above, but by mutating the HA region instead of mutating the PA region.

The Leu and Ser codons of the HA region were therefore replaced by 1-to-Stop synonymous codons.

The genomic RNA HA sequence of this 1-to-Stop Influenza A virus is SEQ ID NO: 86 (mutated nucleotides are in lower case letters):

```
                                             SEQ ID NO: 86
AGUAGAAACAAGGGUGUUUUUCUCAUGCUUCUGAAAUCCUAAUGUUAAAU

ACAUAUUCUACACUGUAauGACCCAUUuGAGCACAUCCAGAAugaGAUUG

CCCCCAacGAGACUACCAaUACCAAUGaugaGGCGACAGUUGAAUAGAUC

GCCAAAAUCUGGUAAAUCCUUGUUGAUUCCAaCUUUACCCCAUCUAUUUC

UUCUCUGUUUAAUUUUGCUUCCUCUGAGUAUUUUGGGUAGUCAUAAGUCC

CAUUUUUGACugaUUCCAUGCACGUGUUAUCGCAUUUGUGGUAAAAUUCA

AAGCAGCCGUUUCCAAUUUCCUUGGCAUUGUUUUUAaCUGCgaUCUUAC

CUUUUCAUAUAAGUUCUUCACAUUUGAAUCGUGGUAGUCCAAAGUUCUUU

CAUUUUCCAAUAaAACCAACAaUUCGGCAUUGUAAGUCCAAAUGUCCAAG

AAACCAUCAUCAACUUUUUUAUUUAAAUUCUCUAUUCUUUUUUCCAaGUG

GUUGAACUCUUUUACCUACUGCUGUGAACUGUGUAUUCAUCUUUUUCAAUAA

CuGAAUUUACUUUGUUAGUAAUCUCGUCAAUGGCAUUCUGUGUcgaCUUC

AaGUCGGCUGCAUAUCCUGACCCCUGCUCAUUUUGAUGGUGAUAACCGUA

CCAUCCAUCUACCAUCCCUGUCCACCCCCCUUCAAUGAAACCGGCAAUGG

CCCCAAAUAaGCCUCUuGAUUGAAUgaCGGGACAUUCCUCAAUCCUGUG

GCCAaUCUCAAUUUUGUcgaUUUUACAUAUUUUGGACAUUUUCCAAUUGU

GAUCGGAUGUAUAUUCUGAAAUGGcAacgaGGUGUUUAUAGCACCCUUGG

GUGUCUGACAAGUUGUAUUGCAAUCGUGGACUGGUGUAUCUGAAAUGAUA

AUACCuGAUCCAGCAUUUCUUUCCAUUGCGAAUGCAUAUCUCGGUACCAC

UAaAUUUCCAGUUGCUUCGAAUGUUAUUUUGUCUCCCGGCUCUACUAaUG

UCCAGUAAUAGUUCAUUCUCCCCUCUUGAUCCCUCACUUUGGGUCUUAUU

GCUAUUUCCGGCUUGAACUUCUUcgaGUAUCUUGAUGACCCCACAAAAAC

AUAUGCAUCUGCAUUCUGAUAcAaugaUUGUUGGUCAGCUgaAGUuGAUG

GAUGGUGAAUGCCCCAUAaCACcAaGACUUCUUUCCCUUUAUCAUUAAUG

UAcGAUUUcgacAaCUUUGGGUAUGAAUUUCCUUUUUUAACUAaCCAUAU

UAAAUUUUUGUAGAAcgaUUUUGCUCCAGCAUGAGGACAUGCUGCCGUUA

CACCUUUUGUUCGAGUCAUGAUUGGGCCAUGAugaUGUCUUGGGGAAUAUC

UCAAACCUUUCAAAUGAUGACACUGAcgaCAAUUGCUCUCUUAaCUCCUC

AUAAUCGAUGAAAUCUCCUGGGUAACACGUUCCAUUGUCUGAUgauGAUG

UUUCCACAAUGUAcGACCAUGAcgaUGCUGUcGAcAaUGAUUCACACUCU

GGAUUUCCCAaGAUCCAGCCAGCAAUGUUACAUUUACCCAAAUGCAAUGG

GGCUACCCCUCUUAaUUUGCAUAaUUUCCCGUUAUGCUUGUCUUCUAauA aGUUAACcGAGUGUGUUACUGUUACAUUCUUUUCUAaUACUGUGUCUACA

GUGUCUGUUGAAUUGUUCGCAUGAUAACCUAUACAUAAUGUGUCUGCAUU

UGCGGUUGCAAAUGUAUAUAaCAaAACUACUAaUAUUGCCUUCAUUUUUG

UUGCUUUUGUUUUCCCCUGCUUUUGCU
```

The cDNA CDS HA sequence of this 1-to-Stop Influenza A virus is SEQ ID NO: 87 (mutated nucleotides are in lower case letters):

```
                                             SEQ ID NO: 87
ATGAAGGCAATAtTAGTAGTTtTGtTATATACATTTGCAACCGCAAATGC

AGACACATTATGTATAGGTTATCATGCGAACAATTCAACAGACACTGTAG

ACACAGTAtTAGAAAAGAATGTAACAGTAACACACTCgGTTAACtTatTA

GAAGACAAGCATAACGGGAAAtTATGCAAAtTAAGAGGGGTAGCCCCATT

GCATTTGGGTAAATGTAACATTGCTGGCTGGATCtTGGGAAATCCAGAGT

GTGAATCAtTgTCgACAGCAtcgTCATGGTCgTACATTGTGGAAACATCa tcaTCAGACAATGGAACGTGTTACCCAGGAGATTTCATCGATTATGAGGA GtTAAGAGAGCAATTGtcgTCAGTGTCATCATTTGAAAGGTTTGAGATAT TCCCCAAGACAtcaTCATGGCCCAATCATGACTCGAACAAAGGTGTAACG GCAGCATGTCCTCATGCTGGAGCAAAAtcgTTCTACAAAAATTTAATATG GtTAGTTAAAAAAGGAAATTCATACCCAAAGtTgtcgAAATCgTACATTA ATGATAAAGGGAAAGAAGTCtTgGTGtTATGGGCATTCACCATCCATCa
```

-continued

ACTtcaGCTGACCAACAAtcatTgTATCAGAATGCAGATGCATATGTTTT

TGTGGGGTCATCAAGATACtcgAAGAAGTTCAAGCCGGAAATAGCAATAA

GACCCAAAGTGAGGGATCAAGAGGGGAGAATGAACTATTACTGGACAtTA

GTAGAGCCGGGAGACAAAATAACATTCGAAGCAACTGGAAATtTAGTGGT

ACCGAGATATGCATTCGCAATGGAAAGAAATGCTGGATCaGGTATTATCA

TTTCAGATACACCAGTCCACGATTGCAATACAACTTGTCAGACACCCAAG

GGTGCTATAAACACCtcgTgCCATTTCAGAATATACATCCGATCACAAT

TGGAAAATGTCCAAAATATGTAAAAtcgACAAAATTGAGAtTGGCCACAG

GATTGAGGAATGTCCCGTCaATTCAATCaAGAGGCtTATTTGGGGCCATT

GCCGGTTTCATTGAAGGGGGGTGGACAGGGATGGTAGATGGATGGTACGG

TTATCACCATCAAAATGAGCAGGGGTCAGGATATGCAGCCGACtTGAAGt cgACACAGAATGCCATTGACGAGATTACTAACAAAGTAAATTCaGTTATT

GAAAAGATGAATACACAGTTCACAGCAGTAGGTAAAGAGTTCAACCACtT

GGAAAAAGAATAGAGAATTTAAATAAAAAAGTTGATGATGGTTTCtTGG

ACATTTGGACTTACAATGCCGAAtTGTTGGTTtTATTGGAAAATGAAAGA

ACTTTGGACTACCACGATTCAAATGTGAAGAACTTATATGAAAAGGTAAG

AtcgCAGtTAAAAAACAATGCCAAGGAAATTGGAAACGGCTGCTTTGAAT

TTTACCACAAATGCGATAACACGTGCATGGAATcaGTCAAAAATGGGACT

TATGACTACCCAAAATACTCAGAGGAAGCAAAATTAAACAGAGAAGAAAT

AGATGGGGTAAAGtTGGAATCAACAAGGATTTACCAGATTTTGGCGATCT

ATTCAACTGTCGCCtcaTCATTGGTAtTGGTAGTCTCgtTGGGGGCAATC tcaTTCTGGATGTGCTCaAATGGGTCatTACAGTGTAGAATATGTATTTA

A

The HA protein coded by the 1-to-Stop Influenza virus is identical to the wild-type HA (SEQ ID NO: 88):

```
                                                SEQ ID NO: 88
MKAILVVLLYTFATANADTLCIGYHANNSTDTVDTVLEKNVTVTHSVNLL

EDKHNGKLCKLRGVAPLHLGKCNIAGWILGNPECESLSTASSWSYIVETS

SSDNGTCYPGDFIDYEELREQLSSVSSFERFEIFPKTSSWPNHDSNKGVT

AACPHAGAKSFYKNLIWLVKKGNSYPKLSKSYINDKGKEVLVLWGIHHPS

TSADQQSLYQNADAYVFVGSSRYSKKFKPEIAIRPKVRDQEGRMNYYWTL

VEPGDKITFEATGNLVVPRYAFAMERNAGSGIIISDTPVHDCNTTCQTPK

GAINTSLPFQNIHPITIGKCPKYVKSTKLRLATGLRNVPSIQSRGLFGAI

AGFIEGGWTGMVDGWYGYHHQNEQGSGYAADLKSTQNAIDEITNKVNSVI

EKMNTQFTAVGKEFNHLEKRIENLNKKVDDGFLDIWTYNAELLVLLENER

TLDYHDSNVKNLYEKVRSQLKNNAKEIGNGCFEFYHKCDNTCMESVKNGT

YDYPKYSEEAKLNREEIDGVKLESTRIYQILAIYSTVASSLVLVVSLGAI

SFWMCSNGSLQCRICI
```

The cDNA CDS HA sequence of the wild-type Influenza A virus is SEQ ID NO: 67.

Table 6 below list the 1-to-Stop mutations made to the wild-type Influenza cDNA HA sequence.

TABLE 6

| Position number of 1st nucleotide in codon (numbering in CDS, starting at A of the ATG) | Wt (SEQ ID NO: 67) | 1-to-Stop (SEQ ID NO: 87) | amino-acid |
|---|---|---|---|
| 13 | CTA | TTA | leucine |
| 22 | CTG | TTG | leucine |
| 25 | CTA | TTA | leucine |
| 58 | TTA | TTA | leucine |
| 85 | TCA | TCA | serine |
| 109 | CTA | TTA | leucine |
| 136 | TCT | TCG | serine |
| 145 | CTT | TTA | leucine |
| 148 | CTA | TTA | leucine |
| 172 | CTA | TTA | leucine |
| 181 | CTA | TTA | leucine |
| 199 | TTG | TTG | leucine |
| 205 | TTG | TTG | leucine |
| 235 | CTG | TTG | leucine |
| 256 | TCA | TCA | serine |
| 259 | CTC | TTG | leucine |
| 262 | TCC | TCG | serine |
| 271 | AGC | TCG | serine |
| 274 | TCA | TCA | serine |
| 280 | TCC | TCG | serine |
| 298 | TCT | TCA | serine |
| 301 | AGT | TCA | serine |
| 304 | TCA | TCA | serine |
| 352 | CTA | TTA | leucine |
| 364 | TTG | TTG | leucine |
| 367 | AGC | TCG | serine |
| 370 | TCA | TCA | serine |
| 376 | TCA | TCA | serine |
| 379 | TCA | TCA | serine |
| 412 | AGT | TCA | serine |
| 415 | TCA | TCA | serine |
| 433 | TCG | TCG | serine |
| 478 | AGC | TCG | serine |
| 493 | TTA | TTA | leucine |
| 502 | CTA | TTA | leucine |
| 520 | TCA | TCA | serine |
| 532 | CTC | TTG | leucine |

TABLE 6-continued

| Position number of 1st nucleotide in codon (numbering in CDS, starting at A of the ATG) | Wt (SEQ ID NO: 67) | 1-to-Stop (SEQ ID NO: 87) | amino-acid |
|---|---|---|---|
| 535 | AGC | TCG | serine |
| 541 | TCC | TCG | serine |
| 571 | CTC | TTG | leucine |
| 577 | CTA | TTA | leucine |
| 598 | TCT | TCA | serine |
| 604 | AGT | TCA | serine |
| 619 | AGT | TCA | serine |
| 622 | CTC | TTG | leucine |
| 658 | TCA | TCA | serine |
| 661 | TCA | TCA | serine |
| 670 | AGC | TCG | serine |
| 748 | CTA | TTA | leucine |
| 793 | CTA | TTA | leucine |
| 838 | TCT | TCA | serine |
| 853 | TCA | TCA | serine |
| 916 | AGC | TCG | serine |
| 919 | CTC | TTG | leucine |
| 976 | AGC | TCG | serine |
| 985 | TTG | TTG | leucine |
| 991 | CTG | TTG | leucine |
| 1003 | TTG | TTG | leucine |
| 1018 | TCT | TCA | serine |
| 1027 | TCT | TCA | serine |
| 1036 | CTA | TTA | leucine |
| 1126 | TCA | TCA | serine |
| 1144 | CTG | TTG | leucine |
| 1150 | AGC | TCG | serine |
| 1192 | TCT | TCA | serine |
| 1249 | CTG | TTG | leucine |
| 1270 | TTA | TTA | leucine |
| 1297 | CTG | TTG | leucine |
| 1324 | CTG | TTG | leucine |
| 1327 | TTG | TTG | leucine |
| 1333 | CTA | TTA | leucine |
| 1336 | TTG | TTG | leucine |
| 1354 | TTG | TTG | leucine |
| 1369 | TCA | TCA | serine |
| 1384 | TTA | TTA | leucine |
| 1402 | AGC | TCG | serine |
| 1408 | CTA | TTA | leucine |
| 1483 | AGT | TCA | serine |
| 1519 | TCA | TCA | serine |
| 1534 | TTA | TTA | leucine |
| 1564 | CTG | TTG | leucine |
| 1570 | TCA | TCA | serine |
| 1591 | TTG | TTG | leucine |
| 1603 | TCA | TCA | serine |
| 1615 | AGT | TCA | serine |
| 1618 | TCA | TCA | serine |
| 1621 | TTG | TTG | leucine |
| 1627 | CTG | TTG | leucine |
| 1636 | TCC | TCG | serine |
| 1639 | CTG | TTG | leucine |
| 1651 | AGT | TCA | serine |
| 1666 | TCT | TCA | serine |
| 1675 | TCT | TCA | serine |
| 1678 | CTA | TTA | leucine |

Figures 18A, 18B:
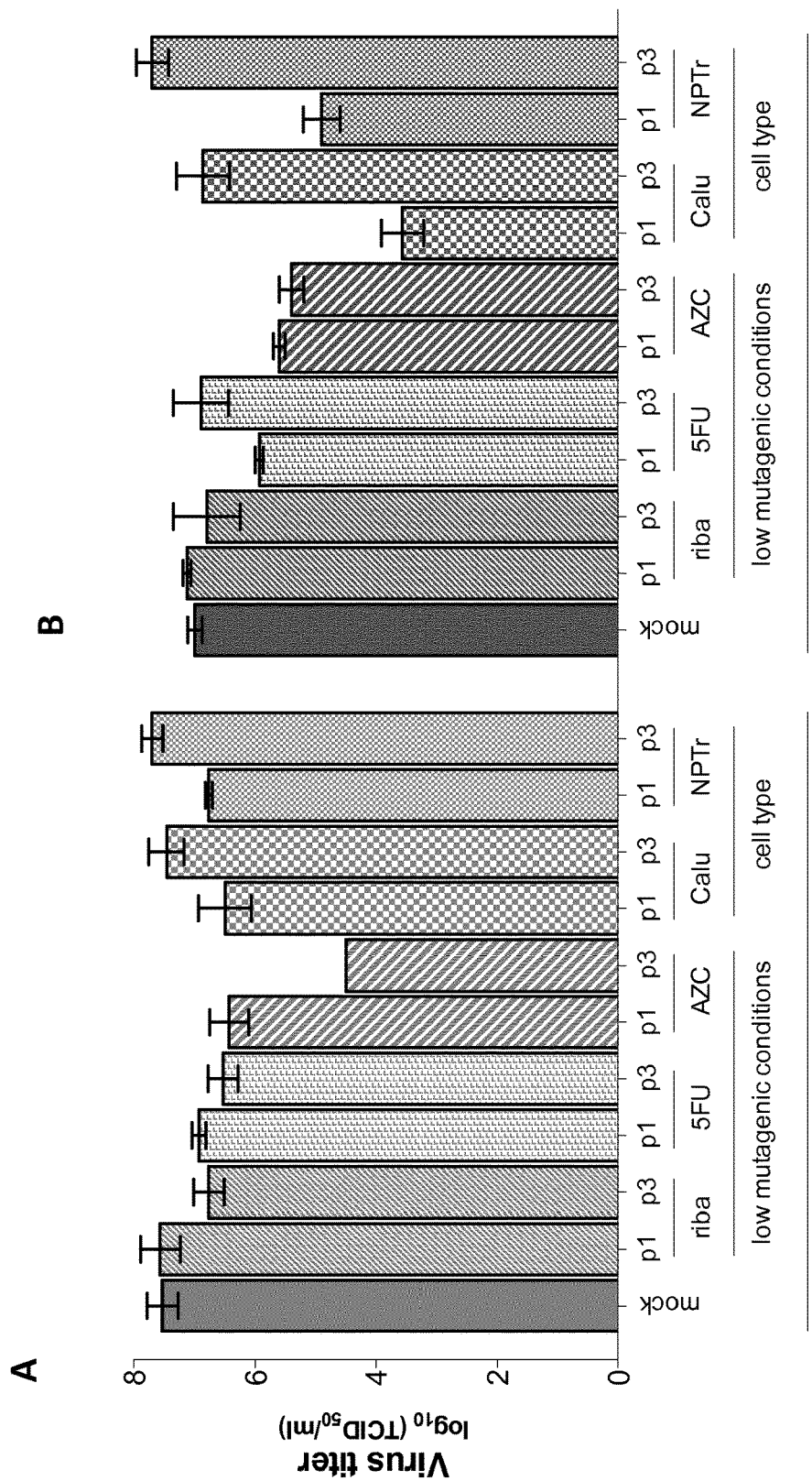
FIGS. 18A and 18B. Influenza 1-to-Stop mutants (HA region). Virus titers at passages 1 and 3 at passages 1 and 3 (m.o.i.=0.001; harvested at 48 h.p.i.) in low mutagenic conditions (5 µM ribavirin or 5-fluorouracil or 5-azacytidine) or in human tracheo-bronchial cells (Calu) or swine tracheal cells (NPTr). (A) wt=wild-type Influenza; (B) HA-1-to-Stop=Influenza with HA mutated in accordance with the application.

FIGS. 18A and 18B show the virus titers at passages 1 and 3 at passages 1 and 3 (m.o.i.=0.001; harvested at 48 h.p.i.) in low mutagenic conditions (5 μM ribavirin or 5-fluorouracil or 5-azacytidine) or in human tracheo-bronchial cells (Calu) or swine tracheal cells (NPTr).

Example 8

1-to-Stop and "Super-Stop" Mutants of CHIKUNGUNYA Virus (E1-E2 Region)

1-to-Stop and Super-Stop mutants of Chikungunya virus were generated in accordance with the methodology described in example 1 above.

The sequence of the wild-type Chikungunya virus was GENBANK® AM258994.1.

The 1-to-Stop and Super-Stop mutations were introduced in the sequence coding the C-E3-E2-6K-E1 polyprotein in accordance with the methodology described in example 1 above.

The 1-to-Stop mutations are the replacement of the Leu and Ser codons (of the coding C-E3-E2-6K-E1 polyprotein) by 1-to-Stop synonymous codons.

The Super-Stop mutations are the replacement of the Leu, Ser, Arg and Gly codons (of the coding C-E3-E2-6K-E1 polyprotein) by 1-to-Stop synonymous codons The sequence of the 1-to-Stop mutant of Chikungunya virus is SEQ ID NO: 101:

SEQ ID NO: 101

ATGGAGTTCATCCCAACCCAAACTTTTTACAATAGGAGGTACCAGCCTCG
ACCCTGGACTCCGCGCCCTACTATCCAAGTCATCAGGCCCAGACCGCGCC
CTCAGAGGCAAGCTGGGCAATTAGCCCAGTTGATCTCAGCAGTTAATAAA
TTGACAATGCGCGCGGTACCCCAACAGAAGCCACGCAGGAATCGGAAGAA
TAAGAAGCAAAAGCAAAAACAACAGGCGCCACAAAACAACACAAATCAAA
AGAAGCAGCCACCTAAAAAGAAACCGGCTCAAAAGAAAAAGAAGCCGGGC
CGCAGAGAGAGGATGTGCATGAAAATCGAAAATGATTGTATTTTCGAAGT
CAAGCACGAAGGTAAGGTAACAGGTTACGCGTGCTTGGTGGGGGACAAAG
TAATGAAACCAGCACACGTAAAGGGGACCATCGATAACGCGGACTTGGCC
AAATTGGCCTTTAAGCGGTCATCAAAGTATGACTTAGAATGCGCGCAGAT
ACCCGTGCACATGAAGTCGGACGCTTCGAAGTTCACCCATGAGAAACCGG
AGGGGTACTACAACTGGCACCACGGAGCAGTACAGTACTCAGGAGGCCGG
TTCACCATCCCTACAGGTGCTGGCAAACCAGGGGACTCGGGCAGACCGAT
CTTCGACAACAAGGGACGCGTGGTGGCCATAGTCTTAGGAGGAGCTAATG
AAGGAGCCCGTACAGCCTTGTCGGTGGTGACCTGGAATAAAGACATTGTC
ACTAAAATCACCCCGAGGGGGCCGAAGAGTGGTCATTAGCCATCCCAGT
TATGTGCTTGTTGGCAAACACCACGTTCCCTGCTCGCAGCCCCCTTGCA
CGCCCTGCTGCTACGAAAAGGAACCGGAGGAAACCTTACGCATGTTAGAG
GACAACGTCATGAGACCTGGGTACTATCAGTTGTTACAAGCATCGTTAAC
ATGTTCACCCCACCGCCAGCGACGCTCGACCAAGGACAACTTCAATGTCT
ATAAAGCCACAAGACCATACTTAGCTCACTGTCCCGACTGTGGAGAAGGG
CACTCGTGCCATTCACCCGTAGCATTAGAACGCATCAGAAATGAAGCGAC
AGACGGGACGTTGAAAATCCAGGTCTCGTTGCAAATCGGAATAAAGACGG
ATGACTCGCACGATTGGACCAAGTTGCGTTATATGGACAACCACATGCCA
GCAGACGCAGAGAGGGCGGGGTTATTTGTAAGAACATCAGCACCGTGTAC
GATTACTGGAACAATGGGACACTTCATCTTGGCCCGATGTCCAAAAGGGG
AAACTTTGACGGTGGGATTCACTGACTCAAGGAAGATTTCACACTCATGT
ACGCACCCATTTCACCACGACCCTCCTGTGATAGGTCGGGAAAAATTCCA
TTCGCGACCGCAGCACGGTAAAGAGTTACCTTGCTCGACGTACGTGCAGT
CGACCGCCGCAACTACCGAGGAGATAGAGGTACACATGCCCCCAGACACC
CCTGATCGCACATTAATGTCACAACAGTCGGGCAACGTAAAGATCACAGT
CAATGGCCAGACGGTGCGGTACAAGTGTAATTGCGGTGGCTCAAATGAAG
GATTAACAACTACAGACAAAGTGATTAATAACTGCAAGGTTGATCAATGT
CATGCCGCGGTCACCAATCACAAAAAGTGGCAGTATAACTCGCCTTTGGT
CCCGCGTAATGCTGAATTAGGGGACCGAAAAGGAAAAATTCACATCCCGT
TTCCGTTGGCAAATGTAACATGCAGGGTGCCTAAAGCAAGGAACCCCACC
GTGACGTACGGGAAAAACCAAGTCATCATGTTATTGTATCCTGACCACCC
AACATTGTTGTCGTACCGGAATATGGGAGAAGAACCAAACTATCAAGAAG
AGTGGGTGATGCATAAGAAGGAAGTCGTGTTAACCGTGCCGACTGAAGGG
TTGGAGGTCACGTGGGGCAACAACGAGCCGTATAAGTATTGGCCGCAGTT

ATCAACAAACGGTACAGCCCATGGCCACCCGCACGAGATAATTTTGTATT
ATTATGAGTTGTACCCCACTATGACTGTAGTAGTTGTGTCAGTGGCCACG
TTCATATTGTTGTCGATGGTGGGTATGGCAGCGGGGATGTGCATGTGTGC
ACGACGCAGATGCATCACACCGTATGAATTGACACCAGGAGCTACCGTCC
CTTTCTTGTTATCGTTAATATGCTGCATCAGAACAGCTAAAGCGGCCACA
TACCAAGAGGCTGCGATATACTTGTGGAACGAGCAGCAACCTTTGTTTTG
GTTACAAGCCTTAATTCCGTTGGCAGCCTTGATTGTTTTATGCAACTGTT
TGAGATTGTTACCATGCTGCTGTAAAACGTTGGCTTTTTTAGCCGTAATG
TCGGTCGGTGCCCACACTGTGTCGGCGTACGAACACGTAACAGTGATCCC
GAACACGGTGGGAGTACCGTATAAGACTTTAGTCAATAGACCTGGCTACT
CGCCCATGGTATTGGAGATGGAATTATTGTCAGTCACTTTGGAGCCAACA
TTATCGTTAGATTACATCACGTGCGAGTACAAAACCGTCATCCCGTCACC
GTACGTGAAGTGCTGCGGTACAGCAGAGTGCAAGGACAAAAACTTACCTG
ACTACTCGTGTAAGGTCTTCACCGGCGTCTACCCATTTATGTGGGGCGGC
GCCTACTGCTTCTGCGACGCTGAAAACACGCAGTTGTCGGAAGCACACGT
GGAGAAGTCGGAATCATGCAAAACAGAATTTGCATCAGCATACAGGGCTC
ATACCGCATCAGCATCAGCTAAGTTGCGCGTCTTATACCAAGGAAATAAC
ATCACTGTAACTGCCTATGCAAACGGCGACCATGCCGTCACAGTTAAGGA
CGCCAAATTCATTGTGGGCCAATGTCATCAGCCTGGACACCTTTCGACA
ACAAAATTGTGGTGTACAAAGGTGACGTCTATAACATGGACTACCCGCCC
TTTGGCGCAGGAAGACCAGGACAATTTGGCGATATCCAATCACGCACACC
TGAGTCAAAAGACGTCTATGCTAATACACAATTGGTATTGCAGAGACCGG
CTGTGGGTACGGTACACGTGCCATACTCACAGGCACCATCAGGCTTTAAG
TATTGGTTAAAAGAACGCGGGCGTCGTTGCAGCACACAGCACCATTTGG
CTGCCAAATAGCAACAAACCCGGTAAGAGCGGTGAACTGCGCCGTAGGGA
ACATGCCCATCTCGATCGACATACCGGAAGCGGCCTTCACTAGGGTCGTC
GACGCGCCCTCATTAACGGACATGTCGTGCGAGGTACCAGCCTGCACCCA
TTCGTCAGACTTTGGGGCGTCGCCATTATTAAATATGCAGCCTCGAAGA
AAGGCAAGTGTGCGGTGCATTCGATGACTAACGCCGTCACTATTCGGGAA
GCTGAGATAGAAGTTGAAGGGAATTCACAGTTGCAAATCTCATTCTCGAC
GGCCTTAGCCTCGGCCGAATTCCGCGTACAAGTCTGTTCAACACAAGTAC
ACTGTGCAGCCGAGTGCCACCCCCGAAGGACCACATAGTCAACTACCCG
GCGTCACATACCACCTTGGGGGTCCAGGACATCTCGGCTACGGCGATGTC
ATGGGTGCAGAAGATCACGGGAGGTGTGGGATTGGTTGTTGCTGTTGCCG
CATTGATTTTAATCGTGGTGTTATGCGTGTCGTTCTCGAGGCACTAA

The sequence of the Super-Stop mutant of Chikungunya virus is SEQ ID NO: 102:

SEQ ID NO: 102

ATGGAGTTCATCCCAACCCAAACTTTTTACAATAGAAGATACCAGCCTCG
ACCCTGGACTCCGCGACCTACTATCCAAGTCATCAGACCCAGACCGCGAC
CTCAGAGACAAGCTGGACAATTAGCCCAGTTGATCTCAGCAGTTAATAAA

-continued

TTGACAATGCGAGCGGTACCCCAACAGAAGCCACGAAGAAATCGAAAGAA
TAAGAAGCAAAAGCAAAAACAACAGGCGCCACAAAACAACACAAATCAAA
AGAAGCAGCCACCTAAAAAGAAACCGGCTCAAAAGAAAAAGAAGCCGGGA
CGAAGAGAGAGAATGTGCATGAAAATCGAAATGATTGTATTTTCGAAGT
CAAGCACGAAGGAAAGGTAACAGGATACGCGTGCTTGGTGGGAGACAAAG
TAATGAAACCAGCACACGTAAAGGGAACCATCGATAACGCGGACTTGGCC
AAATTGGCCTTTAAGCGATCATCAAAGTATGACTTAGAATGCGCGCAGAT
ACCCGTGCACATGAAGTCGGACGCTTCGAAGTTCACCCATGAGAAACCGG
AGGGATACTACAACTGGCACCACGGAGCAGTACAGTACTCAGGAGGACGA
TTCACCATCCCTACAGGAGCTGGAAAACCAGGAGACTCGGGAAGACCGAT
CTTCGACAACAAGGGACGAGTGGTGGCCATAGTCTTAGGAGGAGCTAATG
AAGGAGCCCGAACAGCCTTGTCGGTGGTGACCTGGAATAAAGACATTGTC
ACTAAAATCACCCCCGAGGGAGCCGAAGAGTGGTCATTAGCCATCCCAGT
TATGTGCTTGTTGGCAAACACCACGTTCCCCTGCTCGCAGCCCCCTTGCA
CGCCCTGCTGCTACGAAAAGGAACCGGAGGAAACCTTACGAATGTTAGAG
GACAACGTCATGAGACCTGGATACTATCAGTTGTTACAAGCATCGTTAAC
ATGTTCACCCCACCGACAGCGACGATCGACCAAGGACAACTTCAATGTCT
ATAAAGCCACAAGACCATACTTAGCTCACTGTCCCGACTGTGGAGAAGGA
CACTCGTGCCATTCACCCGTAGCATTAGAACGAATCAGAAATGAAGCGAC
AGACGGAACGTTGAAAATCCAGGTCTCGTTGCAAATCGGAATAAAGACGG
ATGACTCGCACGATTGGACCAAGTTGCGATATATGGACAACCACATGCCA
GCAGACGCAGAGAGCGGGATTATTTGTAAGAACATCAGCACCGTGTAC
GATTACTGGAACAATGGGACACTTCATCTTGGCCCGATGTCCAAAAGGAG
AAACTTTGACGGTGGGATTCACTGACTCAAGAAAGATTTCACACTCATGT
ACGCACCCATTTCACCACGACCCTCCTGTGATAGGACGAGAAAAATTCCA
TTCGCGACCGCAGCACGGAAAAGAGTTACCTTGCTCGACGTACGTGCAGT
CGACCGCCGCAACTACCGAGGAGATAGAGGTACACATGCCCCCAGACACC
CCTGATCGAACATTAATGTCACAACAGTCGGGAAACGTAAAGATCACAGT
CAATGGACAGACGGTGCGATACAAGTGTAATTGCGGAGGATCAAATGAAG
GATTAACAACTACAGACAAAGTGATTAATAACTGCAAGGTTGATCAATGT
CATGCCGCGGTCACCAATCACAAAAAGTGGCAGTATAACTCGCCTTTGGT
CCCGCGAAATGCTGAATTAGGAGACCGAAAAGGAAAAATTCACATCCCGT
TTCCGTTGGCAAATGTAACATGCAGAGTGCCTAAAGCAAGAAACCCCACC
GTGACGTACGGAAAAAACCAAGTCATCATGTTATTGTATCCTGACCACCC
AACATTGTTGTCGTACCGAAATATGGGAGAAGAACCAAACTATCAAGAAG
AGTGGGTGATGCATAAGAAGGAAGTCGTGTTAACCGTGCCGACTGAAGGA

-continued

TTGGAGGTCACGTGGGGAAACAACGAGCCGTATAAGTATTGGCCGCAGTT
ATCAACAAACGGAACAGCCCATGGACACCCGCACGAGATAATTTTGTATT
ATTATGAGTTGTACCCCACTATGACTGTAGTAGTTGTGTCAGTGGCCACG
TTCATATTGTTGTCGATGGTGGGAATGGCAGCGGGAATGTGCATGTGTGC
ACGACGAAGATGCATCACACCGTATGAATTGACACCAGGAGCTACCGTCC
CTTTCTTGTTATCGTTAATATGCTGCATCAGAACAGCTAAAGCGGCCACA
TACCAAGAGGCTGCGATATACTTGTGGAACGAGCAGCAACCTTTGTTTTG
GTTACAAGCCTTAATTCCGTTGGCAGCCTTGATTGTTTTATGCAACTGTT
TGAGATTGTTACCATGCTGCTGTAAAACGTTGGCTTTTTTAGCCGTAATG
TCGGTCGGAGCCCACACTGTGTCGGCGTACGAACACGTAACAGTGATCCC
GAACACGGTGGGAGTACCGTATAAGACTTTAGTCAATAGACCTGGATACT
CGCCCATGGTATTGGAGATGGAATTATTGTCAGTCACTTTGGAGCCAACA
TTATCGTTAGATTACATCACGTGCGAGTACAAAACCGTCATCCCGTCACC
GTACGTGAAGTGCTGCGGAACAGCAGAGTGCAAGGACAAAAACTTACCTG
ACTACTCGTGTAAGGTCTTCACCGGAGTCTACCCATTTATGTGGGGAGGA
GCCTACTGCTTCTGCGACGCTGAAAACACGCAGTTGTCGGAAGCACACGT
GGAGAAGTCGGAATCATGCAAAACAGAATTTGCATCAGCATACAGAGCTC
ATACCGCATCAGCATCAGCTAAGTTGCGAGTCTTATACCAAGGAAATAAC
ATCACTGTAACTGCCTATGCAAACGGAGACCATGCCGTCACAGTTAAGGA
CGCCAAATTCATTGTGGGACCAATGTCATCAGCCTGGACACCTTTCGACA
ACAAAATTGTGGTGTACAAAGGAGACGTCTATAACATGGACTACCCGCCC
TTTGGAGCAGGAAGACCAGGACAATTTGGAGATATCCAATCACGAACACC
TGAGTCAAAAGACGTCTATGCTAATACACAATTGGTATTGCAGAGACCGG
CTGTGGGAACGGTACACGTGCCATACTCACAGGCACCATCAGGATTTAAG
TATTGGTTAAAAGAACGAGGAGCGTCGTTGCAGCACACAGCACCATTTGG
ATGCCAAATAGCAACAAACCCGGTAAGAGCGGTGAACTGCGCCGTAGGAA
ACATGCCCATCTCGATCGACATACCGGAAGCGGCCTTCACTAGAGTCGTC
GACGCGCCCTCATTAACGGACATGTCGTGCGAGGTACCAGCCTGCACCCA
TTCGTCAGACTTTGGAGGAGTCGCCATTATTAAATATGCAGCCTCGAAGA
AAGGAAAGTGTGCGGTGCATTCGATGACTAACGCCGTCACTATTCGAGAA
GCTGAGATAGAAGTTGAAGGAAATTCACAGTTGCAAATCTCATTCTCGAC
GGCCTTAGCCTCGGCCGAATTCCGAGTACAAGTCTGTTCAACACAAGTAC
ACTGTGCAGCCGAGTGCCACCCCCCGAAGGACCACATAGTCAACTACCCG
GCGTCACATACCACCTTGGGAGTCCAGGACATCTCGGCTACGGCGATGTC
ATGGGTGCAGAAGATCACGGGAGGAGTGGGATTGGTTGTTGCTGTTGCCG
CATTGATTTTAATCGTGGTGTTATGCGTGTCGTTCTCGAGACACTAA

The wild-type Chikungunya virus GENBANK® AM258994.1 is (SEQ ID NO: 103):

(SEQ ID NO: 103)

```
  1 caaagcaaga gattaataac ccatcatgga tcctgtgtac gtggacatag acgctgacag 61 cgccttttg aaggccctgc aacgtgcgta ccccatgttt gaggtggaac caaggcaggt
```

-continued

```
 121 cacaccgaat gaccatgcta atgctagagc gttctcgcat ctagctataa aactaataga
 181 gcaggaaatt gaccccgact caaccatcct ggatatcggc agtgcgccag caaggaggat
 241 gatgtcggac aggaagtacc actgcgtctg cccgatgcgc agtgcggaag atcccgagag
 301 actcgccaat tatgcgagaa agctagcatc tgccgcagga aaagtcctgg acagaaacat
 361 ctctggaaag atcggggact tacaagcagt aatggccgtg ccagacacgg agacgccaac
 421 attctgctta cacacagacg tctcatgtag acagagagca gacgtcgcta taccaaga
 481 cgtctatgct gtacacgcac ccacgtcgct ataccaccag gcgattaaag gggtccgagt
 541 ggcgtactgg gttgggttcg acacaacccc gttcatgtac aatgccatgg cgggtgccta
 601 cccctcatac tcgacaaact gggcagatga gcaggtactg aaggctaaga acataggatt
 661 atgttcaaca gacctgacgg aaggtagacg aggcaagttg tctattatga gagggaaaaa
 721 gctaaaaccg tgcgaccgtg tgctgttctc agtagggtca acgctctacc cggaaagccg
 781 caagctactt aagagctggc acctgccatc ggtgttccat ttaaagggca aactcagctt
 841 cacatgccgc tgtgatacag tggtttcgtg tgagggctac gtcgttaaga gaataacgat
 901 gagcccaggc ctttatggaa aaaccacagg gtatgcggta acccaccacg cagacggatt
 961 cctgatgtgc aagactaccg acacggttga cggcgaaaga gtgtcattct cggtgtgcac
1021 atacgtgccg gcgaccattt gtgatcaaat gaccggcatc cttgctacag aagtcacgcc
1081 ggaggatgca cagaagctgt tggtggggct gaaccagaga atagtggtta acggcagaac
1141 gcaacggaat acgaacacca tgaaaaatta tctgcttccc gtggtcgccc aagccttcag
1201 taagtgggca aaggagtgcc ggaaagacat ggaagatgaa aaactcctgg gggtcagaga
1261 aagaacactg acctgctgct gtctatgggc attcaagaag cagaaaacac acacggtcta
1321 caagagacct gatacccagt caattcagaa ggttcaggcc gagtttgaca gctttgtggt
1381 accgagtctg tggtcgtccg ggttgtcaat ccctttgagg actagaatca aatggttgtt
1441 aagcaaggtg ccaaaaaccg acctgatccc atacagcgga gacgcccgag aagcccggga
1501 cgcagaaaaa gaagcagagg aagaacgaga agcagaactg actcgcgaag ccctaccacc
1561 tctacaggca gcacaggaag atgttcaggt cgaaatcgac gtggaacagc ttgaggacag
1621 agcgggcgca ggaataatag agactccgag aggagctatc aaagttactg cccaaccaac
1681 agaccacgtc gtgggagagt acctggtact ctccccgcag accgtactac gtagccagaa
1741 gctcagtctg attcacgctt ggcggagca agtgaagacg tgcacgcaca acggacgagc
1801 agggaggtat gcggtcgaag cgtacgacgg ccgagtccta gtgccctcag gctatgcaat
1861 ctcgcctgaa gacttccaga gtctaagcga aagcgcaacg atggtgtata cgaaagaga
1921 gttcgtaaac agaaagctac accatattgc gatgcacgga ccagccctga caccgacga
1981 agagtcgtat gagctggtga gggcagagag gacagaacac gagtacgtct acgacgtgga
2041 tcagagaaga tgctgtaaga aggaagaagc cgcaggactg tactggtgg gcgacttgac
2101 taatccgccc taccacgaat tcgcatatga agggctaaaa atccgccctg cctgcccata
2161 caaaattgca gtcataggag tcttcggagt accgggatct ggcaagtcag ctattatcaa
2221 gaacctagtt accaggcagg acctggtgac tagcggaaag aaagaaaact gccaagaaat
2281 caccaccgac gtgatgagac agagaggtct agagatatct gcacgtacgg ttgactcgct
2341 gctcttgaat ggatgcaaca gaccagtcga cgtgttgtac gtagacgagg cgtttgcgtg
2401 ccactctgga acgctacttg ctttgatcgc cttggtgaga ccaaggcaga aagttgtact
2461 ttgtggtgac ccgaagcagt gcggcttctt caatatgatg cagatgaaag tcaactataa
```

-continued

```
2521 tcacaacatc tgcacccaag tgtaccacaa aagtatctcc aggcggtgta cactgcctgt 2581 gaccgccatt gtgtcatcgt tgcattacga aggcaaaatg cgcactacga atgagtacaa 2641 caagccgatt gtagtggaca ctacaggctc aacaaaacct gaccctggag acctcgtgtt 2701 aacgtgcttc agagggtggg ttaaacaact gcaaattgac tatcgtggat acgaggtcat 2761 gacagcagcc gcatcccaag ggttaaccag aaaaggagtt tacgcagtta gacaaaaagt 2821 taatgaaaac ccgctctatg catcaacgtc agagcacgtc aacgtactcc taacgcgtac 2881 ggaaggtaaa ctggtatgga agacactttc cggcgacccg tggataaaga cgctgcagaa 2941 cccaccgaaa ggaaacttca aagcaactat taaggagtgg gaggtggagc atgcatcaat 3001 aatggcgggc atctgcagtc accaaatgac cttcgataca ttccaaaata aagccaacgt 3061 ttgttgggct aagagcttgg tccctatcct cgaaacagcg gggataaaac taaatgatag 3121 gcagtggtct cagataattc aagccttcaa agaagacaaa gcatactcac ctgaagtagc 3181 cctgaatgaa atatgtacgc gcatgtatgg ggtggatcta gacagcgggc tattttctaa 3241 accgttggtg tctgtgtatt acgcggataa ccactgggat aataggcctg gagggaaaat 3301 gttcggattt aaccccgagg cagcatccat tctagaaaga aagtatccat tcacaaaagg 3361 gaagtggaac atcaacaagc agatctgcgt gactaccagg aggatagaag actttaaccc 3421 taccaccaac atcataccgg ccaacaggag actaccacac tcattagtgg ccgaacaccg 3481 cccagtaaaa ggggaaagaa tggaatggct ggttaacaag ataaacggcc accacgtgct 3541 cctggtcagt ggctataacc ttgcactgcc tactaagaga gtcacttggg tagcgccgtt 3601 aggtgtccgc ggagcggact acacatacaa cctagagttg gtctgccag caacgcttgg 3661 taggtatgac ctagtggtca taaacatcca cacccttttt cgcatacacc attaccaaca 3721 gtgcgtcgac cacgcaatga aactgcaaat gctcgggggt gactcattga gactgctcaa 3781 accgggcggc tctctattga tcagagcata tggttacgca gatagaacca gtgaacgagt 3841 catctgcgta ttgggacgca agtttagatc gtctagagcg ttgaaaccac catgtgtcac 3901 cagcaacact gagatgtttt tcctattcag caactttgac aatggcagaa ggaatttcac 3961 aactcatgtc atgaacaatc aactgaatgc agccttcgta ggacaggtca cccgagcagg 4021 atgtgcaccg tcgtaccggg taaaacgcat ggacatcgcg aagaacgatg aagagtgcgt 4081 agtcaacgcc gctaaccctc gcgggttacc gggtgacggt gtttgcaagg cagtatacaa 4141 aaaatggccg gagtccttta agaacagtgc aacaccagtg gaaccgcaa aaacagttat 4201 gtgcggtacg tatccagtaa tccacgctgt tggaccaaac ttctctaatt attcggagtc 4261 tgaagggac cgggaattgg cagctgccta tcgagaagtc gcaaggaag taactaggct 4321 gggagtaaat agtgtagcta tacctctcct ctccacaggt gtatactcag gagggaaaga 4381 caggctgacc cagtcactga accacctctt tacagccatg gactcgacgg atgcagacgt 4441 ggtcatctac tgccgcgaca agaatgggga gaagaaaata tctgaggcca tacagatgcg 4501 gacccaagta gagctgctgg atgagcacat ctccatagac tgcgatattg ttcgcgtgca 4561 ccctgacagc agcttggcag cagaaaagg atacagcacc acggaaggcg cactgtactc 4621 atatctagaa gggacccgtt tcatcagac ggctgtggat atggcggaga tacatactat 4681 gtggccaaag caaacagagg ccaatgagca agtctgccta tatgccctgg gggaaagtat 4741 tgaatcgatc aggcagaaat gccggtgga tgatgcagac gcatcatctc cccccaaaac 4801 tgtcccgtgc ctttgccgtt acgctatgac tccagaacgc gtcacccggc ttcgcatgaa 4861 ccacgtcaca agcataattg tgtgttcttc gtttccccctc ccaaagtaca aaatagaagg 4921 agtgcaaaaa gtcaaatgct ctaaggtaat gctatttgac cacaacgtgc catcgcgcgt
```

-continued

```
4981  aagtccaagg gaatatagat cttcccagga gtctgcacag gaggcgagta caatcacgtc
5041  actgacgcat agtcaattcg acctaagcgt tgatggcgag atactgcccg tcccgtcaga
5101  cctggatgct gacgcccag ccctagaacc agcactagac gacggggcga cacacacgct
5161  gccatccaca accggaaacc ttgcggccgt gtctgattgg gtaatgagca ccgtacctgt
5221  cgcgccgccc agaagaaggc gagggagaaa cctgactgtg acatgtgacg agagagaagg
5281  gaatataaca cccatggcta gcgtccgatt ctttagggca gagctgtgtc cggtcgtaca
5341  agaaacagcg gagacgcgtg acacagcaat gtctcttcag gcaccaccga gtaccgccac
5401  ggaaccgaat catccgccga tctccttcgg agcatcaagc gagacgttcc ccattacatt
5461  tggggacttc aacgaaggag aaatcgaaag cttgtcttct gagctactaa ctttcggaga
5521  cttcttacca ggagaagtgg atgacttgac agacagcgac tggtccacgt gctcagacac
5581  ggacgacgag ttatgactag acagggcagg tgggtatata ttctcgtcgg acaccggtcc
5641  aggtcattta caacagaagt cagtacgcca gtcagtgctg ccggtgaaca ccctggagga
5701  agtccacgag gagaagtgtt acccacctaa gctggatgaa gcaaaggagc aactattact
5761  taagaaactc caggagagtg catccatggc caacagaagc aggtatcagt cgcgcaaagt
5821  agaaaacatg aaagcagcaa tcatccagag actaaagaga ggctgtagac tatacttaat
5881  gtcagagacc ccaaaagtcc ctacttaccg gactacatat ccggcgcctg tgtactcgcc
5941  tccgatcaac gtccgattgt ccaatcccga gtccgcagtg gcagcatgca atgagttctt
6001  agctagaaac tatccaactg tctcatcata ccaaattacc gacgagtatg atgcatatct
6061  agacatggtg gacgggtcgg agagttgcct ggaccgagcg acattcaatc cgtcaaaact
6121  caggagctac ccgaaacagc acgcttacca cgcgccctcc atcagaagcg ctgtaccgtc
6181  cccattccag aacacactac agaatgtact ggcagcagcc acgaaaagaa actgcaacgt
6241  cacacagatg agggaattac ccactttgga ctcagcagta ttcaacgtgg agtgtttcaa
6301  aaaattcgca tgcaaccaag aatactggga agaatttgct gccagcccta ttaggataac
6361  aactgagaat ttagcaacct atgttactaa actaaaaggg ccaaaagcag cagcgctatt
6421  cgcaaaaacc cataatctac tgccactaca ggaagtacca atggataggt tcacagtaga
6481  tatgaaaagg gacgtaaagg tgactcctgg tacaaagcat acagaggaaa gacctaaggt
6541  gcaggttata caggcggctg aacccttggc gacagcatac ctatgtggga ttcacagaga
6601  gctggttagg aggctgaacg ccgtcctcct acccaatgta catacactat ttgacatgtc
6661  tgccgaggat ttcgatgcca tcatagccgc acactttaag ccaggagaca ctgtttttgga
6721  aacggacata gcctcctttg ataagagcca agatgattca cttgcgctta ctgctttgat
6781  gctgttagag gatttagggg tggatcactc cctgctggac ttgatagagg ctgctttcgg
6841  agagatttcc agctgtcacc taccgacagg tacgcgcttc aagttcggcg ccatgatgaa
6901  atcaggtatg ttcctaactc tgttcgtcaa cacattgtta aacatcacca tcgccagccg
6961  agtgctggaa gatcgtctga caaaatccgc gtgcgcggcc ttcatcggcg acgacaacat
7021  aatacatgga gtcgtctccg atgaattgat ggcagccaga tgtgccactt ggatgaacat
7081  ggaagtgaag atcatagatg cagttgtatc cttgaaagcc ccttacttt gtggagggtt
7141  tatactgcac gatactgtga caggaacagc ttgcagagtg cagaccccgc taaaaaggct
7201  ttttaaactg gcaaaccgc tagcggcagg tgacgaacaa gatgaagata aagacgagc
7261  gctggctgac gaagtgatca gatggcaacg aacagggcta attgatgagc tggagaaagc
7321  ggtatactct aggtacgaag tgcagggtat atcagttgtg gtaatgtcca tggccacctt
```

-continued

```
7381  tgcaagctcc agatccaact tcgagaagct cagaggaccc gtcataactt tgtacggcgg
7441  tcctaaatag gtacgcacta cagctaccta ttttgcagaa gccgacagca agtatctaaa
7501  cactaatcag ctacaatgga gttcatccca acccaaactt tttacaatag gaggtaccag
7561  cctcgaccct ggactccgcg ccctactatc caagtcatca ggcccagacc gcgccctcag
7621  aggcaagctg ggcaacttgc ccagctgatc tcagcagtta ataaactgac aatgcgcgcg
7681  gtaccccaac agaagccacg caggaatcgg aagaataaga agcaaaagca aaacaacag
7741  gcgccacaaa acaacacaaa tcaaagaag cagccaccta aaaagaaacc ggctcaaaag
7801  aaaaagaagc cgggccgcag agagaggatg tgcatgaaaa tcgaaaatga ttgtattttc
7861  gaagtcaagc acgaaggtaa ggtaacaggt tacgcgtgcc tggtggggga caaagtaatg
7921  aaaccagcac acgtaaaggg gaccatcgat aacgcggacc tggccaaact ggcctttaag
7981  cggtcatcta agtatgacct tgaatgcgcg cagatacccg tgcacatgaa gtccgacgct
8041  tcgaagttca cccatgagaa accggagggg tactacaact ggcaccacgg agcagtacag
8101  tactcaggag gccggttcac catccctaca ggtgctggca aaccagggga cagcggcaga
8161  ccgatcttcg acaacaaggg acgcgtggtg gccatagtct taggaggagc taatgaagga
8221  gcccgtacag ccctctcggt ggtgacctgg aataaagaca ttgtcactaa aatcaccccc
8281  gagggggccg aagagtggag tcttgccatc ccagttatgt gcctgttggc aaacaccacg
8341  ttcccctgct cccagccccc ttgcacgccc tgctgctacg aaaaggaacc ggaggaaacc
8401  ctacgcatgc ttgaggacaa cgtcatgaga cctgggtact atcagctgct acaagcatcc
8461  ttaacatgtt ctccccaccg ccagcgacgc agcaccaagg acaacttcaa tgtctataaa
8521  gccacaagac catacttagc tcactgtccc gactgtggag aagggcactc gtgccatagt
8581  cccgtagcac tagaacgcat cagaaatgaa gcgacagacg ggacgctgaa aatccaggtc
8641  tccttgcaaa tcggaataaa gacggatgac agccacgatt ggaccaagct gcgttatatg
8701  gacaaccaca tgccagcaga cgcagagagg gcggggctat ttgtaagaac atcagcaccg
8761  tgtacgatta ctggaacaat gggacacttc atcctggccc gatgtccaaa aggggaaact
8821  ctgacggtgg gattcactga cagtaggaag attagtcact catgtacgca cccatttcac
8881  cacgaccctc ctgtgatagg tcgggaaaaa ttccattccc gaccgcagca cggtaaagag
8941  ctaccttgca gcacgtacgt gcagagcacc gccgcaacta ccgaggagat agaggtacac
9001  atgcccccag acacccctga tcgcacatta atgtcacaac agtccggcaa cgtaaagatc
9061  acagtcaatg gccgacggt gcggtacaag tgtaattgcg gtggctcaaa tgaaggacta
9121  acaactacag acaaagtgat taataactgc aaggttgatc aatgtcatgc cgcggtcacc
9181  aatcacaaaa agtggcagta aactccccct ctggtcccgc gtaatgctga acttggggac
9241  cgaaaggaa aaattcacat cccgtttccg ctggcaaatg taacatgcag ggtgcctaaa
9301  gcaaggaacc ccaccgtgac gtacgggaaa aaccaagtca tcatgctact gtatcctgac
9361  cacccaacac tcctgtccta ccggaatatg ggagaagaac caaactatca agaagagtgg
9421  gtgatgcata agaaggaagt cgtgctaacc gtgccgactg aagggctcga ggtcacgtgg
9481  ggcaacaacg agccgtataa gtattggccg cagttatcta caaacggtac agcccatggc
9541  cacccgcacg agataattct gtattattat gagctgtacc ccactatgac tgtagtagtt
9601  gtgtcagtgg ccacgttcat actcctgtcg atggtgggta tggcagcggg gatgtgcatg
9661  tgtgcacgac gcagatgcat cacaccgtat gaactgacac caggagctac cgtcccttc
9721  ctgcttagcc taatatgctg catcagaaca gctaaagcgg ccacatacca agaggctgcg
9781  atataccctgt ggaacgagca gcaacctttg ttttggctac aagcccttat tccgctggca
```

-continued

```
 9841 gccctgattg ttctatgcaa ctgtctgaga ctcttaccat gctgctgtaa aacgttggct 9901 tttttagccg taatgagcgt cggtgcccac actgtgagcg cgtacgaaca cgtaacagtg 9961 atcccgaaca cggtgggagt accgtataag actctagtca atagacctgg ctacagcccc 10021 atggtattgg agatggaact actgtcagtc actttggagc caacactatc gcttgattac 10081 atcacgtgcg agtacaaaac cgtcatcccg tctccgtacg tgaagtgctg cggtacagca 10141 gagtgcaagg acaaaaacct acctgactac agctgtaagg tcttcaccgg cgtctaccca 10201 tttatgtggg gcggcgccta ctgcttctgc gacgctgaaa acacgcagtt gagcgaagca 10261 cacgtggaga agtccgaatc atgcaaaaca gaatttgcat cagcatacag ggctcatacc 10321 gcatctgcat cagctaagct ccgcgtcctt taccaaggaa ataacatcac tgtaactgcc 10381 tatgcaaacg gcgaccatgc cgtcacagtt aaggacgcca aattcattgt ggggccaatg 10441 tcttcagcct ggacaccttt cgacaacaaa attgtggtgt acaaggtga cgtctataac 10501 atggactacc cgccctttgg cgcaggaaga ccaggacaat tggcgatat ccaaagtcgc 10561 acacctgaga gtaaagacgt ctatgctaat acacaactgg tactgcagag accggctgtg 10621 ggtacggtac acgtgccata ctctcaggca ccatctggct ttaagtattg gctaaaagaa 10681 cgcggggcgt cgctgcagca cacagcacca tttggctgcc aaatagcaac aaacccggta 10741 agagcggtga actgcgccgt agggaacatg cccatctcca tcgacatacc ggaagcggcc 10801 ttcactaggg tcgtcgacgc gccctcttta acggacatgt cgtgcgaggt accagcctgc 10861 acccattcct cagactttgg gggcgtcgcc attattaaat atgcagccag caagaaaggc 10921 aagtgtgcgg tgcattcgat gactaacgcc gtcactattc gggaagctga gatagaagtt 10981 gaagggaatt ctcagctgca aatctctttc tcgacggcct tagccagcgc cgaattccgc 11041 gtacaagtct gttctacaca agtacactgt gcagccgagt gccacccccc gaaggaccac 11101 atagtcaact acccggcgtc acataccacc ctcggggtcc aggacatctc cgctacggcg 11161 atgtcatggg tgcagaagat cacgggaggt gtgggactgg ttgttgctgt tgccgcactg 11221 attctaatcg tggtgctatg cgtgtcgttc agcaggcact aacttgacaa ttaagtatga 11281 aggtatatgt gtccctaag agacacactg tacatagcaa ataatctata gatcaaaggg 11341 ctacgcaacc cctgaatagt aacaaaatat aaaatcacta aaattataa aaacagaaaa 11401 atacataaat aggtatacgt gtcccctaag agacacattg tatgtaggtg ataagtatag 11461 atcaaagggc cgaataaccc ctgaatagta acaaatatg aaaatcaata aaaatcataa 11521 aatagaaaaa ccataaacag aagtagttca aagggctata aaacccctga atagtaacaa 11581 aacataaaat taataaaaat c
```

Fragment 7516-11262 from SEQ ID NO: 103 is the CDS that codes for the C-E3-E2-6K-E1 polyprotein.

Fragment 8491-11262 from SEQ ID NO: 103 codes for the glycoproteins E1, 6K and E2.

Fragment 8491-9759 from SEQ ID NO: 103 is the CDS that codes for the glycoprotein E2.

Fragment 9943-11262 from SEQ ID NO: 103 is the CDS that codes for the glycoprotein E1.

Fragment 7516-11262 from SEQ ID NO: 103 (SEQ ID NO: 104) is the wild-type version of the sequence of SEQ ID NO: 101 and 102.

SEQ ID NO: 104 is:

```
                                                      SEQ ID NO: 104
7516                  atgga gttcatccca acccaaactt tttacaatag gaggtaccag
7561  cctcgaccct ggactccgcg ccctactatc caagtcatca ggcccagacc gcgccctcag
7621  aggcaagctg ggcaacttgc ccagctgatc tcagcagtta ataaactgac aatgcgcgcg
7681  gtaccccaac agaagccacg caggaatcgg aagaataaga agcaaaagca aaaacaacag
```

-continued

```
7741 gcgccacaaa acaacacaaa tcaaagaag cagccaccta aaaagaaacc ggctcaaaag 7801 aaaaagaagc cgggccgcag agagaggatg tgcatgaaaa tcgaaaatga ttgtattttc 7861 gaagtcaagc acgaaggtaa ggtaacaggt tacgcgtgcc tggtggggga caaagtaatg 7921 aaaccagcac acgtaagggg gaccatcgat aacgcggacc tggccaaact ggcctttaag 7981 cggtcatcta agtatgacct tgaatgcgcg cagatacccg tgcacatgaa gtccgacgct 8041 tcgaagttca cccatgagaa accggagggg tactacaact ggcaccacgg agcagtacag 8101 tactcaggag gccggttcac catccctaca ggtgctggca aaccagggga cagcggcaga 8161 ccgatcttcg acaacaaggg acgcgtggtg gccatagtct taggaggagc taatgaagga 8221 gcccgtacag ccctctcggt ggtgacctgg aataaagaca ttgtcactaa aatcacccc 8281 gaggggggccg aagagtggag tcttgccatc ccagttatgt gcctgttggc aaacaccacg 8341 ttcccctgct cccagccccc ttgcacgccc tgctgctacg aaaaggaacc ggaggaaacc 8401 ctacgcatgc ttgaggacaa cgtcatgaga cctgggtact atcagctgct acaagcatcc 8461 ttaacatgtt ctccccaccg ccagcgacgc agcaccaagg acaacttcaa tgtctataaa 8521 gccacaagac catacttagc tcactgtccc gactgtggag aagggcactc gtgccatagt 8581 cccgtagcac tagaacgcat cagaaatgaa gcgacagacg ggacgctgaa aatccaggtc 8641 tccttgcaaa tcggaataaa gacggatgac agccacgatt ggaccaagct gcgttatatg 8701 gacaaccaca tgccagcaga cgcagagagg gcggggctat ttgtaagaac atcagcaccg 8761 tgtacgatta ctggaacaat gggacacttc atcctggccc gatgtccaaa aggggaaact 8821 ctgacggtgg gattcactga cagtaggaag attagtcact catgtacgca cccatttcac 8881 cacgaccctc ctgtgatagg tcgggaaaaa ttccattccc gaccgcagca cggtaaagag 8941 ctaccttgca gcacgtacgt gcagagcacc gccgcaacta ccgaggagat agaggtacac 9001 atgcccccag acacccctga tcgcacatta atgtcacaac agtccggcaa cgtaaagatc 9061 acagtcaatg gccagacggt gcgtacaag tgtaattgcg gtggctcaaa tgaaggacta 9121 acaactacag acaaagtgat taataactgc aaggttgatc aatgtcatgc cgcggtcacc 9181 aatcacaaaa agtggcagta taactcccct ctggtcccgc gtaatgctga acttgggggac 9241 cgaaaaggaa aaattcacat cccgtttccg ctggcaaatg taacatgcag ggtgcctaaa 9301 gcaaggaacc ccaccgtgac gtacgggaaa aaccaagtca tcatgctact gtatcctgac 9361 cacccaacac tcctgtccta ccggaatatg ggagaagaac caaactatca agaagagtgg 9421 gtgatgcata agaaggaagt cgtgctaacc gtgccgactg aagggctcga ggtcacgtgg 9481 ggcaacaacg agccgtataa gtattggccg cagttatcta caaacggtac agcccatggc 9541 cacccgcacg agataattct gtattattat gagctgtacc ccactatgac tgtagtagtt 9601 gtgtcagtgg ccacgttcat actcctgtcg atggtgggta tggcagcggg gatgtgcatg 9661 tgtgcacgac gcagatgcat cacaccgtat gaactgacac caggagctac cgtccctttc 9721 ctgcttagcc taatatgctg catcagaaca gctaaagcgg ccacatacca agaggctgcg 9781 atatacctgt ggaacgagca gcaacctttg ttttggctac aagcccttat ccgctggca 9841 gccctgattg ttctatgcaa ctgtctgaga ctcttaccat gctgctgtaa aacgttggct 9901 ttttagccg taatgagcgt cggtgcccac actgtgagcg cgtacgaaca cgtaacagtg 9961 atcccgaaca cggtgggagt accgtataag actctagtca atagacctgg ctacagcccc 10021 atggtattgg agatggaact actgtcagtc actttggagc caacactatc gcttgattac 10081 atcacgtgcg agtacaaaac cgtcatcccg tctccgtacg tgaagtgctg cggtacagca 10141 gagtgcaagg acaaaaaccct acctgactac agctgtaagg tcttcaccgg cgtctaccca
```

```
10201 tttatgtggg gcggcgccta ctgcttctgc gacgctgaaa acacgcagtt gagcgaagca 10261 cacgtggaga agtccgaatc atgcaaaaca gaatttgcat cagcatacag ggctcatacc 10321 gcatctgcat cagctaagct ccgcgtcctt taccaaggaa ataacatcac tgtaactgcc 10381 tatgcaaacg gcgaccatgc cgtcacagtt aaggacgcca aattcattgt ggggccaatg 10441 tcttcagcct ggacaccttt cgacaacaaa attgtggtgt acaaaggtga cgtctataac 10501 atggactacc cgccctttgg cgcaggaaga ccaggacaat ttggcgatat ccaaagtcgc 10561 acacctgaga gtaaagacgt ctatgctaat acacaactgg tactgcagag accggctgtg 10621 ggtacggtac acgtgccata ctctcaggca ccatctggct ttaagtattg gctaaaagaa 10681 cgcggggcgt cgctgcagca cacagcacca tttggctgcc aaatagcaac aaacccggta 10741 agagcggtga actgcgccgt agggaacatg cccatctcca tcgacatacc ggaagcggcc 10801 ttcactaggg tcgtcgacgc gccctcttta acggacatgt cgtgcgaggt accagcctgc 10861 acccattcct cagactttgg gggcgtcgcc attattaaat atgcagccag caagaaaggc 10921 aagtgtgcgg tgcattcgat gactaacgcc gtcactattc gggaagctga gatagaagtt 10981 gaagggaatt ctcagctgca aatctctttc tcgacggcct tagccagcgc cgaattccgc 11041 gtacaagtct gttctacaca agtacactgt gcagccgagt gccacccccc gaaggaccac 11101 atagtcaact acccggcgtc acataccacc ctcgggtcc aggacatctc cgctacggcg 11161 atgtcatggg tgcagaagat cacgggaggt gtgggactgg ttgttgctgt tgccgcactg 11221 attctaatcg tggtgctatg cgtgtcgttc agcaggcact aa
```

BIBLIOGRAPHIC REFERENCES

Abramoff, M. D., Magalhaes, P. J., Ram, S. J. 2004, "Image Processing with ImageJ". Biophotonics International, volume 11, issue 7, pp. 36-42.

Archetti 2009, M. Genetic robustness at the codon level as a measure of selection, Gene 443: 64-69.

Atkinson, N. J., Witteveldt, J., Evans, D. J. & Simmonds, P. 2014, The influence of CpG and UpA dinucleotide frequencies on RNA virus replication and characterization of the innate cellular pathways underlying virus attenuation and enhanced replication. Nucleic Acids Res. 42: 4527-4545.

Carrasco P., Daròs J. A., Agudelo-Romero P., Elena S. F. 2007. A real-time RT-PCR assay for quantifying the fitness of tobacco etch virus in competition experiments. J Virol Methods 139:181-188.

Coleman, J. R. et al. 2008, Virus attenuation by genome-scale changes in codon pair bias. Science 320: 1784-1787.

Furuta et al. 2009, T-705 (favipiravir) and related compounds: Novel broad-spectrum inhibitors of RNA viral infections. Antiviral Research 82(3): 95-102.

Gnädig, N. F. et al. 2012, Coxsackie virus B3 mutator strains are attenuated in vivo. Proc. Natl. Acad. Sci. U.S.A. (2012). doi:10.1073/pnas.1204022109.

Harrison, D. N., Gazina, E. V., Purcell, D. F., Anderson, D. A. and S. Petrou, 2008. S. Amiloride Derivatives Inhibit Coxsackie virus B3 RNA Replication. J. Virol. 82:1465-1473.

Hoffmann, E., Neumann, G., Hobom, G., Webster, R. G., and Kawaoka, Y. (2000). "Ambisense" approach for the generation of influenza A virus: vRNA and mRNA synthesis from one template. Virology 267, 310-317.

Lauring, A. S., Acevedo, A. Cooper, S. B. and Andono, R. 2012. Codon usage determines the mutational robustness, evolutionary capacity, and virulence of an RNA virus. Cell Host Microbe 12: 623-632.

Li H. 2013. Aligning sequence reads, clone sequences and assembly contigs with BWA-MEM. arXiv (1303.3997)

McLachlan, A. D. 1972, J. Mol. Biol. 64: 417-437.

Rasband, W. S. 1997-2014, ImageJ, U. S. National Institutes of Health, Bethesda, Md., U.S.A., imagej.nih.gov/ij/.

Schneider, C. A., Rasband, W. S., Eliceiri, K. W. 2012, "NIH Image to ImageJ: 25 years of image analysis". Nature Methods 9: 671-675.

Schuffenecker et al. 2006 "Genome microevolution of Chikungunya viruses causing the Indian ocean outbreak", PLoS Medicine 3(7): e263.

The invention claimed is:

1. A process for producing an attenuated RNA virus or a cDNA clone thereof comprising a RNA-dependent RNA polymerase or a RNA-dependent DNA polymerase, the process comprising:
   providing an infectious RNA virus or a cDNA clone thereof comprising the retrotranscript of the CDS of the genome of the RNA virus; and
   modifying the RNA genome of the infectious RNA virus or the retrotranscript of the CDS of the genome of the RNA virus, respectively;
   wherein the modification comprises changing at least one codon that codes for an amino acid selected from Leu, Ser, Arg and Gly in the infectious RNA virus or cDNA clone thereof to a different but synonymous codon,
   wherein said different but synonymous codon differs by only one nucleotide from a STOP codon.

2. The process of claim 1, wherein
   the at least one codon, which codes for Leu is selected from CUU, CUC, CUA and CUG in the infectious RNA virus, or from CTT, CTC, CTA and CTG in said retrotranscript of the CDS of the genome of the RNA virus, respectively, and wherein the different but synonymous Leu codon is selected from UUA and UUG for attenuation of said RNA virus, or from TTA and TTG for attenuation of said cDNA clone, respectively; and/or
   the at least one codon, which codes for Ser is selected from AGU, AGC, UCU and UCC in said infectious RNA virus, or from AGT, AGC, TCT and TCC in said infectious cDNA clone, and wherein the different but synonymous Ser codon, which replaces it, is selected from UCA and UCG for attenuation of said RNA virus, or from TCA and TCG for attenuation of said cDNA clone, respectively; and/or
   the at least one codon which codes for Arg is selected from AGA, AGG, CGU, CGC and CGG in said infectious RNA virus, or from AGA, AGG, CGT, CGC and CGG in said retrotranscript of the CDS of the genome of the RNA virus, respectively, and wherein the different but synonymous Arg codon, which replaces it, is CGA for attenuation of said RNA virus or for attenuation of said cDNA clone, respectively; and/or the at least one codon which codes for Gly is selected from GGG, GGU and GGC in said retrotranscript of the CDS of the genome of the RNA virus, respectively, and wherein the different but synonymous Gly codon, which replaces it, is GGA for attenuation of said RNA virus or for attenuation of said cDNA clone, respectively.

3. The process of claim 1, wherein the at least one codon which codes for Ser is selected from AGU and AGC in said infectious RNA virus, or from AGT and AGC in said infectious cDNA clone, and wherein the different but synonymous Ser codon, which replaces it, is selected from UCA and UCG for attenuation of said RNA virus, or from TCA and TCG for attenuation of said cDNA clone, respectively; and/or the at least one codon which codes for Arg is selected from AGA and AGG in said infectious RNA virus or in said infectious cDNA clone, and wherein the different but synonymous Arg codon, which replaces it, is CGA for attenuation of said RNA virus or for attenuation of said cDNA clone, respectively.

4. The process of claim 1, wherein the modification comprises:
changing at least one codon which codes for Leu and at least one codon which codes for Ser; or
changing at least one codon which codes for Leu, at least one codon which codes for Ser, at least one codon which codes for Arg and at least one codon which codes for Gly.

5. The process of claim 1, wherein the modification further comprises changing at least one codon which codes for an amino acid selected from Thr and Ala to a different and non-synonymous codon that codes for Ser;
wherein the at least one codon that codes for an amino acid selected from Thr and Ala differs by only one nucleotide from a codon that codes for Ser; and
wherein the different and non-synonymous codon differs by only one nucleotide from a STOP codon.

6. The process of claim 1, wherein said modification comprises changing from 2% to 30% of the total number of codons of the genome of the infectious RNA virus, or of the total number of codons of the retrotranscript of the CDS of the genome of the RNA virus, respectively.

7. The process of claim 1, wherein the coding sequence of the genome of the infectious RNA virus or the retrotranscribed cDNA CDS sequence of said cDNA clone consists of from 2,000 to 30,000 nucleotides.

8. The process of claim 1, wherein the modification comprises changing more than 100 codons.

9. The process of claim 1, wherein the RNA virus is a single-stranded RNA virus.

10. The process of claim 1, wherein the RNA virus is a Coxsackie virus, an Influenza virus, a Chikungunya virus, or an O'Nyong-nyong virus.

11. The process of claim 1, wherein the modification comprises changing a plurality of codons, wherein:
the infectious RNA virus is a Coxsackie virus, and the plurality of codons are codons of the P1 coding sequence of the Coxsackie virus;
the infectious RNA virus is an Influenza virus, and the plurality of codons are codons of the PA and/or HA coding sequence(s) of the Influenza virus, or
the infectious RNA virus is a Chikungunya virus, and the plurality of codons are codons of the C-E3-E2-6K-E1 coding sequence of the Chikungunya virus.

12. The process of claim 1, wherein the Codon-Pair Bias of said modified virus or modified cDNA clone is not different from the Codon-Pair Bias of said infectious RNA virus or infectious cDNA clone, respectively; and/or wherein the CpG and UpA dinucleotide bias of said modified virus is not different from the CpG and UpA dinucleotide bias of said infectious RNA virus, and wherein the CpG and TpA dinucleotide bias of said modified cDNA clone is not different from the CpG and TpA dinucleotide bias of said infectious cDNA clone.

13. The process of claim 1, wherein said modification further comprises changing the RNA-dependent RNA-polymerase of said infectious RNA virus with a RNA-dependent RNA-polymerase having a lower copying fidelity.

14. A live and attenuated virus or a cDNA clone thereof, which is obtainable by the process of claim 1, and
which is a live and attenuated Coxsackie virus or a cDNA clone thereof comprising the retrotranscript of the CDS of the genome of the live and attenuated Coxsackie virus, wherein the codons that codes for Leu in the P1 protein of thelive and attenuated Coxsackie virus or cDNA clone thereof are all selected from UUA and UUG for said live and attenuated virus, or from TTA and TTG for the cDNA clone thereof, respectively, and wherein the codons that code for Ser in the P1 protein of the live and attenuated Coxsackie virus or cDNA clone thereof are all selected from UCA and UCG for the live and attenuated virus, or from TCA and TCG for the cDNA clone thereof, or
which is a live and attenuated Influenza virus or a cDNA clone thereof comprising the retrotranscript of the CDS of the genome of the live and attenuated Influenza virus, wherein the codons that code for Leu in the PA and/or HA protein(s) of said live and attenuated Influenza virus or cDNA clone thereof are all selected from UUA and UUG for the live and attenuated virus, or from TTA and TTG for the cDNA clone thereof, respectively, and wherein the codons that code for Ser in the PA and/or HA protein(s) of said live and attenuated Influenza virus or cDNA clone thereof are all selected from UCA and UCG for the live and attenuated virus, or from TCA and TCG for the cDNA clone thereof, respectively, or
which is a live and attenuated Chikungunya virus or a cDNA clone thereof comprising the retrotranscript of the CDS of the genome of the live and attenuated Chikungunya virus, wherein the codons that code for Leu in the E1 and/or E2 protein(s) of the live and attenuated Chikungunya virus or cDNA clone thereof are all selected from UUA and UUG for said live and attenuated virus, or from TTA and TTG for said cDNA clone thereof, respectively, and wherein the codons that code for Ser in the E1 and/or E2 protein(s) of said live and attenuated Chikungunya virus or cDNA clone thereof are all selected from UCA and UCG for said live and attenuated virus, or from TCA and TCG for said cDNA clone thereof, respectively.

15. The live and attenuated virus or cDNA clone thereof of claim 14,
which is a live and attenuated Coxsackie virus or a cDNA clone thereof comprising the retrotranscript of the CDS of the genome of the live and attenuated Coxsackie virus, wherein the codons that code for Arg in the P1 protein of the live and attenuated Coxsackie virus or cDNA clone thereof all are CGA, and wherein the codons that code for Gly in the P1 protein of the live and attenuated Coxsackie virus or cDNA clone thereof all are GGA; or which is a live and attenuated Influenza virus or a cDNA clone thereof comprising the retrotranscript of the CDS of the genome of the live and attenuated Influenza virus, wherein the codons that code for Arg in the PA and/or HA protein(s) of said live and attenuated Influenza virus or cDNA clone thereof all are CGA, and wherein the codons that code for Gly in the PA and/or HA protein(s) of said live and attenuated Influenza virus or cDNA clone thereof all are GGA; or which is a live and attenuated Chikungunya virus or a cDNA clone thereof comprising the retrotranscript of the CDS of the genome of the live and attenuated Chikungunya virus, wherein the codons that code for Arg in the E1 and/or E2 protein(s) of said live and attenuated Chikungunya virus or cDNA clone thereof all are CGA, and wherein the codons that code for Gly in the E1 and/or E2 protein(s) of said live and attenuated Chikungunya virus or cDNA clone thereof all are GGA.

16. The live and attenuated virus or the cDNA clone thereof of claim 15, which is a live and attenuated Coxsackie virus or cDNA clone thereof, wherein the sequence coding for Coxsackie virus P1 protein comprises the RNA transcript of the cDNA sequence of SEQ ID NO: 85, or the cDNA sequence of SEQ ID NO: 85, respectively; or which is a live and attenuated Chikungunya virus or cDNA clone thereof, and wherein the sequence coding for Chikungunya virus polyprotein C-E3-E2-6K-E1 comprises the RNA transcript of the cDNA sequence of SEQ ID NO: 102 or the cDNA sequence of SEQ ID NO: 102, respectively.

17. An immunogenic composition, which comprises the live and attenuated virus of claim 14 or the cDNA clone thereof.

18. A method to prevent and/or to treat and/or to palliate a RNA virus infection or a disease or disorder induced by a RNA virus comprising administering the immunogenic composition according to claim 17 to a subject in need thereof.

19. A method to produce an immunogenic composition comprising a live and attenuated virus or clone thereof, comprising producing the live and attenuated virus or clone thereof according to claim 1 in a culture medium, and formulating the live and attenuated virus or clone thereof in a composition suitable for administration to an animal.

20. A method to produce an immunogenic composition comprising a live and attenuated virus or clone thereof, comprising producing the live and attenuated virus or clone thereof according to claim 14 in a culture medium, and formulating the live and attenuated virus or clone thereof in a composition suitable for administration to an animal.

21. A nucleic acid selected from the group consisting of: SEQ ID NO: 14, 54, 56, 85, 87, 101 and 102.

22. A nucleic acid vector, which comprises at least one of the nucleic acids as defined in claim 21.

23. A culture medium, which comprises at least one of the live and attenuated virus or cDNA clone thereof according to claim 1.

24. A composition comprising the live and attenuated virus of claim 14 or the cDNA clone thereof.

25. A composition comprising the live and attenuated virus of claim 14 or the cDNA clone thereof, for use in the prevention and/or the treatment and/or the palliation of a RNA virus infection or of a disease or disorder induced by a RNA virus in a mammalian host.

26. The live and attenuated virus or cDNA clone thereof of claim 14, which is a live and attenuated Coxsackie virus or a cDNA clone thereof, wherein the sequence coding for Coxsackie virus P1 protein comprises the RNA transcript of the cDNA sequence of SEQ ID NO: 14, or the cDNA sequence of SEQ ID NO: 14, respectively; or which is a live and attenuated Influenza virus or a cDNA clone thereof, wherein the sequence coding for the Influenza PA protein comprises the RNA transcript of the cDNA sequence of SEQ ID NO: 54 or 56, or the cDNA sequence of SEQ ID NO: 54 or 56, respectively; or which is a live and attenuated Influenza virus or a cDNA clone thereof, wherein the sequence coding for the Influenza HA protein comprises the RNA transcript of the cDNA sequence of SEQ ID NO: 87, or the cDNA sequence of SEQ ID NO: 87, respectively; or which is a live and attenuated Influenza virus or a cDNA clone thereof, wherein the sequence coding for the Influenza PA protein comprises the RNA transcript of the cDNA sequence of SEQ ID NO: 54 or 56, or the cDNA sequence of SEQ ID NO: 54 or 56, respectively, and wherein the sequence coding for the Influenza HA protein comprises the RNA transcript of the cDNA sequence of SEQ ID NO: 87, or the cDNA sequence of SEQ ID NO: 87, respectively; or which is a live and attenuated Chikungunya virus or cDNA clone thereof, and wherein the sequence coding for Chikungunya virus polyprotein C-E3-E2-6K-E1 comprises the RNA transcript of the cDNA sequence of SEQ ID NO: 101 or the cDNA sequence of SEQ ID NO: 101, respectively.

27. An immunogenic composition, which comprises the live and attenuated virus of claim 26 or the cDNA clone thereof.

28. A method to prevent and/or to treat and/or to palliate a RNA virus infection or a disease or disorder induced by a RNA virus comprising administering the immunogenic composition according to claim 27 to a subject in need thereof.

* * * * *

SEQUENCE LISTING

```
<160> NUMBER OF SEQ ID NOS: 105

<210> SEQ ID NO 1
<211> LENGTH: 7452
<212> TYPE: DNA
<213> ORGANISM: Coxsackievirus

<400> SEQUENCE: 1
```

```
gggagacccg aattctccaa gacatccccc ccccaaaaca gcctgtgggt tgatcccacc      60
cacaggccca ttgggcgcta gcactctggt atcacggtac ctttgtgcgc ctgttttata     120
cccccctccc caactgtaac ttagaagtaa cacacaccga tcaacagtca gcgtggcaca     180
ccagccacgt tttgatcaag cacttctgtt accccggact gagtatcaat agactgctca     240
cgcggttgaa ggagaaagcg ttcgttatcc ggccaactac ttcgaaaaac ctagtaacac     300
cgtggaagtt gcagagtgtt tcgctcagca ctacccagt gtagatcagg tcgatgagtc      360
accgcattcc ccacgggcga ccgtggcggt ggctgcgttg gcggcctgcc catggggaaa     420
cccatgggac gctctaatac agacatggtg cgaagagtct attgagctag ttggtagtcc     480
tccggcccct gaatgcggct aatcctaact gcggagcaca caccctcaag ccagagggca     540
gtgtgtcgta acgggcaact ctgcagcgga accgactact ttgggtgtcc gtgtttcatt     600
ttattcctat actggctgct tatggtgaca attgagagat cgttaccata tagctattgg     660
attggccatc cggtgactaa tagagctatt atatatccct ttgttgggtt tataccactt     720
agcttgaaag aggttaaaac attacaattc attgttaagt tgaatacagc aaaatgggag     780
ctcaagtatc aacgcaaaag actggggcac atgagaccag gctgaatgct agcggcaatt     840
ccatcattca ctacacaaat attaattatt acaaggatgc cgcatccaac tcagccaatc     900
ggcaggattt cactcaagac ccgggcaagt tcacagaacc agtgaaagat atcatgatta     960
aatcactacc agctctcaac tcccccacag tagaggagtg cggatacagt gacagggcga    1020
gatcaatcac attaggtaac tccaccataa cgactcagga atgcgccaac gtggtggtgg    1080
gctatggagt atggccagat tatctaaagg atagtgaggc aacagcagag gaccaaccga    1140
cccaaccaga cgttgccaca tgtaggttct atacccttga ctctgtgcaa tggcagaaaa    1200
cctcaccagg atggtggtgg aagctgcccg atgctttgtc gaacttagga ctgtttgggc    1260
agaacatgca gtaccactac ttaggccgaa ctgggtatac cgtacatgtg cagtgcaatg    1320
catctaagtt ccaccaagga tgcttgctag tagtgtgtgt accggaagct gagatgggtt    1380
gcgcaacgct agacaacacc ccatccagtg cagaattgct ggggggcgat agcgcaaagg    1440
agtttgcgga caaaccggtc gcatccgggt ccaacaagtt ggtacagagg gtggtgtata    1500
atgcaggcat gggggtgggt gttggaaacc tcaccatttt cccccaccaa tggatcaacc    1560
tacgcaccaa taatagtgct acaattgtga tgccatacac caacagtgta cctatggata    1620
acatgtttag gcataacaac gtcaccctaa tggttatccc atttgtaccg ctagattact    1680
gccctgggtc caccacgtac gtcccaatta cggtcacgat agcccccaatg tgtgccgagt    1740
acaatgggtt acgtttagca gggcaccagg gcttaccaac catgaatact ccggggagct    1800
gtcaatttct gacatcagac gacttccaat caccatccgc catgccgcaa tatgacgtca    1860
caccagagat gaggatacct ggtgaggtga aaaacttgat ggaaatagct gaggttgact    1920
cagttgtccc agtccaaaat gttggagaga aggtcaactc tatggaagca taccagatac    1980
ctgtgagatc caacgaagga tctggaacgc aagtattcgg ctttccactg caaccagggt    2040
actcgagtgt ttttagtcgg acgctcctag gagagatctt gaactattat acacattggt    2100
caggcagcat aaagcttacg tttatgttct gtggttcggc catggctact ggaaaattcc    2160
ttttggcata ctcaccacca ggtgctggag ctcctacaaa aaggggttgat gctatgcttg    2220
gtactcatgt aatttgggac gtggggctac aatcaagttg cgtgctgtgt atccctggaa    2280
taagccaaac acactaccgg tttgttgctt cagatgagta taccgcaggg ggttttatta    2340
```

-continued

```
cgtgctggta tcaaacaaac atagtggtcc cagcggatgc ccaaagctcc tgttacatca    2400
tgtgtttcgt gtcagcatgc aatgacttct ctgtcaggct attgaaggac actcctttca    2460
tttcgcagca aaacttttc cagggcccag tggaagacgc gataacagcc gctataggga    2520
gagttgcgga taccgtgggt acagggccaa ccaactcaga agctatacca gcactcactg    2580
ctgctgagac gggtcacacg tcacaagtag tgccgggtga cactatgcag acacgccacg    2640
ttaagaacta ccattcaagg tccgagtcaa ccatagagaa cttcctatgt aggtcagcat    2700
gcgtgtactt tacggagtat aaaaactcag gtgccaagcg gtatgctgaa tgggtattaa    2760
caccacgaca agcagcacaa cttaggagaa agctagaatt cttaccttac gtccggttcg    2820
acctggagct gacgtttgtc ataacaagta ctcaacagcc ctcaaccaca cagaaccaag    2880
atgcacagat cctaacacac caaattatgt atgtaccacc aggtggacct gtaccagata    2940
aagttgattc atacgtgtgg caaacatcta cgaatcccag tgtgttttgg accgagggaa    3000
acgccccgcc gcgcatgtcc ataccgtttt tgagcattgg caacgcctat tcaaatttct    3060
atgacggatg gtctgaattt tccaggaacg gagtttacgg catcaacacg ctaaacaaca    3120
tgggcacgct atatgcaaga catgtcaacg ctggaagcac gggtccaata aaaagcacca    3180
ttagaatcta cttcaaaccg aagcatgtca agcgtggat acctagacca cctagactct    3240
gccaatacga aaggcaaag aacgtgaact ccaacccag cggagttacc actactaggc    3300
aaagcatcac tacaatgaca aatacggcg catttggaca caatcaggg gcagtgtatg    3360 tggggaacta cagggtggta aatagacatc tagctaccag tgctgactgg caaaactgtg    3420
tgtgggaaag ttacaacaga gacctcttag tgagcacgac cacagcacat ggatgtgata    3480
ttatagccag atgtcagtgc acaacgggag tgtacttttg tgcgtccaaa aacaagcact    3540
acccaatttc gtttgaagga ccaggtctag tagaggtcca agagagtgaa tactacccca    3600
ggagatacca atcccatgtg ctttagcag ctggattttc cgaaccaggt gactgtggcg    3660
gtatcctaag gtgtgagcat ggtgtcattg gcattgtgac catgggggt gaaggcgtgg    3720 tcggctttgc agacatccgt gatctcctgt ggctggaaga tgatgcaatg gaacagggag    3780
tgaaggacta tgtggaacag cttggaaatg cattcggctc cggctttact aaccaaatat    3840
gtgagcaagt caacctcctg aaagaatcac tagtgggtca agactccatc ttagagaaat    3900
ctctaaaagc cttagttaag ataatatcag ccttagtaat tgtggtgagg aaccacgatg    3960
acctgatcac tgtgactgcc acactagccc ttatcggttg tacctcgtcc ccgtggcggt    4020
ggctcaaaca gaaggtgtca caatattacg gaatccctat ggctgaacgc caaaacaata    4080
gctggcttaa gaaatttact gaaatgacaa atgcttgcaa gggtatggaa tggatagctg    4140
tcaaaattca gaaattcatt gaatggctca agtaaaaat tttgccagag gtcagagaaa    4200
aacacgagtt cctgaacaga cttaaacaac tcccttatt agaaagtcag atcgccacaa    4260
tcgagcagag cgcgccatcc caaagtgacc aggaacaatt attttccaat gtccaatact    4320
ttgcccacta ttgcagaaag tacgctcccc tctacgcagc tgaagcaaag agggtgttct    4380
cccttgagaa gaagatgagc aattacatac agttcaagtc caaatgccgt attgaacctg    4440
tatgtttgct cctgcacggg agccctggtg ccggcaagtc ggtggcaaca aacttaattg    4500
gaaggtcgct tgctgagaaa ctcaacagct cagtgtactc actaccgcca gacccagatc    4560
acttcgacgg atacaaacag caggcgtgg tgattatgga cgatctatgc cagaatcctg    4620
atgggaaaga cgtctccttg ttctgccaaa tggtttccag tgtagatttt gtaccaccca    4680
tggctgccct agaagagaaa ggcattctgt tcacctcacc gtttgtcttg gcatcgacca    4740
```

```
atgcaggatc tattaatgct ccaaccgtgt cagatagcag agccttggca aggagatttc    4800
actttgacat gaacatcgag gttatttcca tgtacagtca gaatggcaag ataaacatgc    4860
ccatgtcagt caagacttgt gacgatgagt gttgcccggt caattttaaa aagtgctgcc    4920
ctcttgtgtg tgggaaggct atacaattca ttgatagaag aacacaggtc agatactctc    4980
tagacatgct agtcaccgag atgtttaggg agtacaatca tagacatagc gtggggacca    5040
cgcttgaggc actgttccag ggaccaccag tatacagaga gatcaaaatt agcgttgcac    5100
cagagacacc accaccgccc gccattgcgg acctgctcaa atcggtagac agtgaggctg    5160
tgagggagta ctgcaaagaa aaaggatggt tggttcctga gatcaactcc accctccaaa    5220
ttgagaaaca tgtcagtcgg gctttcattt gcttacaggc attgaccaca tttgtgtcag    5280
tggctggaat catatatata atatataagc tctttgcggg ttttcaaggt gcttatacag    5340
gagtgcccaa ccagaagccc agagtgccta ccctgaggca agcaaaagtg caaggccctg    5400
cctttgagtt cgccgtcgca atgatgaaaa ggaactcaag cacggtgaaa actgaatatg    5460
gcgagtttac catgctgggc atctatgaca ggtgggccgt tttgccacgc cacgccaaac    5520
ctgggccaac catcttgatg aatgatcaag aggttggtgt gctagatgcc aaggagctag    5580
tagacaagga cggcaccaac ttagaactga cactactcaa attgaaccgg aatgagaagt    5640
tcagagacat cagaggcttc ttagccaagg aggaagtgga ggttaatgag gcagtgctag    5700
caattaacac cagcaagttt cccaacatgt acattccagt aggacaggtc acagaatacg    5760
gcttcctaaa cctaggtggc acacccacca agagaatgct tatgtacaac ttccccacaa    5820
gagcaggcca gtgtggtgga gtgctcatgt ccaccggcaa ggtactgggt atccatgttg    5880
gtggaaatgg ccatcagggc ttctcagcag cactcctcaa acactacttc aatgatgagc    5940
aaggtgaaat agaatttatt gagagctcaa aggacgccgg gtttccagtc atcaacacac    6000
caagtaaaac aaagttggag cctagtgttt tccaccaggt ctttgagggg aacaaagaac    6060
cagcagtact caggagtggg gatccacgtc tcaaggccaa ttttgaagag gctatatttt    6120
ccaagtatat aggaaatgtc aacacacacg tggatgagta catgctggaa gcagtggacc    6180
actacgcagg ccaactagcc accctagata tcagcactga ccaatgaaaa ctggaggacg    6240
cagtgtacgg taccgagggt cttgaggcgc ttgatctaac aacgagtgcc ggttacccat    6300
atgttgcact gggtatcaag aagagggaca tcctctctaa gaagactaag gacctaacaa    6360
agttaaagga atgtatggac aagtatggcc tgaacctacc aatggtgact tatgtaaaag    6420
atgagctcag gtccatagag aaggtagcga aggaaagtc taggctgatt gaggcgtcca    6480
gtttgaatga ttcagtggcg atgagacaga catttggtaa tctgtacaaa actttccacc    6540
taaacccagg ggttgtgact ggtagtgctg ttgggtgtga cccagacctc ttttggagca    6600
agataccagt gatgttagat ggacatctcc tagcatttga ttactctggg tacgatgcta    6660
gcttaagccc tgtctggttt gcttgcctaa aaatgttact tgagaagctt ggatacacgc    6720
acaaagagac aaactacatt gactacttgt gcaactccca tcacctgtac agggataaac    6780
attactttgt gaggggtggc atgccctcgg gatgttctgg taccagtatt ttcaactcaa    6840
tgattaacaa tatcataatt aggacactaa tgctaaaagt gtacaagggg attgacttgg    6900
accaattcag gatgatcgca tatggtgatg atgtgatcgc atcgtaccca tggcctatag    6960
atgcatcttt actcgctgaa gctggtaagg gttacgggct gatcatgaca ccagcagata    7020
agggagagtg ctttaacgaa gttacctgga ccaacgccac tttcctaaag aggtatttta    7080
```

| | |
|---|---:|
| gagcagatga acagtacccc ttcctggtgc atcctgttat gcccatgaaa gacatacacg | 7140 |
| aatcaattag atggaccaag gatccaaaga acacccaaga tcacgtgcgc tcactgtgtc | 7200 |
| tattagcttg gcataacggg gagcacgaat atgaggagtt catccgtaaa attagaagcg | 7260 |
| tcccagtcgg acgttgtttg accctccccg cgttttcaac tctacgcagg aagtggttgg | 7320 |
| actccttttta gattagagac aatttgaaat aatttagatt ggcttaaccc tactgtgcta | 7380 |
| accgaaccag ataacggtac agtaggggta aattctccgc attcggtgcg gaaaaaaaaa | 7440 |
| aaaaaaaag aa | 7452 |

<210> SEQ ID NO 2
<211> LENGTH: 6558
<212> TYPE: DNA
<213> ORGANISM: Coxsackievirus

<400> SEQUENCE: 2

| | |
|---|---:|
| atgggagctc aagtatcaac gcaaaagact ggggcacatg agaccaggct gaatgctagc | 60 |
| ggcaattcca tcattcacta cacaaatatt aattattaca aggatgccgc atccaactca | 120 |
| gccaatcggc aggatttcac tcaagacccg gcaagttca cagaaccagt gaaagatatc | 180 |
| atgattaaat cactaccagc tctcaactcc cccacagtag aggagtgcgg atacagtgac | 240 |
| agggcgagat caatcacatt aggtaactcc accataacga ctcaggaatg cgccaacgtg | 300 |
| gtggtgggct atgagtatg gccagattat ctaaaggata gtgaggcaac agcagaggac | 360 |
| caaccgaccc aaccagacgt tgccacatgt aggttctata cccttgactc tgtgcaatgg | 420 |
| cagaaaacct caccaggatg gtggtggaag ctgcccgatg ctttgtcgaa cttaggactg | 480 |
| tttgggcaga acatgcagta ccactactta ggccgaactg ggtataccgt acatgtgcag | 540 |
| tgcaatgcat ctaagttcca ccaaggatgc ttgctagtag tgtgtgtacc ggaagctgag | 600 |
| atgggttgcg caacgctaga caacacccca tccagtgcag aattgctggg gggcgatagc | 660 |
| gcaaaggagt ttgcggacaa accggtcgca tcgggtcca acaagttggt acagagggtg | 720 |
| gtgtataatg caggcatggg ggtgggtgtt ggaaacctca ccattttccc ccaccaatgg | 780 |
| atcaacctac gcaccaataa tagtgctaca attgtgatgc catacaccaa cagtgtacct | 840 |
| atggataaca tgtttaggca taacaacgtc accctaatgg ttatcccatt tgtaccgcta | 900 |
| gattactgcc ctgggtccac cacgtacgtc ccaattacgg tcacgatagc cccaatgtgt | 960 |
| gccgagtaca atgggttacg tttagcaggg caccagggct taccaaccat gaatactccg | 1020 |
| gggagctgtc aatttctgac atcagacgac ttccaatcac catccgccat gccgcaatat | 1080 |
| gacgtcacac cagagatgag gatacctggt gaggtgaaaa acttgatgga aatagctgag | 1140 |
| gttgactcag ttgtcccagt ccaaaatgtt ggagagaagg tcaactctat ggaagcatac | 1200 |
| cagatacctg tgagatccaa cgaaggatct ggaacgcaag tattcggctt tccactgcaa | 1260 |
| ccagggtact cgagtgtttt tagtcggacg ctcctaggag agatcttgaa ctattataca | 1320 |
| cattggtcag gcagcataaa gcttacgttt atgttctgtg gttcggccat ggctactgga | 1380 |
| aaattccttt tggcatactc accaccaggt gctggagctc tacaaaaag ggttgatgct | 1440 |
| atgcttggta tcatgtaat ttgggacgtg gggctacaat caagttgcgt gctgtgtata | 1500 |
| ccctggataa gccaaacaca ctaccggttt gttgcttcag atgagtatac cgcaggggt | 1560 |
| tttattacgt gctggtatca aacaaacata gtggtcccag cggatgccca aagctcctgt | 1620 |
| tacatcatgt gtttcgtgtc agcatgcaat gacttctctg tcaggctatt gaaggacact | 1680 |
| ccttttcattt cgcagcaaaa cttttttccag ggcccagtgg aagacgcgat aacagccgct | 1740 |

```
ataggagag ttgcggatac cgtgggtaca gggccaacca actcagaagc tataccagca   1800
ctcactgctg ctgagacggg tcacacgtca caagtagtgc cgggtgacac tatgcagaca   1860
cgccacgtta agaactacca ttcaaggtcc gagtcaacca tagagaactt cctatgtagg   1920
tcagcatgcg tgtactttac ggagtataaa aactcaggtg ccaagcggta tgctgaatgg   1980
gtattaacac cacgacaagc agcacaactt aggagaaagc tagaattctt tacctacgtc   2040
cggttcgacc tggagctgac gtttgtcata acaagtactc aacagccctc aaccacacag   2100
aaccaagatg cacagatcct aacacaccaa attatgtatg taccaccagg tggacctgta   2160
ccagataaag ttgattcata cgtgtggcaa acatctacga atcccagtgt gttttggacc   2220
gagggaaacg ccccgccgcg catgtccata ccgttttga gcattggcaa cgcctattca    2280
aatttctatg acggatggtc tgaatttcc aggaacggag tttacggcat caacacgcta    2340
aacaacatgg gcacgctata tgcaagacat gtcaacgctg gaagcacggg tccaataaaa   2400
agcaccatta gaatctactt caaaccgaag catgtcaaag cgtggatacc tagaccacct   2460
agactctgcc aatacgagaa ggcaaagaac gtgaacttcc aacccagcgg agttaccact   2520
actaggcaaa gcatcactac aatgacaaat acgggcgcat ttggacaaca atcaggggca   2580
gtgtatgtgg ggaactacag ggtggtaaat agacatctag ctaccagtgc tgactggcaa   2640
aactgtgtgt gggaaagtta caacagagac ctcttagtga gcacgaccac agcacatgga   2700
tgtgatatta tagccagatg tcagtgcaca acgggagtgt acttttgtgc gtccaaaaac   2760
aagcactacc caattcgtt tgaaggacca ggtctagtag aggtccaaga gagtgaatac   2820
taccccagga gataccaatc ccatgtgctt ttagcagctg gattttccga accaggtgac   2880
tgtggcggta tcctaaggtg tgagcatggt gtcattggca ttgtgaccat gggggtgaa    2940
ggcgtggtcg gctttgcaga catccgtgat ctcctgtggc tggaagatga tgcaatggaa   3000
cagggagtga aggactatgt ggaacagctt ggaaatgcat tcggctccgg ctttactaac   3060
caaatatgtg agcaagtcaa cctcctgaaa gaatcactag tgggtcaaga ctccatctta   3120
gagaaatctc taaaagcctt agttaagata atatcagcct tagtaattgt ggtgaggaac   3180
cacgatgacc tgatcactgt gactgccaca ctagccctta tcggttgtac ctcgtccccg   3240
tggcggtggc tcaaacagaa ggtgtcacaa tattacggaa tccctatggc tgaacgccaa   3300
aacaatagct ggcttaagaa atttactgaa atgacaaatg cttgcaaggg tatggaatgg   3360
atagctgtca aaattcagaa attcattgaa tggctcaaag taaaaatttt gccagaggtc   3420
agagaaaaac acgagttcct gaacagactt aaacaactcc ccttattaga aagtcagatc   3480
gccacaatcg agcagagcgc gccatcccaa agtgaccagg aacaattatt ttccaatgtc   3540
caatactttg cccactattg cagaaagtac gctcccctct acgcagctga agcaaagagg   3600
gtgttctccc ttgagaagaa gatgagcaat acatacagt tcaagtccaa atgccgtatt   3660
gaacctgtat gtttgctcct gcacgggagc cctggtgccg gcaagtcggt ggcaacaaac   3720
ttaattggaa ggtcgcttgc tgagaaactc aacagctcag tgtactcact accgccagac   3780
ccagatcact tcgacggata caaacagcag gccgtggtga ttatggacga tctatgccag   3840
aatcctgatg gaaagacgt ctccttgttc tgccaaatgg tttccagtgt agattttgta    3900
ccacccatgg ctgccctaga agagaaaggc attctgttca cctcaccgtt tgtcttggca   3960
tcgaccaatg caggatctat taatgctcca accgtgtcag atagcagagc cttggcaagg   4020
agatttcact ttgacatgaa catcgaggtt atttccatgt acagtcagaa tggcaagata   4080
```

```
aacatgccca tgtcagtcaa gacttgtgac gatgagtgtt gcccggtcaa tttttaaaaag    4140 tgctgccctc ttgtgtgtgg gaaggctata caattcattg atagaagaac acaggtcaga    4200
tactctctag acatgctagt caccgagatg tttagggagt acaatcatag acatagcgtg    4260
gggaccacgc ttgaggcact gttccaggga ccaccagtat acagagagat caaaattagc    4320
gttgcaccag agacaccacc accgcccgcc attgcggacc tgctcaaatc ggtagacagt    4380
gaggctgtga gggagtactg caaagaaaaa ggatggttgg ttcctgagat caactccacc    4440
ctccaaattg agaaacatgt cagtcgggct ttcatttgct tacaggcatt gaccacattt    4500
gtgtcagtgg ctggaatcat atatataata taagctct  ttgcgggttt tcaaggtgct    4560
tatacaggag tgcccaacca gaagcccaga gtgcctaccc tgaggcaagc aaaagtgcaa    4620
ggccctgcct ttgagttcgc cgtcgcaatg atgaaaagga actcaagcac ggtgaaaact    4680
gaatatggcg agtttaccat gctgggcatc tatgacaggt gggccgtttt gccacgccac    4740
gccaaacctg gccaaccat cttgatgaat gatcaagagg ttggtgtgct agatgccaag    4800
gagctagtag acaaggacgg caccaactta gaactgacac tactcaaatt gaaccggaat    4860
gagaagttca gagacatcag aggcttctta gccaaggagg aagtggaggt taatgaggca    4920
gtgctagcaa ttaacaccag caagtttccc aacatgtaca ttccagtagg acaggtcaca    4980
gaatacggct tcctaaacct aggtggcaca cccaccaaga gaatgcttat gtacaacttc    5040
cccacaagag caggccagtg tggtggagtg ctcatgtcca ccggcaaggt actgggtatc    5100
catgttggtg gaaatggcca tcagggcttc tcagcagcac tcctcaaaca ctacttcaat    5160
gatgagcaag gtgaaataga atttattgag agctcaaagg acgccgggtt tccagtcatc    5220
aacacaccaa gtaaaacaaa gttggagcct agtgtttttcc accaggtctt tgaggggaac    5280
aaagaaccag cagtactcag gagtgggat ccacgtctca aggccaattt tgaagaggct    5340
atattttcca gtatataggg aaatgtcaac acacacgtgg atgagtacat gctggaagca    5400
gtggaccact acgcaggcca actagccacc ctagatatca gcactgaacc aatgaaactg    5460
gaggacgcag tgtacggtac cgagggtctt gaggcgcttg atctaacaac gagtgccggt    5520
tacccatatg ttgcactggg tatcaagaag agggacatcc tctctaagaa gactaaggac    5580
ctaacaaagt taaaggaatg tatggacaag tatggcctga acctaccaat ggtgacttat    5640
gtaaaagatg agctcaggtc catagagaag gtagcgaaag gaaagtctag gctgattgag    5700
gcgtccagtt tgaatgattc agtggcgatg agacagacat ttggtaatct gtacaaaact    5760
ttccacctaa acccagggt tgtgactggt agtgctgttg ggtgtgaccc agacctcttt    5820
tggagcaaga taccagtgat gttagatgga catctcatag catttgatta ctctgggtac    5880
gatgctagct taagccctgt ctggtttgct tgcctaaaaa tgttacttga gaagcttgga    5940
tacacgcaca aagagacaaa ctacattgac tacttgtgca actcccatca cctgtacagg    6000
gataaacatt actttgtgag gggtggcatg ccctcgggat gttctggtac cagtattttc    6060
aactcaatga ttaacaatat cataattagg acactaatgc taaaagtgta caagggatt    6120 gacttggacc aattcaggat gatcgcatat ggtgatgatg tgatcgcatc gtacccatgg    6180
cctatagatg catctttact cgctgaagct ggtaagggtt acgggctgat catgacacca    6240
gcagataagg gagagtgctt taacgaagtt acctggacca acgccacttt cctaaagagg    6300
tattttagag cagatgaaca gtaccccttc ctggtgcatc ctgttatgcc catgaaagac    6360
atacacgaat caattagatg gaccaaggat ccaagaacaa cccaagatca cgtgcgctca    6420
ctgtgtctat tagcttggca taacggggag cacgaatatg aggagttcat ccgtaaaatt    6480
```
agaagcgtcc cagtcggacg ttgtttgacc ctccccgcgt tttcaactct acgcaggaag    6540
tggttggact ccttttag                                                  6558

<210> SEQ ID NO 3
<211> LENGTH: 2185
<212> TYPE: PRT
<213> ORGANISM: Coxsackievirus

<400> SEQUENCE: 3

Met Gly Ala Gln Val Ser Thr Gln Lys Thr Gly Ala His Glu Thr Arg
1 5 10 15

Leu Asn Ala Ser Gly Asn Ser Ile Ile His Tyr Thr Asn Ile Asn Tyr
20 25 30

Tyr Lys Asp Ala Ala Ser Asn Ser Ala Asn Arg Gln Asp Phe Thr Gln
35 40 45

Asp Pro Gly Lys Phe Thr Glu Pro Val Lys Asp Ile Met Ile Lys Ser
50 55 60

Leu Pro Ala Leu Asn Ser Pro Thr Val Glu Glu Cys Gly Tyr Ser Asp
65 70 75 80

Arg Ala Arg Ser Ile Thr Leu Gly Asn Ser Thr Ile Thr Thr Gln Glu
85 90 95

Cys Ala Asn Val Val Val Gly Tyr Gly Val Trp Pro Asp Tyr Leu Lys
100 105 110

Asp Ser Glu Ala Thr Ala Glu Asp Gln Pro Thr Gln Pro Asp Val Ala
115 120 125

Thr Cys Arg Phe Tyr Thr Leu Asp Ser Val Gln Trp Gln Lys Thr Ser
130 135 140

Pro Gly Trp Trp Trp Lys Leu Pro Asp Ala Leu Ser Asn Leu Gly Leu
145 150 155 160

Phe Gly Gln Asn Met Gln Tyr His Tyr Leu Gly Arg Thr Gly Tyr Thr
165 170 175

Val His Val Gln Cys Asn Ala Ser Lys Phe His Gln Gly Cys Leu Leu
180 185 190

Val Val Cys Val Pro Glu Ala Glu Met Gly Cys Ala Thr Leu Asp Asn
195 200 205

Thr Pro Ser Ser Ala Glu Leu Leu Gly Gly Asp Ser Ala Lys Glu Phe
210 215 220

Ala Asp Lys Pro Val Ala Ser Gly Ser Asn Lys Leu Val Gln Arg Val
225 230 235 240

Val Tyr Asn Ala Gly Met Gly Val Gly Val Gly Asn Leu Thr Ile Phe
245 250 255

Pro His Gln Trp Ile Asn Leu Arg Thr Asn Asn Ser Ala Thr Ile Val
260 265 270

Met Pro Tyr Thr Asn Ser Val Pro Met Asp Asn Met Phe Arg His Asn
275 280 285

Asn Val Thr Leu Met Val Ile Pro Phe Val Pro Leu Asp Tyr Cys Pro
290 295 300

Gly Ser Thr Thr Tyr Val Pro Ile Thr Val Thr Ile Ala Pro Met Cys
305 310 315 320

Ala Glu Tyr Asn Gly Leu Arg Leu Ala Gly His Gln Gly Leu Pro Thr
325 330 335

Met Asn Thr Pro Gly Ser Cys Gln Phe Leu Thr Ser Asp Asp Phe Gln
340 345 350

```
Ser Pro Ser Ala Met Pro Gln Tyr Asp Val Thr Pro Glu Met Arg Ile
            355                 360                 365

Pro Gly Glu Val Lys Asn Leu Met Glu Ile Ala Glu Val Asp Ser Val
370                 375                 380

Val Pro Val Gln Asn Val Gly Glu Lys Val Asn Ser Met Glu Ala Tyr
385                 390                 395                 400

Gln Ile Pro Val Arg Ser Asn Glu Gly Ser Gly Thr Gln Val Phe Gly
                405                 410                 415

Phe Pro Leu Gln Pro Gly Tyr Ser Ser Val Phe Ser Arg Thr Leu Leu
            420                 425                 430

Gly Glu Ile Leu Asn Tyr Tyr Thr His Trp Ser Gly Ser Ile Lys Leu
            435                 440                 445

Thr Phe Met Phe Cys Gly Ser Ala Met Ala Thr Gly Lys Phe Leu Leu
450                 455                 460

Ala Tyr Ser Pro Pro Gly Ala Gly Ala Pro Thr Lys Arg Val Asp Ala
465                 470                 475                 480

Met Leu Gly Thr His Val Ile Trp Asp Val Gly Leu Gln Ser Ser Cys
            485                 490                 495

Val Leu Cys Ile Pro Trp Ile Ser Gln Thr His Tyr Arg Phe Val Ala
            500                 505                 510

Ser Asp Glu Tyr Thr Ala Gly Gly Phe Ile Thr Cys Trp Tyr Gln Thr
        515                 520                 525

Asn Ile Val Val Pro Ala Asp Ala Gln Ser Ser Cys Tyr Ile Met Cys
530                 535                 540

Phe Val Ser Ala Cys Asn Asp Phe Ser Val Arg Leu Leu Lys Asp Thr
545                 550                 555                 560

Pro Phe Ile Ser Gln Gln Asn Phe Phe Gln Gly Pro Val Glu Asp Ala
                565                 570                 575

Ile Thr Ala Ala Ile Gly Arg Val Ala Asp Thr Val Gly Thr Gly Pro
            580                 585                 590

Thr Asn Ser Glu Ala Ile Pro Ala Leu Thr Ala Ala Glu Thr Gly His
            595                 600                 605

Thr Ser Gln Val Val Pro Gly Asp Thr Met Gln Thr Arg His Val Lys
610                 615                 620

Asn Tyr His Ser Arg Ser Glu Ser Thr Ile Glu Asn Phe Leu Cys Arg
625                 630                 635                 640

Ser Ala Cys Val Tyr Phe Thr Glu Tyr Lys Asn Ser Gly Ala Lys Arg
                645                 650                 655

Tyr Ala Glu Trp Val Leu Thr Pro Arg Gln Ala Ala Gln Leu Arg Arg
            660                 665                 670

Lys Leu Glu Phe Phe Thr Tyr Val Arg Phe Asp Leu Glu Leu Thr Phe
            675                 680                 685

Val Ile Thr Ser Thr Gln Gln Pro Ser Thr Thr Gln Asn Gln Asp Ala
690                 695                 700

Gln Ile Leu Thr His Gln Ile Met Tyr Val Pro Pro Gly Gly Pro Val
705                 710                 715                 720

Pro Asp Lys Val Asp Ser Tyr Val Trp Gln Thr Ser Thr Asn Pro Ser
                725                 730                 735

Val Phe Trp Thr Glu Gly Asn Ala Pro Pro Arg Met Ser Ile Pro Phe
            740                 745                 750

Leu Ser Ile Gly Asn Ala Tyr Ser Asn Phe Tyr Asp Gly Trp Ser Glu
            755                 760                 765

Phe Ser Arg Asn Gly Val Tyr Gly Ile Asn Thr Leu Asn Asn Met Gly
```

```
            770             775             780
Thr Leu Tyr Ala Arg His Val Asn Ala Gly Ser Thr Gly Pro Ile Lys
785                 790                 795                 800

Ser Thr Ile Arg Ile Tyr Phe Lys Pro Lys His Val Lys Ala Trp Ile
                805                 810                 815

Pro Arg Pro Arg Leu Cys Gln Tyr Glu Lys Ala Lys Asn Val Asn
                820                 825                 830

Phe Gln Pro Ser Gly Val Thr Thr Arg Gln Ser Ile Thr Thr Met
                835                 840                 845

Thr Asn Thr Gly Ala Phe Gly Gln Gln Ser Gly Ala Val Tyr Val Gly
850                 855                 860

Asn Tyr Arg Val Val Asn Arg His Leu Ala Thr Ser Ala Asp Trp Gln
865                 870                 875                 880

Asn Cys Val Trp Glu Ser Tyr Asn Arg Asp Leu Leu Val Ser Thr Thr
                885                 890                 895

Thr Ala His Gly Cys Asp Ile Ile Ala Arg Cys Gln Cys Thr Thr Gly
                900                 905                 910

Val Tyr Phe Cys Ala Ser Lys Asn Lys His Tyr Pro Ile Ser Phe Glu
                915                 920                 925

Gly Pro Gly Leu Val Glu Val Gln Glu Ser Glu Tyr Tyr Pro Arg Arg
                930                 935                 940

Tyr Gln Ser His Val Leu Leu Ala Ala Gly Phe Ser Glu Pro Gly Asp
945                 950                 955                 960

Cys Gly Gly Ile Leu Arg Cys Glu His Gly Val Ile Gly Ile Val Thr
                965                 970                 975

Met Gly Gly Glu Gly Val Val Gly Phe Ala Asp Ile Arg Asp Leu Leu
                980                 985                 990

Trp Leu Glu Asp Asp Ala Met Glu  Gln Gly Val Lys Asp  Tyr Val Glu
                995                  1000                1005

Gln Leu  Gly Asn Ala Phe Gly  Ser Gly Phe Thr Asn  Gln Ile Cys
    1010                 1015                1020

Glu Gln  Val Asn Leu Leu Lys  Glu Ser Leu Val Gly  Gln Asp Ser
    1025                 1030                1035

Ile Leu  Glu Lys Ser Leu Lys  Ala Leu Val Lys Ile  Ile Ser Ala
    1040                 1045                1050

Leu Val  Ile Val Val Arg Asn  His Asp Asp Leu Ile  Thr Val Thr
    1055                 1060                1065

Ala Thr  Leu Ala Leu Ile Gly  Cys Thr Ser Ser Pro  Trp Arg Trp
    1070                 1075                1080

Leu Lys  Gln Lys Val Ser Gln  Tyr Tyr Gly Ile Pro  Met Ala Glu
    1085                 1090                1095

Arg Gln  Asn Asn Ser Trp Leu  Lys Lys Phe Thr Glu  Met Thr Asn
    1100                 1105                1110

Ala Cys  Lys Gly Met Glu Trp  Ile Ala Val Lys Ile  Gln Lys Phe
    1115                 1120                1125

Ile Glu  Trp Leu Lys Val Lys  Ile Leu Pro Glu Val  Arg Glu Lys
    1130                 1135                1140

His Glu  Phe Leu Asn Arg Leu  Lys Gln Leu Pro Leu  Leu Glu Ser
    1145                 1150                1155

Gln Ile  Ala Thr Ile Glu Gln  Ser Ala Pro Ser Gln  Ser Asp Gln
    1160                 1165                1170

Glu Gln  Leu Phe Ser Asn Val  Gln Tyr Phe Ala His  Tyr Cys Arg
    1175                 1180                1185
```

```
Lys Tyr Ala Pro Leu Tyr Ala Ala Glu Ala Lys Arg Val Phe Ser
    1190             1195             1200

Leu Glu Lys Lys Met Ser Asn Tyr Ile Gln Phe Lys Ser Lys Cys
    1205             1210             1215

Arg Ile Glu Pro Val Cys Leu Leu His Gly Ser Pro Gly Ala
    1220             1225             1230

Gly Lys Ser Val Ala Thr Asn Leu Ile Gly Arg Ser Leu Ala Glu
    1235             1240             1245

Lys Leu Asn Ser Ser Val Tyr Ser Leu Pro Pro Asp Pro Asp His
    1250             1255             1260

Phe Asp Gly Tyr Lys Gln Ala Val Val Ile Met Asp Asp Leu
    1265             1270             1275

Cys Gln Asn Pro Asp Gly Lys Asp Val Ser Leu Phe Cys Gln Met
    1280             1285             1290

Val Ser Ser Val Asp Phe Val Pro Pro Met Ala Ala Leu Glu Glu
    1295             1300             1305

Lys Gly Ile Leu Phe Thr Ser Pro Phe Val Leu Ala Ser Thr Asn
    1310             1315             1320

Ala Gly Ser Ile Asn Ala Pro Thr Val Ser Asp Ser Arg Ala Leu
    1325             1330             1335

Ala Arg Arg Phe His Phe Asp Met Asn Ile Glu Val Ile Ser Met
    1340             1345             1350

Tyr Ser Gln Asn Gly Lys Ile Asn Met Pro Met Ser Val Lys Thr
    1355             1360             1365

Cys Asp Asp Glu Cys Cys Pro Val Asn Phe Lys Lys Cys Cys Pro
    1370             1375             1380

Leu Val Cys Gly Lys Ala Ile Gln Phe Ile Asp Arg Arg Thr Gln
    1385             1390             1395

Val Arg Tyr Ser Leu Asp Met Leu Val Thr Glu Met Phe Arg Glu
    1400             1405             1410

Tyr Asn His Arg His Ser Val Gly Thr Thr Leu Glu Ala Leu Phe
    1415             1420             1425

Gln Gly Pro Pro Val Tyr Arg Glu Ile Lys Ile Ser Val Ala Pro
    1430             1435             1440

Glu Thr Pro Pro Pro Pro Ala Ile Ala Asp Leu Leu Lys Ser Val
    1445             1450             1455

Asp Ser Glu Ala Val Arg Glu Tyr Cys Lys Glu Lys Gly Trp Leu
    1460             1465             1470

Val Pro Glu Ile Asn Ser Thr Leu Gln Ile Glu Lys His Val Ser
    1475             1480             1485

Arg Ala Phe Ile Cys Leu Gln Ala Leu Thr Thr Phe Val Ser Val
    1490             1495             1500

Ala Gly Ile Ile Tyr Ile Ile Tyr Lys Leu Phe Ala Gly Phe Gln
    1505             1510             1515

Gly Ala Tyr Thr Gly Val Pro Asn Gln Lys Pro Arg Val Pro Thr
    1520             1525             1530

Leu Arg Gln Ala Lys Val Gln Gly Pro Ala Phe Glu Phe Ala Val
    1535             1540             1545

Ala Met Met Lys Arg Asn Ser Ser Thr Val Lys Thr Glu Tyr Gly
    1550             1555             1560

Glu Phe Thr Met Leu Gly Ile Tyr Asp Arg Trp Ala Val Leu Pro
    1565             1570             1575
```

Arg His Ala Lys Pro Gly Pro Thr Ile Leu Met Asn Asp Gln Glu
1580             1585             1590

Val Gly Val Leu Asp Ala Lys Glu Leu Val Asp Lys Asp Gly Thr
1595             1600             1605

Asn Leu Glu Leu Thr Leu Leu Lys Leu Asn Arg Asn Glu Lys Phe
1610             1615             1620

Arg Asp Ile Arg Gly Phe Leu Ala Lys Glu Glu Val Glu Val Asn
1625             1630             1635

Glu Ala Val Leu Ala Ile Asn Thr Ser Lys Phe Pro Asn Met Tyr
1640             1645             1650

Ile Pro Val Gly Gln Val Thr Glu Tyr Gly Phe Leu Asn Leu Gly
1655             1660             1665

Gly Thr Pro Thr Lys Arg Met Leu Met Tyr Asn Phe Pro Thr Arg
1670             1675             1680

Ala Gly Gln Cys Gly Gly Val Leu Met Ser Thr Gly Lys Val Leu
1685             1690             1695

Gly Ile His Val Gly Gly Asn Gly His Gln Gly Phe Ser Ala Ala
1700             1705             1710

Leu Leu Lys His Tyr Phe Asn Asp Glu Gln Gly Glu Ile Glu Phe
1715             1720             1725

Ile Glu Ser Ser Lys Asp Ala Gly Phe Pro Val Ile Asn Thr Pro
1730             1735             1740

Ser Lys Thr Lys Leu Glu Pro Ser Val Phe His Gln Val Phe Glu
1745             1750             1755

Gly Asn Lys Glu Pro Ala Val Leu Arg Ser Gly Asp Pro Arg Leu
1760             1765             1770

Lys Ala Asn Phe Glu Glu Ala Ile Phe Ser Lys Tyr Ile Gly Asn
1775             1780             1785

Val Asn Thr His Val Asp Glu Tyr Met Leu Glu Ala Val Asp His
1790             1795             1800

Tyr Ala Gly Gln Leu Ala Thr Leu Asp Ile Ser Thr Glu Pro Met
1805             1810             1815

Lys Leu Glu Asp Ala Val Tyr Gly Thr Glu Gly Leu Glu Ala Leu
1820             1825             1830

Asp Leu Thr Thr Ser Ala Gly Tyr Pro Tyr Val Ala Leu Gly Ile
1835             1840             1845

Lys Lys Arg Asp Ile Leu Ser Lys Lys Thr Lys Asp Leu Thr Lys
1850             1855             1860

Leu Lys Glu Cys Met Asp Lys Tyr Gly Leu Asn Leu Pro Met Val
1865             1870             1875

Thr Tyr Val Lys Asp Glu Leu Arg Ser Ile Glu Lys Val Ala Lys
1880             1885             1890

Gly Lys Ser Arg Leu Ile Glu Ala Ser Ser Leu Asn Asp Ser Val
1895             1900             1905

Ala Met Arg Gln Thr Phe Gly Asn Leu Tyr Lys Thr Phe His Leu
1910             1915             1920

Asn Pro Gly Val Val Thr Gly Ser Ala Val Gly Cys Asp Pro Asp
1925             1930             1935

Leu Phe Trp Ser Lys Ile Pro Val Met Leu Asp Gly His Leu Ile
1940             1945             1950

Ala Phe Asp Tyr Ser Gly Tyr Asp Ala Ser Leu Ser Pro Val Trp
1955             1960             1965

Phe Ala Cys Leu Lys Met Leu Leu Glu Lys Leu Gly Tyr Thr His

```
                    1970                1975                1980
Lys Glu Thr Asn Tyr Ile Asp Tyr Leu Cys Asn Ser His His Leu
    1985                1990                1995

Tyr Arg Asp Lys His Tyr Phe Val Arg Gly Gly Met Pro Ser Gly
    2000                2005                2010

Cys Ser Gly Thr Ser Ile Phe Asn Ser Met Ile Asn Asn Ile Ile
    2015                2020                2025

Ile Arg Thr Leu Met Leu Lys Val Tyr Lys Gly Ile Asp Leu Asp
    2030                2035                2040

Gln Phe Arg Met Ile Ala Tyr Gly Asp Asp Val Ile Ala Ser Tyr
    2045                2050                2055

Pro Trp Pro Ile Asp Ala Ser Leu Leu Ala Glu Ala Gly Lys Gly
    2060                2065                2070

Tyr Gly Leu Ile Met Thr Pro Ala Asp Lys Gly Glu Cys Phe Asn
    2075                2080                2085

Glu Val Thr Trp Thr Asn Ala Thr Phe Leu Lys Arg Tyr Phe Arg
    2090                2095                2100

Ala Asp Glu Gln Tyr Pro Phe Leu Val His Pro Val Met Pro Met
    2105                2110                2115

Lys Asp Ile His Glu Ser Ile Arg Trp Thr Lys Asp Pro Lys Asn
    2120                2125                2130

Thr Gln Asp His Val Arg Ser Leu Cys Leu Leu Ala Trp His Asn
    2135                2140                2145

Gly Glu His Glu Tyr Glu Glu Phe Ile Arg Lys Ile Arg Ser Val
    2150                2155                2160

Pro Val Gly Arg Cys Leu Thr Leu Pro Ala Phe Ser Thr Leu Arg
    2165                2170                2175

Arg Lys Trp Leu Asp Ser Phe
    2180                2185

<210> SEQ ID NO 4
<211> LENGTH: 2562
<212> TYPE: DNA
<213> ORGANISM: Coxsackievirus

<400> SEQUENCE: 4
atgggagctc aagtatcaac gcaaaagact ggggcacatg agaccaggct gaatgctagc      60
ggcaattcca tcattcacta cacaaatatt aattattaca aggatgccgc atccaactca     120
gccaatcggc aggatttcac tcaagacccg ggcaagttca cagaaccagt gaaagatatc     180
atgattaaat cactaccagc tctcaactcc cccacagtag aggagtgcgg atacagtgac     240
agggcgagat caatcacatt aggtaactcc accataacga ctcaggaatg cgccaacgtg     300
gtggtgggct atggagtatg gccagattat ctaaggata gtgaggcaac agcagaggac     360
caaccgaccc aaccagacgt tgccacatgt aggttctata cccttgactc tgtgcaatgg     420
cagaaaacct caccaggatg gtggtggaag ctgcccgatg ctttgtcgaa cttaggactg     480
tttgggcaga acatgcagta ccactactta ggccgaactg ggtataccgt acatgtgcag     540
tgcaatgcat ctaagttcca ccaaggatgc ttgctagtag tgtgtgtacc ggaagctgag     600
atgggttgcg caacgctaga caacacccca tccagtgcag aattgctggg gggcgatagc     660
gcaaaggagt ttgcggacaa accggtcgca tccgggtcca acaagttggt acagagggtg     720
gtgtataatg caggcatggg ggtgggtgtt ggaaacctca ccattttccc ccaccaatgg     780
atcaacctac gcaccaataa tagtgctaca attgtgatgc catacaccaa cagtgtacct     840
```

-continued

```
atggataaca tgtttaggca taacaacgtc accctaatgg ttatcccatt tgtaccgcta      900
gattactgcc ctgggtccac cacgtacgtc ccaattacgg tcacgatagc cccaatgtgt      960
gccgagtaca atgggttacg tttagcaggg caccagggct taccaaccat gaatactccg     1020
gggagctgtc aatttctgac atcagacgac ttccaatcac catccgccat gccgcaatat     1080
gacgtcacac cagagatgag gatacctggt gaggtgaaaa acttgatgga aatagctgag     1140
gttgactcag ttgtcccagt ccaaaatgtt ggagagaagg tcaactctat ggaagcatac     1200
cagatacctg tgagatccaa cgaaggatct ggaacgcaag tattcggctt ccactgcaa      1260
ccagggtact cgagtgtttt tagtcggacg ctcctaggag agatcttgaa ctattataca     1320
cattggtcag gcagcataaa gcttacgttt atgttctgtg ttcggccat ggctactgga      1380
aaattccttt tggcatactc accaccaggt gctggagctc ctacaaaaag ggttgatgct     1440
atgcttggta ctcatgtaat ttgggacgtg gggctacaat caagttgcgt gctgtgtata     1500
ccctggataa gccaaacaca ctaccggttt gttgcttcag atgagtatac cgcaggggt      1560
tttattacgt gctggtatca aacaaacata gtggtcccag cggatgccca agctcctgt      1620
tacatcatgt gtttcgtgtc agcatgcaat gacttctctg tcaggctatt gaaggacact     1680
cctttcattt cgcagcaaaa cttttttccag ggcccagtgg aagacgcgat aacagccgct    1740
atagggagag ttgcggatac cgtgggtaca gggccaacca actcagaagc tataccagca    1800
ctcactgctg ctgagacggg tcacacgtca caagtagtgc cgggtgacac tatgcagaca    1860
cgccacgtta agaactacca ttcaaggtcc gagtcaacca tagagaactt cctatgtagg    1920
tcagcatgcg tgtactttac ggagtataaa aactcaggtg ccaagcggta tgctgaatgg    1980
gtattaacac cacgacaagc agcacaactt aggagaaagc tagaattctt tacctacgtc    2040
cggttcgacc tggagctgac gtttgtcata acaagtactc aacagccctc aaccacacag    2100
aaccaagatg cacagatcct aacacaccaa attatgtatg taccaccagg tggacctgta    2160
ccagataaag ttgattcata cgtgtggcaa acatctacga atcccagtgt gttttggacc    2220
gagggaaacg ccccgccgcg catgtccata ccgttttga gcattggcaa cgcctattca    2280
aatttctatg acggatggtc tgaattttcc aggaacggag tttacggcat caacacgcta    2340
aacaacatgg gcacgctata tgcaagacat gtcaacgctg gaagcacggg tccaataaaa    2400
agcaccatta gaatctactt caaaccgaag catgtcaaag cgtggatacc tagaccacct    2460
agactctgcc aatacgagaa ggcaaagaac gtgaacttcc aacccagcgg agttaccact    2520
actaggcaaa gcatcactac aatgacaaat acgggcgcat tt                        2562
```

<210> SEQ ID NO 5
<211> LENGTH: 854
<212> TYPE: PRT
<213> ORGANISM: Coxsackievirus

<400> SEQUENCE: 5

```
Met Gly Ala Gln Val Ser Thr Gln Lys Thr Gly Ala His Glu Thr Arg
1               5                   10                  15

Leu Asn Ala Ser Gly Asn Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60
```

```
Leu Pro Ala Leu Asn Ser Pro Thr Val Glu Glu Cys Gly Tyr Ser Asp
 65                  70                  75                  80

Arg Ala Arg Ser Ile Thr Leu Gly Asn Ser Thr Ile Thr Thr Gln Glu
             85                  90                  95

Cys Ala Asn Val Val Val Gly Tyr Gly Val Trp Pro Asp Tyr Leu Lys
            100                 105                 110

Asp Ser Glu Ala Thr Ala Glu Asp Gln Pro Thr Gln Pro Asp Val Ala
        115                 120                 125

Thr Cys Arg Phe Tyr Thr Leu Asp Ser Val Gln Trp Gln Lys Thr Ser
    130                 135                 140

Pro Gly Trp Trp Trp Lys Leu Pro Asp Ala Leu Ser Asn Leu Gly Leu
145                 150                 155                 160

Phe Gly Gln Asn Met Gln Tyr His Tyr Leu Gly Arg Thr Gly Tyr Thr
                165                 170                 175

Val His Val Gln Cys Asn Ala Ser Lys Phe His Gln Gly Cys Leu Leu
            180                 185                 190

Val Val Cys Val Pro Glu Ala Glu Met Gly Cys Ala Thr Leu Asp Asn
        195                 200                 205

Thr Pro Ser Ser Ala Glu Leu Leu Gly Gly Asp Ser Ala Lys Glu Phe
    210                 215                 220

Ala Asp Lys Pro Val Ala Ser Gly Ser Asn Lys Leu Val Gln Arg Val
225                 230                 235                 240

Val Tyr Asn Ala Gly Met Gly Val Gly Val Gly Asn Leu Thr Ile Phe
                245                 250                 255

Pro His Gln Trp Ile Asn Leu Arg Thr Asn Asn Ser Ala Thr Ile Val
                260                 265                 270

Met Pro Tyr Thr Asn Ser Val Pro Met Asp Asn Met Phe Arg His Asn
        275                 280                 285

Asn Val Thr Leu Met Val Ile Pro Phe Val Pro Leu Asp Tyr Cys Pro
    290                 295                 300

Gly Ser Thr Thr Tyr Val Pro Ile Thr Val Thr Ile Ala Pro Met Cys
305                 310                 315                 320

Ala Glu Tyr Asn Gly Leu Arg Leu Ala Gly His Gln Gly Leu Pro Thr
                325                 330                 335

Met Asn Thr Pro Gly Ser Cys Gln Phe Leu Thr Ser Asp Asp Phe Gln
            340                 345                 350

Ser Pro Ser Ala Met Pro Gln Tyr Asp Val Thr Pro Glu Met Arg Ile
        355                 360                 365

Pro Gly Glu Val Lys Asn Leu Met Glu Ile Ala Glu Val Asp Ser Val
    370                 375                 380

Val Pro Val Gln Asn Val Gly Glu Lys Val Asn Ser Met Glu Ala Tyr
385                 390                 395                 400

Gln Ile Pro Val Arg Ser Asn Glu Gly Ser Gly Thr Gln Val Phe Gly
                405                 410                 415

Phe Pro Leu Gln Pro Gly Tyr Ser Ser Val Phe Ser Arg Thr Leu Leu
            420                 425                 430

Gly Glu Ile Leu Asn Tyr Tyr Thr His Trp Ser Gly Ser Ile Lys Leu
        435                 440                 445

Thr Phe Met Phe Cys Gly Ser Ala Met Ala Thr Gly Lys Phe Leu Leu
    450                 455                 460

Ala Tyr Ser Pro Pro Gly Ala Gly Ala Pro Thr Lys Arg Val Asp Ala
465                 470                 475                 480

Met Leu Gly Thr His Val Ile Trp Asp Val Gly Leu Gln Ser Ser Cys
```

```
                        485                 490                 495
Val Leu Cys Ile Pro Trp Ile Ser Gln Thr His Tyr Arg Phe Val Ala
                    500                 505                 510
Ser Asp Glu Tyr Thr Ala Gly Gly Phe Ile Thr Cys Trp Tyr Gln Thr
                515                 520                 525
Asn Ile Val Val Pro Ala Asp Ala Gln Ser Ser Cys Tyr Ile Met Cys
            530                 535                 540
Phe Val Ser Ala Cys Asn Asp Phe Ser Val Arg Leu Leu Lys Asp Thr
545                 550                 555                 560
Pro Phe Ile Ser Gln Gln Asn Phe Phe Gln Gly Pro Val Glu Asp Ala
                565                 570                 575
Ile Thr Ala Ala Ile Gly Arg Val Ala Asp Thr Val Gly Thr Gly Pro
                580                 585                 590
Thr Asn Ser Glu Ala Ile Pro Ala Leu Thr Ala Ala Glu Thr Gly His
                595                 600                 605
Thr Ser Gln Val Val Pro Gly Asp Thr Met Gln Thr Arg His Val Lys
            610                 615                 620
Asn Tyr His Ser Arg Ser Glu Ser Thr Ile Glu Asn Phe Leu Cys Arg
625                 630                 635                 640
Ser Ala Cys Val Tyr Phe Thr Glu Tyr Lys Asn Ser Gly Ala Lys Arg
                645                 650                 655
Tyr Ala Glu Trp Val Leu Thr Pro Arg Gln Ala Ala Gln Leu Arg Arg
                660                 665                 670
Lys Leu Glu Phe Phe Thr Tyr Val Arg Phe Asp Leu Glu Leu Thr Phe
                675                 680                 685
Val Ile Thr Ser Thr Gln Gln Pro Ser Thr Thr Gln Asn Gln Asp Ala
            690                 695                 700
Gln Ile Leu Thr His Gln Ile Met Tyr Val Pro Pro Gly Gly Pro Val
705                 710                 715                 720
Pro Asp Lys Val Asp Ser Tyr Val Trp Gln Thr Ser Thr Asn Pro Ser
                725                 730                 735
Val Phe Trp Thr Glu Gly Asn Ala Pro Pro Arg Met Ser Ile Pro Phe
            740                 745                 750
Leu Ser Ile Gly Asn Ala Tyr Ser Asn Phe Tyr Asp Gly Trp Ser Glu
            755                 760                 765
Phe Ser Arg Asn Gly Val Tyr Gly Ile Asn Thr Leu Asn Asn Met Gly
        770                 775                 780
Thr Leu Tyr Ala Arg His Val Asn Ala Gly Ser Thr Gly Pro Ile Lys
785                 790                 795                 800
Ser Thr Ile Arg Ile Tyr Phe Lys Pro Lys His Val Lys Ala Trp Ile
                805                 810                 815
Pro Arg Pro Pro Arg Leu Cys Gln Tyr Glu Lys Ala Lys Asn Val Asn
            820                 825                 830
Phe Gln Pro Ser Gly Val Thr Thr Arg Gln Ser Ile Thr Thr Met
            835                 840                 845
Thr Asn Thr Gly Ala Phe
    850

<210> SEQ ID NO 6
<211> LENGTH: 1725
<212> TYPE: DNA
<213> ORGANISM: Coxsackievirus

<400> SEQUENCE: 6
```

```
ggacaacaat cagggcagt gtatgtgggg aactacaggg tggtaaatag acatctagct    60
accagtgctg actggcaaaa ctgtgtgtgg gaaagttaca acagagacct cttagtgagc   120
acgaccacag cacatggatg tgatattata gccagatgtc agtgcacaac gggagtgtac   180
ttttgtgcgt ccaaaaacaa gcactaccca atttcgtttg aaggaccagg tctagtagag   240
gtccaagaga gtgaatacta ccccaggaga taccaatccc atgtgctttt agcagctgga   300
ttttccgaac caggtgactg tggcggtatc ctaaggtgtg agcatggtgt cattggcatt   360
gtgaccatgg ggggtgaagg cgtggtcggc tttgcagaca tccgtgatct cctgtggctg   420
gaagatgatg caatggaaca gggagtgaag gactatgtgg aacagcttgg aaatgcattc   480
ggctccggct ttactaacca aatatgtgag caagtcaacc tcctgaaaga atcactagtg   540
ggtcaagact ccatcttaga gaaatctcta aaagccttag ttaagataat atcagcctta   600
gtaattgtgg tgaggaacca cgatgacctg atcactgtga ctgccacact agcccttatc   660
ggttgtacct cgtccccgtg gcggtggctc aaacagaagg tgtcacaata ttacggaatc   720
cctatggctg aacgccaaaa caatagctgg cttaagaaat ttactgaaat gacaaatgct   780
tgcaagggta tggaatggat agctgtcaaa attcagaaat tcattgaatg gctcaaagta   840
aaaatttttgc cagaggtcag agaaaaacac gagttcctga acagacttaa acaactcccc   900
ttattagaaa gtcagatcgc cacaatcgag cagagcgcgc catcccaaag tgaccaggaa   960
caattatttt ccaatgtcca atactttgcc cactattgca gaaagtacgc tcccctctac  1020
gcagctgaag caaagagggt gttctcccctt gagaagaaga tgagcaatta catacagttc  1080
aagtccaaat gccgtattga acctgtatgt ttgctcctgc acgggagccc tggtgccggc  1140
aagtcggtgg caacaaactt aattggaagg tcgcttgctg agaaactcaa cagctcagtg  1200
tactcactac cgccagaccc agatcacttc gacggataca aacagcaggc cgtggtgatt  1260
atggacgatc tatgccagaa tcctgatggg aaagacgtct ccttgttctg ccaaatggtt  1320
tccagtgtag attttgtacc acccatggct gccctagaag agaaaggcat tctgttcacc  1380
tcaccgtttg tcttggcatc gaccaatgca ggatctatta atgctccaac cgtgtcagat  1440
agcagagcct tggcaaggag atttcacttt gacatgaaca tcgaggttat ttccatgtac  1500
agtcagaatg gcaagataaa catgcccatg tcagtcaaga cttgtgacga tgagtgttgc  1560
ccggtcaatt ttaaaaagtg ctgccctctt gtgtgtggga aggctataca attcattgat  1620
agaagaacac aggtcagata ctctctagac atgctagtca ccgagatgtt tagggagtac  1680
aatcatagac atagcgtggg gaccacgctt gaggcactgt tccag             1725
```

<210> SEQ ID NO 7
<211> LENGTH: 575
<212> TYPE: PRT
<213> ORGANISM: Coxsackievirus

<400> SEQUENCE: 7

Gly Gln Gln Ser Gly Ala Val Tyr Val Gly Asn Tyr Arg Val Val Asn
1               5                   10                  15

Arg His Leu Ala Thr Ser Ala Asp Trp Gln Asn Cys Val Trp Glu Ser
            20                  25                  30

Tyr Asn Arg Asp Leu Leu Val Ser Thr Thr Ala His Gly Cys Asp
        35                  40                  45

Ile Ile Ala Arg Cys Gln Cys Thr Thr Gly Val Tyr Phe Cys Ala Ser
    50                  55                  60

Lys Asn Lys His Tyr Pro Ile Ser Phe Glu Gly Pro Gly Leu Val Glu

```
                65                  70                  75                  80
Val Gln Glu Ser Glu Tyr Tyr Pro Arg Arg Tyr Gln Ser His Val Leu
                    85                  90                  95

Leu Ala Ala Gly Phe Ser Glu Pro Gly Asp Cys Gly Gly Ile Leu Arg
            100                 105                 110

Cys Glu His Gly Val Ile Gly Ile Val Thr Met Gly Gly Glu Gly Val
        115                 120                 125

Val Gly Phe Ala Asp Ile Arg Asp Leu Leu Trp Leu Glu Asp Asp Ala
    130                 135                 140

Met Glu Gln Gly Val Lys Asp Tyr Val Glu Gln Leu Gly Asn Ala Phe
145                 150                 155                 160

Gly Ser Gly Phe Thr Asn Gln Ile Cys Glu Gln Val Asn Leu Leu Lys
                    165                 170                 175

Glu Ser Leu Val Gly Gln Asp Ser Ile Leu Glu Lys Ser Leu Lys Ala
            180                 185                 190

Leu Val Lys Ile Ile Ser Ala Leu Val Ile Val Arg Asn His Asp
        195                 200                 205

Asp Leu Ile Thr Val Thr Ala Thr Leu Ala Leu Ile Gly Cys Thr Ser
    210                 215                 220

Ser Pro Trp Arg Trp Leu Lys Gln Lys Val Ser Gln Tyr Tyr Gly Ile
225                 230                 235                 240

Pro Met Ala Glu Arg Gln Asn Asn Ser Trp Leu Lys Lys Phe Thr Glu
                    245                 250                 255

Met Thr Asn Ala Cys Lys Gly Met Glu Trp Ile Ala Val Lys Ile Gln
            260                 265                 270

Lys Phe Ile Glu Trp Leu Lys Val Lys Ile Leu Pro Glu Val Arg Glu
        275                 280                 285

Lys His Glu Phe Leu Asn Arg Leu Lys Gln Leu Pro Leu Leu Glu Ser
    290                 295                 300

Gln Ile Ala Thr Ile Glu Gln Ser Ala Pro Ser Gln Ser Asp Gln Glu
305                 310                 315                 320

Gln Leu Phe Ser Asn Val Gln Tyr Phe Ala His Tyr Cys Arg Lys Tyr
                    325                 330                 335

Ala Pro Leu Tyr Ala Ala Glu Ala Lys Arg Val Phe Ser Leu Glu Lys
            340                 345                 350

Lys Met Ser Asn Tyr Ile Gln Phe Lys Ser Lys Cys Arg Ile Glu Pro
        355                 360                 365

Val Cys Leu Leu Leu His Gly Ser Pro Gly Ala Gly Lys Ser Val Ala
    370                 375                 380

Thr Asn Leu Ile Gly Arg Ser Leu Ala Glu Lys Leu Asn Ser Ser Val
385                 390                 395                 400

Tyr Ser Leu Pro Pro Asp Pro Asp His Phe Asp Gly Tyr Lys Gln Gln
                    405                 410                 415

Ala Val Val Ile Met Asp Asp Leu Cys Gln Asn Pro Asp Gly Lys Asp
            420                 425                 430

Val Ser Leu Phe Cys Gln Met Val Ser Ser Val Asp Phe Val Pro Pro
        435                 440                 445

Met Ala Ala Leu Glu Glu Lys Gly Ile Leu Phe Thr Ser Pro Phe Val
    450                 455                 460

Leu Ala Ser Thr Asn Ala Gly Ser Ile Asn Ala Pro Thr Val Ser Asp
465                 470                 475                 480

Ser Arg Ala Leu Ala Arg Arg Phe His Phe Asp Met Asn Ile Glu Val
                    485                 490                 495
```

```
Ile Ser Met Tyr Ser Gln Asn Gly Lys Ile Asn Met Pro Met Ser Val
            500                 505                 510

Lys Thr Cys Asp Asp Glu Cys Cys Pro Val Asn Phe Lys Lys Cys Cys
        515                 520                 525

Pro Leu Val Cys Gly Lys Ala Ile Gln Phe Ile Asp Arg Arg Thr Gln
    530                 535                 540

Val Arg Tyr Ser Leu Asp Met Leu Val Thr Glu Met Phe Arg Glu Tyr
545                 550                 555                 560

Asn His Arg His Ser Val Gly Thr Thr Leu Glu Ala Leu Phe Gln
                565                 570                 575
```

<210> SEQ ID NO 8
<211> LENGTH: 2268
<212> TYPE: DNA
<213> ORGANISM: Coxsackievirus

<400> SEQUENCE: 8

```
ggaccaccag tatacagaga gatcaaaatt agcgttgcac cagagacacc accaccgccc     60
gccattgcgg acctgctcaa atcggtagac agtgaggctg tgagggagta ctgcaaagaa    120
aaaggatggt tggttcctga gatcaactcc accctccaaa ttgagaaaca tgtcagtcgg    180
gctttcattt gcttacaggc attgaccaca tttgtgtcag tggctggaat catatatata    240
atatataagc tctttgcggg ttttcaaggt gcttatacag gagtgcccaa ccagaagccc    300
agagtgccta ccctgaggca agcaaaagtg caaggccctg cctttgagtt cgccgtcgca    360
atgatgaaaa ggaactcaag cacggtgaaa actgaatatg gcgagtttac catgctgggc    420
atctatgaca ggtgggccgt tttgccacgc cacgccaaac ctgggccaac catcttgatg    480
aatgatcaag aggttggtgt gctagatgcc aaggagctag tagacaagga cggcaccaac    540
ttagaactga cactactcaa attgaaccgg aatgagaagt tcagagacat cagaggcttc    600
ttagccaagg aggaagtgga ggttaatgag gcagtgctag caattaacac cagcaagttt    660
cccaacatgt acattccagt aggacaggtc acagaatacg gcttcctaaa cctaggtggc    720
acacccacca agagaatgct tatgtacaac ttccccacaa gagcaggcca gtgtggtgga    780
gtgctcatgt ccaccggcaa ggtactgggt atccatgttg gtggaaatgg ccatcagggc    840
ttctcagcag cactcctcaa acactacttc aatgatgagc aaggtgaaat agaatttatt    900
gagagctcaa aggacgccgg gtttccagtc atcaacacac caagtaaaac aaagttggag    960
cctagtgttt tccaccaggt ctttgagggg aacaaagaac cagcagtact caggagtggg   1020
gatccacgtc tcaaggccaa ttttgaagag gctatatttt ccaagtatat aggaaatgtc   1080
aacacacacg tggatgagta catgctggaa gcagtggacc actacgcagg ccaactagcc   1140
accctagata tcagcactga accaatgaaa ctggaggacg cagtgtacgg taccgagggt   1200
cttgaggcgc ttgatctaac aacgagtgcc ggttacccat atgttgcact gggtatcaag   1260
aagagggaca tcctctctaa gaagactaag gacctaacaa agttaaagga atgtatggac   1320
aagtatggcc tgaacctacc aatggtgact tatgtaaaag atgagctcag gtccatagag   1380
aaggtagcga aaggaaagtc taggctgatt gaggcgtcca gtttgaatga ttcagtggcg   1440
atgagacaga catttggtaa tctgtacaaa actttccacc taaacccagg ggttgtgact   1500
ggtagtgctg ttgggtgtga cccagacctc ttttggagca agataccagt gatgttagat   1560
ggacatctca tagcatttga ttactctggg tacgatgcta gcttaagccc tgtctggttt   1620
gcttgcctaa aaatgttact tgagaagctt ggatacacgc acaaagagac aaactacatt   1680
```

```
gactacttgt gcaactccca tcacctgtac agggataaac attactttgt gaggggtggc   1740
atgccctcgg gatgttctgg taccagtatt ttcaactcaa tgattaacaa tatcataatt   1800
aggacactaa tgctaaaagt gtacaaaggg attgacttgg accaattcag gatgatcgca   1860
tatggtgatg atgtgatcgc atcgtaccca tggcctatag atgcatcttt actcgctgaa   1920
gctggtaagg gttacgggct gatcatgaca ccagcagata agggagagtg ctttaacgaa   1980
gttacctgga ccaacgccac tttcctaaag aggtatttta gagcagatga acagtacccc   2040
ttcctggtgc atcctgttat gcccatgaaa gacatacacg aatcaattag atggaccaag   2100
gatccaaaga cacccaaga tcacgtgcgc tcactgtgtc tattagcttg cataacgggg   2160
gagcacgaat atgaggagtt catccgtaaa attagaagcg tcccagtcgg acgttgtttg   2220
accctccccg cgttttcaac tctacgcagg aagtggttgg actccttt        2268
```

<210> SEQ ID NO 9
<211> LENGTH: 756
<212> TYPE: PRT
<213> ORGANISM: Coxsackievirus

<400> SEQUENCE: 9

```
Gly Pro Pro Val Tyr Arg Glu Ile Lys Ile Ser Val Ala Pro Glu Thr
1               5                   10                  15

Pro Pro Pro Pro Ala Ile Ala Asp Leu Leu Lys Ser Val Asp Ser Glu
            20                  25                  30

Ala Val Arg Glu Tyr Cys Lys Glu Lys Gly Trp Leu Val Pro Glu Ile
        35                  40                  45

Asn Ser Thr Leu Gln Ile Glu Lys His Val Ser Arg Ala Phe Ile Cys
    50                  55                  60

Leu Gln Ala Leu Thr Thr Phe Val Ser Val Ala Gly Ile Ile Tyr Ile
65                  70                  75                  80

Ile Tyr Lys Leu Phe Ala Gly Phe Gln Gly Ala Tyr Thr Gly Val Pro
                85                  90                  95

Asn Gln Lys Pro Arg Val Pro Thr Leu Arg Gln Ala Lys Val Gln Gly
            100                 105                 110

Pro Ala Phe Glu Phe Ala Val Ala Met Met Lys Arg Asn Ser Ser Thr
        115                 120                 125

Val Lys Thr Glu Tyr Gly Glu Phe Thr Met Leu Gly Ile Tyr Asp Arg
    130                 135                 140

Trp Ala Val Leu Pro Arg His Ala Lys Pro Gly Pro Thr Ile Leu Met
145                 150                 155                 160

Asn Asp Gln Glu Val Gly Val Leu Asp Ala Lys Glu Leu Val Asp Lys
                165                 170                 175

Asp Gly Thr Asn Leu Glu Leu Thr Leu Leu Lys Leu Asn Arg Asn Glu
            180                 185                 190

Lys Phe Arg Asp Ile Arg Gly Phe Leu Ala Lys Glu Glu Val Glu Val
        195                 200                 205

Asn Glu Ala Val Leu Ala Ile Asn Thr Ser Lys Phe Pro Asn Met Tyr
    210                 215                 220

Ile Pro Val Gly Gln Val Thr Glu Tyr Gly Phe Leu Asn Leu Gly Gly
225                 230                 235                 240

Thr Pro Thr Lys Arg Met Leu Met Tyr Asn Phe Pro Thr Arg Ala Gly
                245                 250                 255

Gln Cys Gly Gly Val Leu Met Ser Thr Gly Lys Val Leu Gly Ile His
            260                 265                 270
```

```
Val Gly Gly Asn Gly His Gln Gly Phe Ser Ala Ala Leu Leu Lys His
        275                 280                 285

Tyr Phe Asn Asp Glu Gln Gly Glu Ile Glu Phe Ile Glu Ser Ser Lys
        290                 295                 300

Asp Ala Gly Phe Pro Val Ile Asn Thr Pro Ser Lys Thr Lys Leu Glu
305                 310                 315                 320

Pro Ser Val Phe His Gln Val Phe Glu Gly Asn Lys Glu Pro Ala Val
                325                 330                 335

Leu Arg Ser Gly Asp Pro Arg Leu Lys Ala Asn Phe Glu Glu Ala Ile
                340                 345                 350

Phe Ser Lys Tyr Ile Gly Asn Val Asn Thr His Val Asp Glu Tyr Met
                355                 360                 365

Leu Glu Ala Val Asp His Tyr Ala Gly Gln Leu Ala Thr Leu Asp Ile
        370                 375                 380

Ser Thr Glu Pro Met Lys Leu Glu Asp Ala Val Tyr Gly Thr Glu Gly
385                 390                 395                 400

Leu Glu Ala Leu Asp Leu Thr Thr Ser Ala Gly Tyr Pro Tyr Val Ala
                405                 410                 415

Leu Gly Ile Lys Lys Arg Asp Ile Leu Ser Lys Lys Thr Lys Asp Leu
                420                 425                 430

Thr Lys Leu Lys Glu Cys Met Asp Lys Tyr Gly Leu Asn Leu Pro Met
        435                 440                 445

Val Thr Tyr Val Lys Asp Glu Leu Arg Ser Ile Glu Lys Val Ala Lys
        450                 455                 460

Gly Lys Ser Arg Leu Ile Glu Ala Ser Ser Leu Asn Asp Ser Val Ala
465                 470                 475                 480

Met Arg Gln Thr Phe Gly Asn Leu Tyr Lys Thr Phe His Leu Asn Pro
                485                 490                 495

Gly Val Val Thr Gly Ser Ala Val Gly Cys Asp Pro Asp Leu Phe Trp
                500                 505                 510

Ser Lys Ile Pro Val Met Leu Asp Gly His Leu Ile Ala Phe Asp Tyr
        515                 520                 525

Ser Gly Tyr Asp Ala Ser Leu Ser Pro Val Trp Phe Ala Cys Leu Lys
        530                 535                 540

Met Leu Leu Glu Lys Leu Gly Tyr Thr His Lys Glu Thr Asn Tyr Ile
545                 550                 555                 560

Asp Tyr Leu Cys Asn Ser His His Leu Tyr Arg Asp Lys His Tyr Phe
                565                 570                 575

Val Arg Gly Gly Met Pro Ser Gly Cys Ser Gly Thr Ser Ile Phe Asn
                580                 585                 590

Ser Met Ile Asn Asn Ile Ile Ile Arg Thr Leu Met Leu Lys Val Tyr
        595                 600                 605

Lys Gly Ile Asp Leu Asp Gln Phe Arg Met Ile Ala Tyr Gly Asp Asp
        610                 615                 620

Val Ile Ala Ser Tyr Pro Trp Pro Ile Asp Ala Ser Leu Leu Ala Glu
625                 630                 635                 640

Ala Gly Lys Gly Tyr Gly Leu Ile Met Thr Pro Ala Asp Lys Gly Glu
                645                 650                 655

Cys Phe Asn Glu Val Thr Trp Thr Asn Ala Thr Phe Leu Lys Arg Tyr
                660                 665                 670

Phe Arg Ala Asp Glu Gln Tyr Pro Phe Leu Val His Pro Val Met Pro
                675                 680                 685
```

```
Met Lys Asp Ile His Glu Ser Ile Arg Trp Thr Lys Asp Pro Lys Asn
    690                 695                 700

Thr Gln Asp His Val Arg Ser Leu Cys Leu Leu Ala Trp His Asn Gly
705                 710                 715                 720

Glu His Glu Tyr Glu Glu Phe Ile Arg Lys Ile Arg Ser Val Pro Val
                725                 730                 735

Gly Arg Cys Leu Thr Leu Pro Ala Phe Ser Thr Leu Arg Arg Lys Trp
            740                 745                 750

Leu Asp Ser Phe
        755

<210> SEQ ID NO 10
<211> LENGTH: 1386
<212> TYPE: DNA
<213> ORGANISM: Coxsackievirus

<400> SEQUENCE: 10
ggtgaaatag aatttattga gagctcaaag gacgccgggt ttccagtcat caacacacca      60
agtaaaacaa agttggagcc tagtgttttc caccaggtct ttgaggggaa caaagaacca     120
gcagtactca ggagtgggga tccacgtctc aaggccaatt tgaagaggc tatattttcc     180 aagtatatag aaatgtcaa cacacacgtg gatgagtaca tgctggaagc agtggaccac     240
tacgcaggcc aactagccac cctagatatc agcactgaac caatgaaact ggaggacgca     300
gtgtacggta ccgagggtct tgaggcgctt gatctaacaa cgagtgccgg ttacccatat     360
gttgcactgg gtatcaagaa gagggacatc ctctctaaga agactaagga cctaacaaag     420
ttaaaggaat gtatggacaa gtatggcctg aacctaccaa tggtgactta tgtaaaagat     480
gagctcaggt ccatagagaa ggtagcgaaa ggaaagtcta ggctgattga ggcgtccagt     540
ttgaatgatt cagtggcgat gagacagaca tttggtaatc tgtacaaaac tttccaccta     600
aacccagggg ttgtgactgg tagtgctgtt gggtgtgacc cagacctctt ttggagcaag     660
ataccagtga tgttagatgg acatctcata gcatttgatt actctgggta cgatgctagc     720
ttaagccctg tctggttttgc ttgcctaaaa atgttacttg agaagcttgg atacacgcac     780
aaagagacaa actacattga ctacttgtgc aactcccatc acctgtacag ggataaacat     840
tactttgtga ggggtggcat gccctcggga tgttctggta ccagtatttt caactcaatg     900
attaacaata tcataattag gacactaatg ctaaaagtgt acaaagggat tgacttggac     960
caattcagga tgatcgcata tggtgatgat gtgatcgcat cgtacccatg gcctatagat    1020
gcatctttac tcgctgaagc tggtaaggggt tacgggctga tcatgacacc agcagataag    1080
ggagagtgct ttaacgaagt tacctggacc aacgccactt tcctaaagag gtatttaga    1140 gcagatgaac agtacccctt cctggtgcat cctgttatgc ccatgaaaga catacacgaa    1200
tcaattagat ggaccaagga tccaaagaac acccaagatc acgtgcgctc actgtgtcta    1260
ttagcttggc ataacgggga gcacgaatat gaggagttca tccgtaaaat tagaagcgtc    1320
ccagtcggac gttgtttgac cctccccgcg ttttcaactc tacgcaggaa gtggttggac    1380
tccttt                                                              1386

<210> SEQ ID NO 11
<211> LENGTH: 462
<212> TYPE: PRT
<213> ORGANISM: Coxsackievirus

<400> SEQUENCE: 11
```

-continued

```
Gly Glu Ile Glu Phe Ile Glu Ser Ser Lys Asp Ala Gly Phe Pro Val
1               5                   10                  15

Ile Asn Thr Pro Ser Lys Thr Lys Leu Glu Pro Ser Val Phe His Gln
            20                  25                  30

Val Phe Glu Gly Asn Lys Glu Pro Ala Val Leu Arg Ser Gly Asp Pro
        35                  40                  45

Arg Leu Lys Ala Asn Phe Glu Glu Ala Ile Phe Ser Lys Tyr Ile Gly
    50                  55                  60

Asn Val Asn Thr His Val Asp Glu Tyr Met Leu Glu Ala Val Asp His
65                  70                  75                  80

Tyr Ala Gly Gln Leu Ala Thr Leu Asp Ile Ser Thr Glu Pro Met Lys
                85                  90                  95

Leu Glu Asp Ala Val Tyr Gly Thr Glu Gly Leu Glu Ala Leu Asp Leu
            100                 105                 110

Thr Thr Ser Ala Gly Tyr Pro Tyr Val Ala Leu Gly Ile Lys Lys Arg
        115                 120                 125

Asp Ile Leu Ser Lys Lys Thr Lys Asp Leu Thr Lys Leu Lys Glu Cys
    130                 135                 140

Met Asp Lys Tyr Gly Leu Asn Leu Pro Met Val Thr Tyr Val Lys Asp
145                 150                 155                 160

Glu Leu Arg Ser Ile Glu Lys Val Ala Lys Gly Lys Ser Arg Leu Ile
                165                 170                 175

Glu Ala Ser Ser Leu Asn Asp Ser Val Ala Met Arg Gln Thr Phe Gly
            180                 185                 190

Asn Leu Tyr Lys Thr Phe His Leu Asn Pro Gly Val Val Thr Gly Ser
        195                 200                 205

Ala Val Gly Cys Asp Pro Asp Leu Phe Trp Ser Lys Ile Pro Val Met
    210                 215                 220

Leu Asp Gly His Leu Ile Ala Phe Asp Tyr Ser Gly Tyr Asp Ala Ser
225                 230                 235                 240

Leu Ser Pro Val Trp Phe Ala Cys Leu Lys Met Leu Leu Glu Lys Leu
                245                 250                 255

Gly Tyr Thr His Lys Glu Thr Asn Tyr Ile Asp Tyr Leu Cys Asn Ser
            260                 265                 270

His His Leu Tyr Arg Asp Lys His Tyr Phe Val Arg Gly Gly Met Pro
        275                 280                 285

Ser Gly Cys Ser Gly Thr Ser Ile Phe Asn Ser Met Ile Asn Asn Ile
    290                 295                 300

Ile Ile Arg Thr Leu Met Leu Lys Val Tyr Lys Gly Ile Asp Leu Asp
305                 310                 315                 320

Gln Phe Arg Met Ile Ala Tyr Gly Asp Asp Val Ile Ala Ser Tyr Pro
                325                 330                 335

Trp Pro Ile Asp Ala Ser Leu Leu Ala Glu Ala Gly Lys Gly Tyr Gly
            340                 345                 350

Leu Ile Met Thr Pro Ala Asp Lys Gly Glu Cys Phe Asn Glu Val Thr
        355                 360                 365

Trp Thr Asn Ala Thr Phe Leu Lys Arg Tyr Phe Arg Ala Asp Glu Gln
    370                 375                 380

Tyr Pro Phe Leu Val His Pro Val Met Pro Met Lys Asp Ile His Glu
385                 390                 395                 400

Ser Ile Arg Trp Thr Lys Asp Pro Lys Asn Thr Gln Asp His Val Arg
                405                 410                 415

Ser Leu Cys Leu Leu Ala Trp His Asn Gly Glu His Glu Tyr Glu Glu
```

420             425             430
Phe Ile Arg Lys Ile Arg Ser Val Pro Val Gly Arg Cys Leu Thr Leu
            435                 440                 445

Pro Ala Phe Ser Thr Leu Arg Arg Lys Trp Leu Asp Ser Phe
450                 455                 460

<210> SEQ ID NO 12
<211> LENGTH: 7452
<212> TYPE: DNA
<213> ORGANISM: Artificial
<220> FEATURE:
<223> OTHER INFORMATION: "1-to-Stop" Coxsackievirus mutant

<400> SEQUENCE: 12

| | | |
|---|---|---|
| gggagacccg aattctccaa gacatccccc ccccaaaaca gcctgtgggt tgatcccacc | 60 |
| cacaggccca ttgggcgcta gcactctggt atcacggtac ctttgtgcgc ctgttttata | 120 |
| cccccctcccc caactgtaac ttagaagtaa cacacaccga tcaacagtca gcgtggcaca | 180 |
| ccagccacgt tttgatcaag cacttctgtt accccggact gagtatcaat agactgctca | 240 |
| cgcggttgaa ggagaaagcg ttcgttatcc ggccaactac ttcgaaaaac ctagtaacac | 300 |
| cgtggaagtt gcagagtgtt tcgctcagca ctaccccagt gtagatcagg tcgatgagtc | 360 |
| accgcattcc ccacgggcga ccgtggcggt ggctgcgttg gcggcctgcc catggggaaa | 420 |
| cccatgggac gctctaatac agacatggtg cgaagagtct attgagctag ttggtagtcc | 480 |
| tccggcccct gaatgcggct aatcctaact gcggagcaca ccctcaag ccagagggca | 540 |
| gtgtgtcgta acgggcaact ctgcagcgga accgactact ttgggtgtcc gtgtttcatt | 600 |
| ttattcctat actggctgct tatggtgaca attgagagat cgttaccata tagctattgg | 660 |
| attggccatc cggtgactaa tagagctatt atatatccct ttgttgggtt tataccactt | 720 |
| agcttgaaag aggttaaaac attacaattc attgttaagt tgaatacagc aaaatgggag | 780 |
| ctcaagtatc aacgcaaaag actggggcac atgagaccag gttgaatgct tcgggcaatt | 840 |
| cgatcattca ctacacaaat attaattatt acaaggatgc cgcatcgaac tcagccaatc | 900 |
| ggcaggattt cactcaagac ccgggcaagt tcacagaacc agtgaaagat atcatgatta | 960 |
| aatcattacc agctttgaac tcgcccacag tagaggagtg cggatactca gacagggcga | 1020 |
| gatcaatcac attaggtaac tcgaccataa cgactcagga atgcgccaac gtggtggtgg | 1080 |
| gctatggagt atggccagat tatttaaagg attcagaggc aacagcagag gaccaaccga | 1140 |
| cccaaccaga cgttgccaca tgtaggttct ataccttaga ctcagtgcaa tggcagaaaa | 1200 |
| cctcaccagg atggtggtgg aagttgcccg atgctttgtc gaacttagga ttgtttgggc | 1260 |
| agaacatgca gtaccactac ttaggccgaa ctgggtatac cgtacatgtg cagtgcaatg | 1320 |
| catcaaagtt ccaccaagga tgcttgttag tagtgtgtgt accggaagct gagatgggtt | 1380 |
| gcgcaacgtt agacaacacc ccatcgtcag cagaattgtt gggggggcgat acggcaaagg | 1440 |
| agtttgcgga caaccggtc gcatcggggt cgaacaagtt ggtacagagg gtggtgtata | 1500 |
| atgcaggcat gggggtgggt gttggaaact tgaccatttt cccccaccaa tggatcaact | 1560 |
| tacgcaccaa taattcagct acaattgtga tgccatacac caactcagta cctatggata | 1620 |
| acatgtttag gcataacaac gtcaccttaa tggttatccc atttgtaccg ttagattact | 1680 |
| gccctgggtc aaccacgtac gtcccaatta cggtcacgat agccccaatg tgtgccgagt | 1740 |
| acaatgggtt acgtttagca gggcaccagg gcttaccaac catgaatact ccggggtcgt | 1800 |
| gtcaattttt gacatcagac gacttccaat caccatcggc catgccgcaa tatgacgtca | 1860 |

```
caccagagat gaggatacct ggtgaggtga aaaacttgat ggaaatagct gaggttgact    1920
cagttgtccc agtccaaaat gttggagaga aggtcaactc aatggaagca taccagatac    1980
ctgtgagatc gaacgaagga tcaggaacgc aagtattcgg ctttccattg caaccagggt    2040
actcgtcagt tttttcacgg acgttgttag gagagatctt gaactattat acacattggt    2100
caggctcgat aaagttaacg tttatgttct gtggttcggc catggctact ggaaaattct    2160
tattggcata ctcaccacca ggtgctggag ctcctacaaa aagggttgat gctatgttag    2220
gtactcatgt aatttgggac gtggggttac aatcatcatg cgtgttgtgt atacCctgga    2280
tatcgcaaac acactaccgg tttgttgctt cagatgagta taccgcaggg ggtttttatta   2340
cgtgctggta tcaaacaaac atagtggtcc cagcggatgc ccaatcgtcg tgttacatca    2400
tgtgtttcgt gtcagcatgc aatgacttct cagtcaggtt attgaaggac actcctttca    2460
tttcgcagca aaacttttcc cagggcccag tggaagacgc gataacagcc gctataggga    2520
gagttgcgga taccgtgggt acagggccaa ccaactcaga agctatacca gcattgactg    2580
ctgctgagac gggtcacacg tcacaagtag tgccgggtga cactatgcag acacgccacg    2640
ttaagaacta ccattcaagg tcggagtcaa ccatagagaa cttcttatgt aggtcagcat    2700
gcgtgtactt tacggagtat aaaaactcag gtgccaagcg gtatgctgaa tgggtattaa    2760
caccacgaca agcagcacaa ttaaggagaa agttagaatt ctttacctac gtccggttcg    2820
acttggagtt gacgtttgtc ataacatcaa ctcaacagcc ctcaaccaca cagaaccaag    2880
atgcacagat cttaacacac caaattatgt atgtaccacc aggtggacct gtaccagata    2940
aagttgattc atacgtgtgg caaacatcaa cgaatccctc agtgttttgg accgagggaa    3000
acgccccgcc gcgcatgtcg ataccgtttt tgtcgattgg caacgcctat tcaaatttct    3060
atgacggatg gtcagaattt tcgaggaacg gagtttacgg catcaacacg ttaaacaaca    3120
tgggcacgtt atatgcaaga catgtcaacg ctggatcgac gggtccaata aaatcgacca    3180
ttagaatcta cttcaaaccg aagcatgtca aagcgtggat acctagacca cctagattgt    3240
gccaatacga aaggcaaag aacgtgaact tccaaccctc gggagttacc actactaggc    3300
aatcgatcac tacaatgaca aatacgggcg catttggaca caatcaggg gcagtgtatg    3360
tggggaacta cagggtggta aatagacatc tagctaccag tgctgactgg caaaactgtg    3420
tgtgggaaag ttcaacagga gacctcttag tgagcacgac cacagcacat ggatgtgata    3480
ttatagccag atgtcagtgc acaacgggag tgtactttg tgcgtccaaa aacaagcact    3540
acccaatttc gtttgaagga ccaggtctag tagaggtcca agagagtgaa tactacccca    3600
ggagatacca atcccatgtg cttttagcag ctggattttc cgaaccaggt gactgtggcg    3660
gtatcctaag gtgtgagcat ggtgtcattg gcattgtgac catggggggt gaaggcgtgg    3720
tcggctttgc agacatccgt gatctcctgt ggctggaaga tgatgcaatg gaacagggag    3780
tgaaggacta tgtggaacag cttggaaatg cattcggctc cggctttact aaccaaatat    3840
gtgagcaagt caacctcctg aaagaatcac tagtgggtca agactccatc ttagagaaat    3900
ctctaaaagc cttagttaag ataatatcag ccttagtaat tgtggtgagg aaccacgatg    3960
acctgatcac tgtgactgcc acactagccc ttatcggttg tacctcgtcc ccgtggcggt    4020
ggctcaaaca gaaggtgtca caatattacg gaatccctat ggctgaacgc caaaacaata    4080
gctggcttaa gaaatttact gaaatgacaa atgcttgcaa gggtatggaa tggatagctg    4140
tcaaaattca gaaattcatt gaatggctca agtaaaaat tttgccagag gtcagagaaa    4200
```

```
aacacgagtt cctgaacaga cttaaacaac tccccttatt agaaagtcag atcgccacaa    4260
tcgagcagag cgcgccatcc caaagtgacc aggaacaatt attttccaat gtccaatact    4320
ttgcccacta ttgcagaaag tacgctcccc tctacgcagc tgaagcaaag agggtgttct    4380
cccttgagaa gaagatgagc aattacatac agttcaagtc caaatgccgt attgaacctg    4440
tatgtttgct cctgcacggg agccctggtg ccggcaagtc ggtggcaaca aacttaattg    4500
gaaggtcgct tgctgagaaa ctcaacagct cagtgtactc actaccgcca gacccagatc    4560
acttcgacgg atacaaacag caggccgtgg tgattatgga cgatctatgc cagaatcctg    4620
atgggaaaga cgtctccttg ttctgccaaa tggtttccag tgtagatttt gtaccaccca    4680
tggctgccct agaagagaaa ggcattctgt tcacctcacc gtttgtcttg gcatcgacca    4740
atgcaggatc tattaatgct ccaaccgtgt cagatagcag agccttggca aggagatttc    4800
actttgacat gaacatcgag gttatttcca tgtacagtca gaatggcaag ataaacatgc    4860
ccatgtcagt caagacttgt gacgatgagt gttgcccggt caattttaaa aagtgctgcc    4920
ctcttgtgtg tgggaaggct atacaattca ttgatagaag aacacaggtc agatactctc    4980
tagacatgct agtcaccgag atgtttaggg agtacaatca tagacatagc gtggggacca    5040
cgcttgaggc actgttccag ggaccaccag tatacagaga gatcaaaatt agcgttgcac    5100
cagagacacc accaccgccc gccattgcgg acctgctcaa atcggtagac agtgaggctg    5160
tgagggagta ctgcaaagaa aaaggatggt tggttcctga tcaactcc accctccaaa     5220
ttgagaaaca tgtcagtcgg gctttcattt gcttacaggc attgaccaca tttgtgtcag    5280
tggctggaat catatatata atatataagc tctttgcggg ttttcaaggt gcttatacag    5340
gagtgcccaa ccagaagccc agagtgccta ccctgaggca agcaaaagtg caaggccctg    5400
cctttgagtt cgccgtcgca atgatgaaaa ggaactcaag cacggtgaaa actgaatatg    5460
gcgagtttac catgctgggc atctatgaca ggtgggccgt tttgccacgc cacgccaaac    5520
ctgggccaac catcttgatg aatgatcaag aggttggtgt gctagatgcc aaggagctag    5580
tagacaagga cggcaccaac ttagaactga cactactcaa attgaaccgg aatgagaagt    5640
tcagagacat cagaggcttc ttagccaagg aggaagtgga ggttaatgag gcagtgctag    5700
caattaacac cagcaagttt cccaacatgt acattccagt aggacaggtc acagaatacg    5760
gcttcctaaa cctaggtggc acacccacca agagaatgct tatgtacaac ttccccacaa    5820
gagcaggcca gtgtggtgga gtgctcatgt ccaccggcaa ggtactgggt atccatgttg    5880
gtggaaatgg ccatcagggc ttctcagcag cactcctcaa acactacttc aatgatgagc    5940
aaggtgaaat agaatttatt gagagctcaa aggacgccgg gtttccagtc atcaacacac    6000
caagtaaaac aaagtggag cctagtgttt tccaccaggt ctttgagggg aacaaagaac    6060
cagcagtact caggagtggg gatccacgtc tcaaggccaa ttttgaagag ctatatttt    6120
ccaagtatat aggaaatgtc aacacacacg tggatgagta catgctggaa gcagtggacc    6180
actacgcagg ccaactagcc accctagata tcagcactga ccaatgaaa ctggaggacg     6240
cagtgtacgg taccgagggt cttgaggcgc ttgatctaac aacgagtgcc ggttacccat    6300
atgttgcact gggtatcaag aagagggaca tcctctctaa gaagactaag gacctaacaa    6360
agttaaagga atgtatggac aagtatggcc tgaacctacc aatggtgact tatgtaaaag    6420
atgagctcag gtccatagag aaggtagcga aggaaagtc taggctgatt gaggcgtcca    6480
gtttgaatga ttcagtggcg atgagacaga catttgttaa tctgtacaaa actttccacc    6540
taaacccagg ggttgtgact ggtagtgctg ttgggtgtga cccagacctc ttttgagca    6600
```

```
agataccagt gatgttagat ggacatctca tagcatttga ttactctggg tacgatgcta    6660
gcttaagccc tgtctggttt gcttgcctaa aaatgttact tgagaagctt ggatacacgc    6720
acaaagagac aaactacatt gactacttgt gcaactccca tcacctgtac agggataaac    6780
attactttgt gaggggtggc atgccctcgg gatgttctgg taccagtatt ttcaactcaa    6840
tgattaacaa tatcataatt aggacactaa tgctaaaagt gtacaaggg attgacttgg    6900 accaattcag gatgatcgca tatggtgatg atgtgatcgc atcgtaccca tggcctatag    6960
atgcatcttt actcgctgaa gctggtaagg gttacgggct gatcatgaca ccagcagata    7020
agggagagtg ctttaacgaa gttacctgga ccaacgccac tttcctaaag aggtatttta    7080
gagcagatga acagtacccc ttcctggtgc atcctgttat gcccatgaaa gacatacacg    7140
aatcaattag atggaccaag gatccaaaga cacccaaga tcacgtgcgc tcactgtgtc    7200
tattagcttg gcataacggg gagcacgaat atgaggagtt catccgtaaa attagaagcg    7260
tcccagtcgg acgttgtttg accctccccg cgttttcaac tctacgcagg aagtggttgg    7320 actccttta gattagagac aatttgaaat aatttagatt ggcttaaccc tactgtgcta    7380
accgaaccag ataacggtac agtaggggta aattctccgc attcggtgcg gaaaaaaaaa    7440 aaaaaaaag aa                                                         7452

<210> SEQ ID NO 13
<211> LENGTH: 6558
<212> TYPE: DNA
<213> ORGANISM: Artificial
<220> FEATURE:
<223> OTHER INFORMATION: "1-to-Stop" Coxsackievirus mutant

<400> SEQUENCE: 13
atgggagctc aagtatcaac gcaaaagact ggggcacatg agaccaggtt gaatgcttcg      60
ggcaattcga tcattcacta cacaaatatt aattattaca aggatgccgc atcgaactca     120
gccaatcggc aggatttcac tcaagacccg ggcaagttca cagaaccagt gaaagatatc     180
atgattaaat cattaccagc tttgaactcg cccacagtag aggagtgcgg atactcagac     240
agggcgagat caatcacatt aggtaactcg accataacga ctcaggaatg cgccaacgtg     300
gtggtgggct atggagtatg ccagattat ttaaaggatt cagaggcaac agcagaggac     360
caaccgaccc aaccagacgt tgccacatgt aggttctata ccttagactc agtgcaatgg     420
cagaaaacct caccaggatg gtggtggaag ttgcccgatg ctttgtcgaa cttaggattg     480
tttgggcaga acatgcagta ccactactta ggccgaactg gtataccgt acatgtgcag     540 tgcaatgcat caaagttcca ccaaggatgc ttgttagtag tgtgtgtacc ggaagctgag     600
atgggttgcg caacgttaga caacacccca tcgtcagcag aattgttggg gggcgatacg     660
gcaaaggagt ttgcggacaa accggtcgca tcggggtcga caagttggt acagagggtg     720 gtgtataatg caggcatggg ggtgggtgtt ggaaacttga ccatttcccc ccaccaatgg     780
atcaacttac gcaccaataa ttcagctaca attgtgatgc atacaccaa ctcagtacct     840 atggataaca tgtttaggca taacaacgtc accttaatgg ttatcccatt tgtaccgtta     900
gattactgcc ctgggtcaac cacgtacgtc ccaattacgg tcacgatagc cccaatgtgt     960
gccgagtaca atgggttacg tttagcaggg caccagggct accaaccat gaatactccg    1020 gggtcgtgtc aattttgac atcagacgac ttccaatcac catcggccat gccgcaatat    1080
gacgtcacac cagagatgag gatacctggt gaggtgaaaa acttgatgga aatagctgag    1140
```

```
gttgactcag ttgtcccagt ccaaaatgtt ggagagaagg tcaactcaat ggaagcatac      1200
cagatacctg tgagatcgaa cgaaggatca ggaacgcaag tattcggctt tccattgcaa      1260
ccagggtact cgtcagtttt ttcacggacg ttgttaggag agatcttgaa ctattataca      1320
cattggtcag gctcgataaa gttaacgttt atgttctgtg gttcggccat ggctactgga      1380
aaattcttat tggcatactc accaccaggt gctggagctc ctacaaaaag ggttgatgct      1440
atgttaggta ctcatgtaat ttgggacgtg gggttacaat catcatgcgt gttgtgtata      1500
ccctggatat cgcaaacaca ctaccggttt gttgcttcag atgagtatac cgcaggggt       1560 tttattacgt gctggtatca aacaaacata gtggtcccag cggatgccca atcgtcgtgt      1620
tacatcatgt gtttcgtgtc agcatgcaat gacttctcag tcaggttatt gaaggacact      1680
cctttcattt cgcagcaaaa cttttttccag ggcccagtgg aagacgcgat aacagccgct     1740
atagggagag ttgcggatac cgtgggtaca gggccaacca actcagaagc tataccagca     1800
ttgactgctg ctgagacggg tcacacgtca caagtagtgc cgggtgacac tatgcagaca     1860
cgccacgtta agaactacca ttcaaggtcg gagtcaacca tagagaactt cttatgtagg     1920
tcagcatgcg tgtactttac ggagtataaa aactcaggtg ccaagcggta tgctgaatgg     1980
gtattaacac cacgacaagc agcacaatta aggagaaagt tagaattctt tacctacgtc     2040
cggttcgact tggagttgac gtttgtcata acatcaactc aacagccctc aaccacacag     2100
aaccaagatg cacagatctt aacacaccaa attatgtatg taccaccagg tggacctgta     2160
ccagataaag ttgattcata cgtgtggcaa acatcaacga atccctcagt gttttggacc     2220
gagggaaacg ccccgccgcg catgtcgata ccgttttgt cgattggcaa cgcctattca      2280
aatttctatg acggatggtc agaattttcg aggaacggag tttacggcat caacacgtta     2340
aacaacatgg gcacgttata tgcaagacat gtcaacgctg gatcgacggg tccaataaaa     2400
tcgaccatta gaatctactt caaaccgaag catgtcaaag cgtggatacc tagaccacct     2460
agattgtgcc aatacgagaa ggcaaagaac gtgaacttcc aaccctcggg agttaccact     2520
actaggcaat cgatcactac aatgacaaat acgggcgcat ttggacaaca atcaggggca     2580
gtgtatgtgg ggaactacag ggtggtaaat agacatctag ctaccagtgc tgactggcaa     2640
aactgtgtgt gggaaagtta acagagagac ctcttagtga gcacgaccac agcacatgga     2700
tgtgatatta tagccagatg tcagtgcaca acggagtgt acttttgtgc gtccaaaaac      2760
aagcactacc caatttcgtt tgaaggacca ggtctagtag aggtccaaga gagtgaatac     2820
taccccagga gataccaatc ccatgtgctt ttagcagctg gatttttccga accaggtgac     2880 tgtggcggta tcctaaggtg tgagcatggt gtcattggca ttgtgaccat ggggggtgaa     2940
ggcgtggtcg gctttgcaga catccgtgat ctcctgtggc tggaagatga tgcaatggaa     3000
cagggagtga aggactatgt ggaacagctt ggaaatgcat tcggctccgg ctttactaac     3060
caaatatgtg agcaagtcaa cctcctgaaa gaatcactag tgggtcaaga ctccatctta     3120
gagaaatctc taaaagcctt agttaagata atatcagcct tagtaattgt ggtgaggaac     3180
cacgatgacc tgatcactgt gactgccaca ctagccctta tcggttgtac ctcgtccccg     3240
tggcggtggc tcaaacagaa ggtgtcacaa tattacggaa tccctatggc tgaacgccaa     3300
aacaatagct ggcttaagaa atttactgaa atgacaaatg cttgcaaggg tatggaatgg     3360
atagctgtca aaattcagaa attcattgaa tggctcaaag taaaaatttt gccagaggtc     3420
agagaaaaac acgagttcct gaacagactt aaacaactcc ccttattaga aagtcagatc     3480
gccacaatcg agcagagcgc gccatcccaa agtgaccagg aacaattatt ttccaatgtc     3540
```

-continued

```
caatactttg cccactattg cagaaagtac gctcccctct acgcagctga agcaaagagg    3600
gtgttctccc ttgagaagaa gatgagcaat tacatacagt tcaagtccaa atgccgtatt    3660
gaacctgtat gtttgctcct gcacgggagc cctggtgccg gcaagtcggt ggcaacaaac    3720
ttaattggaa ggtcgcttgc tgagaaactc aacagctcag tgtactcact accgccagac    3780
ccagatcact tcgacggata caaacagcag gccgtggtga ttatggacga tctatgccag    3840
aatcctgatg ggaaagacgt ctccttgttc tgccaaatgg tttccagtgt agattttgta    3900
ccacccatgg ctgccctaga agagaaaggc attctgttca cctcaccgtt tgtcttggca    3960
tcgaccaatg caggatctat taatgctcca accgtgtcag atagcagagc cttggcaagg    4020
agatttcact ttgacatgaa catcgaggtt atttccatgt acagtcagaa tggcaagata    4080
aacatgccca tgtcagtcaa gacttgtgac gatgagtgtt gcccggtcaa ttttaaaaag    4140
tgctgccctc ttgtgtgtgg aaggctata caattcattg atagaagaac acaggtcaga    4200
tactctctag acatgctagt caccgagatg tttagggagt acaatcatag acatagcgtg    4260
gggaccacgc ttgaggcact gttccaggga ccaccagtat acagagagat caaaattagc    4320
gttgcaccag agacaccacc accgcccgcc attgcggacc tgctcaaatc ggtagacagt    4380
gaggctgtga gggagtactg caaagaaaaa ggatggttgg ttcctgagat caactccacc    4440
ctccaaattg agaaacatgt cagtcgggct ttcatttgct acaggcatt gaccacattt    4500
gtgtcagtgg ctggaatcat atatataata taaagctct ttgcgggttt tcaaggtgct    4560
tatacaggag tgcccaacca gaagcccaga gtgcctaccc tgaggcaagc aaaagtgcaa    4620
ggccctgcct ttgagttcgc cgtcgcaatg atgaaaagga actcaagcac ggtgaaaact    4680
gaatatggcg agtttaccat gctgggcatc tatgacaggg gggccgtttt gccacgccac    4740
gccaaacctg gccaaccat cttgatgaat gatcaagagg ttggtgtgct agatgccaag    4800
gagctagtag acaaggacgg caccaactta gaactgacac tactcaaatt gaaccggaat    4860
gagaagttca gagacatcag aggcttctta gccaaggagg aagtggaggt taatgaggca    4920
gtgctagcaa ttaacaccag caagtttccc aacatgtaca ttccagtagg acaggtcaca    4980
gaatacggct tcctaaacct aggtggcaca cccaccaaga gaatgcttat gtacaacttc    5040
cccacaagag caggccagtg tggtggagtg ctcatgtcca ccggcaaggt actgggtatc    5100
catgttggtg gaaatggcca tcagggcttc tcagcagcac tcctcaaaca ctacttcaat    5160
gatgagcaag gtgaaataga atttattgag agctcaaagg acgccgggtt tccagtcatc    5220
aacacaccaa gtaaaacaaa gttggagcct agtgttttcc accaggtctt tgaggggaac    5280
aaagaaccag cagtactcag gagtgggat ccacgtctca aggccaattt tgaagaggct    5340
atattttcca gtatataggc aaatgtcaac acacacgtgg atgagtacat gctgaagca    5400
gtggaccact acgcaggcca actagccacc ctagatatca gcactgaacc aatgaaactg    5460
gaggacgcag tgtacggtac cgagggtctt gaggcgcttg atctaacaac gagtgccggt    5520
tacccatatg ttgcactggg tatcaagaag agggacatcc tctctaagaa gactaaggac    5580
ctaacaaagt taaggaatg tatggacaag tatggcctga acctaccaat ggtgacttat    5640
gtaaagatg agctcaggtc catagagaag gtagcgaaag gaaagtctag gctgattgag    5700
gcgtccagtt tgaatgattc agtggcgatg agacagacat ttggtaatct gtacaaaact    5760
ttccacctaa acccaggggt tgtgactggt agtgctgttg ggtgtgaccc agacctcttt    5820
tggagcaaga taccagtgat gttagatgga catctcatag catttgatta ctctgggtac    5880
```

-continued

```
gatgctagct taagccctgt ctggtttgct tgcctaaaaa tgttacttga gaagcttgga    5940
tacacgcaca aagagacaaa ctacattgac tacttgtgca actcccatca cctgtacagg    6000
gataaacatt actttgtgag gggtggcatg ccctcgggat gttctggtac cagtattttc    6060
aactcaatga ttaacaatat cataattagg acactaatgc taaaagtgta caaagggatt    6120
gacttggacc aattcaggat gatcgcatat ggtgatgatg tgatcgcatc gtacccatgg    6180
cctatagatg catctttact cgctgaagct ggtaagggtt acgggctgat catgacacca    6240
gcagataagg gagagtgctt taacgaagtt acctggacca acgccacttt cctaaagagg    6300
tattttagag cagatgaaca gtaccccttc ctggtgcatc ctgttatgcc catgaaagac    6360
atacacgaat caattagatg gaccaaggat ccaaagaaca cccaagatca cgtgcgctca    6420
ctgtgtctat tagcttggca taacggggag cacgaatatg aggagttcat ccgtaaaatt    6480
agaagcgtcc cagtcggacg ttgtttgacc ctccccgcgt tttcaactct acgcaggaag    6540
tggttggact ccttttag                                                  6558
```

<210> SEQ ID NO 14
<211> LENGTH: 2562
<212> TYPE: DNA
<213> ORGANISM: Artificial
<220> FEATURE:
<223> OTHER INFORMATION: "1-to-Stop" Coxsackievirus mutant

<400> SEQUENCE: 14

```
atgggagctc aagtatcaac gcaaaagact ggggcacatg agaccaggtt gaatgcttcg      60
ggcaattcga tcattcacta cacaaatatt aattattaca aggatgccgc atcgaactca     120
gccaatcggc aggatttcac tcaagacccg gcaagttca cagaaccagt gaaagatatc      180
atgattaaat cattaccagc tttgaactcg cccacagtag aggagtgcgg atactcagac     240
agggcgagat caatcacatt aggtaactcg accataacga ctcaggaatg cgccaacgtg     300
gtggtgggct atggagtatg gccagattat ttaaaggatt cagaggcaac agcagaggac     360
caaccgaccc aaccagacgt tgccacatgt aggttctata ccttagactc agtgcaatgg     420
cagaaaacct caccaggatg gtggtggaag ttgcccgatg cttttgtcgaa cttaggattg     480 tttgggcaga acatgcagta ccactactta ggccgaactg ggtataccgt acatgtgcag     540
tgcaatgcat caaagttcca ccaaggatgc ttgttagtag tgtgtgtacc ggaagctgag     600
atgggttgcg caacgttaga caacaccccca tcgtcagcag aattgttggg gggcgatacg     660
gcaaaggagt tgcggacaa accggtcgca tcggggtcga acaagttggt acagagggtg      720
gtgtataatg caggcatggg ggtgggtgtt ggaaacttga ccattttccc ccaccaatgg     780
atcaacttac gcaccaataa ttcagctaca attgtgatgc catacaccaa ctcagtacct     840
atggataaca tgtttaggca taacaacgtc accttaatgg ttatcccatt tgtaccgtta     900
gattactgcc ctgggtcaac cacgtacgtc ccaattacgg tcacgatagc cccaatgtgt     960
gccgagtaca atgggttacg tttagcaggg caccagggct taccaaccat gaatactccg    1020
gggtcgtgtc aatttttgac atcagacgac ttccaatcac catcggccat gccgcaatat    1080
gacgtcacac cagagatgag gataccctggt gaggtgaaaa acttgatgga aatagctgag    1140
gttgactcag ttgtcccagt ccaaaatgtt ggagagaagg tcaactcaat ggaagcatac    1200
cagatacctg tgagatcgaa cgaaggatca ggaacgcaag tattcggctt tccattgcaa    1260
ccagggtact cgtcagtttt ttcacggacg ttgttaggag agatcttgaa ctattataca    1320
cattggtcag gctcgataaa gttaacgttt atgttctgtg gttcggccat ggctactgga    1380
```

-continued

```
aaattcttat tggcatactc accaccaggt gctggagctc ctacaaaaag ggttgatgct   1440
atgttaggta ctcatgtaat ttgggacgtg gggttacaat catcatgcgt gttgtgtata   1500
ccctggatat cgcaaacaca ctaccggttt gttgcttcag atgagtatac cgcaggggt    1560 tttattacgt gctggtatca aacaaacata gtggtcccag cggatgccca atcgtcgtgt   1620
tacatcatgt gtttcgtgtc agcatgcaat gacttctcag tcaggttatt gaaggacact   1680
cctttcattt cgcagcaaaa cttttttccag ggcccagtgg aagacgcgat aacagccgct  1740
atagggagag ttgcggatac cgtgggtaca gggccaacca actcagaagc tataccagca   1800
ttgactgctg ctgagacggg tcacacgtca aagtagtgc cgggtgacac tatgcagaca    1860
cgccacgtta agaactacca ttcaaggtcg gagtcaacca tagagaactt cttatgtagg   1920
tcagcatgcg tgtactttac ggagtataaa aactcaggtg ccaagcggta tgctgaatgg   1980
gtattaacac cacgacaagc agcacaatta aggagaaagt tagaattctt tacctacgtc   2040
cggttcgact tggagttgac gtttgtcata acatcaactc aacagccctc aaccacacag   2100
aaccaagatg cacagatctt aacacaccaa attatgtatg taccaccagg tggacctgta   2160
ccagataaag ttgattcata cgtgtggcaa acatcaacga atccctcagt gttttggacc   2220
gagggaaacg ccccgccgcg catgtcgata ccgttttgt cgattggcaa cgcctattca    2280
aatttctatg acggatggtc agaattttcg aggaacggag tttacggcat caacacgtta   2340
aacaacatgg gcacgttata tgcaagacat gtcaacgctg gatcgacggg tccaataaaa   2400
tcgaccatta gaatctactt caaaccgaag catgtcaaag cgtggatacc tagaccacct   2460
agattgtgcc aatacgagaa ggcaaagaac gtgaacttcc aaccctcggg agttaccact   2520
actaggcaat cgatcactac aatgacaaat acgggcgcat tt                      2562
```

<210> SEQ ID NO 15
<211> LENGTH: 462
<212> TYPE: PRT
<213> ORGANISM: Artificial
<220> FEATURE:
<223> OTHER INFORMATION: low fidelity RNA polymerase

<400> SEQUENCE: 15

```
Gly Glu Ile Glu Phe Ile Glu Ser Ser Lys Asp Ala Gly Phe Pro Val
1               5                   10                  15

Ile Asn Thr Pro Ser Lys Thr Lys Leu Glu Pro Ser Val Phe His Gln
            20                  25                  30

Val Phe Glu Gly Asn Lys Glu Pro Ala Val Leu Arg Ser Gly Asp Pro
        35                  40                  45

Arg Leu Lys Ala Asn Phe Glu Glu Ala Ile Phe Ser Lys Tyr Ile Gly
    50                  55                  60

Asn Val Asn Thr His Val Asp Glu Tyr Met Leu Glu Ala Val Asp His
65                  70                  75                  80

Tyr Ala Gly Gln Leu Ala Thr Leu Asp Ile Ser Thr Glu Pro Met Lys
                85                  90                  95

Leu Glu Asp Ala Val Tyr Gly Thr Glu Gly Leu Glu Ala Leu Asp Leu
            100                 105                 110

Thr Thr Ser Ala Gly Tyr Pro Tyr Val Ala Leu Gly Ile Lys Lys Arg
        115                 120                 125

Asp Ile Leu Ser Lys Lys Thr Lys Asp Leu Thr Lys Leu Lys Glu Cys
    130                 135                 140

Met Asp Lys Tyr Gly Leu Asn Leu Pro Met Val Thr Tyr Val Lys Asp
```

```
145                 150                 155                 160
Glu Leu Arg Ser Ile Glu Lys Val Ala Lys Gly Lys Ser Arg Leu Ile
                165                 170                 175
Glu Ala Ser Ser Leu Asn Asp Ser Val Ala Met Arg Gln Thr Phe Gly
                180                 185                 190
Asn Leu Tyr Lys Thr Phe His Leu Asn Pro Gly Val Thr Gly Ser
                195                 200                 205
Ala Val Gly Cys Asp Pro Asp Leu Phe Trp Ser Lys Ile Pro Val Met
            210                 215                 220
Leu Asp Gly His Leu Ile Ala Phe Asp Tyr Ser Gly Tyr Asp Gly Ser
225                 230                 235                 240
Leu Ser Pro Val Trp Phe Ala Cys Leu Lys Met Leu Leu Glu Lys Leu
                245                 250                 255
Gly Tyr Thr His Lys Glu Thr Asn Tyr Ile Asp Tyr Leu Cys Asn Ser
                260                 265                 270
His His Leu Tyr Arg Asp Lys His Tyr Phe Val Arg Gly Gly Met Pro
                275                 280                 285
Ser Gly Cys Ser Gly Thr Ser Ile Phe Asn Ser Met Ile Asn Asn Ile
            290                 295                 300
Ile Ile Arg Thr Leu Met Leu Lys Val Tyr Lys Gly Ile Asp Leu Asp
305                 310                 315                 320
Gln Phe Arg Met Ile Ala Tyr Gly Asp Asp Val Ile Ala Ser Tyr Pro
                325                 330                 335
Trp Pro Ile Asp Ala Ser Leu Leu Ala Glu Ala Gly Lys Gly Tyr Gly
                340                 345                 350
Leu Ile Met Thr Pro Ala Asp Lys Gly Glu Cys Phe Asn Glu Val Thr
                355                 360                 365
Trp Thr Asn Ala Thr Phe Leu Lys Arg Tyr Phe Arg Ala Asp Glu Gln
                370                 375                 380
Tyr Pro Phe Leu Val His Pro Val Met Pro Met Lys Asp Ile His Glu
385                 390                 395                 400
Ser Ile Arg Trp Thr Lys Asp Pro Lys Asn Thr Gln Asp His Val Arg
                405                 410                 415
Ser Leu Cys Leu Leu Ala Trp His Asn Gly Glu His Glu Tyr Glu Glu
                420                 425                 430
Phe Ile Arg Lys Ile Arg Ser Val Pro Val Gly Arg Cys Leu Thr Leu
                435                 440                 445
Pro Ala Phe Ser Thr Leu Arg Arg Lys Trp Leu Asp Ser Phe
450                 455                 460

<210> SEQ ID NO 16
<211> LENGTH: 462
<212> TYPE: PRT
<213> ORGANISM: Artificial
<220> FEATURE:
<223> OTHER INFORMATION: low fidelity RNA polymerase

<400> SEQUENCE: 16

Gly Glu Ile Glu Phe Ile Glu Ser Ser Lys Asp Ala Gly Phe Pro Val
1               5                   10                  15
Ile Asn Thr Pro Ser Lys Thr Lys Leu Glu Pro Ser Val Phe His Gln
                20                  25                  30
Val Phe Glu Gly Asn Lys Glu Pro Ala Val Leu Arg Ser Gly Asp Pro
                35                  40                  45
Arg Leu Lys Ala Asn Phe Glu Glu Ala Ile Phe Ser Lys Tyr Ile Gly
```

```
            50                  55                  60
Asn Val Asn Thr His Val Asp Glu Tyr Met Leu Glu Ala Val Asp His
 65                  70                  75                  80

Tyr Ala Gly Gln Leu Ala Thr Leu Asp Ile Ser Thr Glu Pro Met Lys
                 85                  90                  95

Leu Glu Asp Ala Val Tyr Gly Thr Glu Gly Leu Glu Ala Leu Asp Leu
            100                 105                 110

Thr Thr Ser Ala Gly Tyr Pro Tyr Val Ala Leu Gly Ile Lys Lys Arg
            115                 120                 125

Asp Ile Leu Ser Lys Lys Thr Lys Asp Leu Thr Lys Leu Lys Glu Cys
130                 135                 140

Met Asp Lys Tyr Gly Leu Asn Leu Pro Met Val Thr Tyr Val Lys Asp
145                 150                 155                 160

Glu Leu Arg Ser Ile Glu Lys Val Ala Lys Gly Lys Ser Arg Leu Ile
                165                 170                 175

Glu Ala Ser Ser Leu Asn Asp Ser Val Ala Met Arg Gln Thr Phe Gly
            180                 185                 190

Asn Leu Tyr Lys Thr Phe His Leu Asn Pro Gly Val Val Thr Gly Ser
            195                 200                 205

Ala Val Gly Cys Asp Pro Asp Leu Phe Trp Ser Lys Ile Pro Val Met
210                 215                 220

Leu Asp Gly His Leu Ile Ala Phe Asp Tyr Ser Gly Tyr Asp Ala Ser
225                 230                 235                 240

Leu Ser Pro Val Trp Phe Ala Cys Leu Lys Met Leu Leu Glu Lys Leu
                245                 250                 255

Gly Tyr Thr His Lys Glu Thr Asn Tyr Ile Asp Trp Leu Cys Asn Ser
            260                 265                 270

His His Leu Tyr Arg Asp Lys His Tyr Phe Val Arg Gly Gly Met Pro
            275                 280                 285

Ser Gly Cys Ser Gly Thr Ser Ile Phe Asn Ser Met Ile Asn Asn Ile
            290                 295                 300

Ile Ile Arg Thr Leu Met Leu Lys Val Tyr Lys Gly Ile Asp Leu Asp
305                 310                 315                 320

Gln Phe Arg Met Ile Ala Tyr Gly Asp Asp Val Ile Ala Ser Tyr Pro
                325                 330                 335

Trp Pro Ile Asp Ala Ser Leu Leu Ala Glu Ala Gly Lys Gly Tyr Gly
            340                 345                 350

Leu Ile Met Thr Pro Ala Asp Lys Gly Glu Cys Phe Asn Glu Val Thr
            355                 360                 365

Trp Thr Asn Ala Thr Phe Leu Lys Arg Tyr Phe Arg Ala Asp Glu Gln
370                 375                 380

Tyr Pro Phe Leu Val His Pro Val Met Pro Met Lys Asp Ile His Glu
385                 390                 395                 400

Ser Ile Arg Trp Thr Lys Asp Pro Lys Asn Thr Gln Asp His Val Arg
                405                 410                 415

Ser Leu Cys Leu Leu Ala Trp His Asn Gly Glu His Glu Tyr Glu Glu
            420                 425                 430

Phe Ile Arg Lys Ile Arg Ser Val Pro Val Gly Arg Cys Leu Thr Leu
            435                 440                 445

Pro Ala Phe Ser Thr Leu Arg Arg Lys Trp Leu Asp Ser Phe
450                 455                 460

<210> SEQ ID NO 17
```

<211> LENGTH: 462
<212> TYPE: PRT
<213> ORGANISM: Artificial
<220> FEATURE:
<223> OTHER INFORMATION: low fidelity RNA polymerase

<400> SEQUENCE: 17

```
Gly Glu Ile Glu Phe Ile Glu Ser Ser Lys Asp Ala Gly Phe Pro Val
1               5                   10                  15

Ile Asn Thr Pro Ser Lys Thr Lys Leu Glu Pro Ser Val Phe His Gln
            20                  25                  30

Val Phe Glu Gly Asn Lys Glu Pro Ala Val Leu Arg Ser Gly Asp Pro
        35                  40                  45

Arg Leu Lys Ala Asn Phe Glu Ala Ile Phe Ser Lys Tyr Ile Gly
    50                  55                  60

Asn Val Asn Thr His Val Asp Glu Tyr Met Leu Glu Ala Val Asp His
65                  70                  75                  80

Tyr Ala Gly Gln Leu Ala Thr Leu Asp Ile Ser Thr Glu Pro Met Lys
                85                  90                  95

Leu Glu Asp Ala Val Tyr Gly Thr Glu Gly Leu Glu Ala Leu Asp Leu
            100                 105                 110

Thr Thr Ser Ala Gly Tyr Pro Tyr Val Ala Leu Gly Ile Lys Lys Arg
        115                 120                 125

Asp Ile Leu Ser Lys Lys Thr Lys Asp Leu Thr Lys Leu Lys Glu Cys
130                 135                 140

Met Asp Lys Tyr Gly Leu Asn Leu Pro Met Val Thr Tyr Val Lys Asp
145                 150                 155                 160

Glu Leu Arg Ser Ile Glu Lys Val Ala Lys Gly Lys Ser Arg Leu Ile
                165                 170                 175

Glu Ala Ser Ser Leu Asn Asp Ser Val Ala Met Arg Gln Thr Phe Gly
            180                 185                 190

Asn Leu Tyr Lys Thr Phe His Leu Asn Pro Gly Val Val Thr Gly Ser
        195                 200                 205

Ala Val Gly Cys Asp Pro Asp Leu Phe Trp Ser Lys Ile Pro Val Met
    210                 215                 220

Leu Asp Gly His Leu Phe Ala Phe Asp Tyr Ser Gly Tyr Asp Ala Ser
225                 230                 235                 240

Leu Ser Pro Val Trp Phe Ala Cys Leu Lys Met Leu Leu Glu Lys Leu
                245                 250                 255

Gly Tyr Thr His Lys Glu Thr Asn Tyr Ile Asp Tyr Leu Cys Asn Ser
            260                 265                 270

His His Leu Tyr Arg Asp Lys His Tyr Phe Val Arg Gly Gly Met Pro
        275                 280                 285

Ser Gly Cys Ser Gly Thr Ser Ile Phe Asn Ser Met Ile Asn Asn Ile
    290                 295                 300

Ile Ile Arg Thr Leu Met Leu Lys Val Tyr Lys Gly Ile Asp Leu Asp
305                 310                 315                 320

Gln Phe Arg Met Ile Ala Tyr Gly Asp Asp Val Ile Ala Ser Tyr Pro
                325                 330                 335

Trp Pro Ile Asp Ala Ser Leu Leu Ala Glu Ala Gly Lys Gly Tyr Gly
            340                 345                 350

Leu Ile Met Thr Pro Ala Asp Lys Gly Glu Cys Phe Asn Glu Val Thr
        355                 360                 365

Trp Thr Asn Ala Thr Phe Leu Lys Arg Tyr Phe Arg Ala Asp Glu Gln
    370                 375                 380
```

```
Tyr Pro Phe Leu Val His Pro Val Met Pro Met Lys Asp Ile His Glu
385                 390                 395                 400

Ser Ile Arg Trp Thr Lys Asp Pro Lys Asn Thr Gln Asp His Val Arg
                405                 410                 415

Ser Leu Cys Leu Leu Ala Trp His Asn Gly Glu His Glu Tyr Glu Glu
            420                 425                 430

Phe Ile Arg Lys Ile Arg Ser Val Pro Val Gly Arg Cys Leu Thr Leu
        435                 440                 445

Pro Ala Phe Ser Thr Leu Arg Arg Lys Trp Leu Asp Ser Phe
    450                 455                 460

<210> SEQ ID NO 18
<211> LENGTH: 462
<212> TYPE: PRT
<213> ORGANISM: Artificial
<220> FEATURE:
<223> OTHER INFORMATION: low fidelity RNA polymerase

<400> SEQUENCE: 18

Gly Glu Ile Glu Phe Ile Glu Ser Ser Lys Asp Ala Gly Phe Pro Val
1               5                   10                  15

Ile Asn Thr Pro Ser Lys Thr Lys Leu Glu Pro Ser Val Phe His Gln
            20                  25                  30

Val Phe Glu Gly Asn Lys Glu Pro Ala Val Leu Arg Ser Gly Asp Pro
        35                  40                  45

Arg Leu Lys Ala Asn Phe Glu Glu Ala Ile Phe Ser Lys Tyr Ile Gly
    50                  55                  60

Asn Val Asn Thr His Val Asp Glu Tyr Met Leu Glu Ala Val Asp His
65                  70                  75                  80

Tyr Ala Gly Gln Leu Ala Thr Leu Asp Ile Ser Thr Glu Pro Met Lys
                85                  90                  95

Leu Glu Asp Ala Val Tyr Gly Thr Glu Gly Leu Glu Ala Leu Asp Leu
            100                 105                 110

Thr Thr Ser Ala Gly Tyr Pro Tyr Val Ala Leu Gly Ile Lys Lys Arg
        115                 120                 125

Asp Ile Leu Ser Lys Lys Thr Lys Asp Leu Thr Lys Leu Lys Glu Cys
    130                 135                 140

Met Asp Lys Tyr Gly Leu Asn Leu Pro Met Val Thr Tyr Val Lys Asp
145                 150                 155                 160

Glu Leu Arg Ser Ile Glu Lys Val Ala Lys Gly Lys Ser Arg Leu Ile
                165                 170                 175

Glu Ala Ser Ser Leu Asn Asp Ser Val Ala Met Arg Gln Thr Phe Gly
            180                 185                 190

Asn Leu Tyr Lys Thr Phe His Leu Asn Pro Gly Val Val Thr Gly Ser
        195                 200                 205

Ala Val Gly Cys Asp Pro Asp Leu Phe Trp Ser Lys Ile Pro Val Met
    210                 215                 220

Leu Asp Gly His Leu Ile Ala Phe Asp Tyr Ser Gly Tyr Asp Ala Ser
225                 230                 235                 240

Leu Ser Pro Val Trp Phe Ala Cys Leu Lys Met Leu Leu Glu Lys Leu
                245                 250                 255

Gly Tyr Thr His Lys Glu Thr Asn Tyr Ile Asp His Leu Cys Asn Ser
            260                 265                 270

His His Leu Tyr Arg Asp Lys His Tyr Phe Val Arg Gly Gly Met Pro
        275                 280                 285
```

```
Ser Gly Cys Ser Gly Thr Ser Ile Phe Asn Ser Met Ile Asn Asn Ile
    290                 295                 300

Ile Ile Arg Thr Leu Met Leu Lys Val Tyr Lys Gly Ile Asp Leu Asp
305                 310                 315                 320

Gln Phe Arg Met Ile Ala Tyr Gly Asp Asp Val Ile Ala Ser Tyr Pro
                325                 330                 335

Trp Pro Ile Asp Ala Ser Leu Leu Ala Glu Ala Gly Lys Gly Tyr Gly
            340                 345                 350

Leu Ile Met Thr Pro Ala Asp Lys Gly Glu Cys Phe Asn Glu Val Thr
        355                 360                 365

Trp Thr Asn Ala Thr Phe Leu Lys Arg Tyr Phe Arg Ala Asp Glu Gln
370                 375                 380

Tyr Pro Phe Leu Val His Pro Val Met Pro Met Lys Asp Ile His Glu
385                 390                 395                 400

Ser Ile Arg Trp Thr Lys Asp Pro Lys Asn Thr Gln Asp His Val Arg
                405                 410                 415

Ser Leu Cys Leu Leu Ala Trp His Asn Gly Glu His Glu Tyr Glu Glu
            420                 425                 430

Phe Ile Arg Lys Ile Arg Ser Val Pro Val Gly Arg Cys Leu Thr Leu
        435                 440                 445

Pro Ala Phe Ser Thr Leu Arg Arg Lys Trp Leu Asp Ser Phe
    450                 455                 460

<210> SEQ ID NO 19
<211> LENGTH: 462
<212> TYPE: PRT
<213> ORGANISM: Artificial
<220> FEATURE:
<223> OTHER INFORMATION: low fidelity RNA polymerase

<400> SEQUENCE: 19

Gly Glu Ile Glu Phe Ile Glu Ser Ser Lys Asp Ala Gly Phe Pro Val
1               5                   10                  15

Ile Asn Thr Pro Ser Lys Thr Lys Leu Glu Pro Ser Val Phe His Gln
                20                  25                  30

Val Phe Glu Gly Asn Lys Glu Pro Ala Val Leu Arg Ser Gly Asp Lys
            35                  40                  45

Arg Leu Lys Ala Asn Phe Glu Glu Ala Ile Phe Ser Lys Tyr Ile Gly
        50                  55                  60

Asn Val Asn Thr His Val Asp Glu Tyr Met Leu Glu Ala Val Asp His
65                  70                  75                  80

Tyr Ala Gly Gln Leu Ala Thr Leu Asp Ile Ser Thr Glu Pro Met Lys
                85                  90                  95

Leu Glu Asp Ala Val Tyr Gly Thr Glu Gly Leu Glu Ala Leu Asp Leu
                100                 105                 110

Thr Thr Ser Ala Gly Tyr Pro Tyr Val Ala Leu Gly Ile Lys Lys Arg
            115                 120                 125

Asp Ile Leu Ser Lys Lys Thr Lys Asp Leu Thr Lys Leu Lys Glu Cys
        130                 135                 140

Met Asp Lys Tyr Gly Leu Asn Leu Pro Met Val Thr Tyr Val Lys Asp
145                 150                 155                 160

Glu Leu Arg Ser Ile Glu Lys Val Ala Lys Gly Lys Ser Arg Leu Ile
                165                 170                 175

Glu Ala Ser Ser Leu Asn Asp Ser Val Ala Met Arg Gln Thr Phe Gly
            180                 185                 190
```

-continued

```
Asn Leu Tyr Lys Thr Phe His Leu Asn Pro Gly Val Val Thr Gly Ser
            195                 200                 205

Ala Val Gly Cys Asp Pro Asp Leu Phe Trp Ser Lys Ile Pro Val Met
        210                 215                 220

Leu Asp Gly His Leu Ile Ala Phe Asp Tyr Ser Gly Tyr Asp Ala Ser
225                 230                 235                 240

Leu Ser Pro Val Trp Phe Ala Cys Leu Lys Met Leu Leu Glu Lys Leu
                245                 250                 255

Gly Tyr Thr His Lys Glu Thr Asn Tyr Ile Asp Tyr Leu Cys Asn Ser
            260                 265                 270

His His Leu Tyr Arg Asp Lys His Tyr Phe Val Arg Gly Gly Met Pro
        275                 280                 285

Ser Gly Cys Ser Gly Thr Ser Ile Phe Asn Ser Met Ile Asn Asn Ile
    290                 295                 300

Ile Ile Arg Thr Leu Met Leu Lys Val Tyr Lys Gly Ile Asp Leu Asp
305                 310                 315                 320

Gln Phe Arg Met Ile Ala Tyr Gly Asp Asp Val Ile Ala Ser Tyr Pro
                325                 330                 335

Trp Pro Ile Asp Ala Ser Leu Leu Ala Glu Ala Gly Lys Gly Tyr Gly
            340                 345                 350

Leu Ile Met Thr Pro Ala Asp Lys Gly Glu Cys Phe Asn Glu Val Thr
        355                 360                 365

Trp Thr Asn Ala Thr Phe Leu Lys Arg Tyr Phe Arg Ala Asp Glu Gln
370                 375                 380

Tyr Pro Phe Leu Val His Pro Val Met Pro Met Lys Asp Ile His Glu
385                 390                 395                 400

Ser Ile Arg Trp Thr Lys Asp Pro Lys Asn Thr Gln Asp His Val Arg
                405                 410                 415

Ser Leu Cys Leu Leu Ala Trp His Asn Gly Glu His Glu Tyr Glu Glu
            420                 425                 430

Phe Ile Arg Lys Ile Arg Ser Val Pro Val Gly Arg Cys Leu Thr Leu
        435                 440                 445

Pro Ala Phe Ser Thr Leu Arg Arg Lys Trp Leu Asp Ser Phe
    450                 455                 460

<210> SEQ ID NO 20
<211> LENGTH: 462
<212> TYPE: PRT
<213> ORGANISM: Artificial
<220> FEATURE:
<223> OTHER INFORMATION: low fidelity RNA polymerase

<400> SEQUENCE: 20

Gly Glu Ile Glu Phe Ile Glu Ser Ser Lys Asp Ala Gly Phe Pro Val
1               5                   10                  15

Ile Asn Thr Pro Ser Lys Thr Lys Leu Glu Pro Ser Val Phe His Gln
            20                  25                  30

Val Phe Glu Gly Asn Lys Glu Pro Ala Val Leu Arg Ser Gly Asp Pro
        35                  40                  45

Arg Leu Lys Ala Asn Phe Glu Glu Ala Ile Phe Ser Tyr Ile Gly
    50                  55                  60

Asn Val Asn Thr His Val Asp Glu Tyr Met Leu Glu Ala Val Asp His
65                  70                  75                  80

Tyr Ala Gly Gln Leu Ala Thr Leu Asp Ile Ser Thr Glu Pro Met Lys
                85                  90                  95
```

Leu Glu Asp Ala Val Tyr Gly Thr Glu Gly Leu Ala Leu Asp Leu
                100                 105                 110

Thr Thr Ser Ala Gly Tyr Pro Tyr Val Ala Leu Gly Ile Lys Lys Arg
            115                 120                 125

Asp Ile Leu Ser Lys Lys Thr Lys Asp Leu Thr Lys Leu Lys Glu Cys
        130                 135                 140

Met Asp Lys Tyr Gly Leu Asn Leu Pro Met Val Thr Tyr Val Lys Asp
145                 150                 155                 160

Glu Leu Arg Ser Ile Glu Lys Val Ala Lys Gly Lys Ser Arg Leu Ile
                165                 170                 175

Glu Ala Ser Ser Leu Asn Asp Ser Val Ala Met Arg Gln Thr Phe Gly
            180                 185                 190

Asn Leu Tyr Lys Thr Phe His Leu Asn Pro Gly Val Val Thr Gly Ser
        195                 200                 205

Ala Val Gly Cys Asp Pro Asp Leu Phe Trp Ser Lys Ile Pro Val Met
210                 215                 220

Leu Asp Gly His Leu Ile Ala Tyr Asp Tyr Ser Gly Tyr Asp Ala Ser
225                 230                 235                 240

Leu Ser Pro Val Trp Phe Ala Cys Leu Lys Met Leu Leu Glu Lys Leu
                245                 250                 255

Gly Tyr Thr His Lys Glu Thr Asn Tyr Ile Asp Tyr Leu Cys Asn Ser
            260                 265                 270

His His Leu Tyr Arg Asp Lys His Tyr Phe Val Arg Gly Gly Met Pro
        275                 280                 285

Ser Gly Cys Ser Gly Thr Ser Ile Phe Asn Ser Met Ile Asn Asn Ile
290                 295                 300

Ile Ile Arg Thr Leu Met Leu Lys Val Tyr Lys Gly Ile Asp Leu Asp
305                 310                 315                 320

Gln Phe Arg Met Ile Ala Tyr Gly Asp Asp Val Ile Ala Ser Tyr Pro
                325                 330                 335

Trp Pro Ile Asp Ala Ser Leu Leu Ala Glu Ala Gly Lys Gly Tyr Gly
            340                 345                 350

Leu Ile Met Thr Pro Ala Asp Lys Gly Glu Cys Phe Asn Glu Val Thr
        355                 360                 365

Trp Thr Asn Ala Thr Phe Leu Lys Arg Tyr Phe Arg Ala Asp Glu Gln
370                 375                 380

Tyr Pro Phe Leu Val His Pro Val Met Pro Met Lys Asp Ile His Glu
385                 390                 395                 400

Ser Ile Arg Trp Thr Lys Asp Pro Lys Asn Thr Gln Asp His Val Arg
                405                 410                 415

Ser Leu Cys Leu Leu Ala Trp His Asn Gly Glu His Glu Tyr Glu Glu
            420                 425                 430

Phe Ile Arg Lys Ile Arg Ser Val Pro Val Gly Arg Cys Leu Thr Leu
        435                 440                 445

Pro Ala Phe Ser Thr Leu Arg Arg Lys Trp Leu Asp Ser Phe
450                 455                 460

<210> SEQ ID NO 21
<211> LENGTH: 462
<212> TYPE: PRT
<213> ORGANISM: Artificial Sequence
<220> FEATURE:
<223> OTHER INFORMATION: low fidelity RNA polymerase

<400> SEQUENCE: 21

```
Gly Glu Ile Glu Phe Ile Glu Ser Ser Lys Asp Ala Gly Phe Pro Val
1               5                   10                  15

Ile Asn Thr Pro Ser Lys Thr Lys Leu Glu Pro Ser Val Phe His Gln
            20                  25                  30

Val Phe Glu Gly Asn Lys Glu Pro Ala Val Leu Arg Ser Gly Asp Pro
        35                  40                  45

Arg Leu Lys Ala Asn Phe Glu Glu Ala Ile Phe Ser Lys Tyr Ile Gly
    50                  55                  60

Asn Val Asn Thr His Val Asp Glu Tyr Met Leu Glu Ala Val Asp His
65              70                  75                  80

Tyr Ala Gly Gln Leu Ala Thr Leu Asp Ile Ser Thr Glu Pro Met Lys
                85                  90                  95

Leu Glu Asp Ala Val Tyr Gly Thr Glu Gly Leu Glu Ala Leu Asp Leu
                100                 105                 110

Thr Thr Ser Ala Gly Tyr Pro Tyr Val Ala Leu Gly Ile Lys Lys Arg
            115                 120                 125

Asp Ile Leu Ser Lys Lys Thr Lys Asp Leu Thr Lys Leu Lys Glu Cys
    130                 135                 140

Met Asp Lys Tyr Gly Leu Asn Leu Pro Met Val Thr Tyr Val Lys Asp
145                 150                 155                 160

Glu Leu Arg Ser Ile Glu Lys Val Ala Lys Gly Lys Ser Arg Leu Ile
                165                 170                 175

Glu Ala Ser Ser Leu Asn Asp Ser Val Ala Met Arg Gln Thr Phe Gly
            180                 185                 190

Asn Leu Tyr Lys Thr Phe His Leu Asn Pro Gly Val Val Thr Gly Ser
            195                 200                 205

Ala Val Gly Cys Asp Pro Asp Leu Phe Trp Ser Lys Ile Pro Val Met
    210                 215                 220

Leu Asp Gly His Leu Ile Ala Phe Asp Tyr Ser Gly Tyr Asp Ala Ser
225                 230                 235                 240

Leu Ser Pro Val Trp Phe Ala Cys Leu Lys Met Leu Leu Glu Lys Leu
                245                 250                 255

Gly Tyr Thr His Lys Glu Thr Asn Tyr Ile Asp Tyr Leu Cys Asn Ser
            260                 265                 270

His His Leu Tyr Arg Asp Lys His Tyr Phe Val Arg Gly Gly Met Pro
    275                 280                 285

Ser Gly Cys Ser Gly Thr Ser Ile Phe Asn Thr Met Ile Asn Asn Ile
    290                 295                 300

Ile Ile Arg Thr Leu Met Leu Lys Val Tyr Lys Gly Ile Asp Leu Asp
305                 310                 315                 320

Gln Phe Arg Met Ile Ala Tyr Gly Asp Asp Val Ile Ala Ser Tyr Pro
                325                 330                 335

Trp Pro Ile Asp Ala Ser Leu Leu Ala Glu Ala Gly Lys Gly Tyr Gly
            340                 345                 350

Leu Ile Met Thr Pro Ala Asp Lys Gly Glu Cys Phe Asn Glu Val Thr
            355                 360                 365

Trp Thr Asn Ala Thr Phe Leu Lys Arg Tyr Phe Arg Ala Asp Glu Gln
    370                 375                 380

Tyr Pro Phe Leu Val His Pro Val Met Pro Met Lys Asp Ile His Glu
385                 390                 395                 400

Ser Ile Arg Trp Thr Lys Asp Pro Lys Asn Thr Gln Asp His Val Arg
                405                 410                 415
```

```
Ser Leu Cys Leu Leu Ala Trp His Asn Gly Glu His Glu Tyr Glu Glu
            420                 425                 430

Phe Ile Arg Lys Ile Arg Ser Val Pro Val Gly Arg Cys Leu Thr Leu
        435                 440                 445

Pro Ala Phe Ser Thr Leu Arg Arg Lys Trp Leu Asp Ser Phe
    450                 455                 460

<210> SEQ ID NO 22
<211> LENGTH: 27
<212> TYPE: DNA
<213> ORGANISM: Artificial
<220> FEATURE:
<223> OTHER INFORMATION: viral RNA primer

<400> SEQUENCE: 22
gcatatggtg atgatgtgat cgctagc                                        27

<210> SEQ ID NO 23
<211> LENGTH: 24
<212> TYPE: DNA
<213> ORGANISM: Artificial
<220> FEATURE:
<223> OTHER INFORMATION: viral RNA primer

<400> SEQUENCE: 23
ggggtactgt tcatctgctc taaa                                           24

<210> SEQ ID NO 24
<211> LENGTH: 18
<212> TYPE: DNA
<213> ORGANISM: Artificial
<220> FEATURE:
<223> OTHER INFORMATION: viral RNA probe

<400> SEQUENCE: 24
ggttacgggc tgatcatg                                                  18

<210> SEQ ID NO 25
<211> LENGTH: 16
<212> TYPE: DNA
<213> ORGANISM: Artificial
<220> FEATURE:
<223> OTHER INFORMATION: MGB_CVB3_WT probe

<400> SEQUENCE: 25
cgcatcgtac ccatgg                                                    16

<210> SEQ ID NO 26
<211> LENGTH: 16
<212> TYPE: DNA
<213> ORGANISM: Artificial
<220> FEATURE:
<223> OTHER INFORMATION: MGB_CVB3_Ref probe

<400> SEQUENCE: 26
cgctagctac ccatgg                                                    16

<210> SEQ ID NO 27
<211> LENGTH: 23
<212> TYPE: DNA
<213> ORGANISM: Artificial
<220> FEATURE:
<223> OTHER INFORMATION: RNA primer

<400> SEQUENCE: 27
```

```
gatcgcatat ggtgatgatg tga                                              23

<210> SEQ ID NO 28
<211> LENGTH: 22
<212> TYPE: DNA
<213> ORGANISM: Artificial
<220> FEATURE:
<223> OTHER INFORMATION: RNA primer

<400> SEQUENCE: 28
agcttcagcg agtaaagatg ca                                               22

<210> SEQ ID NO 29
<211> LENGTH: 21
<212> TYPE: DNA
<213> ORGANISM: Artificial
<220> FEATURE:
<223> OTHER INFORMATION: RNA primer

<400> SEQUENCE: 29
gaaaacgcgg ggagggtcaa a                                                21

<210> SEQ ID NO 30
<211> LENGTH: 20
<212> TYPE: DNA
<213> ORGANISM: Artificial
<220> FEATURE:
<223> OTHER INFORMATION: RNA primer

<400> SEQUENCE: 30
accccctccc ccaactgtaa                                                  20

<210> SEQ ID NO 31
<211> LENGTH: 12
<212> TYPE: DNA
<213> ORGANISM: Artificial
<220> FEATURE:
<223> OTHER INFORMATION: RNA primer

<400> SEQUENCE: 31
agcraaagca gg                                                          12

<210> SEQ ID NO 32
<211> LENGTH: 23
<212> TYPE: DNA
<213> ORGANISM: Artificial
<220> FEATURE:
<223> OTHER INFORMATION: Influenza primer

<400> SEQUENCE: 32
gcaaaagcag gtcaattata ttc                                              23

<210> SEQ ID NO 33
<211> LENGTH: 23
<212> TYPE: DNA
<213> ORGANISM: Artificial
<220> FEATURE:
<223> OTHER INFORMATION: Influenza primer

<400> SEQUENCE: 33
caaggtcgtt tttaaacaat tcg                                              23

<210> SEQ ID NO 34
<211> LENGTH: 20
<212> TYPE: DNA
<213> ORGANISM: Artificial
```

<220> FEATURE:
<223> OTHER INFORMATION: Influenza primer

<400> SEQUENCE: 34
caaaagcagg caaaccattt                                               20

<210> SEQ ID NO 35
<211> LENGTH: 22
<212> TYPE: DNA
<213> ORGANISM: Artificial
<220> FEATURE:
<223> OTHER INFORMATION: Influenza primer

<400> SEQUENCE: 35
ttcattattt ttgccgtctg ag                                            22

<210> SEQ ID NO 36
<211> LENGTH: 22
<212> TYPE: DNA
<213> ORGANISM: Artificial
<220> FEATURE:
<223> OTHER INFORMATION: Influenza primer

<400> SEQUENCE: 36
agcaaaagca ggtactgatc ca                                            22

<210> SEQ ID NO 37
<211> LENGTH: 24
<212> TYPE: DNA
<213> ORGANISM: Artificial
<220> FEATURE:
<223> OTHER INFORMATION: Influenza primer

<400> SEQUENCE: 37
tttttggaca gtatggatag caaa                                          24

<210> SEQ ID NO 38
<211> LENGTH: 21
<212> TYPE: DNA
<213> ORGANISM: Artificial
<220> FEATURE:
<223> OTHER INFORMATION: Influenza primer

<400> SEQUENCE: 38
aaaagcaggg gaaaacaaaa g                                             21

<210> SEQ ID NO 39
<211> LENGTH: 22
<212> TYPE: DNA
<213> ORGANISM: Artificial
<220> FEATURE:
<223> OTHER INFORMATION: Influenza primer

<400> SEQUENCE: 39
acaagggtgt ttttctcatg ct                                            22

<210> SEQ ID NO 40
<211> LENGTH: 22
<212> TYPE: DNA
<213> ORGANISM: Artificial
<220> FEATURE:
<223> OTHER INFORMATION: Influenza primer

<400> SEQUENCE: 40
gcaaaagcag ggtagataat ca                                            22

<210> SEQ ID NO 41
<211> LENGTH: 24
<212> TYPE: DNA
<213> ORGANISM: Artificial
<220> FEATURE:
<223> OTHER INFORMATION: Influenza primer

<400> SEQUENCE: 41
gaaacaaggg tatttttcct caac                                          24

<210> SEQ ID NO 42
<211> LENGTH: 22
<212> TYPE: DNA
<213> ORGANISM: Artificial
<220> FEATURE:
<223> OTHER INFORMATION: Influenza primer

<400> SEQUENCE: 42
agcaggagtt taaaatgaat cc                                            22

<210> SEQ ID NO 43
<211> LENGTH: 22
<212> TYPE: DNA
<213> ORGANISM: Artificial
<220> FEATURE:
<223> OTHER INFORMATION: Influenza primer

<400> SEQUENCE: 43
tgtcaatggt aaatggcaac tc                                            22

<210> SEQ ID NO 44
<211> LENGTH: 24
<212> TYPE: DNA
<213> ORGANISM: Artificial
<220> FEATURE:
<223> OTHER INFORMATION: Influenza primer

<400> SEQUENCE: 44
aagatgagtc ttctaaccga ggtc                                          24

<210> SEQ ID NO 45
<211> LENGTH: 22
<212> TYPE: DNA
<213> ORGANISM: Artificial
<220> FEATURE:
<223> OTHER INFORMATION: Influenza primer

<400> SEQUENCE: 45
caaaatgacc atcgtcaaca tc                                            22

<210> SEQ ID NO 46
<211> LENGTH: 19
<212> TYPE: DNA
<213> ORGANISM: Artificial
<220> FEATURE:
<223> OTHER INFORMATION: Influenza primer

<400> SEQUENCE: 46
gcaaaagcag ggtgacaaa                                                19

<210> SEQ ID NO 47
<211> LENGTH: 22
<212> TYPE: DNA
<213> ORGANISM: Artificial
<220> FEATURE:
<223> OTHER INFORMATION: Influenza primer

<400> SEQUENCE: 47
ataagctgaa acgagaaagc tc            22

<210> SEQ ID NO 48
<211> LENGTH: 2233
<212> TYPE: RNA
<213> ORGANISM: Influenza A virus

<400> SEQUENCE: 48

| | | | | | |
|---|---|---|---|---|---|
| aguagaaaca | agguacuuuu | uuggacagua | uggauagcaa | auaguagcau | ugccacaacu |   60 |
| acuucagugc | augugugagg | aaggaguuga | accaagaugc | auuaagcaaa | acccagggau |  120 |
| cauuaaucag | gcacuccucg | auugcuucau | auagccccccc | aagaucgaag | guuccagguu |  180 |
| ccagguuguc | ccuaagugcc | ugaacaauga | gaagcaauuu | ucucgauuca | gccgaaaacc |  240 |
| ccucaaguug | uggagacgca | auagacugu | ugaauacaga | uuuugccagu | aagguccugc |  300 |
| acacuucccc | aauagagccu | uccuccacuc | cccuggguga | cucccgauu | ggccauguuu |  360 |
| ccgauuuguu | uucaaagaau | uccuugguca | ugucuuucuc | uuugacagaa | gacucggccu |  420 |
| caaucaugcu | cucaaucugc | ugaagagacu | gaagaaggca | gcgccucauu | uccaugcccc |  480 |
| auuucaucuu | gaucuuggag | guuccauugg | uucucacaua | uaggaacaug | ggccucgaca |  540 |
| cuuggccuau | cgcagcccuc | aagagcaugu | cuccuauuuc | aagaacacag | uauuuuuccc |  600 |
| auuugugugg | cuccagucuc | ggucaguga | gugagaacuc | cauacuuaca | aaguucacca |  660 |
| caucaguauc | auuucucaaa | ugagaccuuc | cuuuuauaau | gaacccauac | agguuuguuu |  720 |
| uccgucuucc | uucuuugguc | cuacauuugc | uuaucauugg | gaucagcuga | aagucaucca |  780 |
| uggcugcaca | ggaugcauug | agcaaggccg | uauuuaugua | cacucccuuc | auuauguauu |  840 |
| caguagcccu | gcagugggac | acuucugcug | uaaaauaguu | ccuccucaug | cuugcgauau |  900 |
| guucaaucgg | ggcaacaucu | cuccuauuu | caucaaguuc | uaccagcuu | gaaucaguca |  960 |
| auucacaugc | cuuauugaau | ucauuuugga | cccagcuugc | uagagaucug | ggcucuggcu | 1020 |
| caucacuguc | auacuguuua | aggcuccaa | caucuuugca | gucaucaaag | ucuacuuuuu | 1080 |
| cuggugccau | auuucaccg | agugcccacu | ucaauuggcu | uguucucuuc | auguucuuug | 1140 |
| uccuugggau | cuucucuuca | uuuucaaugu | ccuguagcuc | ugcuagcacu | ugcuuccaag | 1200 |
| ccaugaggua | auugggauuu | augccuuucc | caugugguuu | gacauguua | ggcucuuucc | 1260 |
| agccaaagaa | ugucuucaug | cauuugauug | caucauauag | ugguauuccc | ucccccucgu | 1320 |
| gacucgggc | uucaauacuu | aauucagag | cauccaucag | caggaacuuu | gaccgcugau | 1380 |
| ggcaaagagg | cccaucaggc | aaucgaggg | ggcgggugu | cguccucaag | aaugguucaa | 1440 |
| uuuuggcguu | cacuucuuuu | gacauuuggg | aaagcuugcc | cucaaugcag | ccguucggcu | 1500 |
| cgaauccauc | uacauaggcu | cuaaaguuuu | caaggcugga | gaaguucggu | gggagacuuu | 1560 |
| ggucggcaag | cuugcgcaua | guccuguaa | ucucaaauuu | ucuucaauu | gucucuucgc | 1620 |
| cucuuucgga | cugacgaaag | gaaucccaua | gacuccuacu | ggccauuucu | ugucuuauag | 1680 |
| ugaaaagccu | aguuugauuu | cuugcccgc | ucucuucguc | aagguguag | uccgcuuugg | 1740 |
| uggccaucuc | cucuccagug | aaugaaaaga | ugugaaugug | ugucucuca | gauuuauuu | 1800 |
| uguuggcuuu | cucuagguaa | uauaugugga | cuccccuccg | uguuacucca | auucaauga | 1860 |
| accgguucuc | uuuguaauca | uacaaaucag | gaagaaauuu | aggcuucucu | accccuguug | 1920 |
| uguuacauau | acuguucacc | acuguccagg | ccaugauucg | gucucuuccu | ucaauuaucu | 1980 |

| | |
|---|---:|
| caaaucggug cuucaauagu gcauucgggu caccagauuc uacaauuauu gauucacccc | 2040 |
| guucgucgau gaaauggaaa uccgaauaca ugaaacaaac uuccaaaugu gugcauauug | 2100 |
| cagcaaacuu guuaguuucg auuuucggau cuuccccaua uucuuucauu gccuuuccg | 2160 |
| caagcucgac gaucauugga uugaagcauu gucgcacaaa gucuuccauu uuggaucagu | 2220 |
| accugcuuuc gcu | 2233 |

<210> SEQ ID NO 49
<211> LENGTH: 2151
<212> TYPE: DNA
<213> ORGANISM: Influenza A virus

<400> SEQUENCE: 49

| | |
|---|---:|
| atggaagact tgtgcgaca atgcttcaat ccaatgatcg tcgagcttgc ggaaaaggca | 60 |
| atgaaagaat atggggaaga tccgaaaatc gaaactaaca agtttgctgc aatatgcaca | 120 |
| catttggaag tttgtttcat gtattcggat ttccatttca tcgacgaacg gggtgaatca | 180 |
| ataattgtag aatctggtga cccgaatgca ctattgaagc accgatttga gataattgaa | 240 |
| ggaagagacc gaatcatggc ctggacagtg gtgaacagta tatgtaacac aacaggggta | 300 |
| gagaagccta aatttcttcc tgatttgtat gattacaaag agaaccggtt cattgaaatt | 360 |
| ggagtaacac ggagggaagt ccacatatat acctagaga agccaacaa aataaaatct | 420 |
| gagaagacac acattcacat cttttcattc actggagagg atgccac caaagcggac | 480 |
| tacacccttg acgaagagag cagggcaaga atcaaaacta gcttttcac tataagacaa | 540 |
| gaaatggcca gtaggagtct atgggattcc tttcgtcagt ccgaaagagg cgaagagaca | 600 |
| attgaagaaa aatttgagat tacaggaact atgcgcaagc ttgccgacca aagtctccca | 660 |
| ccgaacttct ccagccttga aactttaga gcctatgtag atggattcga ccgaacggc | 720 |
| tgcattgagg gcaagctttc ccaaatgtca aagaagtga cgccaaaat tgaaccattc | 780 |
| ttgaggacga caccacgccc cctcagattg cctgatgggc ctctttgcca tcagcggtca | 840 |
| aagttcctgc tgatggatgc tctgaaatta gtattgaag acccgagtca cgaggggag | 900 |
| ggaataccac tatatgatgc aatcaaatgc atgaagacat ctttggctg aaagagcct | 960 |
| aacatagtca aaccacatgg gaaaggcata atcccaatt acctcatggc ttggaagcaa | 1020 |
| gtgctagcag agctacagga cattgaaaat gaagagaaga tcccaaggac aaagaacatg | 1080 |
| aagagaacaa gccaattgaa gtgggcactc ggtgaaaata tggcaccaga aaagtagac | 1140 |
| tttgatgact gcaaagatgt tggagacctt aacagtatg acagtgatga ccagagccc | 1200 |
| agatctctag caagctgggt ccaaaatgaa ttcaataagg catgtgaatt gactgattca | 1260 |
| agctggatag aacttgatga ataggagaa gatgttgccc cgattgaaca tatcgcaagc | 1320 |
| atgaggagga actatttac agcagaagtg tcccactgca gggctactga atacataatg | 1380 |
| aagggagtgt acataaatac ggccttgctc aatgcatcct gtgcagccat ggatgacttt | 1440 |
| cagctgatcc caatgataag caatgtagg accaagaag gaagacggaa acaaacctg | 1500 |
| tatgggttca ttataaaagg aaggtctcat tgagaaatg atactgatgt ggtgaacttt | 1560 |
| gtaagtatgg agttctcact cactgacccg agactggagc cacacaaatg gaaaaatac | 1620 |
| tgtgttcttg aaataggaga catgctcttg aggactgcga taggccaagt gtcgaggccc | 1680 |
| atgttcctat atgtgagaac caatggaacc tccaagatca agatgaaatg ggcatggaa | 1740 |
| atgaggcgct gccttcttca gtctcttcag cagattgaga gcatgattga ggccgagtct | 1800 |
| tctgtcaaag agaaagacat gaccaaggaa ttctttgaaa acaaatcgga aacatggcca | 1860 |

```
atcggagagt cacccagggg agtggaggaa ggctctattg ggaaagtgtg caggacctta   1920
ctggcaaaat ctgtattcaa cagtctatat gcgtctccac aacttgaggg gttttcggct   1980
gaatcgagaa aattgcttct cattgttcag gcacttaggg acaacctgga acctggaacc   2040
ttcgatcttg ggggctata tgaagcaatc gaggagtgcc tgattaatga tccctgggtt   2100
ttgcttaatg catcttggtt caactccttc ctcacacatg cactgaagta g             2151

<210> SEQ ID NO 50
<211> LENGTH: 716
<212> TYPE: PRT
<213> ORGANISM: Influenza A virus

<400> SEQUENCE: 50

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asp Glu Arg Gly Glu Ser Ile Ile Val Glu
        50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320
```

-continued

Asn Ile Val Lys Pro His Gly Lys Gly Ile Asn Pro Asn Tyr Leu Met
            325                 330                 335

Ala Trp Lys Gln Val Leu Ala Glu Leu Gln Asp Ile Glu Asn Glu Glu
        340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
        370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
        450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
        610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
        690                 695                 700

Ser Trp Phe Asn Ser Phe Leu Thr His Ala Leu Lys
705                 710                 715

<210> SEQ ID NO 51
<211> LENGTH: 699
<212> TYPE: DNA

<213> ORGANISM: Influenza A virus

<400> SEQUENCE: 51

```
atggaagact tgtgcgaca atgcttcaat ccaatgatcg tcgagcttgc ggaaaaggca      60
atgaaagaat atggggaaga tcc <210> SEQ ID NO 53
<211> LENGTH: 2233
<212> TYPE: RNA
<213> ORGANISM: Influenza A virus

<400> SEQUENCE: 53

| | | | | | |
|---|---|---|---|---|---|
| aguagaaaca | agguacuuuu | uuggacagua | uggauagcaa | auaguagcau | ugccacaacu | 60 |
| acuucaaugc | augugucaag | aacgaguuga | accaugaugc | auuuaacaaa | acccagggau | 120 |
| cauuaaucaa | gcacuccucg | auugcuucau | auaacccccc | uaaaucgaag | guuccagguu | 180 |
| ccaaguuguc | ccuuaaugcc | ugaacaauca | auaacaauuu | ucucgauuca | gccgaaaacc | 240 |
| ccucuaauug | uggugacgca | auaaaugagu | ugaauacuga | uuuugccaau | aaggucccugc | 300 |
| acacuuuccc | aauugagccu | uccuccacuc | cccuggguga | cucuccgauu | ggccauguuu | 360 |
| ccgauuuguu | uucaaagaau | uccugguca | ugucuuucuc | uuugacugau | gacucggccu | 420 |
| caaucaucga | cucaaucugc | uguaaugacu | guaauaagca | gcgccucauu | uccaugcccc | 480 |
| auuucaucuu | gaucuucgag | guuccauugg | uucucacaua | uaagaacaug | ggccucgaca | 540 |
| cuuggccuau | cgcaguccuc | aacaacaugu | cccuauuuu | uaaaacacag | uauuuuuccc | 600 |
| auuugugugg | uccaaucuc | gggcaguca | augagaacuc | cauugauaca | aaguucacca | 660 |
| caucaguauc | auuucucaaa | ugugaccuuc | cuuuauaau | gaacccauac | aaguuuguuu | 720 |
| uccgucuucc | uucuuugguc | cuacauuucg | auaucauugg | gaucaacuga | aagucaucca | 780 |
| uggcugcaca | cgaugcauuc | aacaaggccg | uauuuaugua | cacucccuuc | auuauguauu | 840 |
| caguagcccu | gcagugcgac | acuucugcug | uaaaauaguu | ccuccucauc | gaugcgauau | 900 |
| guucaaucgg | ggcaacaucu | ucuccuauuu | caucuaauuc | uauccacgau | gaaucaguca | 960 |
| auucacaugc | cuuauugaau | ucauuuugga | cccacgaugc | uaaugaucug | ggcucuggcu | 1020 |
| caucugagc | auacguuuu | aagcuccaa | caucuuugca | gucaucaaag | ucuacuuuu | 1080 |
| cuggugccau | auuucacccc | aaugcccacu | ucaaugcga | uguucucuuc | auguucuug | 1140 |
| uccuugggau | cuucucuuca | uuuucaaugu | ccguaacuc | ugcuaacacu | ugcuuccaag | 1200 |
| ccaucaagua | auugggauuu | augccuuucc | caugugguuu | gacuauguua | ggcucuuucc | 1260 |
| agccaaagaa | ugcuucaug | cauuugauug | caucauauaa | ugguauuccc | uccccucgu | 1320 |
| gugacggguc | uucaauugau | aauuucaaag | cauccaucaa | caagaacuuu | gaccgcugau | 1380 |
| ggcauaaagg | cccaucaggc | aaucucaagg | ggcguggugu | cguccucaag | aauggucaa | 1440 |
| uuuggcguu | cacucuuuu | gacauuugcg | auaacuugcc | cucaaugcag | ccgucggcu | 1500 |
| cgaauccauc | uacauaggcu | cuaaaguuuu | cuaacgacga | aaguucggu | ggcaaugauu | 1560 |
| ggucggcuaa | cuugcgcaua | guccuguaa | ucucaaauuu | ucuucaauu | gucucuucgc | 1620 |
| cucuuuccga | cugacgaaac | gaaucccaua | augaccuuga | ggccauucu | ugucuuauag | 1680 |
| ugaauaaccu | aguuugauu | cuugcccucg | acuucgcu | uaagguguag | uccgcuuggu | 1740 |
| uggccaucuc | cucuccagug | aaugaaaaga | ugugaaugug | ugucuucucu | gauuuauuu | 1800 |
| uguuggcuuu | cucuaaguaa | uauauggga | cuucccuccg | uguuacucca | auucaauga | 1860 |
| accgguucuc | uuuguaauca | uacaaaucag | guaaaauuu | aggcuucucu | accccuguug | 1920 |
| uguuacauau | ugaguucacc | acugucagg | ccaugauucg | gucucuuccu | ucauuaucu | 1980 |
| caaaucgguug | cuucaauaau | gcaucgggu | caccugauuc | uacaauuauu | gauucacccc | 2040 |
| guucgucgau | gaaauggaaa | uccgaauaca | ugaaacaaac | uuccaaaugu | gugcauauug | 2100 |

| | |
|---|---:|
| cagcaaacuu guuaguuucg auuuucggau cuuccccaua uucuuucauu gccuuuuccg | 2160 |
| cuaacucgac gaucauugga uugaagcauu gucgcacaaa gucuuccauu uuggaucagu | 2220 |
| accugcuuuc gcu | 2233 |

<210> SEQ ID NO 54
<211> LENGTH: 2151
<212> TYPE: DNA
<213> ORGANISM: Influenza A virus

<400> SEQUENCE: 54
atggaagact ttgtgcgaca atgcttcaat ccaatgatcg tcgagttagc ggaaaaggca 60
atgaaagaat atggggaaga tccgaaaatc gaaactaaca agtttgctgc aatatgcaca 120
catttggaag tttgtttcat gtattcggat ttccatttca tcgacgaacg gggtgaatca 180
ataattgtag aatcaggtga cccgaatgca ttattgaagc accgatttga gataattgaa 240
ggaagagacc gaatcatggc ctggacagtg gtgaactcaa tatgtaacac aacaggggta 300
gagaagccta aatttttacc tgatttgtat gattacaaag agaaccggtt cattgaaatt 360
ggagtaacac ggagggaagt ccacatatat tacttagaga aagccaacaa aataaaatca 420
gagaagacac acattcacat cttttcattc actggagagg agatggccac caaagcggac 480
tacaccttag acgaagagtc gagggcaaga atcaaaacta ggttattcac tataagacaa 540
gaaatggcct caaggtcatt atgggattcg tttcgtcagt cggaaagagg cgaagagaca 600
attgaagaaa aatttgagat tacaggaact atgcgcaagt tagccgacca atcattgcca 660
ccgaacttct cgtcgttaga aaactttaga gcctatgtag atggattcga gccgaacggc 720
tgcattgagg gcaagttatc gcaaatgtca aaagaagtga acgccaaaat tgaaccattc 780
ttgaggacga caccacgccc cttgagattg cctgatgggc ctttatgcca tcagcggtca 840
aagttcttgt tgatggatgc tttgaaatta tcaattgaag acccgtcaca cgagggggag 900
ggaataccat tatatgatgc aatcaaatgc atgaagacat tctttggctg gaaagagcct 960
aacatagtca aaccacatgg gaaaggcata aatcccaatt acttgatggc ttggaagcaa 1020
gtgttagcag agttacagga cattgaaaat gaagagaaga tcccaaggac aaagaacatg 1080
aagagaacat cgcaattgaa gtgggcattg ggtgaaaata tggcaccaga aaaagtagac 1140
tttgatgact gcaaagatgt tggagactta aaacagtatg actcagatga gccagagccc 1200
agatcattag catcgtgggt ccaaaatgaa ttcaataagg catgtgaatt gactgattca 1260
tcgtggatag aattagatga aataggagaa gatgttgccc cgattgaaca tatcgcatcg 1320
atgaggagga actattttac agcagaagtg tcgcactgca gggctactga atacataatg 1380
aagggagtgt acataaatac ggccttgttg aatgcatcgt gtgcagccat ggatgacttt 1440
cagttgatcc caatgatatc gaaatgtagg accaaagaag gaagacggaa aacaaacttg 1500
tatgggttca ttataaaagg aaggtcacat ttgagaaatg atactgatgt ggtgaacttt 1560
gtatcaatgg agttctcatt gactgacccg agattggagc cacacaaatg ggaaaaatac 1620
tgtgttttag aaataggaga catgttgttg aggactgcga taggccaagt gtcgaggccc 1680
atgttcttat atgtgagaac caatggaacc tcgaagatca agatgaaatg gggcatggaa 1740
atgaggcgct gcttattaca gtcattacag cagattgagt cgatgattga ggccgagtca 1800
tcagtcaaag agaaagacat gaccaaggaa ttctttgaaa acaaatcgga aacatggcca 1860
atcggagagt cacccagggg agtggaggaa ggctcaattg ggaaagtgtg caggacctta 1920

-continued

```
ttggcaaaat cagtattcaa ctcattatat gcgtcaccac aattagaggg gttttcggct      1980
gaatcgagaa aattgttatt gattgttcag gcattaaggg acaacttgga acctggaacc      2040
ttcgatttag gggggttata tgaagcaatc gaggagtgct tgattaatga tccctgggtt      2100
ttgttaaatg catcatggtt caactcgttc ttgacacatg cattgaagta g               2151
```

<210> SEQ ID NO 55
<211> LENGTH: 716
<212> TYPE: PRT
<213> ORGANISM: Influenza A virus

<400> SEQUENCE: 55

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Gly Lys Gly Ile Asn Pro Asn Tyr Leu Met
                325                 330                 335
```

```
Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715

<210> SEQ ID NO 56
<211> LENGTH: 699
<212> TYPE: DNA
<213> ORGANISM: Influenza A virus

<400> SEQUENCE: 56
```

```
atggaagact tgtgcgaca atgcttcaat ccaatgatcg tcgagttagc ggaaaaggca      60
atgaaagaat atggggaaga tccgaaaatc gaaactaaca agtttgctgc aatatgcaca     120
catttggaag tttgtttcat gtattcggat ttccatttca tcgacgaacg gggtgaatca     180
ataattgtag aatcaggtga cccgaatgca ttattgaagc accgatttga gataattgaa     240
ggaagagacc gaatcatggc ctggacagtg gtgaactcaa tatgtaacac aacaggggta     300
gagaagccta aattttacc tgatttgtat gattacaaag agaaccggtt cattgaaatt      360
ggagtaacac ggagggaagt ccacatatat tacttagaga agccaacaa aataaaatca      420 gagaagacac acattcacat cttttcattc actggagagg agatggccac caaagcggac     480
tacaccttag acgaagagtc gagggcaaga atcaaaacta ggttattcac tataagacaa     540
gaaatggcct caaggtcatt atgggattcg ttcgtcagtc ggaaagaggc gaagagacaa     600
ttgaagaaaa atttgagatt acaggaacta tgcgcaagtt agccgaccaa tcattgccac     660
cgaacttctc gtcgttagaa aactttagag cctatgtag                             699
```

<210> SEQ ID NO 57
<211> LENGTH: 213
<212> TYPE: PRT
<213> ORGANISM: Influenza A virus

<400> SEQUENCE: 57

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Val
            180                 185                 190

Ser Arg Lys Glu Ala Lys Arg Gln Leu Lys Lys Asn Leu Arg Leu Gln
        195                 200                 205

Glu Leu Cys Ala Ser
    210
```

<210> SEQ ID NO 58
<211> LENGTH: 2341
<212> TYPE: RNA

<213> ORGANISM: Influenza A virus

<400> SEQUENCE: 58

```
aguagaaaca aggucguuuu uaaacaauuc gacacuaauu gauggccauc cgaauucuuu      60
uggucgcugu cuggcuguca guaaguaugc uagagucccg uuuucguuuc auuaccaaca     120
cuacgucccc uugcccaauu agcacauuag ccuucucucc uuuugcaaga uugcucaguu     180
cauugaugcu uaaugcuggg ccauaucucu ugucuucuuu gcccaaaaug agaaauccuc     240
ucaggacagc agacuccacc ccagaugugc cuucaucugg aucuucaguc aaugcaccug     300
cauccuuucc aagaacugua agucguuugg ugccuuguu guaauugaau acuggagaau      360
ugccucuuac caguauccuc aacccugauc cucucacauu cacagucaau gaggaaaauu     420
gcauccuacu cuguucuggu ggagcagcag caaaggggag aaguuuuauu auuuggacag     480
ugucaaaugu cccaagcaca ucccgcauuu gcuggaacag uguccuuacg aauccacugu     540
accggcuucu gguugccuua gggacaagag acugaaaugg uucaaauucc auuuuguugu     600
auaacauugu gggaucuugu gaccauugaa uuuucacaau ucccaguuc cugauuaucc      660
auugauaagu guugcuagc acugacucag ggccauugau cucccacauc auugaugacg      720
aauaaguuau ugcaacuuc ucaguccuu gcguuucacu gacuucuucg ggagacaaua       780
auacguuccc ucuuugaucu cuaacccuua aaaaucgguc aauacucacu accacucucu     840
ccgugcugga guauucaucu acucccauuu ugcugacucu uaucccucuc agcgacaucu     900
ccgugcuugg ggucaugucg ggcaguauuc cgaucauucc caucacauug ucgauggauu     960
caauucccca guucuggaaa agcacuuuug caucuuuug gaaaugccuc aagaguuggu    1020
gcauggggu cagucgcugg uuugcccuau ugacaaaguu cagaucgccc cuaacugccu    1080
ugaucaugca auccucugu gagaauacca uggccacaau uauugccuca gcaauugacu    1140
gcucgucucu cccgcuuacu aucaacugga ucaaucuccu gguugccuuu cugagaauag    1200
cuguugcucu ucucccaacc auugugaauu cuucauaccc ucauguacu cuuauuuuca     1260
guguuuggag uugcccguu agcacuucuu cuucuuucuu gacugaugau ccgcuugucc    1320
uuuugaaagu gaacccacca aaacugaaag augagcuaau ccucaacccu auugcugccu    1380
ugcauaugucu uacggcuugu uccucaguug gauucugucu aaggaugucc accauccuua    1440
cuccuccaau cuguguugcug uggcacauuu ccaagagaga ugcuaauggg ucugcugaca    1500
cugcugcucu ucuuacuaug uuucuagcag cgauaaucaa acuuggucaa acaucaucau     1560
uucucacuuc uccuccugga guguacaucu gcuccagca cguucccugg guuaagugca     1620
acacuucaau auaaacacug ccuguuccgc cggcuacugg gagaaaccuu guuuuacgga    1680
ccaauucucu uucuagcaug uacgccacca ucaagggagc aauuuuacaa uccuggagcu    1740
cuucuuucuu cucuuuuguu auugccauuu gacucuga ugcaguauu cugcccca         1800
cuucauuugg gaaacaacu uccauaauca cauccugugc cuccuuggca cugagaucug      1860
cauggccagg guuguauca acucuccccc uuauuuuaac uugauuucug aaguggacag     1920
ggccgaaggu accauguuuc aaccuuucga ccuuuucgaa auaaguuuua uauaccuuag    1980
gguaaugaac uguacuuguu guuggccau uccuauucca ccauguuacg gccgagggug      2040
auaccaucac ucggucugau ccagcaucgu uguuuugcu ccagagggu ugccuuguu        2100
cauuccucuc uggaaucaug uccauuauca ucugucugc uguaauggg uaucucauug       2160
ccaucaucca cuucauucug agucgggu ucuucucuu ccuuccugau guguacuuuu        2220
ugauuauggc cauaugguc cacaguggucu uagugaguau cucgcgagug cgggacugcg    2280
```

```
acauuagauc ucucaguucu uuuauucucu ccauauugaa uauauuugac cugcuuucgc    2340
u                                                                   2341

<210> SEQ ID NO 59
<211> LENGTH: 2280
<212> TYPE: DNA
<213> ORGANISM: Influenza A virus

<400> SEQUENCE: 59
atggagagaa taaagaaact gagagatcta atgtcgcagt cccgcactcg cgagatactc      60
actaagacca ctgtggacca tatggccata atcaaaaagt acacatcagg aaggcaagag     120
aagaaccccg cactcagaat gaagtggatg atggcaatga datacccaat tacagcagac     180
aagagaataa tggacatgat tccagagagg aatgaacaag acaaaccct ctggagcaaa      240 acaaacgatg ctggatcaga ccgagtgatg gtatcacctc tggccgtaac atggtggaat     300
aggaatggcc caacaacaag tacagttcat taccctaagg tatataaaac ttatttcgaa     360
aaggtcgaaa ggttgaaaca tggtaccttc ggccctgtcc acttcagaaa tcaagttaaa     420
ataaggagga gagttgatac aaaccctggc catgcagatc tcagtgccaa ggaggcacag     480
gatgtgatta tggaagttgt tttcccaaat gaagtggggg caagaatact gacatcagag     540
tcacaaatgg caataacaaa agaagagaaa gaagagctcc aggattgtaa aattgctccc     600
ttgatggtgg cgtacatgct agaaagagaa ttggtccgta aaacaaggtt tctcccagta     660
gccggcggaa caggcagtgt ttatattgaa gtgttgcact taacccaagg gacgtgctgg     720
gagcagatgt acactccagg aggagaagtg agaaatgatg atgttgacca agtttgatt      780 atcgctgcta gaaacatagt aagaagagca gcagtgtcag cagacccatt agcatctctc     840
ttggaaatgt gccacagcac acagattgga ggagtaagga tggtggacat ccttagacag     900
aatccaactg aggaacaagc cgtagacata tgcaaggcag caatagggt gaggattagc      960 tcatctttca gttttggtgg gttcactttc aaaaggacaa gcggatcatc agtcaagaaa    1020
gaagaagaag tgctaacggg caacctccaa acactgaaaa taagagtaca tgaagggtat    1080
gaagaattca caatggttgg gagaagagca acagctattc tcagaaaggc aaccaggaga    1140
ttgatccagt tgatagtaag cgggagagac gagcagtcaa ttgctgaggc aataattgtg    1200
gccatggtat tctcacaaga ggattgcatg atcaaggcag ttaggggcga tctgaacttt    1260
gtcaataggg caaaccagcg actgaacccc atgcaccaac tcttgaggca tttccaaaaa    1320
gatgcaaaag tgcttttcca gaactgggga attgaatcca tcgacaatgt gatgggaatg    1380
atcggaatac tgcccgacat gaccccaagc acggagatgt cgctgagagg ataagagtc     1440 agcaaaatgg gagtagatga atactccagc acggagagag tggtagtgag tattgaccga    1500
tttttaaggg ttagagatca agagggaac gtattattgt ctcccgaaga agtcagtgaa     1560
acgcaaggaa ctgagaagtt gacaataact tattcgtcat caatgatgtg ggagatcaat    1620
ggccctgagt cagtgctagt caacacttat caatggataa tcaggaactg ggaaattgtg    1680
aaaattcaat ggtcacaaga tcccacaatg ttatacaaca aaatggaatt tgaaccattt    1740
cagtctcttg tccctaaggc aaccagaagc cggtacagtg gattcgtaag gacactgttc    1800
cagcaaatgc gggatgtgct tgggacattt gacactgtcc aaataataaa acttctcccc    1860
tttgctgctg ctccaccaga acagagtagg atgcaatttt cctcattgac tgtgaatgtg    1920
agaggatcag ggttgaggat actggtaaga ggcaattctc cagtattcaa ttacaacaag    1980
```

```
gcaaccaaac gacttacagt tcttggaaag gatgcaggtg cattgactga agatccagat    2040
gaaggcacat ctggggtgga gtctgctgtc ctgagaggat ttctcatttt gggcaaagaa    2100
gacaagagat atgcccagc attaagcatc aatgaactga gcaatcttgc aaaaggagag     2160
aaggctaatg tgctaattgg gcaaggggac gtagtgttgg taatgaaacg aaaacgggac    2220
tctagcatac ttactgacag ccagacagcg accaaaagaa ttcggatggc catcaattag    2280
```

<210> SEQ ID NO 60
<211> LENGTH: 759
<212> TYPE: PRT
<213> ORGANISM: Influenza A virus

<400> SEQUENCE: 60

```
Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Arg Tyr Pro Ile Thr Ala Asp Lys Arg Ile Met
    50                  55                  60

Asp Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Val His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Thr Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Met Ala Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Gly Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Val Arg Met Val Asp Ile Leu Arg Gln Asn Pro Thr Glu
    290                 295                 300

Glu Gln Ala Val Asp Ile Cys Lys Ala Ala Ile Gly Leu Arg Ile Ser
305                 310                 315                 320

Ser Ser Phe Ser Phe Gly Gly Phe Thr Phe Lys Arg Thr Ser Gly Ser
```

```
            325                 330                 335
Ser Val Lys Lys Glu Glu Val Leu Thr Gly Asn Leu Gln Thr Leu
            340                 345                 350
Lys Ile Arg Val His Glu Gly Tyr Glu Glu Phe Thr Met Val Gly Arg
            355                 360                 365
Arg Ala Thr Ala Ile Leu Arg Lys Ala Thr Arg Leu Ile Gln Leu
            370                 375             380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
                435                 440                 445
Trp Gly Ile Glu Ser Ile Asp Asn Val Met Gly Met Ile Gly Ile Leu
            450                 455                 460
Pro Asp Met Thr Pro Ser Thr Glu Met Ser Leu Arg Gly Ile Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Val Leu
            500                 505                 510
Leu Ser Pro Glu Glu Val Ser Glu Thr Gln Gly Thr Glu Lys Leu Thr
                515                 520                 525
Ile Thr Tyr Ser Ser Ser Met Met Trp Glu Ile Asn Gly Pro Glu Ser
            530                 535                 540
Val Leu Val Asn Thr Tyr Gln Trp Ile Ile Arg Asn Trp Glu Ile Val
545                 550                 555                 560
Lys Ile Gln Trp Ser Gln Asp Pro Thr Met Leu Tyr Asn Lys Met Glu
                565                 570                 575
Phe Glu Pro Phe Gln Ser Leu Val Pro Lys Ala Thr Arg Ser Arg Tyr
            580                 585                 590
Ser Gly Phe Val Arg Thr Leu Phe Gln Gln Met Arg Asp Val Leu Gly
                595                 600                 605
Thr Phe Asp Thr Val Gln Ile Ile Lys Leu Leu Pro Phe Ala Ala Ala
            610                 615                 620
Pro Pro Glu Gln Ser Arg Met Gln Phe Ser Ser Leu Thr Val Asn Val
625                 630                 635                 640
Arg Gly Ser Gly Leu Arg Ile Leu Val Arg Gly Asn Ser Pro Val Phe
                645                 650                 655
Asn Tyr Asn Lys Ala Thr Lys Arg Leu Thr Val Leu Gly Lys Asp Ala
                660                 665                 670
Gly Ala Leu Thr Glu Asp Pro Asp Glu Gly Thr Ser Gly Val Glu Ser
            675                 680                 685
Ala Val Leu Arg Gly Phe Leu Ile Leu Gly Lys Glu Asp Lys Arg Tyr
            690                 695             700
Gly Pro Ala Leu Ser Ile Asn Glu Leu Ser Asn Leu Ala Lys Gly Glu
705                 710                 715                 720
Lys Ala Asn Val Leu Ile Gly Gln Gly Asp Val Val Leu Val Met Lys
                725                 730                 735
Arg Lys Arg Asp Ser Ser Ile Leu Thr Asp Ser Gln Thr Ala Thr Lys
            740                 745                 750
```

Arg Ile Arg Met Ala Ile Asn
      755

<210> SEQ ID NO 61
<211> LENGTH: 2341
<212> TYPE: RNA
<213> ORGANISM: Influenza A virus

<400> SEQUENCE: 61

| | | | | | |
|---|---|---|---|---|---|
| aguagaaaca | aggcauuuuu | ucaugaagga | caaguuaaau | ucauuauuuu | ugccgucuga | 60 |
| guucuucaau | gguggaacag | aucuucauga | ucucagagaa | cucucucuuc | uugauccguc | 120 |
| cagacucgaa | gucgacccug | gcaucaaucc | gggcccuaga | caccauggcc | uccaccaugc | 180 |
| uagaaauucc | aaccggucuc | cuauaugaac | ugcuagggaa | aaauuucucg | aauagauugc | 240 |
| agcacuucug | guacaucugu | ucauccucaa | gaauuccccu | uggcuugug | uugagaauag | 300 |
| aacgauuccu | cuugggaauc | caggaaugug | uaguugcaac | ggcaucauau | uccaugcuuu | 360 |
| uggcuggacc | augggcuggc | auuaccacag | cauuguuuac | agaaucaauc | ucuuuaugac | 420 |
| ugacaaaggg | auucagggga | uuacaaaguc | uuccccgaua | ucaucaucc | auuagcuccc | 480 |
| auuuuaagca | gacuucagga | augugaagau | uccguauauu | guauaaguuu | gguccuccau | 540 |
| cugauacuaa | uagcccuacc | uuugauuggg | uuugauccca | cagcuucuuu | aacucaaaug | 600 |
| aucuucucgu | cugaauuugu | gugucucccc | uauggcaccu | auauguguau | cuguagucuu | 660 |
| ugaugaacaa | uugaagagcc | aucugggccg | ugcaggucc | aaggucauug | uuuaucaugu | 720 |
| uguucuuuau | cacuguuacu | ccaauacuca | ugucagcuga | ucauuuacu | ccagacacuc | 780 |
| caaagcuggg | uagcuccaug | cuaaaauuag | ccacaaauuc | cuagcgauaa | aaaaagcuug | 840 |
| ugaauucaaa | ugucccuguc | uuauuuauau | aggacuucuu | uuugcucaug | uugauuccca | 900 |
| cuaacuugca | gguccuguag | aaucugucca | cuccugcuug | uauucccuca | ugguuuggug | 960 |
| cauucacuau | gagagcaaaa | ucgucggaug | auuggagccc | auccaccag | uauauugucu | 1020 |
| uggguauuu | cuuuugucca | agauucagua | ucgagacucc | caagaccgua | cuuagcaugu | 1080 |
| ugaacaugcc | caucaucauc | ccaggacuca | gugaugcugu | gccaucuauu | agaagaggcc | 1140 |
| uuauuuucuc | aauuucuuc | uuuguugauu | cauugaagua | cuucagguca | augcuugcua | 1200 |
| gcauuucugc | ugguauuugu | guucgaauc | ucauucuuuu | acucucgaac | auguacccuu | 1260 |
| ucccuagucu | ugccauuuug | uuugagaaca | uuaugggugc | caugcucagg | auguuucuga | 1320 |
| accacucggg | uugauuucug | gugauauaug | uaaucaucgc | caggaacauu | cgaggauuuu | 1380 |
| gauuucauu | ccacuuagug | uugccccag | ugauugugaa | agaaaucucu | gugucuugug | 1440 |
| aauuagucau | caucuuucuc | acaacauuug | ccaguuggc | cuucuuuuca | uugccccua | 1500 |
| cugggagccc | agacuguuca | agcuuuucgc | aaaugcuccu | agcuaaaguu | caacaaagu | 1560 |
| auacgaaacc | ucuaaucgc | aucccaggug | uugcgauagc | ccuucuuuuu | aacuugccuc | 1620 |
| ucucugcauc | uuuggucauc | guauuuaaug | ucagggcucu | auuagauag | ccucucuauu | 1680 |
| ucagucuuug | uuuuucuuc | ccuauuguuc | uuugcgugac | caucuucuug | gucauguugu | 1740 |
| cucuuacucu | ccuuuucuu | ugaaaguggg | uuguuaucuc | uauuccucu | uguucauug | 1800 |
| auuccauuac | auccuuuaag | aaaucuauua | gccuuccuga | cucauuagcu | guuaggccau | 1860 |
| ucgaucuaaa | gacucuaug | uguuggcca | augcaguugc | ugccgguuga | uuucuguuua | 1920 |
| auguccaauc | auaagucugg | cgaccuugag | uuaguuuauc | uacccuuguu | uguugaacaa | 1980 |
| cuuccauugu | uucaaggcau | gaauucucaa | auauuccugg | gugggauucu | ucaaggaaag | 2040 |

| | | |
|---|---|---|
| ccauagccuc uagaacacag ucuguuugug cauacccacu ugguucauua uccucaggua | | 2100 |
| gugguccauc aaucggguug agcuggggug caccagucuc uguguuuguc guccacuuuc | | 2160 |
| ccuuuucuga guauuggugu guucuguuua cuguguccau gguguauccu guuccuguuc | | 2220 |
| cauggcugua uggaggaucu ccaguauaag ggaauguggu gcuuauggca uuugcgcug | | 2280 |
| gaauuuuuaa gaaaaguaga gucggauuga cauccauuca aaugguuugc cugcuuucgc | | 2340 |
| u | | 2341 |

<210> SEQ ID NO 62
<211> LENGTH: 2274
<212> TYPE: DNA
<213> ORGANISM: Influenza A virus

<400> SEQUENCE: 62

| | | |
|---|---|---|
| atggatgtca atccgactct acttttctta aaaattccag cgcaaaatgc cataagcacc | | 60 |
| acattcccctt atactggaga tcctccatac agccatggaa caggaacagg atacaccatg | | 120 |
| gacacagtaa acagaacaca ccaatactca gaaaagggaa agtggacgac aaacacagag | | 180 |
| actggtgcac cccagctcaa cccgattgat ggaccactac ctgaggataa tgaaccaagt | | 240 |
| gggtatgcac aaacagactg tgttctagag gctatggctt tccttgaaga atcccaccca | | 300 |
| ggaatatttg agaattcatg ccttgaaaca atggaagttg ttcaacaaac aagggtagat | | 360 |
| aaactaactc aaggtcgcca gacttatgat ggacattaa acagaaatca accggcagca | | 420 |
| actgcattgg ccaacaccat agaagtcttt agatcgaatg gcctaacagc taatgagtca | | 480 |
| ggaaggctaa tagatttctt aaaggatgta atggaatcaa tgaacaaaga ggaaatagag | | 540 |
| ataacaaccc actttcaaag aaaaaggaga gtaagagaca catgaccaa gaagatggtc | | 600 |
| acgcaaagaa caatagggaa gaaaaacaa agactgaata agagaggcta tctaataaga | | 660 |
| gccctgacat taaatacgat gaccaaagat gcagagagag caagttaaa aagaagggct | | 720 |
| atcgcaacac ctgggatgca gattagaggt ttcgtatact tgttgaaac tttagctagg | | 780 |
| agcatttgcg aaaagcttga acagtctggg ctcccagtag ggggcaatga aaagaaggcc | | 840 |
| aaactggcaa atgttgtgag aaagatgatg actaattcac aagacacaga gatttctttc | | 900 |
| acaatcactg ggacaacac taagtggaat gaaaatcaaa atcctcgaat gttcctggcg | | 960 |
| atgattacat atatcaccag aaatcaaccc gagtggttca gaaacatcct gagcatggca | | 1020 |
| cccataatgt tctcaaacaa atggcaagac taggaaag ggtacatgtt cgagagtaaa | | 1080 |
| agaatgaaga ttcgaacaca ataccagca gaaatgctag caagcattga cctgaagtac | | 1140 |
| ttcaatgaat caacaaagaa gaaaattgag aaaataaggc ctcttctaat agatggcaca | | 1200 |
| gcatcactga gtcctgggat gatgatgggc atgttcaaca tgctaagtac ggtcttggga | | 1260 |
| gtctcgatac tgaatcttgg acaaaagaaa tacaccaaga caatatactg gtgggatggg | | 1320 |
| ctccaatcat ccgacgattt tgctctcata gtgaatgcac caaaccatga gggaatacaa | | 1380 |
| gcaggagtgg acagattcta caggacctgc aagttagtgg aatcaacat gagcaaaaag | | 1440 |
| aagtcctata taataagac agggacattt gaattcacaa gctttttta tcgctatgga | | 1500 |
| tttgtggcta tttttagcat ggagctaccc agctttgag tgtctggagt aaatgaatca | | 1560 |
| gctgacatga gtattggagt aacagtgata agaacaaca tgataaacaa tgaccttgga | | 1620 |
| cctgcaacgg cccagatggc tcttcaattg ttcatcaaag actacagata cacatatagg | | 1680 |
| tgccataggg gagacacaca aattcagacg agaagatcat ttgagttaaa gaagctgtgg | | 1740 |

-continued

```
gatcaaaccc aatcaaaggt agggctatta gtatcagatg gaggaccaaa cttatacaat    1800
atacggaatc ttcacattcc tgaagtctgc ttaaaatggg agctaatgga tgatgattat    1860
cggggaagac tttgtaatcc cctgaatccc tttgtcagtc ataaagagat tgattctgta    1920
aacaatgctg tggtaatgcc agcccatggt ccagccaaaa gcatggaata tgatgccgtt    1980
gcaactacac attcctggat tcccaagagg aatcgttcta ttctcaacac aagccaaagg    2040
ggaattcttg aggatgaaca gatgtaccag aagtgctgca atctattcga gaattttttc    2100
cctagcagtt catataggag accggttgga atttctagca tggtggaggc catggtgtct    2160
agggcccgga ttgatgccag ggtcgacttc gagtctggac ggatcaagaa agaagagttc    2220
tctgagatca tgaagatctg ttccaccatt gaagaactca gacggcaaaa ataa           2274
```

<210> SEQ ID NO 63
<211> LENGTH: 757
<212> TYPE: PRT
<213> ORGANISM: Influenza A virus

<400> SEQUENCE: 63

```
Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285
```

```
Met Met Thr Asn Ser Gln Asp Thr Glu Ile Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
            340                 345                 350

Lys Gly Tyr Met Phe Glu Ser Lys Arg Met Lys Ile Arg Thr Gln Ile
        355                 360                 365

Pro Ala Glu Met Leu Ala Ser Ile Asp Leu Lys Tyr Phe Asn Glu Ser
370                 375                 380

Thr Lys Lys Lys Ile Glu Lys Ile Arg Pro Leu Leu Ile Asp Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Lys Lys Tyr Thr
                420                 425                 430

Lys Thr Ile Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Val Asn Glu Ser Ala Asp Met Ser Ile Gly Val Thr
        515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Val Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Asp Tyr Arg Gly Arg Leu
610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
        690                 695                 700
```

Tyr Arg Arg Pro Val Gly Ile Ser Ser Met Val Glu Ala Met Val Ser
705                 710                 715                 720

Arg Ala Arg Ile Asp Ala Arg Val Asp Phe Glu Ser Gly Arg Ile Lys
            725                 730                 735

Lys Glu Glu Phe Ser Glu Ile Met Lys Ile Cys Ser Thr Ile Glu Glu
            740                 745                 750

Leu Arg Arg Gln Lys
        755

<210> SEQ ID NO 64
<211> LENGTH: 36
<212> TYPE: DNA
<213> ORGANISM: Influenza A virus

<400> SEQUENCE: 64
atggaacagg aacaggatac accatggaca cagtaa                        36

<210> SEQ ID NO 65
<211> LENGTH: 11
<212> TYPE: PRT
<213> ORGANISM: Influenza A virus

<400> SEQUENCE: 65

Met Glu Gln Glu Gln Asp Thr Pro Trp Thr Gln
1               5                   10

<210> SEQ ID NO 66
<211> LENGTH: 1777
<212> TYPE: RNA
<213> ORGANISM: Influenza A virus

<400> SEQUENCE: 66
aguagaaaca agggguguuuu ucucaugcuu cugaaauccu aauguuaaau acauauucua    60
cacuguagag acccauuaga gcacauccag aaacugauug ccccaggga gacuaccagu     120 accaaugaac uggcgacagu ugaauagauc gccaaaaucu gguaaauccu guugauucc     180 agcuuuaccc caucuauuuc uucucuguuu aauuuugcuu ccucugagua uuuugggguag   240 ucauaagucc cauuuuugac acuuuccaug cacguguuau cgcauuugug guaaaauuca    300
aagcagccgu uccaauuuc cuggcauug uuuuuuagcu ggcuucuuac cuuucauau       360 aaguucuuca cauuugaauc guggguagucc aaaguucuuu cauuuccaa uagaaccaac    420 aguucggcau uguaagucca aauuccaagg aaaccaucau caacuuuuuu auuuaaauuc    480
ucuauucuuu uuuccaggug guugaacucu uuaccacug cuguguaacug uguauucauc   540 uuuucaauaa cagaauuuac uuguuuaugua aucucgucaa uggcauucug guugcucuuc   600
aggucggcug cauauccuga ccccugcuca uuuugauggu gauaaccgua ccauccaucu    660 accauccccug uccaccccc uucaaugaaa ccggcaaugg ccccaaaauag gcucucuagau  720 ugaauagacg ggacauuccu caauccugug gccagucuca auuugugcu uuuuacauau    780 uuggacauu uccaauugu gaucggaugu auaauucgaa augggaggcu ggguguuaua     840 gcacccuuggg gugucugaca aguuguaauu gcaaucgugga cugguguauc ugaaaugaua   900
auaccagauc cagcauuucu uuccauggcg aaugcauauc ucggguaccac uagauuucca    960 guugcuucga auguuauuu ugucucccggc ucuacuaguug uccaguaaua guucauucuc   1020
cccucuugau cccucacuuu gggcuuauau gcuauuccg gcuugaacuu cuugcuguau     1080
cuugaugacc ccacaaaaac auaugcaucu gcauucugau agagacuuug uuggucagca    1140

| | |
|---|---:|
| cuaguagaug gauggugaau gccccauagc acgaggacuu cuuucccuuu aucauuaaug | 1200 |
| uaggauuugc ugagcuuugg guaugaauuu ccuuuuuuaa cuagccauau uaaauuuuug | 1260 |
| uagaagcuuu uugcuccagc augaggacau gcugccguua caccuuuguu cgagucauga | 1320 |
| uugggccaug aacuugucuu ggggaauauc ucaaaccuuu caaaugauga cacugagcuc | 1380 |
| aauugcucuc uuagcucccuc auaaucgaug aaaucuccug gguaacacgu uccauugucu | 1440 |
| gaacuagaug uuuccacaau guaggaccau gagcuugcug uggagaguga uucacacucu | 1500 |
| ggauuuccca ggauccagcc agcaauguua cauuuaccca aaugcaaugg ggcuaccccu | 1560 |
| cuuaguuugc auaguuuccc guuaugcuug ucuucuagaa gguuaacaga gugguguuacu | 1620 |
| guuacauucu uuucuaguac uguguccuaca gugucuguug aauuguucgc augauaaccu | 1680 |
| auacauaaug ugucucauu ugcgguugca aauguauaua gcagaacuac uaguauugcc | 1740 |
| uucauuuuug uugcuuuugu uuuccccugc uuuugcu | 1777 |

<210> SEQ ID NO 67
<211> LENGTH: 1701
<212> TYPE: DNA
<213> ORGANISM: Influenza A virus

<400> SEQUENCE: 67

| | |
|---|---:|
| atgaaggcaa tactagtagt tctgctatat acatttgcaa ccgcaaatgc agacacatta | 60 |
| tgtataggtt atcatgcgaa caattcaaca gacactgtag acacagtact agaaaagaat | 120 |
| gtaacagtaa cacactctgt taaccttcta agagacaagc ataacgggaa actatgcaaa | 180 |
| ctaagagggg tagccccatt gcatttgggt aaatgtaaca ttgctggctg atcctgggga | 240 |
| aatccagagt gtgaatcact ctccacagca agctcatggt cctacattgt ggaaacatct | 300 |
| agttcagaca atggaacgtg ttacccagga gatttcatcg attatgagga gctaagagag | 360 |
| caattgagct cagtgtcatc atttgaaagg tttgagatat cccccaagac aagttcatgg | 420 |
| cccaatcatg actcgaacaa aggtgtaacg gcagcatgtc ctcatgctgg agcaaaaagc | 480 |
| ttctacaaaa atttaatatg gctagttaaa aaaggaaatt catacccaaa gctcagcaaa | 540 |
| tcctacatta atgataaagg aaagaagtc ctcgtgctat ggggcattca ccatccatct | 600 |
| actagtgctg accaacaaag tctctatcag aatgcagatg catatgtttt tgtggggtca | 660 |
| tcaagataca gcaagaagtt caagccggaa atagcaataa gacccaaagt gagggatcaa | 720 |
| gagggagaa tgaactatta ctggacacta gtagagccgg gagacaaaat aacattcgaa | 780 |
| gcaactggaa atctagtggt accgagatat gcattcgcaa tggaaagaaa tgctggatct | 840 |
| ggtattatca tttcagatac accagtccac gattgcaata caacttgtca gacacccaag | 900 |
| ggtgctataa acaccagcct cccatttcag aatatacatc cgatcacaat tggaaaatgt | 960 |
| ccaaaatatg taaaaagcac aaaattgaga ctggccacag gattgaggaa tgtcccgtct | 1020 |
| attcaatcta gaggcctatt tggggccatt gccggtttca ttgaaggggg gtggacaggg | 1080 |
| atggtagatg gatggtacgg ttatcaccat caaaatgagc aggggtcagg atatgcagcc | 1140 |
| gacctgaaga gcacacagaa tgccattgac gagattacta acaaagtaaa ttctgttatt | 1200 |
| gaaaagatga tacacagtt cacagcagta ggtaaagagt caaccaccct ggaaaaaaga | 1260 |
| atagagaatt taaataaaaa agttgatgat ggtttcctgg catttggac ttacaatgcc | 1320 |
| gaactgttgg ttctattgga aaatgaaaga actttggact accacgattc aaatgtgaag | 1380 |
| aacttatatg aaaaggtaag aagccagcta aaaacaatg ccaaggaaat tggaaacggc | 1440 |
| tgctttgaat tttaccacaa atgcgataac acgtgcatgg aaagtgtcaa aatgggact | 1500 |

```
tatgactacc caaaatactc agaggaagca aaattaaaca gagaagaaat agatggggta    1560
aagctggaat caacaaggat ttaccagatt ttggcgatct attcaactgt cgccagttca    1620
ttggtactgg tagtctccct gggggcaatc agtttctgga tgtgctctaa tgggtctcta    1680
cagtgtagaa tatgtattta a                                              1701
```

```
<210> SEQ ID NO 68
<211> LENGTH: 566
<212> TYPE: PRT
<213> ORGANISM: Influenza A virus

<400> SEQUENCE: 68
```

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335
```

-continued

```
Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 69
<211> LENGTH: 1565
<212> TYPE: RNA
<213> ORGANISM: Influenza A virus

<400> SEQUENCE: 69

```
aguagaaaca aggguauuuu uccucaacug ucauacuccu cugcauuguc uccgaagaaa      60
uaagacccuu cauuacucau gucaaaggaa ggcacgaucg gguucguugc cuuuucgucc     120
gagagcucga agacuccccg ccccuggaag gacaaaucuu cuggcuuugc acuuuccauc     180
auucuuauaa cuucuguucg caugucggau guccguccuu cauuguuccc gcugaaugcu     240
gccauaacgg uugcucuuuc aaaagggaga uuccgcugca cugagaaugu aggcugcaca     300
cugaucuggc cugcggaugc cuuuuguuga uugguauuuc cuccacuccu gguccuuaug     360
gcccaguauc ugcuucucag uuccagggua uuggagucca ugguuuccac auucucauuu     420
gaagcaaucu ggaccccucu uguggaaagc uuuccucuug gaaucacuuu cuuuccucuu     480
augaaacuug auacucuuaa aucuucaaau gcagcagagu ggcaugccau ccacaccaau     540
ugacucuugu gagcugggiu uucauuuggc cucaucaggc ugaccacuug gcuguuuugg     600
aguaauuuga augggucuau cccgaccagu gaguacccuu cccuuucaaa gucaugccca     660
cuugcuacug caagcccaua cacacaagca ggcaggcagg auuuaugugc aacugauccc     720
cucagaauga gugcugaccg ugccaggaaa augaggucuu caaucucagc guuuccuggg     780
```

| | |
|---|---:|
| uuucgacuuu cucuuacuug auccaucauu gcccucuggg cagcuguuug aaauuuuccu | 840 |
| uugaggauau ugcacauucu uucauaagca acccuuguuc uucguccauu uucaccccuc | 900 |
| cagaaauuuc ggucauugau uccacguuug aucauucuga uuaacuccau ugcuauuguu | 960 |
| ccaacuccuu ucaccgcagc accugcggca ccagaccuuu ugggaagugu ugaaccuugc | 1020 |
| auuagagagc acauucuggg auccauuccg gugcgaacaa gcgcucuugu ucucugauau | 1080 |
| guggcaucau ucagguugga augccaaauc augauaugaa uaagaccugc uguugcaucu | 1140 |
| ucgccauugu uugcuuggcg ccaaacucuc cuuauuucuu cuuugucaua aaggaugagu | 1200 |
| ucucucaucc acuuuccguc uacucuucua uauauggguc cuccuguuuu cuuagggucc | 1260 |
| uucccagcac uggggaugcuc uucuagguau uuauuucuuc ucucaucaaa agcagaaagc | 1320 |
| accauccucu cuauuguuau gcauucuugg auuagucguc caucauaauc acugaguuug | 1380 |
| aguucagugc acauuuggau guagaaucuc ccgauuccac caaucauucu uccgacagau | 1440 |
| gcucugauuu cuguggcauc cuggcgcucc ccaccagucu ccauuuguuc auaugaucgu | 1500 |
| uuggugccuu gagacgccau ggcuucgaug ucacucauug agugauuauc uacccugcuu | 1560 |
| uugcu | 1565 |

<210> SEQ ID NO 70
<211> LENGTH: 1497
<212> TYPE: DNA
<213> ORGANISM: Influenza A virus

<400> SEQUENCE: 70

| | |
|---|---:|
| atggcgtctc aaggcaccaa acgatcatat gaacaaatgg agactggtgg ggagcgccag | 60 |
| gatgccacag aaatcagagc atctgtcgga gaatgattg gtggaatcgg agattctac | 120 |
| atccaaatgt gcactgaact caaactcagt gattatgatg acgactaat ccagaatagc | 180 |
| ataacaatag agaggatggt gctttctgct tttgatgaga aagaaataa atacctagaa | 240 |
| gagcatccca gtgctgggaa ggaccctaag aaaacaggag gacccatata tagaagagta | 300 |
| gacggaaagt ggatgagaga actcatcctt tatgacaaag aagaaataag agagtttggg | 360 |
| cgccaagcaa acaatggcga agatgcaaca gcaggtctta ctcatatcat gatttggcat | 420 |
| tccaacctga tgatgccac atatcagaga acaagagcgc ttgttcgcac cggaatggat | 480 |
| cccagaatgt gctctctaat gcaaggttca acacttccca gaaggtctgg tgccgcaggt | 540 |
| gctgcggtga aggagttgg aacaatagca atggagttaa tcagaatgat caaacgtgga | 600 |
| atcaatgacc gaaatttctg gaggggtgaa atggacgaa ggacaagggt tgcttatgaa | 660 |
| agaatgtgca atatcctcaa ggaaaatttt caaacagctg cccagagggc aatgatggat | 720 |
| caagtaagag aaagtcgaaa cccaggaaac gctgagattg aagacctcat tttcctggca | 780 |
| cggtcagcac tcattctgag gggatcagtt gcacataaat cctgcctgcc tgcttgtgtg | 840 |
| tatgggcttg cagtagcaag tgggcatgac tttgaaaggg aagggtactc actggtcggg | 900 |
| atagacccat tcaaattact ccaaaacagc caagtggtca gcctgatgag gccaaatgaa | 960 |
| aacccagctc acaagagtca attggtgtgg atgcatgcc actctgctgc attgaagat | 1020 |
| ttaagagtat caagtttcat aagaggaaag aaagtgattc aagaggaaa gctttccaca | 1080 |
| agaggggtcc agattgcttc aaatgagaat gtggaaacca tggactccaa taccctggaa | 1140 |
| ctgagaagca gatactgggc cataaggacc aggagtggag gaaataccaa tcaacaaaag | 1200 |
| gcatccgcag gccagatcag tgtgcagcct acattctcag tgcagcggaa tctcccttttt | 1260 |

```
gaaagagcaa ccgttatggc agcattcagc gggaacaatg aaggacggac atccgacatg     1320
cgaacagaag ttataagaat gatggaaagt gcaaagccag aagatttgtc cttccagggg     1380
cggggagtct tcgagctctc ggacgaaaag gcaacgaacc cgatcgtgcc ttcctttgac     1440
atgagtaatg aagggtctta tttcttcgga gacaatgcag aggagtatga cagttga       1497
```

<210> SEQ ID NO 71
<211> LENGTH: 498
<212> TYPE: PRT
<213> ORGANISM: Influenza A virus

<400> SEQUENCE: 71

```
Met Ala Ser Gln Gly Thr Lys Arg Ser Tyr Glu Gln Met Glu Thr Gly
1               5                   10                  15

Gly Glu Arg Gln Asp Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Asp Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Ile Leu Tyr Asp
            100                 105                 110

Lys Glu Glu Ile Arg Arg Val Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Val Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
    290                 295                 300

Lys Leu Leu Gln Asn Ser Gln Val Val Ser Leu Met Arg Pro Asn Glu
305                 310                 315                 320

Asn Pro Ala His Lys Ser Gln Leu Val Trp Met Ala Cys His Ser Ala
                325                 330                 335
```

| | | | | | | | | | | | | |
|---|---|---|---|---|---|---|---|---|---|---|---|---|
|Ala|Phe|Glu|Asp|Leu|Arg|Val|Ser|Ser|Phe|Ile|Arg|Gly|Lys|Lys|Val|
| | | |340| | | |345| | | | |350| | | |

Ala Phe Glu Asp Leu Arg Val Ser Ser Phe Ile Arg Gly Lys Lys Val
            340              345                    350

Ile Pro Arg Gly Lys Leu Ser Thr Arg Gly Val Gln Ile Ala Ser Asn
355                    360                    365

Glu Asn Val Glu Thr Met Asp Ser Asn Thr Leu Glu Leu Arg Ser Arg
        370                375                380

Tyr Trp Ala Ile Arg Thr Arg Ser Gly Gly Asn Thr Asn Gln Gln Lys
385                    390                    395              400

Ala Ser Ala Gly Gln Ile Ser Val Gln Pro Thr Phe Ser Val Gln Arg
            405                  410                415

Asn Leu Pro Phe Glu Arg Ala Thr Val Met Ala Ala Phe Ser Gly Asn
        420                425                430

Asn Glu Gly Arg Thr Ser Asp Met Arg Thr Glu Val Ile Arg Met Met
            435                  440              445

Glu Ser Ala Lys Pro Glu Asp Leu Ser Phe Gln Gly Arg Gly Val Phe
        450                455                460

Glu Leu Ser Asp Glu Lys Ala Thr Asn Pro Ile Val Pro Ser Phe Asp
465                    470                    475              480

Met Ser Asn Glu Gly Ser Tyr Phe Phe Gly Asp Asn Ala Glu Glu Tyr
                485                490              495

Asp Ser

<210> SEQ ID NO 72
<211> LENGTH: 1458
<212> TYPE: RNA
<213> ORGANISM: Influenza A virus

<400> SEQUENCE: 72

```
aguagaaaca aggaguuuuu ugaacaaauu acuugucaau gguaaauggc aacucagcac    60
cgucuggcca agaccaaccc acagugucac uguuuacacc acaaaaggau augcugcucc   120
cgcuagucca gauuguguuc ucuuggguc gcccucugau uaguucaacc cagaagcaag   180
gucuuauaca auccagcccu guuaguucug gaugcugaac aaaacucccg cuauauccug   240
accacucauu uauuccuacg auaucuugcu uuauugagaa guuauugcu gucccagucc   300
auccguucgg aucccaaauc aucucaaaac cguuucuuga acuaaugcuu uuaguucuc   360
cuauccaaac accauugccg uauuugaaug aaaauccuuu uacuccauuu gcuccauuag   420
acgauacugg accacaacug ccugucuuau cauuagggcg uggauugucu ccgaaaaucc   480
cacugcauau guauccuauc ugauauucca gauucggguu gaaagacacc cacggucgau   540
ucgagccaug ccaguuaucc cugcacacac augugauuuc acuagaauca ggauaacagg   600
agcauuccuc auagugauaa uuaggggcau ucauucgac ugauuugacu aucuuucccu   660
uuucuauucu gaagaucuug uaugaggccu guccauuacu ggucccaucg gucauuacag   720
uaaagcaaga accauuuaca caugcacauu cagacucuug uguucucaau auauuguuuc   780
uccaacucuu gauagugucu guuauuaugc cguuguacuu aacacagcc acugccccau   840
ugucugggcc agaaauucca auuguuagcc aauugaugcc aucaugacaa gcacuugcug   900
accaagcgac ugacucaaau cuugaguugu auggagaggg aacuucacca auaggacagc   960
ucauuagggu ucgauauggg cuccugucuu uaaugguucc auggaaugu uugcauuua  1020
gcaaggcccc uugagucaag aagaagguuc ugcauuccaa ggggagcau gauaugaaug  1080
guucccuuau gacaaacaca uccccuugg aaccgauucu uacacuguug ucuuuacugu  1140
auauagccca uccacuaaca gggcagagag aggaauugcc cgcuaauuuc acggaaacca  1200
```

```
cugacugucc agcagcaaag uugguguugc ugauguuaac auaugucuga uuuacccaag 1260
uguuguuuuc auaaguaaug acgcuuugau ugcauguuuc aaucugauuu ugauucccaa 1320
guugaauuga guggcuaauc cauauugaga uuauguuucc aauuuguaau auuaaguuag 1380
ccauuccaau ugucauacag accgaaccaa ugguuauuau cuuuugguuu ggauucauuu 1440
uaaacuccug cuuuugcu 1458

<210> SEQ ID NO 73
<211> LENGTH: 1410
<212> TYPE: DNA
<213> ORGANISM: Influenza A virus
<400> SEQUENCE: 73
atgaatccaa accaaaagat aataaccatt ggttcggtct gtatgacaat tggaatggct 60
aacttaatat tacaaattgg aaacataatc tcaatatgga ttagccactc aattcaactt 120
gggaatcaaa atcagattga aacatgcaat caaagcgtca ttacttatga aaacaacact 180
tgggtaaatc agacatatgt taacatcagc aacaccaact ttgctgctgg acagtcagtg 240
gtttccgtga aattagcggg caattcctct ctctgccctg ttagtggatg ggctatatac 300
agtaaagaca acagtgtaag aatcggttcc aagggggatg tgtttgtcat aagggaacca 360
ttcatatcat gctccccctt ggaatgcaga accttcttct tgactcaagg ggccttgcta 420
aatgacaaac attccaatgg aaccattaaa gacaggagcc catatcgaac cctaatgagc 480
tgtcctattg gtgaagttcc ctctccatac aactcaagat ttgagtcagt cgcttggtca 540
gcaagtgctt gtcatgatgg catcaattgg ctaacaattg gaatttctgg cccagacaat 600
ggggcagtgg ctgtgttaaa gtacaacggc ataataacag acactatcaa gagttggaga 660
aacaatatat tgagaacaca agagtctgaa tgtgcatgtg taaatggttc ttgctttact 720
gtaatgaccg atggaccaag taatggacag gcctcataca agatcttcag aatagaaaag 780
ggaaagatag tcaaatcagt cgaaatgaat gcccctaatt atcactatga ggaatgctcc 840
tgttatcctg attctagtga aatcacatgt gtgtgcaggg ataactggca tggctcgaat 900
cgaccgtggg tgtctttcaa ccagaatctg gaatatcaga taggatacat atgcagtggg 960
attttcggag acaatccacg ccctaatgat aagacaggca gttgtggtcc agtatcgtct 1020
aatggagcaa atggagtaaa aggattttca ttcaaatacg gcaatggtgt ttggataggg 1080
agaactaaaa gcattagttc aagaaacggt tttgagatga tttgggatcc gaacggatgg 1140
actgggacag acaataactt ctcaataaag caagatatcg taggaataaa tgagtggtca 1200
ggatatagcg ggagttttgt tcagcatcca gaactaacag ggctggattg tataagacct 1260
tgcttctggg ttgaactaat cagagggcga cccaaagaga acacaatctg gactagcggg 1320
agcagcatat ccttttgtgg tgtaaacagt gacactgtgg gttggtcttg gccagacggt 1380
gctgagttgc catttaccat tgacaagtaa 1410

<210> SEQ ID NO 74
<211> LENGTH: 469
<212> TYPE: PRT
<213> ORGANISM: Influenza A virus

<400> SEQUENCE: 74

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile

```
                    20                  25                  30
Trp Ile Ser His Ser Ile Gln Leu Gly Asn Gln Asn Gln Ile Glu Thr
                35                  40                  45
Cys Asn Gln Ser Val Ile Thr Tyr Glu Asn Asn Thr Trp Val Asn Gln
            50                  55                  60
Thr Tyr Val Asn Ile Ser Asn Thr Asn Phe Ala Ala Gly Gln Ser Val
65                  70                  75                  80
Val Ser Val Lys Leu Ala Gly Asn Ser Ser Leu Cys Pro Val Ser Gly
                85                  90                  95
Trp Ala Ile Tyr Ser Lys Asp Asn Ser Val Arg Ile Gly Ser Lys Gly
                100                 105                 110
Asp Val Phe Val Ile Arg Glu Pro Phe Ile Ser Cys Ser Pro Leu Glu
                115                 120                 125
Cys Arg Thr Phe Phe Leu Thr Gln Gly Ala Leu Leu Asn Asp Lys His
                130                 135                 140
Ser Asn Gly Thr Ile Lys Asp Arg Ser Pro Tyr Arg Thr Leu Met Ser
145                 150                 155                 160
Cys Pro Ile Gly Glu Val Pro Ser Pro Tyr Asn Ser Arg Phe Glu Ser
                165                 170                 175
Val Ala Trp Ser Ala Ser Ala Cys His Asp Gly Ile Asn Trp Leu Thr
                180                 185                 190
Ile Gly Ile Ser Gly Pro Asp Asn Gly Ala Val Ala Val Leu Lys Tyr
                195                 200                 205
Asn Gly Ile Ile Thr Asp Thr Ile Lys Ser Trp Arg Asn Asn Ile Leu
                210                 215                 220
Arg Thr Gln Glu Ser Glu Cys Ala Cys Val Asn Gly Ser Cys Phe Thr
225                 230                 235                 240
Val Met Thr Asp Gly Pro Ser Asn Gly Gln Ala Ser Tyr Lys Ile Phe
                245                 250                 255
Arg Ile Glu Lys Gly Lys Ile Val Lys Ser Val Glu Met Asn Ala Pro
                260                 265                 270
Asn Tyr His Tyr Glu Glu Cys Ser Cys Tyr Pro Asp Ser Ser Glu Ile
                275                 280                 285
Thr Cys Val Cys Arg Asp Asn Trp His Gly Ser Asn Arg Pro Trp Val
                290                 295                 300
Ser Phe Asn Gln Asn Leu Glu Tyr Gln Ile Gly Tyr Ile Cys Ser Gly
305                 310                 315                 320
Ile Phe Gly Asp Asn Pro Arg Pro Asn Asp Lys Thr Gly Ser Cys Gly
                325                 330                 335
Pro Val Ser Ser Asn Gly Ala Asn Gly Val Lys Gly Phe Ser Phe Lys
                340                 345                 350
Tyr Gly Asn Gly Val Trp Ile Gly Arg Thr Lys Ser Ile Ser Ser Arg
                355                 360                 365
Asn Gly Phe Glu Met Ile Trp Asp Pro Asn Gly Trp Thr Gly Thr Asp
                370                 375                 380
Asn Asn Phe Ser Ile Lys Gln Asp Ile Val Gly Ile Asn Glu Trp Ser
385                 390                 395                 400
Gly Tyr Ser Gly Ser Phe Val Gln His Pro Glu Leu Thr Gly Leu Asp
                405                 410                 415
Cys Ile Arg Pro Cys Phe Trp Val Glu Leu Ile Arg Gly Arg Pro Lys
                420                 425                 430
Glu Asn Thr Ile Trp Thr Ser Gly Ser Ser Ile Ser Phe Cys Gly Val
                435                 440                 445
```

Asn Ser Asp Thr Val Gly Trp Ser Trp Pro Asp Gly Ala Glu Leu Pro
    450                 455                 460

Phe Thr Ile Asp Lys
465

<210> SEQ ID NO 75
<211> LENGTH: 1027
<212> TYPE: RNA
<213> ORGANISM: Influenza A virus

<400> SEQUENCE: 75

| | | | | | |
|---|---|---|---|---|---|
| aguagaaaca | agguaguuuu | uuacucuagc | ucuauguuga | caaaaugacc | aucgucaaca | 60 |
| uccacagcac | ucugcuguuc | cuguugauau | ucuucccuca | uggacucagg | cacuccuucc | 120 |
| guagaaggcc | cucuuuucaa | accguauuua | aagcgacgau | aaauacauuu | gaaaaaaaga | 180 |
| cgaucaguaa | uccacaauau | caggugcaag | aucccaauga | uauuugcugc | aaugacgaga | 240 |
| ggaucacuug | aaucgcugca | ucugcacucc | cauucgcuuc | ugguaggccu | gcaaauuuuc | 300 |
| aagaagguca | ucuuucagac | cagcacugga | gcuaggauga | gucccaauag | uucucauugc | 360 |
| auguaccauc | ugccuagucu | gauuagcaac | cuccauggcc | uccgcugccu | guucacucga | 420 |
| uccagccauc | uguccauag | ccuuugccgu | agugcuagcc | agcaccauuc | uguuucaug | 480 |
| ccugauuagu | ggauuggugg | uaguagccau | cugucuguga | gaccgaugcu | gugaaucagc | 540 |
| aaucuguuca | caaguggcac | acacuagacc | aaaagcagcu | ucuggguca | cuguucccau | 600 |
| ccuguuguau | augaggccca | ugcaacuggc | aagugcacca | guugaauagc | uuagugacac | 660 |
| cuccuuggcc | ccauggaacg | uuauuucucu | uuugagcuuc | uguauaguu | uaacugcucu | 720 |
| auccauguug | uucgggucc | cauucccauu | uagggcauuu | uggacaaagc | gucuacgcug | 780 |
| caguccucgc | ucacugggca | cggugagcgu | gaacacaaau | ccuaaaauuc | ccuuagucag | 840 |
| aggugacaag | auuggucuug | ucuuuagcca | auccaugaga | gccucaagau | cuguguucuu | 900 |
| uccugcaaag | acacuuucca | gucucugcgc | gaucucggcu | uugaggggc | cugacgggau | 960 |
| gauagaaaga | acguacguuu | cgaccucggu | uagaagacuc | aucuuuaaau | aucuaccugc | 1020 |
| uuuugcu | | | | | | 1027 |

<210> SEQ ID NO 76
<211> LENGTH: 759
<212> TYPE: DNA
<213> ORGANISM: Influenza A virus

<400> SEQUENCE: 76

| | | | | | |
|---|---|---|---|---|---|
| atgagtcttc | taaccgaggt | cgaaacgtac | gttctttcta | tcatcccgtc | aggccccctc | 60 |
| aaagccgaga | tcgcgcagag | actggaaagt | gtctttgcag | gaaagaacac | agatcttgag | 120 |
| gctctcatgg | aatggctaaa | gacaagacca | atcttgtcac | ctctgactaa | gggaatttta | 180 |
| ggatttgtgt | tcacgctcac | cgtgcccagt | gagcgaggac | tgcagcgtag | acgctttgtc | 240 |
| caaaatgccc | taaatgggaa | tggggacccg | aacaacatgg | atagagcagt | taaactatac | 300 |
| aagaagctca | aaagagaaat | aacgttccat | ggggccaagg | aggtgtcact | aagctattca | 360 |
| actggtgcac | ttgccagttg | catgggcctc | atatacaaca | ggatgggaac | agtgaccaca | 420 |
| gaagctgctt | ttggtctagt | gtgtgccact | tgtgaacaga | ttgctgattc | acagcatcgg | 480 |
| tctcacagac | agatggctac | taccaccaat | ccactaatca | ggcatgaaaa | cagaatggtg | 540 |
| ctggctagca | ctacggcaaa | ggctatggaa | cagatggctg | gatcgagtga | acaggcagcg | 600 |

```
gaggccatgg aggttgctaa tcagactagg cagatggtac atgcaatgag aactattggg    660
actcatccta gctccagtgc tggtctgaaa gatgaccttc ttgaaaattt gcaggcctac    720
cagaagcgaa tgggagtgca gatgcagcga ttcaagtga                           759
```

<210> SEQ ID NO 77
<211> LENGTH: 252
<212> TYPE: PRT
<213> ORGANISM: Influenza A virus

<400> SEQUENCE: 77

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Ser Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Ala Ala Phe
130                 135                 140

Gly Leu Val Cys Ala Thr Cys Glu Gln Ile Ala Asp Ser Gln His Arg
145                 150                 155                 160

Ser His Arg Gln Met Ala Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Thr Arg Gln Met Val His Ala Met Arg Thr Ile Gly Thr His Pro Ser
210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 78
<211> LENGTH: 294
<212> TYPE: DNA
<213> ORGANISM: Influenza A virus

<400> SEQUENCE: 78

```
atgagtcttc taaccgaggt cgaaacgcct accagaagcg aatgggagtg cagatgcagc     60
gattcaagtg atcctctcgt cattgcagca aatatcattg ggatcttgca cctgatattg    120
tggattactg atcgtctttt tttcaaatgt atttatcgtc gctttaaata cggtttgaaa    180
agagggcctt ctacggaagg agtgcctgag tccatgaggg aagaatatca acaggaacag    240
cagagtgctg tggatgttga cgatggtcat tttgtcaaca tagagctaga gtaa          294
```

<210> SEQ ID NO 79
<211> LENGTH: 97
<212> TYPE: PRT
<213> ORGANISM: Influenza A virus

<400> SEQUENCE: 79

```
Met Ser Leu Leu Thr Glu Val Glu Thr Pro Thr Arg Ser Glu Trp Glu
1               5                   10                  15

Cys Arg Cys Ser Asp Ser Ser Asp Pro Leu Val Ile Ala Ala Asn Ile
            20                  25                  30

Ile Gly Ile Leu His Leu Ile Leu Trp Ile Thr Asp Arg Leu Phe Phe
        35                  40                  45

Lys Cys Ile Tyr Arg Arg Phe Lys Tyr Gly Leu Lys Arg Gly Pro Ser
    50                  55                  60

Thr Glu Gly Val Pro Glu Ser Met Arg Glu Glu Tyr Gln Gln Glu Gln
65                  70                  75                  80

Gln Ser Ala Val Asp Val Asp Asp Gly His Phe Val Asn Ile Glu Leu
                85                  90                  95

Glu
```

<210> SEQ ID NO 80
<211> LENGTH: 890
<212> TYPE: RNA
<213> ORGANISM: Influenza A virus

<400> SEQUENCE: 80

```
aguagaaaca agggguguuuu uuaucauuaa auaagcugaa acgagaaagc ucuuaucucu      60
uguucuacuu caagcaguag uuguaaggcu ugcauaaaug uuauuuguuc gaaacuauuc     120
ucugucgcuu ucaaucugug ccgcauuucu ucaauuaacc accuuauuuc cucaaauuuc     180
ugucccaauu gcucucgcca cuuuucauuu cugcucugga gguagugaag gucucccauu     240
cucaucacag uuucuccaag cgaaucucug uauauuuuca gagacucgaa ccguguuacc     300
auuccauuca aguccuccga ugaggacccc aacugcauuu uugacauccu cauaaguaug     360
uccuggaaga gaaggugaug gugaaauuuc uccaacuauu gcucccuccu cagugaaagc     420
ccuuaguagu aucaaggucu cuaaucgguu aaagauuaca cugaaguucg cuuucaguac     480
uauguucuuu uccaugaucg ccugguccaa ucgcacgcaa agagggccua uuaucuuuug     540
ccuaggcaug agcaugaacc agucucguga cauuuccucg agggucaugu cagaaaggua     600
gcgcgaagua gguacagaug caauugucau ucuaagugu ucgcuggauu ccucuuucaa     660
uauccauucc acgauuuguu ucccaacaag aguggcuguu ucgauaucga ggccaagggu     720
guugccucuu ccuuuuaagg acuuuugauc ucggcggagc cgaucaagga auggggcauc     780
acccaaucca uugucugcaa aucgcuugcg gauaugccaa aggaaacagu cuaccugaaa     840
gcuugacaug guguuggagu ccauuauguu uuugucaccc ugcuuuugcu                890
```

<210> SEQ ID NO 81
<211> LENGTH: 660
<212> TYPE: DNA
<213> ORGANISM: Influenza A virus

<400> SEQUENCE: 81

```
atggactcca acaccatgtc aagctttcag gtagactgtt tcctttggca tatccgcaag      60
cgatttgcag acaatggatt gggtgatgcc ccattccttg atcggctccg ccgagatcaa     120
```

```
aagtccttaa aaggaagagg caacacccct tggcctcgata tcgaaacagc cactcttgtt    180
gggaaacaaa tcgtggaatg gatattgaaa gaggaatcca gcgagacact tagaatgaca    240
attgcatctg tacctacttc gcgctacctt tctgacatga ccctcgagga aatgtcacga    300
gactggttca tgctcatgcc taggcaaaag ataataggcc ctctttgcgt gcgattggac    360
caggcgatca tggaaaagaa catagtactg aaagcgaact tcagtgtaat ctttaaccga    420
ttagagacct tgatactact aagggctttc actgaggagg gagcaatagt tggagaaatt    480
tcaccatcac cttctcttcc aggacatact tatgaggatg tcaaaaatgc agttggggtc    540
ctcatcggag acttgaatgg aatggtaaca cggttcgagt ctctgaaaaa tatacagaga    600
ttcgcttgga gaaactgtga tgagaatggg agaccttcac tacctccaga gcagaaatga    660
```

<210> SEQ ID NO 82
<211> LENGTH: 219
<212> TYPE: PRT
<213> ORGANISM: Influenza A virus

<400> SEQUENCE: 82

```
Met Asp Ser Asn Thr Met Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Asn
        35                  40                  45

Thr Leu Gly Leu Asp Ile Glu Thr Ala Thr Leu Val Gly Lys Gln Ile
    50                  55                  60

Val Glu Trp Ile Leu Lys Glu Glu Ser Ser Glu Thr Leu Arg Met Thr
65                  70                  75                  80

Ile Ala Ser Val Pro Thr Ser Arg Tyr Leu Ser Asp Met Thr Leu Glu
                85                  90                  95

Glu Met Ser Arg Asp Trp Phe Met Leu Met Pro Arg Gln Lys Ile Ile
            100                 105                 110

Gly Pro Leu Cys Val Arg Leu Asp Gln Ala Ile Met Glu Lys Asn Ile
        115                 120                 125

Val Leu Lys Ala Asn Phe Ser Val Ile Phe Asn Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Ser Pro Ser Leu Pro Gly His Thr Tyr Glu Asp Val Lys Asn
                165                 170                 175

Ala Val Gly Val Leu Ile Gly Gly Leu Glu Trp Asn Gly Asn Thr Val
            180                 185                 190

Arg Val Ser Glu Asn Ile Gln Arg Phe Ala Trp Arg Asn Cys Asp Glu
        195                 200                 205

Asn Gly Arg Pro Ser Leu Pro Pro Glu Gln Lys
    210                 215
```

<210> SEQ ID NO 83
<211> LENGTH: 366
<212> TYPE: DNA
<213> ORGANISM: Influenza A virus

<400> SEQUENCE: 83

```
atggactcca acaccatgtc aagctttcag gacatactta tgaggatgtc aaaaatgcag    60
ttggggtcct catcggagga cttgaatgga atggtaacac ggttcgagtc tctgaaaata   120
```

| | |
|---|---|
| tacagagatt cgcttggaga aactgtgatg agaatgggag accttcacta cctccagagc | 180 |
| agaaatgaaa agtggcgaga gcaattggga cagaaatttg aggaaataag gtggttaatt | 240 |
| gaagaaatgc ggcacagatt gaaagcgaca gagaatagtt tcgaacaaat aacatttatg | 300 |
| caagccttac aactactgct tgaagtagaa caagagataa gagctttctc gtttcagctt | 360 |
| atttaa | 366 |

<210> SEQ ID NO 84
<211> LENGTH: 121
<212> TYPE: PRT
<213> ORGANISM: Influenza A virus

<400> SEQUENCE: 84

```
Met Asp Ser Asn Thr Met Ser Ser Phe Gln Asp Ile Leu Met Arg Met
1               5                   10                  15
Ser Lys Met Gln Leu Gly Ser Ser Glu Asp Leu Asn Gly Met Val
            20                  25                  30
Thr Arg Phe Glu Ser Leu Lys Ile Tyr Arg Asp Ser Leu Gly Glu Thr
        35                  40                  45
Val Met Arg Met Gly Asp Leu His Tyr Leu Gln Ser Arg Asn Glu Lys
    50                  55                  60
Trp Arg Glu Gln Leu Gly Gln Lys Phe Glu Glu Ile Arg Trp Leu Ile
65                  70                  75                  80
Glu Glu Met Arg His Arg Leu Lys Ala Thr Glu Asn Ser Phe Glu Gln
                85                  90                  95
Ile Thr Phe Met Gln Ala Leu Gln Leu Leu Leu Glu Val Glu Gln Glu
            100                 105                 110
Ile Arg Ala Phe Ser Phe Gln Leu Ile
        115                 120
```

<210> SEQ ID NO 85
<211> LENGTH: 2553
<212> TYPE: DNA
<213> ORGANISM: Coxsackievirus

<400> SEQUENCE: 85

| | |
|---|---|
| atgggagctc aagtatcaac gcaaaagact ggagcacatg agaccagatt gaatgcttcg | 60 |
| ggaaattcga tcattcacta cacaaatatt aattattaca aggatgccgc atcgaactca | 120 |
| gccaatcgac aggatttcac tcaagacccg ggaaagttca cagaaccagt gaaagatatc | 180 |
| atgattaaat cattaccagc tttgaactcg cccacagtag aggagtgcgg atactcagac | 240 |
| agagcgagat caatcacatt aggaaactcg accataacga ctcaggaatg cgccaacgtg | 300 |
| gtggtgggat atgagagtatg gccagattat ttaaaggatt cagaggcaac agcagaggac | 360 |
| caaccgaccc aaccagacgt tgccacatgt agattctata ccttagactc agtgcaatgg | 420 |
| cagaaaacct caccaggatg gtggtggaag ttgcccgatg ctttgtcgaa cttaggattg | 480 |
| tttggacaga acatgcagta ccactactta ggacgaactg gatataccgt acatgtgcag | 540 |
| tgcaatgcat caaagttcca ccaaggatgc ttgttagtag tgtgtgtacc ggaagctgag | 600 |
| atgggatgcg caacgttaga caacacccca tcgtcagcag aattgttggg aggagataeg | 660 |
| gcaaaggagt tgcggacaa accggtcgca tcgggatcga acaagttggt acagagagtg | 720 |
| gtgtataatg caggaatggg agtgggagtt ggaaacttga ccattttccc ccaccaatgg | 780 |
| atcaacttac gaaccaataa ttcagctaca attgtgatgc catacaccaa ctcagtacct | 840 |

-continued

```
atggataaca tgtttagaca taacaacgtc accttaatgg ttatcccatt tgtaccgtta    900
gattactgcc ctggatcaac cacgtacgtc ccaattacgg tcacgatagc cccaatgtgt    960
gccgagtaca atggattacg attagcagga caccagggat taccaaccat gaatactccg   1020
ggatcgtgtc aatttttgac atcagacgac ttccaatcac catcggccat gccgcaatat   1080
gacgtcacac cagagatgag aatacctgga gaggtgaaaa acttgatgga aatagctgag   1140
gttgactcag ttgtcccagt ccaaaatgtt ggagagaagg tcaactcaat ggaagcatac   1200
cagatacctg tgagatcgaa cgaaggatca ggaacgcaag tattcggatt tccattgcaa   1260
ccaggatact cgtcagtttt ttcacgaacg ttgttaggag agatcttgaa ctattataca   1320
cattggtcag gatcgataaa gttaacgttt atgttctgtg gatcggccat ggctactgga   1380
aaattcttat tggcatactc accaccagga gctggagctc ctacaaaaag agttgatgct   1440
atgttaggaa ctcatgtaat ttgggacgtg ggattacaat catcatgcgt gttgtgtata   1500
ccctggatat cgcaaacaca ctaccgattt gttgcttcag atgagtatac cgcaggagga   1560
tttattacgt gctggtatca aacaaacata gtggtcccag cggatgccca atcgtcgtgt   1620
tacatcatgt gtttcgtgtc agcatgcaat gacttctcag tcagattatt gaaggacact   1680
cctttcattt cgcagcaaaa ctttttccag ggaccagtgg aagacgcgat aacagccgct   1740
ataggaagag ttgcggatac cgtgggaaca ggaccaacca actcagaagc tataccagca   1800
ttgactgctg ctgagacggg acacacgtca caagtagtgc cgggagacac tatgcagaca   1860
cgacacgtta agaactacca ttcaagatcg gagtcaacca tagagaactt cttatgtaga   1920
tcagcatgcg tgtactttac ggagtataaa aactcaggag ccaagcgata tgctgaatgg   1980
gtattaacac cacgacaagc agcacaatta agaagaaagt tagaattctt tacctacgtc   2040
cgattcgact tggagttgac gtttgtcata acatcaactc aacagccctc aaccacacag   2100
aaccaagatg cacagatctt aacacaccaa attatgtatg taccaccagg aggacctgta   2160
ccagataaag ttgattcata cgtgtggcaa acatcaacga atccctcagt gttttggacc   2220
gagggaaacg ccccgccgcg aatgtcgata ccgtttttgt cgattggaaa cgcctattca   2280
aatttctatg acggatggtc agaattttcg agaaacggag tttacggaat caacacgtta   2340
aacaacatgg gaacgttata tgcaagacat gtcaacgctg gatcgacggg accaataaaa   2400
tcgaccatta gaatctactt caaaccgaag catgtcaaag cgtggatacc tagaccacct   2460
agattgtgcc aatacgagaa ggcaaagaac gtgaacttcc aaccctcggg agttaccact   2520
actagacaat cgatcactac aatgacaaat acg                                2553
```

```
<210> SEQ ID NO 86
<211> LENGTH: 1777
<212> TYPE: RNA
<213> ORGANISM: Influenza A virus

<400> SEQUENCE: 86
aguagaaaca agggguguuuu ucucaugcuu cugaaauccu aauguuaaau acauauucua     60
cacuguaaug acccauuuga gcacauccag aaugagauug cccccaacga gacuaccaau    120
accaaugaug aggcgacagu ugaauagauc gccaaaaucu gguaaauccu uguugauucc    180
aacuuuaccc caucuauuuc uucucuguuu aauuuugcuu ccucugagua uuuuggguag    240
ucauaagucc cauuuuugac ugauuccaug cacguguuau cgcauuugug guaaaauuca    300
aagcagccgu uuccaauuuc cuuggcauug uuuuuuaacu gcgaucuuac cuuuucauau    360
aaguucuuca cauuugaauc gugguagucc aaaguucuuu cauuuuccaa uaaaaccaac    420
```

```
aauucggcau uguaagucca aauguccaag aaaccaucau caacuuuuuu auuuaaauuc       480
ucuauucuuu uuccaagug guugaacucu uuaccuacug cugugaacug uguauucauc        540
uuuucaauaa cugaauuuac uuuguuagua aucucgucaa uggcauucug ugucgacuuc       600
aagucggcug cauauccuga ccccugcuca uuuugauggu gauaaccgua ccauccaucu       660
accaucccug uccaccccc uucaaugaaa ccggcaaugg ccccaaauaa gccucuugau        720
ugaauugacg ggacauuccu caauccugug gccaaucuca auuugucga uuuuacauau       780 uuuggacauu uuccaaugu gaucggaugu auauucgaa auggcaacga ggguuuaua         840 gcacccuugg gugucugaca aguuguauug caaucgugga cuggguguauc ugaaaugaua     900 auaccugauc cagcauuucu uuccauugcg aaugcauauc ucgguaccac uaaauuucca      960
guugcuucga auguuauuuu gucucccggc ucuacuaaug uccaguaaua guucauucuc      1020
cccucuugau cccucacuuu ggucuuauu gcauuuccg gcuugaacuu cuucgaguau        1080
cuugaugacc ccacaaaaac auaugcaucu gcauucugaa acaaugauug uuggucagcu      1140
gaaguugaug gauggugaau gccccauaac accaagacuu cuucccuuu ucauuaaug       1200 uacgauuucg acaacuuugg guaugaauuu ccuuuuuuaa cuaaccauau uaaauuuug      1260 uagaacgauu uugcuccagc augaggacau gcugccguua caccuuuguu cgagucauga     1320
uugggccaug augaugucuu ggggaauauc ucaaaccuuu caaaugauga cacugacgac    1380
aauugcucuc uuaacuccuc auaaucgaug aaaucuccug gguaacacgu uccauugucu      1440
gaugaugaug uuuccacaau guacgaccau gacgaugcug ucgacaauga uucacacucu      1500
ggauucccca agauccagcc agcaauguua cauuuaccca aaugcaaugg ggcuaccccu      1560
cuuaauuugc auaauuuccc guuaugcuug ucuucuaaua aguuaaccga guguguuacu      1620
guuacauucu uuucuaauac uguugucuaca guguucuguug aauuguucgc augauaaccu    1680
auacauaaug ugucucauu ugcgguugca aauguauaua acaaaacuac uaauauugcc       1740
uucauuuuug uugcuuuugu uuuccccugc uuuugcu                              1777

<210> SEQ ID NO 87
<211> LENGTH: 1701
<212> TYPE: DNA
<213> ORGANISM: Influenza A virus

<400> SEQUENCE: 87
atgaaggcaa tattagtagt tttgttatat acatttgcaa ccgcaaatgc agacacatta      60
tgtataggtt atcatgcgaa caattcaaca gacactgtag acacagtatt agaaaagaat     120
gtaacagtaa cacactcggt taacttatta gaagacaagc ataacgggaa attatgcaaa    180
ttaagagggg tagccccatt gcatttgggt aaatgtaaca ttgctggctg atcttgggga   240
aatccagagt gtgaatcatt gtcgacagca tcgtcatggt cgtacattgt ggaaacatca   300
tcatcagaca atggaacgtg ttacccagga gatttcatcg attatgagga gttaagagag   360
caattgtcgt cagtgtcatc atttgaaagg tttgagatat cccccaagac atcatcatgg   420
cccaatcatg actcgaacaa aggtgtaacg gcagcatgtc ctcatgctgg agcaaaatcg   480
ttctacaaaa atttaatatg gttagttaaa aaggaaatt catacccaaa gttgtcgaaa    540
tcgtacatta atgataaagg gaaagaagtc ttggtgttat ggggcattca ccatccatca   600
acttcagctg accaacaatc attgtatcag aatgcagatg catatgtttt tgtggggtca   660
tcaagatact cgaagaagtt caagccggaa atagcaataa gacccaaagt gagggatcaa   720
```

```
gaggggagaa tgaactatta ctggacatta gtagagccgg gagacaaaat aacattcgaa    780
gcaactggaa atttagtggt accgagatat gcattcgcaa tggaaagaaa tgctggatca    840
ggtattatca tttcagatac accagtccac gattgcaata caacttgtca gacacccaag    900
ggtgctataa acacctcgtt gccatttcag aatatacatc cgatcacaat ggaaaatgt     960 ccaaaatatg taaaatcgac aaaattgaga ttggccacag gattgaggaa tgtcccgtca   1020
attcaatcaa gaggcttatt tggggccatt gccggtttca ttgaaggggg gtggacaggg   1080
atggtagatg gatggtacgg ttatcaccat caaaatgagc aggggtcagg atatgcagcc   1140
gacttgaagt cgacacagaa tgccattgac gagattacta caaagtaaa ttcagttatt    1200 gaaagatga atacacagtt cacagcagta ggtaaagagt caaccactt ggaaaaaga     1260 atagagaatt taaataaaaa agttgatgat ggtttcttgg acatttggac ttacaatgcc   1320
gaattgttgg ttttattgga aaatgaaaga actttggact accacgattc aaatgtgaag   1380
aacttatatg aaaaggtaag atcgcagtta aaaaacaatg ccaaggaaat tggaaacggc   1440
tgctttgaat tttaccacaa atgcgataac acgtgcatgg aatcagtcaa aaatgggact   1500
tatgactacc caaatactc agaggaagca aaattaaaca gagaagaaat agatggggta    1560
aagttggaat caacaaggat ttaccagatt ttggcgatct attcaactgt cgcctcatca   1620
ttggtattgg tagtctcgtt gggggcaatc tcattctgga tgtgctcaaa tgggtcatta   1680
cagtgtagaa tatgtattta a                                              1701
```

<210> SEQ ID NO 88
<211> LENGTH: 566
<212> TYPE: PRT
<213> ORGANISM: Influenza A virus

<400> SEQUENCE: 88

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
```

```
                195                 200                 205
Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 89
<211> LENGTH: 2474
<212> TYPE: PRT
<213> ORGANISM: Chikungunya virus
<220> FEATURE:
<221> NAME/KEY: misc_feature
<222> LOCATION: (1857)..(1857)
```

<223> OTHER INFORMATION: Xaa can be any naturally occurring amino acid

<400> SEQUENCE: 89

```
Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

Arg Ile Thr Met Ser Pro Gly Leu Tyr Gly Lys Thr Thr Gly Tyr Ala
290                 295                 300

Val Thr His His Ala Asp Gly Phe Leu Met Cys Lys Thr Thr Asp Thr
305                 310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
370                 375                 380

Pro Val Val Ala Gln Ala Phe Ser Lys Trp Ala Lys Glu Cys Arg Lys
385                 390                 395                 400
```

```
Asp Met Glu Asp Glu Lys Leu Leu Gly Val Arg Glu Arg Thr Leu Thr
                405                 410                 415
Cys Cys Cys Leu Trp Ala Phe Lys Lys Gln Lys Thr His Thr Val Tyr
        420                 425                 430
Lys Arg Pro Asp Thr Gln Ser Ile Gln Lys Val Gln Ala Glu Phe Asp
            435                 440                 445
Ser Phe Val Val Pro Ser Leu Trp Ser Ser Gly Leu Ser Ile Pro Leu
    450                 455                 460
Arg Thr Arg Ile Lys Trp Leu Leu Ser Lys Val Pro Lys Thr Asp Leu
465                 470                 475                 480
Ile Pro Tyr Ser Gly Asp Ala Arg Glu Ala Arg Asp Ala Glu Lys Glu
                485                 490                 495
Ala Glu Glu Glu Arg Glu Ala Glu Leu Thr Arg Glu Ala Leu Pro Pro
            500                 505                 510
Leu Gln Ala Ala Gln Glu Asp Val Gln Val Glu Ile Asp Val Glu Gln
        515                 520                 525
Leu Glu Asp Arg Ala Gly Ala Gly Ile Ile Glu Thr Pro Arg Gly Ala
    530                 535                 540
Ile Lys Val Thr Ala Gln Pro Thr Asp His Val Val Gly Glu Tyr Leu
545                 550                 555                 560
Val Leu Ser Pro Gln Thr Val Leu Arg Ser Gln Lys Leu Ser Leu Ile
                565                 570                 575
His Ala Leu Ala Glu Gln Val Lys Thr Cys Thr His Asn Gly Arg Ala
            580                 585                 590
Gly Arg Tyr Ala Val Glu Ala Tyr Asp Gly Arg Val Leu Val Pro Ser
        595                 600                 605
Gly Tyr Ala Ile Ser Pro Glu Asp Phe Gln Ser Leu Ser Glu Ser Ala
    610                 615                 620
Thr Met Val Tyr Asn Glu Arg Glu Phe Val Asn Arg Lys Leu His His
625                 630                 635                 640
Ile Ala Met His Gly Pro Ala Leu Asn Thr Asp Glu Glu Ser Tyr Glu
                645                 650                 655
Leu Val Arg Ala Glu Arg Thr Glu His Glu Tyr Val Tyr Asp Val Asp
            660                 665                 670
Gln Arg Arg Cys Cys Lys Lys Glu Glu Ala Ala Gly Leu Val Leu Val
        675                 680                 685
Gly Asp Leu Thr Asn Pro Pro Tyr His Glu Phe Ala Tyr Glu Gly Leu
    690                 695                 700
Lys Ile Arg Pro Ala Cys Pro Tyr Lys Ile Ala Val Ile Gly Val Phe
705                 710                 715                 720
Gly Val Pro Gly Ser Gly Lys Ser Ala Ile Ile Lys Asn Leu Val Thr
                725                 730                 735
Arg Gln Asp Leu Val Thr Ser Gly Lys Lys Glu Asn Cys Gln Glu Ile
            740                 745                 750
Thr Thr Asp Val Met Arg Gln Arg Gly Leu Glu Ile Ser Ala Arg Thr
        755                 760                 765
Val Asp Ser Leu Leu Leu Asn Gly Cys Asn Arg Pro Val Asp Val Leu
    770                 775                 780
Tyr Val Asp Glu Ala Phe Ala Cys His Ser Gly Thr Leu Leu Ala Leu
785                 790                 795                 800
Ile Ala Leu Val Arg Pro Arg Gln Lys Val Val Leu Cys Gly Asp Pro
                805                 810                 815
Lys Gln Cys Gly Phe Phe Asn Met Met Gln Met Lys Val Asn Tyr Asn
```

```
                820                 825                 830
His Asn Ile Cys Thr Gln Val Tyr His Lys Ser Ile Ser Arg Arg Cys
            835                 840                 845

Thr Leu Pro Val Thr Ala Ile Val Ser Ser Leu His Tyr Glu Gly Lys
            850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
            885                 890                 895

Gly Trp Val Lys Gln Leu Gln Ile Asp Tyr Arg Gly Tyr Glu Val Met
            900                 905                 910

Thr Ala Ala Ser Gln Gly Leu Thr Arg Lys Gly Val Tyr Ala Val
            915                 920                 925

Arg Gln Lys Val Asn Glu Asn Pro Leu Tyr Ala Ser Thr Ser Glu His
            930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Lys Gly
            965                 970                 975

Asn Phe Lys Ala Thr Ile Lys Glu Trp Glu Val Glu His Ala Ser Ile
            980                 985                 990

Met Ala Gly Ile Cys Ser His Gln Met Thr Phe Asp Thr Phe Gln Asn
            995                 1000                1005

Lys Ala Asn Val Cys Trp Ala Lys Ser Leu Val Pro Ile Leu Glu
   1010             1015                1020

Thr Ala Gly Ile Lys Leu Asn Asp Arg Gln Trp Ser Gln Ile Ile
   1025             1030                1035

Gln Ala Phe Lys Glu Asp Lys Ala Tyr Ser Pro Glu Val Ala Leu
   1040             1045                1050

Asn Glu Ile Cys Thr Arg Met Tyr Gly Val Asp Leu Asp Ser Gly
   1055             1060                1065

Leu Phe Ser Lys Pro Leu Val Ser Val Tyr Tyr Ala Asp Asn His
   1070             1075                1080

Trp Asp Asn Arg Pro Gly Gly Lys Met Phe Gly Phe Asn Pro Glu
   1085             1090                1095

Ala Ala Ser Ile Leu Glu Arg Lys Tyr Pro Phe Thr Lys Gly Lys
   1100             1105                1110

Trp Asn Ile Asn Lys Gln Ile Cys Val Thr Thr Arg Arg Ile Glu
   1115             1120                1125

Asp Phe Asn Pro Thr Thr Asn Ile Ile Pro Ala Asn Arg Arg Leu
   1130             1135                1140

Pro His Ser Leu Val Ala Glu His Arg Pro Val Lys Gly Glu Arg
   1145             1150                1155

Met Glu Trp Leu Val Asn Lys Ile Asn Gly His His Val Leu Leu
   1160             1165                1170

Val Ser Gly Tyr Asn Leu Ala Leu Pro Thr Lys Arg Val Thr Trp
   1175             1180                1185

Val Ala Pro Leu Gly Val Arg Gly Ala Asp Tyr Thr Tyr Asn Leu
   1190             1195                1200

Glu Leu Gly Leu Pro Ala Thr Leu Gly Arg Tyr Asp Leu Val Val
   1205             1210                1215

Ile Asn Ile His Thr Pro Phe Arg Ile His His Tyr Gln Gln Cys
   1220             1225                1230
```

```
Val Asp His Ala Met Lys Leu Gln Met Leu Gly Gly Asp Ser Leu
    1235                1240                1245

Arg Leu Leu Lys Pro Gly Gly Ser Leu Leu Ile Arg Ala Tyr Gly
    1250                1255                1260

Tyr Ala Asp Arg Thr Ser Glu Arg Val Ile Cys Val Leu Gly Arg
    1265                1270                1275

Lys Phe Arg Ser Ser Arg Ala Leu Lys Pro Pro Cys Val Thr Ser
    1280                1285                1290

Asn Thr Glu Met Phe Phe Leu Phe Ser Asn Phe Asp Asn Gly Arg
    1295                1300                1305

Arg Asn Phe Thr Thr His Val Met Asn Asn Gln Leu Asn Ala Ala
    1310                1315                1320

Phe Val Gly Gln Val Thr Arg Ala Gly Cys Ala Pro Ser Tyr Arg
    1325                1330                1335

Val Lys Arg Met Asp Ile Ala Lys Asn Asp Glu Glu Cys Val Val
    1340                1345                1350

Asn Ala Ala Asn Pro Arg Gly Leu Pro Gly Asp Gly Val Cys Lys
    1355                1360                1365

Ala Val Tyr Lys Lys Trp Pro Glu Ser Phe Lys Asn Ser Ala Thr
    1370                1375                1380

Pro Val Gly Thr Ala Lys Thr Val Met Cys Gly Thr Tyr Pro Val
    1385                1390                1395

Ile His Ala Val Gly Pro Asn Phe Ser Asn Tyr Ser Glu Ser Glu
    1400                1405                1410

Gly Asp Arg Glu Leu Ala Ala Ala Tyr Arg Glu Val Ala Lys Glu
    1415                1420                1425

Val Thr Arg Leu Gly Val Asn Ser Val Ala Ile Pro Leu Leu Ser
    1430                1435                1440

Thr Gly Val Tyr Ser Gly Gly Lys Asp Arg Leu Thr Gln Ser Leu
    1445                1450                1455

Asn His Leu Phe Thr Ala Met Asp Ser Thr Asp Ala Asp Val Val
    1460                1465                1470

Ile Tyr Cys Arg Asp Lys Glu Trp Glu Lys Lys Ile Ser Glu Ala
    1475                1480                1485

Ile Gln Met Arg Thr Gln Val Glu Leu Leu Asp Glu His Ile Ser
    1490                1495                1500

Ile Asp Cys Asp Ile Val Arg Val His Pro Asp Ser Ser Leu Ala
    1505                1510                1515

Gly Arg Lys Gly Tyr Ser Thr Thr Glu Gly Ala Leu Tyr Ser Tyr
    1520                1525                1530

Leu Glu Gly Thr Arg Phe His Gln Thr Ala Val Asp Met Ala Glu
    1535                1540                1545

Ile His Thr Met Trp Pro Lys Gln Thr Glu Ala Asn Glu Gln Val
    1550                1555                1560

Cys Leu Tyr Ala Leu Gly Glu Ser Ile Glu Ser Ile Arg Gln Lys
    1565                1570                1575

Cys Pro Val Asp Asp Ala Asp Ala Ser Ser Pro Pro Lys Thr Val
    1580                1585                1590

Pro Cys Leu Cys Arg Tyr Ala Met Thr Pro Glu Arg Val Thr Arg
    1595                1600                1605

Leu Arg Met Asn His Val Thr Ser Ile Ile Val Cys Ser Ser Phe
    1610                1615                1620
```

-continued

Pro Leu Pro Lys Tyr Lys Ile Glu Gly Val Gln Lys Val Lys Cys
    1625                1630                1635

Ser Lys Val Met Leu Phe Asp His Asn Val Pro Ser Arg Val Ser
    1640                1645                1650

Pro Arg Glu Tyr Arg Ser Ser Gln Glu Ser Ala Gln Glu Ala Ser
    1655                1660                1665

Thr Ile Thr Ser Leu Thr His Ser Gln Phe Asp Leu Ser Val Asp
    1670                1675                1680

Gly Glu Ile Leu Pro Val Pro Ser Asp Leu Asp Ala Asp Ala Pro
    1685                1690                1695

Ala Leu Glu Pro Ala Leu Asp Asp Gly Ala Thr His Thr Leu Pro
    1700                1705                1710

Ser Thr Thr Gly Asn Leu Ala Ala Val Ser Asp Trp Val Met Ser
    1715                1720                1725

Thr Val Pro Val Ala Pro Pro Arg Arg Arg Gly Arg Asn Leu
    1730                1735                1740

Thr Val Thr Cys Asp Glu Arg Glu Gly Asn Ile Thr Pro Met Ala
    1745                1750                1755

Ser Val Arg Phe Phe Arg Ala Glu Leu Cys Pro Val Val Gln Glu
    1760                1765                1770

Thr Ala Glu Thr Arg Asp Thr Ala Met Ser Leu Gln Ala Pro Pro
    1775                1780                1785

Ser Thr Ala Thr Glu Pro Asn His Pro Pro Ile Ser Phe Gly Ala
    1790                1795                1800

Ser Ser Glu Thr Phe Pro Ile Thr Phe Gly Asp Phe Asn Glu Gly
    1805                1810                1815

Glu Ile Glu Ser Leu Ser Ser Glu Leu Leu Thr Phe Gly Asp Phe
    1820                1825                1830

Leu Pro Gly Glu Val Asp Asp Leu Thr Asp Ser Asp Trp Ser Thr
    1835                1840                1845

Cys Ser Asp Thr Asp Asp Glu Leu Xaa Leu Asp Arg Ala Gly Gly
    1850                1855                1860

Tyr Ile Phe Ser Ser Asp Thr Gly Pro Gly His Leu Gln Gln Lys
    1865                1870                1875

Ser Val Arg Gln Ser Val Leu Pro Val Asn Thr Leu Glu Glu Val
    1880                1885                1890

His Glu Glu Lys Cys Tyr Pro Pro Lys Leu Asp Glu Ala Lys Glu
    1895                1900                1905

Gln Leu Leu Leu Lys Lys Leu Gln Glu Ser Ala Ser Met Ala Asn
    1910                1915                1920

Arg Ser Arg Tyr Gln Ser Arg Lys Val Glu Asn Met Lys Ala Ala
    1925                1930                1935

Ile Ile Gln Arg Leu Lys Arg Gly Cys Arg Leu Tyr Leu Met Ser
    1940                1945                1950

Glu Thr Pro Lys Val Pro Thr Tyr Arg Thr Thr Tyr Pro Ala Pro
    1955                1960                1965

Val Tyr Ser Pro Pro Ile Asn Val Arg Leu Ser Asn Pro Glu Ser
    1970                1975                1980

Ala Val Ala Ala Cys Asn Glu Phe Leu Ala Arg Asn Tyr Pro Thr
    1985                1990                1995

Val Ser Ser Tyr Gln Ile Thr Asp Glu Tyr Asp Ala Tyr Leu Asp
    2000                2005                2010

Met Val Asp Gly Ser Glu Ser Cys Leu Asp Arg Ala Thr Phe Asn

```
                   2015                2020                2025
Pro Ser Lys Leu Arg Ser Tyr Pro Lys Gln His Ala Tyr His Ala
    2030                2035                2040

Pro Ser Ile Arg Ser Ala Val Pro Ser Pro Phe Gln Asn Thr Leu
    2045                2050                2055

Gln Asn Val Leu Ala Ala Ala Thr Lys Arg Asn Cys Asn Val Thr
    2060                2065                2070

Gln Met Arg Glu Leu Pro Thr Leu Asp Ser Ala Val Phe Asn Val
    2075                2080                2085

Glu Cys Phe Lys Lys Phe Ala Cys Asn Gln Glu Tyr Trp Glu Glu
    2090                2095                2100

Phe Ala Ala Ser Pro Ile Arg Ile Thr Thr Glu Asn Leu Ala Thr
    2105                2110                2115

Tyr Val Thr Lys Leu Lys Gly Pro Lys Ala Ala Ala Leu Phe Ala
    2120                2125                2130

Lys Thr His Asn Leu Leu Pro Leu Gln Glu Val Pro Met Asp Arg
    2135                2140                2145

Phe Thr Val Asp Met Lys Arg Asp Val Lys Val Thr Pro Gly Thr
    2150                2155                2160

Lys His Thr Glu Glu Arg Pro Lys Val Gln Val Ile Gln Ala Ala
    2165                2170                2175

Glu Pro Leu Ala Thr Ala Tyr Leu Cys Gly Ile His Arg Glu Leu
    2180                2185                2190

Val Arg Arg Leu Asn Ala Val Leu Leu Pro Asn Val His Thr Leu
    2195                2200                2205

Phe Asp Met Ser Ala Glu Asp Phe Asp Ala Ile Ile Ala Ala His
    2210                2215                2220

Phe Lys Pro Gly Asp Thr Val Leu Glu Thr Asp Ile Ala Ser Phe
    2225                2230                2235

Asp Lys Ser Gln Asp Asp Ser Leu Ala Leu Thr Ala Leu Met Leu
    2240                2245                2250

Leu Glu Asp Leu Gly Val Asp His Ser Leu Leu Asp Leu Ile Glu
    2255                2260                2265

Ala Ala Phe Gly Glu Ile Ser Ser Cys His Leu Pro Thr Gly Thr
    2270                2275                2280

Arg Phe Lys Phe Gly Ala Met Met Lys Ser Gly Met Phe Leu Thr
    2285                2290                2295

Leu Phe Val Asn Thr Leu Leu Asn Ile Thr Ile Ala Ser Arg Val
    2300                2305                2310

Leu Glu Asp Arg Leu Thr Lys Ser Ala Cys Ala Ala Phe Ile Gly
    2315                2320                2325

Asp Asp Asn Ile Ile His Gly Val Val Ser Asp Glu Leu Met Ala
    2330                2335                2340

Ala Arg Cys Ala Thr Trp Met Asn Met Glu Val Lys Ile Ile Asp
    2345                2350                2355

Ala Val Val Ser Leu Lys Ala Pro Tyr Phe Cys Gly Gly Phe Ile
    2360                2365                2370

Leu His Asp Thr Val Thr Gly Thr Ala Cys Arg Val Ala Asp Pro
    2375                2380                2385

Leu Lys Arg Leu Phe Lys Leu Gly Lys Pro Leu Ala Ala Gly Asp
    2390                2395                2400

Glu Gln Asp Glu Asp Arg Arg Arg Ala Leu Ala Asp Glu Val Ile
    2405                2410                2415
```

-continued

Arg Trp Gln Arg Thr Gly Leu Ile Asp Glu Leu Glu Lys Ala Val
    2420                2425                2430

Tyr Ser Arg Tyr Glu Val Gln Gly Ile Ser Val Val Val Met Ser
    2435                2440                2445

Met Ala Thr Phe Ala Ser Ser Arg Ser Asn Phe Glu Lys Leu Arg
2450                2455                2460

Gly Pro Val Ile Thr Leu Tyr Gly Gly Pro Lys
    2465                2470

<210> SEQ ID NO 90
<211> LENGTH: 2474
<212> TYPE: PRT
<213> ORGANISM: Chikungunya virus
<220> FEATURE:
<221> NAME/KEY: misc_feature
<222> LOCATION: (1857)..(1857)
<223> OTHER INFORMATION: Xaa can be any naturally occurring amino acid

<400> SEQUENCE: 90

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
    210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

```
Arg Ile Thr Met Ser Pro Gly Leu Tyr Gly Lys Thr Thr Gly Tyr Ala
290                 295                 300
Val Thr His His Ala Asp Gly Phe Leu Met Cys Lys Thr Thr Asp Thr
305                 310                 315                 320
Val Asp Gly Glu Arg Val Ser Phe Ser Val Cys Thr Tyr Val Pro Ala
                325                 330                 335
Thr Ile Cys Asp Gln Met Thr Gly Ile Leu Ala Thr Glu Val Thr Pro
                340                 345                 350
Glu Asp Ala Gln Lys Leu Leu Val Gly Leu Asn Gln Arg Ile Val Val
                355                 360                 365
Asn Gly Arg Thr Gln Arg Asn Thr Asn Thr Met Lys Asn Tyr Leu Leu
370                 375                 380
Pro Val Val Ala Gln Ala Phe Ser Lys Trp Ala Lys Glu Cys Arg Lys
385                 390                 395                 400
Asp Met Glu Asp Glu Lys Leu Leu Gly Val Arg Glu Arg Thr Leu Thr
                405                 410                 415
Cys Cys Cys Leu Trp Ala Phe Lys Lys Gln Lys Thr His Thr Val Tyr
                420                 425                 430
Lys Arg Pro Asp Thr Gln Ser Ile Gln Lys Val Gln Ala Glu Phe Asp
                435                 440                 445
Ser Phe Val Val Pro Ser Leu Trp Ser Ser Gly Leu Ser Ile Pro Leu
                450                 455                 460
Arg Thr Arg Ile Lys Trp Leu Leu Ser Lys Val Pro Lys Thr Asp Leu
465                 470                 475                 480
Ile Pro Tyr Ser Gly Asp Ala Arg Glu Ala Arg Asp Ala Glu Lys Glu
                485                 490                 495
Ala Glu Glu Glu Arg Glu Ala Glu Leu Thr Arg Glu Ala Leu Pro Pro
                500                 505                 510
Leu Gln Ala Ala Gln Glu Asp Val Gln Val Glu Ile Asp Val Glu Gln
                515                 520                 525
Leu Glu Asp Arg Ala Gly Ala Gly Ile Ile Glu Thr Pro Arg Gly Ala
                530                 535                 540
Ile Lys Val Thr Ala Gln Pro Thr Asp His Val Val Gly Glu Tyr Leu
545                 550                 555                 560
Val Leu Ser Pro Gln Thr Val Leu Arg Ser Gln Lys Leu Ser Leu Ile
                565                 570                 575
His Ala Leu Ala Glu Gln Val Lys Thr Cys Thr His Asn Gly Arg Ala
                580                 585                 590
Gly Arg Tyr Ala Val Glu Ala Tyr Asp Gly Arg Val Leu Val Pro Ser
                595                 600                 605
Gly Tyr Ala Ile Ser Pro Glu Asp Phe Gln Ser Leu Ser Glu Ser Ala
                610                 615                 620
Thr Met Val Tyr Asn Glu Arg Glu Phe Val Asn Arg Lys Leu His His
625                 630                 635                 640
Ile Ala Met His Gly Pro Ala Leu Asn Thr Asp Glu Glu Ser Tyr Glu
                645                 650                 655
Leu Val Arg Ala Glu Arg Thr Glu His Glu Tyr Val Tyr Asp Val Asp
                660                 665                 670
Gln Arg Arg Cys Cys Lys Lys Glu Ala Ala Gly Leu Val Leu Val
                675                 680                 685
Gly Asp Leu Thr Asn Pro Pro Tyr His Glu Phe Ala Tyr Glu Gly Leu
690                 695                 700
Lys Ile Arg Pro Ala Cys Pro Tyr Lys Ile Ala Val Ile Gly Val Phe
```

```
             705                 710                 715                 720
Gly Val Pro Gly Ser Gly Lys Ser Ala Ile Ile Lys Asn Leu Val Thr
                725                 730                 735
Arg Gln Asp Leu Val Thr Ser Gly Lys Lys Glu Asn Cys Gln Glu Ile
                740                 745                 750
Thr Thr Asp Val Met Arg Gln Arg Gly Leu Glu Ile Ser Ala Arg Thr
                755                 760                 765
Val Asp Ser Leu Leu Asn Gly Cys Asn Arg Pro Val Asp Val Leu
    770                 775                 780
Tyr Val Asp Glu Ala Phe Ala Cys His Ser Gly Thr Leu Leu Ala Leu
785                 790                 795                 800
Ile Ala Leu Val Arg Pro Arg Gln Lys Val Val Leu Cys Gly Asp Pro
                805                 810                 815
Lys Gln Cys Gly Phe Phe Asn Met Met Gln Met Lys Val Asn Tyr Asn
                820                 825                 830
His Asn Ile Cys Thr Gln Val Tyr His Lys Ser Ile Ser Arg Arg Cys
                835                 840                 845
Thr Leu Pro Val Thr Ala Ile Val Ser Ser Leu His Tyr Glu Gly Lys
    850                 855                 860
Met Arg Thr Thr Asn Glu Tyr Asn Lys Pro Ile Val Val Asp Thr Thr
865                 870                 875                 880
Gly Ser Thr Lys Pro Asp Pro Gly Asp Leu Val Leu Thr Cys Phe Arg
                885                 890                 895
Gly Trp Val Lys Gln Leu Gln Ile Asp Tyr Arg Gly Tyr Glu Val Met
                900                 905                 910
Thr Ala Ala Ala Ser Gln Gly Leu Thr Arg Lys Gly Val Tyr Ala Val
                915                 920                 925
Arg Gln Lys Val Asn Glu Asn Pro Leu Tyr Ala Ser Thr Ser Glu His
                930                 935                 940
Val Asn Val Leu Leu Thr Arg Thr Glu Gly Lys Leu Val Trp Lys Thr
945                 950                 955                 960
Leu Ser Gly Asp Pro Trp Ile Lys Thr Leu Gln Asn Pro Pro Lys Gly
                965                 970                 975
Asn Phe Lys Ala Thr Ile Lys Glu Trp Glu Val Glu His Ala Ser Ile
                980                 985                 990
Met Ala Gly Ile Cys Ser His Gln Met Thr Phe Asp Thr Phe Gln Asn
                995                 1000                1005
Lys Ala Asn Val Cys Trp Ala Lys Ser Leu Val Pro Ile Leu Glu
    1010                1015                1020
Thr Ala Gly Ile Lys Leu Asn Asp Arg Gln Trp Ser Gln Ile Ile
    1025                1030                1035
Gln Ala Phe Lys Glu Asp Lys Ala Tyr Ser Pro Glu Val Ala Leu
    1040                1045                1050
Asn Glu Ile Cys Thr Arg Met Tyr Gly Val Asp Leu Asp Ser Gly
    1055                1060                1065
Leu Phe Ser Lys Pro Leu Val Ser Val Tyr Tyr Ala Asp Asn His
    1070                1075                1080
Trp Asp Asn Arg Pro Gly Gly Lys Met Phe Gly Phe Asn Pro Glu
    1085                1090                1095
Ala Ala Ser Ile Leu Glu Arg Lys Tyr Pro Phe Thr Lys Gly Lys
    1100                1105                1110
Trp Asn Ile Asn Lys Gln Ile Cys Val Thr Arg Arg Ile Glu
    1115                1120                1125
```

-continued

```
Asp Phe Asn Pro Thr Thr Asn Ile Ile Pro Ala Asn Arg Arg Leu
    1130                1135            1140

Pro His Ser Leu Val Ala Glu His Arg Pro Val Lys Gly Glu Arg
    1145                1150            1155

Met Glu Trp Leu Val Asn Lys Ile Asn Gly His His Val Leu Leu
    1160                1165            1170

Val Ser Gly Tyr Asn Leu Ala Leu Pro Thr Lys Arg Val Thr Trp
    1175                1180            1185

Val Ala Pro Leu Gly Val Arg Gly Ala Asp Tyr Thr Tyr Asn Leu
    1190                1195            1200

Glu Leu Gly Leu Pro Ala Thr Leu Gly Arg Tyr Asp Leu Val Val
    1205                1210            1215

Ile Asn Ile His Thr Pro Phe Arg Ile His His Tyr Gln Gln Cys
    1220                1225            1230

Val Asp His Ala Met Lys Leu Gln Met Leu Gly Gly Asp Ser Leu
    1235                1240            1245

Arg Leu Leu Lys Pro Gly Gly Ser Leu Leu Ile Arg Ala Tyr Gly
    1250                1255            1260

Tyr Ala Asp Arg Thr Ser Glu Arg Val Ile Cys Val Leu Gly Arg
    1265                1270            1275

Lys Phe Arg Ser Ser Arg Ala Leu Lys Pro Pro Cys Val Thr Ser
    1280                1285            1290

Asn Thr Glu Met Phe Phe Leu Phe Ser Asn Phe Asp Asn Gly Arg
    1295                1300            1305

Arg Asn Phe Thr Thr His Val Met Asn Asn Gln Leu Asn Ala Ala
    1310                1315            1320

Phe Val Gly Gln Val Thr Arg Ala Gly Cys Ala Pro Ser Tyr Arg
    1325                1330            1335

Val Lys Arg Met Asp Ile Ala Lys Asn Asp Glu Glu Cys Val Val
    1340                1345            1350

Asn Ala Ala Asn Pro Arg Gly Leu Pro Gly Asp Gly Val Cys Lys
    1355                1360            1365

Ala Val Tyr Lys Lys Trp Pro Glu Ser Phe Lys Asn Ser Ala Thr
    1370                1375            1380

Pro Val Gly Thr Ala Lys Thr Val Met Cys Gly Thr Tyr Pro Val
    1385                1390            1395

Ile His Ala Val Gly Pro Asn Phe Ser Asn Tyr Ser Glu Ser Glu
    1400                1405            1410

Gly Asp Arg Glu Leu Ala Ala Ala Tyr Arg Glu Val Ala Lys Glu
    1415                1420            1425

Val Thr Arg Leu Gly Val Asn Ser Val Ala Ile Pro Leu Leu Ser
    1430                1435            1440

Thr Gly Val Tyr Ser Gly Gly Lys Asp Arg Leu Thr Gln Ser Leu
    1445                1450            1455

Asn His Leu Phe Thr Ala Met Asp Ser Thr Asp Ala Asp Val Val
    1460                1465            1470

Ile Tyr Cys Arg Asp Lys Glu Trp Glu Lys Lys Ile Ser Glu Ala
    1475                1480            1485

Ile Gln Met Arg Thr Gln Val Glu Leu Leu Asp Glu His Ile Ser
    1490                1495            1500

Ile Asp Cys Asp Ile Val Arg Val His Pro Asp Ser Ser Leu Ala
    1505                1510            1515
```

```
Gly Arg Lys Gly Tyr Ser Thr Thr Glu Gly Ala Leu Tyr Ser Tyr
1520                1525                1530

Leu Glu Gly Thr Arg Phe His Gln Thr Ala Val Asp Met Ala Glu
1535                1540                1545

Ile His Thr Met Trp Pro Lys Gln Thr Glu Ala Asn Glu Gln Val
1550                1555                1560

Cys Leu Tyr Ala Leu Gly Glu Ser Ile Glu Ser Ile Arg Gln Lys
1565                1570                1575

Cys Pro Val Asp Asp Ala Asp Ala Ser Ser Pro Pro Lys Thr Val
1580                1585                1590

Pro Cys Leu Cys Arg Tyr Ala Met Thr Pro Glu Arg Val Thr Arg
1595                1600                1605

Leu Arg Met Asn His Val Thr Ser Ile Ile Val Cys Ser Ser Phe
1610                1615                1620

Pro Leu Pro Lys Tyr Lys Ile Glu Gly Val Gln Lys Val Lys Cys
1625                1630                1635

Ser Lys Val Met Leu Phe Asp His Asn Val Pro Ser Arg Val Ser
1640                1645                1650

Pro Arg Glu Tyr Arg Ser Ser Gln Glu Ser Ala Gln Glu Ala Ser
1655                1660                1665

Thr Ile Thr Ser Leu Thr His Ser Gln Phe Asp Leu Ser Val Asp
1670                1675                1680

Gly Glu Ile Leu Pro Val Pro Ser Asp Leu Asp Ala Asp Ala Pro
1685                1690                1695

Ala Leu Glu Pro Ala Leu Asp Asp Gly Ala Thr His Thr Leu Pro
1700                1705                1710

Ser Thr Thr Gly Asn Leu Ala Ala Val Ser Asp Trp Val Met Ser
1715                1720                1725

Thr Val Pro Val Ala Pro Pro Arg Arg Arg Arg Gly Arg Asn Leu
1730                1735                1740

Thr Val Thr Cys Asp Glu Arg Glu Gly Asn Ile Thr Pro Met Ala
1745                1750                1755

Ser Val Arg Phe Phe Arg Ala Glu Leu Cys Pro Val Val Gln Glu
1760                1765                1770

Thr Ala Glu Thr Arg Asp Thr Ala Met Ser Leu Gln Ala Pro Pro
1775                1780                1785

Ser Thr Ala Thr Glu Pro Asn His Pro Pro Ile Ser Phe Gly Ala
1790                1795                1800

Ser Ser Glu Thr Phe Pro Ile Thr Phe Gly Asp Phe Asn Glu Gly
1805                1810                1815

Glu Ile Glu Ser Leu Ser Ser Glu Leu Leu Thr Phe Gly Asp Phe
1820                1825                1830

Leu Pro Gly Glu Val Asp Asp Leu Thr Asp Ser Asp Trp Ser Thr
1835                1840                1845

Cys Ser Asp Thr Asp Asp Glu Leu Xaa Leu Asp Arg Ala Gly Gly
1850                1855                1860

Tyr Ile Phe Ser Ser Asp Thr Gly Pro Gly His Leu Gln Gln Lys
1865                1870                1875

Ser Val Arg Gln Ser Val Leu Pro Val Asn Thr Leu Glu Glu Val
1880                1885                1890

His Glu Glu Lys Cys Tyr Pro Pro Lys Leu Asp Glu Ala Lys Glu
1895                1900                1905

Gln Leu Leu Leu Lys Lys Leu Gln Glu Ser Ala Ser Met Ala Asn
```

-continued

```
                1910                1915                1920
Arg Ser Arg Tyr Gln Ser Arg Lys Val Glu Asn Met Lys Ala Ala
            1925                1930                1935

Ile Ile Gln Arg Leu Lys Arg Gly Cys Arg Leu Tyr Leu Met Ser
            1940                1945                1950

Glu Thr Pro Lys Val Pro Thr Tyr Arg Thr Thr Tyr Pro Ala Pro
            1955                1960                1965

Val Tyr Ser Pro Pro Ile Asn Val Arg Leu Ser Asn Pro Glu Ser
            1970                1975                1980

Ala Val Ala Ala Cys Asn Glu Phe Leu Ala Arg Asn Tyr Pro Thr
            1985                1990                1995

Val Ser Ser Tyr Gln Ile Thr Asp Glu Tyr Asp Ala Tyr Leu Asp
            2000                2005                2010

Met Val Asp Gly Ser Glu Ser Cys Leu Asp Arg Ala Thr Phe Asn
            2015                2020                2025

Pro Ser Lys Leu Arg Ser Tyr Pro Lys Gln His Ala Tyr His Ala
            2030                2035                2040

Pro Ser Ile Arg Ser Ala Val Pro Ser Pro Phe Gln Asn Thr Leu
            2045                2050                2055

Gln Asn Val Leu Ala Ala Ala Thr Lys Arg Asn Cys Asn Val Thr
            2060                2065                2070

Gln Met Arg Glu Leu Pro Thr Leu Asp Ser Ala Val Phe Asn Val
            2075                2080                2085

Glu Cys Phe Lys Lys Phe Ala Cys Asn Gln Glu Tyr Trp Glu Glu
            2090                2095                2100

Phe Ala Ala Ser Pro Ile Arg Ile Thr Thr Glu Asn Leu Ala Thr
            2105                2110                2115

Tyr Val Thr Lys Leu Lys Gly Pro Lys Ala Ala Leu Phe Ala
            2120                2125                2130

Lys Thr His Asn Leu Leu Pro Leu Gln Glu Val Pro Met Asp Arg
            2135                2140                2145

Phe Thr Val Asp Met Lys Arg Asp Val Lys Val Thr Pro Gly Thr
            2150                2155                2160

Lys His Thr Glu Glu Arg Pro Lys Val Gln Val Ile Gln Ala Ala
            2165                2170                2175

Glu Pro Leu Ala Thr Ala Tyr Leu Cys Gly Ile His Arg Glu Leu
            2180                2185                2190

Val Arg Arg Leu Asn Ala Val Leu Leu Pro Asn Val His Thr Leu
            2195                2200                2205

Phe Asp Met Ser Ala Glu Asp Phe Asp Ala Ile Ile Ala Ala His
            2210                2215                2220

Phe Lys Pro Gly Asp Thr Val Leu Glu Thr Asp Ile Ala Ser Phe
            2225                2230                2235

Asp Lys Ser Gln Asp Asp Ser Leu Ala Leu Thr Ala Leu Met Leu
            2240                2245                2250

Leu Glu Asp Leu Gly Val Asp His Ser Leu Leu Asp Leu Ile Glu
            2255                2260                2265

Ala Ala Phe Gly Glu Ile Ser Ser Cys His Leu Pro Thr Gly Thr
            2270                2275                2280

Arg Phe Lys Phe Gly Ala Met Met Lys Ser Gly Met Phe Leu Thr
            2285                2290                2295

Leu Phe Val Asn Thr Leu Leu Asn Ile Thr Ile Ala Ser Arg Val
            2300                2305                2310
```

```
Leu Glu Asp Arg Leu Thr Lys Ser Ala Cys Ala Ala Phe Ile Gly
    2315            2320                2325

Asp Asp Asn Ile Ile His Gly Val Val Ser Asp Glu Leu Met Ala
    2330            2335                2340

Ala Arg Ala Ala Thr Trp Met Asn Met Glu Val Lys Ile Ile Asp
    2345            2350                2355

Ala Val Val Ser Leu Lys Ala Pro Tyr Phe Cys Gly Gly Phe Ile
    2360            2365                2370

Leu His Asp Thr Val Thr Gly Thr Ala Cys Arg Val Ala Asp Pro
    2375            2380                2385

Leu Lys Arg Leu Phe Lys Leu Gly Lys Pro Leu Ala Ala Gly Asp
    2390            2395                2400

Glu Gln Asp Glu Asp Arg Arg Ala Leu Ala Asp Glu Val Ile
    2405            2410                2415

Arg Trp Gln Arg Thr Gly Leu Ile Asp Glu Leu Glu Lys Ala Val
    2420            2425                2430

Tyr Ser Arg Tyr Glu Val Gln Gly Ile Ser Val Val Val Met Ser
    2435            2440                2445

Met Ala Thr Phe Ala Ser Ser Arg Ser Asn Phe Glu Lys Leu Arg
    2450            2455                2460

Gly Pro Val Ile Thr Leu Tyr Gly Gly Pro Lys
    2465            2470

<210> SEQ ID NO 91
<211> LENGTH: 2474
<212> TYPE: PRT
<213> ORGANISM: Chikungunya virus
<220> FEATURE:
<221> NAME/KEY: misc_feature
<222> LOCATION: (1857)..(1857)
<223> OTHER INFORMATION: Xaa can be any naturally occurring amino acid

<400> SEQUENCE: 91

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175
```

-continued

```
Gly Phe Asp Thr Thr Pro Phe Met Tyr Asn Ala Met Ala Gly Ala Tyr
                180                 185                 190
Pro Ser Tyr Ser Thr Asn Trp Ala Asp Glu Gln Val Leu Lys Ala Lys
            195                 200                 205
Asn Ile Gly Leu Cys Ser Thr Asp Leu Thr Glu Gly Arg Arg Gly Lys
        210                 215                 220
Leu Ser Ile Met Arg Gly Lys Lys Leu Lys Pro Cys Asp Arg Val Leu
225                 230                 235                 240
Phe Ser Val Gly Ser Thr Leu Tyr Pro Glu Ser Arg Lys Leu Leu Lys
                245                 250                 255
Ser Trp His Leu Pro Ser Val Phe His Leu Lys Gly Lys Leu Ser Phe
            260                 265                 270
Thr Cys Arg Cys Asp Thr Val Ser Cys Glu Gly Tyr Val Val Lys
        275                 280                 285
Arg Ile Thr Met Ser Pro Gly Leu Tyr Gly Lys Thr Thr Gly Tyr Ala
        290                 295                 300
Val Thr His His Ala Asp Gly Phe Leu Met Cys Lys Thr Thr Asp Thr
305                 310                 315                 320
Val Asp Gly Glu Arg Val Ser Phe Ser Val Cys Thr Tyr Val Pro Ala
                325                 330                 335
Thr Ile Cys Asp Gln Met Thr Gly Ile Leu Ala Thr Glu Val Thr Pro
            340                 345                 350
Glu Asp Ala Gln Lys Leu Leu Val Gly Leu Asn Gln Arg Ile Val Val
        355                 360                 365
Asn Gly Arg Thr Gln Arg Asn Thr Asn Thr Met Lys Asn Tyr Leu Leu
370                 375                 380
Pro Val Val Ala Gln Ala Phe Ser Lys Trp Ala Lys Glu Cys Arg Lys
385                 390                 395                 400
Asp Met Glu Asp Glu Lys Leu Leu Gly Val Arg Glu Arg Thr Leu Thr
                405                 410                 415
Cys Cys Cys Leu Trp Ala Phe Lys Lys Gln Lys Thr His Thr Val Tyr
            420                 425                 430
Lys Arg Pro Asp Thr Gln Ser Ile Gln Lys Val Gln Ala Glu Phe Asp
        435                 440                 445
Ser Phe Val Val Pro Ser Leu Trp Ser Ser Gly Leu Ser Ile Pro Leu
450                 455                 460
Arg Thr Arg Ile Lys Trp Leu Leu Ser Lys Val Pro Lys Thr Asp Leu
465                 470                 475                 480
Ile Pro Tyr Ser Gly Asp Ala Arg Glu Ala Arg Asp Ala Glu Lys Glu
                485                 490                 495
Ala Glu Glu Glu Arg Glu Ala Glu Leu Thr Arg Glu Ala Leu Pro Pro
            500                 505                 510
Leu Gln Ala Ala Gln Glu Asp Val Gln Val Glu Ile Asp Val Glu Gln
        515                 520                 525
Leu Glu Asp Arg Ala Gly Ala Gly Ile Ile Glu Thr Pro Arg Gly Ala
        530                 535                 540
Ile Lys Val Thr Ala Gln Pro Thr Asp His Val Val Gly Glu Tyr Leu
545                 550                 555                 560
Val Leu Ser Pro Gln Thr Val Leu Arg Ser Gln Lys Leu Ser Leu Ile
                565                 570                 575
His Ala Leu Ala Glu Gln Val Lys Thr Cys Thr His Asn Gly Arg Ala
            580                 585                 590
Gly Arg Tyr Ala Val Glu Ala Tyr Asp Gly Arg Val Leu Val Pro Ser
```

-continued

```
            595                 600                 605
Gly Tyr Ala Ile Ser Pro Glu Asp Phe Gln Ser Leu Ser Glu Ser Ala
    610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Ala Ala Gly Leu Val Leu Val
            675                 680                 685

Gly Asp Leu Thr Asn Pro Pro Tyr His Glu Phe Ala Tyr Glu Gly Leu
    690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
            755                 760                 765

Val Asp Ser Leu Leu Asn Gly Cys Asn Arg Pro Val Asp Val Leu
770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
            805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
        835                 840                 845

Thr Leu Pro Val Thr Ala Ile Val Ser Ser Leu His Tyr Glu Gly Lys
    850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly Tyr Glu Val Met
            900                 905                 910

Thr Ala Ala Ala Ser Gln Gly Leu Thr Arg Lys Gly Val Tyr Ala Val
        915                 920                 925

Arg Gln Lys Val Asn Glu Asn Pro Leu Tyr Ala Ser Thr Ser Glu His
    930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
            980                 985                 990

Met Ala Gly Ile Cys Ser His Gln Met Thr Phe Asp Thr Phe Gln Asn
        995                 1000                1005

Lys Ala Asn Val Cys Trp Ala Lys Ser Leu Val Pro Ile Leu Glu
    1010                1015                1020
```

```
Thr Ala Gly Ile Lys Leu Asn Asp Arg Gln Trp Ser Gln Ile Ile
    1025            1030                1035

Gln Ala Phe Lys Glu Asp Lys Ala Tyr Ser Pro Glu Val Ala Leu
    1040            1045                1050

Asn Glu Ile Cys Thr Arg Met Tyr Gly Val Asp Leu Asp Ser Gly
    1055            1060                1065

Leu Phe Ser Lys Pro Leu Val Ser Val Tyr Tyr Ala Asp Asn His
    1070            1075                1080

Trp Asp Asn Arg Pro Gly Gly Lys Met Phe Gly Phe Asn Pro Glu
    1085            1090                1095

Ala Ala Ser Ile Leu Glu Arg Lys Tyr Pro Phe Thr Lys Gly Lys
    1100            1105                1110

Trp Asn Ile Asn Lys Gln Ile Cys Val Thr Thr Arg Arg Ile Glu
    1115            1120                1125

Asp Phe Asn Pro Thr Thr Asn Ile Ile Pro Ala Asn Arg Arg Leu
    1130            1135                1140

Pro His Ser Leu Val Ala Glu His Arg Pro Val Lys Gly Glu Arg
    1145            1150                1155

Met Glu Trp Leu Val Asn Lys Ile Asn Gly His His Val Leu Leu
    1160            1165                1170

Val Ser Gly Tyr Asn Leu Ala Leu Pro Thr Lys Arg Val Thr Trp
    1175            1180                1185

Val Ala Pro Leu Gly Val Arg Gly Ala Asp Tyr Thr Tyr Asn Leu
    1190            1195                1200

Glu Leu Gly Leu Pro Ala Thr Leu Gly Arg Tyr Asp Leu Val Val
    1205            1210                1215

Ile Asn Ile His Thr Pro Phe Arg Ile His His Tyr Gln Gln Cys
    1220            1225                1230

Val Asp His Ala Met Lys Leu Gln Met Leu Gly Gly Asp Ser Leu
    1235            1240                1245

Arg Leu Leu Lys Pro Gly Gly Ser Leu Leu Ile Arg Ala Tyr Gly
    1250            1255                1260

Tyr Ala Asp Arg Thr Ser Glu Arg Val Ile Cys Val Leu Gly Arg
    1265            1270                1275

Lys Phe Arg Ser Ser Arg Ala Leu Lys Pro Pro Cys Val Thr Ser
    1280            1285                1290

Asn Thr Glu Met Phe Phe Leu Phe Ser Asn Phe Asp Asn Gly Arg
    1295            1300                1305

Arg Asn Phe Thr Thr His Val Met Asn Asn Gln Leu Asn Ala Ala
    1310            1315                1320

Phe Val Gly Gln Val Thr Arg Ala Gly Cys Ala Pro Ser Tyr Arg
    1325            1330                1335

Val Lys Arg Met Asp Ile Ala Lys Asn Asp Glu Glu Cys Val Val
    1340            1345                1350

Asn Ala Ala Asn Pro Arg Gly Leu Pro Gly Asp Gly Val Cys Lys
    1355            1360                1365

Ala Val Tyr Lys Lys Trp Pro Glu Ser Phe Lys Asn Ser Ala Thr
    1370            1375                1380

Pro Val Gly Thr Ala Lys Thr Val Met Cys Gly Thr Tyr Pro Val
    1385            1390                1395

Ile His Ala Val Gly Pro Asn Phe Ser Asn Tyr Ser Glu Ser Glu
    1400            1405                1410
```

```
Gly Asp Arg Glu Leu Ala Ala Ala Tyr Arg Glu Val Ala Lys Glu
    1415                1420                1425

Val Thr Arg Leu Gly Val Asn Ser Val Ala Ile Pro Leu Leu Ser
    1430                1435                1440

Thr Gly Val Tyr Ser Gly Gly Lys Asp Arg Leu Thr Gln Ser Leu
    1445                1450                1455

Asn His Leu Phe Thr Ala Met Asp Ser Thr Asp Ala Asp Val Val
    1460                1465                1470

Ile Tyr Cys Arg Asp Lys Glu Trp Glu Lys Lys Ile Ser Glu Ala
    1475                1480                1485

Ile Gln Met Arg Thr Gln Val Glu Leu Leu Asp Glu His Ile Ser
    1490                1495                1500

Ile Asp Cys Asp Ile Val Arg Val His Pro Asp Ser Ser Leu Ala
    1505                1510                1515

Gly Arg Lys Gly Tyr Ser Thr Thr Glu Gly Ala Leu Tyr Ser Tyr
    1520                1525                1530

Leu Glu Gly Thr Arg Phe His Gln Thr Ala Val Asp Met Ala Glu
    1535                1540                1545

Ile His Thr Met Trp Pro Lys Gln Thr Glu Ala Asn Glu Gln Val
    1550                1555                1560

Cys Leu Tyr Ala Leu Gly Glu Ser Ile Glu Ser Ile Arg Gln Lys
    1565                1570                1575

Cys Pro Val Asp Asp Ala Asp Ala Ser Ser Pro Lys Thr Val
    1580                1585                1590

Pro Cys Leu Cys Arg Tyr Ala Met Thr Pro Glu Arg Val Thr Arg
    1595                1600                1605

Leu Arg Met Asn His Val Thr Ser Ile Ile Val Cys Ser Ser Phe
    1610                1615                1620

Pro Leu Pro Lys Tyr Lys Ile Glu Gly Val Gln Lys Val Lys Cys
    1625                1630                1635

Ser Lys Val Met Leu Phe Asp His Asn Val Pro Ser Arg Val Ser
    1640                1645                1650

Pro Arg Glu Tyr Arg Ser Ser Gln Glu Ser Ala Gln Glu Ala Ser
    1655                1660                1665

Thr Ile Thr Ser Leu Thr His Ser Gln Phe Asp Leu Ser Val Asp
    1670                1675                1680

Gly Glu Ile Leu Pro Val Pro Ser Asp Leu Asp Ala Asp Ala Pro
    1685                1690                1695

Ala Leu Glu Pro Ala Leu Asp Asp Gly Ala Thr His Thr Leu Pro
    1700                1705                1710

Ser Thr Thr Gly Asn Leu Ala Ala Val Ser Asp Trp Val Met Ser
    1715                1720                1725

Thr Val Pro Val Ala Pro Pro Arg Arg Arg Gly Arg Asn Leu
    1730                1735                1740

Thr Val Thr Cys Asp Glu Arg Glu Gly Asn Ile Thr Pro Met Ala
    1745                1750                1755

Ser Val Arg Phe Phe Arg Ala Glu Leu Cys Pro Val Val Gln Glu
    1760                1765                1770

Thr Ala Glu Thr Arg Asp Thr Ala Met Ser Leu Gln Ala Pro Pro
    1775                1780                1785

Ser Thr Ala Thr Glu Pro Asn His Pro Pro Ile Ser Phe Gly Ala
    1790                1795                1800

Ser Ser Glu Thr Phe Pro Ile Thr Phe Gly Asp Phe Asn Glu Gly
```

```
            1805                1810                1815
Glu Ile Glu Ser Leu Ser Ser Glu Leu Leu Thr Phe Gly Asp Phe
            1820                1825                1830

Leu Pro Gly Glu Val Asp Asp Leu Thr Asp Ser Asp Trp Ser Thr
            1835                1840                1845

Cys Ser Asp Thr Asp Asp Glu Leu Xaa Leu Asp Arg Ala Gly Gly
            1850                1855                1860

Tyr Ile Phe Ser Ser Asp Thr Gly Pro Gly His Leu Gln Gln Lys
            1865                1870                1875

Ser Val Arg Gln Ser Val Leu Pro Val Asn Thr Leu Glu Glu Val
            1880                1885                1890

His Glu Glu Lys Cys Tyr Pro Pro Lys Leu Asp Glu Ala Lys Glu
            1895                1900                1905

Gln Leu Leu Leu Lys Lys Leu Gln Glu Ser Ala Ser Met Ala Asn
            1910                1915                1920

Arg Ser Arg Tyr Gln Ser Arg Lys Val Glu Asn Met Lys Ala Ala
            1925                1930                1935

Ile Ile Gln Arg Leu Lys Arg Gly Cys Arg Leu Tyr Leu Met Ser
            1940                1945                1950

Glu Thr Pro Lys Val Pro Thr Tyr Arg Thr Thr Tyr Pro Ala Pro
            1955                1960                1965

Val Tyr Ser Pro Pro Ile Asn Val Arg Leu Ser Asn Pro Glu Ser
            1970                1975                1980

Ala Val Ala Ala Cys Asn Glu Phe Leu Ala Arg Asn Tyr Pro Thr
            1985                1990                1995

Val Ser Ser Tyr Gln Ile Thr Asp Glu Tyr Asp Ala Tyr Leu Asp
            2000                2005                2010

Met Val Asp Gly Ser Glu Ser Cys Leu Asp Arg Ala Thr Phe Asn
            2015                2020                2025

Pro Ser Lys Leu Arg Ser Tyr Pro Lys Gln His Ala Tyr His Ala
            2030                2035                2040

Pro Ser Ile Arg Ser Ala Val Pro Ser Pro Phe Gln Asn Thr Leu
            2045                2050                2055

Gln Asn Val Leu Ala Ala Ala Thr Lys Arg Asn Cys Asn Val Thr
            2060                2065                2070

Gln Met Arg Glu Leu Pro Thr Leu Asp Ser Ala Val Phe Asn Val
            2075                2080                2085

Glu Cys Phe Lys Lys Phe Ala Cys Asn Gln Glu Tyr Trp Glu Glu
            2090                2095                2100

Phe Ala Ala Ser Pro Ile Arg Ile Thr Thr Glu Asn Leu Ala Thr
            2105                2110                2115

Tyr Val Thr Lys Leu Lys Gly Pro Lys Ala Ala Ala Leu Phe Ala
            2120                2125                2130

Lys Thr His Asn Leu Leu Pro Leu Gln Glu Val Pro Met Asp Arg
            2135                2140                2145

Phe Thr Val Asp Met Lys Arg Asp Val Lys Val Thr Pro Gly Thr
            2150                2155                2160

Lys His Thr Glu Glu Arg Pro Lys Val Gln Val Ile Gln Ala Ala
            2165                2170                2175

Glu Pro Leu Ala Thr Ala Tyr Leu Cys Gly Ile His Arg Glu Leu
            2180                2185                2190

Val Arg Arg Leu Asn Ala Val Leu Leu Pro Asn Val His Thr Leu
            2195                2200                2205
```

```
Phe Asp Met Ser Ala Glu Asp Phe Asp Ala Ile Ile Ala Ala His
    2210                2215                2220

Phe Lys Pro Gly Asp Thr Val Leu Glu Thr Asp Ile Ala Ser Phe
    2225                2230                2235

Asp Lys Ser Gln Asp Ser Leu Ala Leu Thr Ala Leu Met Leu
    2240                2245                2250

Leu Glu Asp Leu Gly Val Asp His Ser Leu Leu Asp Leu Ile Glu
    2255                2260                2265

Ala Ala Phe Gly Glu Ile Ser Ser Cys His Leu Pro Thr Gly Thr
    2270                2275                2280

Arg Phe Lys Phe Gly Ala Met Met Lys Ser Gly Met Phe Leu Thr
    2285                2290                2295

Leu Phe Val Asn Thr Leu Leu Asn Ile Thr Ile Ala Ser Arg Val
    2300                2305                2310

Leu Glu Asp Arg Leu Thr Lys Ser Ala Cys Ala Ala Phe Ile Gly
    2315                2320                2325

Asp Asp Asn Ile Ile His Gly Val Val Ser Asp Glu Leu Met Ala
    2330                2335                2340

Ala Arg Trp Ala Thr Trp Met Asn Met Glu Val Lys Ile Ile Asp
    2345                2350                2355

Ala Val Val Ser Leu Lys Ala Pro Tyr Phe Cys Gly Gly Phe Ile
    2360                2365                2370

Leu His Asp Thr Val Thr Gly Thr Ala Cys Arg Val Ala Asp Pro
    2375                2380                2385

Leu Lys Arg Leu Phe Lys Leu Gly Lys Pro Leu Ala Ala Gly Asp
    2390                2395                2400

Glu Gln Asp Glu Asp Arg Arg Arg Ala Leu Ala Asp Glu Val Ile
    2405                2410                2415

Arg Trp Gln Arg Thr Gly Leu Ile Asp Glu Leu Glu Lys Ala Val
    2420                2425                2430

Tyr Ser Arg Tyr Glu Val Gln Gly Ile Ser Val Val Val Met Ser
    2435                2440                2445

Met Ala Thr Phe Ala Ser Ser Arg Ser Asn Phe Glu Lys Leu Arg
    2450                2455                2460

Gly Pro Val Ile Thr Leu Tyr Gly Gly Pro Lys
    2465                2470

<210> SEQ ID NO 92
<211> LENGTH: 2474
<212> TYPE: PRT
<213> ORGANISM: Chikungunya virus
<220> FEATURE:
<221> NAME/KEY: misc_feature
<222> LOCATION: (1857)..(1857)
<223> OTHER INFORMATION: Xaa can be any naturally occurring amino acid

<400> SEQUENCE: 92

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60
```

```
Gly Ser Ala Pro Ala Arg Met Met Ser Asp Arg Lys Tyr His Cys
 65                  70                  75                  80

Val Cys Pro Met Arg Ser Ala Glu Asp Pro Glu Arg Leu Ala Asn Tyr
             85                  90                  95

Ala Arg Lys Leu Ala Ser Ala Ala Gly Lys Val Leu Asp Arg Asn Ile
        100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
        130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
            195                 200                 205

Asn Ile Gly Leu Cys Ser Thr Asp Leu Thr Glu Gly Arg Arg Gly Lys
        210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

Arg Ile Thr Met Ser Pro Gly Leu Tyr Gly Lys Thr Thr Gly Tyr Ala
        290                 295                 300

Val Thr His His Ala Asp Gly Phe Leu Met Cys Lys Thr Thr Asp Thr
305                 310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
            355                 360                 365

Asn Gly Arg Thr Gln Arg Asn Thr Asn Thr Met Lys Asn Tyr Leu Leu
        370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
        450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
```

```
                485                 490                 495
Ala Glu Glu Glu Arg Glu Ala Glu Leu Thr Arg Glu Ala Leu Pro Pro
                500                 505                 510

Leu Gln Ala Ala Gln Glu Asp Val Gln Val Glu Ile Asp Val Glu Gln
                515                 520                 525

Leu Glu Asp Arg Ala Gly Ala Gly Ile Ile Glu Thr Pro Arg Gly Ala
                530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
                580                 585                 590

Gly Arg Tyr Ala Val Glu Ala Tyr Asp Gly Arg Val Leu Val Pro Ser
                595                 600                 605

Gly Tyr Ala Ile Ser Pro Glu Asp Phe Gln Ser Leu Ser Glu Ser Ala
                610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
                660                 665                 670

Gln Arg Arg Cys Cys Lys Lys Glu Ala Ala Gly Leu Val Leu Val
                675                 680                 685

Gly Asp Leu Thr Asn Pro Pro Tyr His Glu Phe Ala Tyr Glu Gly Leu
                690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
                740                 745                 750

Thr Thr Asp Val Met Arg Gln Arg Gly Leu Glu Ile Ser Ala Arg Thr
                755                 760                 765

Val Asp Ser Leu Leu Leu Asn Gly Cys Asn Arg Pro Val Asp Val Leu
                770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
                820                 825                 830

His Asn Ile Cys Thr Gln Val Tyr His Lys Ser Ile Ser Arg Arg Cys
                835                 840                 845

Thr Leu Pro Val Thr Ala Ile Val Ser Ser Leu His Tyr Glu Gly Lys
                850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly Tyr Glu Val Met
                900                 905                 910
```

```
Thr Ala Ala Ala Ser Gln Gly Leu Thr Arg Lys Gly Val Tyr Ala Val
            915                 920                 925

Arg Gln Lys Val Asn Glu Asn Pro Leu Tyr Ala Ser Thr Ser Glu His
    930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
                980                 985                 990

Met Ala Gly Ile Cys Ser His Gln Met Thr Phe Asp Thr Phe Gln Asn
            995                 1000                1005

Lys Ala Asn Val Cys Trp Ala Lys Ser Leu Val Pro Ile Leu Glu
    1010                1015                1020

Thr Ala Gly Ile Lys Leu Asn Asp Arg Gln Trp Ser Gln Ile Ile
    1025                1030                1035

Gln Ala Phe Lys Glu Asp Lys Ala Tyr Ser Pro Glu Val Ala Leu
    1040                1045                1050

Asn Glu Ile Cys Thr Arg Met Tyr Gly Val Asp Leu Asp Ser Gly
    1055                1060                1065

Leu Phe Ser Lys Pro Leu Val Ser Val Tyr Tyr Ala Asp Asn His
    1070                1075                1080

Trp Asp Asn Arg Pro Gly Gly Lys Met Phe Gly Phe Asn Pro Glu
    1085                1090                1095

Ala Ala Ser Ile Leu Glu Arg Lys Tyr Pro Phe Thr Lys Gly Lys
    1100                1105                1110

Trp Asn Ile Asn Lys Gln Ile Cys Val Thr Thr Arg Arg Ile Glu
    1115                1120                1125

Asp Phe Asn Pro Thr Thr Asn Ile Ile Pro Ala Asn Arg Arg Leu
    1130                1135                1140

Pro His Ser Leu Val Ala Glu His Arg Pro Val Lys Gly Glu Arg
    1145                1150                1155

Met Glu Trp Leu Val Asn Lys Ile Asn Gly His His Val Leu Leu
    1160                1165                1170

Val Ser Gly Tyr Asn Leu Ala Leu Pro Thr Lys Arg Val Thr Trp
    1175                1180                1185

Val Ala Pro Leu Gly Val Arg Gly Ala Asp Tyr Thr Tyr Asn Leu
    1190                1195                1200

Glu Leu Gly Leu Pro Ala Thr Leu Gly Arg Tyr Asp Leu Val Val
    1205                1210                1215

Ile Asn Ile His Thr Pro Phe Arg Ile His His Tyr Gln Gln Cys
    1220                1225                1230

Val Asp His Ala Met Lys Leu Gln Met Leu Gly Gly Asp Ser Leu
    1235                1240                1245

Arg Leu Leu Lys Pro Gly Gly Ser Leu Leu Ile Arg Ala Tyr Gly
    1250                1255                1260

Tyr Ala Asp Arg Thr Ser Glu Arg Val Ile Cys Val Leu Gly Arg
    1265                1270                1275

Lys Phe Arg Ser Ser Arg Ala Leu Lys Pro Pro Cys Val Thr Ser
    1280                1285                1290

Asn Thr Glu Met Phe Phe Leu Phe Ser Asn Phe Asp Asn Gly Arg
    1295                1300                1305
```

```
Arg Asn Phe Thr Thr His Val Met Asn Asn Gln Leu Asn Ala Ala
1310                1315                1320

Phe Val Gly Gln Val Thr Arg Ala Gly Cys Ala Pro Ser Tyr Arg
1325                1330                1335

Val Lys Arg Met Asp Ile Ala Lys Asn Asp Glu Glu Cys Val Val
1340                1345                1350

Asn Ala Ala Asn Pro Arg Gly Leu Pro Gly Asp Gly Val Cys Lys
1355                1360                1365

Ala Val Tyr Lys Lys Trp Pro Glu Ser Phe Lys Asn Ser Ala Thr
1370                1375                1380

Pro Val Gly Thr Ala Lys Thr Val Met Cys Gly Thr Tyr Pro Val
1385                1390                1395

Ile His Ala Val Gly Pro Asn Phe Ser Asn Tyr Ser Glu Ser Glu
1400                1405                1410

Gly Asp Arg Glu Leu Ala Ala Ala Tyr Arg Glu Val Ala Lys Glu
1415                1420                1425

Val Thr Arg Leu Gly Val Asn Ser Val Ala Ile Pro Leu Leu Ser
1430                1435                1440

Thr Gly Val Tyr Ser Gly Gly Lys Asp Arg Leu Thr Gln Ser Leu
1445                1450                1455

Asn His Leu Phe Thr Ala Met Asp Ser Thr Asp Ala Asp Val Val
1460                1465                1470

Ile Tyr Cys Arg Asp Lys Glu Trp Glu Lys Lys Ile Ser Glu Ala
1475                1480                1485

Ile Gln Met Arg Thr Gln Val Glu Leu Leu Asp Glu His Ile Ser
1490                1495                1500

Ile Asp Cys Asp Ile Val Arg Val His Pro Asp Ser Ser Leu Ala
1505                1510                1515

Gly Arg Lys Gly Tyr Ser Thr Thr Glu Gly Ala Leu Tyr Ser Tyr
1520                1525                1530

Leu Glu Gly Thr Arg Phe His Gln Thr Ala Val Asp Met Ala Glu
1535                1540                1545

Ile His Thr Met Trp Pro Lys Gln Thr Glu Ala Asn Glu Gln Val
1550                1555                1560

Cys Leu Tyr Ala Leu Gly Glu Ser Ile Glu Ser Ile Arg Gln Lys
1565                1570                1575

Cys Pro Val Asp Asp Ala Asp Ala Ser Ser Pro Lys Thr Val
1580                1585                1590

Pro Cys Leu Cys Arg Tyr Ala Met Thr Pro Glu Arg Val Thr Arg
1595                1600                1605

Leu Arg Met Asn His Val Thr Ser Ile Ile Val Cys Ser Ser Phe
1610                1615                1620

Pro Leu Pro Lys Tyr Lys Ile Glu Gly Val Gln Lys Val Lys Cys
1625                1630                1635

Ser Lys Val Met Leu Phe Asp His Asn Val Pro Ser Arg Val Ser
1640                1645                1650

Pro Arg Glu Tyr Arg Ser Ser Gln Glu Ser Ala Gln Glu Ala Ser
1655                1660                1665

Thr Ile Thr Ser Leu Thr His Ser Gln Phe Asp Leu Ser Val Asp
1670                1675                1680

Gly Glu Ile Leu Pro Val Pro Ser Asp Leu Asp Ala Asp Ala Pro
1685                1690                1695

Ala Leu Glu Pro Ala Leu Asp Asp Gly Ala Thr His Thr Leu Pro
```

-continued

```
            1700                1705                1710
Ser Thr Thr Gly Asn Leu Ala Ala Val Ser Asp Trp Val Met Ser
            1715                1720                1725
Thr Val Pro Val Ala Pro Pro Arg Arg Arg Gly Arg Asn Leu
            1730                1735                1740
Thr Val Thr Cys Asp Glu Arg Glu Gly Asn Ile Thr Pro Met Ala
            1745                1750                1755
Ser Val Arg Phe Phe Arg Ala Glu Leu Cys Pro Val Val Gln Glu
            1760                1765                1770
Thr Ala Glu Thr Arg Asp Thr Ala Met Ser Leu Gln Ala Pro Pro
            1775                1780                1785
Ser Thr Ala Thr Glu Pro Asn His Pro Pro Ile Ser Phe Gly Ala
            1790                1795                1800
Ser Ser Glu Thr Phe Pro Ile Thr Phe Gly Asp Phe Asn Glu Gly
            1805                1810                1815
Glu Ile Glu Ser Leu Ser Ser Glu Leu Leu Thr Phe Gly Asp Phe
            1820                1825                1830
Leu Pro Gly Glu Val Asp Asp Leu Thr Asp Ser Asp Trp Ser Thr
            1835                1840                1845
Cys Ser Asp Thr Asp Asp Glu Leu Xaa Leu Asp Arg Ala Gly Gly
            1850                1855                1860
Tyr Ile Phe Ser Ser Asp Thr Gly Pro Gly His Leu Gln Gln Lys
            1865                1870                1875
Ser Val Arg Gln Ser Val Leu Pro Val Asn Thr Leu Glu Glu Val
            1880                1885                1890
His Glu Glu Lys Cys Tyr Pro Pro Lys Leu Asp Glu Ala Lys Glu
            1895                1900                1905
Gln Leu Leu Leu Lys Lys Leu Gln Glu Ser Ala Ser Met Ala Asn
            1910                1915                1920
Arg Ser Arg Tyr Gln Ser Arg Lys Val Glu Asn Met Lys Ala Ala
            1925                1930                1935
Ile Ile Gln Arg Leu Lys Arg Gly Cys Arg Leu Tyr Leu Met Ser
            1940                1945                1950
Glu Thr Pro Lys Val Pro Thr Tyr Arg Thr Thr Tyr Pro Ala Pro
            1955                1960                1965
Val Tyr Ser Pro Pro Ile Asn Val Arg Leu Ser Asn Pro Glu Ser
            1970                1975                1980
Ala Val Ala Ala Cys Asn Glu Phe Leu Ala Arg Asn Tyr Pro Thr
            1985                1990                1995
Val Ser Ser Tyr Gln Ile Thr Asp Glu Tyr Asp Ala Tyr Leu Asp
            2000                2005                2010
Met Val Asp Gly Ser Glu Ser Cys Leu Asp Arg Ala Thr Phe Asn
            2015                2020                2025
Pro Ser Lys Leu Arg Ser Tyr Pro Lys Gln His Ala Tyr His Ala
            2030                2035                2040
Pro Ser Ile Arg Ser Ala Val Pro Ser Pro Phe Gln Asn Thr Leu
            2045                2050                2055
Gln Asn Val Leu Ala Ala Ala Thr Lys Arg Asn Cys Asn Val Thr
            2060                2065                2070
Gln Met Arg Glu Leu Pro Thr Leu Asp Ser Ala Val Phe Asn Val
            2075                2080                2085
Glu Cys Phe Lys Lys Phe Ala Cys Asn Gln Glu Tyr Trp Glu Glu
            2090                2095                2100
```

```
Phe Ala Ala Ser Pro Ile Arg Ile Thr Thr Glu Asn Leu Ala Thr
    2105                2110                2115

Tyr Val Thr Lys Leu Lys Gly Pro Lys Ala Ala Ala Leu Phe Ala
    2120                2125                2130

Lys Thr His Asn Leu Leu Pro Leu Gln Glu Val Pro Met Asp Arg
    2135                2140                2145

Phe Thr Val Asp Met Lys Arg Asp Val Lys Val Thr Pro Gly Thr
    2150                2155                2160

Lys His Thr Glu Glu Arg Pro Lys Val Gln Val Ile Gln Ala Ala
    2165                2170                2175

Glu Pro Leu Ala Thr Ala Tyr Leu Cys Gly Ile His Arg Glu Leu
    2180                2185                2190

Val Arg Arg Leu Asn Ala Val Leu Leu Pro Asn Val His Thr Leu
    2195                2200                2205

Phe Asp Met Ser Ala Glu Asp Phe Asp Ala Ile Ile Ala Ala His
    2210                2215                2220

Phe Lys Pro Gly Asp Thr Val Leu Glu Thr Asp Ile Ala Ser Phe
    2225                2230                2235

Asp Lys Ser Gln Asp Asp Ser Leu Ala Leu Thr Ala Leu Met Leu
    2240                2245                2250

Leu Glu Asp Leu Gly Val Asp His Ser Leu Leu Asp Leu Ile Glu
    2255                2260                2265

Ala Ala Phe Gly Glu Ile Ser Ser Cys His Leu Pro Thr Gly Thr
    2270                2275                2280

Arg Phe Lys Phe Gly Ala Met Met Lys Ser Gly Met Phe Leu Thr
    2285                2290                2295

Leu Phe Val Asn Thr Leu Leu Asn Ile Thr Ile Ala Ser Arg Val
    2300                2305                2310

Leu Glu Asp Arg Leu Thr Lys Ser Ala Cys Ala Ala Phe Ile Gly
    2315                2320                2325

Asp Asp Asn Ile Ile His Gly Val Val Ser Asp Glu Leu Met Ala
    2330                2335                2340

Ala Arg Gly Ala Thr Trp Met Asn Met Glu Val Lys Ile Ile Asp
    2345                2350                2355

Ala Val Val Ser Leu Lys Ala Pro Tyr Phe Cys Gly Gly Phe Ile
    2360                2365                2370

Leu His Asp Thr Val Thr Gly Thr Ala Cys Arg Val Ala Asp Pro
    2375                2380                2385

Leu Lys Arg Leu Phe Lys Leu Gly Lys Pro Leu Ala Ala Gly Asp
    2390                2395                2400

Glu Gln Asp Glu Asp Arg Arg Arg Ala Leu Ala Asp Glu Val Ile
    2405                2410                2415

Arg Trp Gln Arg Thr Gly Leu Ile Asp Glu Leu Glu Lys Ala Val
    2420                2425                2430

Tyr Ser Arg Tyr Glu Val Gln Gly Ile Ser Val Val Val Met Ser
    2435                2440                2445

Met Ala Thr Phe Ala Ser Ser Arg Ser Asn Phe Glu Lys Leu Arg
    2450                2455                2460

Gly Pro Val Ile Thr Leu Tyr Gly Gly Pro Lys
    2465                2470

<210> SEQ ID NO 93
<211> LENGTH: 7425
```

<212> TYPE: DNA
<213> ORGANISM: Chikungunya virus

<400> SEQUENCE: 93

```
atggatcctg tgtacgtgga catagacgct gacagcgcct ttttgaaggc cctgcaacgt    60
gcgtacccca tgtttgaggt ggaaccaagg caggtcacac cgaatgacca tgctaatgct   120
agagcgttct cgcatctagc tataaaacta atagagcagg aaattgaccc cgactcaacc   180
atcctggata tcggcagtgc gccagcaagg aggatgatgt cggacaggaa gtaccactgc   240
gtctgcccga tgcgcagtgc ggaagatccc gagagactcg ccaattatgc gagaaagcta   300
gcatctgccg caggaaaagt cctggacaga aacatctctg aaagatcgg ggacttacaa    360
gcagtaatgg ccgtgccaga cacggagacg ccaacattct gcttacacac agacgtctca   420
tgtagacaga gagcagacgt cgctatatac aagacgtct atgctgtaca cgcacccacg    480
tcgctatacc accaggcgat taaggggtc cgagtggcgt actgggttgg gttcgacaca    540
accccgttca tgtacaatgc catggcgggt gcctacccct catactcgac aaactgggca   600
gatgagcagg tactgaaggc taagaacata ggattatgtt caacagacct gacggaaggt   660
agacgaggca agttgtctat tatgagaggg aaaaagctaa accgtgcga ccgtgtgctg    720
ttctcagtag ggtcaacgct ctacccggaa agccgcaagc tacttaagag ctggcacctg   780
ccatcggtgt tccatttaaa gggcaaactc agcttcacat gccgctgtga tacagtggtt   840
tcgtgtgagg gctacgtcgt taagagaata cgatgagcc aggccttta tggaaaaaacc    900
acagggtatg cggtaaccca ccacgcagac ggattcctga tgtgcaagac taccgacacg   960
gttgacggcg aaagagtgtc attctcggtg tgcacatacg tgccggcgac catttgtgat  1020
caaatgaccg gcatccttgc tacagaagtc acgccggagg atgcacagaa gctgttggtg  1080
gggctgaacc agagaatagt ggttaacggc agaacgcaac ggaatacgaa caccatgaaa  1140
aattatctgc ttcccgtggt cgcccaagcc ttcagtaagt gggcaaagga gtgccggaaa  1200
gacatggaag atgaaaaact cctgggggtc agagaaagaa cactgacctg ctgctgtcta  1260
tgggcattca gaagcagaa acacacacg gtctacaaga gacctgatac ccagtcaatt   1320
cagaaggttc aggccgagtt tgacagcttt gtggtaccga gtctgtggtc gtccgggttg  1380
tcaatcccctt tgaggactag aatcaaatgg ttgttaagca aggtgccaaa aaccgacctg  1440
atcccataca gcggagacgc ccgagaagcc cgggacgcag aaaagaagc agaggaagaa   1500
cgagaagcag aactgactcg cgaagcccta ccacctctac aggcagcaca ggaagatgtt  1560
caggtcgaaa tcgacgtgga acagcttgag gacagagcgg gcagaggaat aatagagact  1620
ccgagaggag ctatcaaagt tactgcccaa ccaacagacc acgtcgtggg agagtacctg  1680
gtactctccc cgcagaccgt actacgtagc cagaagctca gtctgattca cgctttggcg  1740
gagcaagtga agacgtgcac gcacaacgga cgagcaggga ggtatgcggt cgaagcgtac  1800
gacggccgag tcctagtgcc ctcaggctat gcaatctcgc ctgaagactt ccagagtcta  1860
agcgaaagcg caacgatggt gtataacgaa agagagttcg taaacagaaa gctacaccat  1920
attgcgatgc acggaccagc cctgaacacc gacgaagagt cgtatgagct ggtgagggca  1980
gagaggacag aacacgagta cgtctacgac gtggatcaga agatgctg taagaaggaa   2040
gaagccgcag gactggtact ggtgggcgac ttgactaatc cgcctacca gaattcgca   2100
tatgaagggc taaaaatccg ccctgcctgc ccatacaaaa ttgcagtcat aggagtcttc  2160
ggagtaccgg gatctggcaa gtcagctatt atcaagaacc tagttaccag gcaggaccct  2220
```

```
gtgactagcg gaaagaaaga aaactgccaa gaaatcacca ccgacgtgat gagacagaga    2280
ggtctagaga tatctgcacg tacggttgac tcgctgctct tgaatggatg caacagacca    2340
gtcgacgtgt tgtacgtaga cgaggcgttt gcgtgccact ctggaacgct acttgctttg    2400
atcgccttgg tgagaccaag gcagaaagtt gtactttgtg gtgacccgaa gcagtgcggc    2460
ttcttcaata tgatgcagat gaaagtcaac tataatcaca acatctgcac ccaagtgtac    2520
cacaaaagta tctccaggcg gtgtacactg cctgtgaccg ccattgtgtc atcgttgcat    2580
tacgaaggca aaatgcgcac tacgaatgag tacaacaagc cgattgtagt ggacactaca    2640
ggctcaacaa aacctgaccc tggagacctc gtgttaacgt gcttcagagg gtgggttaaa    2700
caactgcaaa ttgactatcg tggatacgag gtcatgacag cagccgcatc ccaagggtta    2760
accagaaaag gagtttacgc agttagacaa aaagttaatg aaaacccgct ctatgcatca    2820
acgtcagagc acgtcaacgt actcctaacg cgtacggaag gtaaactggt atggaagaca    2880
cttccggcg acccgtggat aaagacgctg cagaacccac cgaaaggaaa cttcaaagca    2940
actattaagg agtgggaggt ggagcatgca tcaataatgg cgggcatctg cagtcaccaa    3000
atgaccttcg atacattcca aaataaagcc aacgtttgtt gggctaagag cttggtccct    3060
atcctcgaaa cagcggggat aaaactaaat gataggcagt ggtctcagat aattcaagcc    3120
ttcaaagaag acaaagcata ctcacctgaa gtagccctga tgaaatatg tacgcgcatg    3180
tatgggtgg atctagacag cgggctattt tctaaaccgt tggtgtctgt gtattacgcg    3240
gataaccact gggataatag gcctggaggg aaaatgttcg gatttaaccc cgaggcagca    3300
tccattctag aaagaagta tccattcaca aaagggaagt ggaacatcaa caagcagatc    3360
tgcgtgacta ccaggaggat agaagacttt aaccctacca ccaacatcat accggccaac    3420
aggagactac cacactcatt agtggccgaa caccgcccag taaaggggga agaatggaa     3480
tggctggtta acaagataaa cggccaccac gtgctcctgg tcagtggcta taaccttgca    3540
ctgcctacta agagagtcac ttgggtagcg ccgttaggtg tccgcggagc ggactacaca    3600
tacaacctag agttgggtct gccagcaacg cttggtaggt atgacctagt ggtcataaac    3660
atccacacac cttttcgcat acaccattac caacagtgcg tcgaccacgc aatgaaactg    3720
caaatgctcg ggggtgactc attgagactg ctcaaaccgg gcggctctct attgatcaga    3780
gcatatggtt acgcagatag aaccagtgaa cgagtcatct gcgtattggg acgcaagttt    3840
agatcgtcta gagcgttgaa accaccatgt gtcaccagca cactgagat gttttttccta    3900
ttcagcaact ttgacaatgg cagaaggaat tcacaactc atgtcatgaa caatcaactg    3960
aatgcagcct tcgtaggaca ggtcacccga gcaggatgtg caccgtcgta ccgggtaaaa    4020
cgcatggaca tcgcgaagaa cgatgaagag tgcgtagtca acgccgctaa ccctcgcggg    4080
ttaccgggtg acggtgtttg caaggcagta tacaaaaaat ggccggagtc ctttaagaac    4140
agtgcaacac cagtgggaac cgcaaaaaca gttatgtgcg gtacgtatcc agtaatccac    4200
gctgttggac caaacttctc taattattcg gagtctgaag gggaccggga attggcagct    4260
gcctatcgag aagtcgcaaa ggaagtaact aggctgggag taaatagtgt agctatacct    4320
ctcctctcca caggtgtata ctcaggaggg aaagacaggc tgacccagtc actgaaccac    4380
ctctttacag ccatggactc gacggatgca gacgtggtca tctactgccg cgacaaagaa    4440
tgggagaaga aaatatctga ggccatacag atgcggaccc aagtagagct gctggatgag    4500
cacatctcca tagactgcga tattgttcgc gtgcaccctg acagcagctt ggcaggcaga    4560
aaaggataca gcaccacgga aggcgcactg tactcatatc tagaagggac ccgttttcat    4620
```

```
cagacggctg tggatatggc ggagatacat actatgtggc caaagcaaac agaggccaat    4680
gagcaagtct gcctatatgc cctgggggaa agtattgaat cgatcaggca gaaatgcccg    4740
gtggatgatg cagacgcatc atctcccccc aaaactgtcc cgtgcctttg ccgttacgct    4800
atgactccag aacgcgtcac ccggcttcgc atgaaccacg tcacaagcat aattgtgtgt    4860
tcttcgtttc ccctcccaaa gtacaaaata gaaggagtgc aaaaagtcaa atgctctaag    4920
gtaatgctat ttgaccacaa cgtgccatcg cgcgtaagtc caagggaata tagatcttcc    4980
caggagtctg cacaggaggc gagtacaatc acgtcactga cgcatagtca attcgaccta    5040
agcgttgatg gcgagatact gcccgtcccg tcagacctgg atgctgacgc cccagccta    5100 gaaccagcac tagacgacgg ggcgacacac acgctgccat ccacaaccgg aaaccttgcg    5160
gccgtgtctg attgggtaat gagcaccgta cctgtcgcgc cgcccagaag aaggcgaggg    5220
agaaacctga ctgtgacatg tgacgagaga gaagggaata taacacccat ggctagcgtc    5280
cgattcttta gggcagagct gtgtccggtc gtacaagaaa cagcggagac gcgtgacaca    5340
gcaatgtctc ttcaggcacc accgagtacc gccacggaac cgaatcatcc gccgatctcc    5400
ttcggagcat caagcgagac gttccccatt acatttgggg acttcaacga aggagaaatc    5460
gaaagcttgt cttctgagct actaactttc ggagacttct taccaggaga agtggatgac    5520
ttgacagaca gcgactggtc cacgtgctca gacacggacg acgagttatg actagacagg    5580
gcaggtgggt atatattctc gtcggacacc ggtccaggtc atttacaaca gaagtcagta    5640
cgccagtcag tgctgccggt gaacaccctg gaggaagtcc acgaggagaa gtgttaccca    5700
cctaagctgg atgaagcaaa ggagcaacta ttacttaaga aactccagga gagtgcatcc    5760
atggccaaca gaagcaggta tcagtcgcgc aaagtagaaa acatgaaagc agcaatcatc    5820
cagagactaa agagaggctg tagactatac ttaatgtcag agaccccaaa agtccctact    5880
taccggacta catatccggc gcctgtgtac tcgcctccga tcaacgtccg attgtccaat    5940
cccgagtccg cagtggcagc atgcaatgag ttcttagcta gaaactatcc aactgtctca    6000
tcataccaaa ttaccgacga gtatgatgca tatctagaca tggtggacgg gtcggagagt    6060
tgcctggacc gagcgacatt caatccgtca aaactcagga gctacccgaa acagcacgct    6120
taccacgcgc cctccatcag aagcgctgta ccgtccccat tccagaacac actacagaat    6180
gtactggcag cagccacgaa aagaaactgc aacgtcacac agatgaggga attaccact    6240 ttggactcag cagtattcaa cgtggagtgt ttcaaaaaat tcgcatgcaa ccaagaatac    6300
tgggaagaat ttgctgccag ccctattagg ataacaactg agaatttagc aacctatgtt    6360
actaaactaa aagggccaaa agcagcagcg ctattcgcaa aaacccataa tctactgcca    6420
ctacaggaag taccaatgga taggttcaca gtagatatga aaagggacgt aaaggtgact    6480
cctggtacaa agcatacaga ggaaagacct aaggtgcagg ttatacaggc ggctgaaccc    6540
ttggcgacag cataccctat gtgggattca agagagctgg ttaggaggct gaacgccgtc    6600
ctcctaccca atgtacatac actatttgac atgtctgccg aggatttcga tgccatcata    6660
gccgcacact ttaagccagg agacactgtt ttggaaacgg acatagcctc ctttgataag    6720
agccaagatg attcacttgc gcttactgct ttgatgctgt tagaggattt aggggtggat    6780
cactccctgc tggacttgat agaggctgct ttcggagaga tttccagctg tcacctaccg    6840
acaggtacgc gcttcaagtt cggcgccatg atgaaatcag gtatgttcct aactctgttc    6900
gtcaacacat tgttaaacat caccatcgcc agccgagtgc tggaagatcg tctgacaaaa    6960
```

| | |
|---|---|
| tccgcgtgcg cggccttcat cggcgacgac aacataatac atggagtcgt ctccgatgaa | 7020 |
| ttgatggcag ccagatgtgc cacttggatg aacatggaag tgaagatcat agatgcagtt | 7080 |
| gtatccttga aagccccctta cttttgtgga gggtttatac tgcacgatac tgtgacagga | 7140 |
| acagcttgca gagtggcaga cccgctaaaa aggcttttta aactgggcaa accgctagcg | 7200 |
| gcaggtgacg aacaagatga agatagaaga cgagcgctgg ctgacgaagt gatcagatgg | 7260 |
| caacgaacag ggctaattga tgagctggag aaagcggtat actctaggta cgaagtgcag | 7320 |
| ggtatatcag ttgtggtaat gtccatggcc acctttgcaa gctccagatc caacttcgag | 7380 |
| aagctcagag acccgtcat aactttgtac ggcggtccta aatag | 7425 |

```
<210> SEQ ID NO 94
<211> LENGTH: 7545
<212> TYPE: DNA
<213> ORGANISM: O'nyong-nyong virus

<400> SEQUENCE: 94
```

| | |
|---|---|
| atggattcag tgtatgtaga catagatgct gacagcgcgt tctgaaggc gttgcagcaa | 60 |
| gcatacccca tgtttgaggt ggaaccaaag caggtcacgc caaatgacca tgcaaacgct | 120 |
| agagcatttt cgcatctagc aataaaactg atagagcagg aaattgatcc agactcaacc | 180 |
| attctagaca ttggtagcgc accagctagg aggatgatgt ctgatagaaa ataccactgc | 240 |
| gtctgcccga tgcgcagcgc agaagaccct gagaggctcg cgaattacgc gagaaaactt | 300 |
| gcgtcagccg ctggaaaggt gacagataaa acatctccg gaaaaattaa tgatctacaa | 360 |
| gctgtgatgg ccgtaccgaa tatggaaaca tccacattct gcctacacac tgatgctaca | 420 |
| tgcaaacaaa gaggagacgt cgccatttat caagacgtct acgccgtcca tgcacctacc | 480 |
| tcgctgtacc atcaggcgat taaaggagtc gcgtggcat actggatagg gttcgatacg | 540 |
| acacctttca tgtacaatgc aatggctggc gcataccat catattcaac aaactgggct | 600 |
| gatgagcagg tactgaaagc taagaacata gggctgtgtt caacagacct atctgaggt | 660 |
| agacgaggca aactatccat catgagaggc aaaaaattga agccatgcga ccgagtgcta | 720 |
| ttctcggtcg gctcaacact ctaccctgaa agtcgtaaac ttctacaaag ctggcattta | 780 |
| ccatcggtat ttcatctgaa gggtaaactc agcttcacct gccgctgtga cacgatcgtc | 840 |
| tcatgcgaag gatacgttgt caagagagtg accatgagtc caggcatcta cggaaagaca | 900 |
| tcggggtatg ctgtaactca tcatgccggc ggcttcctga tgtgcaagac gacagataca | 960 |
| gtagacggcg aaagggtatc attctccgtg tgtacttacg taccagctac tatctgcgac | 1020 |
| cagatgactg gaatccttgc cactgaggta ccccagaag acgcacagaa actactggtt | 1080 |
| gggctaaacc aacggatagt ggtcaatggc aggacgcaac gtaatacaaa caccatgaaa | 1140 |
| aactacctgc tcccaatagt tgctcaggcc ttcagcaagt gggccaaaga atgtcgaaag | 1200 |
| gacatggagg acgaaaaact cttgggtgtc cgagagagga ccttaacgtg ctgttgccta | 1260 |
| tgggcattta gaaagcacaa gacgcatacg gtgtacaaaa gaccggatac ccagtcaatc | 1320 |
| caaaaggtcc ctgccgaatt tgacagcttt gtgataccaa gtctgtggtc gtcaggttta | 1380 |
| tcaattccgc tgagaaccag aatcaagtgg ctcttgagca agctccaaa atacgagcaa | 1440 |
| ctaccgcaca gcggaaacgc cgaggaagca gcccaggctg aaacagatgc ggtagaagaa | 1500 |
| caggaggcag agctaacccg agaagctatg ccaccattgc aggcgacaca ggatgacatt | 1560 |
| caggtagaaa ttgatgtaga gcaacttgaa gaccgagcag gagcgggcat agtcgaaaca | 1620 |
| ccaagaggag caatcaaagt cacagcccaa ccgtcagacc ttgttgtcgg agagtactta | 1680 |

```
gtactgacac cgcaggcggt cctgcgcagc caaaaactca gtctgattca cgcgcttgca    1740
gagcaggtaa aaacgtgcac acatagtggg cgagcaggca ggtacgcggt tgaagcatac    1800
gatgggcgtg ttctagtgcc ctcgggctac gcgataccCC aggaagactt ccagagctta    1860
agcgaaagtg ccaccatggt atttaacgag cgagagtttg tgaaccggaa gttacaccac    1920
atcgccatgc acggcccagc gctgaacact gatgaagagt catatgaact ggtaagggta    1980
gagaaaacag aacacgagta cgtctatgac gttgatcaga gaaatgttg  taagagggag    2040 gaagcaacag gactagtgct agtaggcgac ttaactagcc caccatacca tgagttcgcc    2100
tacgaaggac taaaaatccg cccagcatgt ccatacaaaa cggcagttat aggtgtcttc    2160
ggagtaccgg gttctggcaa gtcggctata atcaaaaacc tggtaaccag gcaagacttg    2220
gtgactagtg gaaaaaaaga aaactgccaa gaaatctcca atgacgtaat gcggcaaagg    2280
aaattggaga tatctgcacg tacagtcgac tcactactcc tgaatggatg taacaagcca    2340
gtggaagtac tgtacgtgga cgaggcattc gcttgtcatt cgggaacCCt gttggcactg    2400
atagccatgg ttagaccgcg tcagaaggtc gtactttgtg gcgacccaaa gcagtgcgga    2460
ttcttcaata tgatgcaaat gaaggtcaac tataatcaca acatctgcac acaggtgtac    2520
cataaaagca tatcaaggcg gtgtacactg cctgtaacag ccatcgtgtc ctcgttgcat    2580
tacgagagca agatgcgcac tacaaatgag tacaaccagc caatcgtagt ggatactacg    2640
ggcataacaa aaccagaacc cggggactta gtgttaacgt gtttccgggg atgggttaag    2700
cagctgcaaa tagactaccg tggaaacgaa gtcatgacag cagctgcttc tcagggctg    2760 accagaaaag gtgtttatgc agtaaggcag aaagtcaacg aaaaccctct gtatgcacca    2820
acatcagaac acgttaacgt gctattgaca cgcacagagg gcaagttgac atggaagaca    2880
ctctcaggcg acccatggat aaagatactg cagaaccCCC caaaagggga ctttaaggca    2940
acaatcaagg agtgggaagc agaacacgcc tccatcatgg caggaatatg caatcaccag    3000
atggcttttg acacatttca gaacaaagct aatgtatgct gggctaaatg cctggtccct    3060
attcttgaca ctgctggaat caaattaagt gacaggcagt ggtctcagat agtgcaagct    3120
tttaaagaag atagggccta ctctccagaa gttgcactga tgaaatatg  cactcgcata    3180 tatgggtag  acctggacag cggactattc tcaaagccac tgatatccgt ctactatgca    3240
gacaaccact gggacaatag accaggagga aaaatgttcg ggttcaaccc tgaggtggca    3300
cttatgcttg aaaagaaata ccctttaca  aaaggtaagt ggaacattaa caagcagata    3360
tgtataacta ccagaaaggt tgacgaattt aaccccgaaa ccaacataat accggccaac    3420
cgcagactgc cgcactcact cgtggctgaa caccactcag tgagggggga aagaatggaa    3480
tggctggtaa acaaaatcag cggtcaccac atgttgttgg ttagcggtca taatcttata    3540
ttaccaacaa aaagagtcac ctgggtagca ccgttaggca cccgaggtgc agactacaca    3600
tataacctgg aacttggtct accagccaca ctaggcagat atgacctggt agttatcaat    3660
atccatactc cattccgcat acatcattac cagcagtgtg tagatcacgc aatgaagctc    3720
cagatgctag gggggactc  tctacggctg ttaaagccgg gaggttcact tctgattaga    3780
gcttacgggt acgccgaccg aaccagtgaa agggtcatta gcgtattggg acgcaagttc    3840
agatcgtcca gggctctgaa acctcagtgc atcacgagca atacagaaat gttcttccta    3900
tttagccgat cgacaatgg  aagaaggaac ttcaccacac atgttatgaa caaccagctg    3960
aacgcagtgt atgcaggact ggccactaga gcgggctgtg ccccgtcata ccgagtgaaa    4020
```

```
cggatggaca tcgcaaagaa cactgaggaa tgcgtggtaa acgccgccaa tccgcgcgga    4080
gtaccaggcg atggagtatg taaagccgtg tatagaaaat ggccagaatc attcagaaac    4140
agtgcaacac cagtggggac tgcaaagaca atcatgtgcg gtcaataccc cgtcatccac    4200
gcagtaggcc ctaacttctc aaactattct gaggctgaag gggatagggga attggcttca    4260 gtgtatagag aagtggcgaa agaagtgtct aggctaggag tgagcagtgt agccatccct    4320
ttgctctcaa ccggtgtgta ctcaggaggc aaagacagac tgctgcaatc actaaaccat    4380
cttttcgcag cgatggattc gacagatgca gacgttgtca tctactgcag ggacaaggaa    4440
tgggagaaga agatcactga agccatatca ctaagatccc aggtagaatt actagatgat    4500
cacatctcag tggattgcga cattgtacgc gttcatccag acagcagctt ggcaggccga    4560
aaggggtaca gcacagtaga gggagcactc tactcgtacc tagagggaac aagattccac    4620
caaactgcag tagatatggc agagatatat accatgtggc cgaaacaaac tgaagccaac    4680
gaacaggtct gcctatatgc tctgggggag agtatagagt ccgtcaggca aaaatgtccc    4740
gtagacgacg ccgacgcctc attccctccg aaaacagtcc cgtgcctatg ccgttatgct    4800
atgacgcctg aacgagttgc acgtctacgc atgaatcata ccaccagcat catagtgtgc    4860
tcgtcttttc cgctgccgaa atacaaaatc gagggcgtgc aaaaagtaaa atgttcgaaa    4920
gcactcttgt ttgatcacaa cgtaccgtct cgagtgagcc cgagaacgta caggcctgcg    4980
gacgaaatca tacagacacc tcaaacacca actgaagcgt gtcaggacgc acaactcgtg    5040
cagtcaataa atgatgaagc agtgccagtt ccctcagact tagaggcttg tgacgcaact    5100
atggactggc cctctatcgg caccgtatca acaagacaaa gacacgactc atctgacagc    5160
gagtatagtg gctccagaag taacatacaa ctagtgacgg cggacgtgca tgcaccaatg    5220
tacgcacatt cgctggcgtc cagcggaggt tcaatgctgt cgctgtccag tgaaccagct    5280
cagaacggca caatgatact acttgactca gaagacacag acagtataag cagagtaagc    5340
acaccgatcg ccccgcccag aagacgtttg ggaaggacca taaatgtgac ctgcgacgag    5400
cgggaaggga aaatactccc tatggccagc gacaggttct tcactgctaa gccatacact    5460
gtcgcactga gcgtatcaac agcagatatg actgtgtatc ccatccaggc accgctagga    5520
ttgataccac cacctaccct cgaaccgatc actttcggag acttcgccga aggtgaaata    5580
gacaacctcc tgacagggc attgacattt gggacttcg agccaggtga agtgaagag     5640 ctgacggata gcgagtggtc aacgtgctcg gacacagacg aagagttacg actagacaga    5700
gcagggggtt acatattctc ctctgacact ggtcaaggtc atctacagca aaaatcagta    5760
cgtcaaacga cgctaccggt aaacattgtt gaagaggtcc acgaagagaa atgctatcca    5820
cctaaattgg atgagatcaa agagcaacta ctacttaaga acttcagga gagtgcttcc    5880 acggctaacc ggagtaggta ccaatctaga aaagtggaaa acatgaaagc cacgattatc    5940
cacagactga agagggttg cagactctat ttggcgtcag aaacaccgag ggtcccatct    6000
taccgagtca catacccggc gcccatctac tcgccttcaa tcaatatcaa actgactaac    6060
ccagagactg cagtagcagt gtgtaacgag ttttggcca gaaactatcc aactgtggca    6120
tcctaccaag tcactgacga gtacgacgcg tacttggata tggtagacgg gtccgaaagt    6180
tgcctagaca gagctacatt caacccgtct aaactcagga gttacccaaa acaacactct    6240
taccacgcac ccaccatcag aagtgcagtg ccatcaccat tccaaaatac gttgcagaat    6300
gtcttggcag cggccacaaa aagaaactgc aacgtacgc agatgaggga actacccact    6360
atggactccg cagtgtttaa cgtggagtgt tttaagaagt acgcttgcaa ccaagagtac    6420
```

```
tggagagagt tcgcctcaag ccctataagg gtaacgacag agaatctgac aatgtatgtg    6480
acgaaactaa aggggcctaa agcggcggca ctcttcgcaa aaacacacaa cttgctgccg    6540
ctacaagagg taccgatgga caggttcaca atggacatga acgtgatgt gaaagtgaca     6600 ccaggtacaa agcacaccga ggaaaggccg aaagtacagg tcatacaggc ggcagaacca    6660
ctggcaacag catacctgtg tggcatacac agagagttgg tgagaagact aaatgcagtt    6720
ctgctaccga atgtccacac actgttcgat atgtcagccg aagacttcga tgcaattata    6780
gccacccatt tcaaaccggg cgatgctgta ctagaaactg acatagcctc atttgataag    6840
agtcaagacg actcgcttgc gtcgaccgcc atgatgttgc tagaagacct tggggtagat    6900
caacctatcc tggatctgat agaagcagca ttcggcgaaa tatccagttg tcatctaccg    6960
acgggtacgc ggttcaagtt cggcgcaatg atgaaatcag gcatgtttct aaccctgttt    7020
gtcaataccc tcctgaacat caccattgcc agtcgggtgt tagaggagcg attgactact    7080
tcagcctgtg cagctttcat tggggacgac aacataatac atgggggttgt ctctgacgca   7140 ctaatggctg cacgttgtgc tacgtggatg aacatggaag tgaaaatcat cgatgcagta    7200
gtgtcagaga aggcgccata cttctgtggg ggatttattt tacacgacac ggtgacaggc    7260
acgtcgtgca gagtagcaga ccctttaaag agactgttca agctaggcaa acctctggca    7320
gctggagacg aacaggatga ggacagaaga cgtgctctgg cagatgaggt tactagatgg    7380
caaagaaccg gcttagtcac agaattggaa aaagcagtat attcaaggta tgaagtacaa    7440
ggaataacag ccgtaataac atcaatggct acctttgcga atagcaaaga aaactttaag    7500
aaactaagag ggcccgtcgt aaccttgtac ggcggaccta aatag                    7545
```

<210> SEQ ID NO 95
<211> LENGTH: 27
<212> TYPE: DNA
<213> ORGANISM: Artificial Sequence
<220> FEATURE:
<223> OTHER INFORMATION: RNA primer

<400> SEQUENCE: 95
gcatatggtg atgatgtgat cgctagc                                          27

<210> SEQ ID NO 96
<211> LENGTH: 24
<212> TYPE: DNA
<213> ORGANISM: Artificial Sequence
<220> FEATURE:
<223> OTHER INFORMATION: RNA primer

<400> SEQUENCE: 96
ggggtactgt tcatctgctc taaa                                             24

<210> SEQ ID NO 97
<211> LENGTH: 16
<212> TYPE: DNA
<213> ORGANISM: Artificial Sequence
<220> FEATURE:
<223> OTHER INFORMATION: Coxsackie probe

<400> SEQUENCE: 97
cgcatcgtac ccatgg                                                      16

<210> SEQ ID NO 98
<211> LENGTH: 16
<212> TYPE: DNA

<213> ORGANISM: Artificial Sequence
<220> FEATURE:
<223> OTHER INFORMATION: Coxsackie probe

<400> SEQUENCE: 98
cgctagctac ccatgg                                                       16

<210> SEQ ID NO 99
<211> LENGTH: 23
<212> TYPE: DNA
<213> ORGANISM: Artificial Sequence
<220> FEATURE:
<223> OTHER INFORMATION: Coxsackie primer

<400> SEQUENCE: 99
gatcgcatat ggtgatgatg tga                                               23

<210> SEQ ID NO 100
<211> LENGTH: 22
<212> TYPE: DNA
<213> ORGANISM: Artificial Sequence
<220> FEATURE:
<223> OTHER INFORMATION: Coxsackie primer

<400> SEQUENCE: 100
agcttcagcg agtaaagatg ca                                                22

<210> SEQ ID NO 101
<211> LENGTH: 3747
<212> TYPE: DNA
<213> ORGANISM: Chikungunya virus

<400> SEQUENCE: 101
atggagttca tcccaaccca aacttttttac aataggaggt accagcctcg accctggact        60
ccgcgcccta ctatccaagt catcaggccc agaccgcgcc ctcagaggca agctgggcaa       120
ttagcccagt tgatctcagc agttaataaa ttgacaatgc gcgcggtacc ccaacgaaag       180
ccacgcagga atcggaagaa taagaagcaa agcaaaaaac aacaggcgcc acaaaacaac       240
acaaatcaaa agaagcagcc acctaaaaag aaaccggctc aaaagaaaaa gaagccgggc       300
cgcagagaga ggatgtgcat gaaaatcgaa atgattgtta ttttcgaagt caagcacgaa       360
ggtaaggtaa caggttacgc gtgcttggtg ggggacaaag taatgaaacc agcacacgta       420
aagggaccca tcgataacgc ggacttggcc aaattggcct ttaagcggtc atcaaagtat       480
gacttagaat gcgcgcagat accgtgcac atgaagtcgg acgcttcgaa gttcacccat       540
gagaaaccgg agggtacta caactggcac cacggagcag tacagtactc aggaggccgg       600
ttcaccatcc ctacaggtgc tgcaaaacca gggactcgg gcagaccgat cttcgacaac       660
aagggacgcg tggtggccat agtcttagga ggagctaatg aaggagcccg tacagccttg       720
tcggtggtga cctggaataa agacattgtc actaaaatca cccccgaggg ggccgaagag       780
tggtcattag ccatcccagt tatgtgcttg ttggcaaaca ccacgttccc ctgctcgcag       840 ccccccttgca cgccctgctg ctacgaaaag gaaccggagg aaaccttacg catgttagag       900
gacaacgtca tgagacctgg gtactatcag ttgttacaag catcgttaac atgttcaccc       960
caccgccagc gacgctcgac caaggacaac ttcaatgtct ataagccac aagaccatac      1020 ttagctcact gtcccgactg tggagaaggg cactcgtgcc attcacccgt agcattagaa      1080
cgcatcagaa atgaagcgac agacgggacg ttgaaaatcc aggtctcgtt gcaaatcgga      1140
ataaagacgg atgactcgca cgattggacc aagttgcgtt atatggacaa ccacatgcca      1200

```
gcagacgcag agagggcggg gttatttgta agaacatcag caccgtgtac gattactgga    1260
acaatgggac acttcatctt ggcccgatgt ccaaaagggg aaactttgac ggtgggattc    1320
actgactcaa ggaagatttc acactcatgt acgcacccat ttcaccacga ccctcctgtg    1380
ataggtcggg aaaaattcca ttcgcgaccg cagcacggta aagagttacc ttgctcgacg    1440
tacgtgcagt cgaccgccgc aactaccgag gagatagagg tacacatgcc cccagacacc    1500
cctgatcgca cattaatgtc acaacagtcg ggcaacgtaa agatcacagt caatggccag    1560
acggtgcggt acaagtgtaa ttgcggtggc tcaaatgaag gattaacaac tacagacaaa    1620
gtgattaata actgcaaggt tgatcaatgt catgccgcgg tcaccaatca caaaaagtgg    1680
cagtataact cgccttttgg cccgcgtaat gctgaattag gggaccgaaa aggaaaaatt    1740
cacatcccgt ttccgttggc aaatgtaaca tgcagggtgc ctaaagcaag gaaccccacc    1800
gtgacgtacg ggaaaaacca agtcatcatg ttattgtatc ctgaccaccc aacattgttg    1860
tcgtaccgga atatgggaga agaaccaaac tatcaagaag agtgggtgat gcataagaag    1920
gaagtcgtgt taaccgtgcc gactgaaggg ttggaggtca cgtggggcaa caacgagccg    1980
tataagtatt ggccgcagtt atcaacaaac ggtacagccc atggccaccc gcacgagata    2040
attttgtatt attatgagtt gtaccccact atgactgtag tagttgtgtc agtggccacg    2100
ttcatattgt tgtcgatggt gggtatggca gcggggatgt gcatgtgtgc acgacgcaga    2160
tgcatcacac cgtatgaatt gacaccagga gctaccgtcc ctttcttgtt atcgttaata    2220
tgctgcatca gaacagctaa agcggccaca taccaagagg ctgcgatata cttgtggaac    2280
gagcagcaac ctttgttttg gttacaagcc ttaattccgt tggcagcctt gattgtttta    2340
tgcaactgtt tgagattgtt accatgctgc tgtaaaacgt tggcttttttt agccgtaatg    2400 tcggtcggtg cccacactgt gtcggcgtac gaacacgtaa cagtgatccc gaacacggtg    2460
ggagtaccgt ataagacttt agtcaataga cctggctact cgcccatggt attggagatg    2520
gaattattgt cagtcacttt ggagccaaca ttatcgttag attacatcac gtgcgagtac    2580
aaaaccgtca tcccgtcacc gtacgtgaag tgctgcggta cagcagagtg caaggacaaa    2640
aacttacctg actactcgtg taaggtcttc accggcgtct acccatttat gtggggcggc    2700
gcctactgct tctgcgacgc tgaaaacacg cagttgtcgg aagcacacgt ggagaagtcg    2760
gaatcatgca aaacagaatt tgcatcagca tacagggctc ataccgcatc agcatcagct    2820
aagttgcgcg tcttataccA aggaaataac atcactgtaa ctgcctatgc aaacggcgac    2880
catgccgtca cagttaagga cgccaaattc attgtggggc caatgtcatc agcctggaca    2940
cctttcgaca acaaaattgt ggtgtacaaa ggtgacgtct ataacatgga ctacccgccc    3000
tttggcgcag aagaccagg acaatttggc gatatccaat cacgcacacc tgagtcaaaa    3060
gacgtctatg ctaatacaca attggtattg cagagaccgg ctgtgggtac ggtacacgtg    3120
ccatactcac aggcaccatc aggctttaag tattggttaa agaacgcgg ggcgtcgttg    3180 cagcacacag caccatttgg ctgccaaata gcaacaaacc cggtaagagc ggtgaactgc    3240
gccgtaggga acatgcccat ctcgatcgac ataccggaag cggccttcac tagggtcgtc    3300
gacgcgccct cattaacgga catgtcgtgc gaggtaccag cctgcaccca ttcgtcagac    3360
tttgggggcg tcgccattat taaatatgca gcctcgaaga aaggcaagtg tgcggtgcat    3420
tcgatgacta acgccgtcac tattcgggaa gctgagatag aagttgaagg gaattcacag    3480
ttgcaaatct cattctcgac ggccttagcc tcggccgaat tccgcgtaca agtctgttca    3540
```

-continued

| | |
|---|---|
| acacaagtac actgtgcagc cgagtgccac cccccgaagg accacatagt caactacccg | 3600 |
| gcgtcacata ccaccttggg ggtccaggac atctcggcta cggcgatgtc atgggtgcag | 3660 |
| aagatcacgg gaggtgtggg attggttgtt gctgttgccg cattgatttt aatcgtggtg | 3720 |
| ttatgcgtgt cgttctcgag gcactaa | 3747 |

<210> SEQ ID NO 102
<211> LENGTH: 3747
<212> TYPE: DNA
<213> ORGANISM: Chikungunya virus

<400> SEQUENCE: 102

| | |
|---|---|
| atggagttca tcccaaccca aacttttttac aatagaagat accagcctcg accctggact | 60 |
| ccgcgaccta ctatccaagt catcagaccc agaccgcgac ctcagagaca agctggacaa | 120 |
| ttagcccagt tgatctcagc agttaataaa ttgacaatgc gagcggtacc ccaacagaag | 180 |
| ccacgaagaa atcgaagaa taagaagcaa agcaaaaac aacaggcgcc acaaaacaac | 240 |
| acaaatcaaa agaagcagcc acctaaaaag aaaccggctc aaaagaaaaa gaagccggga | 300 |
| cgaagagaga gaatgtgcat gaaaatcgaa atgattgta ttttcgaagt caagcacgaa | 360 |
| ggaaaggtaa caggatacgc gtgcttggtg ggagacaaag taatgaaacc agcacacgta | 420 |
| aagggaacca tcgataacgc ggacttggcc aaattggcct ttaagcgatc atcaaagtat | 480 |
| gacttagaat gcgcgcagat acccgtgcac atgaagtcgg acgcttcgaa gttcacccat | 540 |
| gagaaaccgg agggatacta caactggcac acggagcag tacagtactc aggaggacga | 600 |
| ttcaccatcc ctacaggagc tggaaaacca ggagactcgg gaagaccgat cttcgacaac | 660 |
| aagggacgag tggtggccat agtcttagga ggagctaatg aaggagcccg aacagccttg | 720 |
| tcggtggtga cctggaataa agacattgtc actaaaatca cccccgaggg agccgaagag | 780 |
| tggtcattag ccatcccagt tatgtgcttg ttggcaaaca ccacgttccc ctgctcgcag | 840 |
| cccccttgca cgcccctgct ctacgaaaag gaaccggagg aaaccttacg aatgttagag | 900 |
| gacaacgtca tgagacctgg atactatcag ttgttacaag catcgttaac atgttcacc | 960 |
| caccgacagc gacgatcgac caaggacaac ttcaatgtct ataaagccac aagaccatac | 1020 |
| ttagctcact gtcccgactg tggagaagga cactcgtgcc attcacccgt agcattagaa | 1080 |
| cgaatcagaa atgaagcgac agacggaacg ttgaaaatcc aggtctcgtt gcaaatcgga | 1140 |
| ataaagacgg atgactcgca cgattggacc aagttgcgat atatggacaa ccacatgcca | 1200 |
| gcagacgcag agagagcggg attatttgta agaacatcag caccgtgtac gattactgga | 1260 |
| acaatgggac acttcatctt ggcccgatgt ccaaaggag aaactttgac ggtgggattc | 1320 |
| actgactcaa gaaagatttc acactcatgt acgcacccat tcaccacga ccctcctgtg | 1380 |
| ataggacgag aaaaattcca ttcgcgaccg cagcacggaa aagagttacc ttgctcgacg | 1440 |
| tacgtgcagt cgaccgccgc aactaccgag gagatagagg tacacatgcc cccagacacc | 1500 |
| cctgatcgaa cattaatgtc acaacagtcg ggaaacgtaa agatcacagt caatggacag | 1560 |
| acggtgcgat acaagtgtaa ttgcggagga tcaaatgaag gattaacaac tacagacaaa | 1620 |
| gtgattaata actgcaaggt tgatcaatgt catgccgcgg tcaccaatca aaaaagtgg | 1680 |
| cagtataact cgcctttggt cccgcgaaat gctgaattag agaccgaaa aggaaaaatt | 1740 |
| cacatcccgt ttccgttggc aaatgtaaca tgcagagtgc ctaaagcaag aaaccccacc | 1800 |
| gtgacgtacg gaaaaaacca agtcatcatg ttattgtatc ctgaccaccc aacattgttg | 1860 |
| tcgtaccgaa atatgggaga agaaccaaac tatcaagaag agtgggtgat gcataagaag | 1920 |

```
gaagtcgtgt taaccgtgcc gactgaagga ttggaggtca cgtgggaaa caacgagccg      1980 tataagtatt ggccgcagtt atcaacaaac ggaacagccc atggacaccc gcacgagata     2040
attttgtatt attatgagtt gtaccccact atgactgtag tagttgtgtc agtggccacg     2100
ttcatattgt tgtcgatggt gggaatggca gcgggaatgt gcatgtgtgc acgacgaaga     2160
tgcatcacac cgtatgaatt gacaccagga gctaccgtcc ctttcttgtt atcgttaata     2220
tgctgcatca gaacagctaa agcggccaca taccaagagg ctgcgatata cttgtggaac     2280
gagcagcaac ctttgttttg gttacaagcc ttaattccgt tggcagcctt gattgtttta     2340
tgcaactgtt tgagattgtt accatgctgc tgtaaaacgt tggcttttttt agccgtaatg    2400 tcggtcggag cccacactgt gtcggcgtac gaacacgtaa cagtgatccc gaacacggtg     2460
ggagtaccgt ataagacttt agtcaataga cctggatact cgcccatggt attggagatg     2520
gaattattgt cagtcacttt ggagccaaca ttatcgttag attacatcac gtgcgagtac     2580
aaaaccgtca tcccgtcacc gtacgtgaag tgctgcggaa cagcagagtg caaggacaaa     2640
aacttacctg actactcgtg taaggtcttc accggagtct acccatttat gtggggagga     2700
gcctactgct tctgcgacgc tgaaaacacg cagttgtcgg aagcacacgt ggagaagtcg     2760
gaatcatgca aaacagaatt tgcatcagca tacagagctc ataccgcatc agcatcagct     2820
aagttgcgag tcttatacca aggaaataac atcactgtaa ctgcctatgc aaacggagac     2880
catgccgtca cagttaagga cgccaaattc attgtgggac caatgtcatc agcctggaca     2940
cctttcgaca caaaaattgt ggtgtacaaa ggagacgtct ataacatgga ctacccgccc     3000
tttggagcag gaagaccagg acaatttgga gatatccaat cacgaacacc tgagtcaaaa     3060
gacgtctatg ctaatacaca attggtattg cagagaccgg ctgtgggaac ggtacacgtg     3120
ccatactcac aggcaccatc aggatttaag tattggttaa agaacgagg agcgtcgttg     3180 cagcacacag caccatttgg atgccaaata gcaacaaacc cggtaagagc ggtgaactgc     3240
gccgtaggaa acatgcccat ctcgatcgac ataccggaag cggccttcac tagagtcgtc     3300
gacgcgccct cattaacgga catgtcgtgc gaggtaccag cctgcaccca ttcgtcagac     3360 tttgaggag tcgccattat taaatatgca gcctcgaaga aggaaagtg tgcggtgcat     3420 tcgatgacta acgccgtcac tattcgagaa gctgagatag aagttgaagg aaattcacag     3480
ttgcaaatct cattctcgac ggccttagcc tcggccgaat ccgagtaca agtctgttca     3540 acacaagtac actgtgcagc cgagtgccac cccccgaagg accacatagt caactacccg     3600
gcgtcacata ccaccttggg agtccaggac atctcggcta cggcgatgtc atgggtgcag     3660
aagatcacgg gaggagtggg attggttgtt gctgttgccg cattgatttt aatcgtggtg     3720
ttatgcgtgt cgttctcgag acactaa                                          3747
```

<210> SEQ ID NO 103
<211> LENGTH: 11601
<212> TYPE: DNA
<213> ORGANISM: Chikungunya virus

<400> SEQUENCE: 103

```
caaagcaaga gattaataac ccatcatgga tcctgtgtac gtggacatag acgctgacag       60 cgccttttg aaggccctgc aacgtgcgta ccccatgttt gaggtggaac caaggcaggt     120
cacaccgaat gaccatgcta atgctagagc gttctcgcat ctagctataa aactaataga     180
gcaggaaatt gaccccgact caaccatcct ggatatcggc agtgcgccag caaggaggat     240
```

-continued

```
gatgtcggac aggaagtacc actgcgtctg cccgatgcgc agtgcggaag atcccgagag    300
actcgccaat tatgcgagaa agctagcatc tgccgcagga aaagtcctgg acagaaacat    360
ctctggaaag atcggggact acaagcagt aatggccgtg ccagacacgg agacgccaac     420
attctgctta cacacagacg tctcatgtag acagagagca gacgtcgcta tataccaaga    480
cgtctatgct gtacacgcac ccacgtcgct ataccaccag gcgattaaag gggtccgagt    540
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaccacagg gtatgcggta acccaccacg cagacggatt     960
cctgatgtgc aagactaccg acacggttga cggcgaaaga gtgtcattct cggtgtgcac    1020
atacgtgccg gcgaccattt gtgatcaaat gaccggcatc cttgctacag aagtcacgcc    1080
ggaggatgca cagaagctgt ggtggggct gaaccagaga atagtggtta acggcagaac     1140
gcaacggaat acgaacacca tgaaaaatta tctgcttccc gtggtcgccc aagccttcag    1200
taagtgggca aaggagtgcc ggaaagacat ggaagatgaa aaactcctgg gggtcagaga    1260
aagaacactg acctgctgct gtctatgggc attcaagaag cagaaaacac acacggtcta    1320
caagagacct gatacccagt caattcagaa ggttcaggcc gagtttgaca gctttgtggt    1380
accgagtctg tggtcgtccg ggttgtcaat ccctttgagg actagaatca atggttgtt    1440 aagcaaggtg ccaaaaaccg acctgatccc atacagcgga gacgcccgag aagcccggga    1500
cgcagaaaaa gaagcagagg aagaacgaga agcagaactg actcgcgaag ccctaccacc    1560
tctacaggca gcacaggaag atgttcaggt cgaaatcgac gtggaacagc ttgaggacag    1620
agcgggcgca ggaataatag agactccgag aggagctatc aaagttactg cccaaccaac    1680
agaccacgtc gtgggagagt acctggtact ctccccgcag accgtactac gtagccagaa    1740
gctcagtctg attcacgctt tggcggagca agtgaagacg tgcacgcaca acggacgagc    1800
agggaggtat gcggtcgaag cgtacgacgg ccgagtccta gtgccctcag gctatgcaat    1860
ctcgcctgaa gacttccaga gtctaagcga aagcgcaacg atggtgtata cgaaagaga    1920 gttcgtaaac agaaagctac accatattgc gatgcacgga ccagccctga caccgacga    1980 agagtcgtat gagctggtga gggcagagag gacagaacac gagtacgtct acgacgtgga    2040
tcagagaaga tgctgtaaga aggaagaagc cgcaggactg gtactggtgg gcgacttgac    2100
taatccgccc taccacgaat cgcatatga agggctaaaa atccgccctg cctgcccata    2160
caaaattgca gtcataggag tcttcggagt accgggatct ggcaagtcag ctattatcaa    2220
gaacctagtt accaggcagg acctggtgac tagcggaaag aaagaaaact gccaagaaat    2280
caccaccgac gtgatgagac agagaggtct agagatatct gcacgtacgg ttgactcgct    2340
gctcttgaat ggatgcaaca gaccagtcga cgtgttgtac gtagacgagg cgtttgcgtg    2400
ccactctgga acgctacttg ctttgatcgc cttggtgaga ccaaggcaga aagttgtact    2460
ttgtggtgac ccgaagcagt gcggcttctt caatatgatg cagatgaaag tcaactataa    2520
tcacaacatc tgcacccaag tgtaccacaa agtatctcc aggcggtgta cactgcctgt     2580
gaccgccatt gtgtcatcgt tgcattacga aggcaaaatg cgcactacga atgagtacaa    2640
```

```
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
gacagcagcc gcatcccaag ggttaaccag aaaaggagtt tacgcagtta gacaaaaagt   2820
taatgaaaac ccgctctatg catcaacgtc agagcacgtc aacgtactcc taacgcgtac   2880
ggaaggtaaa ctggtatgga agacactttc cggcgacccg tggataaaga cgctgcagaa   2940
cccaccgaaa ggaaacttca agcaactat taaggagtgg gaggtggagc atgcatcaat    3000
aatggcgggc atctgcagtc accaaatgac cttcgataca ttccaaaata agccaacgt    3060 ttgtttgggct aagagcttgg tccctatcct cgaaacagcg gggataaaac taaatgatag  3120
gcagtggtct cagataattc aagccttcaa agaagacaaa gcatactcac ctgaagtagc   3180
cctgaatgaa atatgtacgc gcatgtatgg ggtggatcta gacagcgggc tattttctaa   3240
accgttggtg tctgtgtatt acgcggataa ccactgggat aataggcctg gagggaaaat   3300
gttcggattt aaccccgagg cagcatccat tctagaaaga aagtatccat tcacaaaagg   3360
gaagtggaac atcaacaagc agatctgcgt gactaccagg aggatagaag actttaaccc   3420
taccaccaac atcataccgg ccaacaggag actaccacac tcattagtgg ccgaacaccg   3480
cccagtaaaa ggggaaagaa tggaatggct ggttaacaag ataaacggcc accacgtgct   3540
cctggtcagt ggctataacc ttgcactgcc tactaagaga gtcacttggg tagcgccgtt   3600
aggtgtccgc ggagcggact acacatacaa cctagagttg ggtctgccag caacgcttgg   3660
taggtatgac ctagtggtca taaacatcca cacacctttt cgcatacacc attaccaaca   3720
gtgcgtcgac cacgcaatga aactgcaaat gctcgggggt gactcattga gactgctcaa   3780
accgggcggc tctctattga tcagagcata tggttacgca gatagaacca gtgaacgagt   3840
catctgcgta ttgggacgca agtttagatc gtctagagcg ttgaaaccac catgtgtcac   3900
cagcaacact gagatgtttt tcctattcag caactttgac aatggcagaa ggaatttcac   3960
aactcatgtc atgaacaatc aactgaatgc agccttcgta ggacaggtca cccgagcagg   4020
atgtgcaccg tcgtaccggg taaaacgcat ggacatcgcg aagaacgatg aagagtgcgt   4080
agtcaacgcc gctaaccctc gcgggttacc gggtgacggt gtttgcaagg cagtatacaa   4140
aaaatggccg gagtccttta gaacagtgc aacaccagtg ggaaccgcaa aaacagttat   4200
gtgcggtacg tatccagtaa tccacgctgt tggaccaaac ttctctaatt attcggagtc   4260
tgaaggggac cgggaattgg cagctgccta tcgagaagtc gcaaaggaag taactaggct   4320
gggagtaaat agtgtagcta tacctctcct ctccacaggt gtatactcag agggaaagaa   4380
caggctgacc cagtcactga accacctctt tacagccatg gactcgacgg atgcagacgt   4440
ggtcatctac tgccgcgaca agaatgggaa gaagaaaata tctgaggcca tacagatgcg   4500
gacccaagta gagctgctgg atgagcacat ctccatagac tgcgatattg ttcgcgtgca   4560
ccctgacagc agcttggcag gcagaaaagg atacagcacc acggaaggcg cactgtactc   4620
atatctagaa gggacccgtt ttcatcagac ggctgtggat atggcggaga tacatactat   4680
gtggccaaag caaacagagg ccaatgagca agtctgccta tatgccctgg gggaaagtat   4740
tgaatcgatc aggcagaaat gcccggtgga tgatgcagac gcatcatctc cccccaaaac   4800
tgtcccgtgc ctttgccgtt acgctatgac tccagaacgc gtcacccggc ttcgcatgaa   4860
ccacgtcaca agcataattg tgtgttcttc gtttccctc ccaaagtaca aaatagaagg   4920
agtgcaaaaa gtcaaatgct ctaaggtaat gctatttgac cacaacgtgc catcgcgcgt   4980
```

```
aagtccaagg gaatatagat cttcccagga gtctgcacag gaggcgagta caatcacgtc    5040
actgacgcat agtcaattcg acctaagcgt tgatggcgag atactgcccg tcccgtcaga    5100
cctggatgct gacgcccag ccctagaacc agcactagac gacggggcga cacacacgct    5160
gccatccaca accggaaacc ttgcggccgt gtctgattgg gtaatgagca ccgtacctgt    5220
cgcgccgccc agaagaaggc gagggagaaa cctgactgtg acatgtgacg agagagaagg    5280
gaatataaca cccatggcta gcgtccgatt ctttagggca gagctgtgtc cggtcgtaca    5340
agaaacagcg gagacgcgtg acacagcaat gtctcttcag gcaccaccga gtaccgccac    5400
ggaaccgaat catccgccga tctccttcgg agcatcaagc gagacgttcc ccattacatt    5460
tggggacttc aacgaaggag aaatcgaaag cttgtcttct gagctactaa ctttcggaga    5520
cttcttacca ggagaagtgg atgacttgac agacagcgac tggtccacgt gctcagacac    5580
ggacgacgag ttatgactag acagggcagg tgggtatata ttctcgtcgg acaccggtcc    5640
aggtcattta caacagaagt cagtacgcca gtcagtgctg ccggtgaaca ccctggagga    5700
agtccacgag gagaagtgtt acccacctaa gctggatgaa gcaaaggagc aactattact    5760
taagaaactc caggagagtg catccatggc caacagaagc aggtatcagt cgcgcaaagt    5820
agaaaacatg aaagcagcaa tcatccgaga actaaagaga ggctgtagac tatacttaat    5880
gtcagagacc ccaaaagtcc ctacttaccg gactacatat ccggcgcctg tgtactcgcc    5940
tccgatcaac gtccgattgt ccaatcccga gtccgcagtg gcagcatgca atgagttctt    6000
agctagaaac tatccaactg tctcatcata ccaaattacc gacgagtatg atgcatatct    6060
agacatggtg gacgggtcgg agagttgcct ggaccgagcg acattcaatc cgtcaaaact    6120
caggagctac ccgaaacagc acgcttacca cgcgccctcc atcagaagcg ctgtaccgtc    6180
cccattccag aacacactac agaatgtact ggcagcagcc acgaaaagaa actgcaacgt    6240
cacacagatg agggaattac ccactttgga ctcagcagta ttcaacgtgg agtgtttcaa    6300
aaaattcgca tgcaaccaag aatactggga agaatttgct gccagcccta ttaggataac    6360
aactgagaat ttagcaacct atgttactaa actaaagggg ccaaaagcag cagcgctatt    6420
cgcaaaaacc cataatctac tgccactaca ggaagtacca atggataggt tcacagtaga    6480
tatgaaaagg gacgtaaagg tgactcctgg tacaaagcat acagaggaaa gacctaaggt    6540
gcaggttata caggcggctg aacccttggc gacagcatac ctatgtggga ttcacagaga    6600
gctggttagg aggctgaacg ccgtcctcct acccaatgta catacactat ttgacatgtc    6660
tgccgaggat ttcgatgcca tcatagccgc acactttaag ccaggagaca ctgttttgga    6720
aacggacata gcctcctttg ataagagcca agatgattca cttgcgctta ctgctttgat    6780
gctgttagag gatttagggg tggatcactc cctgctggac ttgatagagg ctgctttcgg    6840
agagatttcc agctgtcacc taccgacagg tacgcgcttc aagttcggcg ccatgatgaa    6900
atcaggtatg ttcctaactc tgttcgtcaa cacattgtta aacatcacca tcgccagccg    6960
agtgctggaa gatcgtctga caaaatccgc gtgcgcggcc ttcatcggcg acgacaacat    7020
aatacatgga gtcgtctccg atgaattgat ggcagccaga tgtgccactt ggatgaacat    7080
ggaagtgaag atcatagatg cagttgtatc cttgaaagcc ccttactttt gtgggggtt    7140 tatactgcac gatactgtga caggaacagc ttgcagagtg cagacccgc taaaaaggct    7200 ttttaaactg gcaaaccgc tagcggcagg tgacgaacaa gatgaagata aagacgagc    7260 gctggctgac gaagtgatca gatggcaacg aacaggcta attgatgagc tggagaaagc    7320
ggtatactct aggtacgaag tgcagggtat atcagttgtg gtaatgtcca tggccacctt    7380
```

```
tgcaagctcc agatccaact tcgagaagct cagaggaccc gtcataactt tgtacggcgg    7440
tcctaaatag gtacgcacta cagctaccta ttttgcagaa gccgacagca agtatctaaa    7500
cactaatcag ctacaatgga gttcatccca acccaaactt tttacaatag gaggtaccag    7560
cctcgaccct ggactccgcg ccctactatc caagtcatca ggcccagacc cgcccctcag    7620
aggcaagctg ggcaacttgc ccagctgatc tcagcagtta ataaactgac aatgcgcgcg    7680
gtaccccaac agaagccacg caggaatcgg aagaataaga agcaaagca aaacaacag     7740 gcgccacaaa acaacacaaa tcaaagaag cagccaccta aaagaaacc ggctcaaaag      7800 aaaaagaagc cgggccgcag agagaggatg tgcatgaaaa tcgaaaatga ttgtattttc    7860
gaagtcaagc acgaaggtaa ggtaacaggt tacgcgtgcc tggtggggga caaagtaatg    7920
aaaccagcac acgtaaaggg gaccatcgat aacgcggacc tggccaaact ggcctttaag    7980
cggtcatcta agtatgacct tgaatgcgcg cagataccg tgcacatgaa gtccgacgct     8040
tcgaagttca cccatgagaa accgaggggg tactacaact ggcaccacgg agcagtacag    8100
tactcaggag gccggttcac catccctaca ggtgctggca accaggggga cagcggcaga    8160
ccgatcttcg acaacaaggg acgcgtggtg gccatagtct taggaggagc taatgaagga    8220
gcccgtacag ccctctcggt ggtgacctgg aataaagaca ttgtcactaa aatcacccc     8280 gaggggggccg aagagtggag tcttgccatc ccagttatgt gcctgttggc aaacaccacg    8340
ttcccctgct cccagccccc ttgcacgccc tgctgctacg aaaaggaacc ggaggaaacc    8400
ctacgcatgc ttgaggacaa cgtcatgaga cctgggtact atcagctgct acaagcatcc    8460
ttaacatgtt ctccccaccg ccagcgacgc agcaccaagg acaacttcaa tgtctataaa    8520
gccacaagac catacttagc tcactgtccc gactgtggag aagggcactc gtgccatagt    8580
cccgtagcac tagaacgcat cagaaatgaa gcgacagacg ggacgctgaa aatccaggtc    8640
tccttgcaaa tcggaataaa gacggatgac agccacgatt ggaccaagct gcgttatatg    8700
gacaaccaca tgccagcaga cgcagagagg gcggggctat ttgtaagaac atcagcaccg    8760
tgtacgatta ctggaacaat gggacacttc atcctggccc gatgtccaaa aggggaaact    8820
ctgacggtgg gattcactga cagtaggaag attagtcact catgtacgca cccatttcac    8880
cacgaccctc ctgtgatagg tcgggaaaaa ttccattccc gaccgcagca cggtaaagag    8940
ctaccttgca gcacgtacgt gcagagcacc gccgcaacta ccgaggagat agaggtacac    9000 atgccccag acacccctga tcgcacatta atgtcacaac agtccggcaa cgtaaagatc    9060
acagtcaatg ccagacggt gcggtacaag tgtaattgcg gtggctcaaa tgaaggacta    9120
acaactacag acaaagtgat taataactgc aaggttgatc aatgtcatgc cgcggtcacc    9180
aatcacaaaa agtggcagta taactcccct ctggtcccgc gtaatgctga acttgggga     9240 cgaaaaggaa aaattcacat cccgtttccg ctggcaaatg taacatgcag ggtgcctaaa    9300
gcaaggaacc ccaccgtgac gtacgggaaa accaagtca tcatgctact gtatcctgac     9360
cacccaacac tcctgtccta ccggaatatg ggagaagaac caaactatca agaagagtgg    9420
gtgatgcata gaaggaagt cgtgctaacc gtgccgactg aagggctcga ggtcacgtgg    9480
ggcaacaacg agccgtataa gtattggccg cagttatcta caaacggtac agcccatggc    9540
cacccgcacg agataattct gtattattat gagctgtacc ccactatgac tgtagtagtt    9600
gtgtcagtgg ccacgttcat actcctgtcg atggtgggta tggcagcggg gatgtgcatg    9660
tgtgcacgac gcagatgcat cacaccgtat gaactgacac caggagctac cgtccctttc    9720
```

```
ctgcttagcc taatatgctg catcagaaca gctaaagcgg ccacatacca agaggctgcg    9780
atatacctgt ggaacgagca gcaacctttg ttttggctac aagcccttat tccgctggca    9840
gccctgattg ttctatgcaa ctgtctgaga ctcttaccat gctgctgtaa aacgttggct    9900
tttttagccg taatgagcgt cggtgcccac actgtgagcg cgtacgaaca cgtaacagtg    9960
atcccgaaca cggtgggagt accgtataag actctagtca atagacctgg ctacagcccc   10020
atggtattgg agatggaact actgtcagtc actttggagc caacactatc gcttgattac   10080
atcacgtgcg agtacaaaac cgtcatcccg tctccgtacg tgaagtgctg cggtacagca   10140
gagtgcaagg acaaaaacct acctgactac agctgtaagg tcttcaccgg cgtctaccca   10200
tttatgtggg gcggcgccta ctgcttctgc gacgctgaaa acacgcagtt gagcgaagca   10260
cacgtggaga agtccgaatc atgcaaaaca gaatttgcat cagcatacag ggctcatacc   10320
gcatctgcat cagctaagct ccgcgtcctt taccaaggaa ataacatcac tgtaactgcc   10380
tatgcaaacg gcgaccatgc cgtcacagtt aaggacgcca aattcattgt ggggccaatg   10440
tcttcagcct ggacaccttt cgacaacaaa attgtggtgt acaaaggtga cgtctataac   10500
atggactacc cgccctttgg cgcaggaaga ccaggacaat tggcgatatc caaagtcgc a   10560 acacctgaga gtaagacgt ctatgctaat acacaactgg tactgcagag accggctgtg    10620
ggtacggtac acgtgccata ctctcaggca ccatctggct ttaagtattg gctaaaagaa   10680 cgcgggggcgt cgctgcagca cacagcacca tttggctgcc aaatagcaac aaacccggta   10740
agagcggtga actgcgccgt agggaacatg cccatctcca tcgacatacc ggaagcggcc   10800
ttcactaggg tcgtcgacgc gccctcttta acggacatgt cgtgcgaggt accagcctgc   10860
acccattcct cagactttgg gggcgtcgcc attattaaat atgcagccag caagaaaggc   10920
aagtgtgcgg tgcattcgat gactaacgcc gtcactattc gggaagctga gatagaagtt   10980
gaagggaatt ctcagctgca aatctctttc tcgacggcct tagccagcgc cgaattccgc   11040
gtacaagtct gttctacaca agtacactgt gcagccgagt gccaccccc gaaggaccac   11100 atagtcaact acccggcgtc acataccacc ctcgggtcc aggacatctc cgctacggcg    11160
atgtcatggg tgcagaagat cacgggaggt gtgggactgg ttgttgctgt tgccgcactg   11220
attctaatcg tggtgctatg cgtgtcgttc agcaggcact aacttgacaa ttaagtatga   11280
aggtatatgt gtcccctaag agacacactg tacatagcaa ataatctata gatcaaaggg   11340
ctacgcaacc cctgaatagt aacaaaatat aaaatcacta aaattataa aaacagaaaa    11400 atacataaat aggtatacgt gtcccctaag agacacattg tatgtaggtg ataagtatag   11460
atcaaagggc cgaataaccc ctgaatagta acaaaatatg aaaatcaata aaaatcataa   11520
aatagaaaaa ccataaacag aagtagttca aagggctata aaacccctga atagtaacaa   11580
aacataaaat taataaaaat c                                             11601
```

<210> SEQ ID NO 104
<211> LENGTH: 3747
<212> TYPE: DNA
<213> ORGANISM: Chikungunya virus

<400> SEQUENCE: 104

```
atggagttca tcccaaccca acttttttac aataggaggt accagcctcg accctggact     60
ccgcgcccta ctatccaagt catcaggccc agaccgcgcc ctcagaggca agctgggcaa    120
cttgcccagc tgatctcagc agttaataaa ctgacaatgc gcgcggtacc ccaacagaag    180
ccacgcagga atcggaagaa taagaagcaa aagcaaaaac aacaggcgcc acaaaacaac    240
```

```
acaaatcaaa agaagcagcc acctaaaaag aaaccggctc aaaagaaaaa gaagccgggc         300
cgcagagaga ggatgtgcat gaaaatcgaa aatgattgta ttttcgaagt caagcacgaa         360
ggtaaggtaa caggttacgc gtgcctggtg ggggacaaag taatgaaacc agcacacgta         420
aaggggacca tcgataacgc ggacctggcc aaactggcct ttaagcggtc atctaagtat         480
gaccttgaat gcgcgcagat acccgtgcac atgaagtccg acgcttcgaa gttcacccat         540
gagaaaccgg aggggtacta caactggcac acggagcag tacagtactc aggaggccgg          600
ttcaccatcc ctacaggtgc tggcaaacca ggggacagcg gcagaccgat cttcgacaac         660
aagggacgcg tggtggccat agtcttagga ggagctaatg aaggagcccg tacagccctc         720
tcggtggtga cctggaataa agacattgtc actaaaatca cccccgaggg ggccgaagag         780
tggagtcttg ccatcccagt tatgtgcctg ttggcaaaca ccacgttccc ctgctcccag         840 ccccccttgca cgccctgctg ctacgaaaag gaaccggagg aaaccctacg catgcttgag         900
gacaacgtca tgagacctgg gtactatcag ctgctacaag catccttaac atgttctccc         960
caccgccagc gacgcagcac caaggacaac ttcaatgtct ataaagccac aagaccatac        1020
ttagctcact gtcccgactg tggagaaggg cactcgtgcc atagtcccgt agcactagaa        1080
cgcatcagaa atgaagcgac agacgggacg ctgaaaatcc aggtctcctt gcaaatcgga        1140
ataaagacgg atgacagcca cgattggacc aagctgcgtt atatggacaa ccacatgcca        1200
gcagacgcag agagggcggg gctatttgta agaacatcag caccgtgtac gattactgga        1260
acaatgggac acttcatcct ggcccgatgt ccaaaagggg aaactctgac ggtgggattc        1320
actgacagta ggaagattag tcactcatgt acgcacccat ttcaccacga ccctcctgtg        1380
ataggtcggg aaaaattcca ttcccgaccg cagcacggta aagagctacc ttgcagcacg        1440
tacgtgcaga gcaccgccgc aactaccgag gagatagagg tacacatgcc cccagacacc        1500
cctgatcgca cattaatgtc acaacagtcc ggcaacgtaa agatcacagt caatggccag        1560
acggtgcggt acaagtgtaa ttgcggtggc tcaaatgaag gactaacaac tacagacaaa        1620
gtgattaata actgcaaggt tgatcaatgt catgccgcgg tcaccaatca caaaagtggg        1680
cagtataact cccctctggt cccgcgtaat gctgaacttg ggaccgaaa aggaaaaatt         1740 cacatcccgt ttccgctggc aaatgtaaca tgcagggtgc ctaaagcaag gaaccccacc        1800
gtgacgtacg ggaaaaacca agtcatcatg ctactgtatc ctgaccaccc aacactcctg        1860
tcctaccgga atatgggaga agaaccaaac tatcaagaag agtgggtgat gcataagaag        1920
gaagtcgtgc taaccgtgcc gactgaaggg ctcgaggtca cgtggggcaa caacgagccg        1980
tataagtatt ggccgcagtt atctacaaac ggtacagccc atggccaccc gcacgagata        2040
attctgtatt attatgagct gtaccccact atgactgtag tagttgtgtc agtggccacg        2100
ttcatactcc tgtcgatggt gggtatggca gcggggatgt gcatgtgtgc acgacgcaga        2160
tgcatcacac cgtatgaact gacaccagga gctaccgtcc cttcctgct agcctaata         2220 tgctgcatca gaacagctaa agcggccaca taccaagagg ctgcgatata cctgtggaac        2280
gagcagcaac ctttgttttg gctacaagcc cttattccgc tggcagccct gattgttcta        2340
tgcaactgtc tgagactctt accatgctgc tgtaaaacgt tggcttttt agccgtaatg        2400 agcgtcggtg cccacactgt gagcgcgtac gaacacgtaa cagtgatccc gaacacggtg        2460
ggagtaccgt ataagactct agtcaataga cctggctaca gccccatggt attggagatg        2520
gaactactgt cagtcacttt ggagccaaca ctatcgcttg attacatcac gtgcgagtac        2580
```

-continued

```
aaaaccgtca tcccgtctcc gtacgtgaag tgctgcggta cagcagagtg caaggacaaa   2640
aacctacctg actacagctg taaggtcttc accggcgtct acccatttat gtggggcggc   2700
gcctactgct tctgcgacgc tgaaaacacg cagttgagcg aagcacacgt ggagaagtcc   2760
gaatcatgca aaacagaatt tgcatcagca tacagggctc ataccgcatc tgcatcagct   2820
aagctccgcg tcctttacca aggaaataac atcactgtaa ctgcctatgc aaacggcgac   2880
catgccgtca cagttaagga cgccaaattc attgtggggc caatgtcttc agcctggaca   2940
cctttcgaca acaaaattgt ggtgtacaaa ggtgacgtct ataacatgga ctacccgccc   3000
tttggcgcag gaagaccagg acaatttggc gatatccaaa gtcgcacacc tgagagtaaa   3060
gacgtctatg ctaatacaca actggtactg cagagaccgg ctgtgggtac ggtacacgtg   3120
ccatactctc aggcaccatc tggctttaag tattggctaa aagaacgcgg ggcgtcgctg   3180
cagcacacag caccatttgg ctgccaaata gcaacaaacc cggtaagagc ggtgaactgc   3240
gccgtaggga acatgcccat ctccatcgac ataccggaag cggccttcac tagggtcgtc   3300
gacgcgccct ctttaacgga catgtcgtgc gaggtaccag cctgcaccca ttcctcagac   3360
tttgggggcg tcgccattat taaatatgca gccagcaaga aaggcaagtg tgcggtgcat   3420
tcgatgacta acgccgtcac tattcgggaa gctgagatag aagttgaagg gaattctcag   3480
ctgcaaatct ctttctcgac ggccttagcc agcgccgaat tccgcgtaca agtctgttct   3540
acacaagtac actgtgcagc cgagtgccac cccccgaagg accacatagt caactacccg   3600
gcgtcacata ccaccctcgg ggtccaggac atctccgcta cggcgatgtc atgggtgcag   3660
aagatcacgg gaggtgtggg actggttgtt gctgttgccg cactgattct aatcgtggtg   3720
ctatgcgtgt cgttcagcag gcactaa                                       3747
```

<210> SEQ ID NO 105
<211> LENGTH: 854
<212> TYPE: PRT
<213> ORGANISM: Coxsackievirus

<400> SEQUENCE: 105

```
Met Gly Ala Gln Val Ser Thr Gln Lys Thr Gly Ala His Glu Thr Arg
1               5                   10                  15

Leu Asn Ala Ser Gly Asn Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60

Leu Pro Ala Leu Asn Ser Pro Thr Val Glu Glu Cys Gly Tyr Ser Asp
65                  70                  75                  80

Arg Ala Arg Ser Ile Thr Leu Gly Asn Ser Thr Ile Thr Thr Gln Glu
                85                  90                  95

Cys Ala Asn Val Val Val Gly Tyr Gly Val Trp Pro Asp Tyr Leu Lys
            100                 105                 110

Asp Ser Glu Ala Thr Ala Glu Asp Gln Pro Thr Gln Pro Asp Val Ala
        115                 120                 125

Thr Cys Arg Phe Tyr Thr Leu Asp Ser Val Gln Trp Gln Lys Thr Ser
    130                 135                 140

Pro Gly Trp Trp Trp Lys Leu Pro Asp Ala Leu Ser Asn Leu Gly Leu
145                 150                 155                 160

Phe Gly Gln Asn Met Gln Tyr His Tyr Leu Gly Arg Thr Gly Tyr Thr
```

```
            165                 170                 175
Val His Val Gln Cys Asn Ala Ser Lys Phe His Gln Gly Cys Leu Leu
            180                 185                 190

Val Val Cys Val Pro Glu Ala Glu Met Gly Cys Ala Thr Leu Asp Asn
            195                 200                 205

Thr Pro Ser Ser Ala Glu Leu Leu Gly Gly Asp Thr Ala Lys Glu Phe
            210                 215                 220

Ala Asp Lys Pro Val Ala Ser Gly Ser Asn Lys Leu Val Gln Arg Val
225                 230                 235                 240

Val Tyr Asn Ala Gly Met Gly Val Gly Asn Leu Thr Ile Phe
                    245                 250                 255

Pro His Gln Trp Ile Asn Leu Arg Thr Asn Asn Ser Ala Thr Ile Val
                    260                 265                 270

Met Pro Tyr Thr Asn Ser Val Pro Met Asp Asn Met Phe Arg His Asn
                    275                 280                 285

Asn Val Thr Leu Met Val Ile Pro Phe Val Pro Leu Asp Tyr Cys Pro
            290                 295                 300

Gly Ser Thr Thr Tyr Val Pro Ile Thr Val Thr Ile Ala Pro Met Cys
305                 310                 315                 320

Ala Glu Tyr Asn Gly Leu Arg Leu Ala Gly His Gln Gly Leu Pro Thr
                    325                 330                 335

Met Asn Thr Pro Gly Ser Cys Gln Phe Leu Thr Ser Asp Asp Phe Gln
                    340                 345                 350

Ser Pro Ser Ala Met Pro Gln Tyr Asp Val Thr Pro Glu Met Arg Ile
                    355                 360                 365

Pro Gly Glu Val Lys Asn Leu Met Glu Ile Ala Glu Val Asp Ser Val
            370                 375                 380

Val Pro Val Gln Asn Val Gly Glu Lys Val Asn Ser Met Glu Ala Tyr
385                 390                 395                 400

Gln Ile Pro Val Arg Ser Asn Glu Gly Ser Gly Thr Gln Val Phe Gly
                    405                 410                 415

Phe Pro Leu Gln Pro Gly Tyr Ser Ser Val Phe Ser Arg Thr Leu Leu
                    420                 425                 430

Gly Glu Ile Leu Asn Tyr Tyr Thr His Trp Ser Gly Ser Ile Lys Leu
            435                 440                 445

Thr Phe Met Phe Cys Gly Ser Ala Met Ala Thr Gly Lys Phe Leu Leu
            450                 455                 460

Ala Tyr Ser Pro Pro Gly Ala Gly Ala Pro Thr Lys Arg Val Asp Ala
465                 470                 475                 480

Met Leu Gly Thr His Val Ile Trp Asp Val Gly Leu Gln Ser Ser Cys
                    485                 490                 495

Val Leu Cys Ile Pro Trp Ile Ser Gln Thr His Tyr Arg Phe Val Ala
                    500                 505                 510

Ser Asp Glu Tyr Thr Ala Gly Gly Phe Ile Thr Cys Trp Tyr Gln Thr
                    515                 520                 525

Asn Ile Val Val Pro Ala Asp Ala Gln Ser Ser Cys Tyr Ile Met Cys
            530                 535                 540

Phe Val Ser Ala Cys Asn Asp Phe Ser Val Arg Leu Leu Lys Asp Thr
545                 550                 555                 560

Pro Phe Ile Ser Gln Gln Asn Phe Phe Gln Gly Pro Val Glu Asp Ala
                    565                 570                 575

Ile Thr Ala Ala Ile Gly Arg Val Ala Asp Thr Val Gly Thr Gly Pro
                    580                 585                 590
```

-continued

```
Thr Asn Ser Glu Ala Ile Pro Ala Leu Thr Ala Ala Glu Thr Gly His
        595             600             605
Thr Ser Gln Val Val Pro Gly Asp Thr Met Gln Thr Arg His Val Lys
    610             615             620
Asn Tyr His Ser Arg Ser Glu Ser Thr Ile Glu Asn Phe Leu Cys Arg
625             630             635             640
Ser Ala Cys Val Tyr Phe Thr Glu Tyr Lys Asn Ser Gly Ala Lys Arg
                645             650             655
Tyr Ala Glu Trp Val Leu Thr Pro Arg Gln Ala Ala Gln Leu Arg Arg
                660             665             670
Lys Leu Glu Phe Phe Thr Tyr Val Arg Phe Asp Leu Glu Leu Thr Phe
        675             680             685
Val Ile Thr Ser Thr Gln Gln Pro Ser Thr Thr Gln Asn Gln Asp Ala
    690             695             700
Gln Ile Leu Thr His Gln Ile Met Tyr Val Pro Pro Gly Gly Pro Val
705             710             715             720
Pro Asp Lys Val Asp Ser Tyr Val Trp Gln Thr Ser Thr Asn Pro Ser
                725             730             735
Val Phe Trp Thr Glu Gly Asn Ala Pro Pro Arg Met Ser Ile Pro Phe
                740             745             750
Leu Ser Ile Gly Asn Ala Tyr Ser Asn Phe Tyr Asp Gly Trp Ser Glu
        755             760             765
Phe Ser Arg Asn Gly Val Tyr Gly Ile Asn Thr Leu Asn Asn Met Gly
    770             775             780
Thr Leu Tyr Ala Arg His Val Asn Ala Gly Ser Thr Gly Pro Ile Lys
785             790             795             800
Ser Thr Ile Arg Ile Tyr Phe Lys Pro Lys His Val Lys Ala Trp Ile
                805             810             815
Pro Arg Pro Pro Arg Leu Cys Gln Tyr Glu Lys Ala Lys Asn Val Asn
                820             825             830
Phe Gln Pro Ser Gly Val Thr Thr Thr Arg Gln Ser Ile Thr Thr Met
        835             840             845
Thr Asn Thr Gly Ala Phe
850
```